United States Patent
Kerns et al.

(10) Patent No.: US 10,604,509 B2
(45) Date of Patent: Mar. 31, 2020

(54) NRF2 REGULATORS

(71) Applicants: GlaxoSmithKline Intellectual Property Development Limited, Brentford, Middlesex (GB); Astex Therapeutics, Limited, Milton Road, Cambridge (GB)

(72) Inventors: Jeffrey K. Kerns, King of Prussia, PA (US); James Callahan, King of Prussia, PA (US); Thomas Daniel Heightman, Harpenden (GB); Alison Jo-Anne Woolford, Cambridge (GB); Ami Lakdawala Shah, Collegeville, PA (US); Roderick S. Davis, King of Prussia, PA (US); David Norton, Cambridge (GB); Jeffrey Charles Boehm, King of Prussia, PA (US); Nicole Cathleen Goodwin, King of Prussia, PA (US)

(73) Assignees: GlaxoSmithKline Intellectual Property Development Limited, Brentford, Middlesex (GB); Astex Therapeutics Limited, Cambridge, Cambridgeshire (GB)

(*) Notice: Subject to any disclaimer, the term of this patent is extended or adjusted under 35 U.S.C. 154(b) by 0 days.

(21) Appl. No.: 15/736,075

(22) PCT Filed: Jun. 15, 2016

(86) PCT No.: PCT/CN2016/085806
§ 371 (c)(1),
(2) Date: Dec. 13, 2017

(87) PCT Pub. No.: WO2016/202253
PCT Pub. Date: Dec. 22, 2016

(65) Prior Publication Data
US 2018/0179187 A1 Jun. 28, 2018

Related U.S. Application Data

(60) Provisional application No. 62/175,510, filed on Jun. 15, 2015.

(51) Int. Cl.
| | | |
|---|---|---|
| C07D 417/10 | (2006.01) |
| C07D 403/10 | (2006.01) |
| C07D 249/04 | (2006.01) |
| C07D 249/18 | (2006.01) |
| C07D 401/14 | (2006.01) |
| C07D 405/14 | (2006.01) |
| C07D 413/14 | (2006.01) |
| C07D 401/10 | (2006.01) |
| C07D 403/14 | (2006.01) |
| C07D 413/10 | (2006.01) |
| C07D 471/04 | (2006.01) |
| C07D 487/04 | (2006.01) |
| C07D 498/04 | (2006.01) |
| C07D 267/14 | (2006.01) |
| C07D 233/60 | (2006.01) |
| C07D 487/08 | (2006.01) |
| C07D 451/02 | (2006.01) |
| A61P 9/00 | (2006.01) |
| A61P 25/00 | (2006.01) |
| A61P 11/00 | (2006.01) |
| A61P 27/00 | (2006.01) |
| A61P 35/00 | (2006.01) |

(Continued)

(52) U.S. Cl.
CPC .............. *C07D 403/10* (2013.01); *A61P 9/00* (2018.01); *A61P 11/00* (2018.01); *A61P 25/00* (2018.01); *A61P 27/00* (2018.01); *A61P 35/00* (2018.01); *A61P 37/00* (2018.01); *C07D 233/60* (2013.01); *C07D 233/64* (2013.01); *C07D 249/18* (2013.01); *C07D 255/04* (2013.01); *C07D 267/14* (2013.01); *C07D 273/01* (2013.01); *C07D 401/10* (2013.01); *C07D 401/14* (2013.01); *C07D 403/14* (2013.01); *C07D 405/10* (2013.01); *C07D 405/14* (2013.01); *C07D 413/10* (2013.01); *C07D 413/14* (2013.01); *C07D 451/02* (2013.01); *C07D 471/04* (2013.01); *C07D 487/04* (2013.01); *C07D 487/08* (2013.01); *C07D 498/04* (2013.01)

(58) Field of Classification Search
CPC .. C07D 417/10; C07D 403/10; C07D 249/04; C07D 249/18
See application file for complete search history.

(56) References Cited

U.S. PATENT DOCUMENTS

| | | |
|---|---|---|
| 2003/0191115 A1 | 10/2003 | Pinto et al. |
| 2004/0157919 A1 | 8/2004 | Wu et al. |
| 2015/0018422 A1 | 1/2015 | Miwatashi et al. |

FOREIGN PATENT DOCUMENTS

| | | |
|---|---|---|
| EP | 528586 B1 | 2/1995 |
| EP | 0478328 B1 | 1/1996 |

(Continued)

OTHER PUBLICATIONS

Antonio R. Damasio, Alzheimer's Disease and Related Dementias, Cecil Textbook of Medicine, 20th edition (1996), vol. 2, pp. 1992-1996 (Year: 1996).

(Continued)

*Primary Examiner* — Bruck Kifle
(74) *Attorney, Agent, or Firm* — Nora L. Stein; Fang Qian; Edward R. Gimmi

(57) ABSTRACT

Provided are aryl analogs, pharmaceutical compositions containing them and their use as NRF2 regulators.

26 Claims, No Drawings

(51) Int. Cl.
*A61P 37/00* (2006.01)
*C07D 233/64* (2006.01)
*C07D 255/04* (2006.01)
*C07D 273/01* (2006.01)
*C07D 405/10* (2006.01)

(56) References Cited

FOREIGN PATENT DOCUMENTS

| WO | 1993012075 A1 | 6/1993 |
|---|---|---|
| WO | 1995032710 A1 | 12/1995 |
| WO | 2001025181 A1 | 4/2001 |
| WO | 2001053267 A1 | 7/2001 |
| WO | 2002059080 A2 | 8/2002 |
| WO | 2002080899 A1 | 10/2002 |
| WO | 2002100812 A1 | 12/2002 |
| WO | 2003026652 A1 | 4/2003 |
| WO | 2004007464 A1 | 1/2004 |
| WO | 2004092140 A1 | 10/2004 |
| WO | 2006044133 A1 | 4/2006 |
| WO | 2006118320 A1 | 11/2006 |
| WO | 2008002490 A2 | 1/2008 |
| WO | 2009032249 A1 | 3/2009 |
| WO | 2010005922 A1 | 1/2010 |
| WO | 2010099054 A2 | 9/2010 |
| WO | 2011097300 A1 | 8/2011 |
| WO | 2012068589 A2 | 5/2012 |
| WO | WO 2013/067036 A1 | 5/2013 |
| WO | WO 2013/122028 A1 | 8/2013 |
| WO | 2013155528 A2 | 10/2013 |
| WO | WO 2014/145642 A2 | 9/2014 |
| WO | WO 2015/092713 A1 | 6/2015 |
| WO | 2016/203400 A1 | 12/2016 |
| WO | 2016/203401 A1 | 12/2016 |
| WO | 2017060854 A1 | 4/2017 |
| WO | 2017060855 A1 | 4/2017 |

OTHER PUBLICATIONS

FDA mulls drug to slow late-stage Alzheimer's, [retrieved on Sep. 23, 2003]. Retrieved online via Internet, URL: http://www.cnn.com/2003/HEALTH/conditions/09/24/alzheimers.drug.ap/index.html (Year: 2003).

Robert B. Layzer, Section Five—Degenerative Diseases of the Nervous System, Cecil Textbook of Medicine, 20th edition (1996), vol. 2, pp. 2050-2057 (Year: 1996).

TG Davies, et al, "Journal of Medicinal Chemistry Paper—Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based discovery." J Med Chem. Apr. 28, 2016;59(8):3991-4006.

NRF2 REGULATORS

This application is a 371 of International Application No. PCT/CN2016/085806, filed Jun. 15, 2016, which claims the benefit of U.S. Provisional Application No. U.S. 62/175,510, filed Jun. 15, 2015, which is incorporated herein in its entirety.

FIELD OF THE INVENTION

The present invention relates to aryl analogs, pharmaceutical compositions containing them and their use as NRF2 regulators.

BACKGROUND OF THE INVENTION

NRF2 (NF-E2 related factor 2) is a member of the cap-n-collar (CNC) family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cytosol are low in normal conditions but the system is designed to respond immediately to environmental stress by increasing NRF2 activity.

Inappropriately low NRF2 activity in the face of on-going oxidative stress appears to be a pathological mechanism underlying chronic obstructive pulmonary disease (COPD). This may be a result of an altered equilibrium between NRF2 regulators with both inappropriate lack of positive regulators such as DJ1, and overabundance of negative regulators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 modulators may treat COPD (Boutten, A., et al. 2011. *Trends Mol. Med.* 17:363-371) and other respiratory diseases, including asthma and pulmonary fibrosis (Cho, H. Y., and Kleeberger, S. R. 2010. *Toxicol. Appl. Pharmacol.* 244:43-56).

An example of inappropriately low NRF2 activity is found in pulmonary macrophages from COPD patients. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infections. This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa*, non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, al antitrypsin disease, and cystic fibrosis (C F, Chen, J. et al. 2008. *PLoS One,* 2008; 3(10):e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International,* June 19. doi: 10.1038/ki.2013.248), and kidney disease or malfunction seen during kidney transplantation.

In the cardiac area, bardoxolone methyl is currently under investigation in patients with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [*Arterioscler Thromb Vasc Biol* (2009) 29(11); 1843-1850; *PLOS ONE* (2012) 7(9); e44899]. In addition, NRF2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29(11); *J of Mol & Cell Cardio* (2014) 72; 305-315; and 1843-1850; *PLOS ONE* (2012) 7(9); e44899]. NRF2 activation has also been shown to protect against cardiac I/R injury in mice [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064; Epub 2012 Jan. 12) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res. (Phila)* 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis. Sci.*, Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In pre-clinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology,* 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 modulator may be useful in treating the dermatitis/topical effects of radiation (Schifer, M. et al. 2010. *Genes & Devl.* 24:1045-1058); and The Immunosuppression due to Radiation Exposure, Kim, J. H. et al, *J. Clin. Invest.* 2014 Feb. 3:124(2): 730-41).

There are also data suggesting that an NRF2 activator may be beneficial in preeclampsia, a disease that occurs in 2-5% of pregnancies and involves hypertension and proteinuria (*Annals of Anatomy—Anatomischer Anzeiger Volume* 196, *Issue* 5, September 2014, *Pages* 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, *Free Radic Biol Med.* October 2013; 63: 264-273.)

SUMMARY OF THE INVENTION

In one aspect this invention provides for aryl analogs, pharmaceutically acceptable salts thereof, and pharmaceutical compositions containing them. In particular, the compounds of this invention include a compound of Formula (I).

In a second aspect, this invention provides for the use of a compound of Formula (I) as NRF2 regulators.

In another aspect, this invention provides for the use of a compound of Formula (I) for treating and preventing conditions associated with NRF2 imbalance.

In one aspect, the invention is provides a pharmaceutical composition comprising a compound of the invention according to Formula (I), or a pharmaceutically acceptable salt thereof, and a pharmaceutically acceptable excipient. Particularly, this invention is directed to a pharmaceutical composition for the treatment of an NRF2 regulated disease or disorder, wherein the composition comprises a compound according to Formula (I), or a pharmaceutically acceptable salt thereof, and a pharmaceutically acceptable excipient.

In a further aspect, this invention provides for a method of treating respiratory and non-respiratory disorders, including COPD, asthma, fibrosis, chronic asthma, acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I).

In yet another aspect, this invention provides for the use of a compound of Formula (I) for the treatment of respiratory and non-respiratory disorders, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to use of a compound of Formula (I) or a pharmaceutically acceptable salt thereof in the manufacture of a medicament for the treatment of respiratory and non-respiratory disorders, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to a compound of Formula (I) or a pharmaceutically acceptable salt thereof, for use in medical therapy.

In a further aspect, this invention relates to a compound of Formula (I) or a pharmaceutically acceptable salt thereof, for use in the treatment of respiratory and non-respiratory disorders, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to the use of a compound of Formula (I) for the treatment of COPD.

In a further aspect, this invention relates to use of a compound of Formula (I) or a pharmaceutically acceptable salt thereof in the manufacture of a medicament for the treatment of COPD.

In a further aspect, this invention relates to a compound of Formula (I) or a pharmaceutically acceptable salt thereof, for use in the treatment COPD.

In a further aspect, this invention relates to a method of treating COPD which comprises administering to a human in need thereof, a compound of Formula (I).

In a further aspect, this invention relates to the use of a compound of Formula (I) for the treatment of heart failure.

In a further aspect, this invention relates to use of a compound of Formula (I) or a pharmaceutically acceptable salt thereof in the manufacture of a medicament for the treatment of heart failure.

In a further aspect, this invention relates to a method of treating heart failure which comprises administering to a human in need thereof, a compound of Formula (I).

In a further aspect, this invention relates to a compound of Formula (I) or a pharmaceutically acceptable salt thereof, for use in the treatment of heart failure.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, and insulin.

The compounds may be used in combination with antihypertensives such as diuretics, ACE inhibitors, ARBS, calcium channel blockers, and beta blockers.

In one embodiment, the invention is directed to the use of a compound of Formula (I), or a pharmaceutically acceptable salt thereof, as an active therapeutic substance. More specifically, this invention provides for the use of the compounds described herein for the treatment of a respiratory and non-respiratory disorder, specifically, a disease or disorder recited herein. Accordingly, the invention provides for the use of a compound of Formula (I), or a pharmaceutically acceptable salt thereof, as an active therapeutic substance in the treatment of a human in need thereof with a respiratory and non-respiratory disorder, specifically, a disease or disorder recited herein. Specifically, the invention provides for the use of a compound of Formula (I), or a pharmaceutically acceptable salt thereof, as an active therapeutic substance in the treatment of COPD. Specifically, the invention provides for the use of a compound of Formula (I), or a pharmaceutically acceptable salt thereof, as an active therapeutic substance in the treatment of heart failure.

Other aspects and advantages of the present invention are described further in the following detailed description of the preferred embodiments thereof.

DETAILED DESCRIPTION OF THE INVENTION

The present invention provides for compounds of Formula (I):

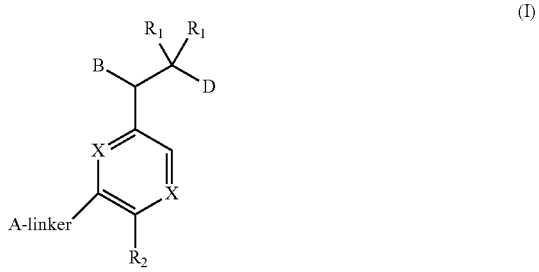

wherein:
B is benzotriazolyl, phenyl, triazolopyridinyl, or —$(CH_2)_2$triazolyl each of which may be unsubstituted or substituted by 1, 2, or 3 substituents independently chosen from —$C_{1-3}$alkyl, —O—$C_{1-3}$alkyl, CN, —$(CH_2)_2$—O—$(CH_2)_2$—$OR_4$ and halo;
D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;
$R_1$ is independently hydrogen, $C_{1-3}$alkyl, F, $C_{3-6}$spirocycloalkyl, oxetane, or the two $R_1$ groups together with the carbon to which they are attached form a cyclopropyl group;
$R_2$ is hydrogen, methyl, CF$_3$, or halo;
$R_4$ is hydrogen or —$C_{1-3}$alkyl;
Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
All of which may be unsubstituted or substituted by 1, 2, or 3 substituents independently chosen from: —$C_{1-3}$alkyl, $C_{3-6}$spirocycloalkyl, halo, CN, —O—$C_{1-3}$alkyl, —CH$_2$—O—CH$_3$, and OH;
And the piperidinyl may additionally be independently substituted by pyrazolyl, —CH$_2$pyrazolyl, or oxadiazolyl each of which may be further independently substituted by —$C_{1-3}$alkyl, or, when A is piperidinyl, it may be substituted by —SO$_2$R, wherein R is $C_{1-3}$alkyl, phenyl or $C_{3-7}$cycloalkyl;
And the oxazepane may additionally be independently substituted by 1 or 2 of —$C_{1-3}$alkyl or —$C_{3-7}$cycloalkyl;
And the morpholinyl may additionally be substituted by a phenyl which itself may be independently substituted by $C_{1-3}$ alkyl or —O—$C_{1-3}$ alkyl;
And the pyrrolidinyl may be additionally substituted by a triazolyl group which itself is may be substituted by —$C_{1-3}$alkyl;
And the imidazolyl, triazolyl, pyrazolyl, and tetrazolyl groups may be additionally independently substituted by —CH$_2$—$C_{4-7}$ cycloalkyl, —CH$_2$—$C_{5-7}$heterocycloalkyl, —CH$_2$— azabicycloheptanyl, —CH$_2$-oxepane, or —CH$_2$-azabicyclohexanyl, all of which, including the —CH$_2$—, may be further substituted independently by 1 or 2 of —$C_{1-3}$ alkyl or F; and
X is independently CH or N;
or a pharmaceutically acceptable salt thereof.

"Alkyl" refers to a monovalent saturated hydrocarbon chain having the specified number of carbon member atoms. For example, $C_{1-4}$alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), and butyl (n-butyl, isobutyl, s-butyl, and t-butyl).

"Cycloalkyl" refers to a monovalent saturated or unsaturated hydrocarbon ring having the specified number of carbon member atoms. For example, $C_{3-6}$cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

"$C_{5-7}$ heterocycloalkyl" refers to pyrrolidine, piperidine, morpholine, azepane, 1,4-oxazepane, 1,4-thiazepane, 1,4-thiazepane 1-oxide, 1,4-thiazepane 1,1-dioxide, thiomorpholine, thiomorpholine 1-oxide, and thiomorpholine 1,1-dioxide.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}$H, $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Representative Embodiments

In one embodiment:
B is benzotriazolyl, phenyl, triazolopyridinyl, or —(CH$_2$)$_2$ triazolyl each of which may be unsubstituted or substituted by 1, 2, or 3 substituents independently chosen from —C$_{1-3}$alkyl, —O—C$_{1-3}$alkyl, CN, —(CH$_2$)$_2$—O—(CH$_2$)$_2$—OR$_4$ and halo;
D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;
R$_1$ is independently hydrogen, C$_{1-3}$alkyl, F, C$_{3-6}$spirocycloalkyl, oxetane, or the two R$_1$ groups together with the carbon to which they are attached form a cyclopropyl group;
R$_2$ is hydrogen, methyl, CF$_3$, or halo;
R$_4$ is hydrogen or —C$_{1-3}$alkyl;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
All of which may be unsubstituted or substituted by 1, 2, or 3 substituents independently chosen from: —C$_{1-3}$alkyl, C$_{3-6}$spirocycloalkyl, halo, CN, —O—C$_{1-3}$alkyl, —CH$_2$—O—CH$_3$, and OH;
And the piperidinyl may additionally be independently substituted by pyrazolyl, —CH$_2$pyrazolyl, or oxadiazolyl each of which may be further independently substituted by —C$_{1-3}$alkyl, or, when A is piperidinyl, it may be substituted by —SO$_2$R, wherein R is —C$_{1-3}$alkyl, phenyl or C$_{3-7}$cycloalkyl;
And the oxazepane may additionally be independently substituted by 1 or 2 of —C$_{1-3}$alkyl or —C$_{3-7}$cycloalkyl;
And the morpholinyl may additionally be substituted by a phenyl which itself may be independently substituted by —C$_{1-3}$alkyl or —O—C$_{1-3}$alkyl;
And the pyrrolidinyl may be additionally substituted by a triazolyl group which itself is may be substituted by —C$_{1-3}$alkyl;
And the imidazolyl, triazolyl, pyrazolyl, and tetrazolyl groups may be additionally independently substituted by —CH$_2$—C$_{4-7}$ cycloalkyl, —CH$_2$—C$_{5-7}$heterocycloalkyl, —CH$_2$-azabicycloheptanyl, —CH$_2$-oxepane, or —CH$_2$-azabicyclohexanyl, all of which, including the —CH$_2$—, may be further substituted independently by 1 or 2 of —C$_{1-3}$alkyl or F; and
X is independently CH or N;
or a pharmaceutically acceptable salt thereof.

In another embodiment:
B is benzotriazolyl or —(CH$_2$)$_2$ triazolyl each of which may be unsubstituted or substituted by 1, 2, or 3 substituents independently chosen from: —C$_{1-3}$alkyl and halo;
D is —C(O)OH, —C(O)NHSO$_2$CH$_3$, or tetrazolyl;
R$_1$ is independently hydrogen or methyl or the two R$_1$ groups together with the carbon to which they are attached form a cyclopropyl group;
R$_2$ is methyl or halo;
Linker is —CH$_2$—;
A is tetrahydrobenzoxazepinyl, tetrahydro-pyrido-oxazepinyl, piperidinyl, tetrahydrobenzazepinyl, pyrazolyl, imidazolyl, triazolyl, tetrazolyl, or tetrahydrobenzodiazepinyl;
All of which may be unsubstituted or substituted by 1, 2, or 3 substituents independently chosen from —C$_{1-3}$ alkyl, halo, CN, or —OC$_{1-3}$alkyl;
And the piperidinyl may additionally be substituted by pyrazolyl or oxadiazolyl each of which may be further substituted by —C$_{1-3}$alkyl or, when A is piperidinyl, it may be substituted by —SO$_2$R, wherein R is —C$_{1-3}$alkyl, phenyl or C$_{3-7}$cycloalkyl;
And the imidazolyl, triazolyl, pyrazolyl, and tetrazolyl groups may be additionally independently substituted by —CH$_2$—C$_{4-7}$ cycloalkyl, —CH$_2$-oxepane or a —CH$_2$—C$_{5-7}$; and
X is independently CH or N;
or a pharmaceutically acceptable salt thereof.

In yet another embodiment:
B is benzotriazolyl, or —(CH$_2$)$_2$ triazolyl each of which may be unsubstituted or substituted by 1, 2, or 3 substituents independently chosen from —C$_{1-3}$alkyl and halo;
D is —C(O)OH;
R$_1$ is independently hydrogen or methyl or the two R$_1$ groups together with the carbon to which they are attached form a cyclopropyl group;
R$_2$ is methyl or halo;
Linker is —CH$_2$—;
A is tetrahydrobenzoxazepinyl, tetrahydro-pyrido-oxazepinyl, piperidinyl, tetrahydrobenzazepinyl, pyrazolyl, imidazolyl, triazolyl, tetrazolyl, or tetrahydrobenzodiazepinyl;
All of which may be unsubstituted or substituted by 1, 2, or 3 substituents independently chosen from —C$_{1-3}$ alkyl, halo, CN, or —OC$_{1-3}$alkyl;
And the piperidinyl may additionally be substituted by pyrazolyl or oxadiazolyl each of which may be further substituted by —C$_{1-3}$alkyl or, when A is piperidinyl, it may be substituted by —SO$_2$R, wherein R is —C$_{1-3}$alkyl, phenyl or C$_{3-7}$cycloalkyl;

And the imidazolyl, triazolyl, pyrazolyl, and tetrazolyl groups may be additionally independently substituted by —CH$_2$—C$_{4-7}$ cycloalkyl, —CH$_2$-oxepane or a —CH$_2$—C$_{5-7}$; and X is CH;

or a pharmaceutically acceptable salt thereof.

In another embodiment:

B is benzotriazolyl unsubstituted or substituted by 1, 2, or 3 substituents independently chosen from —C$_{1-3}$alkyl and halo;

D is —C(O)OH;

R$_1$ is independently hydrogen or C$_{1-3}$alkyl;

R$_2$ is methyl or chloro;

Linker is —CH$_2$—;

A is tetrahydrobenzoxazepinyl, tetrahydro-pyrido-oxazepinyl, piperidinyl, tetrahydrobenzazepinyl, pyrazolyl, imidazolyl, triazolyl, tetrazolyl, or tetrahydrobenzodiazepinyl;

All of which may be unsubstituted or substituted by 1, 2, or 3 substituents independently chosen from —C$_{1-3}$ alkyl, halo, CN, or —OC$_{1-3}$alkyl;

And the piperidinyl may additionally be substituted by pyrazolyl or oxadiazolyl each of which may be further substituted by —C$_{1-3}$alkyl or, when A is piperidinyl, it may be substituted by —SO$_2$R, wherein R is —C$_{1-3}$alkyl, phenyl or C$_{3-7}$cycloalkyl;

And the imidazolyl, triazolyl, pyrazolyl, and tetrazolyl groups may be additionally independently substituted by —CH$_2$—C$_{4-7}$ cycloalkyl, —CH$_2$-oxepane or a —CH$_2$—C$_{5-7}$; and X is CH;

or a pharmaceutically acceptable salt thereof.

In a further embodiment:

B is triazolopyridinyl which may be unsubstituted or substituted by 1, 2, or 3 substituents which are —C$_{1-3}$alkyl;

D is —C(O)OH;

R$_1$ is independently hydrogen or C$_{1-3}$alkyl;

R$_2$ is methyl or chloro;

Linker is —CH$_2$—;

A is tetrahydrobenzoxazepinyl which may be unsubstituted or substituted by 1, 2, or 3 substituents which are —C$_{1-3}$alkyl; and X is CH;

or a pharmaceutically acceptable salt thereof.

In yet another embodiment:

B is —(CH$_2$)$_2$ triazolyl which may be unsubstituted or substituted by 1, 2, or 3 substituents which are —C$_{1-3}$alkyl;

D is —C(O)OH;

R$_1$ is independently hydrogen or methyl;

R$_2$ is methyl or halo;

Linker is —CH$_2$—;

A is tetrahydrobenzoxazepinyl or imidazolyl;

Each of which may be unsubstituted or substituted by 1, 2, or 3 substituents which are —C$_{1-3}$ alkyl;

And the imidazolyl may be additionally substituted by —CH$_2$—C$_{4-7}$ cycloalkyl; and X is CH;

or a pharmaceutically acceptable salt thereof.

In still another embodiment:

B is benzotriazolyl which may be unsubstituted or substituted by 1, 2, or 3 substituents independently chosen from —C$_{1-3}$alkyl and halo;

D is —C(O)OH;

R$_1$ is independently hydrogen or C$_{1-3}$alkyl;

R$_2$ is methyl or chloro;

Linker is —CH$_2$—;

A is tetrahydrobenzoxazepinyl, imidazolyl or piperidinyl;

All of which may be unsubstituted or substituted by 1, 2, or 3 substituents independently chosen from —C$_{1-3}$alkyl, halo and OH;

And the piperidinyl may additionally be substituted by pyrazolyl and —CH$_2$pyrazolyl;

And the imidazolyl may be additionally optionally substituted by —CH$_2$—C$_{4-7}$ cycloalkyl, —CH$_2$—C$_{5-7}$heterocloalkyl, each of which, including the —CH$_2$—, may be further substituted by 1 or 2 of —C$_{1-3}$ alkyl; and X is CH;

or a pharmaceutically acceptable salt thereof.

It is to be understood that the present invention covers all combinations of particular groups described hereinabove.

Specific examples of compounds of the present invention include the following:

3-(3-((2,3-Dihydrobenzo[f][1,4]oxazepin-4(5H)-yl)methyl)-4-methylphenyl)-3-(1,4-dimethyl-1H-benzo[d][1,2,3]triazol-5-yl)propanoic acid, trifluoroacetic acid salt;

3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic acid, trifluoroacetic acid salt;

Ethyl 3-(1,4-dimethyl-1H-benzo[d][1,2,3]triazol-5-yl)-3-(4-methyl-3-((2-methyl-2,3-dihydrobenzo[f][1,4]oxazepin-4(5H)-yl)methyl)phenyl)propanoate, trifluoroacetic acid salt;

5-(1-Ethyl-1H-1,2,3-triazol-4-yl)-3-(3-((2-ethyl-2,3-dihydrobenzo[f][1,4]oxazepin-4(5H)-yl)methyl)-4-methylphenyl)pentanoic acid, trifluoroacetic acid salt;

(3S)-3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic acid, trifluoroacetic acid salt;

(3R)-3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic acid, trifluoroacetic acid salt;

3-(1,4-dimethyl-1H-benzo[d][1,2,3]triazol-5-yl)-3-(3-((7-methoxy-4-methyl-4,5-dihydro-1H-benzo[c]azepin-2(3H)-yl)methyl)-4-methylphenyl)propanoic acid;

3-(1,4-Dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)-2,2-dimethylpropanoic acid, formic acid salt;

Ammonium 3-(3-((3-(1H-pyrazol-1-yl)piperidin-1-yl)methyl)-4-methylphenyl)-3-(1,4-dimethyl-1H-benzo[d][1,2,3]triazol-5-yl)propanoate;

Ammonium 3-(1,4-dimethyl-1H-benzo[d][1,2,3]triazol-5-yl)-3-(3-((2-(5-isopropyl-4H-1,2,4-triazol-3-yl)pyrrolidin-1-yl)methyl)-4-methylphenyl)propanoate;

Ammonium 3-(1,4-dimethyl-1H-benzo[d][1,2,3]triazol-5-yl)-3-(3-((2-isopropyl-5,6-dihydropyrido[3,4-d]pyrimidin-7(8H)-yl)methyl)-4-methylphenyl)propanoate;

Ammonium 3-(1,4-dimethyl-1H-benzo[d][1,2,3]triazol-5-yl)-3-(3-((2-(5-ethyl-1,2,4-oxadiazol-3-yl)piperidin-1-yl)methyl)-4-methylphenyl)propanoate;

Ammonium 3-(1,4-dimethyl-1H-benzo[d][1,2,3]triazol-5-yl)-3-(3-((2-ethyl-5,6-dihydropyrido[3,4-d]pyrimidin-7(8H)-yl)methyl)-4-methylphenyl)propanoate;

Ammonium 3-(3-((7-cyano-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoate;

Ammonium 3-(3-(((2-bromobenzyl)(methyl)amino)methyl)-4-methylphenyl)-3-(1,4-dimethyl-1H-benzo[d][1,2,3]triazol-5-yl)propanoate;
Ammonium 3-(3-(((4-bromobenzyl)(methyl)amino)methyl)-4-methylphenyl)-3-(1,4-dimethyl-1H-benzo[d][1,2,3]triazol-5-yl)propanoate Ammonium 3-(3-(((3-bromobenzyl)(methyl)amino)methyl)-4-methylphenyl)-3-(1,4-dimethyl-1H-benzo[d][1,2,3]triazol-5-yl)propanoate;
3-(1,4-Dimethyl-1H-benzo[d][1,2,3]triazol-5-yl)-3-(4-methyl-3-((2-methyl-2-(p-tolyl)morpholino)methyl)phenyl)propanoate, formic acid salt;
3-(1,4-Dimethyl-1H-benzo[d][1,2,3]triazol-5-yl)-3-(3-((1-ethyl-3,4-dihydropyrrolo[1,2-a]pyrazin-2(1H)-yl)methyl)-4-methylphenyl)propanoic acid, formic acid salt;
3-(3-(((cyclopropyl(4-methoxybenzyl)amino)methyl)-4-methylphenyl)-3-(1,4-dimethyl-1H-benzo[d][1,2,3]triazol-5-yl)propanoic acid, formic acid salt;
3-(1,4-dimethyl-1H-benzo[d][1,2,3]triazol-5-yl)-3-(3-((3-(4-methoxyphenyl)morpholino)methyl)-4-methylphenyl)propanoic acid, formic acid salt;
3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2,2-dimethylpropanoic acid, trifluoroacetic acid salt;
3-(1,4-Dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2,2-dimethylpropanoic acid, trifluoroacetic acid salt;
(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid, formic acid salt;
(S)-3-(1,4-Dimethyl-1H-benzo[d][1,2,3]triazol-5-yl)-3-(3-(((R)-2-ethyl-9-fluoro-2,3-dihydropyrido[3,4-f][1,4]oxazepin-4(5H)-yl)methyl)-4-methylphenyl)-2,2-dimethylpropanoic acid;
(S)-3-(3-(((R)-8-Chloro-2-ethyl-2,3-dihydropyrido[3,4-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid;
(S)-Methyl 3-(1,4-dimethyl-1H-benzo[d][1,2,3]triazol-5-yl)-3-(3-((2,2-dimethyl-2,3-dihydropyrido[2,3-f][1,4]oxazepin-4(5H)-yl)methyl)-4-methylphenyl)-2,2-dimethylpropanoate, formic acid salt;
3-(1,4-Dimethyl-1H-benzo[d][1,2,3]triazol-5-yl)-3-(3-((9-fluoro-2,2-dimethyl-2,3-dihydrobenzo[f][1,4]oxazepin-4(5H)-yl)methyl)-4-methylphenyl)-2,2-dimethylpropanoic acid;
3-(3-((6,7-Dihydro-5H-imidazo[1,5-a][1,4]diazepin-8(9H)-yl)methyl)-4-methylphenyl)-3-(1,4-dimethyl-1H-benzo[d][1,2,3]triazol-5-yl)-2,2-dimethylpropanoate, Sodium salt;
(S)-3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)-2,2-dimethylpropanoic acid, trifluoroacetic acid salt;
(S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoic acid, trifluoroacetic acid salt;
(R)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoic acid;
3-(1,4-Dimethyl-1H-benzo[d][1,2,3]triazol-5-yl)-3-(3-(((R)-2-ethyl-6-fluoro-2,3-dihydrobenzo[f][1,4]oxazepin-4(5H)-yl)methyl)-4-methylphenyl)-2,2-dimethylpropanoic acid, formic acid salt;
3-(1,4-Dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)-2,2-dimethylpropanoic acid, formic acid salt;
3-(1,4-Dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)-2,2-dimethylpropanoic acid, formic acid salt;
3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)-2,2-dimethylpropanoic acid, formic acid salt;
(2R,3S)-3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic acid, formic acid salt;
(2S,3R)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic acid;
(2R,3R)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic acid;
(2S,3S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic acid;
(2R,3S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic acid;
(3R)-3-(1,4-Dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)-2-methylpropanoic acid, trifluoroacetic acid salt;
(R)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)propanoic acid, formic acid salt;
3-(3-((2,3-Dihydrobenzo[f][1,4]oxazepin-4(5H)-yl)methyl)-4-methylphenyl)-3-(1,4-dimethyl-1H-benzo[d][1,2,3]triazol-5-yl)-2,2-dimethylpropanoic acid, formic acid salt;
3-(3-(((R)-2-Ethyl-2,3-dihydrobenzo[f][1,4]oxazepin-4(5H)-yl)methyl)-4-methylphenyl)-3-(7-methoxy-1,4-dimethyl-1H-benzo[d][1,2,3]triazol-5-yl)propanoic acid, formic acid salt
3-(3-((2-Ethyl-2,3-dihydrobenzo[f][1,4]oxazepin-4(5H)-yl)methyl)-4-methylphenyl)-3-(7-methoxy-1-methyl-1H-benzo[d][1,2,3]triazol-5-yl)propanoic acid, trifluoroacetic acid salt;
3-(3,7-Dimethyl-3H-[1,2,3]triazolo[4,5-b]pyridin-6-yl)-3-(3-(((R)-2-ethyl-2,3-dihydrobenzo[f][1,4]oxazepin-4(5H)-yl)methyl)-4-methylphenyl)propanoic acid, trifluoroacetic acid salt;
3-(3,7-Dimethyl-3H-[1,2,3]triazolo[4,5-c]pyridin-6-yl)-3-(3-(((R)-2-ethyl-2,3-dihydrobenzo[f][1,4]oxazepin-4(5H)-yl)methyl)-4-methylphenyl)propanoic acid, trifluoroacetic acid salt;
(S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid, formic acid salt;

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)propanoic acid, formic acid salt;

(R)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid, formic acid salt;

(S)-3-(1-Ethyl-4-fluoro-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)propanoic acid, 0.5 formic acid salt;

(S)-3-(3-(((R)-2-Ethyl-2,3-dihydropyrido[3,4-f][1,4]oxazepin-4(5H)-yl)methyl)-4-methylphenyl)-3-(1-ethyl-4-fluoro-1H-benzo[d][1,2,3]triazol-5-yl)propanoic acid;

(S)-3-(4-Chloro-1-ethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic acid, hydrochloride;

(S)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid;

(R)-3-(1,4-Dimethyl-1H-benzo[d][1,2,3]triazol-5-yl)-3-(3-((7-fluoro-2,2-dimethyl-2,3-dihydrobenzo[f][1,4]oxazepin-4(5H)-yl)methyl)-4-methylphenyl)propanoic acid, 0.7 formic acid salt;

(S)-3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)propanoic acid, Sodium salt;

(R)-3-(1,4-Dimethyl-1H-benzo[d][1,2,3]triazol-5-yl)-3-(3-((8-fluoro-2,2-dimethyl-2,3-dihydrobenzo[f][1,4]oxazepin-4(5H)-yl)methyl)-4-methylphenyl)propanoic acid;

(R)-3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)propanoic acid, Sodium salt;

(R)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid;

(S)-3-(1,4-Dimethyl-1H-benzo[d][1,2,3]triazol-5-yl)-3-(3-((7-fluoro-2,2-dimethyl-2,3-dihydrobenzo[f][1,4]oxazepin-4(5H)-yl)methyl)-4-methylphenyl)propanoic acid, 1.5 formic acid salt;

(S)-3-(1,4-Dimethyl-1H-benzo[d][1,2,3]triazol-5-yl)-3-(3-((8-fluoro-2,2-dimethyl-2,3-dihydrobenzo[f][1,4]oxazepin-4(5H)-yl)methyl)-4-methylphenyl)propanoic acid;

(S)-3-(3-((2,2-Dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid;

(R)-3-(3-((2,2-Dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid, Hydrochloride;

(S)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate, Sodium salt;

(R)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate, Sodium salt;

(3R)-3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic acid, trifluoroacetic acid salt;

(S)-3-(3-(((R)-2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)propanoic acid, formic acid salt;

3-(3-((2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)propanoic acid, formic acid salt;

3-(3-((2-Ethyl-2,3-dihydrobenzo[f][1,4]oxazepin-4(5H)-yl)methyl)-4-methylphenyl)-3-(7-methoxy-1,4-dimethyl-1H-benzo[d][1,2,3]triazol-5-yl)propanoic acid, formic acid salt 3-(1,4-dimethyl-1H-benzo[d][1,2,3]triazol-5-yl)-3-(4-methyl-3-((2-propyl-2,3-dihydrobenzo[f][1,4]oxazepin-4(5H)-yl)methyl)phenyl)propanoic acid, formic acid salt;

3-(1,4-dimethyl-1H-benzo[d][1,2,3]triazol-5-yl)-3-(3-((2-isopropyl-2,3-dihydrobenzo[f][1,4]oxazepin-4(5H)-yl)methyl)-4-methylphenyl)propanoic acid, formic acid salt;

3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid, formic acid salt;

3-(1,4-Dimethyl-1H-benzo[d][1,2,3]triazol-5-yl)-3-(3-((2-(methoxymethyl)-2,3-dihydrobenzo[f][1,4]oxazepin-4(5H)-yl)methyl)-4-methylphenyl)propanoic acid, formic acid salt;

3-(1,4-Dimethyl-1H-benzo[d][1,2,3]triazol-5-yl)-3-(4-methyl-3-((2-methyl-2,3-dihydrobenzo[f][1,4]oxazepin-4(5H)-yl)methyl)phenyl)propanoic Acid, Trifluoroacetic Acid salt;

3-(1,4-Dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)propanoic acid, formic acid salt;

Ammonium 3-(1,4-dimethyl-1H-benzo[d][1,2,3]triazol-5-yl)-3-(3-(((R)-2-ethyl-9-methyl-2,3-dihydrobenzo[f][1,4]oxazepin-4(5H)-yl)methyl)-4-methylphenyl)propanoate;

Ammonium 3-(3-(((R)-7-chloro-2-ethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoate;

3-(1,4-Dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)propanoic acid, formic acid salt;

3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid;

3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)propanoic acid, formic acid salt;

Ammonium 3-(1,4-dimethyl-1H-benzo[d][1,2,3]triazol-5-yl)-3-(3-(((R)-2-ethyl-7-methyl-2,3-dihydrobenzo[f][1,4]oxazepin-4(5H)-yl)methyl)-4-methylphenyl)propanoate;

3-(3-((8-Bromo-2-ethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid;

3-(1,4-Dimethyl-1H-benzo[d][1,2,3]triazol-5-yl)-3-(3-(((R)-2-ethyl-6-fluoro-2,3-dihydrobenzo[f][1,4]oxazepin-4(5H)-yl)methyl)-4-methylphenyl)propanoic acid;

3-(1,4-Dimethyl-1H-benzo[d][1,2,3]triazol-5-yl)-3-(3-((2-ethyl-8-methoxy-2,3-dihydrobenzo[f][1,4]oxazepin-4(5H)-yl)methyl)-4-methylphenyl)propanoic acid, formic acid salt;

Ammonium 3-(1,4-dimethyl-1H-benzo[d][1,2,3]triazol-5-yl)-3-(3-(((R)-2-ethyl-8-methyl-2,3-dihydrobenzo[f][1,4]oxazepin-4(5H)-yl)methyl)-4-methylphenyl)propanoate;

3-(1,4-Dimethyl-1H-benzo[d][1,2,3]triazol-5-yl)-3-(3-
(((R)-2-ethyl-2,3-dihydropyrido[3,4-f][1,4]oxazepin-4
(5H)-yl)methyl)-4-methylphenyl)propanoic acid;
3-(1,4-Dimethyl-1H-benzo[d][1,2,3]triazol-5-yl)-3-(3-((2-
ethyl-7-fluoro-2,3-dihydrobenzo[f][1,4]oxazepin-4(5H)-
yl)methyl)-4-methylphenyl)propanoic acid;
3-(3-((6-Chloro-2-ethyl-2,3-dihydrobenzo[f][1,4]oxazepin-
4(5H)-yl)methyl)-4-methylphenyl)-3-(1,4-dimethyl-1H-
benzo[d][1,2,3]triazol-5-yl)propanoic acid;
3-(1,4-Dimethyl-1H-benzo[d][1,2,3]triazol-5-yl)-3-(3-((2,
2-dimethyl-2,3-dihydrobenzo[f][1,4]oxazepin-4(5H)-yl)
methyl)-4-methylphenyl)propanoic acid;
3-(1,4-Dimethyl-1H-benzo[d][1,2,3]triazol-5-yl)-3-(3-
(((R)-2-ethyl-2,3-dihydropyrido[4,3-f][1,4]oxazepin-4
(5H)-yl)methyl)-4-methylphenyl)propanoic acid;
3-(3-(((R)-2-Ethyl-2,3-dihydrobenzo[f][1,4]oxazepin-4
(5H)-yl)methyl)-4-methylphenyl)-3-(1-methyl-1H-benzo
[d][1,2,3]triazol-5-yl)propanoic acid;
3-(3-(((S)-8-bromo-2-methyl-2,3-dihydrobenzo[f][1,4]ox-
azepin-4(5H)-yl)methyl)-4-methylphenyl)-3-(1,4-dim-
ethyl-1H-benzo[d][1,2,3]triazol-5-yl)propanoic acid, for-
mic acid salt;
3-(1,4-Dimethyl-1H-benzo[d][1,2,3]triazol-5-yl)-3-(4-
methyl-3-(((R)-2-methyl-2,3-dihydrobenzo[f][1,4]oxaze-
pin-4(5H)-yl)methyl)phenyl)propanoic acid, formic acid
salt;
3-(1,4-Dimethyl-1H-benzo[d][1,2,3]triazol-5-yl)-3-(4-
fluoro-3-(((S)-2-methyl-2,3-dihydrobenzo[f][1,4]oxaze-
pin-4(5H)-yl)methyl)phenyl)propanoic acid, formic acid
salt;
3-(1,4-Dimethyl-1H-benzo[d][1,2,3]triazol-5-yl)-3-(3-((2,
2-dimethyl-2,3-dihydropyrido[3,2-f][1,4]oxazepin-4
(5H)-yl)methyl)-4-methylphenyl)propanoic acid;
3-(1-Ethyl-4-methyl-1H-benzo[d][1,2,3]triazol-5-yl)-3-(4-
methyl-3-(((S)-2-methyl-2,3-dihydrobenzo[f][1,4]oxaze-
pin-4(5H)-yl)methyl)phenyl)propanoic acid, formic acid
salt;
3-(1,4-Dimethyl-1H-benzo[d][1,2,3]triazol-5-yl)-3-(4-
methyl-3-(((S)-2-methyl-2,3-dihydrobenzo[f][1,4]oxaze-
pin-4(5H)-yl)methyl)phenyl)propanoic acid, formic acid
salt;
3-(4-Chloro-3-((2,3-dihydrobenzo[f][1,4]oxazepin-4(5H)-
yl)methyl)phenyl)-3-(1,4-dimethyl-1H-benzo[d][1,2,3]
triazol-5-yl)propanoic acid, formic acid salt;
(3S)-3-(1,4-dimethyl-1H-benzo[d][1,2,3]triazol-5-yl)-3-(3-
((2-ethyl-2,3-dihydrobenzo[f][1,4]oxazepin-4(5H)-yl)
methyl)-4-methylphenyl)-2-methylpropanoic acid;
Ammonium (2S,3R)-3-(3-(((R)-2-ethyl-2,3-dihydrobenzo
[f][1,4]oxazepin-4(5H)-yl)methyl)-4-methylphenyl)-3-
(1-ethyl-4-methyl-1H-benzo[d][1,2,3]triazol-5-yl)-2-
methylpropanoate;
(3R)-3-(1,4-dimethyl-1H-benzo[d][1,2,3]triazol-5-yl)-3-(3-
((2-ethyl-2,3-dihydrobenzo[f][1,4]oxazepin-4(5H)-yl)
methyl)-4-methylphenyl)-2-methylpropanoic acid;
Ammonium 3-(3-(((R)-2-Ethyl-2,3-dihydrobenzo[f][1,4]
oxazepin-4(5H)-yl)methyl)-4-methylphenyl)-2,2-dim-
ethyl-3-(1-methyl-1H-benzo[d][1,2,3]triazol-5-yl)pro-
panoate;
3-(3-((4,5-Dihydro-1H-benzo[c]azepin-2(3H)-yl)methyl)-
4-methylphenyl)-3-(1,4-dimethyl-1H-benzo[d][1,2,3]tri-
azol-5-yl)-2,2-dimethylpropanoic acid;
Ammonium 3-(1,4-dimethyl-1H-benzo[d][1,2,3]triazol-5-
yl)-3-(3-((4,4-dimethyl-4,5-dihydro-1H-benzo[c]azepin-
2(3H)-yl)methyl)-4-methylphenyl)propanoate;
3-(1,4-Dimethyl-1H-benzo[d][1,2,3]triazol-5-yl)-3-(3-((4-
ethyl-4,5-dihydro-1H-benzo[c]azepin-2(3H)-yl)methyl)-
4-methylphenyl)propanoic acid;
3-(1,4-dimethyl-1H-benzo[d][1,2,3]triazol-5-yl)-3-(3-((4-
ethyl-8-fluoro-4,5-dihydro-1H-benzo[c]azepin-2(3H)-yl)
methyl)-4-methylphenyl)propanoic acid;
3-(1,4-dimethyl-1H-benzo[d][1,2,3]triazol-5-yl)-3-(4-
methyl-3-((2,2,8-trimethyl-2,3-dihydropyrido[3,4-f][1,4]
oxazepin-4(5H)-yl)methyl)phenyl)propanoic acid, formic
acid salt;
(S)-3-(1,4-dimethyl-1H-benzo[d][1,2,3]triazol-5-yl)-3-(3-
((2,2-dimethyl-2,3-dihydrobenzo[f][1,4]oxazepin-4(5H)-
yl)methyl)-4-methylphenyl)propanoic acid, formic acid
salt;
(R)-3-(1,4-dimethyl-1H-benzo[d][1,2,3]triazol-5-yl)-3-(3-
((2,2-dimethyl-2,3-dihydrobenzo[f][1,4]oxazepin-4(5H)-
yl)methyl)-4-methylphenyl)propanoic acid, formic acid
salt;
3-(1,4-dimethyl-1H-benzo[d][1,2,3]triazol-5-yl)-3-(3-((1-
ethyl-2,3-dihydro-1H-benzo[e][1,4]diazepin-4(5H)-yl)
methyl)-4-methylphenyl)-2,2-dimethylpropanoic acid,
formic acid salt;
(2R)-4-(5-(1-(1,4-dimethyl-1H-benzo[d][1,2,3]triazol-5-
yl)-2-(1H-tetrazol-5-yl)ethyl)-2-methylbenzyl)-2-ethyl-2,
3,4,5-tetrahydrobenzo[f][1,4]oxazepine, formic acid salt;
3-(1,4-Dimethyl-1H-benzo[d][1,2,3]triazol-5-yl)-3-(3-
(((R)-2-ethyl-2,3-dihydropyrido[3,2-f][1,4]oxazepin-4
(5H)-yl)methyl)-4-methylphenyl)-2,2-dimethylpropanoic
acid;
3-(1,4-Dimethyl-1H-benzo[d][1,2,3]triazol-5-yl)-3-(3-
(((R)-2-ethyl-2,3-dihydrobenzo[f][1,4]oxazepin-4(5H)-
yl)methyl)-4-methylphenyl)-2,2-dimethylpropanoic acid,
lithium salt;
3-(3-(((R)-2-ethyl-2,3-dihydrobenzo[f][1,4]oxazepin-4
(5H)-yl)methyl)-4-methylphenyl)-3-(4-fluoro-2-methyl-
phenyl)-2,2-dimethylpropanoic acid, formic acid salt;
3-(1,4-Dimethyl-1H-benzo[d][1,2,3]triazol-5-yl)-3-(3-
(((R)-2-ethyl-2,3-dihydropyrido[3,2-f][1,4]oxazepin-4
(5H)-yl)methyl)-4-methylphenyl)propanoic acid, formic
acid salt;
3-(2,4-difluorophenyl)-3-(3-(((R)-2-ethyl-2,3-dihydrobenzo
[f][1,4]oxazepin-4(5H)-yl)methyl)-4-methylphenyl)pro-
panoic acid, formic acid salt;
5-(1-Ethyl-1H-1,2,3-triazol-4-yl)-3-(3-(((R)-2-ethyl-2,3-di-
hydrobenzo[f][1,4]oxazepin-4(5H)-yl)methyl)-4-methyl-
phenyl)-2-methylpentanoic acid;
(S)-3-(3-((2-(Cycloheptylmethyl)-1H-imidazol-1-yl)
methyl)-4-methylphenyl)-3-(1,4-dimethyl-1H-benzo[d]
[1,2,3]triazol-5-yl)-2,2-dimethylpropanoate, sodium salt;
(S)-3-(3-((2-(Azepan-1-ylmethyl)-1H-imidazol-1-yl)
methyl)-4-methylphenyl)-3-(1,4-dimethyl-1H-benzo[d]
[1,2,3]triazol-5-yl)-2,2-dimethylpropanoate, Sodium salt;
(S)-3-(1,4-Dimethyl-1H-benzo[d][1,2,3]triazol-5-yl)-3-(3-
((2-((4-ethylpiperidin-1-yl)methyl)-1H-imidazol-1-yl)
methyl)-4-methylphenyl)-2,2-dimethylpropanoate,
sodium salt;
3-(1,4-Dimethyl-1H-benzo[d][1,2,3]triazol-5-yl)-2,2-dim-
ethyl-3-(4-methyl-3-((2-(piperidin-1-ylmethyl)-1H-imi-
dazol-1-yl)methyl)phenyl)propanoate, sodium salt;
3-(1,4-Dimethyl-1H-benzo[d][1,2,3]triazol-5-yl)-2,2-dim-
ethyl-3-(4-methyl-3-((2-(pyrrolidin-1-ylmethyl)-1H-imi-
dazol-1-yl)methyl)phenyl)propanoate, sodium salt;
(R)-3-(3-((2-(Cycloheptylmethyl)-1H-imidazol-1-yl)
methyl)-4-methylphenyl)-3-(1,4-dimethyl-1H-benzo[d]
[1,2,3]triazol-5-yl)-2,2-dimethylpropanoate, sodium salt;
3-(3-((2-(Cyclohexylmethyl)-1H-imidazol-1-yl)methyl)-4-
methylphenyl)-3-(1,4-dimethyl-1H-benzo[d][1,2,3]tri-
azol-5-yl)propanoic acid;

3-(3-((1-(Cyclohexylmethyl)-1H-1,2,3-triazol-5-yl)
methyl)-4-methylphenyl)-3-(1,4-dimethyl-1H-benzo[d]
[1,2,3]triazol-5-yl)propanoic acid;

3-(1,4-Dimethyl-1H-benzo[d][1,2,3]triazol-5-yl)-3-(4-
methyl-3-((2-((tetrahydro-2H-pyran-4-yl)methyl)-1H-
imidazol-1-yl)methyl)phenyl)propanoic acid;

3-(3-((2-(Cyclohexylmethyl)-1H-imidazol-1-yl)methyl)-4-
methylphenyl)-5-(1-methyl-1H-1,2,3-triazol-4-yl)pen-
tanoic acid;

3-(3-((2-(Cycloheptylmethyl)-1H-imidazol-1-yl)methyl)-4-
methylphenyl)-3-(1,4-dimethyl-1H-benzo[d][1,2,3]tri-
azol-5-yl)-2,2-dimethylpropanoic acid;

3-(1,4-Dimethyl-1H-benzo[d][1,2,3]triazol-5-yl)-3-(3-((2-
((4-ethylcyclohexyl)methyl)-1H-imidazol-1-yl)methyl)-
4-methylphenyl)propanoic acid;

Ammonium 3-(3-((2-(1-cyclohexylethyl)-1H-imidazol-1-
yl)methyl)-4-methylphenyl)-3-(1,4-dimethyl-1H-benzo
[d][1,2,3]triazol-5-yl)propanoate;

3-(3-((1-(Cyclohexylmethyl)-1H-tetrazol-5-yl)methyl)-4-
methylphenyl)-3-(1,4-dimethyl-1H-benzo[d][1,2,3]tri-
azol-5-yl)propanoic acid, hydrochloride salt;

3-(3-((2-(Cyclohexylmethyl)-1H-imidazol-1-yl)methyl)-4-
methylphenyl)-5-(1-methyl-1H-1,2,3-triazol-4-yl)pen-
tanoic acid;

3-(3-((2-(Cyclohexylmethyl)-1H-imidazol-1-yl)methyl)-4-
methylphenyl)-3-(4-fluoro-2-methylphenyl)propanoic
acid;

3-(1,4-Dimethyl-1H-benzo[d][1,2,3]triazol-5-yl)-3-(4-
methyl-3-((2-((tetrahydro-2H-pyran-4-yl)methyl)-1H-
imidazol-1-yl)methyl)phenyl)propanoic acid;

3-(3-((4-(Cyclohexylmethyl)-1H-imidazol-1-yl)methyl)-4-
methylphenyl)-3-(1,4-dimethyl-1H-benzo[d][1,2,3]tri-
azol-5-yl)propanoic acid;

3-(3-((3-(Cyclohexylmethyl)-5-methyl-1H-1,2,4-triazol-1-
yl)methyl)-4-methylphenyl)-3-(1,4-dimethyl-1H-benzo
[d][1,2,3]triazol-5-yl)propanoic acid;

3-(3-((2-((1,4-Oxazepan-4-yl)methyl)-1H-imidazol-1-yl)
methyl)-4-methylphenyl)-3-(1,4-dimethyl-1H-benzo[d]
[1,2,3]triazol-5-yl)-2,2-dimethylpropanoic acid;

3-(1,4-Dimethyl-1H-benzo[d][1,2,3]triazol-5-yl)-2,2-dim-
ethyl-3-(4-methyl-3-((2-((4-methylpiperidin-1-yl)
methyl)-1H-imidazol-1-yl)methyl)phenyl)propanoic
acid;

3-(1,4-Dimethyl-1H-benzo[d][1,2,3]triazol-5-yl)-3-(3-((2-
((4-ethylpiperidin-1-yl)methyl)-1H-imidazol-1-yl)
methyl)-4-methylphenyl)-2,2-dimethylpropanoic acid,
formic acid salt;

3-(3-((2-(Azepan-1-ylmethyl)-1H-imidazol-1-yl)methyl)-4-
methylphenyl)-3-(1,4-dimethyl-1H-benzo[d][1,2,3]tri-
azol-5-yl)-2,2-dimethylpropanoic acid, trifluoroacetic
acid salt;

3-(1,4-Dimethyl-1H-benzo[d][1,2,3]triazol-5-yl)-2,2-dim-
ethyl-3-(4-methyl-3-((2-(morpholinomethyl)-1H-imida-
zol-1-yl)methyl)phenyl)propanoic acid, trifluoroacetic
acid salt;

3-(3-((2-(Cyclohexylmethyl)-1H-imidazol-1-yl)methyl)-4-
methylphenyl)-3-(1,4-dimethyl-1H-benzo[d][1,2,3]tri-
azol-5-yl)-2,2-dimethylpropanoic acid, trifluoroacetic
acid salt;

3-(1,4-Dimethyl-1H-benzo[d][1,2,3]triazol-5-yl)-2,2-dim-
ethyl-3-(4-methyl-3-((2-(((R)-2-methylmorpholino)
methyl)-1H-imidazol-1-yl)methyl)phenyl)propanoic
acid, trifluoroacetic acid salt;

3-(1,4-Dimethyl-1H-benzo[d][1,2,3]triazol-5-yl)-2,2-dim-
ethyl-3-(4-methyl-3-((2-((tetrahydro-2H-pyran-4-yl)
methyl)-1H-imidazol-1-yl)methyl)phenyl)propanoic
Acid, Trifluoroacetic Acid salt;

3-(3-((2-(Cycloheptylmethyl)-1H-imidazol-1-yl)methyl)-4-
methylphenyl)-3-(1,4-dimethyl-1H-benzo[d][1,2,3]tri-
azol-5-yl)propanoic acid, formic acid salt;

3-(3-((2-(Azepan-1-ylmethyl)-1H-imidazol-1-yl)methyl)-4-
methylphenyl)-3-(1,4-dimethyl-1H-benzo[d][1,2,3]tri-
azol-5-yl)propanoic acid, formic acid salt;

3-(3-((2-(Cyclopentylmethyl)-1H-imidazol-1-yl)methyl)-4-
methylphenyl)-3-(1,4-dimethyl-1H-benzo[d][1,2,3]tri-
azol-5-yl)propanoic acid;

3-(3-((2-((4,4-Difluoropiperidin-1-yl)methyl)-1H-imidazol-
1-yl)methyl)-4-methylphenyl)-3-(1,4-dimethyl-1H-benzo
[d][1,2,3]triazol-5-yl)propanoic acid;

(S)-3-(1,4-Dimethyl-1H-benzo[d][1,2,3]triazol-5-yl)-2,2-
dimethyl-3-(4-methyl-3-((2-(piperidin-1-ylmethyl)-1H-
imidazol-1-yl)methyl)phenyl)propanoic acid;

3-(3-((2-(Azepan-1-ylmethyl)-1H-imidazol-1-yl)methyl)-4-
methylphenyl)-3-(1,4-dimethyl-1H-benzo[d][1,2,3]tri-
azol-5-yl)-2,2-dimethylpropanoic acid, 0.3 formic acid
salt;

(3R)-3-(1,4-Dimethyl-1H-benzo[d][1,2,3]triazol-5-yl)-3-(3-
((2-((4-ethylpiperidin-1-yl)methyl)-1H-imidazol-1-yl)
methyl)-4-methylphenyl)-2-methylpropanoic acid, trif-
luoroacetic acid salt;

3-(1,4-Dimethyl-1H-benzo[d][1,2,3]triazol-5-yl)-3-(4-
methyl-3-((2-(pyrrolidin-1-ylmethyl)-1H-imidazol-1-yl)
methyl)phenyl)propanoic acid, formic acid salt 3-(1,4-dimethyl-1H-benzo[d][1,2,3]triazol-5-yl)-3-(4-
methyl-3-((2-(piperidin-1-ylmethyl)-1H-imidazol-1-yl)
methyl)phenyl)propanoic acid, trifluoroacetic acid salt;

3-(3-((2-(cyclohexylmethyl)-1H-imidazol-1-yl)methyl)-4-
methylphenyl)-3-(1,4-dimethyl-1H-benzo[d][1,2,3]tri-
azol-5-yl)propanoic acid, Trifluoroacetic acid salt;

3-(3-((2-(7-Azabicyclo[2.2.1]heptan-7-ylmethyl)-1H-imi-
dazol-1-yl)methyl)-4-methylphenyl)-3-(1,4-dimethyl-
1H-benzo[d][1,2,3]triazol-5-yl)-2,2-dimethylpropanoic
Acid, Trifluoroacetic Acid salt;

3-(3-((2-(8-Azabicyclo[3.2.1]octan-8-ylmethyl)-1H-imida-
zol-1-yl)methyl)-4-methylphenyl)-3-(1,4-dimethyl-1H-
benzo[d][1,2,3]triazol-5-yl)-2,2-dimethylpropanoic Acid,
Trifluoroacetic Acid salt;

(3R)-3-(3-((3-(1H-Pyrazol-1-yl)piperidin-1-yl)methyl)-4-
methylphenyl)-3-(1,4-dimethyl-1H-benzo[d][1,2,3]tri-
azol-5-yl)propanoic acid (isomer 1);

(3R)-3-(3-((3-(1H-Pyrazol-1-yl)piperidin-1-yl)methyl)-4-
methylphenyl)-3-(1,4-dimethyl-1H-benzo[d][1,2,3]tri-
azol-5-yl)propanoic acid (isomer 2);

(3S)-3-(3-((3-(1H-Pyrazol-1-yl)piperidin-1-yl)methyl)-4-
methylphenyl)-3-(1,4-dimethyl-1H-benzo[d][1,2,3]tri-
azol-5-yl)propanoic acid (isomer 1);

3-(3-((3-(1H-Pyrazol-1-yl)piperidin-1-yl)methyl)-4-chloro-
phenyl)-3-(1,4-dimethyl-1H-benzo[d][1,2,3]triazol-5-yl)
propanoic acid, formic acid salt;

3-(4-chloro-3-((3-hydroxypiperidin-1-yl)methyl)phenyl)-3-
(1,4-dimethyl-1H-benzo[d][1,2,3]triazol-5-yl)propanoic
acid;

3-(3-((3-(1H-Pyrazol-1-yl)piperidin-1-yl)methyl)-4-methyl-
phenyl)-3-(1,4-dimethyl-1H-benzo[d][1,2,3]triazol-5-yl)-
2,2-dimethylpropanoic acid;

3-(3-((3-(1H-pyrazol-1-yl)piperid in-1-yl)methyl)-4-meth-
ylphenyl)-5-(1-propyl-1H-1,2,3-triazol-4-yl)pentanoic
acid, formic acid salt;

3-(3-((3-(1H-pyrazol-1-yl)piperidin-1-yl)methyl)-4-chloro-
phenyl)-3-(7-methoxy-1,4-dimethyl-1H-benzo[d][1,2,3]
triazol-5-yl)propanoic acid, formic acid salt;

3-(3-((6,7-Dihydro-5H-imidazo[1,5-a][1,4]diazepin-8(9H)-
yl)methyl)-4-methylphenyl)-3-(1,4-dimethyl-1H-benzo
[d][1,2,3]triazol-5-yl)propanoic acid, Sodium salt;

(S)-3-(1,4-Dimethyl-1H-benzo[d][1,2,3]triazol-5-yl)-3-(3-((7-methoxy-2,2-dimethyl-2,3-dihydrobenzo[f][1,4]oxazepin-4(5H)-yl)methyl)-4-methylphenyl)propanoic acid, 0.5 Formic acid salt;

(R)-3-(1,4-Dimethyl-1H-benzo[d][1,2,3]triazol-5-yl)-3-(3-((7-methoxy-2,2-dimethyl-2,3-dihydrobenzo[f][1,4]oxazepin-4(5H)-yl)methyl)-4-methylphenyl)propanoic acid;

(R)-3-(1,4-Dimethyl-1H-benzo[d][1,2,3]triazol-5-yl)-3-(3-((8-methoxy-2,2-dimethyl-2,3-dihydrobenzo[f][1,4]oxazepin-4(5H)-yl)methyl)-4-methylphenyl)propanoic acid;

(S)-3-(1,4-Dimethyl-1H-benzo[d][1,2,3]triazol-5-yl)-3-(3-((8-methoxy-2,2-dimethyl-2,3-dihydrobenzo[f][1,4]oxazepin-4(5H)-yl)methyl)-4-methylphenyl)propanoic acid;

(R)-3-(1,4-Dimethyl-1H-benzo[d][1,2,3]triazol-5-yl)-3-(3-((2,2-dimethyl-2,3-dihydropyrido[2,3-f][1,4]oxazepin-4(5H)-yl)methyl)-4-methylphenyl)propanoic acid, 0.5 Formic acid salt;

(S)-3-(1,4-Dimethyl-1H-benzo[d][1,2,3]triazol-5-yl)-3-(3-((2,2-dimethyl-2,3-dihydropyrido[2,3-f][1,4]oxazepin-4(5H)-yl)methyl)-4-methylphenyl)propanoic acid, 0.5 Formic acid salt;

rel-(R)-3-(3-((7-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid;

rel-(S)-3-(3-((7-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid;

rel-(R)-3-(3-((8-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid;

rel-(S)-3-(3-((8-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid;

(R)-3-(1,4-Dimethyl-1H-benzo[d][1,2,3]triazol-5-yl)-3-(4-methyl-3-((2,2,7-trimethyl-2,3-dihydrobenzo[f][1,4]oxazepin-4(5H)-yl)methyl)phenyl)propanoic acid;

(S)-3-(1,4-Dimethyl-1H-benzo[d][1,2,3]triazol-5-yl)-3-(4-methyl-3-((2,2,7-trimethyl-2,3-dihydrobenzo[f][1,4]oxazepin-4(5H)-yl)methyl)phenyl)propanoic acid;

(R)-3-(1,4-Dimethyl-1H-benzo[d][1,2,3]triazol-5-yl)-3-(3-((9-fluoro-2,2-dimethyl-2,3-dihydrobenzo[f][1,4]oxazepin-4(5H)-yl)methyl)-4-methylphenyl)propanoic acid;

(S)-3-(1,4-Dimethyl-1H-benzo[d][1,2,3]triazol-5-yl)-3-(3-((9-fluoro-2,2-dimethyl-2,3-dihydrobenzo[f][1,4]oxazepin-4(5H)-yl)methyl)-4-methylphenyl)propanoic acid;

(R)-3-(1,4-Dimethyl-1H-benzo[d][1,2,3]triazol-5-yl)-3-(4-methyl-3-((2,2,8-trimethyl-2,3-dihydrobenzo[f][1,4]oxazepin-4(5H)-yl)methyl)phenyl)propanoic acid;

(S)-3-(1,4-Dimethyl-1H-benzo[d][1,2,3]triazol-5-yl)-3-(4-methyl-3-((2,2,8-trimethyl-2,3-dihydrobenzo[f][1,4]oxazepin-4(5H)-yl)methyl)phenyl)propanoic acid;

rel-(R)-3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid;

rel-(S)-3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid;

(S)-3-(3-(((S)-3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic acid;

(S)-3-(3-(((R)-3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic acid;

3-(1,4-Dimethyl-1H-benzo[d][1,2,3]triazol-5-yl)-3-(4-methyl-3-((3-(phenylsulfonyl)piperidin-1-yl)methyl)phenyl)propanoic acid;

3-(3-((3-(cyclohexylsulfonyl)piperidin-1-yl)methyl)-4-methylphenyl)-3-(1,4-dimethyl-1H-benzo[d][1,2,3]triazol-5-yl)propanoic acid;

3-(1,4-Dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)-N-(methylsulfonyl)propanamide;

(S)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid;

(R)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid;

(2R,3S)-3-(3-((2,2-Dimethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoic acid;

(2R,3S)-3-(3-(((R)-2-Ethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoic acid;

(2R,3S)-3-(1-Ethyl-4-fluoro-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)-2-methylpropanoic acid;

(2R,3S)-3-(3-((2,2-Dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)-2-methylpropanoic acid Sodium salt;

(2R,3S)-3-(4-Chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoic acid;

(2R,3S)-3-(3-((2,2-Dimethyl-2,3-dihydropyrido[3,2-f][1,4]oxazepin-4(5H)-yl)methyl)-4-methylphenyl)-3-(1-ethyl-4-fluoro-1H-benzo[d][1,2,3]triazol-5-yl)-2-methylpropanoic acid;

(2R,3S)-3-(3-((2,2-Dimethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoic acid, Trifluoroacetic acid salt;

(2S,3R)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoate, Sodium salt;

(2S,3R)-3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoic acid, 0.1 formic acid salt;

(2S,3R)-3-(3-(((R)-2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid;

(2S,3R)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid, 2Trifluoroacetic acid salt;

(2S,3R)-3-(1-Ethyl-4-methyl-1H-benzo[d][1,2,3]triazol-5-yl)-2-methyl-3-(4-methyl-3-((2-(piperidin-1-ylmethyl)-1H-imidazol-1-yl)methyl)phenyl)propanoic acid;

(2R,3S)-3-(4-chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoic acid;

(2R,3S)-3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoic acid, 0.2 formic acid salt;

(R)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid, 0.5 Ethanol;

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(methylsulfonyl)propanamide, Trifluoroacetic acid salt;

rel-(R)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid [enantiomer A (first to elute from SFC)];

rel-(R)-3-(3-((2,2-dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid;

(2R,3S)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid, 2 Trifluoroacetic acid salt;

(2R,3S)-3-(7-Chloro-1-ethyl-4-methyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoic acid;

(2R,3S)-3-(1-Ethyl-4-methyl-1H-benzo[d][1,2,3]triazol-5-yl)-2-methyl-3-(4-methyl-3-((2-(piperidin-1-ylmethyl)-1H-imidazol-1-yl)methyl)phenyl)propanoic acid;

1-((1,4-Dimethyl-1H-benzo[d][1,2,3]triazol-5-yl)(3-((2,2-dimethyl-2,3-dihydropyrido[3,4-f][1,4]oxazepin-4(5H)-yl)methyl)-4-methylphenyl)methyl)cyclopropanecarboxylic acid, Trifluoroacetic acid salt;

3-(1,4-Dimethyl-1H-benzo[d][1,2,3]triazol-5-yl)-3-(6-(((R)-2-ethyl-2,3-dihydropyrido[3,4-f][1,4]oxazepin-4(5H)-yl)methyl)-5-methylpyridin-2-yl)-2,2-dimethylpropanoic acid, formic acid salt;

3-(1,4-Dimethyl-1H-benzo[d][1,2,3]triazol-5-yl)-3-(5-(((R)-2-ethyl-2,3-dihydropyrido[3,4-f][1,4]oxazepin-4(5H)-yl)methyl)-6-methylpyridin-3-yl)-2,2-dimethylpropanoic acid, Trifluoroacetic acid salt;

3-(5-((2-(Cycloheptylmethyl)-1H-imidazol-1-yl)methyl)-6-methylpyridin-3-yl)-3-(1,4-dimethyl-1H-benzo[d][1,2,3]triazol-5-yl)-2,2-dimethylpropanoic acid, Trifluoroacetic acid salt;

(3S)-3-(3-((3-((1H-Pyrazol-1-yl)methyl)piperidin-1-yl)methyl)-4-methylphenyl)-3-(1,4-dimethyl-1H-benzo[d][1,2,3]triazol-5-yl)propanoic acid;

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid;

5-(1-Ethyl-1H-1,2,3-triazol-4-yl)-3-(3-(((R)-2-ethyl-2,3-dihydropyrido[3,2-f][1,4]oxazepin-4(5H)-yl)methyl)-4-methylphenyl)-2,2-dimethylpentanoic acid;

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-2,2-dimethylpropanoic acid, Trifluoroacetate;

(S)-3-(1,4-Dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)-2,2-dimethylpropanoic acid, Trifluoroacetate;

5-(1-Ethyl-1H-1,2,3-triazol-4-yl)-3-(3-(((R)-2-ethyl-2,3-dihydropyrido[4,3-f][1,4]oxazepin-4(5H)-yl)methyl)-4-methylphenyl)-2,2-dimethylpentanoic acid, 3.2 Trifluoroacetic acid salt;

3-(3-((2,2-Dimethyl-2,3-dihydropyrido[2,3-f][1,4]oxazepin-4(5H)-yl)methyl)-4-methylphenyl)-5-(1-ethyl-1H-1,2,3-triazol-4-yl)-2,2-dimethylpentanoic acid;

(S)-3-(1,4-Dimethyl-1H-benzo[d][1,2,3]triazol-5-yl)-3-(3-(((R)-2-ethyl-6-fluoro-2,3-dihydropyrido[3,4-f][1,4]oxazepin-4(5H)-yl)methyl)-4-methylphenyl)-2,2-dimethylpropanoic acid;

3-(3-((2,2-Dimethyl-2,3-dihydropyrido[3,2-f][1,4]oxazepin-4(5H)-yl)methyl)-4-methylphenyl)-5-(1-ethyl-1H-1,2,3-triazol-4-yl)-2,2-dimethylpentanoic acid;

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2-methylpentanoic acid, 0.20 formic acid salt;

5-(1-Ethyl-1H-1,2,3-triazol-4-yl)-3-(3-((2-((4-ethylpiperidin-1-yl)methyl)-1H-imidazol-1-yl)methyl)-4-methylphenyl)-2-methylpentanoic acid, Trifluoroacetic acid salt;

5-(1-Ethyl-1H-1,2,3-triazol-4-yl)-3-(3-((2-((4-ethylpiperidin-1-yl)methyl)-1H-imidazol-1-yl)methyl)-4-methylphenyl)-2-methylpentanoic acid, Trifluoroacetic acid salt;

3-(3-((2,2-Dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoic acid, Trifluoroacetic acid salt;

3-(3-((2,2-Dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoic acid;

Benzyl 3-(4-chloro-3-((2-(cycloheptylmethyl)-1H-imidazol-1-yl)methyl)phenyl)-5-(1-ethyl-1H-1,2,3-triazol-4-yl)-2,2-dimethylpentanoate;

3-(4-Chloro-3-((2-((4-ethylpiperidin-1-yl)methyl)-1H-imidazol-1-yl)methyl)phenyl)-5-(1-ethyl-1H-1,2,3-triazol-4-yl)-2,2-dimethylpentanoic acid;

3-(4-Chloro-3-(((R)-2-ethyl-2,3-dihydropyrido[2,3-f][1,4]oxazepin-4(5H)-yl)methyl)phenyl)-5-(1-ethyl-1H-1,2,3-triazol-4-yl)pentanoic acid;

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoic acid;

3-(4-Chloro-3-((2,2-dimethyl-2,3-dihydropyrido[3,2-f][1,4]oxazepin-4(5H)-yl)methyl)phenyl)-5-(1-ethyl-1H-1,2,3-triazol-4-yl)pentanoic acid;

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)-N-(methylsulfonyl)pentanamide;

(S)-3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic acid;

3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic acid;

(S)-3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic acid;

(R)-3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic acid;

(S)-3-(1-Ethyl-4-methyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoic acid;

(3S)-3-(1,4-Dimethyl-1H-benzo[d][1,2,3]triazol-5-yl)-3-(3-((2-ethyl-2-methyl-2,3-dihydrobenzo[f][1,4]oxazepin-4(5H)-yl)methyl)-4-methylphenyl)-2,2-dimethylpropanoic acid;

rel-(S)-3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic acid;

rel-(R)-3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic acid;

3-(3-((3H-spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoic acid;

3-(3-((3H-spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoic acid;

3-(1,4-Dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoic acid;

3-(3-((7-Cyclopropyl-2-ethyl-1,4-oxazepan-4-yl)methyl)-4-methylphenyl)-3-(1,4-dimethyl-1H-benzo[d][1,2,3]triazol-5-yl)-2,2-dimethylpropanoic acid;

3-(3-((2-((4-Ethylpiperidin-1-yl)methyl)-1H-imidazol-1-yl)methyl)-4-methylphenyl)-2,2-dimethyl-5-(1-propyl-1H-1,2,3-triazol-4-yl)pentanoic acid;

3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoic acid;

5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoic acid;

5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoic acid;

5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid;

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid;

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate;

(S)-((Diphenoxyphosphoryl)oxy)methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate;

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate;

3-((S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoyl)thiazolidin-2-one, Trifluoroacetic acid salt;

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate;

(S)-ethyl 3-(1,4-dimethyl-1H-benzo[d][1,2,3]triazol-5-yl)-3-(3-(((R)-2-ethyl-2.3-dihydropyrido[2,3-t][1,4]oxazepin-4(5H)-yl)methyl)-4-methylphenyl)propionate;

(S)-3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-fluorophenyl)propanoic acid;

rel-(R)-3-(1,4-dimethyl-1H-benzo[d]-[1,2,3]triazol-5-yl)-3-(3-((2,2-dimethyl-2,3-dihydropyrido[2,3-f][1,4]oxazepin-4(5H)-yl)methyl)-4-fluorophenyl)-propanoic acid (isomer 1);

rel-(R)-3-(4-chloro-3-((2,2-dimethyl-2,3-dihydropyrido[2,3-f][1,4]oxazepin-4(5H)-yl)methyl)phenyl)-3-(1,4-dimethyl-1H-benzo[d][1,2,3]triazol-5-yl)propanoic acid (isomer 1);

(S)-3-(4-chloro-3-(((R)-2-ethyl-2,3-dihydropyrido[2,3-f][1,4]oxazepin-4(5H)-yl)methyl)phenyl)-3-(1,4-dimethyl-1H-benzo[d][1,2,3]triazol-5-yl)propanoic acid; and (S)-3-(1,4-dimethyl-1H-benzo[d][1,2,3]triazol-5-yl)-3-(3-((2,2-dimethyl-2,3-dihydropyrido[4,3-f][1,4]oxazepin-4(5H)-yl)methyl)-4-methylphenyl)propanoic acid;

or a pharmaceutically acceptable salt thereof.

In one embodiment, the invention is a compound of Formula (I) which is (S)-ethyl 3-(1,4-dimethyl-1H-benzo[d][1,2,3]triazol-5-yl)-3-(3-(((R)-2-ethyl-2.3-dihydropyrido[2,3-t][1,4]oxazepin-4(5H)-yl)methyl)-4-methylphenyl)propionate, or a pharmaceutically acceptable salt thereof.

In another embodiment, the invention is a compound of Formula (I) which is:

(S)-3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-fluorophenyl)propanoic acid;

rel-(R)-3-(1,4-dimethyl-1H-benzo[d]-[1,2,3]triazol-5-yl)-3-(3-((2,2-dimethyl-2,3-dihydropyrido[2,3-f][1,4]oxazepin-4(5H)-yl)methyl)-4-fluorophenyl)-propanoic acid (isomer 1);

rel-(R)-3-(1,4-dimethyl-1H-benzo[d]-[1,2,3]triazol-5-yl)-3-(3-((2,2-dimethyl-2,3-dihydropyrido[2,3-f][1,4]oxazepin-4(5H)-yl)methyl)-4-fluorophenyl)-propanoic acid (isomer 1);

rel-(R)-3-(4-chloro-3-((2,2-dimethyl-2,3-dihydropyrido[2,3-f][1,4]oxazepin-4(5H)-yl)methyl)phenyl)-3-(1,4-dimethyl-1H-benzo[d][1,2,3]triazol-5-yl)propanoic acid (isomer 1);

(S)-3-(4-chloro-3-(((R)-2-ethyl-2,3-dihydropyrido[2,3-f][1,4]oxazepin-4(5H)-yl)methyl)phenyl)-3-(1,4-dimethyl-1H-benzo[d][1,2,3]triazol-5-yl)propanoic acid; and (S)-3-(1,4-dimethyl-1H-benzo[d][1,2,3]triazol-5-yl)-3-(3-((2,2-dimethyl-2,3-dihydropyrido[4,3-f][1,4]oxazepin-4(5H)-yl)methyl)-4-methylphenyl)propanoic acid, or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes 1-30. In the following description, the groups are as defined above for compounds of Formula (I) unless otherwise indicated. Abbreviations are as defined in the Examples section. Starting materials are commercially available or are made from commercially available starting materials using methods known to those skilled in the art.

Scheme 1

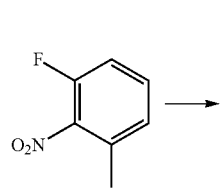

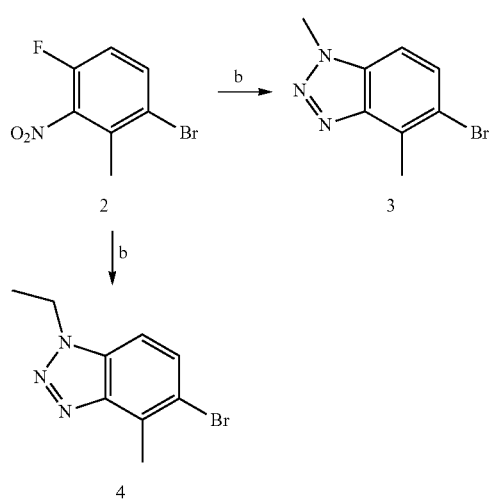

Conditions: a) NBS, TFA, H₂SO₄; b) i) MeNH₂ (or) EtNH₂ THF; ii) Zn, HOAc; iii) NaNO₂, H₂SO₄

Scheme 1 shows a general scheme for the preparation of 5-bromo-4-methyl-1-methyl-1H-benzo[d][1,2,3]triazole. Starting with commercially available 1-fluoro-3-methyl-2-nitrobenzene, bromination with NBS provides intermediate 2. Displacement of the fluoride using an appropriate amine followed by zinc metal reduction of the nitro to the aniline and diazotization and cyclization provides the required triazole 3. Completion of the fully elaborated analog can be accomplished in a fashion analogous to that shown in scheme 23.

Scheme 2

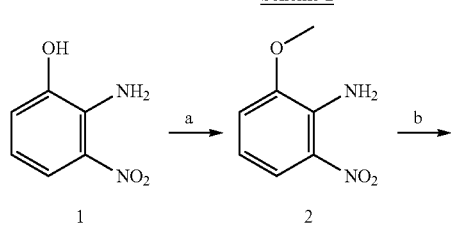

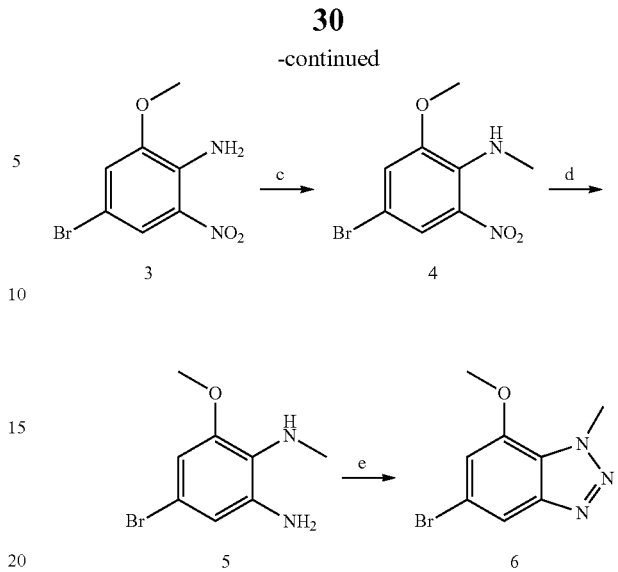

Conditions: a) K₂CO₃, MeI, DMF; b) Br₂, acetic acid, c) NaH, MeI, DMF; d) Zinc, acetic acid; e) NaNO₂, H₂SO₄

Scheme 2 shows a general scheme for the preparation of 5-bromo-7-methoxy-1-methyl-1H-benzo[d][1,2,3]triazole. Starting with commercially available 2-amino-3-nitrophenol, methylation of the phenol using K₂CO₃ and MeI (step a) provides intermediate 2 which can be brominated with NBS (step c). Methylation of the aniline (step d) followed by reduction of the nitro group (step d) and diazotization and cyclization (step e) provide the required triazole 5. Completion of the fully elaborated analog can be accomplished in a fashion analogous to that shown in Scheme 23.

Scheme 3

Conditions: a) NaIO₄/H₂SO₄, I₂, Ac₂O/AcOH; b) CuI, Cs₂CO₃, MeOH;

Scheme 3 shows a general scheme for the preparation of 5-bromo-7-methoxy-1,4-dimethyl-1H-benzo[d][1,2,3]triazole. This two step process starts with iodination at C7 of 5-bromo-1,4-dimethyl-1H-benzo[d][1,2,3]triazole. Copper mediated replacement of the iodide with methanol provides the desired material. Completion of the fully elaborated analog can be accomplished in a fashion analogous to that shown in Scheme 23.

Scheme 4

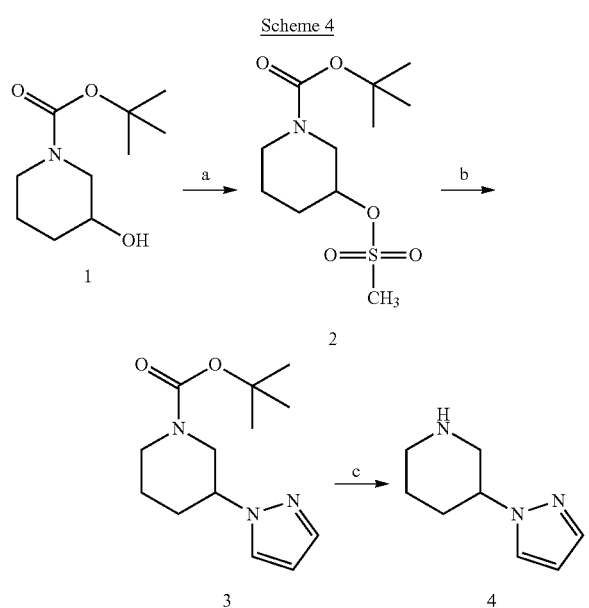

Conditions: a) MsCl, TEA, DCM; b) Pyrazole, NaH, DMF; c) HCl (4M in dioxane), DCM Scheme 4 represents a general scheme for the preparation of 3-(1H-pyrazol-1-yl)piperidine used in the invention. In this, tert-butyl 3-hydroxypiperidine-1-carboxylate depicted as starting material are commercially available. Reaction conditions are as described above in the scheme; however, the skilled artisan will appreciate that certain modifications in the reaction conditions and/or reagents used are possible.

Starting with commercially available tert-butyl 3-hydroxypiperidine-1-carboxylate, mesylation with methanesulfonyl chloride in the presence of triethylamine in DCM provided mesylate 2. Displacement of the mesylate with pyrazole and NaH in DMF gave intermediate 3. Removal of the Boc group with HCl (4 M in dioxane) in DCM gave the required piperidine 4.

Scheme 5

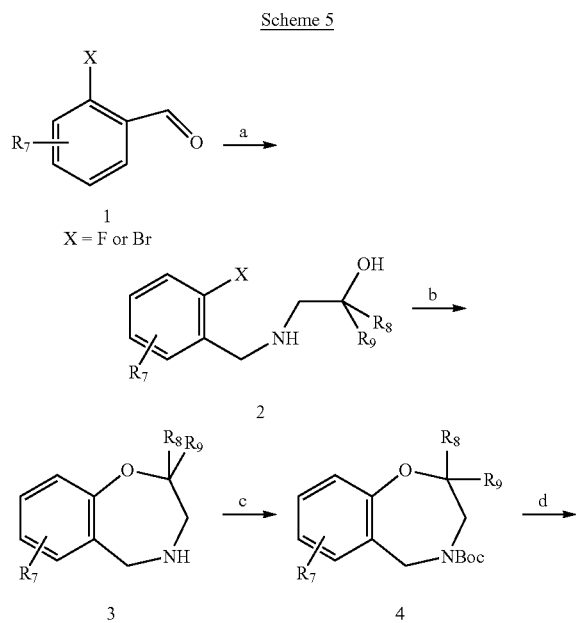

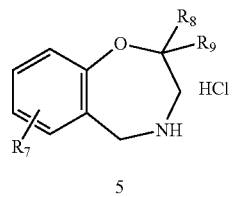

Conditions: a) H$_2$NCH$_2$C(R$_8$)(R$_9$)OH, NaBH$_4$, NaOH, MeOH; b) Cs$_2$CO$_3$, CuI, IPA; or KO$_t$Bu, DMSO; c) Boc anhydride, Et$_3$N, THF; d) HCl, dioxane Scheme 5 represents a general scheme for the preparation of 2-ethyl-2,3,4,5-tetrahydrobenzo[f][1,4]oxazepines, and 2,2-dimethyl-2,3,4,5-tetrahydrobenzo[f][1,4]oxazepines used in the invention. In Scheme 5, R$_7$ is —C$_{1-3}$ alkyl, halo, CN, —OC$_{1-3}$alkyl, —CH$_2$—O—CH$_3$, or OH; R$_8$ and R$_9$ are hydrogen, C$_{1-3}$alkyl, or C$_{3-6}$spirocycloalkyl. Substituted 2-bromobenzaldehyde or substituted 2-fluorobenzaldehyde depicted as starting material are commercially available. Reaction conditions are as described above in the scheme; however, the skilled artisan will appreciate that certain modifications in the reaction conditions and/or reagents used are possible.

Reductive amination of the starting aldehyde with the appropriate aminoalcohol followed by displacement of the bromide or fluoro provides the required intermediate 3. This was then protected as the Boc carbamate to facilitate purification. It will be appreciated by the skilled artisan that alternative protecting groups may be used. Deprotection yields the requisite amine 5.

Scheme 6

Conditions: a) H$_2$NCH$_2$C(R$_8$)OH, NaBH$_4$, NaOH, MeOH; b) PPh$_3$, DEAD, THF; c) Boc anhydride, Et$_3$N, THF; d) HCl, dioxane Scheme 6 represents a general scheme for the preparation of (R)-2-ethyl-2,3,4,5-tetrahydrobenzo[f][1,4]oxazepines, and 2,2-dimethyl-2,3,4,5-tetrahydrobenzo[f][1,4]oxazepines used in the invention. In Scheme 6, $R_7$ and $R_8$ are defined previously. Substituted 2-hydroxybenzaldehyde depicted as starting material is commercially available. Reaction conditions are as described above in the scheme; however, the skilled artisan will appreciate that certain modifications in the reaction conditions and/or reagents used are possible.

Reductive amination of aldehyde with the appropriate aminoalcohol followed by Mitsunobo reaction provides the required intermediate 3. This was then protected as the Boc carbamate to facilitate purification. It will be appreciated by the skilled artisan that alternative protecting groups may be used. Deprotection yields the requisite amine 5.

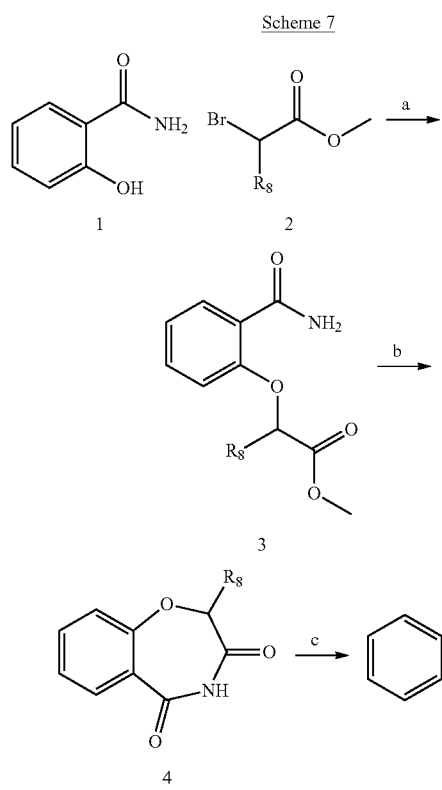

Conditions: a) $K_2CO_3$, THF; b) NaOMe, DMF; c) LAH, THF

Scheme 7 represents a general scheme for the preparation of substituted-tetrahydrobenzo[f][1,4]oxazepines used in the invention. In scheme 7, $R_8$ is as defined previously. In this, 2-hydroxybenzamide depicted as starting material is commercially available. Reaction conditions are as described above in the scheme; however, the skilled artisan will appreciate that certain modifications in the reaction conditions and/or reagents used are possible.

Reaction of 2-hydroxybenzamide with the appropriate bromoacetate yields the intermediate 3. Cyclization under basic conditions followed by reduction of the resulting imide with LAH yields the required amine 5.

Scheme 8

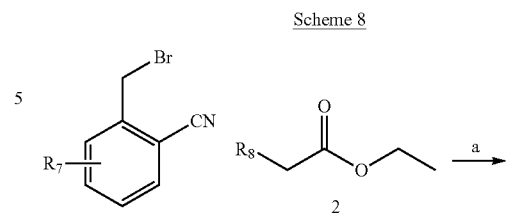

Conditions: a) LDA, THF; b) LAH, THF; c) Boc anhydride, DCM; d) $MeSO_2Cl$, $Et_3N$, DCM; (e) $Cs_2CO_3$, CuI, IPA Scheme 8 represents a general scheme for the preparation of 2,3,4,5-tetrahydro-1H-benzo[c]azepines used in the invention. In Scheme 8, $R_7$ and $R_8$ are as defined previously. The substituted 2-(bromomethyl)benzonitrile depicted as starting material is commercially available. Reaction conditions are as described above in the scheme; however, the skilled artisan will appreciate that certain modifications in the reaction conditions and/or reagents used are possible.

Reaction of starting 2-(bromomethyl)benzonitrile with the enolated generated from the appropriate ester 2 yields nitrile 3. Reduction of the nitrile and ester functions with LAH followed by protection of the amine group and conversion of the alcohol to the mesylate leaving group affords intermediate 6. Completion of the desired 7 is accomplished by cyclization under basic condition with CuI.

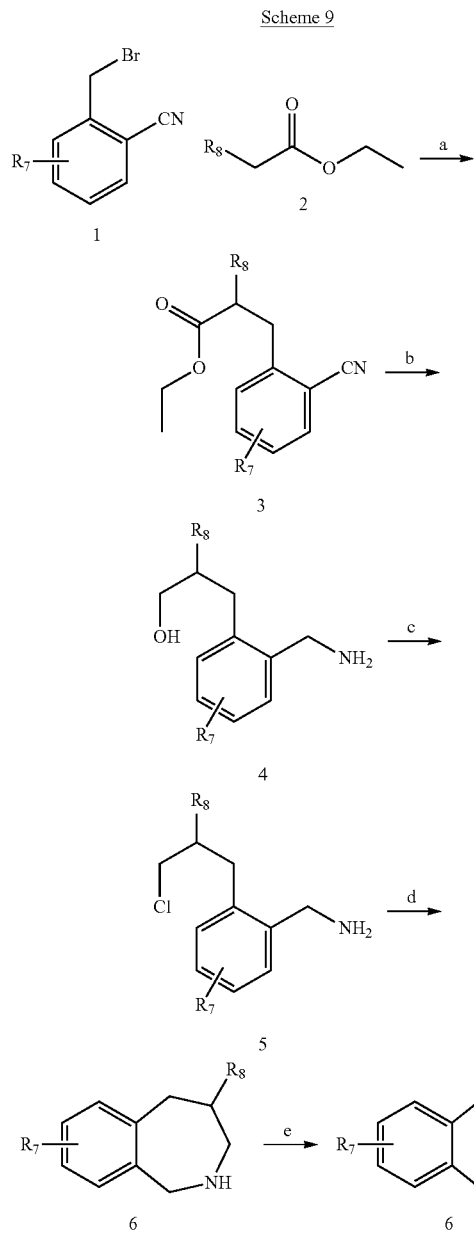

Conditions: a) LDA, THF; b) LAH, THF; c) SOCl$_2$, DCE; d) DIPEA, CH$_3$CN; e) (i) (Boc)$_2$O, TEA, DCM, (ii) HCl in dioxane, THF Scheme 9 represents a general scheme for the preparation of 2,3,4,5-tetrahydro-1H-benzo[c]azepines used in the invention. In Scheme 9, R$_7$ and R$_8$ are as defined previously. The substituted 2-(bromomethyl)benzonitrile depicted as starting material are commercially available. Reaction conditions are as described above in the scheme; however, the skilled artisan will appreciate that certain modifications in the reaction conditions and/or reagents used are possible.

Reaction of starting 2-(bromomethyl)benzonitrile with the enolate generated from the appropriate ester 2 yields nitrile 3. Reduction of the nitrile and ester functions with LAH. Alcohol was then converted intermediate 5 with thionyl chloride. Displacement of the chloride provides the intermediate 6 It was then protected with Boc group and then deprotection to give desired 7 as hydrochloride salt.

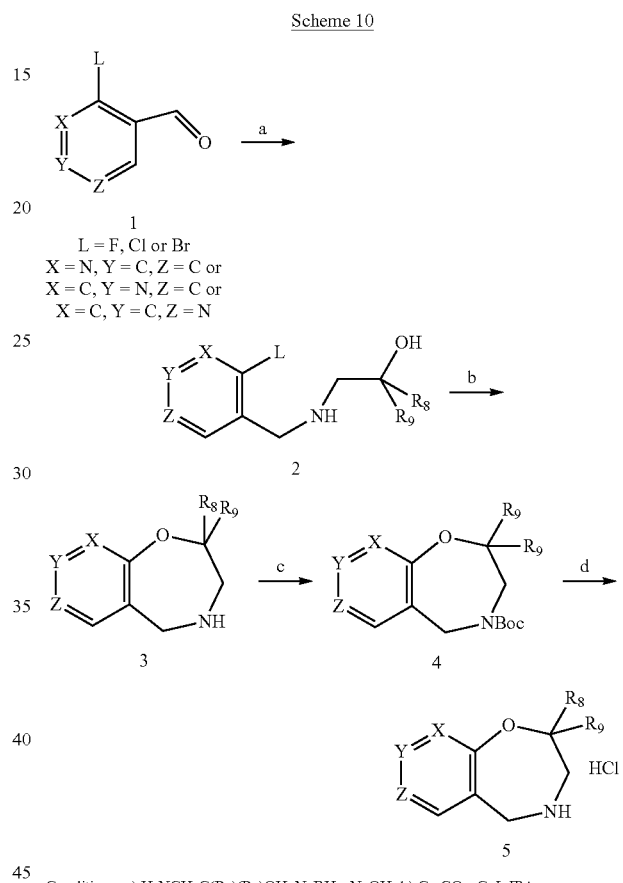

Conditions: a) H$_2$NCH$_2$C(R$_6$)(R$_7$)OH, NaBH$_4$, NaOH; b) Cs$_2$CO$_3$, CuI, IPA; or KO$_t$Bu, DMSO c) Boc anhydride, Et$_3$N, THF; d) HCl, dioxane Scheme 10 represents a general scheme for the preparation of tetrahydropyrido[1,4]oxazepine hydrochloride used in the invention. In Scheme 10, R$_8$ and R$_9$ are as defined previously. The fluoronicotinaldehyde, chloronicotinaldehyde or bromonicotinaldehyde depicted as starting material are commercially available. Reaction conditions are as described above in the scheme; however, the skilled artisan will appreciate that certain modifications in the reaction conditions and/or reagents used are possible.

Reductive amination of the starting aldehyde with the appropriate aminoalcohol followed by displacement of the bromide or fluoro provides the required intermediate 3. This was then protected as the Boc carbamate to facilitate purification. It will be appreciated by the skilled artisan that alternative protecting groups may be used. Deprotection yields the requisite amine 5 as hydrochloride salt.

Scheme 11

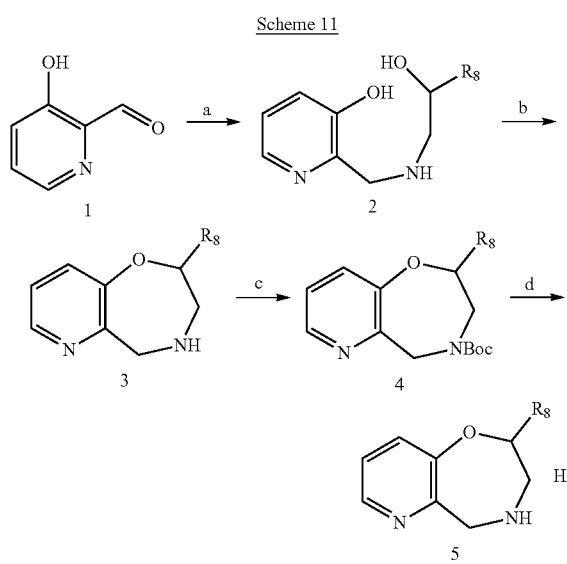

Conditions: a) H$_2$NCH$_2$CH(R$_8$)OH, NaBH$_4$, NaOH, MeOH; b) PPh$_3$, DEAD, THF; c) Boc anhydride, Et$_3$N, THF; d) HCl, dioxane Scheme 11 represents a general scheme for the preparation of (R)-2-ethyl-2,3,4,5-tetrahydropyrido[2,3-f][1,4]oxazepine hydrochloride, and 2,2-dimethyl-2,3,4,5-tetrahydropyrido[2,3-f][1,4]oxazepine hydrochloride used in the invention. In Scheme 11, R$_8$ is as defined previously. The 3-hydroxypicolinaldehyde depicted as starting material is commercially available. Reaction conditions are as described above in the scheme; however, the skilled artisan will appreciate that certain modifications in the reaction conditions and/or reagents used are possible.

Reductive amination of the commercially available aldehyde with the appropriate aminoalcohol followed by Mitsunobo reaction provides the required intermediate 3. This was then protected as the Boc carbamate to facilitate purification. It will be appreciated by the skilled artisan that alternative protecting groups may be used. Deprotection yields the requisite amine 5.

Scheme 12

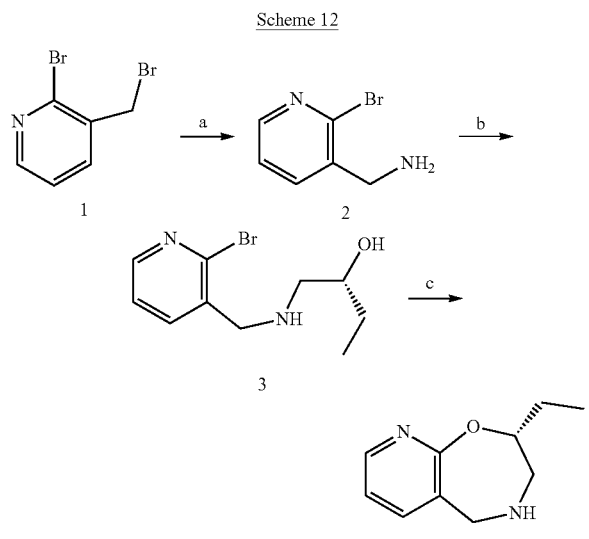

Conditions: a) NH$_4$OH; b) (R)-(2)-ethyloxirane, EtOH: c) KO$_t$Bu, DMF

Scheme 12 represents a general scheme for the preparation of (R)-2-ethyl-2,3,4,5-tetrahydropyrido[3,2-f][1,4]oxazepine used in the invention. In this, 2-bromo-3-(bromomethyl)pyridine depicted as starting material are commercially available. Reaction conditions are as described above in the scheme; however, the skilled artisan will appreciate that certain modifications in the reaction conditions and/or reagents used are possible.

Treatment of commercially available 2-bromo-3-(bromomethyl)pyridine with ammonium hydroxide yields primary amine 2. Alkylation via epoxide opening followed by displacement of the bromide provides intermediate 4.

Scheme 13

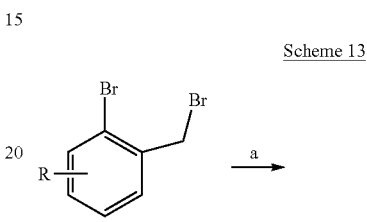

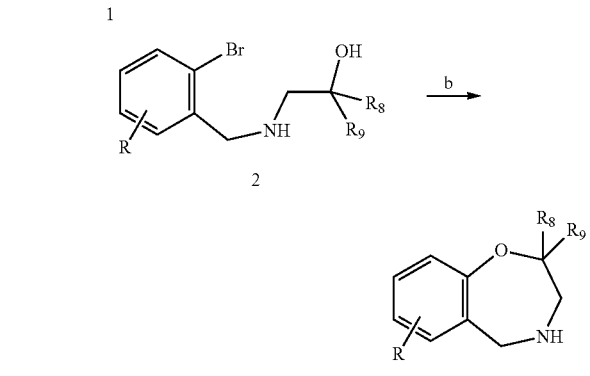

Conditions: a) amine, K$_2$CO$_3$, THF, water; b) Cs$_2$CO$_3$, CuI, IPA

Scheme 13 represents a general scheme for the preparation of 2-ethyl-2,3,4,5-tetrahydrobenzo[f][1,4]oxazepine hydrochloride, and 2,2-dimethyl-2,3,4,5-tetrahydrobenzo[f][1,4]oxazepine hydrochloride used in the invention. In Scheme 13, R$_8$ and R$_9$ are as defined previously. The substituted 1-bromo-2-(bromomethyl)benzene depicted as starting material are commercially available. Reaction conditions are as described above in the scheme; however, the skilled artisan will appreciate that certain modifications in the reaction conditions and/or reagents used are possible.

Alkylation with the appropriate aminoalcohol followed by displacement of the bromide provides the required intermediate 3.

Scheme 14

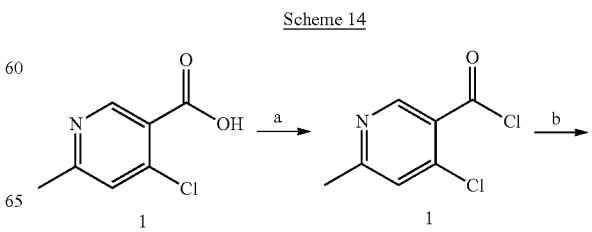

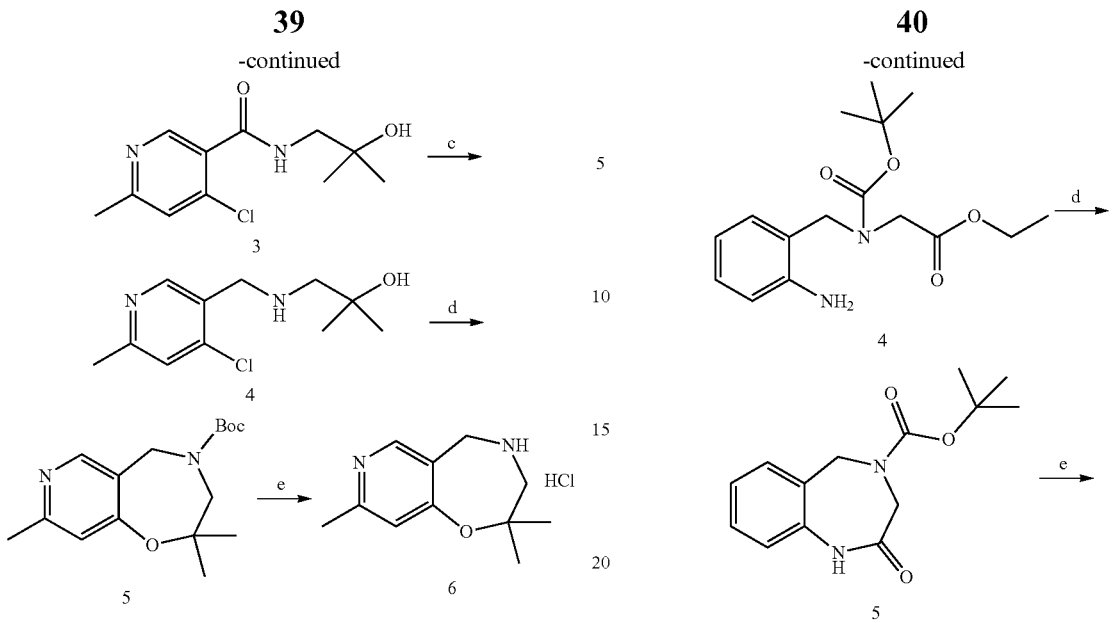

Conditions: a) POCl₃; b) NaOH, DCM; c) borane dimethyl sulfide, THF; d) (i) KOtBu, DMSO; (ii) Boc anhydride, Et₃N, THF; d) HCl, dioxane Scheme 14 represents a general scheme for the preparation of 2,2,8-trimethyl-2,3,4,5-tetrahydropyrido[3,4-f][1,4] oxazepine hydrochloride used in the invention. In this, 4-hydroxy-6-methylnicotinic acid depicted as starting material is commercially available. Reaction conditions are as described above in the scheme; however, the skilled artisan will appreciate that certain modifications in the reaction conditions and/or reagents used are possible.

Commercially available acid 1 was converted to the acid chloride with POCl₃, followed by amide formation to give intermediate 3. Reduction of the amide with borane dimethyl sulfide produces amine 4. Cyclization with potassium tert-butoxide as base followed by amine protection as the tert-butylcarbamate group yields compound 5. Deprotection under acidic condition yields the requisite amine 6.

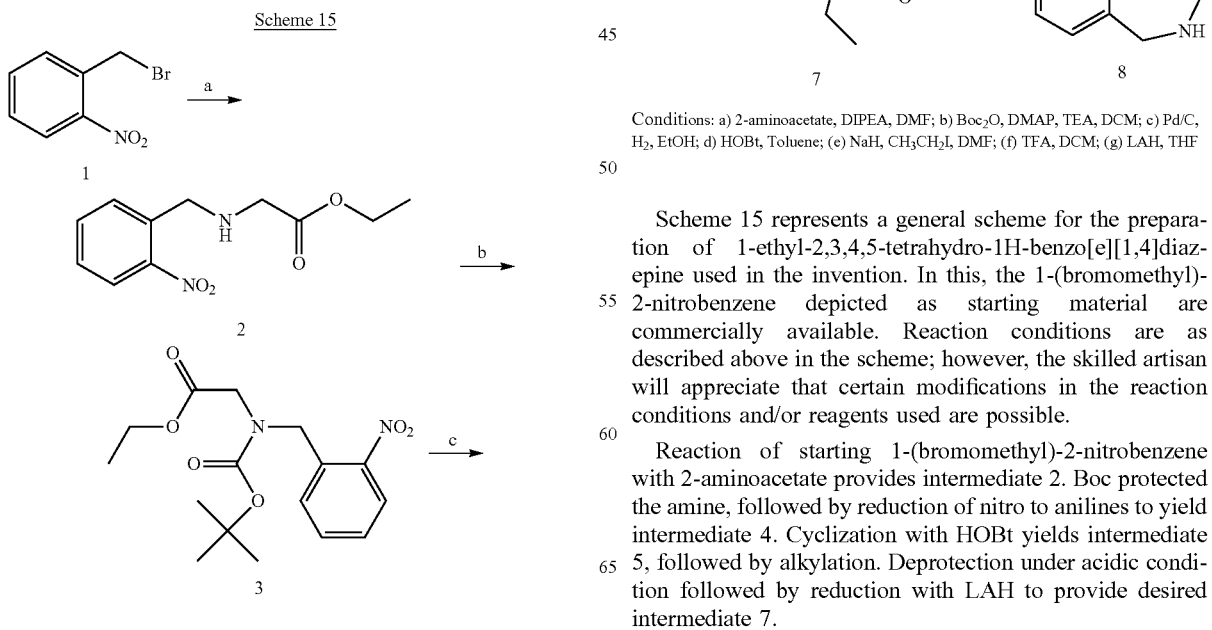

Conditions: a) 2-aminoacetate, DIPEA, DMF; b) Boc₂O, DMAP, TEA, DCM; c) Pd/C, H₂, EtOH; d) HOBt, Toluene; (e) NaH, CH₃CH₂I, DMF; (f) TFA, DCM; (g) LAH, THF Scheme 15 represents a general scheme for the preparation of 1-ethyl-2,3,4,5-tetrahydro-1H-benzo[e][1,4]diazepine used in the invention. In this, the 1-(bromomethyl)-2-nitrobenzene depicted as starting material are commercially available. Reaction conditions are as described above in the scheme; however, the skilled artisan will appreciate that certain modifications in the reaction conditions and/or reagents used are possible.

Reaction of starting 1-(bromomethyl)-2-nitrobenzene with 2-aminoacetate provides intermediate 2. Boc protected the amine, followed by reduction of nitro to anilines to yield intermediate 4. Cyclization with HOBt yields intermediate 5, followed by alkylation. Deprotection under acidic condition followed by reduction with LAH to provide desired intermediate 7.

Scheme 16

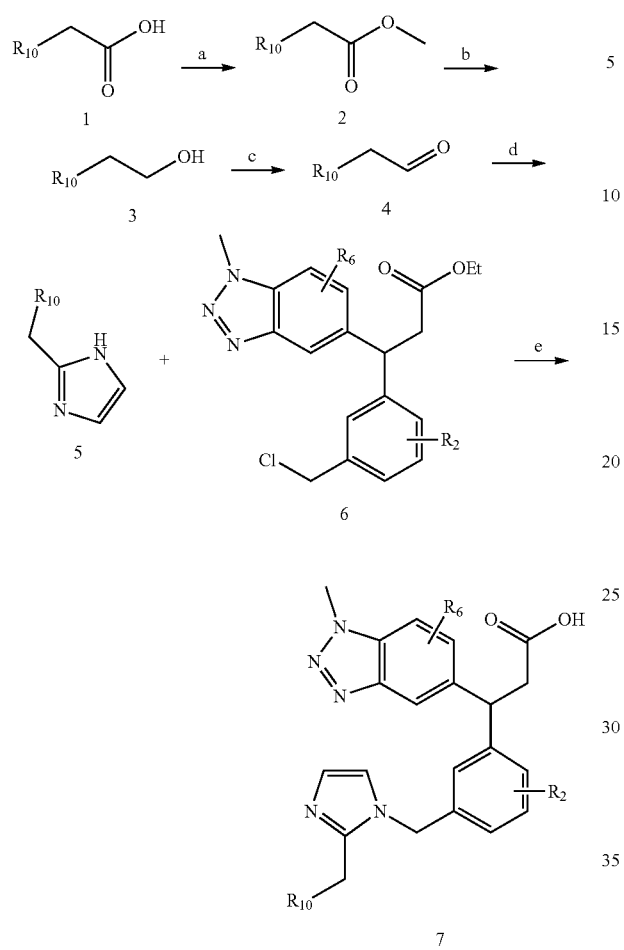

Conditions: a) sulfuric acid, methanol; b) LiAlH₄, THF; c) PCC, DCM; d) oxaldehyde, NH₄OH, H₂O; e) (i) NaH, DMF (ii) NaOH, MeOH Scheme 17

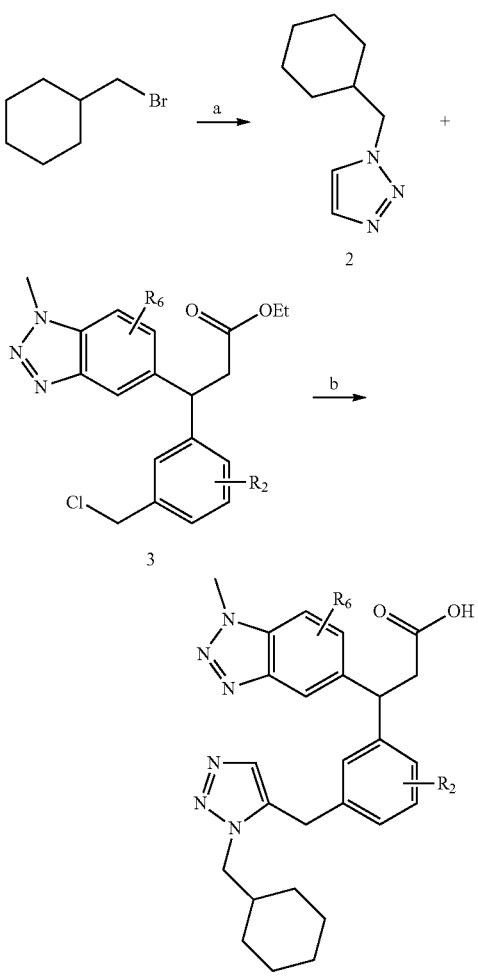

Conditions: a) 1H-1,2,3-triazole, Cs₂CO₃ NaI, DMF; b) (i) NaH, DMF (ii) NaOH, MeOH/H₂O Scheme 16 represents a general scheme for the preparation of compounds according to Formula (I). In Scheme 16 $R_2$ is as in Formula 1 and $R_6$ is $C_{1-3}$alkyl, halo, or —$OC_{1-3}$alkyl. $R_{10}$ is —$C_{1-3}$ alkyl —$C_{4-7}$ cycloalkyl —$C_{5-7}$ heterocycloalkyl, —CH₂-azabicycloheptanyl, or —CH₂-azabicyclohexanyl. The carboxylic acid 1 depicted as starting material is commercially available or may be synthesized from readily available materials. Reaction conditions are as described above in the scheme; however, the skilled artisan will appreciate that certain modifications in the reaction conditions and/or reagents used are possible.

The commercially available carboxylic acid 1 was treated with sulfuric acid in methanol to produce methyl ester 2, which can be reduced by LiAlH₄ in THF and oxided with PCC in DCM to obtain the intermediate aldehyde 4. Compound 4 is treated with oxaldehyde and NH₄OH to afford the desired imidazole 5. Alkylation of 5 by treating with intermediate 6 under basic conditions followed by hydrolysis with NaOH in a suitable solvent produces desired product 7.

Scheme 17 represents a general scheme for the preparation of compounds according to Formula (I). In scheme 17, $R_2$ and $R_5$ are as defined previously. The triazole 1 depicted as starting material is commercially available. Reaction conditions are as described above in the scheme; however, the skilled artisan will appreciate that certain modifications in the reaction conditions and/or reagents used are possible.

Commercially available 1H-1,2,3-triazole 1 is treated with (bromomethyl)cyclohexane in the presence of Cs₂CO₃ and NaI in DMF to afford intermediate 2. Completion of the synthesis is accomplished via reaction with 3 under basic conditions followed by hydrolysis with NaOH in a suitable solvent to produce 4.

Scheme 18

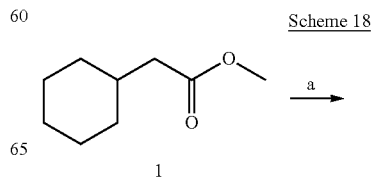

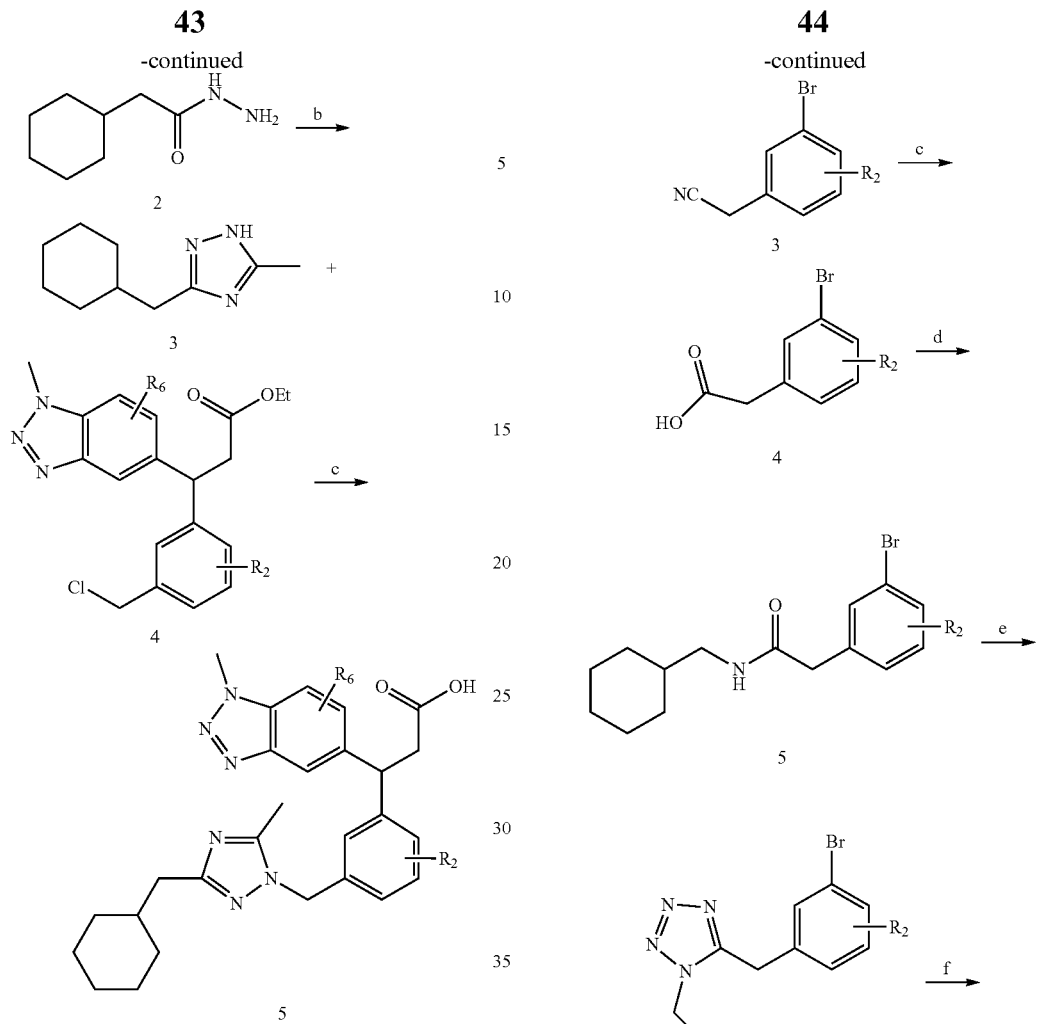

Conditions: a) hydrazine monohydrate, methanol; b) ethanethioamide, pyrinde, butanol; c) (i) NaH, DMF (ii) NaOH, MeOH/H₂O Scheme 18 represents a general scheme for the preparation of compounds according to Formula (I). In Scheme 18, $R_2$ and $R_6$ are as defined previously. The carboxylic acid ester 1 depicted as starting material is commercially available. Reaction conditions are as described above in the scheme; however, the skilled artisan will appreciate that certain modifications in the reaction conditions and/or reagents used are possible.

The commercially available methyl ester 1 is treated with hydrazine in methanol to obtain hydrazide compound 2. Reaction with ethanethioamide and pyrinde in 1-butanol produces triazole 3. Alkylation of intermediate 3 with chloride 4 in the presence of NaH in DMF, followed by hydrolysis with NaOH in a suitable solvent produces desired product 5.

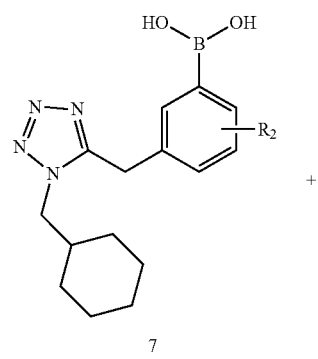

Scheme 19

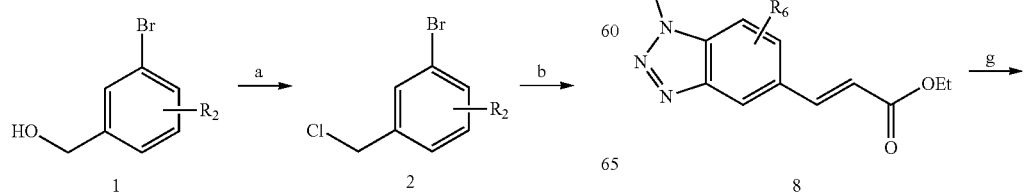

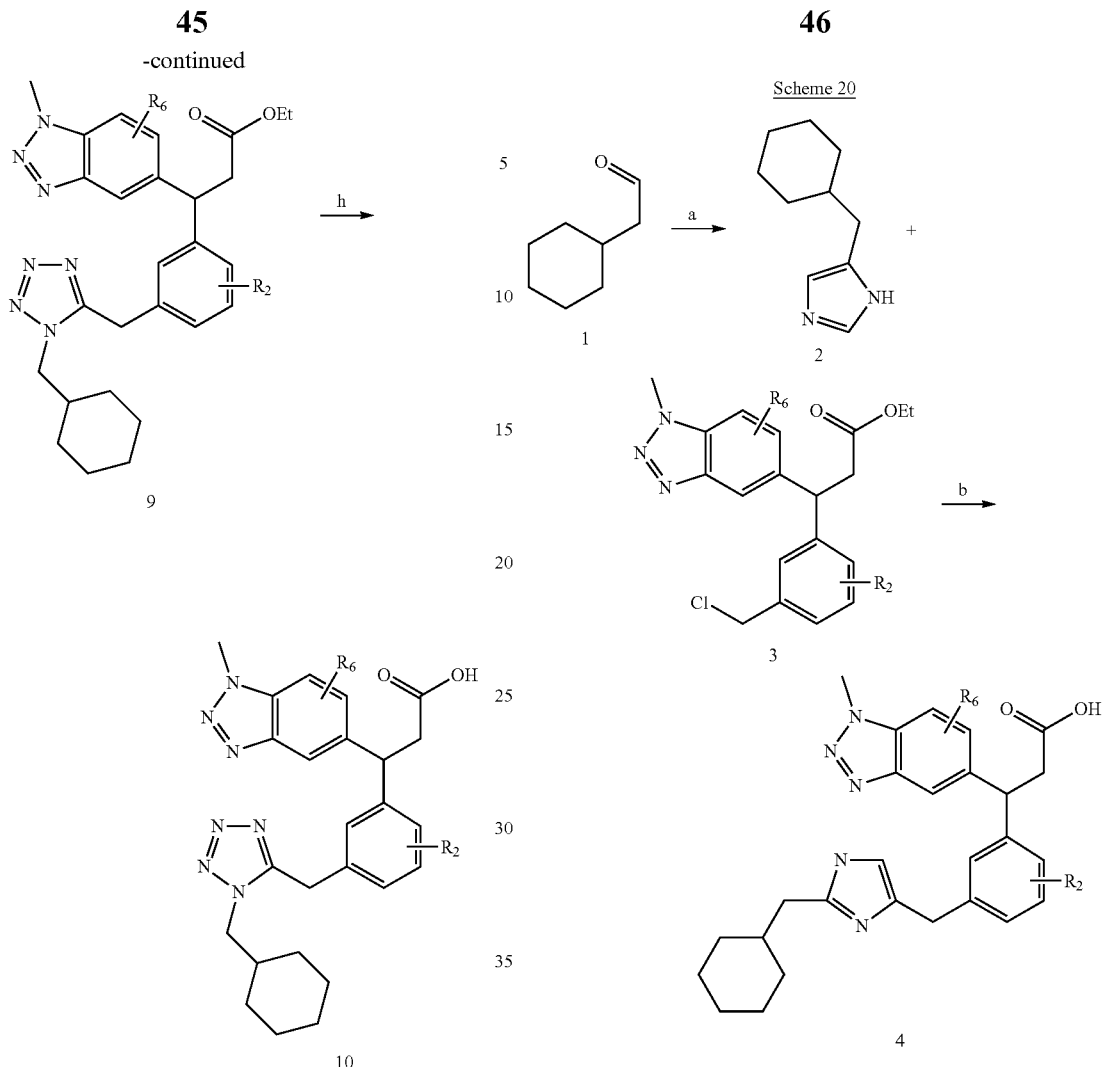

Conditions: a) SOCl$_2$, DCM; b) KCN, ethanol/water; c) NaOH, ethanol, HCl; d) oxalyl chloride, acyclohexylmethanamine, TEA, DCM; e) PCl$_5$, TMSM$_3$, toluene; f) diboron, KOAc, PdCl$_2$(dppf)-CH$_2$Cl$_2$ adduct, 1,4-dioxane; g) [RhCl(cod)]$_2$, TEA H$_2$O, 1,4-dioxane; h) NaOH, MeOH/H$_2$O Scheme 19 represents a general scheme for the preparation of compounds according to Formula (I). In Scheme 19, $R_2$ and $R_6$ are as defined previously. The alcohol 1 depicted as starting material is commercially available or may be synthesized from readily available materials. Reaction conditions are as described above in the scheme; however, the skilled artisan will appreciate that certain modifications in the reaction conditions and/or reagents used are possible.

Alcohol 1 is converted to acid 4 in a 3 step sequence involving conversion to the chloride with SOCl$_2$ in DCM first, followed by treating with KCN in a mixture of ethanol and water to produce the nitrile 3 and hydrolysis of nitrile 3 with NaOH in ethanol. Compound 4 is treated with oxalyl chloride followed by cyclohexylmethanamine and Et$_3$N to produce intermediate 5. Tetrazole 6 is formed by treating 5 with PCl$_5$ and TMSN$_3$ in toluene. Conversion of the bromide to the boronate 7 was accomplished by treating with diboron in presence of PdCl$_2$ (dppf) and KOAc in 1,4-dioxane. The synthesis can be completed by rhodium catalyzed Michael addition of 7 with intermediate 8 followed by hydrolysis with NaOH in suitable solvents.

Conditions: a) TOSMIC, NH$_3$ in methanol; b) (i) NaH, DMF, RT (ii) NaOH, MeOH/H$_2$O Scheme 20 represents a general scheme for the preparation of compounds according to Formula (I). In Scheme 20, $R_2$ and $R_6$ are as defined previously. The aldehyde 1 depicted as starting material is commercially available or may be synthesized from readily available materials. Reaction conditions are as described above in the scheme; however, the skilled artisan will appreciate that certain modifications in the reaction conditions and/or reagents used are possible.

The commercially available aldehyde 1 is treated with TOSMIC and NH$_3$ in methanol to provide intermediate 2. Alkylation of intermediate 2 with intermediate 3 in presence of NaH in DMF, followed by hydrolysis in NaOH and suitable solvents to produce desired product 4.

Scheme 21

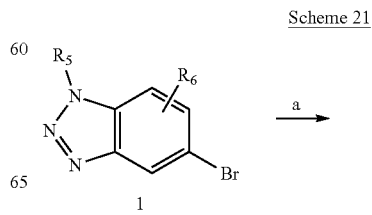

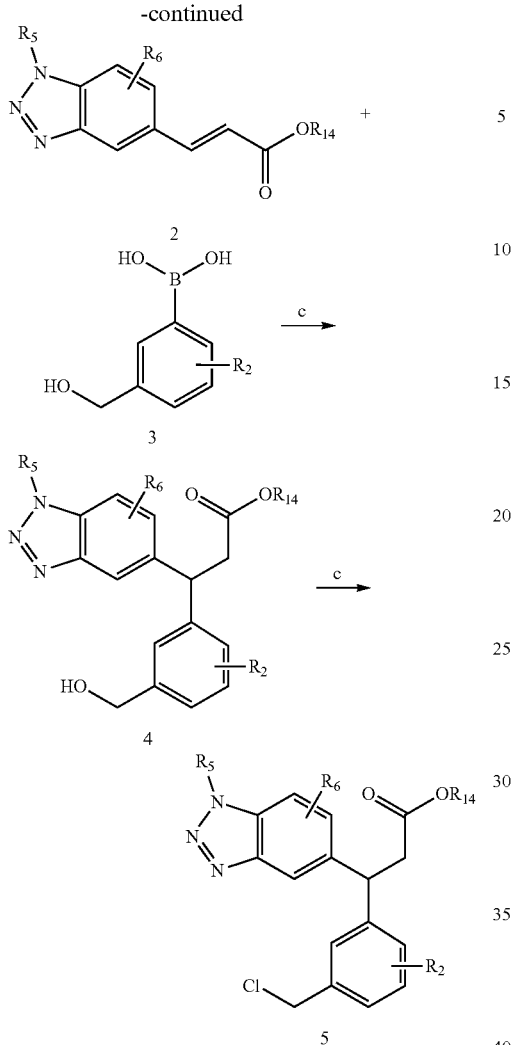

Conditions: a) Methyl acrylate, Ethyl acrylate (or) benzyl acrylate, Pd(OAc)$_2$, DIEA, DMF; b) [RhCl(cod)]$_2$, TEA, H$_2$O, 1,4-dioxane; c) SOCl$_2$, DCM Scheme 21 represents a general scheme for the preparation of compounds according to Formula (I). In Scheme 21, $R_{14}$ is $C_{1-3}$alkyl or Benzyl, $R_5$ is $C_{1-3}$alkyl or —(CH$_2$)$_2$—O—(CH$_2$)$_2$—OR$_4$ (as defined in Formula 1), $R_2$ and $R_6$, are as defined previously. The triazole 1 depicted as starting material may be synthesized from readily available materials. Reaction conditions are as described above in the scheme; however, the skilled artisan will appreciate that certain modifications in the reaction conditions and/or reagents used are possible.

Treatment of triazole 1 with ethyl acrylate or benzyl acrylate in the presence of palladium (II) acetate and diisopropylethyl amine in the presence of a suitable solvent produces the desired Heck cross-coupling product 2. It will appreciated by the skilled artisan that other acrylates may be used for the Heck cross-coupling and that compound 2 may also be obtained via a Wittig olefination reaction starting from the appropriate aldehyde of compound 1. Further transformation of the olefin 2 can be achieved through rhodium mediated cross-coupling of the appropriate boronic acid or boronic ester 3 in the presence of triethylamine. It will be recognized by the skilled artisan that the conditions for this Rh catalyzed Michael reaction may be modified by the appropriate selection of ligands, Rh source, solvent and temperature in order to achieve enantioselectivity wherein the chirality at the carbon β to the carboxylate may favor one or the other of the possible enantiomers. Benzylic alcohol 4 can be transformed to the requisite chloride 5 using thionyl chloride.

Scheme 22

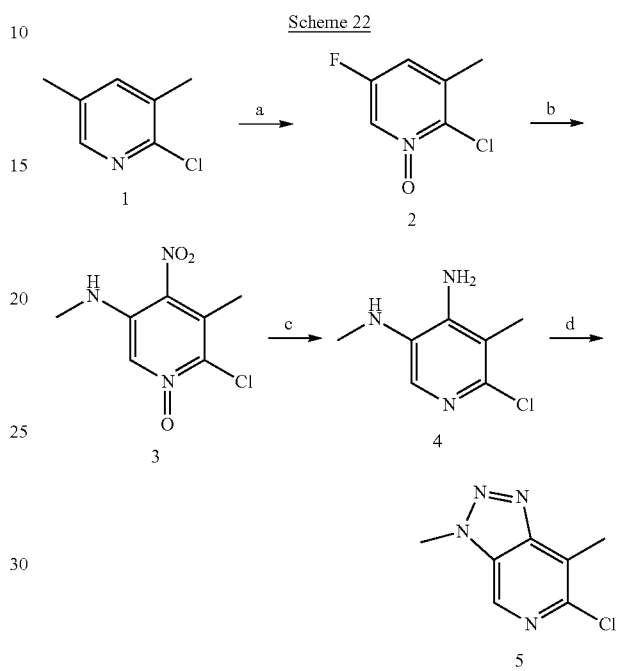

Conditions: a) H$_2$O$_2$, TFA; b) (ii) KNO$_3$, H$_2$SO$_4$; (ii) CH$_3$NH$_2$; c) Ni, EtOH, 40 psi; d) NaNO$_2$, H$_2$SO$_4$ Scheme 22 shows a general scheme for the preparation of 6-chloro-3,7-dimethyl-3H-[1,2,3]triazolo[4,5-c]pyridine. Starting with commercially available 2-chloro-5-fluoro-3-methylpyridine, oxidation provides intermediate 2. This is subsequently converted to nitro intermediate 3. Displacement of the fluoride using an appropriate amine followed by nickel metal reduction of the nitro to the aniline, yields 4. Diazotization and cyclization provides the required triazole 5.

Scheme 23

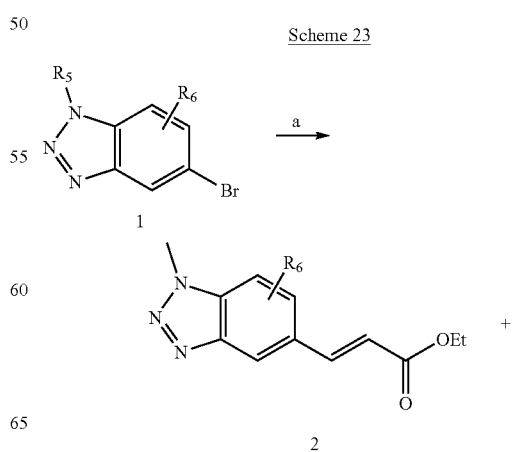

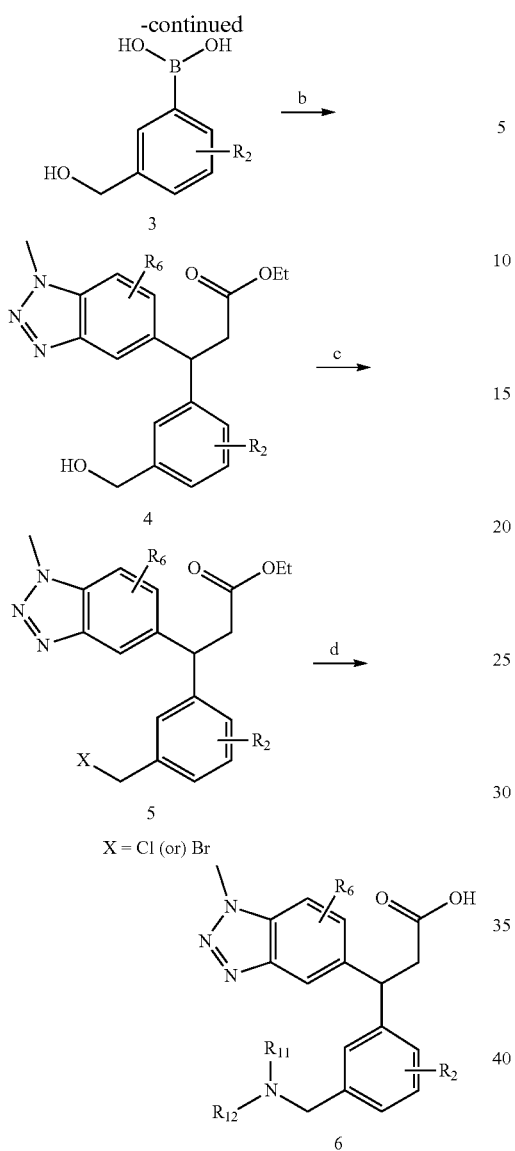

Conditions: a) Ethyl acrylate, Pd(OAc)$_2$, DIEA, DMF; b) [RhCl(cod)]$_2$, TEA H$_2$O, 1,4-dioxane; c) SOCl$_2$, DCM; (or) PBr$_3$ d) (i) R$_{11}$R$_{12}$NH, TEA, MeCN; (ii) NaOH, MeOH/H$_2$O Scheme 23 represents a general scheme for the preparation of compounds according to Formula (I). In Scheme 23, R$_2$ and R$_6$ are as defined previously. R$_{11}$ is methyl or cyclopropyl and R$_{12}$ is CH$_2$-A where A is as defined in Formula (I). The triazole 1 depicted as starting material may be synthesized from readily available materials. Reaction conditions are as described above in the scheme; however, the skilled artisan will appreciate that certain modifications in the reaction conditions and/or reagents used are possible.

Treatment of triazole 1 with ethyl acrylate in the presence of palladium (II) acetate and diisopropylethyl amine in the presence of a suitable solvent produces the desired Heck cross-coupling product 2. It will appreciated by the skilled artisan that other acrylates may be used for the Heck cross-coupling and that compound 2 may also be obtained via a Wittig olefination reaction starting from the appropriate aldehyde of compound 1. Further transformation of the olefin 2 can be achieved through rhodium mediated cross-coupling of the appropriate boronic acid or boronic ester 3 in the presence of triethylamine. Benzylic alcohol 4 can be transformed to the requisite chloride 5 using thionyl chloride. Completion of the desired acid 6 is accomplished in a two step sequence involving reaction of the chloride with the requisite amine, and conversion of the ester to the acid.

Scheme 24

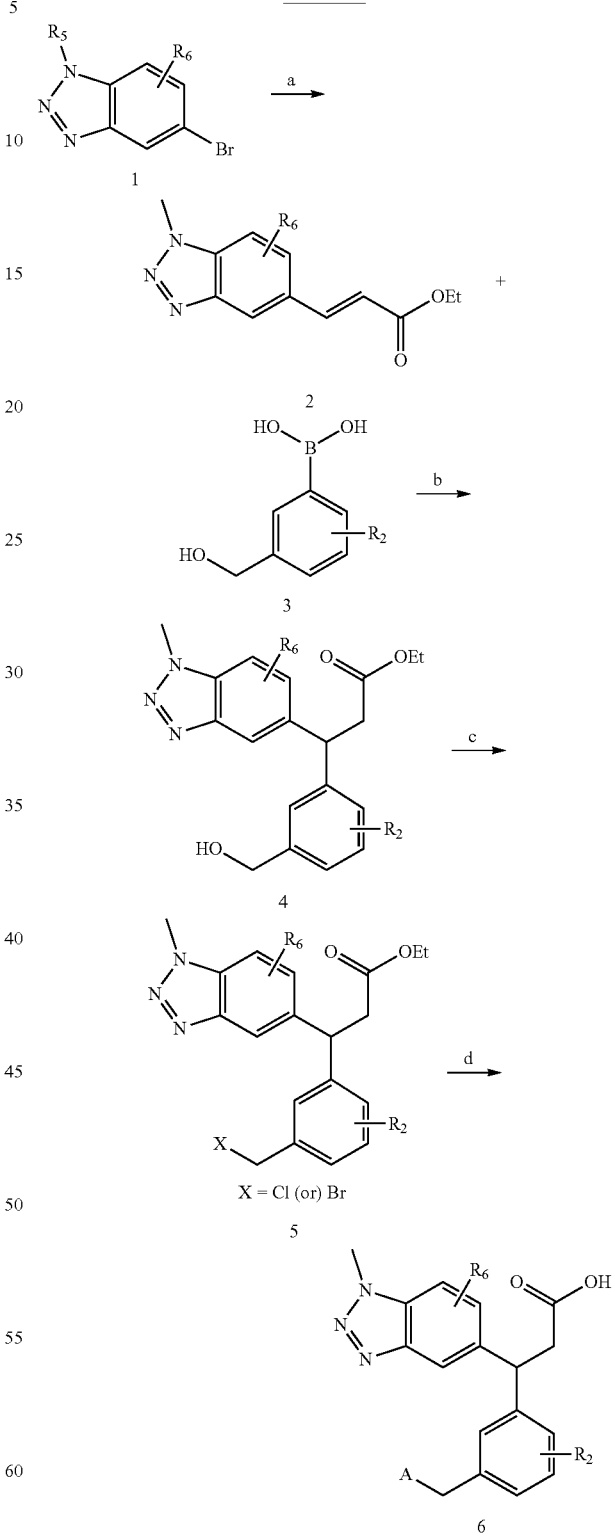

Conditions: a) Ethyl acrylate, Pd(OAc)$_2$, DIEA, DMF; b) [RhCl(cod)]$_2$, TEA, H$_2$O, 1,4-dioxane; c) SOCl$_2$, DCM; (or) PBr$_3$ d) (i) A, NaH (or) A, TEA, MeCN (or) A, DIPEA, DMF; (or) A, nBuLi, THF (ii) NaOH, MeOH/H$_2$O Scheme 24 represents a general scheme for the preparation of compounds according to Formula (I). In Scheme 24, $R_2$, $R_6$, and A are as defined previously. The triazole 1 depicted as starting material may be synthesized from readily available materials. Reaction conditions are as described above in the scheme; however, the skilled artisan will appreciate that certain modifications in the reaction conditions and/or reagents used are possible.

Treatment of triazole 1 with ethyl acrylate in the presence of palladium (II) acetate and diisopropylethyl amine in the presence of a suitable solvent produces the desired Heck cross-coupling product 2. It will appreciated by the skilled artisan that other acrylates may be used for the Heck cross-coupling and that compound 2 may also be obtained via a Wittig olefination reaction starting from the appropriate aldehyde of compound 1. Further transformation of the olefin 2 can be achieved through rhodium mediated cross-coupling of the appropriate boronic acid or boronic ester 3 in the presence of triethylamine. Benzylic alcohol 4 can be transformed to the requisite chloride 5 using thionyl chloride. Completion of the desired acid 6 is accomplished in a two step sequence involving reaction of the chloride with the requisite amine, and conversion of the ester to the acid.

Scheme 25

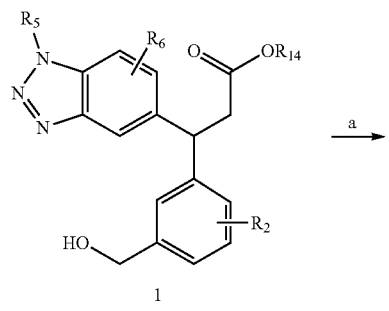

1

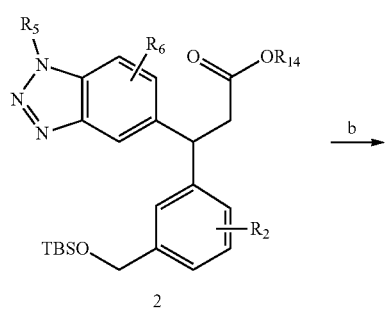

2

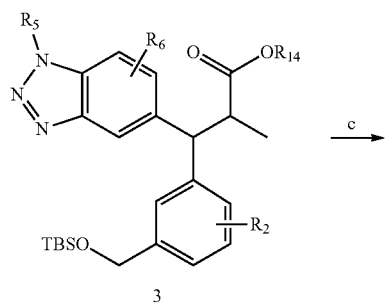

3

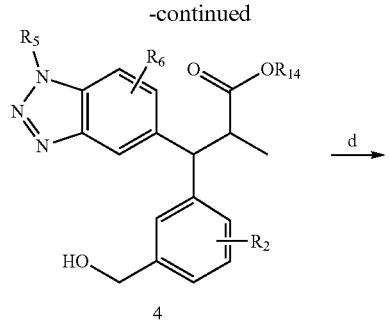

4

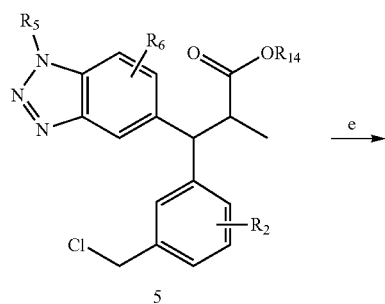

5

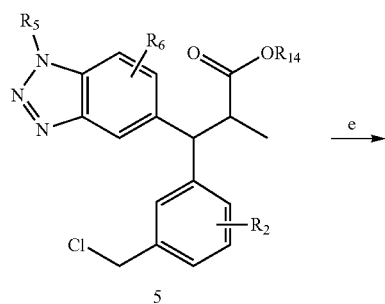

5

$Z = R_{11}R_{12}N$, or A

Conditions: a) TBSCl, imidazole, DCM; b) LDA, MeI, THF; c) TBAF, THF; d) SOCl$_2$, DCM, e) (i) $R_{11}R_{12}NH$, TEA, MeCN; (or) A, TEA, MeCN (or) A, NaH (or) DIPEA, DMF; (or) A, nBuLi, THF (ii) NaOH, MeOH/H$_2$O (or) H$_2$, Pd/C Scheme 25 represents a general scheme for the preparation of compounds according to Formula (I). In Scheme 25, $R_2$, $R_5$, $R_6$, $R_{11}$, $R_{12}$, $R_{14}$ and A are as defined previously. The starting material 1 can be synthesized from readily available materials. Reaction conditions are as described above in the scheme; however, the skilled artisan will appreciate that certain modifications in the reaction conditions and/or reagents used are possible.

Treatment of 1 with t-butyldimethylsilyl chloride and imidazole provides the silyl ether 2. Enolate formation with lithium diisopropylamide and reaction with methyl iodide gives alpha methylated product 3. Reaction with tetrabutylammonium fluoride furnishes benzylic alcohol 4 which can be converted to the chloride with thionyl chloride. The synthesis can be completed as previously described via reaction with the appropriate amine followed by conversion of the ester to the acid.

Scheme 26

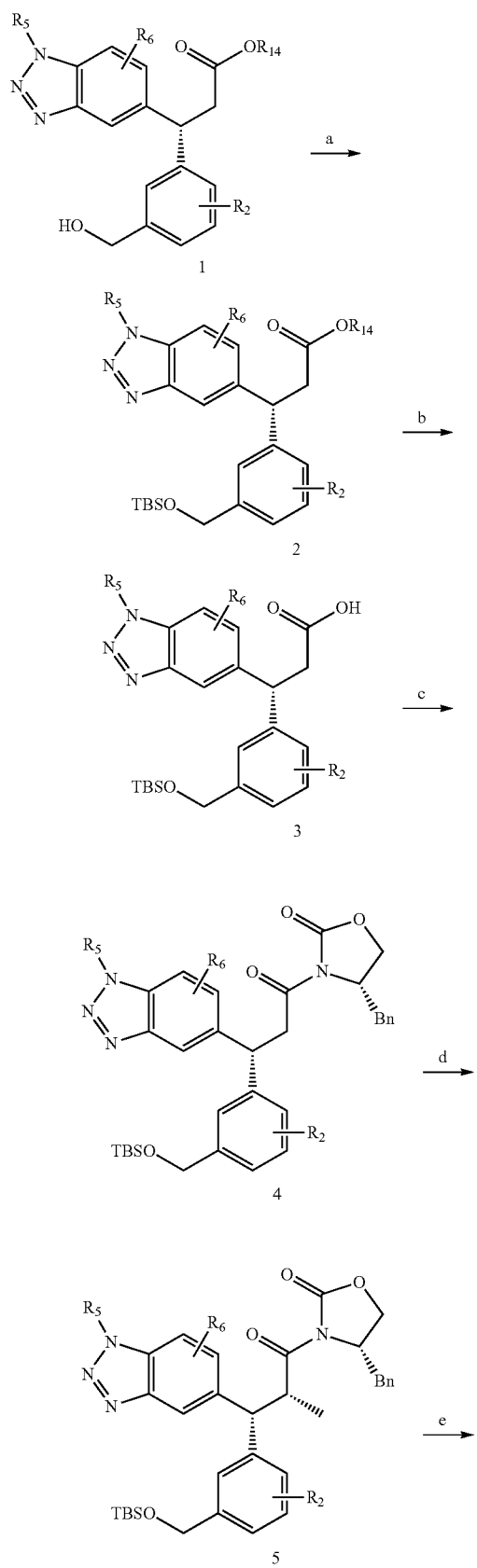

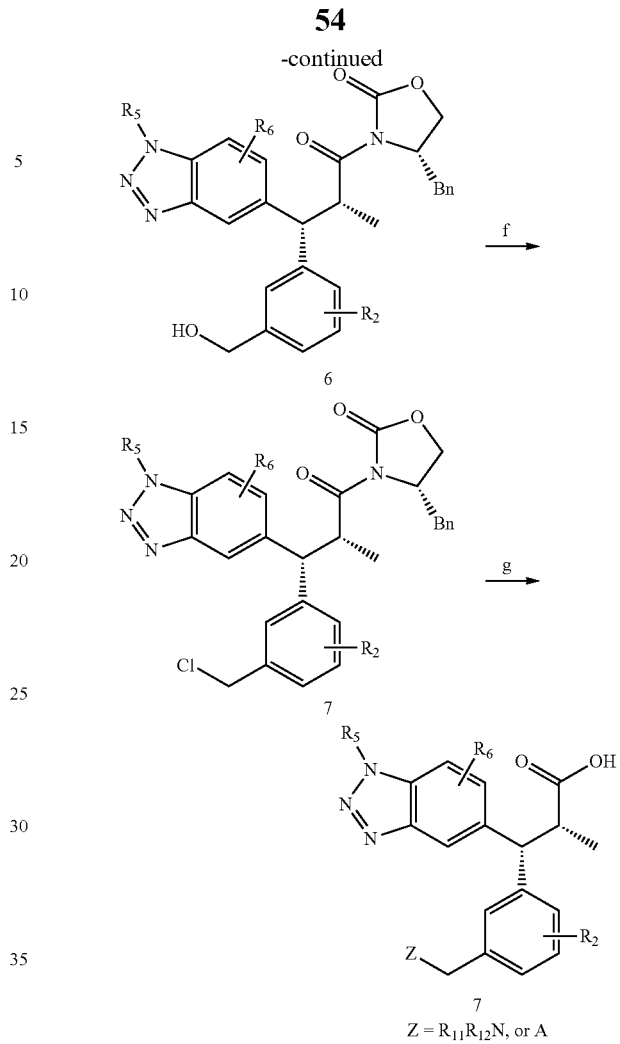

Conditions:
a) TBSCl, imidazole, DCM;
b) NaOH, water (or) H₂ 10% Pd—C, EtOH;
c) CDI, DBU, (S)-4-benzyloxazin-2-one, THF, MeCN;
d) NaHMDS, MeI, THF;
e) TBAF, THF;
f) SOCl₂, DCM
g) (i) R₁₁R₁₂NH, TEA, MeCN; (or) A, NaH (or) DIPEA, DMF; (or) A, nBuLi, THF
(ii) LiOH, H₂O₂

Scheme 26 represents a general scheme for the preparation of compounds according to Formula (I). In Scheme 26, $R_2$, $R_5$, $R_6$, $R_{11}$, $R_{12}$, $R_{14}$ and A are as defined previously. The starting material 1 can be synthesized from readily available materials. Reaction conditions are as described above in the scheme; however, the skilled artisan will appreciate that certain modifications in the reaction conditions and/or reagents used are possible.

Treatment of 1 with t-butyldimethylsilyl chloride and imidazole provides the silyl ether 2. Conversion of the ester to the acid can be accomplished either via hydrolysis under basic conditions such as NaOH and water with a suitable co-solvent or in the case where R9 is a benzyl group via hydrogenation with 10% Pd—C to furnishes acid 3. Treatment with carbonyl diimidazole in tetrahydrofuran followed by reaction with 1,8-Diazabicyclo[5.4.0]undec-7-ene and (S)-4-benzyloxazolidin-2-one provides 4. Enolate formation with sodium bis(trimethylsilyl)amide and stereoselective trapping with methyl iodide gives 5. Removal of the t-bu-

Scheme 27

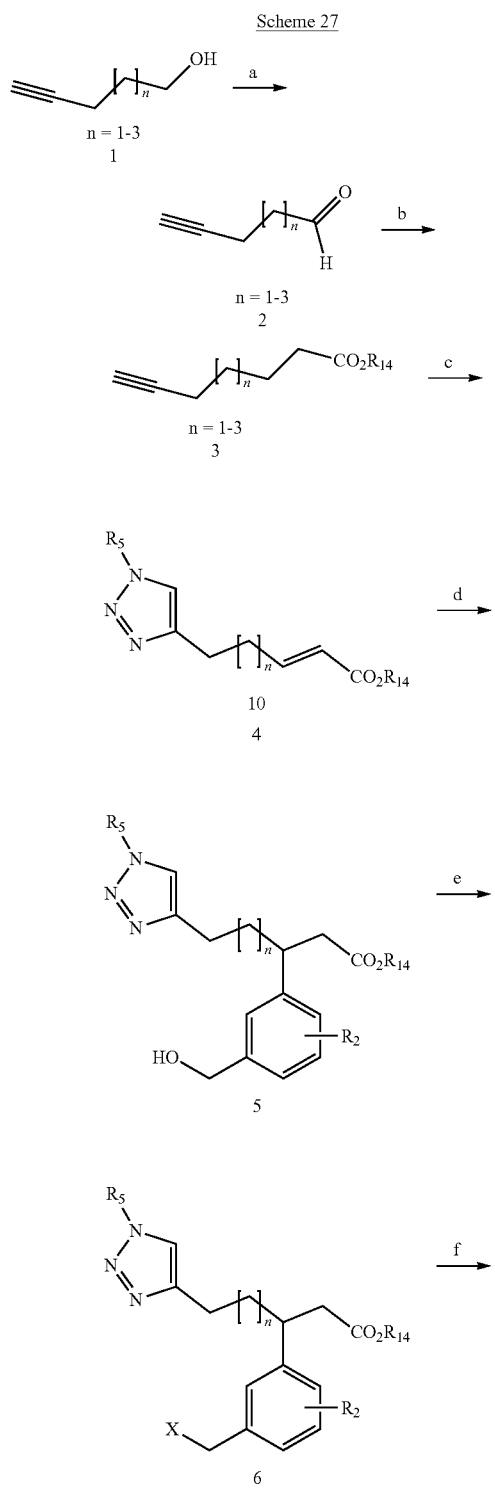

Conditions:
a) oxalyl chloride, DMSO, triethylamine, DCM, -78° C.;
b) $CO_2R_{14}CH=PPh_3$, DCM, reflux, 16 h;
c) $R_5$—I, $NaN_3$, CuI or $R_5$—$N_3$, $CuSO_4$, sodium ascorbate;
d) $(Rh[COD]Cl)_2$, 3-(Hydroxymethyl)-phenyl boronic acids; triethylamine, 1,4-dioxane, water;
e) $SOCl_2$, DCM; (or) $PBr_3$;
f) (i) $R_{13}H$, DIPEA, DMF; or NaH, DMF
(ii) LiOH, MeOH, THF (or) $H_2$ 10% Pd—C, EtOH Scheme 27 represents a general scheme for the preparation of compounds according to formula I. In Scheme 27, $R_2$, $R_5$ and $R_{14}$ are as defined previously. $R_{13}$ is A or A-linker as in Formula (I). The acetylenic alkyl alcohols 1 depicted are commercially available. Reaction conditions are as described above in the scheme; however, the skilled artisan will appreciate that certain modifications in the reaction conditions and/or reagents used are possible.

Aldehyde 2 is best obtained from the alcohols 1 by Swern oxidation. Other well known methods for oxidation of alkyl alcohols to aldehydes, such as pyridinium chlorochromate oxidation or use of the Dess Martin reagent may also be applied. It will be appreciated by the skilled artisan that compound 3 may be obtained by either the Horner Wadsworth Emmons reaction or a Wittig olefination reaction starting from the appropriate aldehyde 2 and the stabilized phosphonium ylide as shown in the scheme or the unstabilized ylide. The triazines 4 are prepared by standard click conditions either using commercially available organo-azides, Cu(II), and a suitable reducing agent such as sodium ascorbate to generate the Cu(I) catalyst or alternatively by in situ formation of an alkyl azide by reaction of an alkyl halide with sodium azide followed by reaction in the presence of a commercially available source of Cu(I) such as CuI. Further transformation of the olefin 4 can be achieved through rhodium mediated cross-coupling of the appropriate boronic acid or boronic ester in the presence of triethylamine to afford the methylphenyl alcohol 5. It will also be recognized by the skilled artisan that the conditions for this Rh catalyzed Michael reaction may be modified by the appropriate selection of ligands, Rh source, solvent and temperature in order to achieve enantioselectivity wherein the chirality at the carbon 3 to the carboxylate may favor one or the other of the possible enantiomers. Completion of the analog synthesis is accomplished via conversion of the alcohol to the chloride or bromide. It will appreciated by the skilled artisan that the benzylic alcohol 5 may be converted to an alternative leaving group such as, but not limited to, mesylate, tosylate, or iodide. Reaction of intermediate 6 with $R_{13}H$ followed by conversion of the ester in the presence of suitable co-solvents to assure adequate solubility of the reactants affords the final target carboxylic acids 7.

Scheme 28

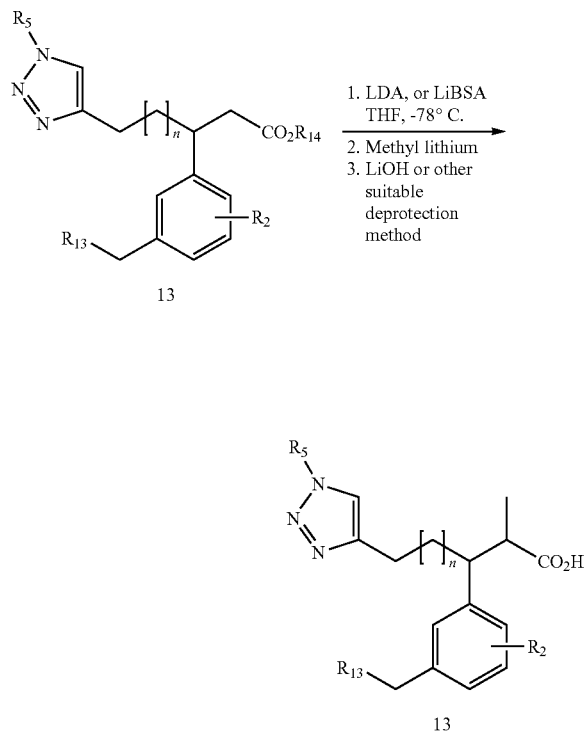

Scheme 28 depicts a method for further elaboration of the obtained compounds by alkylation α to the carboxylate. In Scheme 28, $R_2$, $R_5$ $R_{13}$ and $R_{14}$ are as defined previously. As is well known in the chemical literature ester enolate alkylation requires formation of the kinetic enolate with relatively strong, nonnucleophillic bases such as lithium diisopropyl amide or lithium bis-silyl amide at low temperature in order to prevent self reaction of the enolate with starting ester. However, in order to control the reaction at other acidic centers the base must be carefully selected to have just enough basicity to effect the deprotonation of methylene alpha to the ester while avoiding other acidic centers within the molecule. Alkylation of the dianion where $R_5$=H for acids can also be achieved. For cases where the substrate is an ester, appropriate choice of ester may be advantageous after alkylation because of the potential for steric hinderance of normal aqueous hydrolysis upon addition of the alkylating agent exemplified by MeI.

Scheme 29

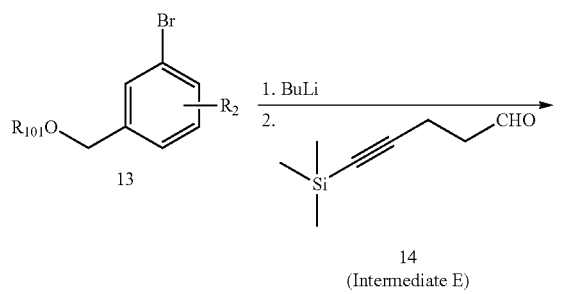

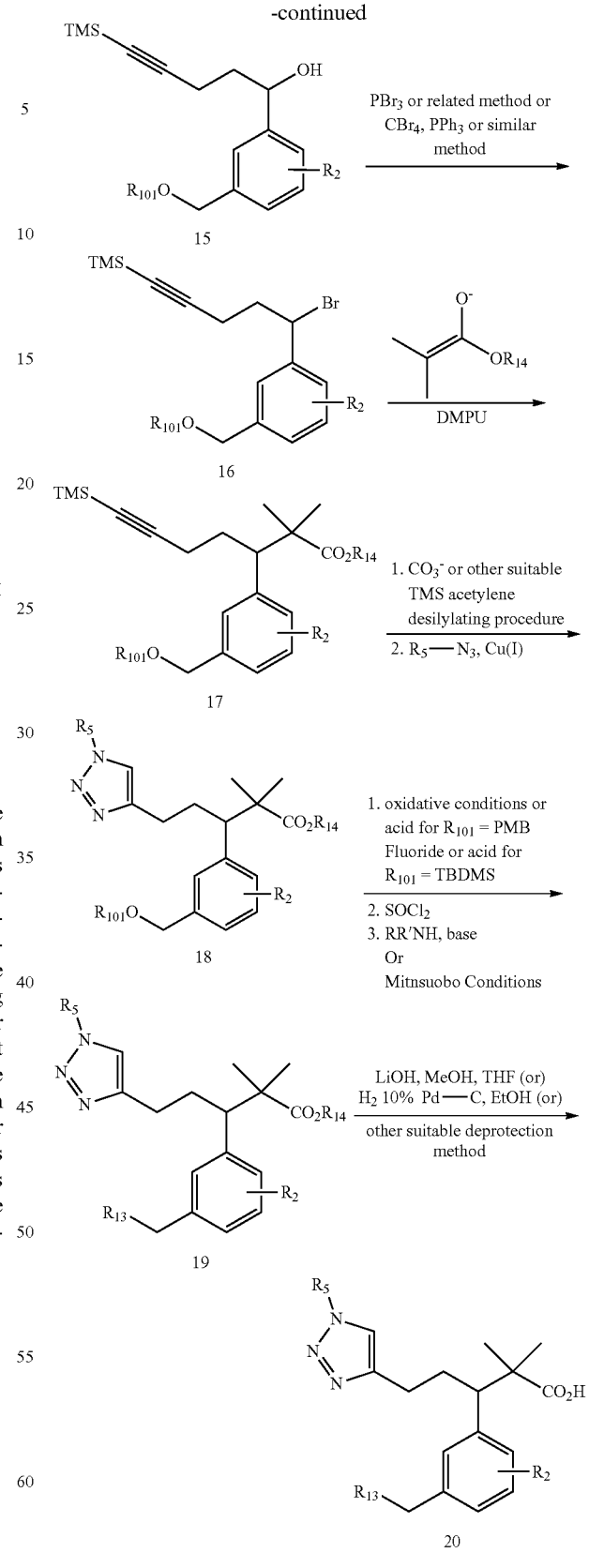

In Scheme 29, $R_2$, $R_5$ and $R_{13}$ are as previously defined. $R_{101}$ is a protecting group linked to an oxygen; for example dimethy-tert-butyl-silyl or para-methoxy benzyl. Similar to the ester hydrolysis there may be a steric influence on the addition of a second alkylating agent to the ester and an alternative route could be achieved as depicted in Scheme 29. By this method the aryl halide exemplified by 13 is metallated by halogen metal exchange with a suitable organometallic such as alkyl lithium or alkyl magnesium. Alternatively, the use of lithium trialkyl magnesium ate complexes (for example i-PrBu$_2$MgLi) have been effective for halogen metal exchange for some substrates. Additionally certain Grignard reagents complexed with one equivalent of LiCl have been identified by some as so-called "turbogrignard reagents" for their useful reactivity in halogen-metal exchange reactions as well as compatibility in these reactions with functional groups having reactivity towards organolithium reagents. These "turbogrignard" reagents might also be useful for the halogen metal exchange in certain cases. Some of these reagents, such as i-PrMgCl·LiCl are commercially available. Upon generation of the aryl metal reagent the addition of acetylenic aldehyde 14 will afford the secondary benzylic alcohol 15. Conversion of the alcohol to the benzylic bromide 16 as might then be mildly achieved with CBr$_4$ and triphenyl phosphine as well as other methods such as PBr$_3$ to afford a somewhat reactive electrophillic substrate. Reaction of 16 with enolates such as that derived from iso-butyates as depicted in the Scheme 29 affords the sterically hindered esters 17. The use of an additive such as 1,3-Dimethyl-3,4,5,6-tetrahydro-2(1H)-pyrimidinone (DMPU) may improve the effectiveness of this reaction. The resulting dialkylated ester 17 containing the TMS protected acetylene can be de-silylated with aqueous carbonate and subjected to click reaction as described above to afford the triazoles such as 18 followed by removal of the hydroxyl protecting group and then activation of the benzylic alcohol to a benzylic chloride and subsequent displacement of the chloride with a suitable electrophile such as a secondary amine or a sulfonamide to afford 19. Alternatively the benzylic alcohol may also be displaced by a suitably acidic nucleophile such as a sulfonamide to afford 19 under Mitsunobu conditions. The ester in 19 is then removed by methods which are suitable for ester cleavage of a highly sterically hindered ester such as 19, affording the carboxylic acid product 20. Furthermore, in some cases it may be advantageous to prepare the α-carboxy monoalkylated compounds by this same route replacing the butyrate with a propionate. One possible advantage of doing this is that by using an appropriately chosen chiral auxillary to replace the ester it may be possible to effect diastereoselective additions to the bromide allowing for synthesis of the preferred stereoisomers.

Scheme 30

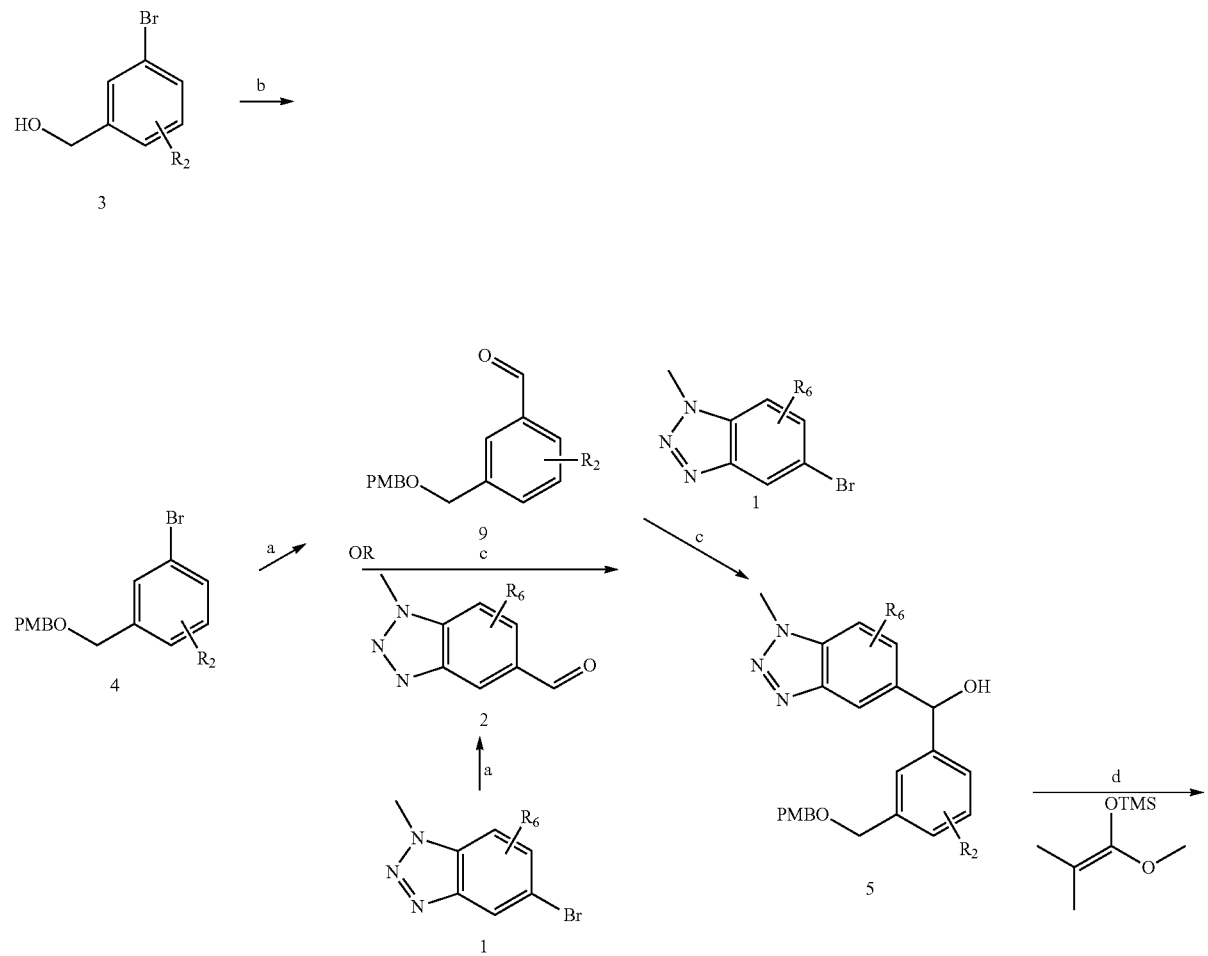

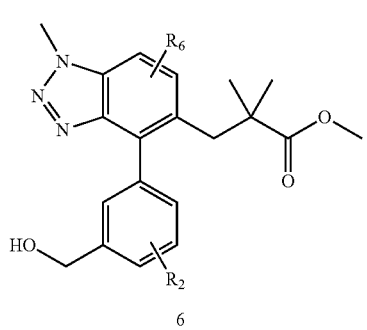 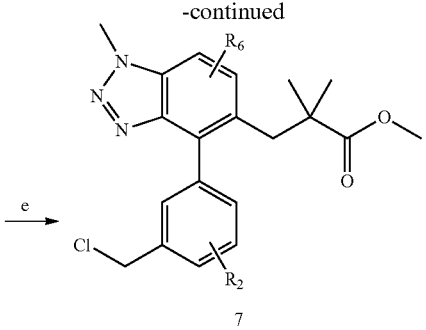 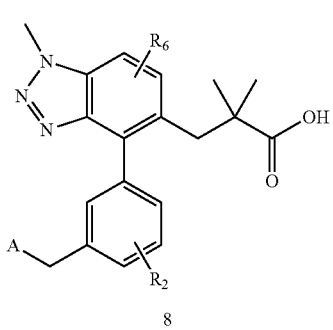

Conditions:
a) n-BuLi, DMF, THF
b) NaH, PMBCl, DMF
c) t-BuLi or n-BuLi, THF
d) TiCl$_4$, DCM (or)
(i) DBU, Cl$_3$CCN, CH$_3$CN; ii) Tf$_2$NH, iii) DDQ, DCM/H$_2$O
e) SO$_2$Cl, DCM
f) R$_{13}$H, DIPEA, CH$_3$CN; (or) R$_{13}$H, NaH, DMF
g) LiOH, MeOH, THF.

Scheme 30 represents a general scheme for the preparation of compounds according to Formula (I). In Scheme 30, R$_2$, R$_6$ and A are as defined previously. Triazole 1 is either commercially available or may be synthesized from readily available materials. Reaction conditions are as described above in the scheme; however, the skilled artisan will appreciate that certain modifications in the reaction conditions and/or reagents used are possible.

Treatment of triazole 1 with n-butyl lithium and DMF in presence of a suitable solvent produces the desired aldehyde product 2. The coupling partner for aldehyde 2 is obtained by first protecting the benzylic alcohol 3 as its para-methoxybenzylether. It will be appreciated that alternative protecting groups are possible. Coupling of the aldehyde 2 and bromide 4 can be accomplished via treatment of the bromide first with t-butyl lithium or n-butyl lithium followed by addition of the aldehyde. However, the skilled artisan will appreciate that other aldehydes, such as substituted phenyl aldehyde may also be applied.

Intermediate alcohol 6, arises from treatment of alcohol 5 with the appropriate silylketene acetal in the presence of a Lewis acid or via one-pot brønsted base/brønsted acid system, followed by deprotection with DDQ. Benzylic alcohol 6 can be transformed to the requisite chloride 7 using thionyl chloride. Completion of the synthesis can be accomplished by deplacement of chloride, following by hydrolysis of the ester to produce 8

It will be also be appreciated by the skilled artisan that intermediate 5 may be prepared by coupling bromide 1 with aldehyde 9.

Scheme 31

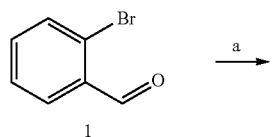

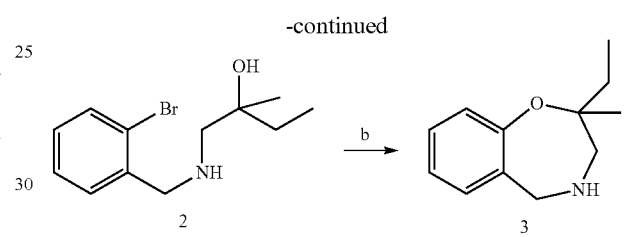

Conditions:
a) 1-amino-2-methylbutan-2-ol, NaBH$_4$, NaOH, MeOH;
b) Cs$_2$CO$_3$, CuI, isopropanol Scheme 31 represents a general scheme for the preparation of 2-ethyl-2-methyl-2,3,4,5-tetrahydrobenzo[f][1,4]oxazepine used in the invention. In Scheme 31, substituted 2-bromobenzaldehyde depicted as starting material is commercially available. Reaction conditions are as described above in the scheme; however, the skilled artisan will appreciate that certain modifications in the reaction conditions and/or reagents used are possible.

Reductive amination of aldehyde 1 with the appropriate aminoalcohol followed by alkylation reaction provides the required intermediate 3.

Scheme 32

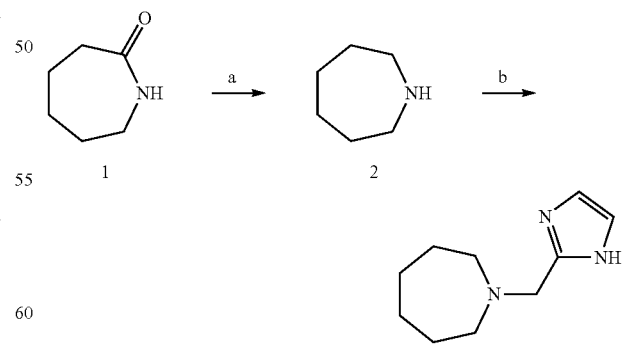

Conditions:
a) LiAlH$_4$, THF;
b) 1H-imidazole-2-carbaldehyde, acetic acid, NaBH(OAc)$_3$, DCE Scheme 32 represents a general scheme for the preparation of 1-((1H-imidazol-2-yl)methyl)azepane used in the invention. Substituted 1-azepan-2-one depicted as starting material is commercially available. Reaction conditions are as described above in the scheme; however, the skilled artisan will appreciate that certain modifications in the reaction conditions and/or reagents used are possible.

Reducing the amide with the appropriate reducing reagent followed by a reductive amination reaction provides the required intermediate 3.

Scheme 33

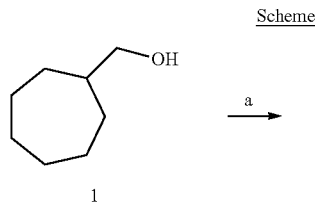

Conditions:
a) TFA, DCM;
b) IH-imidazole-2-carbaldehyde, titanium(IV) isopropoxide, NaCNBH₃, ethanol Scheme 33 represents a general scheme for the preparation of 1-((1H-imidazol-2-yl)methyl)-4-ethylpiperidine used in the invention. Substituted 1-tert-butyl 4-ethylpiperidine-1-carboxylate depicted as starting material is commercially available. Reaction conditions are as described above in the scheme; however, the skilled artisan will appreciate that certain modifications in the reaction conditions and/or reagents used are possible.

Deprotection under acidic conditions followed by a reductive amination reaction provides the required intermediate 3.

Scheme 34

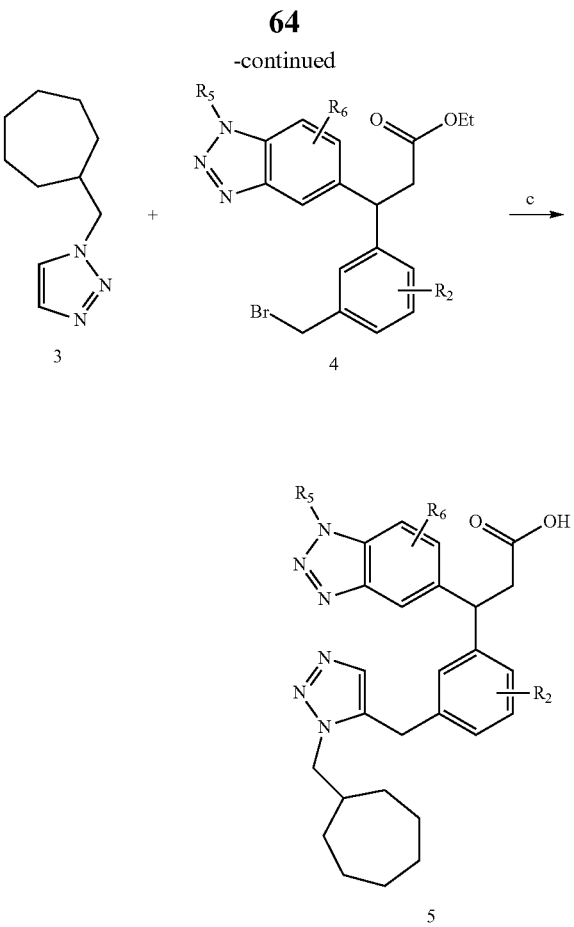

Conditions:
a) Et₃N, TsCl, DCM;
b) 1H-1,2,3-triazole, Cs₂CO₃, DMF;
c) (i) n-butyllithium, THF, -78° C.; (ii) LiOH, ethylene glycol, THF/H₂O Scheme 34 represents a general scheme for the preparation of compounds according to Formula (I). In Scheme 34, R₂, R₅ and R₆ are as defined previously. The cycloheptylmethanol 1 depicted as starting material is commercially available. Reaction conditions are as described above in the scheme; however, the skilled artisan will appreciate that certain modifications in the reaction conditions and/or reagents used are possible.

Commercially available cycloheptylmethanol 1 is treated with TsCl in the presence of Et₃N in DCM to afford intermediate 2 followed by reductive amination reaction provides the required intermediate 3. Completion of the synthesis is accomplished via reaction with 4 under basic conditions followed by hydrolysis with LiOH in a suitable solvent to produce 5.

Scheme 35

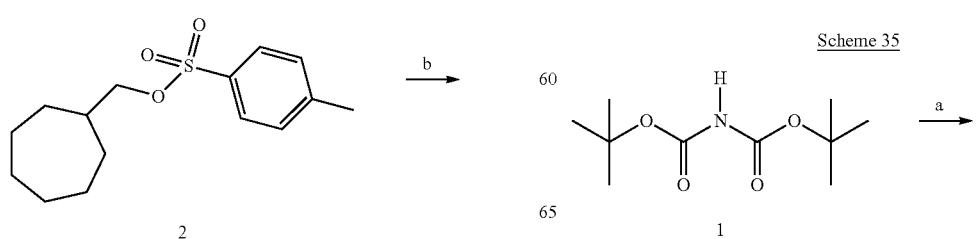

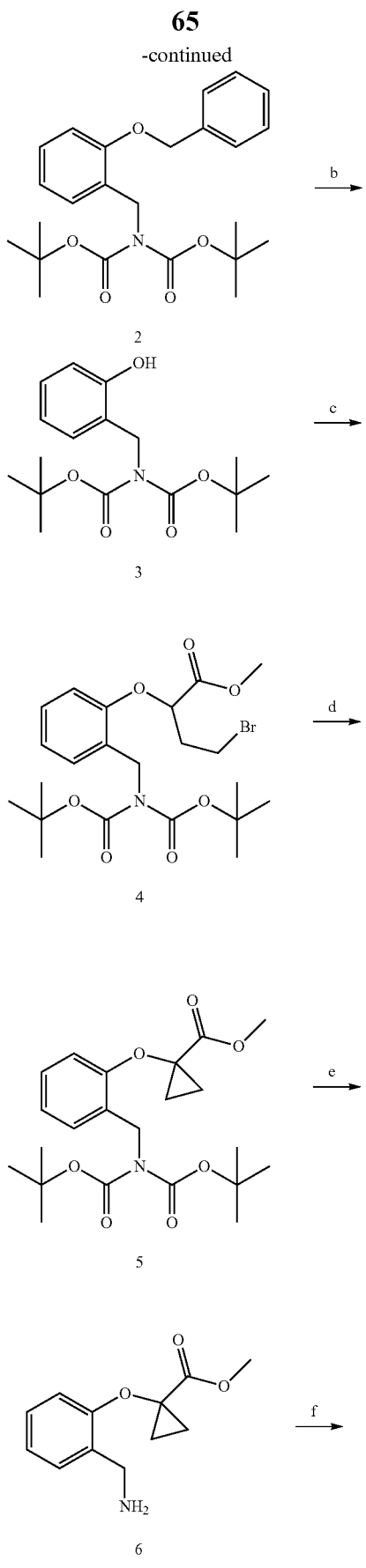

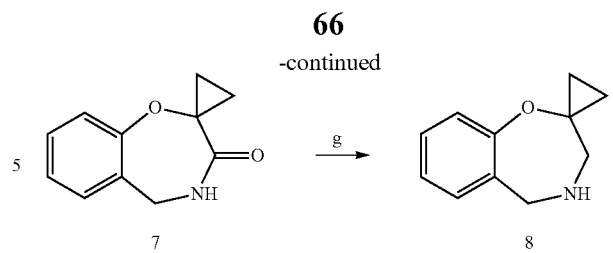

Conditions:
a) 1-(benzyloxy)-2-(chloromethyl)benzene, Cs₂CO₃, NaI, DMF;
b) Pd/C, H₂, MeOH/THF;
c) 2,4-dibromobutanoate, Cs₂CO₃, CH3CN;
d) potassium tert-butoxide, THF;
(e) HCl;
(f) DIPEA, 1,4-dioxane;
(g) LAH, THF Scheme 35 represents a general scheme for the preparation of 4,5-dihydro-3H-spiro[benzo[f][1,4]oxazepine-2,1'-cyclopropane] used in the invention. In this, the (bis-tert-butoxycarbonyl)amine depicted as starting material are commercially available. Reaction conditions are as described above in the scheme; however, the skilled artisan will appreciate that certain modifications in the reaction conditions and/or reagents used are possible.

Reaction of starting (bis-tert-butoxycarbonyl)amine with 1-(benzyloxy)-2-(chloromethyl)benzene provides intermediate 2. Deprotection of the phenol by hydrogenation, followed by reacting with 2,4-dibromobutanoate under basic conditions to yield intermediate 4. Treatment of intermediate 4 with potassium tert-butoxide is to yield intermediate 5. Deprotection under acidic conditions followed by cyclolization and reduction with LAH provides desired intermediate 8.

Scheme 36

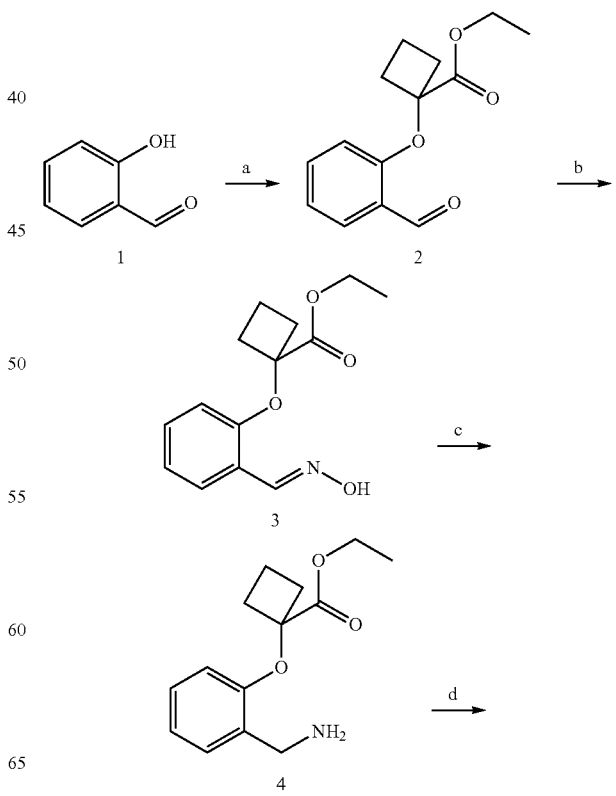

67

-continued

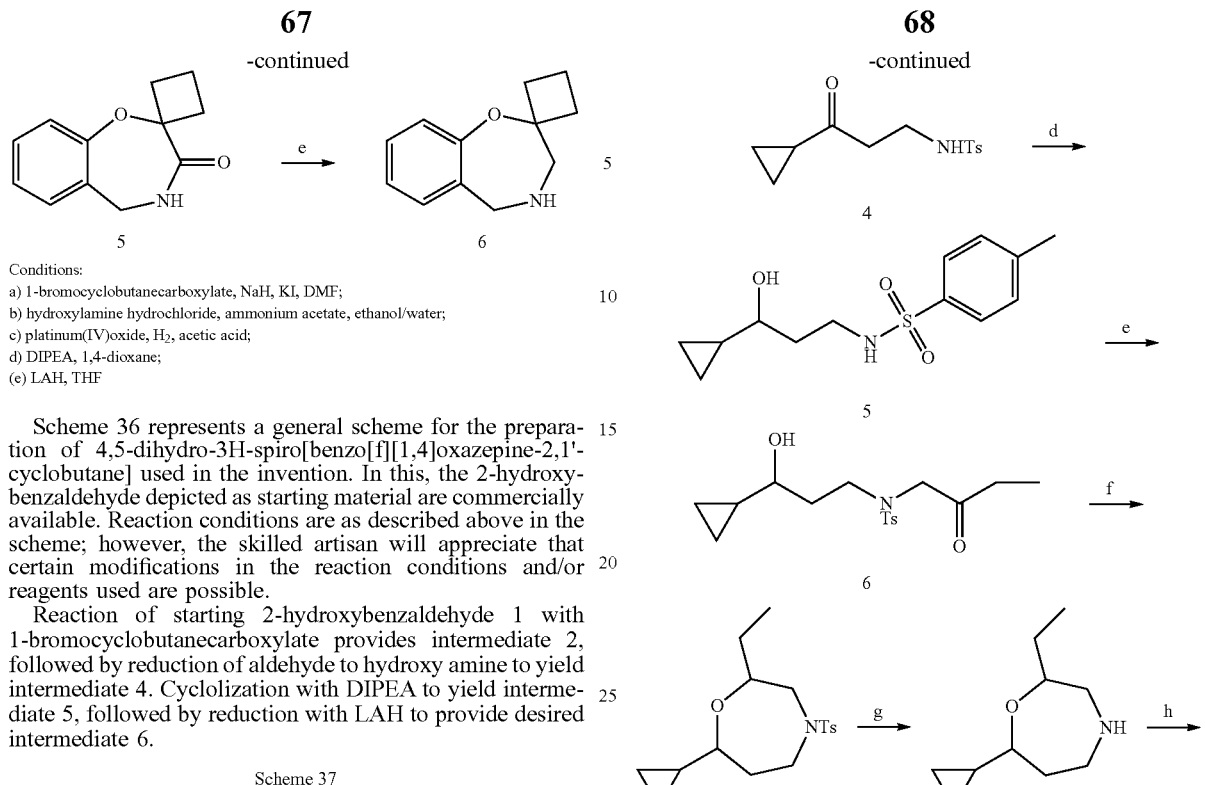

Conditions:
a) 1-bromocyclobutanecarboxylate, NaH, KI, DMF;
b) hydroxylamine hydrochloride, ammonium acetate, ethanol/water;
c) platinum(IV)oxide, H$_2$, acetic acid;
d) DIPEA, 1,4-dioxane;
e) LAH, THF Scheme 36 represents a general scheme for the preparation of 4,5-dihydro-3H-spiro[benzo[f][1,4]oxazepine-2,1'-cyclobutane] used in the invention. In this, the 2-hydroxybenzaldehyde depicted as starting material are commercially available. Reaction conditions are as described above in the scheme; however, the skilled artisan will appreciate that certain modifications in the reaction conditions and/or reagents used are possible.

Reaction of starting 2-hydroxybenzaldehyde 1 with 1-bromocyclobutanecarboxylate provides intermediate 2, followed by reduction of aldehyde to hydroxy amine to yield intermediate 4. Cyclolization with DIPEA to yield intermediate 5, followed by reduction with LAH to provide desired intermediate 6.

Scheme 37

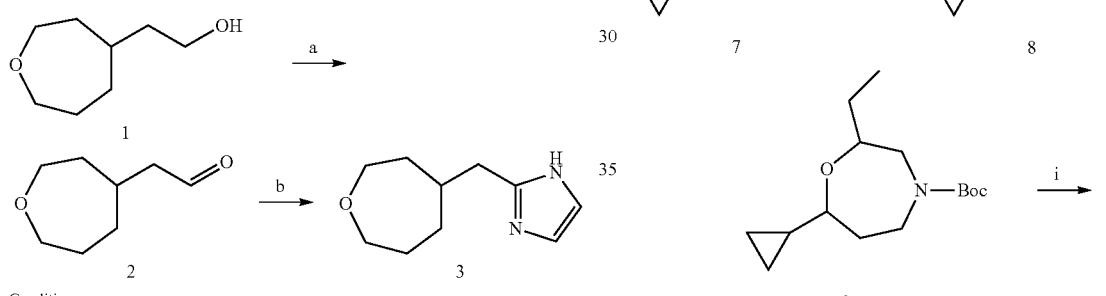

Conditions:
a) PCC, DCM;
b) oxalaldehyde, ammonia hydrate, methanol/water;

Scheme 37 represents a general scheme for the preparation of 2-(oxepan-4-ylmethyl)-1H-imidazole used in the invention. In this, the 2-(oxepan-4-yl)ethanol depicted as starting material are commercially available. Reaction conditions are as described above in the scheme; however, the skilled artisan will appreciate that certain modifications in the reaction conditions and/or reagents used are possible.

The commercially available 2-(oxepan-4-yl)ethanol 1 is treated with PCC in DCM to produce aldehyde 2, which can be reacted with oxalaldehyde, and ammonia hydrate to produce intermediate 3.

Scheme 38

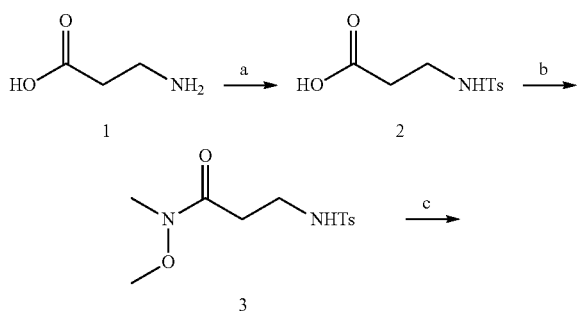

68

-continued

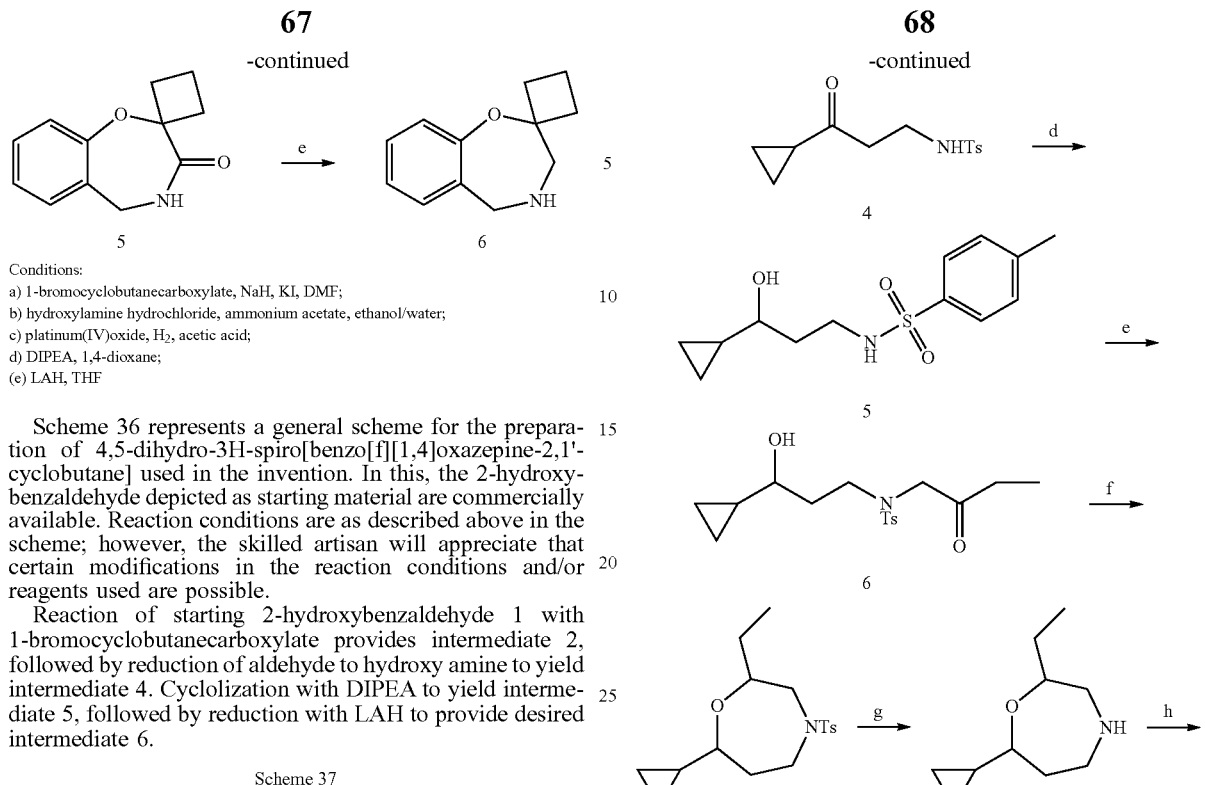

Conditions:
a) TsCl, NaH, water;
b) N,O-dimethylhydroxylamine, 1H-benzo[d][1,2,3]triazol-4-ol, N-ethyl-N-isopropylpropan-2-amine, N1-((ethylimino)methylene)-N3,N3-dimethylpropane-1,3-diamine, ammonia hydrate, DCM;
c) cyclopropylmagnesium bromide, THF;
d) NaBH$_4$, methanol;
e) 1-bromobutan-2-one, K$_2$CO$_3$, acetone;
f) triethylsilane, trimethylsilyl trifluoromethanesulfone, DCM;
g) sodium, naphthalene, DME;
h) di-tert-butyl dicarbonate, water;
i) HCl, ether Scheme 38 represents a general scheme for the preparation of 7-cyclopropyl-2-ethyl-1,4-oxazepane used in the invention. In this, the 3-aminopropanoic acid depicted as starting material is commercially available. Reaction conditions are as described above in the scheme; however, the skilled artisan will appreciate that certain modifications in the reaction conditions and/or reagents used are possible.

Protection of 3-aminopropanoic acid 1 with TsCl is followed by forming N-Methoxy-N-methyl intermediate 3. Then it is treated with cyclopropylmagnesium bromide to provide intermediate 4, followed by reduction with NaBH$_4$ to yield alcohol 5. Intermediate 5 is treated with 1-bromobutan-2-one under basic condition to yield intermediate 6, followed by cyclolization and depretection to yield intermediate 8. After, it is protected with BOC, followed by depretection to yield intermediate 10.

Scheme 39

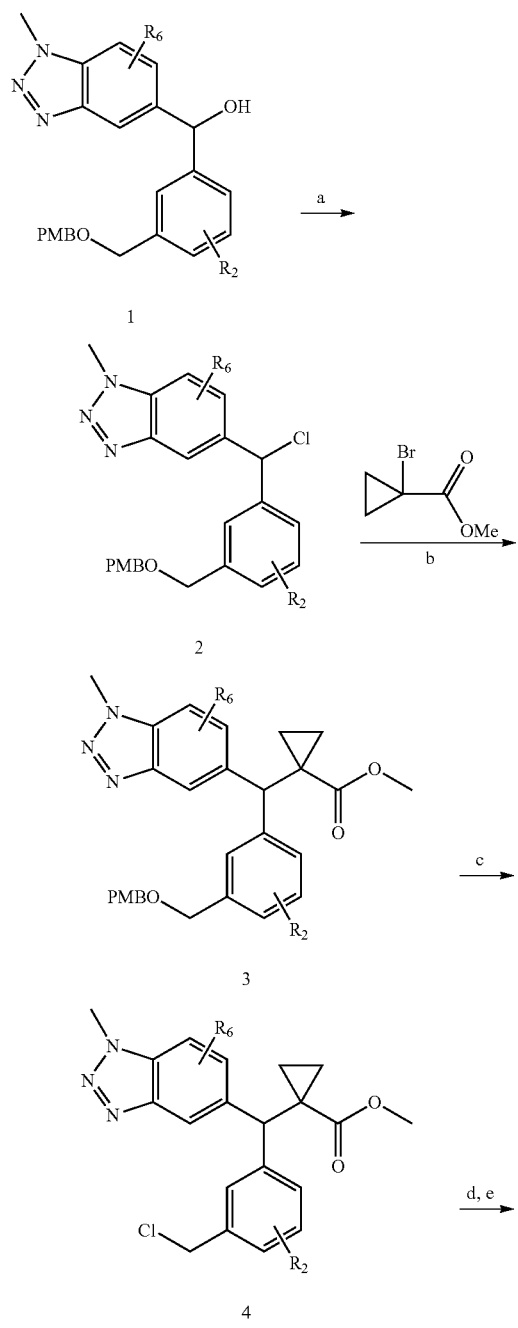

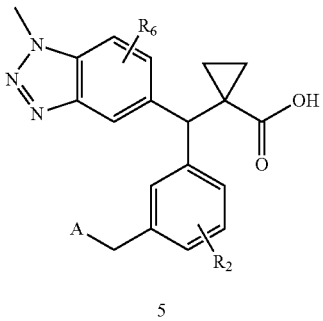

5

Conditions:
a) SO$_2$Cl, DCM
b) Zn, TMSCl, THF
c) 1, DDQ, DCM, 0° C.; 2. SO$_2$Cl, DCM
d) R$_{13}$H, DIPEA, CH$_3$CN; (or) R$_{13}$H, NaH, DMF
e) LiOH, MeOH, THF.

Scheme 39 represents a general scheme for the preparation of compounds according to Formula (I). In Scheme 39, R$_2$, R$_6$, R$_{13}$, and A are as defined previously.

Alcohol 1 is synthesized according to scheme 30. Reaction conditions are as described above in the scheme; however, the skilled artisan will appreciate that certain modifications in the reaction conditions and/or reagents used are possible.

Treatment of alcohol 1 with thionyl chloride in DCM gives the chloride intermediate 2. Reformatsky reaction with Zn yields the ester 3. Deprotection of PMB group with DDQ followed by treatment with thionyl chloride produces intermediate 4. Completion of the synthesis can be accomplished by displacement of the chloride, following by hydrolysis of the ester to produce 5

Scheme 40

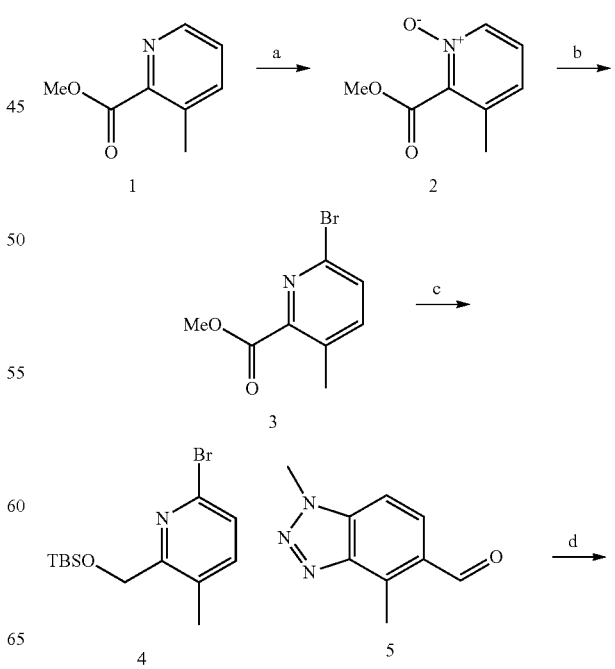

-continued

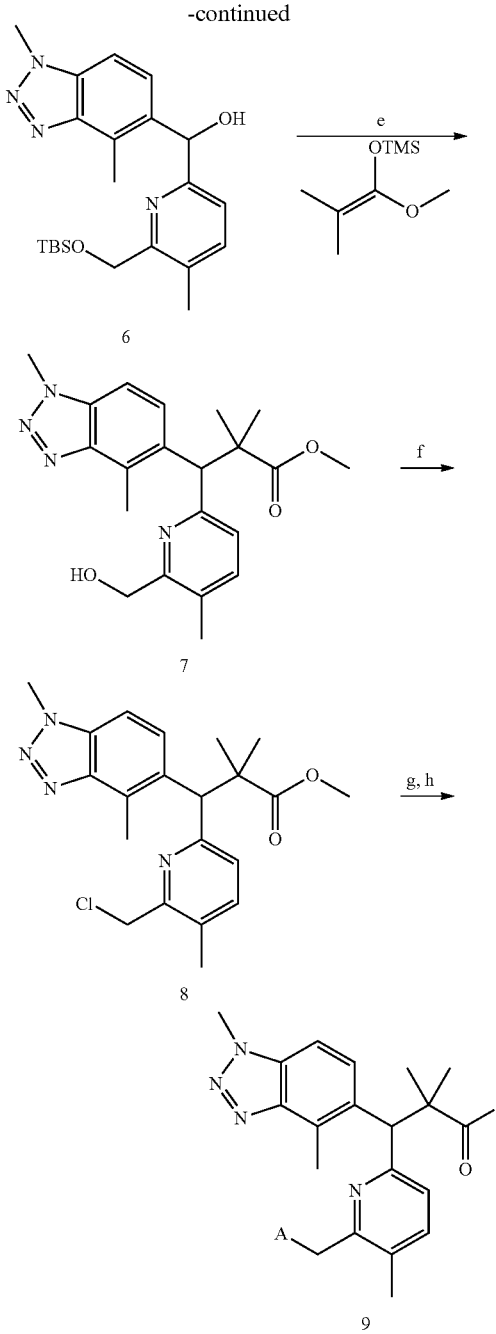

Conditions:
a) m-CPBA, DCM, 0 °C.
b) POBr₃, 84° C.
c) 1, LAH, THF, -45° C.; 2. Imidazole, TBSCl, DCM;
d) nBuLi, diethyl ether, -78° C.;
e) i) DBU, Cl₃CCN, CH₃CN; ii) Tf₂NH, iii) TBAF, THF, 0° C.;
e) SO₂Cl, DCM;
f) R₁₃H, DIPEA, CH₃CN; (or) R₁₃H, NaH, DMF;
g) LiOH, MeOH, THF.

Scheme 40 represents a general scheme for the preparation of compounds according to Formula (I). In Scheme 40, $R_{13}$ and A are as defined previously. Methyl 3-methylpicolinate 1 is commercially available. Reaction conditions are as described above in the scheme; however, the skilled artisan will appreciate that certain modifications in the reaction conditions and/or reagents used are possible.

Treatment of Methyl 3-methylpicolinate 1 with m-CPBA in DCM produces the desired pyridine oxide 2. Bromination of 2 with phosphoryl tribromide produces intermediate bromide 3. Reduction of 3 with LAH, followed by protection of the alcohol as the TBS ether yields intermediate 4. Coupling of the aldehyde 5 and bromide 4 can be accomplished via treatment of the bromide first with n-butyl lithium followed by addition of the aldehyde.

Intermediate benzyl alcohol 7, arises from treatment of alcohol 6 with the appropriate silylketene acetal in the presence of a Lewis acid or via one-pot Brønsted base/Brønsted acid system, followed by deprotection with TBAF. Benzylic alcohol 7 can be transformed to the requisite chloride 8 using thionyl chloride. Completion of the synthesis can be accomplished by displacement of the chloride, followed by hydrolysis of the ester to produce 9.

Scheme 41

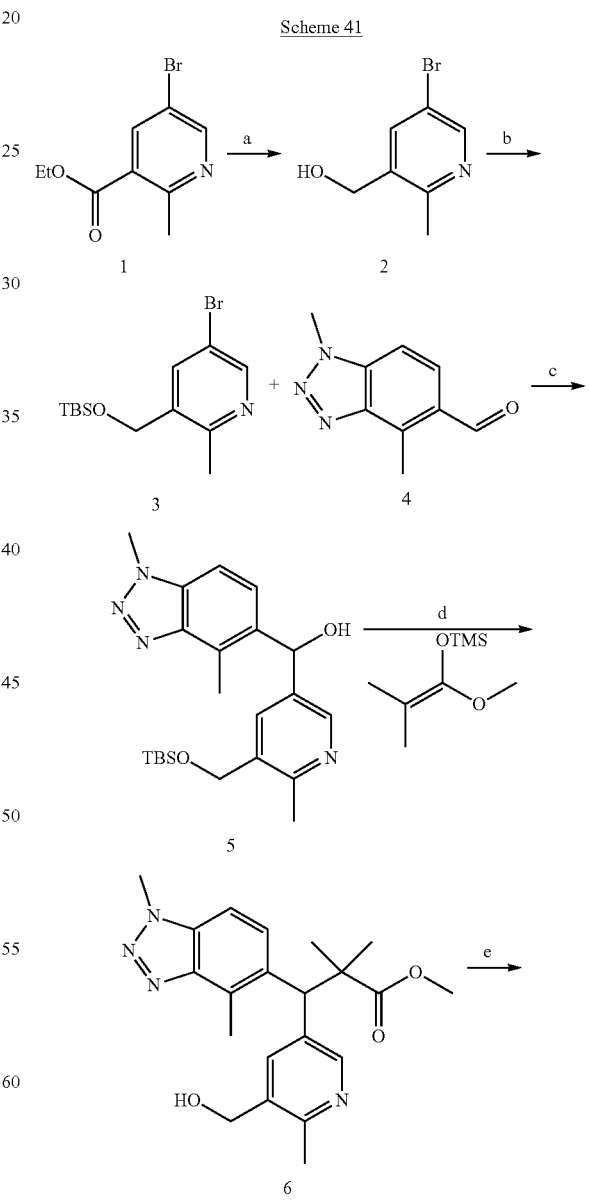

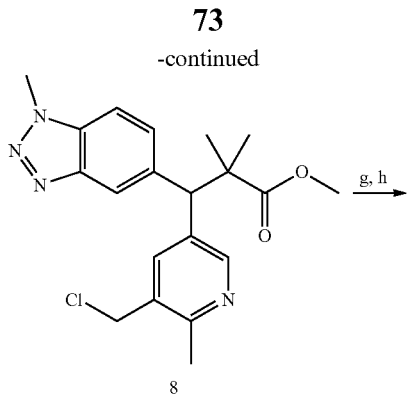

8

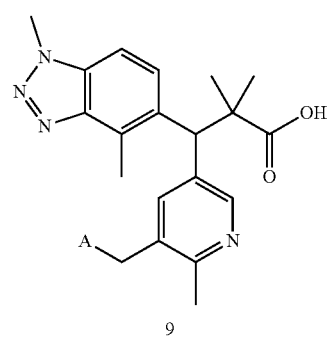

9

Conditions: a) LAH, THF, 0° C.; b) Imidazole, TBSCl, DCM; c) nBuLi, diethyl ether, -78° C.; e) i) DBU, Cl₃CCN, CH₃CN; ii) Tf₂NH, iii) TBAF, THF, 0° C.; e) SO₂Cl, DCM; f) R₁₃H, DIPEA, CH₃CN; (or) R₁₃H, NaH, DMF; g) LiOH, MeOH, THF.

Scheme 41 represents a general scheme for the preparation of compounds according to Formula (I). Ethyl 5-bromo-2-methylnicotinate 1 is commercially available. In Scheme 41, R₁₃ and A are as defined previously. Reaction conditions are as described above in the scheme; however, the skilled artisan will appreciate that certain modifications in the reaction conditions and/or reagents used are possible.

Reduction of ethyl 5-bromo-2-methylnicotinate 1 accomplished with LAH. The resulting alcohol was protected as the TBS ether to yield intermediate 3. Coupling of the aldehyde 4 and bromide 3 can be accomplished via treatment of the bromide first with n-butyl lithium followed by addition of the aldehyde. Intermediate benzyl alcohol 6, arises from treatment of alcohol 5 with the appropriate silylketene acetal in the presence of a Lewis acid or via one-pot Brønsted base/Brønsted acid system, followed by deprotection with TBAF. Benzylic alcohol 6 can be transformed to the requisite chloride 7 using thionyl chloride. Completion of the synthesis can be accomplished by displacement of the chloride, followed by hydrolysis of the ester to produce 8

Scheme 42

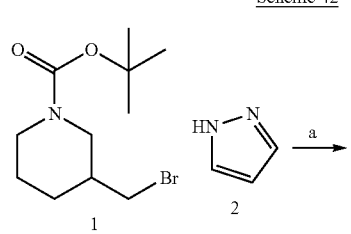

1  2

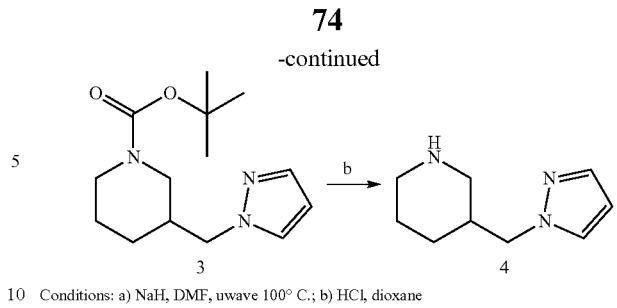

3  4

Conditions: a) NaH, DMF, uwave 100° C.; b) HCl, dioxane

Scheme 42 represents a general scheme for the preparation of 3-((1H-Pyrazol-1-yl)methyl)piperidine 4 used in the invention. Tert-Butyl 3-(bromomethyl)piperidine-1-carboxylate 1 is commercially available. Reaction conditions are as described above in the scheme; however, the skilled artisan will appreciate that certain modifications in the reaction conditions and/or reagents used are possible.

Starting with the bromide 1, displacement of the bromide with pyrazole 2 in the presence of NaH gives Boc protected intermediate 3. Removal of the Boc group under acidic conditions yields product 4.

Scheme 43

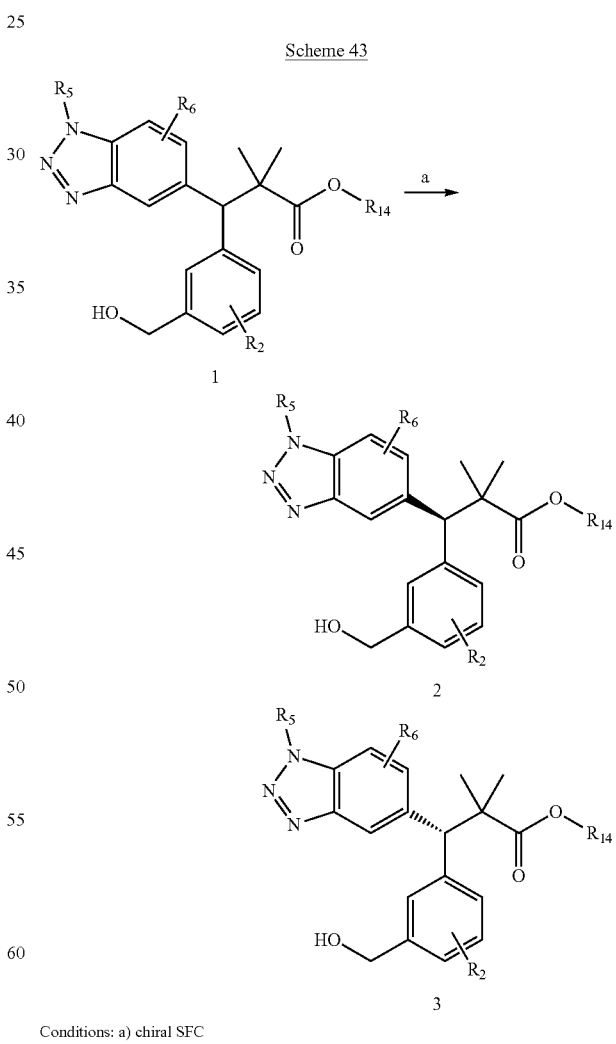

Conditions: a) chiral SFC

Scheme 43 represents a general scheme for the preparation of compounds according to Formula (I). In Scheme 43, $R_2$, $R_5$, $R_6$, and $R_{14}$ are as defined previously. Ester 1 is synthesized according to Scheme 30. Reaction conditions are as described above in the scheme; however, the skilled artisan will appreciate that certain modifications in the reaction conditions and/or reagents used are possible.

Ester 1 was separated by Chiral SFC to give a single enantiomerically pure product 2 and a single enantiomerically pure product 3.

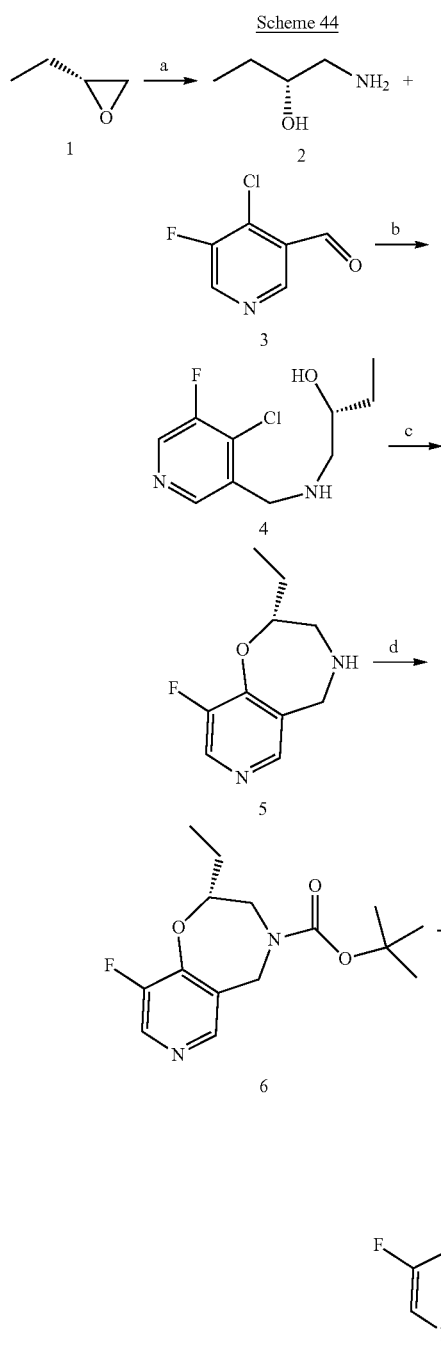

Conditions: a) NH$_4$OH; b) NaBH$_4$, NaOH, MeOH c) KO$_t$Bu, DMSO, 90° C.; d) Boc anhydride, Et$_3$N, THF; d) HCl, dioxane Scheme 44 represents a general scheme for the preparation of (R)-2-Ethyl-9-fluoro-2,3,4,5-tetrahydropyrido[3,4-f] [1,4]oxazepine, hydrochloride used in the invention. The 4-chloro-5-fluoronicotinaldehyde as starting material is commercially available. Reaction conditions are as described above in the scheme; however, the skilled artisan will appreciate that certain modifications in the reaction conditions and/or reagents used are possible.

Commercially available (R)-2-ethyloxirane 1 was opened with ammonium hydroxide to obtain (R)-1-aminobutan-2-ol 2. Reductive amination of the commercially available aldehyde 3 with (R)-1-aminobutan-2-ol 2 followed by displacement of the chloride provides the required intermediate 5. This was then protected as the Boc carbamate to facilitate purification. It will be appreciated by the skilled artisan that alternative protecting groups may be used. Deprotection yields the requisite amine 7.

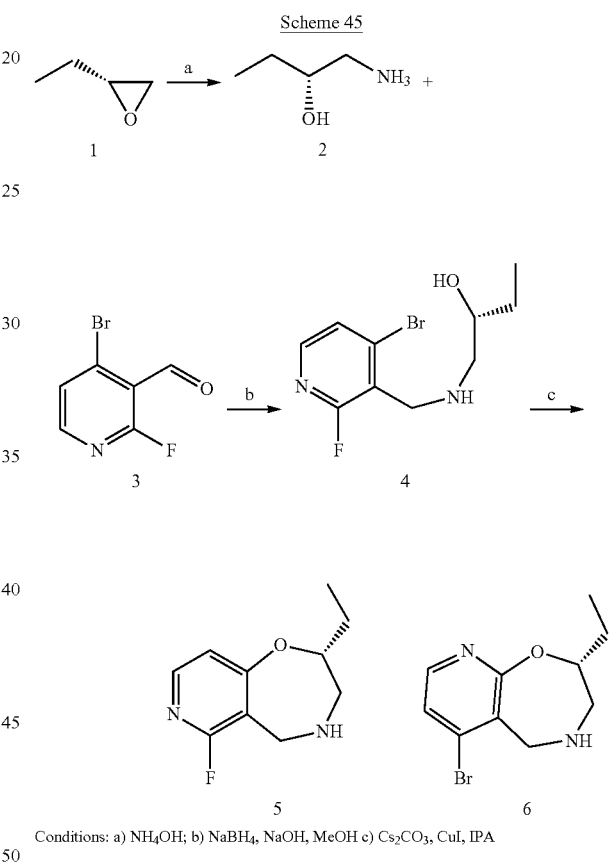

Conditions: a) NH$_4$OH; b) NaBH$_4$, NaOH, MeOH c) Cs$_2$CO$_3$, CuI, IPA

Scheme 45 represents a general scheme for the preparation of (R)-2-Ethyl-6-fluoro-2,3,4,5-tetrahydropyrido[3,4-f] [1,4]oxazepine and (R)-6-Bromo-2-ethyl-2,3,4,5-tetrahydropyrido[3,2-f][1,4]oxazepine used in the invention. The 4-bromo-2-fluoronicotinaldehyde as starting material is commercially available. Reaction conditions are as described above in the scheme; however, the skilled artisan will appreciate that certain modifications in the reaction conditions and/or reagents used are possible.

Commercially available (R)-2-ethyloxirane 1 was opened with ammonium hydroxide to obtain enantiomerically pure (R)-1-aminobutan-2-ol 2. Reductive amination of the commercially available aldehyde 3 with (R)-1-aminobutan-2-ol 2 followed by displacement of the halogen gives amine 5 and amine 6.

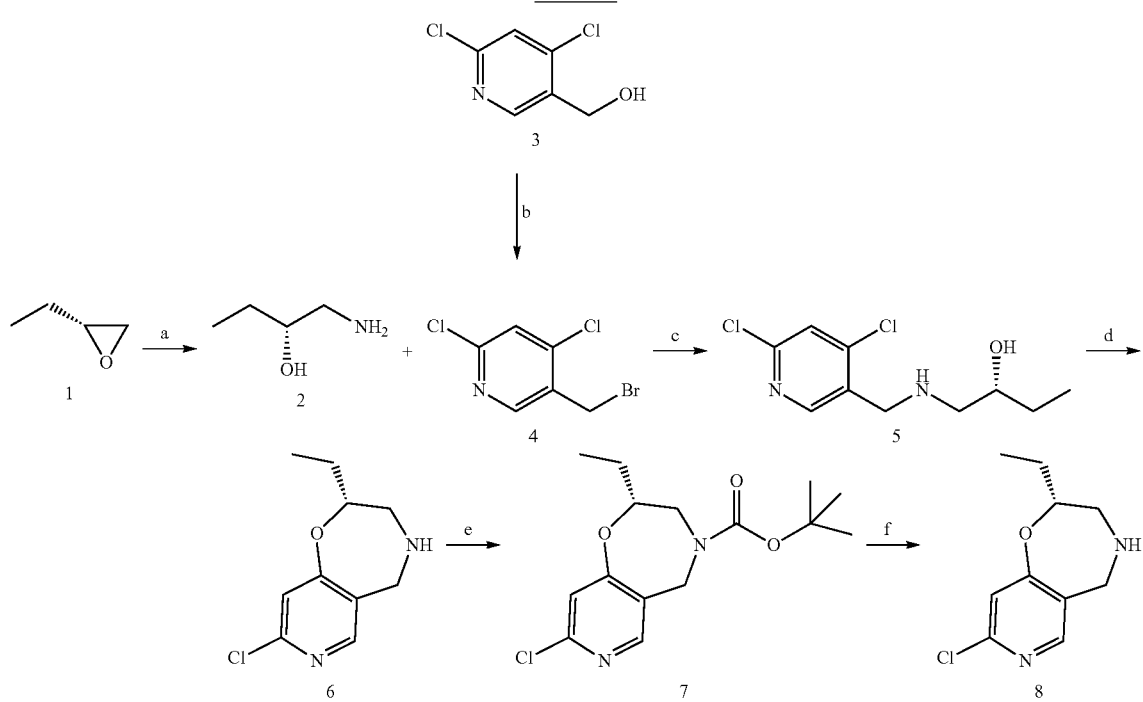

Conditions: a) NH₄OH; b) PBr₃, DCM; c) Et₃N, DCM c) KO_tBu, DMSO, 65° C.: d) Boc anhydride, Et₃N, THF; d) HCl, dioxane Scheme 46 represents a general scheme for the preparation of (R)-8-Chloro-2-ethyl-2,3,4,5-tetrahydropyrido[3,4-f][1,4]oxazepine hydrochloride used in the invention. The (4,6-dichloropyridin-3-yl)methanol as starting material is commercially available. Reaction conditions are as described above in the scheme; however, the skilled artisan will appreciate that certain modifications in the reaction conditions and/or reagents used are possible.

Commercially available (R)-2-ethyloxirane 1 was opened with ammonium hydroxide to obtain (R)-1-aminobutan-2-ol 2. Bromination of alcohol 3 with PBr₃ in DCM produces intermediate 4. Alkylation of 4 with (R)-1-aminobutan-2-ol 2 followed by displacement of the chloride provides the required intermediate 6. This was then protected as the Boc carbamate to facilitate purification. It will be appreciated by the skilled artisan that alternative protecting groups may be used. Deprotection yields the requisite amine 8.

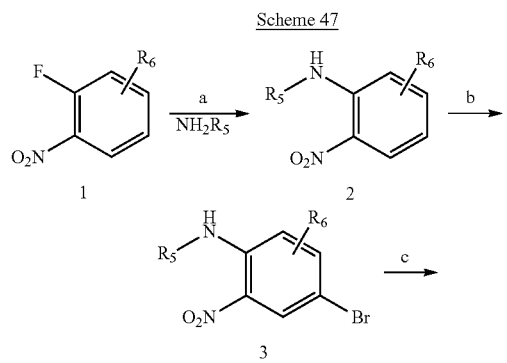

Scheme 47

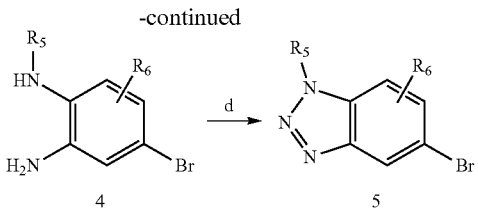

Conditions: a) EtOH; b) NBS, DMF; c) Raney nickel in water, hydrazine hydrate, DCE, EtOH, 0° C. d) NaNO₂, H₂SO₄, H₂O, 0° C.

Scheme 47 represents a general scheme for the preparation of triazole 5 used in the invention. In Scheme xx, R₅ and R₆ are defined previously. Substituted 1-fluoro-2-nitrobenzene depicted as starting material is commercially available. Reaction conditions are as described above in the scheme; however, the skilled artisan will appreciate that certain modifications in the reaction conditions and/or reagents used are possible.

Starting with commercially available substituted 1-fluoro-2-nitrobenzene 1, displacement of the fluoride using an appropriate amine followed by bromination with NBS provides intermediate 3. Reduction of the nitro using Raney nickel in water provides the aniline 4. Diazotization and cyclization provides the required triazole 5. Completion of the fully elaborated analog can be accomplished in a fashion analogous to that shown in scheme 23.

Scheme 48

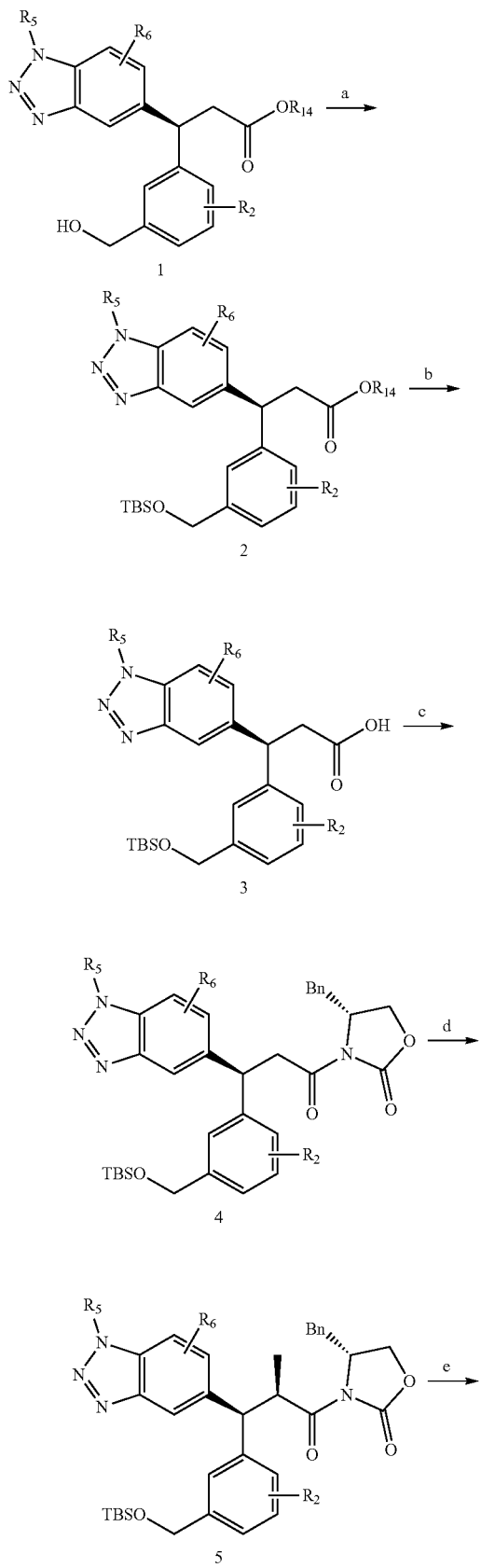

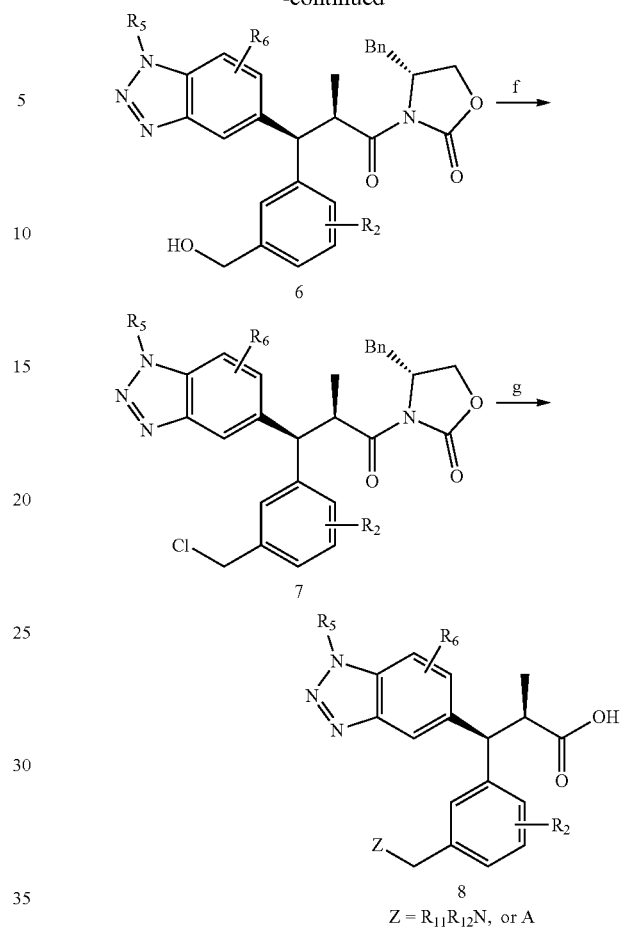

Conditions: a) TBSCl, imidazole, DCM; b) NaOH, water (or) $H_2$ 10% Pd—C, $Et_3N$, EtOAc; c) CDI, DBU, (R)-4-benzyloxazolidin-2-one, THF, MeCN; d) NaHMDS, MeI, THF; e) HCl, MeOH; f) $SOCl_2$, DCM g) (i) $R_{11}R_{12}NH$, TEA, MeCN; (or) A, NaH (ii) LiOH, $H_2O_2$, THF, $H_2O$ Scheme 48 represents a general scheme for the preparation of compounds according to Formula (I). In Scheme 48, $R_2$, $R_5$, $R_6$, $R_{14}$, A and Z are as defined previously. The starting material 1 can be synthesized from readily available materials. Reaction conditions are as described above in the scheme; however, the skilled artisan will appreciate that certain modifications in the reaction conditions and/or reagents used are possible.

Treatment of 1 with t-butyldimethylsilyl chloride and imidazole provides the silyl ether 2. Conversion of the ester to the acid can be accomplished either via hydrolysis under basic conditions such as NaOH and water with a suitable co-solvent or in the case where $R_{14}$ is a benzyl group via hydrogenation with 10% Pd—C to furnish acid 3. Treatment with carbonyl diimidazole in tetrahydrofuran followed by reaction with 1,8-Diazabicyclo[5.4.0]undec-7-ene and (R)-4-benzyloxazolidin-2-one provides 4. Enolate formation with sodium bis(trimethylsilyl)amide and stereoselective trapping with methyl iodide gives 5. Removal of the t-butyldimethylsilyl ether with HCl furnishes benzylic alcohol 6, which is converted to the requisite chloride with thionyl chloride. The synthesis can be completed as previously described via reaction with the appropriate amine followed by conversion of the ester to the acid 8.

Scheme 49

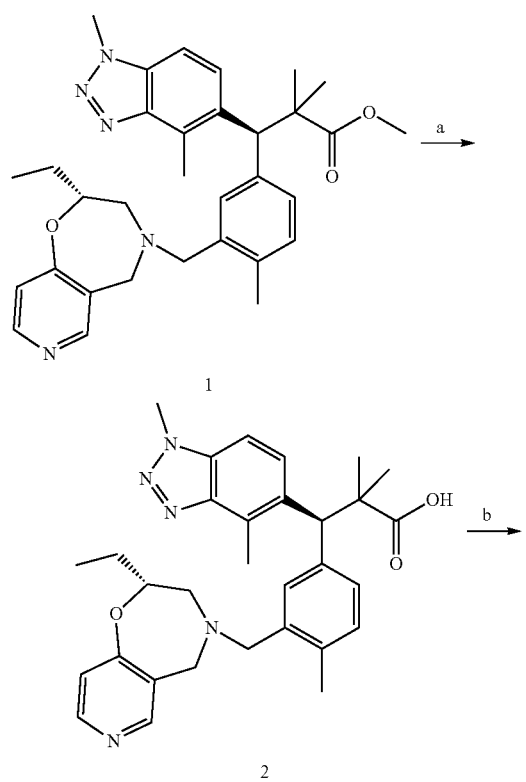

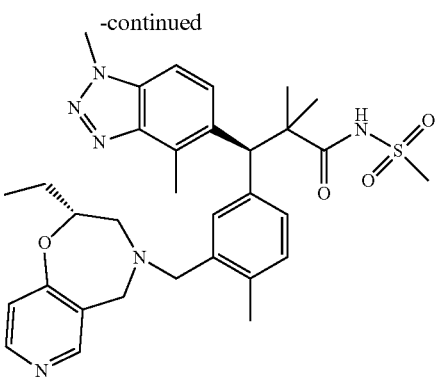

Conditions: a) LiOH, MeOH, H₂O; b) NH₂SO₂Me, EDC, DMAP, DIEA, DCM

Scheme 49 represents a general scheme for the preparation of acyl sulfonamide 3 used in the invention. The starting material 1 can be synthesized from readily available materials. Reaction conditions are as described above in the scheme; however, the skilled artisan will appreciate that certain modifications in the reaction conditions and/or reagents used are possible.

Conversion of the ester 1 to the acid 2 can be accomplished via hydrolysis under basic conditions such as LiOH and water with a suitable co-solvent. The synthesis can be completed by the coupling of acid 2 with methanesulfonamide in the presence of EDC and DMAP to give 3. It will be appreciated by the skilled artisan that alternative coupling reagents may be used.

Scheme 50

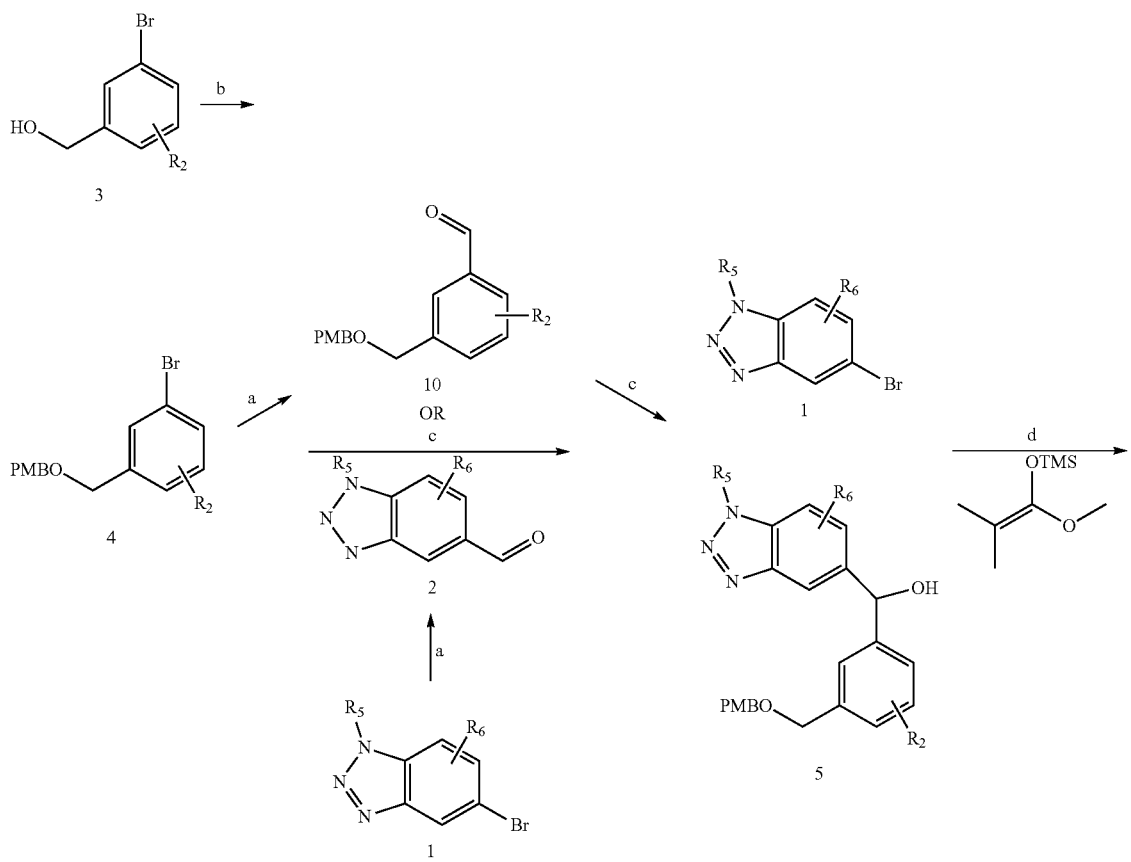

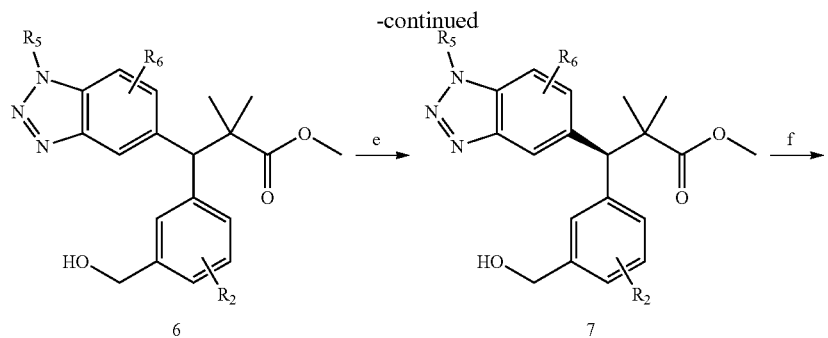

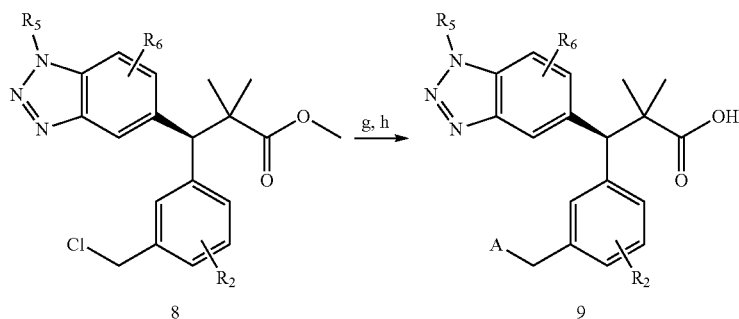

Conditions: a) n-BuLi, DMF, THF b) NaH, PMBCl, DMF c) t-BuLi, THF d) TiCl₄, DCM (or) (i) DBU, Cl₃CCN, CH₃CN; ii) Tf₂NH, iii) DDQ, DCM/H₂O e) Chiral SFC; f) SO₂Cl, DCM g) R₁₃H, DIPEA, CH₃CN; (or) R₁₃H, NaH, DMF h) LiOH, MeOH, THF.

Scheme 50 represents a general scheme for the preparation of compounds according to Formula (I). In Scheme 50, R₂, R₅, R₆ and A are as defined previously. Triazole 1 is either commercially available or may be synthesized from readily available materials. Reaction conditions are as described above in the scheme; however, the skilled artisan will appreciate that certain modifications in the reaction conditions and/or reagents used are possible.

Treatment of triazole 1 with n-butyl lithium and DMF in presence of a suitable solvent produces the desired aldehyde product 2. The coupling partner for aldehyde 2 is obtained by first protecting the benzylic alcohol 3 as its para-methoxybenzylether. It will be appreciated that alternative protecting groups are possible. Coupling of the aldehyde 2 and bromide 4 can be accomplished via treatment of the bromide first with t-butyl lithium or n-butyl lithium followed by addition of the aldehyde. However, the skilled artisan will appreciate that other aldehydes, such as substituted phenyl aldehyde may also be applied. Intermediate benzyl alcohol 6, arises from treatment of alcohol 5 with the appropriate silylketene acetal in the presence of a Lewis acid or via one-pot Brønsted base/Brønsted acid system, followed by deprotection with DDQ. Benzylic alcohol 6 was separated by Chiral SFC to give a single enantiomerically pure product 7. Alcohol 7 can be transformed to the requisite chloride 8 using thionyl chloride. Completion of the synthesis can be accomplished by displacement of chloride, following by hydrolysis of the ester to produce 9

It will be also be appreciated by the skilled artisan that intermediate 5 may be prepared by coupling bromide 1 with aldehyde 10.

Scheme 51

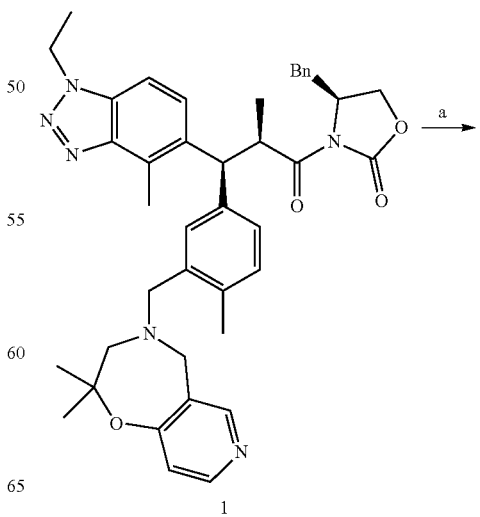

1

-continued

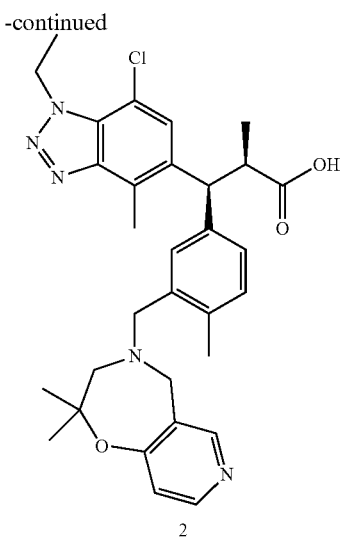

Conditions: a) LiOH, H₂O₂, THF, H₂O, HCl

Scheme 51 represents a general scheme for the preparation of acid 2 used in the invention. The starting material 1 can be synthesized from readily available materials. Reaction conditions are as described above in the scheme; however, the skilled artisan will appreciate that certain modifications in the reaction conditions and/or reagents used are possible.

Hydrolysis of the ester 1 using LiOH and peroxide then quenching with HCl produces acid 2.

Scheme 52

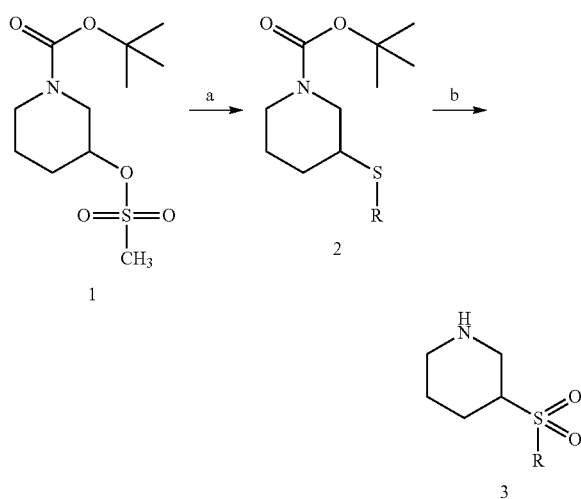

Conditions: a) RSH, NaH, DMF; b) (i) mCPBA, DCM (ii) HCl (4M in dioxane), DCM

Scheme 52 represents a general scheme for the preparation of 3-sulfone substitute-1-piperidine used in the invention. In this, the preparation of tert-butyl 3-mesylpiperidine-1-carboxylate depicted as starting material was described before. Reaction conditions are as described above in the scheme; however, the skilled artisan will appreciate that certain modifications in the reaction conditions and/or reagents used are possible.

Starting tert-butyl 3-mesylpiperidine-1-carboxylate 1 was treated with thiol under NaH condition to afford intermediate sulfide 2. Further oxidation of sulfide into sulfone followed by deprotection of tert-butylcarboxylate group gave the required piperidine 3.

Biological Activity

As stated above, the compounds according to Formula I are NRF2 regulators, and are useful in the treatment or prevention of human diseases that exhibit oxidative stress components such as respiratory and non-respiratory disorders, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a NRF2 antagonist, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% $CO_2$ overnight. On day two, plates are centrifuged and 50 nL of compound or controls are added to the cells. Plates are then incubated at 37° C., 5% $CO_2$ for 48 hours. On day four, medium is aspirated from the plate and crude cell lysates are made by adding 13 uL of 1× Cell Signaling Technologies lysis buffer with 1 Complete, Mini, EDTA-free Protease Inhibitor Tablet (Roche) for each 10 mL of lysis buffer. After lysis plates are incubated for 20 minutes at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation is measured kinetically and the $EC_{50}$ of NQO1 specific activity induction is calculated by plotting the change in absorbance (Delta OD/min) versus the log of compound concentration followed by 3-parameter fitting.

All examples described herein possessed NQO1 specific enzyme activity in BEAS-2B cells with $EC_{50}$s between >10 uM-<1 nM unless otherwise noted (see table below). $EC_{50}$s<1 nM (+++++), $EC_{50}$s 10 nM-1 nM (++++), $EC_{50}$s 10-100 nM (+++), $EC_{50}$s 100 nM-1 uM (++), $EC_{50}$s 1-10 uM (+), $EC_{50}$s>10 uM (−), or were not determined (ND).

fluorescence polarization (FP) assay, a TAMRA-labeled 16mer peptide (AFFAQLQLDEETGEFL) containing the ETGE motif of NRF2 and the Kelch domain (321-609) of Keap1 is used. The assay determines if a compound interferes with the binding between Keap1 (361-609) and the TAMRA-labeled peptide. Binding of TAMRA-labeled

| Ex # | EC50 | Ex # | EC50 | Ex # | EC50 | Ex # | EC50 | Ex # | EC50 |
|---|---|---|---|---|---|---|---|---|---|
| 1 | + | 30 | ++++ | 59 | +++ | 88 | ++ | 117 | + |
| 2 | ++ | 31 | +++++ | 60 | +++ | 89 | +++ | 118 | + |
| 3 | + | 32 | ++++ | 61 | +++ | 90 | +++ | 119 | +++ |
| 4 | + | 33 | +++ | 62 | +++ | 91 | ++ | 120 | ++++ |
| 5 | +++ | 34 | ++ | 63 | +++ | 92 | + | 121 | +++++ |
| 6 | ++ | 35 | ++++ | 64 | +++ | 93 | ++++ | 122 | +++ |
| 7 | + | 36 | ++++ | 65 | +++ | 94 | ++++ | 123 | +++ |
| 8 | ++++ | 37 | + | 66 | +++ | 95 | ++ | 124 | +++ |
| 9 | + | 38 | +++ | 67 | +++ | 96 | ++ | 125 | ++ |
| 10 | + | 39 | +++ | 68 | +++ | 97 | ++ | 126 | ++++ |
| 11 | + | 40 | +++ | 69 | +++ | 98 | ++ | 127 | +++ |
| 12 | ++ | 41 | ++ | 70 | +++ | 99 | + | 128 | + |
| 13 | + | 42 | ++ | 71 | ++ | 100 | +++ | 129 | ++ |
| 14 | + | 43 | + | 72 | + | 101 | +++++ | 130 | ++ |
| 15 | + | 44 | +++ | 73 | ++ | 102 | +++++ | 131 | ++ |
| 16 | + | 45 | ++ | 74 | ++ | 103 | +++++ | 132 | + |
| 17 | + | 46 | ++ | 75 | ++ | 104 | ++++ | 133 | ++ |
| 18 | + | 47 | ++ | 76 | ++ | 105 | +++ | 134 | ++ |
| 19 | + | 48 | ++ | 77 | + | 106 | ++ | 135 | +++ |
| 20 | ++ | 49 | ++ | 78 | + | 107 | +++ | 136 | +++ |
| 21 | + | 50 | +++ | 79 | + | 108 | + | 137 | ++ |
| 22 | ++++ | 51 | ++ | 80 | +++ | 109 | ++ | 138 | + |
| 23 | +++ | 52 | ++++ | 81 | +++ | 110 | +++++ | 139 | + |
| 24 | +++++ | 53 | ++ | 82 | +++ | 111 | +++ | 140 | + |
| 25 | +++++ | 54 | +++ | 83 | ++ | 112 | ++ | 141 | + |
| 26 | ++++ | 55 | +++ | 84 | ++ | 113 | ++ | 142 | ++ |
| 27 | ++ | 56 | +++ | 85 | ++ | 114 | ++ | 143 | + |
| 28 | +++++ | 57 | +++ | 86 | ++ | 115 | + | 144 | ++ |
| 29 | +++++ | 58 | +++ | 87 | +++ | 116 | + | 145 | ++ |
| 146 | +++ | 147 | + | 148 | ++ | 149 | ++ | 150 | +++++ |
| 151 | ++++ | 152 | ++ | 153 | + | 154 | ++ | 155 | +++ |
| 156 | +++ | 157 | ++ | 158 | + | 159 | + | 160 | + |
| 161 | + | 162 | ++ | 163 | + | 164 | ++ | 165 | ++++ |
| 166 | +++ | 167 | +++ | 168 | +++ | 169 | +++ | 170 | +++ |
| 171 | +++ | 172 | +++ | 173 | +++ | 174 | +++ | 175 | +++ |
| 176 | +++ | 177 | +++ | 178 | +++ | 179 | +++ | 180 | +++ |
| 181 | +++ | 182 | ++ | 183 | +++ | 184 | ++ | 185 | +++ |
| 186 | ++ | 187 | ++ | 188 | +++++ | 189 | ++++ | 190 | ++++ |
| 191 | ++++ | 192 | ++++ | 193 | ++++ | 194 | +++ | 195 | +++ |
| 196 | ++++ | 197 | +++ | 198 | +++ | 199 | +++ | 200 | +++ |
| 201 | ++ | 202 | +++ | 203 | +++ | 204 | ++ | 205 | ++ |
| 206 | ++++ | 207 | +++ | 208 | ++++ | 209 | ++++ | 210 | +++ |
| 211 | +++ | 212 | +++ | 213 | ++ | 214 | ++ | 215 | + |
| 216 | ++++ | 217 | +++ | 218 | ++++ | 219 | ++++ | 220 | +++ |
| 221 | +++ | 222 | +++++ | 223 | ++++ | 224 | ++ | 225 | +++ |
| 226 | +++ | 227 | ++ | 228 | ++ | 229 | ++++ | 230 | ++++ |
| 231 | ++ | 232 | ++ | 233 | + | 234 | + | 235 | +++++ |
| 236 | +++++ | 237 | +++++ | 238 | ++++ | 239 | +++++ | 240 | ++++ |
| 241 | +++++ | 242 | +++ | 243 | ++ | 244 | +++ | 245 | +++ |
| 246 | ++ | 247 | ++++ | 248 | +++ | 249 | ++++ | 250 | +++ |
| 251 | ++++ | 252 | +++ | 253 | +++++ | 254 | ++++ | 255 | +++ |
| 256 | +++ | 257 | ++ | 258 | +++ | 259 | ++ | 260 | ++ |
| 261 | ++ | 262 | +++ | 263 | +++ | 264 | + | | |

\* in some determinations $EC_{50}$ values were >10 uM
\# in some determinations $EC_{50}$ values were <170 pM NRF2-Keap1 FP Assay One model for the NRF2-Keap1 interaction is through two binding sites in the Neh2 domain on NRF2. The two sites are referred to as the DLG binding motif (latch domain, uM affinity) and the ETGE binding motif (hinge domain, nM affinity). The Keap1 protein consists of an N-terminal region (NTR), a broad complex, tramtrack, and brick a'brac domain (BTB), an intervening region (IVR), a double glycine repeat domain (DGR or Kelch), and a C-terminal region. The DLG and ETGE motifs of NRF2's Neh2 domain bind to the Kelch domain of Keap1 at different affinities. In the Keap1 Kelch NRF2 peptide to Keap1 (321-609) results in a high FP signal. If a compound interferes with the binding between the peptide and the protein, it will cause the assay signal to decrease. Thus, assay signal is inversely proportional to binding inhibition.

FP Assay:

100 nl of 100× compound dose response curves (serial 3-fold dilutions) in DMSO are stamped using an Echo liquid handling system (Labcyte) into 384-well low volume black assay plates (Greiner, #784076), with DMSO in columns 6 and 18. The top concentration of compound is located in columns 1 and 13. Keap1 (321-609) is diluted to 40 nM (2×) in 1× assay buffer (50 mM Tris, pH 8.0, 100 mM NaCl, 5 mM MgCl$_2$, 1 mM DTT, 2 mM CHAPS, and 0.005% BSA) and 5 ul is added using a Multidrop Combi (Thermo Electron Corporation) equipped with a metal tip dispenser to all wells of the compound plate, except column 18. Column 18 receives only 5 ul of assay buffer. Immediately, 5 uL of 16 nM (2×) of Tamra labeled peptide (AFFAQLQLDEET-GEFL, 21$^{st}$ Century Biochemicals) is added to all wells of the plate. The plates are spun at 500 rpm for 1 min, incubated for 1 hr at room temperature, and read on an Analyst GT (Molecular Devices) equipped with excitation (530/25 nm) and emission (580/10 nm) filters designed for Tamra probes. A 561 nm dichroic mirror is also used in the Analyst. The final assay concentrations of Keap1 (321-609) and Tamra labelled peptide are 20 nM and 8 nM, respectively. Fluorescence measurements, represented as mP, are used in the transformation of the data. Compound activity is calculated based on percent inhibition, normalized against controls in the assay (Control 1 contains the Tamra peptide and Keap1 (321-609) together (0% response) and control 2 contains the Tamra peptide alone (100% response)). Data analysis is handled using the software package Abase XE (Surrey, United Kingdom. The % inhibition values are calculated by the equation:

$$100-(100*((\text{compound response}-\text{average control 2})/(\text{average control 1}-\text{average control2}))).$$

For calculation of pIC$_{50}$s, Abase XE uses a four parameter equation.

All examples described herein possessed activity in the Keap1/NRF2 FP assay.

NRF2-Keap1 TR-FRET Assay

In the NRF2-Keap1 TR-FRET (time-resolved fluorescence resonance energy transfer) assay, full length NRF2 protein and full length Keap1 protein (Keap1 exists a dimer) are used. The assay detects the ability of compound to displace the binding of FlagHis-tagged Keap1 with biotinylated, Avi-tagged NRF2 protein. Biotin-NRF2 binds to streptavidin-europium (a component of the detection mix) and Keap1-FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential Keap1 inhibitor will cause a reduction in the TR-FRET signal by interfering with the binding of Keap1 to NRF2.

One hundred nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. The top concentration of compound is located in columns 1 and 13. All reagents are diluted in assay buffer (50 mM Tris, pH 8.0, 5 mM MgCl2, 100 mM NaCl, 0.005% BSA, 1 mM DTT, and 2 mM CHAPS). The BSA, DTT, and CHAPS are added to the assay buffer on the day of assay. Using a Multidrop Combi (Thermo Electron Corporation) equipped with a metal tip dispenser, 5 ul of 25 nM Keap1-FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 50 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the absence of protein). Data analysis is handled using the software package Abase XE (Surrey, United Kingdom). The % inhibition values are calculated from the ratio (transformed) data by the equation:

$$100-(100*(\text{compound response}-\text{average control 2})/(\text{average control 1}-\text{average control2})).$$

For calculation of pIC50s, Abase XE uses a four parameter equation.

Methods of Use

The compounds of Formula (I) are useful in treating respiratory and non-respiratory disorders, including COPD, asthma, fibrosis, chronic asthma, acute asthma, lung disease secondary to environmental exposures, acute lung infection, chronic lung infection, a1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, said disorders are treated by administering to a human in need thereof, a compound of Formula (I). Accordingly, in another aspect the invention is directed to methods of treating such conditions.

In one embodiment, the compounds of Formula (I) are useful in treating respiratory disorders including COPD, asthma, including chronic asthma and acute asthma.

In one embodiment, the compounds of Formula (I) are useful in treating hypertension, heart failure, acute coronary syndrome, myocardial infarction, myocardial repair, cardiac remodeling, cardiac arrhythmias, heart failure with preserved ejection fraction, heart failure with reduced ejection fraction and diabetic cardiomyopathy.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 uug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g. in separate pharmaceutical compositions, for example as described in WO 03/061743 A1 WO 2007/012871 A1 and/or WO2007/068896. In one embodiment an inhalation device permitting separate containment of components is an inhaler device having two peelable blister strips, each strip containing pre-metered doses in blister pockets arranged along its length, e.g., multiple containers within each blister strip. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (e.g. fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, insulin.

The compounds may be used in combination with anti-hypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The invention will now be described by reference to the following examples which are merely illustrative and are not to be construed as a limitation of the scope of the present invention. All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on silica gel 230-400, 100-200 & 60-120 Cilicant Brand. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson or Waters Preparative System with variable wavelength UV detection or an Agilent Mass Directed AutoPrep (MDAP) system or Shimadzu PREP LC 20AP with both mass and variable wavelength UV detection. A variety of reverse phase columns, e.g., Luna C18(2), SunFire C18, XBridge C18, Atlantics T3, Kromasil C18, Xbridge Phenyl-Hexyl columns were used in the purification with the choice of column support dependent upon the conditions used in the purification. The compounds are eluted using a gradient of $CH_3CN$ or methanol and water. Neutral conditions used an $CH_3CN$ and water gradient with no additional modifier, acidic conditions used an acid modifier, usually 0.1% TFA or 0.1% formic acid and basic conditions used a basic modifier, usually 0.1% $NH_4OH$ (added to the water) or 10 mM ammonium bicarbonate (added to the water), or 0.05% $NH_4HCO_3$ (added to water).

Analytical HPLC was run using an Agilent system or Waters Alliance HPLC with 2996 PDA detector, Waters Acquity UPLC-MS or Agilent Infinity 1290 with PDA or conducted on a Sunfire C18 column, alternative on XSE-LECT CSH C18 column using reverse phase chromatography with a $CH_3CN$ and water gradient with 0.1% formic acid modifier (added to each solvent) and basic conditions used a basic modifier, usually 5 mM ammonium bicarbonate or 10 mM ammonium bicarbonate in water adjusted pH to 10 with ammonia solution. The compound was analyzed by LCMS using a Shimadzu LC system with UV 214 nm wavelength detection and $H_2O$—$CH_3CN$ gradient elution (4-95% over 1.9 min.) acidified to 0.02% TFA. The reversed-phase column was a 2.1×20 mm Thermo Hypersil Gold $C_{18}$ (1.9 u particles) at 50'C. The single quadrupole MS detector was either a Sciex 150EX or a Waters ZQ operated in positive-ion. Alternatively, LC-MS was determined using either a PE Sciex Single Quadrupole 150EX LC-MS, or Waters ZQ Single Quadrupole, Waters 3100 Single Quadrupole, Agilent 6130 SQD or Agilent 6120 Single Quadrupole LC-MS instruments. The compound is analyzed using a reverse phase column, e.g., Thermo Hypersil Gold $C_{18}$ and/or Luna $C_{18}$ eluted using a gradient of $CH_3CN$ and water with a low percentage of an acid modifier such as 0.02% or 0.1% TFA.

Preparative Chiral SFC was performed using a Thar/Waters Preparative SFC System with single wavelength UV detection system. A variety of chiral SFC columns, e.g. Chiralpak IA, IC, AY, AD, IF, OJ were used in the purification. The compounds are eluted using supercritical fluid $CO_2$ and co-solvents, such as MeOH, EtOH, IPA, and combination of these solvent in different ratio based on the compound. Modifiers (0.1% to 0.4% of TFA, $NH_4OH$, DEA, TEA) can be used as needed. Normal phase chromatography is performed using the above mentioned chiral columns & pyridyl amide, ethyl pyridine achiral columns are used for chiral & achiral purifications respectively. Modifiers (0.1% of TFA, NH4OH, DEA) would be used as needed. K PREP Lab 100 G-YMC instruments are used in normal phase preparative scale purifications.

Analytical Chiral SFC was run using a Thar/Waters SFC system with variable wavelength UV detection. A variety of chiral SFC columns, e.g. Chiralpak IA, IB, IC, ID, IF, AY, AD, OD, C2, AS, OJ, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% to 0.4% of TFA, $NH_4OH$, DEA, TEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 spectrometer or Varian MR400 spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiation was carried out on a Biotage Initiator® microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

Table of Abbreviations

[Rh(cod)Cl]2 or [RhCl(cod)]2: di-µ-chlorido-bis[η2,η2-(cycloocta-1,5-diene)rhodium
®T3P: 2,4,6-tripropyl-1,3,5,2,4,6-trioxatriphosphorinane 2,4,6-trioxide
° C.: degree Celsius
AcOH: acetic acid
ADDP: (E)-diazene-1,2-diylbis(piperidin-1-ylmethanone)
aq = aqueous
BINAP: 2,2'-bis(diphenylphosphino)-1,1'-binaphthalene
CDI: Carbonyl dimidazole
$CH_2Cl_2$: dichloromethane
$CH_3CN$: acetonitrile
$CH_3CN$: acetonitrile
$CHCl_3$: chloroform
$Cs_2CO_3$: cesium carbonate
DBU: 1,8-diazabicyclo[5.4.0]undec-7-ene
DCE: dichloroethane
DCM: dichloromethane
DIPEA or DIEA: diisopropylethyl amine
DME: dimethyl ether
DMF: N,N-dimethylformamide
DMF-DMA or DMF-dimethyl acetal: N,N-dimethylformaide-dimethyl acetal
DMSO: dimethyl sulfoxide
EDC: 1-ethyl-3-(3-dimethylaminopropyl)carbodiimide
$Et_2O$: diethyl ether
$Et_3N$: triethylamine
EtOAc: ethyl acetate
EtOH: ethanol
g: gram(s)
h: hour(s)
HATU: O-(7-azabenzotriazol-1-yl)-N,N,N',N'-tetramethyluronium hexafluorophosphate
HBTU: N,N,N',N'-tetramethyl-O-(1H-benzotriazol-1-yl)uronium hexafluorophosphate
HCl: hydrochloric acid
HOAt: 1-hydroxy-7-azabenzotriazole
HPLC: high performance liquid chromatography
IPA: isopropyl alcohol
$K_2CO_3$: potassium carbonate
KOAc: Potassium acetate
LAH: lithium aluminum hydride
LC: liquid chromatography
LC-MS: liquid chromatography-mass spectroscopy
$LiBH_4$: lithium borohydride
LiHMDS: lithium hexamethyldisilazane
LiOH: lithium hydroxide
M: molar
MeCN: acetonitrile
MeI: methyl iodide
MeOH: methanol
mg: milligram(s)
$MgCl_2$: magnesium chloride
$MgSO_4$: magnesium sulfate
MHz: megahertz
min: minute(s)
mL: milliliter(s)
mmol: millimole(s)
MS: mass spectroscopy
$N_2$: nitrogen gas
$Na_2CO_3$: sodium carbonate
$Na_2SO_4$: sodium sulfate
$NaBH_3CN$ or NaCNBH3: sodium cyanoborohydride
NaCl: sodium chloride
NaH: sodium hydride
$NaHCO_3$: sodium bicarbonate
NaHMDS: sodium hexamethyldisilazane
$NaHSO_4$: sodium bisulfate
NaOAc: sodium acetate

Table of Abbreviations

NaOH: sodium hydroxide
NBS: N-Bromosuccinimide
nBuLi: n-butyl lithium
$NH_4Cl$: ammonium chloride
NMR: nuclear magnetic resonance
$P(tBu)_3$: tri-t-butyl phosphine
$Pd(PhP_3)4$: tetrakistriphenylphosphine palladium
Pd/C: pallidium on carbon
$Pd_2(dba)_3$: tris(dibenzylideneacetone)-dipalladium(0)
$PdCl_2(dppf)$ or Pd(dppf)Cl2: [1,1'-bis(diphenylphosphino)-ferrocene] dichloropalladium(II)
Petrol: petroleum ether
PS-PPh3: polymer supported triphenylphosphine
$PtO_2$: platinum(IV) oxide
RT: room temperature
T3P: 2,4,6-tripropyl-1,3,5,2,4,6-trioxatriphosphorinane-2,4,6-trioxide solution
TEA: triethylamine
TFA: trifluoroacetic acid
TFFH: Tetrafluoroformamidinium hexafluorophosphate
THF: tetrahydrofuran
triflic anhydride: trifluoromethanesulfonic anhydride
TsOH: p-toluenesulfonic acid
wt %: weight percent

Intermediate 1

Tert-butyl 3-((methylsulfonyl)oxy)piperidine-1-carboxylate

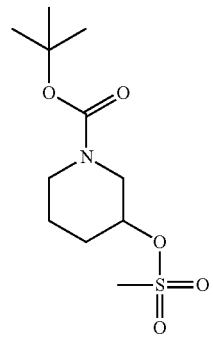 [SMILES: CC(C)(C)OC(=O)N1CCCC(OS(C)(=O)=O)C1]

To a solution of tert-butyl 3-hydroxypiperidine-1-carboxylate (1.05 g, 5.22 mmol) and triethylamine (0.792 g, 7.83 mmol) in dichloromethane (DCM) (30 mL), methanesulfonyl chloride (0.657 g, 5.74 mmol) was added. The reaction mixture was stirred at 0° C. to 25° C. for 3 h after which it was washed with water (3×50 mL) and HCl (1 M, 30 mL), dried over $MgSO_4$, filtered and concentrated to give the title compound tert-butyl 3-((methylsulfonyl)oxy)piperidine-1-carboxylate (1.0 g, 3.44 mmol, 65.9% yield) as a yellow oil. LC-MS m/z 302 (M+Na)+, 1.54 min (ret. time).

Intermediate 2

Tert-butyl 3-(1H-pyrazol-1-yl)piperidine-1-carboxylate

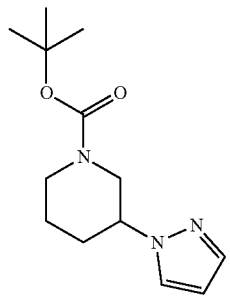 [SMILES: CC(C)(C)OC(=O)N1CCCC(n2cccn2)C1]

To a solution of 1H-pyrazole (0.487 g, 7.16 mmol) in N,N-dimethylformamide (DMF) (20 mL) was added sodium hydride (0.258 g, 10.74 mmol) in small portions at 0° C. The reaction mixture was stirred at 25° C. for 1 h. tert-Butyl 3-((methylsulfonyl)oxy)piperidine-1-carboxylate (1.0 g, 3.58 mmol) was added, and the mixture was heated at 100° C. for 16 h. The reaction mixture was quenched with saturated $NH_4Cl$ (10 mL), and extracted with EtOAc (3×30 mL). The organic layer was washed with water (2×10 mL), brine (2×10 mL), dried over $MgSO_4$ and concentrated. The residue was purified by silica gel chromatography (petroleum ether/ethyl acetate=15%) to give the title compound tert-butyl 3-(1H-pyrazol-1-yl)piperidine-1-carboxylate (0.5 g, 1.631 mmol, 45.6% yield) as a yellow oil. LCMS m/z 252.2 $(M+H)^+$, 1.61 min (ret. time).

Intermediate 3

3-(1H-Pyrazol-1-yl)piperidine

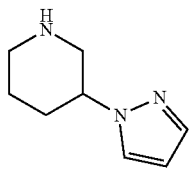 [SMILES: c1cnn(C2CCCNC2)c1]

To a solution of tert-butyl 3-(1H-pyrazol-1-yl)piperidine-1-carboxylate (900 mg, 3.58 mmol) in 1,4-dioxane (10 mL) was added hydrogen chloride (292 mg, 8.00 mmol) in 1,4-dioxane (705 mg). The reaction mixture was stirred at 25° C. for 1 h. The solvent was removed and the residue was purified by reverse-phase HPLC (MeOH/0.05% $NH_3H_2O$/ $H_2O$=38%) to give the title compound 3-(1H-pyrazol-1-yl) piperidine (190 mg, 1.257 mmol, 35.1% yield) as a yellow solid. LC-MS m/z 152.2 $(M+H)^+$, 1.13 min (ret. time)

Intermediate 4

(5-Bromo-2-methylphenyl)methanol

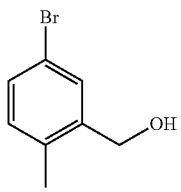

To a solution of 5-bromo-2-methylbenzoic acid (70 g, 326 mmol) in tetrahydrofuran (THF) (700 mL) stirred under nitrogen at 0° C. was added a toluene solution of borane-methyl sulfide complex (244 mL, 488 mmol) drop wise during 15 min. The reaction mixture was stirred for 16 h. The reaction was cooled to 0° C. and quenched with methanol (500 mL) drop wise. The reaction mixture was stirred at ambient temperature for 3 h and then concentrated. The crude residue was diluted with ethyl acetate (1 L) and washed with 1N HCl (500 mL), brine solution (500 mL) and dried over $Na_2SO_4$, filtered and concentrated to give the title compound (49 g, 244 mmol, 74.9% yield). $^1H$ NMR (400 MHz, DMSO) δ=7.52 (d, J=2.6 Hz, 1H), 7.31 (dd, J=8.0, 2.2 Hz, 1H), 7.12-7.03 (m, 1H), 5.22 (td, J=5.5, 1.8 Hz, 1H), 4.48 (dd, J=5.1, 1.8 Hz, 2H), 2.17 (s, 3H).

Intermediate 5

4-Bromo-2-(((4-methoxybenzyl)oxy)methyl)-1-methylbenzene

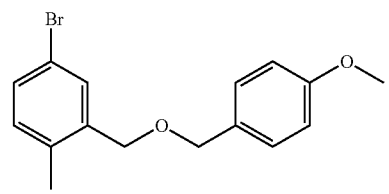 [SMILES: COc1ccc(COCc2cc(Br)ccc2C)cc1]

To a stirred solution of (5-bromo-2-methylphenyl)methanol (100 g, 497 mmol) in dry DMF (800 mL) was added NaH (21.88 g, 547 mmol). After the reaction mixture was stirred for 30 minutes, 1-(chloromethyl)-4-methoxybenzene (82 g, 522 mmol) was added at 0° C. and the reaction mixture was stirred for another 2 h at ambient temperature. The reaction was then diluted with $Et_2O$ (200 mL) and water (200 mL). The organic phase was washed with brine (300 mL) and dried with $Na_2SO_4$ and concentrated under reduced pressure. The residue was purified via silica gel column to yield 4-bromo-2-(((4-methoxybenzyl)oxy)methyl)-1-methylbenzene (140 g, 436 mmol, 88% yield) as a clear oil. $^1H$ NMR (400 MHz, CHLOROFORM-d) δ ppm 2.27 (s, 3H) 3.84 (s, 3H) 4.49 (s, 2H), 4.54 (s, 2H), 6.92 (d, J=8.8, 2H), 6.94 (d, J=8.4, 1H), 7.31-7.35 (m, 3H), 7.54 (d, J=2, 1H).

Intermediate 6

3-(4-Methoxybenzyl)oxy)methyl)-4-methylbenzaldehyde

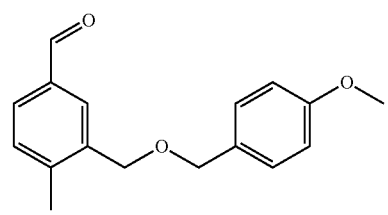 [SMILES: COc1ccc(COCc2cc(C=O)ccc2C)cc1]

To a stirred solution of 4-bromo-2-(((4-methoxybenzyl) oxy)methyl)-1-methylbenzene (80 g, 249 mmol) in THF (800 mL) at −78° C. under $N_2$, 2.5 M n-BuLi in hexane (120 mL, 299 mmol) was carefully added. The reaction mixture was stirred at −78° C. for 65 min, and then DMF (38.6 mL, 498 mmol) was added. The reaction mixture was stirred at −78° C. to 25° C. for another 30 min. The mixture was quenched with saturated NH$_4$Cl (300 mL), and extracted with EtOAc (2×500 mL). The organic layer was washed with water (300 mL) and brine (2×100 mL), dried (Na$_2$SO$_4$) and concentrated. The residue was washed with petroleum ether: EtOAc=10/1 (2000 mL) to give the title compound (50 g, 185 mmol, 74.3% yield) as a solid. LC-MS m/z 288.1 (M+H$_2$O)$^+$, 2.04 min (ret. time).

Intermediate 7

(4-Fluoro-2-methylphenyl)(3-(((4-methoxybenzyl)oxy)methyl)-4-methylphenyl)methanol

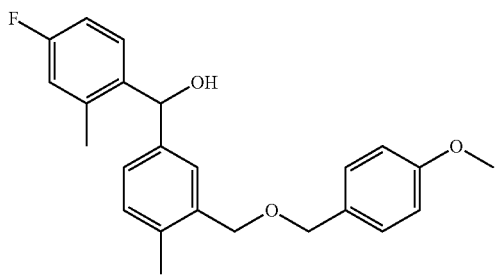 [SMILES: COc1ccc(COCc2cc(C(O)c3ccc(F)cc3C)ccc2C)cc1]

To a solution of 4-bromo-2-(((4-methoxybenzyl)oxy)methyl)-1-methylbenzene (16.04 g, 49.9 mmol) in tetrahydrofuran (THF) (200 mL) was added 2.5 M n-BuLi in hexane (23.98 mL, 59.9 mmol) at −78° C. under N$_2$ atmosphere. The reaction mixture was stirred at −78° C. for 30 min, then 4-fluoro-2-methylbenzaldehyde (6.9 g, 49.9 mmol) in 20 mL of THF was added. Then the reaction mixture was stirred at −78° C. for 1 h and at ambient temperature for 3 h. 100 mL of NH$_4$Gl (saturated) was added. The organic layer was separated and the aqueous layer was extracted with ethyl acetate (3×100 mL). The combined organic layer was washed with brine (50 mL) and dried over Na$_2$SO$_4$ and concentrated. The residue was purified by silica gel chromatography (petroleum ether/ethyl acetate=5:1) to give the title compound (4-fluoro-2-methylphenyl)(3-(((4-methoxybenzyl)oxy)methyl)-4-methylphenyl)methanol (15 g, 39.4 mmol, 79%). LC-MS m/z 363.1 (M+H-18)$^+$, 2.18 min (ret. time)

Intermediate 8

Methyl 3-(4-fluoro-2-methylphenyl)-3-(3-(hydroxymethyl)-4-methylphenyl)-2,2-dimethylpropanoate

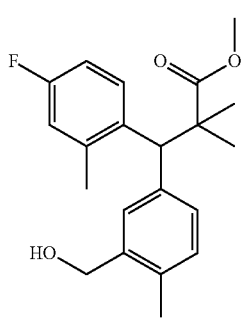 [SMILES: COC(=O)C(C)(C)C(c1ccc(C)c(CO)c1)c1ccc(F)cc1C]

To a solution of (4-fluoro-2-methylphenyl)(3-(((4-methoxybenzyl)oxy)methyl)-4-methylphenyl)methanol (7.8 g, 20.50 mmol) in dichloromethane (DCM) (100 mL) was added ((1-methoxy-2-methylprop-1-en-1-yl)oxy)trimethylsilane (7.15 g, 41.0 mmol), then boron trifluoride diethyl etherate (10.09 mL, 82 mmol) was slowly dropped into the reaction at 0° C. under N$_2$ protection. The reaction mixture was stirred at 0° C. for 30 min and at ambient temperature for 4 h. Then the reaction mixture was poured into the 100 mL of saturated NaHCO$_3$ aqueous solution at 0° C. The organic layer was separated and the aqueous layer was extracted with DCM (3×100 mL). The combined organic layer was washed with brine (100 mL) and dried over anhydrous Na$_2$SO$_4$ and concentrated. The residue was purified by silica gel chromatography (petroleum ether/ethyl acetate=4:1) to give the title compound methyl 3-(4-fluoro-2-methylphenyl)-3-(3-(hydroxymethyl)-4-methylphenyl)-2,2-dimethylpropanoate (7.0 g, 19.91 mmol, 97%). LCMS m/z 327.2 (M+H-18)$^+$, 367.2 (M+23)$^+$, 2.10 min (ret. time)

Intermediate 9

Pent-4-ynal

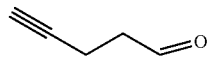

DMSO (25.3 mL, 357 mmol) was added to a solution of oxalyl chloride (15.61 mL, 178 mmol) in CH$_2$Cl$_2$ (900 mL) at −78° C. After it was stirred for 15 min, pent-4-yn-1-ol (10 g, 119 mmol) in CH$_2$Cl$_2$ (100 mL) was added dropwise and the reaction mixture was stirred for a further 15 min. Triethylamine (74.6 mL, 535 mmol) was added to the reaction mixture which was left to stir for an additional 15 min after which it was warmed to 0° C. and quenched with water (100 mL). The aqueous layer was extracted with DCM (3×150 mL). The combined organic layer was washed with water (2×300 mL), brine (300 mL) and dried over Na$_2$SO$_4$ and concentrated under reduced pressure to give the title compound pent-4-ynal (6.7 g, 82 mmol, 68.6% yield). $^1$H NMR (400 MHz, CDCl$_3$) δ=9.81 (s, 1H), 2.72-2.69 (m, 2H), 2.53-2.50 (m, 2H), 2.00-1.99 (m, 1H).

Intermediate 10

(E)-Ethyl hept-2-en-6-ynoate

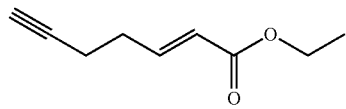

To ethyl 2-(diethoxyphosphoryl)acetate (24.03 g, 107 mmol) in tetrahydrofuran (THF) (150 mL) was added sodium hydride (4.68 g, 117 mmol)) in small portions. After 5 min, pent-4-ynal (8.0 g, 97 mmol) was added slowly. The reaction mixture was stirred at ambient temperature for 30 min. Then saturated NH$_4$Cl (200 mL) was added and the mixture extracted with DCM (200 mL×3). The combined organic layer was washed with brine (200 mL), dried over MgSO$_4$ and concentrated. The residue was purified by silica gel chromatography (petroleum ether/ethyl acetate=50:1) to give the title compound (E)-ethyl hept-2-en-6-ynoate (12 g, 79 mmol, 81% yield) as an oil. $^1$H NMR (400 MHz, CDCl$_3$) δ=6.96 (m, 1H), 5.9 (d, J=15.6 Hz, 1H), 4.22-4.17 (q, J=14, 6.8, 1H), 2.45-2.36 (m, 4H), 2.01 (m, 1H), 1.31-1.27 (m, 3H).

Intermediate 11

(E)-Ethyl 5-(1-propyl-1H-1,2,3-triazol-4-yl)pent-2-enoate

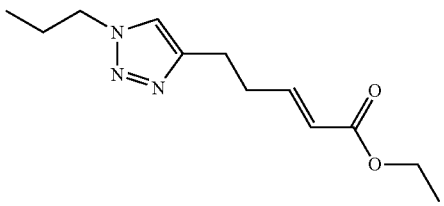 [SMILES: CCCn1cc(CC/C=C/C(=O)OCC)nn1]

A mixture of 1-iodopropane (11.17 g, 65.7 mmol), (E)-ethyl hept-2-en-6-ynoate (5.0 g, 32.9 mmol), sodium azide (4.27 g, 65.7 mmol) and copper(I) iodide (2.503 g, 13.14 mmol) in water (10 mL) and THF (20 mL) was stirred at 70° C. for 8 h. The reaction mixture was concentrated and the residue was extracted with ethyl acetate (3×50 mL). The combined organic layer was dried over MgSO$_4$, concentrated and purified by silica gel chromatography (petroleum ether/ethyl acetate=1:1) to give the title compound (E)-ethyl 5-(1-propyl-1H-1,2,3-triazol-4-yl)pent-2-enoate (2.6 g, 10.41 mmol, 31.7% yield) as an oil. LCMS m/z 238.1 (M+H)$^+$, 1.50 (ret. time)

Intermediate 12

7-((1H-Imidazol-2-yl)methyl)-7-azabicyclo[2.2.1]heptane

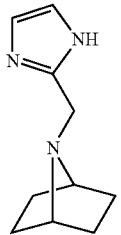 [SMILES: c1c[nH]c(CN2C3CCC2CC3)n1]

To a solution of 7-azabicyclo[2.2.1]heptane (860 mg, 8.85 mmol) in 1,2-dichloroethane (DCE) (10 mL), 1H-imidazole-2-carbaldehyde (851 mg, 8.85 mmol) and acetic acid (0.5 mL) were added. After it was stirred for 1 h at ambient temperature, sodium triacetoxyhydroborate (3752 mg, 17.70 mmol) was added. The reaction mixture was stirred at 25° C. for 2 h. The solvent was evaporated and the residue was adjusted to pH 7 with NH$_4$OH solution, then extracted with ethyl acetate (2×20 mL). The crude product was purified by reverse-phase HPLC (A: 10 mmol/L NH$_4$HCO$_3$, B: MeOH) to give the title compound 7-((1H-imidazol-2-yl)methyl)-7-azabicyclo[2.2.1]heptane (103 mg, 0.552 mmol, 6.24% yield), as a yellow solid. LC-MS m/z 178.2 (M+H)$^+$, 1.12 min (ret. time).

Intermediate 13

8-((1H-imidazol-2-yl)methyl)-8-azabicyclo[3.2.1]octane

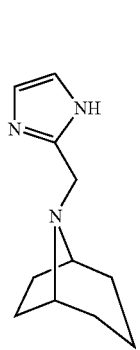

To a solution of 8-azabicyclo[3.2.1]octane (860 mg, 7.73 mmol) in 1,2-dichloroethane (DCE) (10 mL), 1H-imidazole-2-carbaldehyde (743 mg, 7.73 mmol) and acetic acid (0.5 mL) was added. After it was stirred for 1 h at ambient temperature, sodium triacetoxyhydroborate (3752 mg, 17.70 mmol) was added. The reaction mixture was stirred at 25° C. for 2 h. The solvent was evaporated and the residue was adjusted to pH 7 with NH$_4$OH solution, then extracted with ethyl acetate (20 mL×2). The crude product was purified by reverse-phase HPLC (A: 10 mmol/L NH$_4$HCO$_3$, B: MeOH) to give the title compound the 8-((1H-imidazol-2-yl)methyl)-8-azabicyclo[3.2.1]octane (300 mg, 1.490 mmol, 19.26% yield) as a yellow solid. LC-MS m/z 192.3 (M+H)$^+$, 1.27 min (ret. time).

Intermediate 14

Ethyl 5-(1-ethyl-1H-1,2,3-triazol-4-yl)-3-(3-(hydroxymethyl)-4-methylphenyl)pentanoate

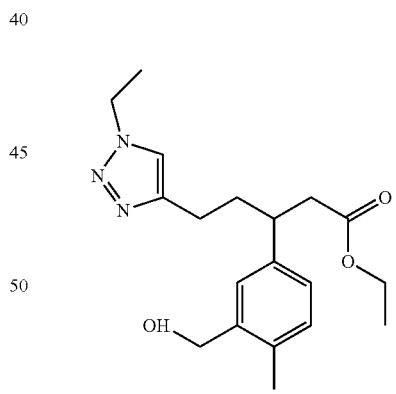

To a solution of (E)-ethyl 5-(1-ethyl-1H-1,2,3-triazol-4-yl)pent-2-enoate (10 g, 44.8 mmol) in 1,4-dioxane (80 mL) and water (40 mL) was added (2-methyl-5-(4,4,5,5-tetramethyl-1,3,2-dioxaborolan-2-yl)phenyl)methanol (22.23 g, 90 mmol) and triethylamine (12.49 mL, 90 mmol). The reaction mixture was stirred for 5 min after which chloro(1,5-cyclooctadiene)rhodium(I) dimer (1.104 g, 2.239 mmol) was added under the protection of nitrogen. The reaction mixture was stirred at 90° C. for 16 h. After it was cooled to ambient temperature, the reaction mixture was quenched with water (10 mL) and extracted with EtOAc (3×80 mL). The combined organic layer was washed with water (2×5 mL) and brine (2×5 mL), dried over Na₂SO₄ and concentrated. The residue was purified by silica gel chromatography (petroleum ether/ethyl acetate=65:1) to give the title compound ethyl 5-(1-ethyl-1H-1,2,3-triazol-4-yl)-3-(3-(hydroxymethyl)-4-methylphenyl)pentanoate (5 g, 13.32 mmol, 29.7% yield) as yellow oil. LC-MS m/z 346.2 (M+H)⁺, 1.73 min (ret. time).

Intermediate 15

Ethyl 3-(3-(((tert-butyldimethylsilyl)oxy)methyl)-4-methylphenyl)-5-(1-ethyl-1H-1,2,3-triazol-4-yl)pentanoate

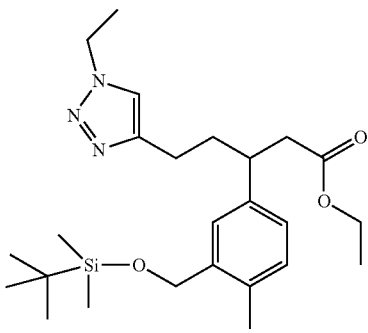 [SMILES: CCOC(=O)CC(CCc1cn(CC)nn1)c1ccc(C)c(CO[Si](C)(C)C(C)(C)C)c1]

To a solution of ethyl 5-(1-ethyl-1H-1,2,3-triazol-4-yl)-3-(3-(hydroxymethyl)-4-methylphenyl)pentanoate (4.65 g, 13.46 mmol) in dichloromethane (DCM) (60 mL) at 0° C., imidazole (1.833 g, 26.9 mmol), DMAP (0.082 g, 0.673 mmol) and tert-butylchlorodimethylsilane (3.04 g, 20.19 mmol) were added. The reaction mixture was stirred at 0° C. to 25° C. for 2 h. The reaction mixture was quenched with water (15 mL) and extracted with DCM (3×40 mL). The combined organic layer was washed with water (2×8 mL), brine (2×8 mL), dried over Na₂SO₄ and concentrated. The residue was purified with silica gel chromatography (petroleum ether/ethyl acetate=30%) to give the title compound ethyl 3-(3-(((tert-butyldimethylsilyl)oxy)methyl)-4-methylphenyl)-5-(1-ethyl-1H-1,2,3-triazol-4-yl)pentanoate (4 g, 8.18 mmol, 60.8% yield) as yellow oil. LC/MS m/z 460.3 (M+H)⁺, 1.98 min (ret. time).

Intermediate 16

Tert-butyl 4-ethylidenepiperidine-1-carboxylate

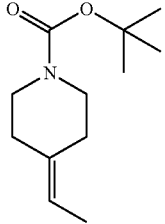

Ethyltriphenylphosphonium bromide (27.9 g, 75 mmol) was added portionwise to the LiHMDS (75 mL, 75 mmol) in THF (60 mL) at 0° C. After the reaction mixture was stirred at 0° C. for 1 h, a solution of tert-butyl 4-oxopiperidine-1-carboxylate (10.0 g, 50.2 mmol) in tetrahydrofuran (THF) (60 mL) was added and stirred for a further 2 h at ambient temperature. Brine was added to quench the reaction and extracted with ethyl acetate (2×200 mL). The combined organic layer was washed with brine, dried over MgSO₄ and concentrated. The residue was purified by silica gel chromatography (petroleum ether/ethyl acetate=10/1) to give the title compound tert-butyl 4-ethylidenepiperidine-1-carboxylate (6.2 g, 29.3 mmol, 58.5% yield) as an oil. LC-MS m/z 156.2 (M+H-56)⁺, 2.21 min (ret. time).

Intermediate 17

Tert-Butyl-4-ethylpiperidine-1-carboxylate

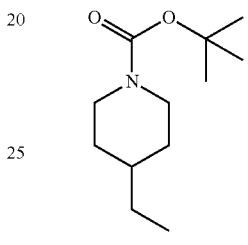

A mixture of tert-butyl 4-ethylidenepiperidine-1-carboxylate (6200 mg, 29.3 mmol) and Pd/C (1561 mg, 14.67 mmol) in methanol (100 mL) was hydrogenated with H₂ balloon for 5 h. The mixture was filtered through celite and the organic layer was concentrated to give the title compound tert-butyl 4-ethylpiperidine-1-carboxylate (6200 mg, 29.1 mmol, 99% yield) as oil. LC-MS m/z 158.1 (M+H)⁺, 2.28 min (ret. time).

Intermediate 18

4-Ethylpiperidine

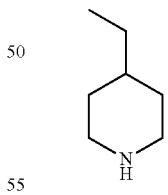

The mixture of tert-butyl 4-ethylpiperidine-1-carboxylate (6200 mg, 29.1 mmol), trifluoroacetic acid (2.239 mL, 29.1 mmol) in dichloromethane (DCM) (50 mL) was stirred at ambient temperature for 5 h. The solvent was concentrated to give the title compound 4-ethylpiperidine (2500 mg, 22.08 mmol, 76% yield) as an oil which was carried to the next step without further purification. LC-MS m/z 114.2 (M+H)⁺, 1.03 min (ret. time).

Intermediate 19

1-((1H-Imidazol-2-yl)methyl)-4-ethylpiperidine

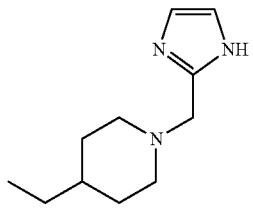

To a mixture of 4-ethylpiperidine (1200 mg, 10.60 mmol) and 1H-imidazole-2-carbaldehyde (1019 mg, 10.60 mmol) was added titanium(IV) isopropoxide (3.73 mL, 12.72 mmol) dropwise. After it was stirred at 25° C. for 2 h, ethanol (120 mL) and NaCNBH$_3$ (666 mg, 10.60 mmol) were added and stirred for another 8 h. Water (2 mL) was added to quench the reaction. The solvent was concentrated. The residue was purified by reverse-phase HPLC (MeOH/0.05% NH$_3$H$_2$O/H$_2$O=50%) to give the title compound 1-((1H-imidazol-2-yl)methyl)-4-ethylpiperidine (850 mg, 4.18 mmol, 39.4% yield) as a solid. LC-MS m/z 194.2 (M+H)$^+$, 1.53 min (ret. time)

Intermediate 20

1-((1H-Imidazol-2-yl)methyl)piperidine

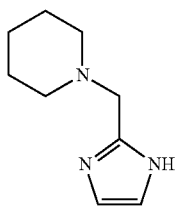

To a solution of 1H-imidazole-2-carbaldehyde (2 g, 20.81 mmol) in 1,2-dichloroethane (DCE) (100 mL), piperidine (1.772 g, 20.81 mmol) and acetic acid (0.5 mL) were added. After it was stirred at ambient temperature for 16 h, NaBH(OAc)$_3$ (8.82 g, 41.6 mmol) was added. The reaction mixture was stirred at 25° C. for a further 2 h. The solvent was removed and the residue was purified by reverse-phase HPLC (0.05% NH$_4$HCO$_3$/H$_2$O: CH$_3$CN=5%~95%) to give the title compound 1-((1H-imidazol-2-yl)methyl)piperidine (1.6 g, 9.68 mmol, 46.5% yield) as a yellow solid. LC-MS m/z 166.2 (M+H)$^+$, 1.27 min (ret. time)

Intermediate 21

Benzyl 4-methylenepiperidine-1-carboxylate

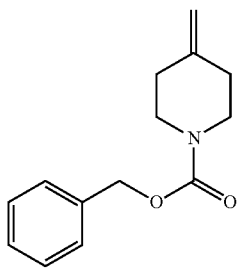 [SMILES: C=C1CCN(C(=O)OCc2ccccc2)CC1]

Methyltriphenylphosphonium bromide (18.38 g, 51.4 mmol) was added portionwise to LiHMDS (51.4 mL, 51.4 mmol) in THF (60 mL) at 0° C. After it was stirred for 1 h, a solution of benzyl 4-oxopiperidine-1-carboxylate (10.0 g, 42.9 mmol) in tetrahydrofuran (THF) (60 mL) was added and stirred for a further 2 h. Then brine was added to quench the reaction followed by extraction with ethyl acetate (2×200 mL). The organic layer was washed with brine, dried and concentrated. The residue was purified by silica gel chromatography (petroleum ether/ethyl acetate=10/1) to give the title compound benzyl 4-methylenepiperidine-1-carboxylate (8.0 g, 34.6 mmol, 81% yield) as an oil. LC-MS m/z 232.2 (M+H)$^+$, 2.00 min (ret. time)

Intermediate 22

4-Methylpiperidine

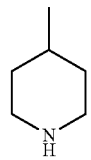

A mixture of benzyl 4-methylenepiperidine-1-carboxylate (8000 mg, 34.6 mmol) and Pd/C (1840 mg, 17.29 mmol) in methanol (100 mL) was hydrogenated at ambient temperature for 5 h. The mixture was filtered through celite and the filtrate was concentrated to give the title compound 4-methylpiperidine (3000 mg, 30.2 mmol, 87% yield) as oil. LC-MS: m/z 100.2 (M+H)$^+$, 0.32 min (ret. time)

Intermediate 23

1-((1H-Imidazol-2-yl)methyl)-4-methylpiperidine

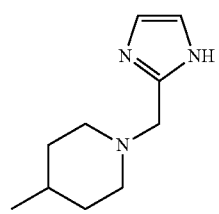

To a mixture of 4-methylpiperidine (2000 mg, 20.17 mmol) and 1H-imidazole-2-carbaldehyde (1938 mg, 20.17 mmol) was added titanium(IV) isopropoxide (7.09 mL, 24.20 mmol) dropwise. After it was stirred at 25° C. for 2 h. ethanol (120 mL) and NaCNBH$_3$ (1267 mg, 20.17 mmol) were added and the reaction stirred for another 8 hrs. Water (2 mL) was added to quench the reaction. The solid was filtered and the solvent was concentrated. The residue was purified by reverse-phase HPLC to give the title compound 1-((1H-imidazol-2-yl)methyl)-4-methylpiperidine (1500 mg, 7.95 mmol, 39.4% yield) as a solid. LC-MS m/z 180.2 (M+H)$^+$, 1.39 min (ret. time)

Intermediate 24

4-((1H-Imidazol-2-yl)methyl)-1,4-oxazepane

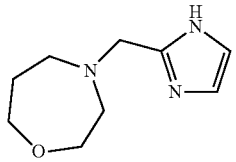 [SMILES: c1c[nH]c(CN2CCCOCC2)n1]

To a solution of 1,4-oxazepane (900 mg, 8.90 mmol) in 1,2-dichloroethane (DCE) (10 mL), 1H-imidazole-2-carbaldehyde (855 mg, 8.90 mmol) and acetic acid (0.5 mL) were added. After it was stirred for 1 h, sodium triacetoxyborohydride (3772 mg, 17.80 mmol) was added. The reaction mixture was stirred at 25° C. for a further 2 h. The solvent was removed and the residue was purified by reverse-phase HPLC (0.05% $NH_4HCO_3/H_2O$: $CH_3CN$=5%~95%) to give the title compound 4-((1H-imidazol-2-yl)methyl)-1,4-oxazepane (533 mg, 2.88 mmol, 32.4% yield) as a yellow solid. LC-MS m/z 182.1 $(M+H)^+$, 1.19 min (ret. time)

Intermediate 25

2-(Pyrrolidin-1-ylmethyl)-1H-imidazole

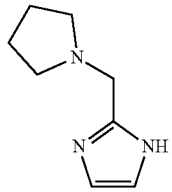 [SMILES: c1c[nH]c(CN2CCCC2)n1]

To a solution of 1H-imidazole-2-carbaldehyde (2 g, 20.81 mmol) in 1,2-dichloroethane (DCE) (100 mL), pyrrolidine (1.480 g, 20.81 mmol) and acetic acid (0.5 mL) were added. After it was stirred for 16 h at ambient temperature, NaBH(OAc)$_3$ (8.82 g, 41.6 mmol) was added. The reaction mixture was stirred at 25° C. for 2 h. The solvent was removed and the residue was purified by reverse-phase HPLC (0.05% $NH_4HCO_3/H_2O$: $CH_3CN$=5%~95%) to give the title compound 2-(pyrrolidin-1-ylmethyl)-1H-imidazole (1 g, 6.48 mmol, 31.1% yield) as a yellow solid. LC-MS m/z 152.3 $(M+H)^+$, 1.09 min (ret. time).

Intermediate 26

4-((1H-Imidazol-2-yl)methyl)morpholine

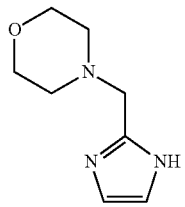 [SMILES: c1c[nH]c(CN2CCOCC2)n1]

To a solution of 1H-imidazole-2-carbaldehyde (2 g, 20.81 mmol) in 1,2-dichloroethane (DCE) (100 mL), morpholine (1.813 g, 20.81 mmol) and acetic acid (0.5 mL) were added. After it was stirred for 16 h at ambient temperature, NaBH(OAc)$_3$ (8.82 g, 41.6 mmol) was added. The reaction mixture was stirred at 25° C. for 2 h. The solvent was removed and the residue was purified by reverse-phase HPLC (0.05% $NH_4HCO_3/H_2O$: $CH_3CN$=5%~95%) to give the title compound 4-((1H-imidazol-2-yl)methyl)morpholine (1.2 g, 6.46 mmol, 31.0% yield) as a yellow solid. LC-MS m/z 168.1 $(M+H)^+$, 1.09 min (ret. time)

Intermediate 27

(R)-4-((1H-Imidazol-2-yl)methyl)-2-methylmorpholine

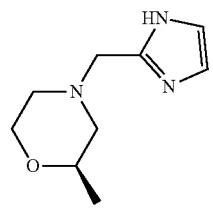

To a solution of (R)-2-methylmorpholine (860 mg, 8.50 mmol) in 1,2-dichloroethane (DCE) (10 mL), 1H-imidazole-2-carbaldehyde (817 mg, 8.50 mmol) and acetic acid (0.5 mL) were added. After it was stirred for 1 h, sodium triacetoxyborohydride (3604 mg, 17.00 mmol) was added. The reaction mixture was stirred at 25° C. for 2 h. The solvent was removed and the residue was purified by reverse-phase HPLC (0.05% $NH_4HCO_3/H_2O$: $CH_3CN$=5%-95%) to give the title compound (R)-4-((1H-imidazol-2-yl)methyl)-2-methylmorpholine (930 mg, 5.03 mmol, 59.1% yield) as a yellow solid. LC-MS m/z 182.2 $(M+H)^+$, 1.21 min (ret. time)

Intermediate 28

2-Bromo-N-methoxy-N-methylacetamide

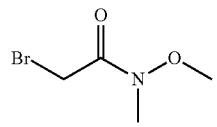

To a stirred solution of N,O-dimethylhydroxylamine hydrochloride (5 g, 51.3 mmol) in diethyl ether (65 mL) and water (65 mL) at ambient temperature was added $K_2CO_3$ (7.08 g, 51.3 mmol). The reaction mixture was cooled to 0° C., 2-bromoacetyl bromide (10.35 g, 51.3 mmol) was added slowly. It was stirred for 4 h at ambient temperature. It was extracted with diethyl ether twice. The organic layer was washed with brine, dried over $Na_2SO_4$, filtered and concentrated to give the title compound (5 g, 26.0 mmol, 50.8% yield) as liquid. LC-MS m/z 183.8 $(M+H)^+$, 1.43 min (ret. time)

Intermediate 29

2-(4,4-Difluoropiperidin-1-yl)-N-methoxy-N-methylacetamide

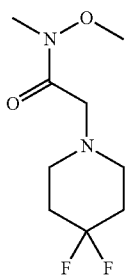

To a solution of 4,4-difluoropiperidine hydrochloride (6.93 g, 44.0 mmol) in tetrahydrofuran (THF) (80 mL) at 0° C. was added TEA (12.25 mL, 88 mmol). The reaction mixture was stirred at ambient temperature for 20 min, and then 2-bromo-N-methoxy-N-methylacetamide (8 g, 44.0 mmol) in tetrahydrofuran (THF) (80 mL) was added at 0° C. The reaction mixture was stirred at ambient temperature for 48 h. The reaction mixture was diluted with water and extracted with EtOAc twice. The combined organic layer was washed with brine, dried over $Na_2SO_4$, filtered and then concentrated. The crude compound was purified by silica gel chromatography to give the title compound (6 g, 27.0 mmol, 61.4% yield) as liquid. 1H NMR (400 MHz, cdcl3) δ=3.71 (s, 3H), 3.45 (s, 2H), 3.19 (s, 3H), 2.79 (br t, J=5.4 Hz, 4H), 2.16-2.02 (m, 4H).

Intermediate 30

2-(4,4-Difluoropiperidin-1-yl)acetaldehyde

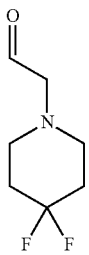

To a solution of 2-(4,4-difluoropiperidin-1-yl)-N-methoxy-N-methylacetamide (6 g, 27.0 mmol) in tetrahydrofuran (THF) (50 mL) at 0° C. was added LAH (1N in THF) (25 mL, 27.0 mmol). The reaction mixture was stirred at ambient temperature for 90 min. The reaction mixture was quenched with saturated $Na_2SO_4$ solution at 0° C. The reaction mixture was passed through celite and extracted with EtOAc (2×200 mL) and brine (100 mL), dried over $Na_2SO_4$, filtered and concentrated to give the title compound (2 g, 12.26 mmol, 45.4% yield). $^1$H NMR (400 MHz, $CDCl_3$) δ=9.89-9.59 (m, 1H), 3.24 (d, J=1.1 Hz, 2H), 2.73-2.56 (m, 4H), 2.13-1.92 (m, 4H).

Intermediate 31

1-((1H-Imidazol-2-yl)methyl)-4,4-difluoropiperidine

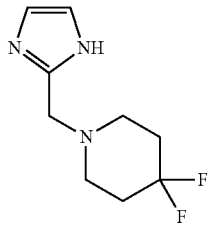 [SMILES: FC1(F)CCN(Cc2ncc[nH]2)CC1]

To a solution of 2-(4,4-difluoropiperidin-1-yl)acetaldehyde (2 g, 12.26 mmol) in water (50 mL) at ambient temperature was added glyoxal hydrate (0.515 g, 2.452 mmol) and ammonia (0.265 mL, 12.26 mmol). The reaction was stirred at ambient temperature for 18 h. The reaction mixture was diluted with water and extracted twice with DCM. The organic layer was dried under anhydrous $Na_2SO_4$, filtered and concentrated to give the crude product. The crude compound was purified by silica gel chromatography to give the title compound (300 mg, 1.491 mmol, 12.16% yield) as liquid. LC-MS m/z 202.35 $(M+H)^+$, 2.40 min (ret. time).

Intermediate 32

3-Methyl-2-nitrobenzamide

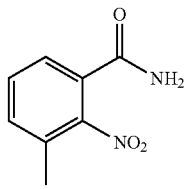

To a solution of 3-methyl-2-nitrobenzoic acid (100 g, 552 mmol) in Dichloromethane (DCM) (1000 mL), oxalyl chloride (72.5 mL, 828 mmol) was added at 25° C. The reaction mixture was stirred at ambient temperature for 1 h. The solvent was removed under reduced pressure. The residue was dissolved in $CH_2Cl_2$ (100 mL). The solvent was added to ammonium hydroxide (1000 mL, 7704 mmol) at ambient temperature and was stirred for 30 minutes. Then the reaction mixture was extracted with ethyl acetate (3×500 mL). The combined organic layer was dried over $MgSO_4$ and concentrated to give 67 g (60.6%) of the title compound. LC-MS m/z 181.1 $(M+H)^+$, 1.40 (ret. time).

Intermediate 33

3-Methyl-2-nitroaniline

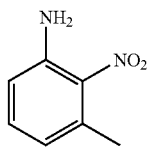

To a mixture of NaOH (2.220 g, 55.5 mmol) in water (12 mL), Br$_2$ (0.322 mL, 6.26 mmol) was added at 00° C. Then 3-methyl-2-nitrobenzamide (1 g, 5.55 mmol) was added in one portion, and the mixture was warmed slowly in a water bath. The material soon darked in color, and at 50-55° C. (internal temperature) oil droplets began to separate. The temperature was raised gradually to 70° and maintained at this point for one hour. A solution of 0.7 g. of sodium hydroxide in 4 cc. of water was added slowly and the temperature was increased to 80° C. for an additional hour. The reaction was cooled to ambient temperature and extracted with ethyl acetate (3×50 mL). The combined organic layer was dried and concentrated to give 0.7 g (90%) of the title compound. LC-MS m/z 153.1 (M+H)$^+$, 1.65 (ret. time).

Intermediate 34

4-bromo-3-methyl-2-nitroaniline

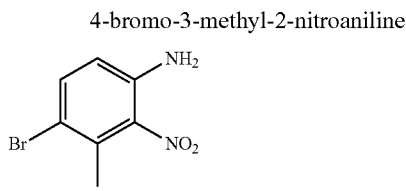

A mixture of NBS (51.5 g, 289 mmol), 3-methyl-2-nitroaniline (44 g, 289 mmol) and acetic acid (450 mL) was stirred at 110° C. for 1 h. The mixture was cooled to ambient temperature and poured into water (100 mL). The solid was collected to give 55 g (78%) of the title compound. LC-MS m/z 230.9 (M+H)$^+$, 1.78 (ret. time).

Intermediate 35

4-Bromo-N,3-dimethyl-2-nitroaniline

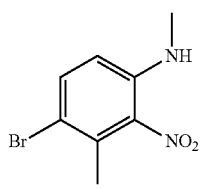

To a solution of 4-bromo-3-methyl-2-nitroaniline (20 g, 87 mmol) in N,N-dimethylformamide (DMF) (200 mL), NaH (3.81 g, 95 mmol) was added at 25° C. The reaction mixture was stirred at 25° C. for 30 minutes. Then iodomethane (12.90 g, 91 mmol) was added. The reaction mixture was stirred for 12 h. The reaction mixture was poured into water and the solid was collected to give 18 g (59.4%) of the title compound. LC-MS m/z 247.0 (M+H)$^+$, 1.90 (ret. time).

Intermediate 36

4-Bromo-N$^1$,3-dimethylbenzene-1,2-diamine

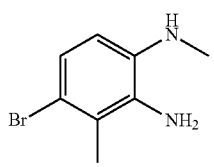

To a solution of 4-Bromo-N,3-dimethyl-2-nitroaniline (30 g, 122 mmol) in ethanol (600 mL), tin(II) chloride (93 g, 490 mmol), was added. The reaction mixture was stirred at 75° C. for 2 h. Then the solvent was adjusted to pH=14 by using 40% NaOH. It was extracted with ethyl acetate (3×500 mL). The combined organic layer was dried over MgSO$_4$ and concentrated to give 26 g (39.5%) of the title compound.

Intermediate 37

5-bromo-1,4-dimethyl-1H-benzo[d][1,2,3]triazole

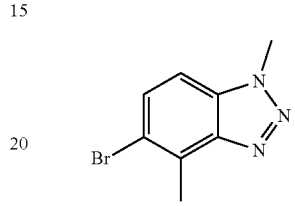

To 4-bromo-N,3-dimethylbenzene-1,2-diamine (30 g, 139 mmol) in 17 ml of 10% H$_2$SO$_4$ at 0° C., sodium nitrite (13.47 g, 195 mmol) was added in small portions over a 20 minute period. After the reaction mixture was stirred for 30 minutes further, 200 mL of water was added. The resulting precipitate was collected by filtration, washed with water and dried. The mother liquid was left to stand 16 h and a second batch of precipitate formed, which was collected as before. The combined solids were purified by silica gel chromatography eluting with ethyl acetate to give the title compound 10 g (21.57%). LC-MS m/z 226.0 (M+H)$^+$, 1.71 (ret. time).

Intermediate 38

(E)-ethyl 3-(1,4-dimethyl-1H-benzo[d][1,2,3]triazol-5-yl)acrylate

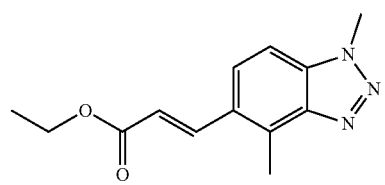 [SMILES: CCOC(=O)/C=C/c1ccc2c(nnn2C)c1C]

To a solution of 5-bromo-1,4-dimethyl-1H-benzo[d][1,2,3]triazole (10 g, 44.2 mmol) in N,N-dimethylformamide (DMF) (20 mL), tri-o-tolylphosphine (2.69 g, 8.85 mmol), methyl acrylate (7.62 g, 88 mmol) and DIPEA (23.18 mL, 133 mmol) were added. Then Pd(OAc)$_2$ (0.993 g, 4.42 mmol) was added. The reaction mixture was stirred at 100° C. for 12 h. The mixture was poured into water and extracted with ethyl acetate (30 mL). The organic layer was dried and concentrated to get crude product. It was purified by silica gel chromatography column (petroleum ether: ethyl acetate=4:1) to give 8.2 g (76%) of the title compound. LC-MS m/z 246.1 (M+H)$^+$, 1.68 (ret. time).

Intermediate 39

Ethyl 3-(1,4-dimethyl-1H-benzo[d][1,2,3]triazol-5-yl)-3-(3-(hydroxymethyl)-4-methylphenyl)propanoate

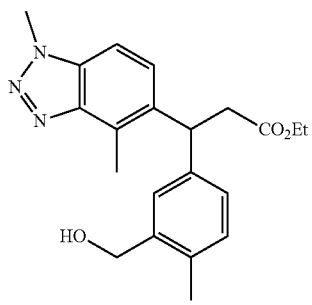 [SMILES: CCOC(=O)CC(c1ccc(C)c(CO)c1)c1ccc2c(nnn2C)c1C]

To a solution of (E)-ethyl 3-(1,4-dimethyl-1H-benzo[d][1,2,3]triazol-5-yl)acrylate (1 g, 4.08 mmol) in 1,4-dioxane (30 mL) and water (10 ml) were added (3-(hydroxymethyl)-4-methylphenyl)boronic acid (1.015 g, 6.12 mmol), triethylamine (0.852 mL, 6.12 mmol) and [RhCl(cod)]$_2$ (0.113 g, 0.204 mmol). The resulting reaction mixture was stirred at 90° C. for 18.5 h. The reaction mixture was extracted with EtOAc (3×30 mL). The combined organic layer was dried over MgSO$_4$, filtered, concentrated under reduced pressure, purified by silica gel chromatography to afford the desired product ethyl 3-(1,4-dimethyl-1H-benzo[d][1,2,3]triazol-5-yl)-3-(3-(hydroxymethyl)-4-methylphenyl)propanoate (1.1954 g, 3.25 mmol, 80% yield). LC-MS m/z 368 (M+H)$^+$, 0.88 (ret. time).

Intermediate 40

2-methoxy-6-nitroaniline

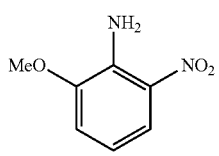

To a solution of 2-amino-3-nitrophenol (2.55 g, 16.55 mmol) in N,N-dimethylformamide (DMF) (35 mL) was added potassium carbonate (2.52 g, 18.20 mmol). The mixture was stirred for 5 min before adding iodomethane (1.138 mL, 18.20 mmol). It was stirred at room temperature for 2 h. Water (75 mL) was added to quench the reaction and the precipitates was collected by filtration, washed with water to give 2.26 g of 2-methoxy-6-nitroaniline (81%). LC-MS m/z 168.9 (M+H)$^+$, 0.74 (ret. time)

Intermediate 41

4-bromo-2-methoxy-6-nitroaniline

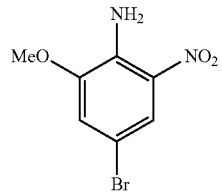 [SMILES: COc1cc(Br)cc([N+](=O)[O-])c1N]

To a solution of 2-methoxy-6-nitroaniline (2.26 g, 13.44 mmol) in acetic acid (50 mL) was added sodium acetate (1.654 g, 20.16 mmol) and bromine (0.762 mL, 14.78 mmol). The mixture was stirred at room temperature for 30 min. Water was added (75 mL) to quench the reaction and the precipitate product was collected by filtration, washed with water and dried over vacuum to give 2.78 g of 4-bromo-2-methoxy-6-nitroaniline (84%). LC-MS m/z 246.9/248.9 (M+H)$^+$, 0.93 (ret. time).

Intermediate 42

4-bromo-2-methoxy-N-methyl-6-nitroaniline

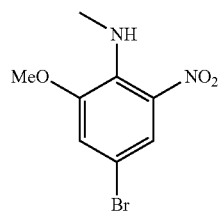

To a solution of 4-bromo-2-methoxy-6-nitroaniline (2.76 g, 11.17 mmol) dissolved in N,N-dimethylformamide (DMF) (50 mL) was added sodium hydride (300 mg, 12.50 mmol) slowly at 0° C. and the reaction mixture was stirred for 30 min. Then methyl iodide (0.768 mL, 12.29 mmol) was added. Water was added (60 mL) to quench the reaction and the precipitate product was collected by filtration, washed with water and dried over vacuum to give 2.82 g of 4-bromo-2-methoxy-N-methyl-6-nitroaniline (97%). LC-MS m/z 260.9/263 (M+H)$^+$, 1.03 (ret. time).

Intermediate 43

5-bromo-7-methoxy-1-methyl-1H-benzo[d][1,2,3]triazole

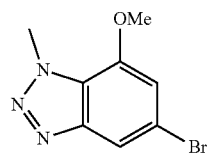

To a solution of 4-bromo-2-methoxy-N-methyl-6-nitroaniline (2.82 g, 10.80 mmol) in glacial acetic acid (100 ml, 1747 mmol) was added zinc (4.94 g, 76 mmol). The reaction mixture was stirred at room temperature for 2 h and 30 min. More zinc (150 mg, 2.294 mmol) was added to the mixture and the solution was stirred until the orange color disappeared (around 30 min). The mixture was filtered and the solid was washed with ethyl acetate. Then the filtrate was concentrated. The crude product was dissolved in sulfuric acid (10%) (50 mL, 10.80 mmol), sodium nitrite was added (0.745 g, 10.80 mmol) in small portions at 0° C. and the mixture was stirred at 0° C. for 1 h and 45 min. Water (100 mL) was added to quench the reaction and the precipitate product was collected by filtration, washed with water and dried under vacuum to give 1.28 g of 5-bromo-7-methoxy-1-methyl-1H-benzo[d][1,2,3]triazole (49%). LC-MS m/z 241.9/243.9 (M+H)$^+$, 0.83 (ret. time).

Intermediate 44

(E)-ethyl 3-(7-methoxy-1-methyl-1H-benzo[d][1,2,3]triazol-5-yl)acrylate

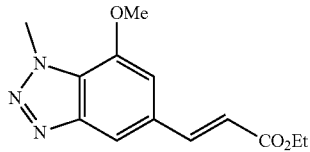 [SMILES: CCOC(=O)/C=C/c1cc(OC)c2c(c1)nnn2C]

To a solution of 5-bromo-7-methoxy-1-methyl-1H-benzo[d][1,2,3]triazole (974 mg, 4.02 mmol) dissolved into DMF (15 mL) were added N,N-diisopropylethylamine (2.108 mL, 12.07 mmol), ethyl acrylate (4.29 mL, 40.2 mmol), diacetoxypalladium (271 mg, 1.207 mmol) and tri-o-tolylphosphine (980 mg, 3.22 mmol). The reaction mixture was heated in microwave at 150° C. for 2 h. Water was added (50 mL) to quench the reaction. Ethyl acetate was added and the layers were separated. Aqueous layer was then extracted with ethyl acetate twice. The combined organic layer was dried with MgSO$_4$, filtered and concentrated. It was then purified by silica gel chromatography to give 820 mg of (E)-ethyl 3-(7-methoxy-1-methyl-1H-benzo[d][1,2,3]triazol-5-yl)acrylate (78%). LC-MS m/z 262 (M+H)$^+$, 0.90 (ret. time).

Intermediate 45

Ethyl 3-(3-(hydroxymethyl)-4-methylphenyl)-3-(7-methoxy-1-methyl-1H-benzo[d][1,2,3]triazol-5-yl)propanoate

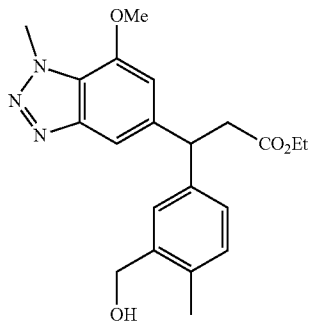 [SMILES: CCOC(=O)CC(c1ccc(C)c(CO)c1)c1cc(OC)c2c(c1)nnn2C]

To a solution of (E)-ethyl 3-(7-methoxy-1-methyl-1H-benzo[d][1,2,3]triazol-5-yl)acrylate (790 mg, 3.02 mmol) in 1,4-dioxane (10 mL) and water (10 mL) was added [RhCl(cod)]$_2$ (502 mg, 0.907 mmol), (3-(hydroxymethyl)-4-methylphenyl)boronic acid (1506 mg, 9.07 mmol) and Et$_3$N (0.969 mL, 6.95 mmol). The mixture was heated in microwave at 150° C. for 45 min. Water (25 mL) and ethyl acetate (25 mL) were added and the layers were separated. The aqueous layer was extracted with ethyl acetate twice. The combined organic layer was dried with MgSO$_4$, filtered, concentrated and purified by silica gel chromatography to give 560 mg of ethyl 3-(3-(hydroxymethyl)-4-methylphenyl)-3-(7-methoxy-1-methyl-1H-benzo[d][1,2,3]triazol-5-yl)propanoate (48%). LC-MS m/z 384.1 (M+H)$^+$, 0.91 (ret. time).

Intermediate 46

2-Chloro-5-fluoro-3-methylpyridine 1-oxide

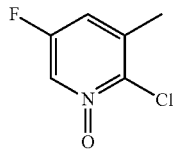

To 2-chloro-5-fluoro-3-methylpyridine (100 mg, 0.687 mmol) in trifluoroacetic acid (TFA) (10 mL) was added H$_2$O$_2$(0.351 mL, 3.43 mmol) slowly under nitrogen at 70° C. The reaction mixture was stirred at 70° C. for 16 h and concentrated. Water (5 mL) and 20 mL of DCM were added. It was adjusted to pH 7 with 28% ammonium hydroxide solution and then extracted with DCM (3×20 mL). The combined organic layer was dried with MgSO$_4$, filtered and concentrated to give the title compound 2-chloro-5-fluoro-3-methylpyridine 1-oxide (100 mg, 0.532 mmol, 77% yield). LC-MS m/z 162.0 (M+H)$^+$, 1.11 min (ret. Time).

Intermediate 47

2-Chloro-3-methyl-5-(methylamino)-4-nitropyridine 1-oxide

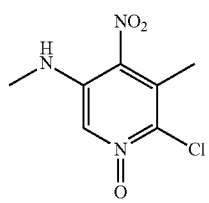

To a solution of 2-chloro-5-fluoro-3-methylpyridine 1-oxide (100 mg, 0.619 mmol) in H$_2$SO$_4$ (5 ml, 94 mmol) at ambient temperature under nitrogen was added potassium nitrate (250 mg, 2.476 mmol) slowly. The reaction mixture was stirred at 110° C. for 16 h after which it was poured into 50 mL of ice/water. Solid was filtered and dried with high vacuum to give 2-chloro-5-fluoro-3-methyl-4-nitropyridine 1-oxide (100 mg, 0.339 mmol, 54.8% yield) as a yellow solid. A mixture of 2-chloro-5-fluoro-3-methyl-4-nitropyridine 1-oxide (100 mg, 0.484 mmol) and methanamine (10 mL, 85 mmol) was stirred at 20° C. for 4 h. After it was concentrated, 10 mL of water was added. Solid was filtered and dried with high vacuum to give the title compound 2-chloro-3-methyl-5-(methylamino)-4-nitropyridine 1-oxide (100 mg, 0.409 mmol, 84% yield) as a yellow solid. LC-MS m/z 218.0 (M+H)$^+$, 1.36 min (ret. Time)

Intermediate 48

6-Chloro-N3,5-dimethylpyridine-3,4-diamine

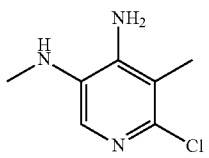

To 2-chloro-3-methyl-5-(methylamino)-4-nitropyridine 1-oxide (100 mg, 0.460 mmol) in ethanol (10 mL) at 20° C. under nitrogen was added nickel (27.0 mg, 0.460 mmol) slowly. It was hydrogenated at 40 psi in a Parr vessel at ambient temperature for 16 h. The mixture was filtered and the filtrate was concentrated to give the title compound 6-chloro-N3,5-dimethylpyridine-3,4-diamine (80 mg, 0.308 mmol, 66.9% yield) as a dark solid. LC-MS m/z 172.1 (M+H)$^+$, 1.01 min (ret. time).

Intermediate 49

6-Chloro-3,7-dimethyl-3H-[1,2,3]triazolo[4,5-c]pyridine

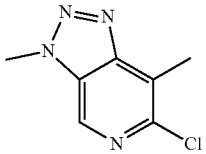

To a solution of 6-chloro-N3,5-dimethylpyridine-3,4-diamine (80 mg, 0.466 mmol) in H$_2$SO$_4$ (0.5 mL, 9.38 mmol) solution and 5 mL of water was added sodium nitrite (260 mg, 3.77 mmol) in water (5 mL) slowly under nitrogen at 0° C. The reaction mixture was stirred at 0° C. for 4 h. Solid was filtered to give the title compound 6-Chloro-3,7-dimethyl-3H-[1,2,3]triazolo[4,5-c]pyridine (50 mg, 0.137 mmol, 29.4% yield). LC-MS m/z 183.0 (M+H)$^+$, 1.45 min (ret. time).

Intermediate 50

(E)-Ethyl 3-(3,7-dimethyl-3H-[1,2,3]triazolo[4,5-c]pyridin-6-yl)acrylate

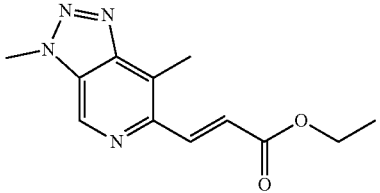 [SMILES: CCOC(=O)/C=C/c1ncc2c(nnn2C)c1C]

A mixture of 6-chloro-3,7-dimethyl-3H-[1,2,3]triazolo[4,5-c]pyridine (100 mg, 0.548 mmol), (E)-ethyl 3-(4,4,5,5-tetramethyl-1,3,2-dioxaborolan-2-yl)acrylate (124 mg, 0.548 mmol), tetrakis(triphenylphosphine)palladium(0) (31.6 mg, 0.027 mmol), and potassium carbonate (151 mg, 1.095 mmol) in 1,2-dimethoxyethane (DME) (3 mL) and ethanol (0.3 mL) was heated in microwave at 150° C. for 2 h (high absorption). Then the reaction mixture was filtered and the filtrate was purified by reverse-phase HPLC (MeOH/0.05% NH$_3$H$_2$O/H$_2$O=50%) to give the title compound (E)-ethyl 3-(3,7-dimethyl-3H-[1,2,3]triazolo[4,5-c]pyridin-6-yl)acrylate (15 mg, 0.059 mmol, 10.59% yield). LCMS m/z 247.1 (M+H)$^+$, 1.67 min (ret. time).

Intermediate 51

(R)-Ethyl 3-(1,4-dimethyl-1H-benzo[d][1,2,3]triazol-5-yl)-3-(3-(hydroxymethyl)-4-methylphenyl)propanoate

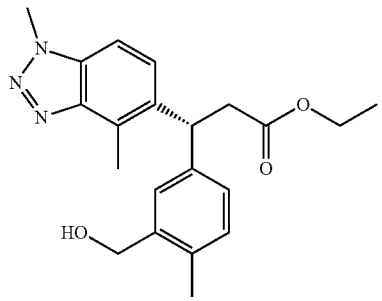 [SMILES: CCOC(=O)C[C@H](c1ccc(C)c(CO)c1)c1ccc2c(nnn2C)c1C]

To a solution of (E)-ethyl 3-(1,4-dimethyl-1H-benzo[d][1,2,3]triazol-5-yl)acrylate (7.5 g, 30.6 mmol) in 1,4-dioxane (60 mL) and water (30 mL) was added (2-methyl-5-(4,4,5,5-tetramethyl-1,3,2-dioxaborolan-2-yl)phenyl)methanol (15.17 g, 61.2 mmol) and TEA (8.52 mL, 61.2 mmol). The reaction mixture was stirred for 10 min and then chloro(1,5-cyclooctadiene)rhodium(I) dimer (0.754 g, 1.529 mmol) was added under the protection of nitrogen after which it was stirred at 90° C. for 16 h. The reaction mixture was extracted with EtOAc (3×100 mL). The combined organic layer was dried over MgSO$_4$ and concentrated. The residue was purified by silica gel chromatography (petroleum ether/ethyl acetate=5:4) to give racemic compound which was separated by chiral SFC chromatography to give the title compound (R)-ethyl 3-(1,4-dimethyl-1H-benzo[d][1,2,3]triazol-5-yl)-3-(3-(hydroxymethyl)-4-methylphenyl)propanoate (3.2 g, 8.45 mmol, 27.6% yield). LC-MS m/z 368.2 (M+H)$^+$, 1.53 min (ret. time).

Intermediate 52

(R)-Ethyl 3-(3-(((tert-butyldimethylsilyl)oxy)methyl)-4-methylphenyl)-3-(1,4-dimethyl-1H-benzo[d][1,2,3]triazol-5-yl)propanoate

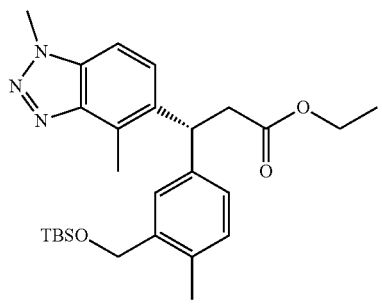 [SMILES: CCOC(=O)C[C@H](c1ccc(C)c(CO[Si](C)(C)C(C)(C)C)c1)c1ccc2c(nnn2C)c1C]

To a solution of (R)-ethyl 3-(1,4-dimethyl-1H-benzo[d][1,2,3]triazol-5-yl)-3-(3-(hydroxymethyl)-4-methylphenyl)propanoate (3.2 g, 8.71 mmol) in dichloromethane (DCM) (30 mL) at 0° C. was added imidazole (1.186 g, 17.42 mmol), DMAP (0.053 g, 0.435 mmol) and tert-butylchlorodimethylsilane (1.969 g, 13.06 mmol). The reaction mixture was stirred at 0° C. to 25° C. for 2 h. The mixture was quenched with water (10 mL) and extracted with DCM (3×20 mL). The combined organic layer was washed with water (2×8 mL) and brine (2×8 mL), dried over Na$_2$SO$_4$, filtered and concentrated. The residue was purified by silica gel chromatography (petroleum ether/ethyl acetate=5%) to give the title compound (R)-ethyl 3-(3-(((tert-butyldimethylsilyl)oxy)methyl)-4-methylphenyl)-3-(1,4-dimethyl-1H-benzo[d][1,2,3]triazol-5-yl)propanoate (3.2 g, 6.44 mmol, 74.0% yield) as yellow oil. LC-MS m/z 482.2 (M+H)$^+$, 1.98 min (ret. time).

Intermediate 53

(R)-3-(3-(((Tert-butyldimethylsilyl)oxy)methyl)-4-methylphenyl)-3-(1,4-dimethyl-1H-benzo[d][1,2,3]triazol-5-yl)propanoic Acid

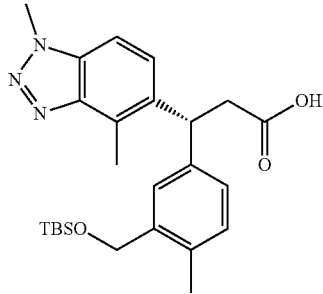 [SMILES: Cc1ccc([C@@H](CC(=O)O)c2ccc3c(nnn3C)c2C)cc1CO[Si](C)(C)C(C)(C)C]

To a solution of (R)-ethyl 3-(3-(((tert-butyldimethylsilyl)oxy)methyl)-4-methylphenyl)-3-(1,4-dimethyl-1H-benzo[d][1,2,3]triazol-5-yl)propanoate (3.1 g, 6.44 mmol) in tetrahydrofuran (THF) (5.00 mL)/methanol (10 mL) was added LiOH (0.462 g, 19.31 mmol) in water (5.00 mL). The reaction mixture was stirred at 25° C. for 16 h. Solvent was concentrated. The residue was adjusted to pH 5 with 3M HCl (3.0 mL) and extracted with ethyl acetate (2×100 mL). The organic phase was washed with water (50 mL), dried over sodium sulfate, filtered and evaporated in vacuum to give the title compound (R)-3-(3-(((tert-butyldimethylsilyl)oxy)methyl)-4-methylphenyl)-3-(1,4-dimethyl-1H-benzo[d][1,2,3]triazol-5-yl)propanoic acid (2.9 g, 4.67 mmol, 72.5% yield) as a yellow oil. LC-MS m/z 454.2 min (M+H)$^+$, 1.84 (ret. time).

Intermediate 54

(R)-Benzyl 3-(3-(((tert-butyldimethylsilyl)oxy)methyl)-4-methylphenyl)-3-(1,4-dimethyl-1H-benzo[d][1,2,3]triazol-5-yl)propanoate

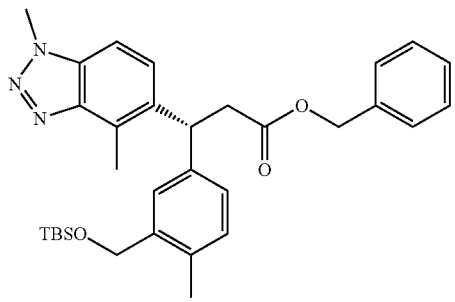 [SMILES: Cc1ccc([C@@H](CC(=O)OCc2ccccc2)c2ccc3c(nnn3C)c2C)cc1CO[Si](C)(C)C(C)(C)C]

To a solution of (R)-3-(3-(((tert-butyldimethylsilyl)oxy)methyl)-4-methylphenyl)-3-(1,4-dimethyl-1H-benzo[d][1,2,3]triazol-5-yl)propanoic acid (2.8 g, 6.17 mmol) in acetonitrile (30 mL) were added (bromomethyl)benzene (1.161 g, 6.79 mmol) and K$_2$CO$_3$ (1.706 g, 12.34 mmol). The reaction mixture was stirred at 25° C. for 16 h. Solvent was evaporated and the residue was purified by silica gel chromatography (petroleum ether/ethyl acetate=10:1) to give the title compound (R)-benzyl 3-(3-(((tert-butyldimethylsilyl)oxy)methyl)-4-methylphenyl)-3-(1,4-dimethyl-1H-benzo[d][1,2,3]triazol-5-yl)propanoate (2.5 g, 3.68 mmol, 59.6% yield) as a yellow oil. LC-MS m/z 544.3 (M+H)$^+$, 2.48 min (ret. time).

Intermediate 55

(3R)-Benzyl 3-(3-(((tert-butyldimethylsilyl)oxy)methyl)-4-methylphenyl)-3-(1,4-dimethyl-1H-benzo[d][1,2,3]triazol-5-yl)-2-methylpropanoate

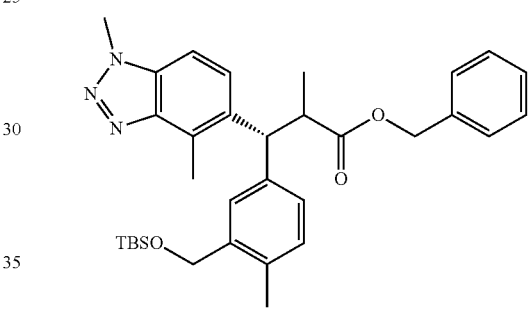

To a solution of (R)-Benzyl 3-(3-(((tert-butyldimethylsilyl)oxy)methyl)-4-methylphenyl)-3-(1,4-dimethyl-1H-benzo[d][1,2,3]triazol-5-yl)propanoate (300 mg, 0.552 mmol) in tetrahydrofuran (THF) (10 mL) at −78° C. was added solution of 1 M LDA in THF (118 mg, 1.103 mmol). The wine red solution was stirred at −78° C. for 45 min and then MeI (0.034 mL, 0.552 mmol) was added in one portion. Then the red wine color was turned to light yellow. The reaction mixture was stirred at −78° C. for 45 min after which it was diluted with EtOAc (75 mL) and water (25 mL). The aqueous layer was extracted with EtOAc (25 mL). The combined organic layer was washed with saturated NaCl (25 mL), dried over Na$_2$SO$_4$ and concentrated. This reaction was repeated 4 times (Total 1.5 g starting material). Those five batches are combined and purified by reverse-phase HPLC (0.05% HN$_4$HCO$_3$/H$_2$O: CH$_3$CN=5%-95%) to give the title compound (3R)-benzyl 3-(3-(((tert-butyldimethylsilyl)oxy)methyl)-4-methylphenyl)-3-(1,4-dimethyl-1H-benzo[d][1,2,3]triazol-5-yl)-2-methylpropanoate (250 mg, 0.426 mmol, 15.44% yield) as a yellow oil. LC-MS m/z 558.3 (M+H)$^+$, 2.50 min (ret. time).

Intermediate 56

(3R)-Benzyl 3-(1,4-dimethyl-1H-benzo[d][1,2,3]triazol-5-yl)-3-(3-(hydroxymethyl)-4-methylphenyl)-2-methylpropanoate

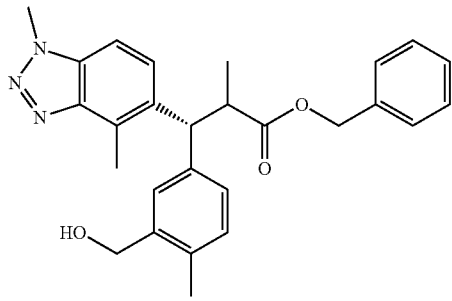

To a solution of (3R)-benzyl 3-(3-(((tert-butyldimethylsilyl)oxy)methyl)-4-methylphenyl)-3-(1,4-dimethyl-1H-benzo[d][1,2,3]triazol-5-yl)-2-methylpropanoate (240 mg, 0.430 mmol) in tetrahydrofuran (THF) (10 mL) at 0° C. was added TBAF (124 mg, 0.473 mmol). The reaction mixture was stirred at 0° C. for 1 h. The mixture was quenched with saturated NH$_4$Cl (20 mL) and extracted with ethyl acetate (3×50 mL). The organic layer was washed with water (30 mL) and brine (30 mL), dried over Na$_2$SO$_4$ and concentrated. The residue was purified by silica gel TLC (petroleum ether/ethyl acetate=3:1) to give the title compound (3R)-benzyl 3-(1,4-dimethyl-1H-benzo[d][1,2,3]triazol-5-yl)-3-(3-(hydroxymethyl)-4-methylphenyl)-2-methylpropanoate (154 mg, 0.330 mmol, 77% yield) as a white solid. LC-MS m/z 444.2 (M+H)$^+$, 1.90 min (ret. time).

Intermediate 57

(Z)-((1-(Benzyloxy)prop-1-en-1-yl)oxy)(tert-butyl)dimethylsilane

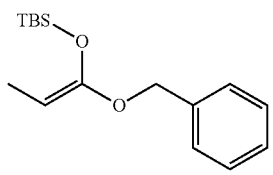

To a solution of diisopropylamine (19.10 mL, 134 mmol) in tetrahydrofuran (THF) (200 mL) at 0° C. was added butyllithium (53.6 mL, 134 mmol, 2.5M solution in hexanes). The reaction mixture was stirred at 0° C. for 30 min. Then it was cooled to −78° C., benzyl propionate (20 g, 122 mmol) in THF (10 mL) and chlorotrimethylsilane (15.88 g, 146 mmol) were added. The reaction mixture was stirred at −78° C. for 1 h. After the mixture was warmed to ambient temperature, solvent was removed. Water (50 mL) was added and the mixture was extracted with petroleum ether (2×150 mL), dried over MgSO$_4$, filtered and concentrated. The residue was purified by distillation (0.5 Hg, 82-90° C.) to give the title compound as colorless oil. $^1$H NMR (400 MHz, CDCl$_3$) δ=7.18-7.07 (m, 6H), 4.63 (s, 2H), 1.38 (d, J=2.4 Hz, 3H), 0.03 (s, 9H).

Intermediate 58

Benzyl 3-(1,4-dimethyl-1H-benzo[d][1,2,3]triazol-5-yl)-3-(3-(((4-methoxybenzyl)oxy)methyl)-4-methylphenyl)-2-methylpropanoate

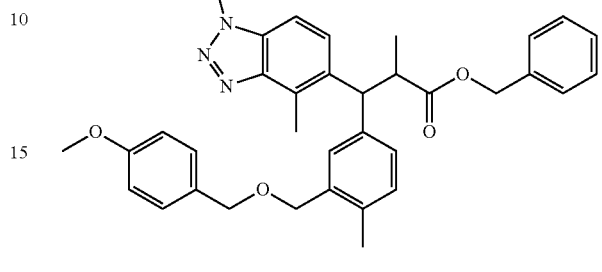

To a solution of (Z)-((1-(benzyloxy)prop-1-en-1-yl)oxy)trimethylsilane (6.79 g, 28.7 mmol) in dry acetonitrile (40 mL) was slowly added DBU (0.029 mL, 0.192 mmol) and 2,2,2-trichloroacetonitrile (1.660 g, 11.50 mmol) under N$_2$ protection. After the mixture was stirred at ambient temperature for 30 min, (1,4-dimethyl-1H-benzo[d][1,2,3]triazol-5-yl)(3-(((4-methoxybenzyl)oxy)methyl)-4-methylphenyl)methanol (4 g, 9.58 mmol) and 1,1,1-trifluoro-N-((trifluoromethyl)sulfonyl)methanesulfonamide (0.135 g, 0.479 mmol) was added into the reaction. The reaction mixture was stirred at ambient temperature for 2 h. Water (20 mL) was added to quench the reaction. The mixture was extracted with ethyl acetate (3×100 mL) and the organic layer was washed with brine, dried over MgSO$_4$, filtered and concentrated to give the title compound benzyl 3-(1,4-dimethyl-1H-benzo[d][1,2,3]triazol-5-yl)-3-(3-(((4-methoxybenzyl)oxy)methyl)-4-methylphenyl)-2-methylpropanoate (1.2 g, 2.086 mmol, 21.78% yield) which was carried to the next step without further purification. LC-MS m/z 563.8 (M+H)$^+$, 1.95 min (ret. time).

Intermediate 59

3-(((4-Methoxybenzyl)oxy)methyl)-4-methylbenzaldehyde

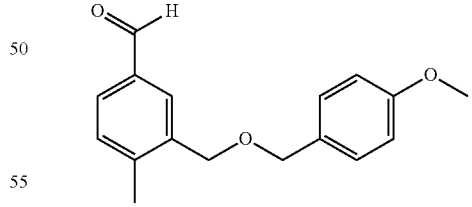

To a solution of 4-bromo-2-(((4-methoxybenzyl)oxy)methyl)-1-methylbenzene (80 g, 249 mmol) in tetrahydrofuran (THF) (800 mL) at −78° C. under nitrogen, butyllithium (120 mL, 299 mmol) was carefully added. The reaction mixture was stirred at −78° C. for 65 min, and then DMF (38.6 mL, 498 mmol) was added. The reaction mixture was stirred at −78° C. to 25° C. for another 30 min. It was quenched with sat. NH$_4$Cl (300 mL), and extracted with ethyl acetate (2×500 mL), the organic layer was washed with water (300 mL) and brine (2×100 mL), dried over Na$_2$SO$_4$, filtered and concentrated. The residue was washed with petroleum ether/ethyl acetate=10/1 (2000 mL) to obtain the title compound 3-(((4-methoxybenzyl)oxy)methyl)-4-methylbenzaldehyde (50 g, 185 mmol, 74.3% yield) as a solid. LC-MS m/z 288.1 (M+H$_2$O), 2.044 min (ret. time).

Intermediate 60

(1,4-Dimethyl-1H-benzo[d][1,2,3]triazol-5-yl)(3-(((4-methoxybenzyl)oxy)methyl)-4-methylphenyl)methanol

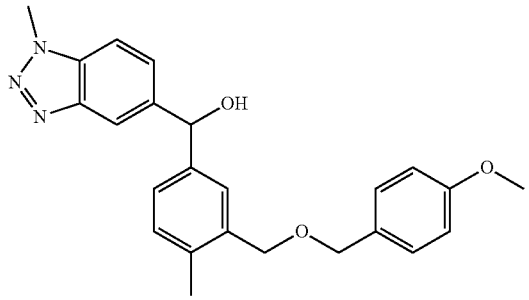 [SMILES: COc1ccc(COCc2cc(C(O)c3ccc4c(c3)nnn4C)ccc2C)cc1]

To a solution of 5-bromo-1,4-dimethyl-1H-benzo[d][1,2,3]triazole (36 g, 159 mmol) in dry tetrahydrofuran (THF) (500 mL) was added tert-butyllithium (147 mL, 191 mmol) at −78° C. under the protection of nitrogen. It was stirred at −78° C. for 0.5 h. Then a solution of 3-(((4-methoxybenzyl)oxy)methyl)-4-methylbenzaldehyde (43.0 g, 159 mmol) in dry tetrahydrofuran (THF) (500 mL) was added into the reaction mixture. After it was stirred at −78° C. for 1.5 hr, the reaction mixture was warmed to 25° C. and continuously stirred for an additional 1 h. Saturated NH$_4$Cl aqueous solution (100 mL) was added to quench the reaction. Then the reaction mixture was extracted with EtOAc (2×300 mL). The combined the organic layer was washed with brine (2×200 mL), dried with MgSO$_4$ and concentrated. The residue was purified by silica gel chromatography (EtOAc: PE=1:5) to obtain the title compound (1,4-dimethyl-1H-benzo[d][1,2,3]triazol-5-yl)(3-(((4-methoxybenzyl)oxy)methyl)-4-methylphenyl)methanol (24 g, 57.5 mmol, 36.1% yield) as a clear oil. LCMS m/z 418.2 (M+H)$^+$, 2.05 min (ret. time).

Intermediate 61

Methyl 3-(1,4-dimethyl-1H-benzo[d][1,2,3]triazol-5-yl)-3-(3-(hydroxymethyl)-4-methylphenyl)-2,2-dimethylpropanoate

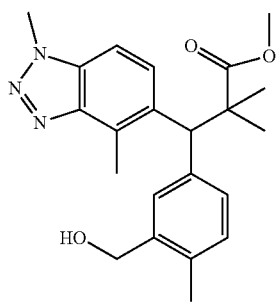 [SMILES: COC(=O)C(C)(C)C(c1ccc(C)c(CO)c1)c1ccc2c(nnn2C)c1C]

To a solution of (1,4-dimethyl-1H-benzo[d][1,2,3]triazol-5-yl)(3-(((4-methoxybenzyl)oxy)methyl)-4-methylphenyl)methanol (15.0 g, 35.9 mmol) in dichloromethane (DCM) (250.0 mL) was added ((1-methoxy-2-methylprop-1-en-1-yl)oxy)trimethylsilane (12.53 g, 71.9 mmol), then titanium tetrachloride (3.96 mL, 35.9 mmol) in DCM (20 ml) was slowly dropped into the reaction at 0° C. under N$_2$ protection. The reaction mixture was stirred at 0° C. for 30 min under N$_2$ protection, then was warmed to ambient temperature and continuously stirred for an additional 4 h. Then the reaction mixture was poured into saturated NaHCO$_3$ aqueous solution (100 mL) at 0° C. The organic layer was separated and the aqueous layer was extracted with DCM (3×50 mL). The combined organic layer was washed with brine (100 mL) and dried over anhydrous Na$_2$SO$_4$ and concentrated. The residue was purified with a silica gel chromatography (petroleum ether/ethyl acetate=1:1) to obtain the title compound methyl 3-(1,4-dimethyl-1H-benzo[d][1,2,3]triazol-5-yl)-3-(3-(hydroxymethyl)-4-methylphenyl)-2,2-dimethylpropanoate (3.0 g, 7.63 mmol, 21.23% yield) as a solid. LCMS m/z 382.2 (M+H)$^+$, 1.82 min (ret. time).

Intermediate 62

(S)-Methyl 3-(1,4-dimethyl-1H-benzo[d][1,2,3]triazol-5-yl)-3-(3-(hydroxymethyl)-4-methylphenyl)-2,2-dimethylpropanoate and (R)-methyl 3-(1,4-dimethyl-1H-benzo[d][1,2,3]triazol-5-yl)-3-(3-(hydroxymethyl)-4-methylphenyl)-2,2-dimethylpropanoate

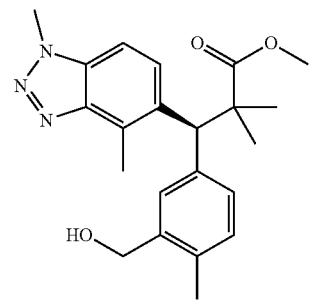

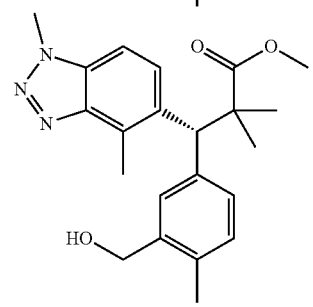

Methyl 3-(1,4-dimethyl-1H-benzo[d][1,2,3]triazol-5-yl)-3-(3-(hydroxymethyl)-4-methylphenyl)-2,2-dimethylpropanoate (4.5 g, 11.80 mmol) was separated by chiral SFC chromatography to obtain isomer 1-(S)-methyl 3-(1,4-dimethyl-1H-benzo[d][1,2,3]triazol-5-yl)-3-(3-(hydroxymethyl)-4-methylphenyl)-2,2-dimethylpropanoate (1.4 g, 3.49 mmol, 29.6%) and isomer 2-(R)-methyl 3-(1,4-dimethyl- 1H-benzo[d][1,2,3]triazol-5-yl)-3-(3-(hydroxymethyl)-4-methylphenyl)-2,2-dimethylpropanoate (1.1 g, 2.74 mmol, 23.22%).

Intermediate 63

1-((2,3-Difluorobenzyl)amino)-2-methylpropan-2-ol

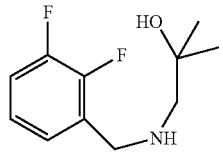

To a solution of 2,3-difluorobenzaldehyde (10 g, 70.4 mmol) in methanol (100 mL) was added 1-amino-2-methylpropan-2-ol (6.27 g, 70.4 mmol) and NaOH (7.04 mL, 7.04 mmol). It was stirred under nitrogen atmosphere for 1 h, and then NaBH$_4$ (1.065 g, 28.1 mmol) was added portion wise over 10 min. The reaction was stirred at ambient temperature for 24 h. The crude product was purified by silica gel chromatography. The fractions were concentrated to give the title compound (10 g, 44.0 mmol, 62.5% yield) as an off-white solid. LC-MS: m/z: 216.13 (M+H)$^+$, 1.915 min (ret. time).

Intermediate 64

9-Fluoro-2,2-dimethyl-2,3,4,5-tetrahydrobenzo[f][1,4]oxazepine

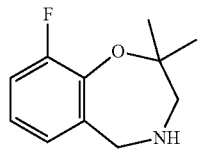

To a solution of 1-((2,3-difluorobenzyl)amino)-2-methylpropan-2-ol (2 g, 9.29 mmol) in dimethyl sulfoxide (DMSO) (20 mL) was added potassium tert-butoxide (2.085 g, 18.58 mmol) and the reaction mixture was stirred at 80° C. for 2 h. The reaction mixture was poured in ice water (100 mL) and extracted with ethyl acetate (2×100 mL). The combined organic layer was washed with water (2×100 mL), brine (100 mL) and then dried over Na$_2$SO$_4$. It was filtered and concentrated. The crude residue was purified with silica gel chromatography to give the title compound (2 g, 5.77 mmol, 62.1% yield) as gummy liquid. LC-MS: m/z: 196.09 (M+H)$^+$, 1.875 min (ret. time).

Intermediate 65

Tert-Butyl 9-fluoro-2,2-dimethyl-2,3-dihydrobenzo[f][1,4]oxazepine-4(5H)-carboxylate

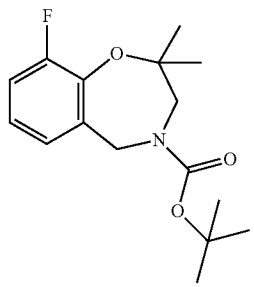 [SMILES: CC(C)(C)OC(=O)N1Cc2cccc(F)c2OC(C)(C)C1]

To a solution of 9-fluoro-2,2-dimethyl-2,3,4,5-tetrahydrobenzo[f][1,4]oxazepine (5 g, 25.6 mmol) in dichloromethane (DCM) (50 mL) at 0° C. was added TEA (7.14 mL, 51.2 mmol) and Boc-anhydride (7.73 mL, 33.3 mmol). The reaction was stirred at ambient temperature for 3 h, diluted with water (100 mL) and extracted with ethyl acetate (2×100 mL), washed with brine solution (100 mL), dried over anhydrous Na$_2$SO$_4$, filtered and concentrated. The crude residue was purified with silica gel chromatography to give the title compound (6.5 g, 21.47 mmol, 84% yield) as an off-white solid. LC-MS: m/z: 239.94 (M-56)$^+$, 6.256 min (ret. time).

Intermediate 66

9-Fluoro-2,2-dimethyl-2,3,4,5-tetrahydrobenzo[f][1,4]oxazepine hydrochloride

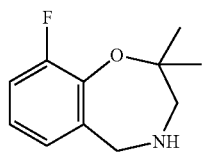

To a solution of tert-butyl 9-fluoro-2,2-dimethyl-2,3-dihydrobenzo[f][1,4]oxazepine-4(5H)-carboxylate (6.5 g, 22.01 mmol) in dichloromethane (DCM) (20 mL) at 10° C. was added 4 M HCl in 1,4-dioxane (16.51 mL, 66.0 mmol). It was stirred for 1 h. The obtained precipitate was filtered and triturated with hexane, dried well to give the title compound (4.47 g, 18.99 mmol, 86% yield) as an off-white solid. LC-MS m/z: 196.0 (M-HCl)$^+$, 3.335 min (ret. time).

Intermediate 67

(R)-1-((2-Bromo-3-fluorobenzyl)amino)butan-2-ol

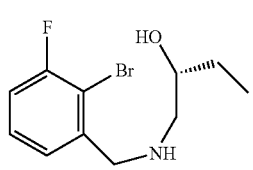

To a solution of 2-bromo-3-fluorobenzaldehyde (600 mg, 2.96 mmol) in methanol (8 mL) was added (R)-1-aminobutan-2-ol (263 mg, 2.96 mmol) and 1 N NaOH (0.5 mL, 0.500 mmol) under nitrogen atmosphere. NaBH$_4$ (224 mg, 5.91 mmol) was added at 0° C. portionwise over 10 min. The reaction was stirred at ambient temperature for 72 h. The resulting mixture was concentrated and the crude residue was purified with silica gel chromatography to give the title compound (600 mg, 2.173 mmol, 73.5% yield) as colorless liquid. LC-MS: m/z 278.17 (M+H)$^+$, 1.307 min (ret. time).

Intermediate 68

(R)-2-Ethyl-9-fluoro-2,3,4,5-tetrahydrobenzo[f][1,4]oxazepine

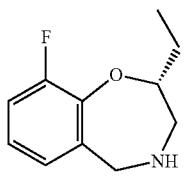

To a solution of (R)-1-((2-bromo-3-fluorobenzyl)amino)butan-2-ol (600 mg, 2.173 mmol) in isopropanol (15 mL) was added Cs$_2$CO$_3$ (601 mg, 4.35 mmol) and copper(I) iodide (41.4 mg, 0.217 mmol) and the reaction mixture was stirred at 90° C. in microwave reactor for 48 h. The reaction mixture was quenched with cold water, extracted twice with EtOAC followed by brine solution. The organic layer was dried over anhydrous Na$_2$SO$_4$ and filtered and concentrated. The crude compound was purified with silica gel chromatography to afford the title compound (300 mg, 1.430 mmol, 65.8% yield) as liquid. LC-MS: m/z 196.21 (M+H)$^+$, 1.26 min (ret. time).

Intermediate 69

(R)-2-Ethyl-9-fluoro-2,3,4,5-tetrahydrobenzo[f][1,4]oxazepine hydrochloride

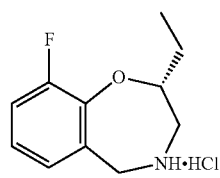

To a solution of (R)-2-ethyl-9-fluoro-2,3,4,5-tetrahydrobenzo[f][1,4]oxazepine (250 mg, 1.281 mmol) in 1,4-dioxane (10 mL) at 0° C. was added 4 M HCl in dioxane (2 mL, 8.00 mmol). The reaction mixture was stirred at ambient temperature for 3 h. The reaction mixture was concentrated and triturated with hexane, diethyl ether to give the title compound (280 mg, 1.139 mmol, 89% yield) as yellow solid. LC-MS: m/z 196.1 (M+H)$^+$, 3.3 min (ret. time).

The compounds in Table 1 were prepared by a method similar to the one described for the preparation of (R)-2-Ethyl-9-fluoro-2,3,4,5-tetrahydrobenzo[f][1,4]oxazepine hydrochloride using potassium tert-butoxide for cyclization. As is appreciated by those skilled in the art, these analogous examples may involve variations in general reaction conditions.

TABLE 1

| Reagent | Product Name | Product Structure | (M + H)$^+$ | Ret. Time (min) |
|---|---|---|---|---|
| 2-bromo-6-fluorobenzaldehyde | (R)-2-Ethyl-6-fluoro-2,3,4,5-tetrahydrobenzo[f][1,4]oxazepine hydrochloride | | 196.1 | 3.38 |
| 2-bromo-4-fluorobenzaldehyde | (R)-2-Ethyl-8-fluoro-2,3,4,5-tetrahydrobenzo[f][1,4]oxazepine hydrochloride | | 196.0 | 3.38 |
| 2-bromo-5-fluorobenzaldehyde | (R)-2-Ethyl-7-fluoro-2,3,4,5-tetrahydrobenzo[f][1,4]oxazepine hydrochloride | | 196.15 | 1.20 |

TABLE 1-continued

| Reagent | Product Name | Product Structure | (M + H)+ | Ret. Time (min) |
|---|---|---|---|---|
| 2-bromo-5-methylbenzaldehyde | (R)-2-Ethyl-7-methyl-2,3,4,5-tetrahydrobenzo[f][1,4]oxazepine | | 192.35 | 3.02 |
| 2-bromo-5-chlorobenzaldehyde | (R)-7-Chloro-2-ethyl-2,3,4,5-tetrahydrobenzo[f][1,4]oxazepine | | 212.17 | 3.41 |
| 2-bromo-3-methylbenzaldehyde | (R)-2-Ethyl-9-methyl-2,3,4,5-tetrahydrobenzo[f][1,4]oxazepine | | 192.0 | 3.47 |
| 2-bromo-4-methoxybenzaldehyde | 2-Ethyl-8-methoxy-2,3,4,5-tetrahydrobenzo[f][1,4]oxazepine | | 1H NMR (400 MHz, D6-DMSO) δ = 7.03 (d, J = 7.9 Hz, 1H), 6.57-6.45 (m, 2H), 3.77-3.69 (m, 5H), 3.79-3.61 (m, 1H), 3.55-3.44 (m, 1H), 3.05 (br d, J = 13.4 Hz, 1H), 2.76-2.66 (m, 1H), 1.60-1.41 (m, 2H), 1.01 (t, J = 7.3 Hz, 3H). | |
| 2-bromo-4-methylbenzaldehyde | (R)-2-Ethyl-8-methyl-2,3,4,5-tetrahydrobenzo[f][1,4]oxazepine | | 192.35 | 3.00 |
| 2-bromobenzaldehyde | 2,2-Dimethyl-2,3,4,5-tetrahydrobenzo[f][1,4]oxazepine | | 178.19 | 2.72 |
| 3-bromoisonicotinaldehyde | (R)-2-Ethyl-2,3,4,5-tetrahydropyrido[4,3-f][1,4]oxazepine | | 179.26 | 2.37 |
| 2-bromobenzaldehyde | (R)-2-Ethyl-2,3,4,5-tetrahydrobenzo[f][1,4]oxazepine hydrochloride | | 178.1 | 1.563 |

TABLE 1-continued

| Reagent | Product Name | Product Structure | (M + H)⁺ | Ret. Time (min) |
|---|---|---|---|---|
| | 7-Methoxy-2,2-dimethyl-2,3,4,5-tetrahydrobenzo[f][1,4]oxazepine | | 208.1 | 3.17 |
| | 7-chloro-2,2-dimethyl-2,3,4,5-tetrahydrobenzo[f][1,4]oxazepine | | 212.0 | 3.49 |
| | 2,2,8-Trimethyl-2,3,4,5-tetrahydrobenzo[f][1,4]oxazepine | | 192.20 | 1.36 |
| | 7-Fluoro-2,2-dimethyl-2,3,4,5-tetrahydrobenzo[f][1,4]oxazepine | | 196.11 | 1.22 |
| | 7-Bromo-2,2-dimethyl-2,3,4,5-tetrahydrobenzo[f][1,4]oxazepine | | 256.07 | 1.45 |
| | 8-Bromo-2,2-dimethyl-2,3,4,5-tetrahydrobenzo[f][1,4]oxazepine | | 256.15 | 1.52 |
| | 2,2-Dimethyl-2,3,4,5-tetrahydropyrido[3,4-f][1,4]oxazepine hydrochloride | | 179.0 | 2.7 |
| | (R)-2-Methyl-2,3,4,5-tetrahydrobenzo[f][1,4]oxazepine hydrochloride | | 164.23 | 2.36 |

TABLE 1-continued

| Reagent | Product Name | Product Structure | (M + H)+ | Ret. Time (min) |
|---|---|---|---|---|
| (R)-2-Ethyl-4-bromo-3-formyl-2-fluoropyridine | (R)-2-Ethyl-6-fluoro-2,3,4,5-tetrahydropyrido[3,4-f][1,4]oxazepine | | 197.0 | 4.3 |
| (R)-4-bromo-2-fluoro-3-formylpyridine | (R)-6-Bromo-2-ethyl-2,3,4,5-tetrahydropyrido[3,2-f][1,4]oxazepine | | 256.9, 258.9 | 4.23 |
| 3-bromo-4-formylpyridine | 2,2-dimethyl-2,3,4,5-tetrahydropyrido[4,3-f][1,4]oxazepine | | 179.0 (M − HCl)+ | 3.33 |

Intermediate 70

Tert-Butyl 7-bromo-2,2-dimethyl-2,3-dihydrobenzo[f][1,4]oxazepine-4(5H)-carboxylate To a solution of 7-bromo-2,2-dimethyl-2,3,4,5-tetrahydrobenzo[f][1,4]oxazepine (700 mg, 2.73 mmol) in dichloromethane (DCM) (5 mL) at ambient temperature was added TEA (0.381 mL, 2.73 mmol). Tert-butyl dicarbonate (596 mg, 2.73 mmol) was added at 0° C. The reaction mixture was stirred at ambient temperature for 1 h. It was diluted with water and extracted with ethyl acetate, dried over Na₂SO₄, filtered and concentrated. The crude residue was purified with silica gel chromatography to give the title compound (900 mg, 2.444 mmol, 89% yield) as liquid. LC-MS m/z 300.13 (M+H)+, 4.23 min (ret. time).

Intermediate 71

2,2-Dimethyl-2,3,4,5-tetrahydrobenzo[f][1,4]oxazepine-7-carbonitrile

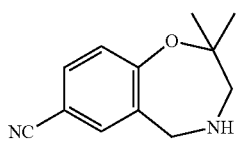

To a solution of tert-butyl 7-bromo-2,2-dimethyl-2,3-dihydrobenzo[f][1,4]oxazepine-4(5H)-carboxylate (300 mg, 0.842 mmol) in N,N-dimethylformamide (DMF) (5 mL) at ambient temperature was added Zn(CN)₂ (99 mg, 0.842 mmol). The reaction mixture was degassed for 20 min, followed by the addition of tetrakis(triphenylphosphine)palladium(0) (97 mg, 0.084 mmol). The reaction mixture was heated in microwave reactor for 1 h at 95° C. The reaction mixture was concentrated and purified with silica gel chromatography to give the title compound (90 mg, 0.101 mmol, 12.02% yield) as liquid. LC-MS m/z 203.21 (M+H)+, 1.22 min (ret. time).

Intermediate 72 tert-Butyl 7-cyano-2,2-dimethyl-2,3-dihydrobenzo[f][1,4]oxazepine-4(5H)-carboxylate

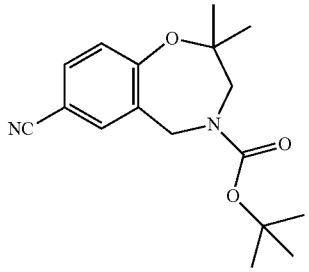 [SMILES: CC(C)(C)OC(=O)N1Cc2cc(C#N)ccc2OC(C)(C)C1]

To a solution of 2,2-dimethyl-2,3,4,5-tetrahydrobenzo[f][1,4]oxazepine-7-carbonitrile (270 mg, 1.335 mmol) and TEA (0.186 mL, 1.335 mmol) in dichloromethane (DCM) (5 mL) at 0° C. was added tert-butyl dicarbonate (291 mg, 1.335 mmol). The reaction mixture was stirred at ambient temperature for 1 h. The reaction mixture was diluted with water and extracted with ethyl acetate, dried over Na$_2$SO$_4$, filtered and concentrated. The crude residue was purified with silica gel chromatography to give the title compound (300 mg, 0.930 mmol, 69.7% yield) as liquid. LC-MS m/z 247.15 (M+H)$^+$, 2.63 min (ret. time).

Intermediate 73

2,2-Dimethyl-2,3,4,5-tetrahydrobenzo[f][1,4]oxazepine-7-carbonitrile hydrochloride

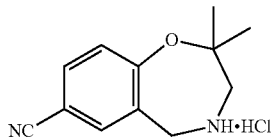

To a solution of tert-butyl 7-cyano-2,2-dimethyl-2,3-dihydrobenzo[f][1,4]oxazepine-4(5H)-carboxylate (300 mg, 0.992 mmol) in 1,4-dioxane (5 mL) at 0° C. was added 4M HCl in dioxane (1 mL, 4.00 mmol). The reaction mixture was stirred at ambient temperature for 2 h. The reaction mixture was concentrated and triturated with 1:4 diethyl ether:hexane. It was dried to give the title compound (190 mg, 0.776 mmol, 78% yield) as solid. LC-MS m/z 203.24 (M+H)$^+$, 1.17 min (ret. time).

Intermediate 74

Tert-Butyl 8-bromo-2,2-dimethyl-2,3-dihydrobenzo[f][1,4]oxazepine-4(5H)-carboxylate

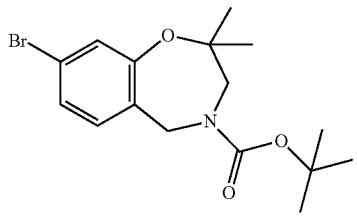 [SMILES: CC(C)(C)OC(=O)N1Cc2ccc(Br)cc2OC(C)(C)C1]

To a solution of 8-bromo-2,2-dimethyl-2,3,4,5-tetrahydrobenzo[f][1,4]oxazepine (800 mg, 3.12 mmol) in dichloromethane (DCM) (15 mL) at 0° C. was added TEA (0.871 mL, 6.25 mmol) and boc-anhydride (0.870 mL, 3.75 mmol). The reaction was stirred at ambient temperature for 2 h. The reaction mixture was concentrated, and then quenched with ice water and extracted with DCM twice. The organic layer was dried with Na$_2$SO$_4$, filtered, and concentrated. The crude residue was purified with silica gel chromatography to give the title compound (900 mg, 2.429 mmol, 78% yield) as color less liquid. LC-MS m/z 255.9 (M-Boc)$^+$, 4.33 min (ret. time).

Intermediate 75

2,2-Dimethyl-2,3,4,5-tetrahydrobenzo[f][1,4]oxazepine-8-carbonitrile

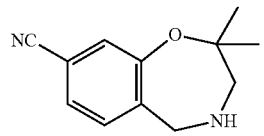

To a solution of tert-butyl 8-bromo-2,2-dimethyl-2,3-dihydrobenzo[f][1,4]oxazepine-4(5H)-carboxylate (450 mg, 1.263 mmol) in N,N-dimethylformamide (DMF) (5 mL) was added Zn(CN)$_2$ (178 mg, 1.516 mmol). The reaction mixture was degassed for 10 min followed by addition of tetrakis(triphenylphosphine)palladium(0) (146 mg, 0.126 mmol). The reaction mixture was heated in microwave reactor for 1 h at 90° C. The reaction mixture was quenched with ice water, extracted twice with EtOAc, washed with water and brine solution. The organic layer was dried over anhydrous Na$_2$SO$_4$ and filtered and concentrated. The crude residue was purified with silica gel chromatography to give the title compound (200 mg, 0.989 mmol, 78% yield). LC-MS m/z 203.16 (M+H)$^+$, 1.30 min (ret. time).

Intermediate 76 tert-Butyl 8-cyano-2,2-dimethyl-2,3-dihydrobenzo[f][1,4]oxazepine-4(5H)-carboxylate

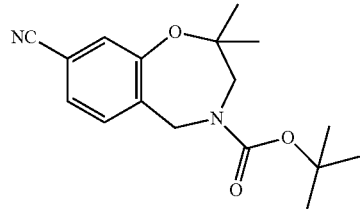 [SMILES: CC(C)(C)OC(=O)N1Cc2ccc(C#N)cc2OC(C)(C)C1]

To a solution of 2,2-dimethyl-2,3,4,5-tetrahydrobenzo[f][1,4]oxazepine-8-carbonitrile (400 mg, 1.978 mmol) in dichloromethane (DCM) (15 mL) at 0° C. was added TEA (0.551 mL, 3.96 mmol) and BOC-anhydride (0.551 mL, 2.373 mmol). The reaction was stirred at ambient temperature for 2 h. The reaction mixture was concentrated and quenched with ice water and extracted with twice DCM. The organic layer was dried over anhydrous Na$_2$SO$_4$, filtered and concentrated. The crude residue was purified with silica gel chromatography to give the title compound (210 mg, 0.690 mmol, 34.9% yield) as color less liquid. LC-MS m/z 203.0 (M-BOC)$^+$, 3.94 min (ret. time).

Intermediate 77

2,2-Dimethyl-2,3,4,5-tetrahydrobenzo[f][1,4]oxazepine-8-carbonitrile hydrochloride

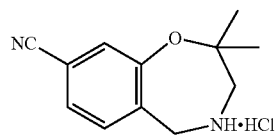

To a solution of tert-butyl 8-cyano-2,2-dimethyl-2,3-dihydrobenzo[f][1,4]oxazepine-4(5H)-carboxylate (200 mg, 0.661 mmol) in 1,4-dioxane (5 mL) at 0° C. was added 4M HCl in dioxane (1 mL, 4.00 mmol). The reaction was stirred at ambient temperature for 2 h. The reaction mixture was concentrated and triturated with diethyl ether to give the title compound (130 mg, 0.537 mmol, 81% yield) as yellow solid. LCMS: 203.24 m/z: M+H)+, 1.17 min (ret. time)

Intermediate 78

(S)-2-(((2-Hydroxybutyl)amino)methyl)pyridin-3-ol

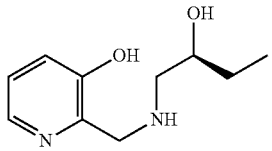

To a solution of (S)-1-aminobutan-2-ol (0.724 g, 8.12 mmol) in methanol (10 mL) was added NaOH (0.812 mL, 0.812 mmol). After 30 min, NaBH$_4$ (0.246 g, 6.50 mmol) was added at 0° C. The reaction was stirred at ambient temperature for 16 h and then concentrated. The crude residue was dissolved in water (5 mL), extracted with 10% MeOH in DCM. The combined organic layer was dried over anhydrous Na$_2$SO$_4$, filtered and concentrated to give the title compound (800 mg, 3.61 mmol, 44.5% yield). LC-MS: m/z 197.0 (M+H)+, 2.31 min (ret. time).

Intermediate 79

(R)-2-Ethyl-2,3,4,5-tetrahydropyrido[2,3-f][1,4]oxazepine

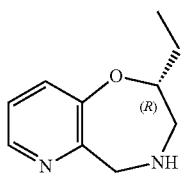

To a solution of (S)-2-(((2-hydroxybutyl)amino)methyl)pyridin-3-ol (800 mg, 4.08 mmol) in tetrahydrofuran (THF) (15 mL) at 0° C. was added triphenylphosphine (1604 mg, 6.11 mmol) and DEAD (0.968 mL, 6.11 mmol). The reaction was stirred at 25° C. for 2 h. The crude residue was concentrated and purified with silica gel chromatography to give the title compound (250 mg, 0.711 mmol, 17.44% yield). LCMS: m/z–179.0 (M+H)+, 2.86 min (ret. time)

Intermediate 80

(R)-tert-Butyl 2-ethyl-2,3-dihydropyrido[2,3-f][1,4]oxazepine-4(5H)-carboxylate

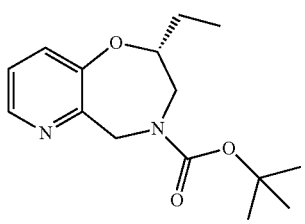 [SMILES: CC[C@@H]1CN(C(=O)OC(C)(C)C)Cc2ncccc2O1]

To a solution of (R)-2-ethyl-2,3,4,5-tetrahydropyrido[2,3-f][1,4]oxazepine (250 mg, 1.403 mmol) in dichloromethane (DCM) (5 mL) was added TEA (0.293 mL, 2.104 mmol) and BOC-anhydride (0.326 mL, 1.403 mmol). The reaction was stirred at 25° C. for 1 h. It was diluted with water and extracted with DCM (3×10 mL). The combined organic layer was dried over anhydrous Na$_2$SO$_4$, filtered and concentrated to give the title compound (200 mg, 0.533 mmol, 38.0% yield). LCMS: m/z–279.29 (M+H)+, 2.07 min (ret. time)

Intermediate 81

(R)-2-Ethyl-2,3,4,5-tetrahydropyrido[2,3-f][1,4]oxazepine

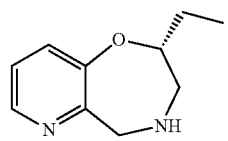

To a solution of (R)-tert-butyl 2-ethyl-2,3-dihydropyrido[2,3-f][1,4]oxazepine-4(5H)-carboxylate (200 mg, 0.719 mmol) in 1,4-dioxane (2 mL) at 0° C. was added 4 M HCl in 1,4-dioxane (0.359 mL, 0.719 mmol). The reaction was stirred at ambient temperature for 1 h. The reaction mixture was concentrated and then dissolved in DCM (20 mL), and washed with saturated NaHCO$_3$ solution (2×15 mL). The organic layer was dried over anhydrous Na$_2$SO$_4$, filtered and concentrated to give the title compound (80 mg, 0.282 mmol, 39.3% yield). LCMS: m/z=179.23 (M+H)+, 2.66 min (ret. time)

Intermediate 82

1-((2,4-Dibromobenzyl)amino)butan-2-ol

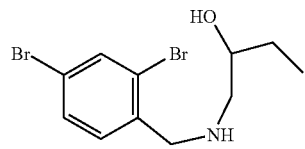

To a solution of 2,4-dibromo-1-(bromomethyl)benzene (700 mg, 2.129 mmol) and 1-aminobutan-2-ol (190 mg, 2.129 mmol) in tetrahydrofuran (THF) (20 mL) and water (4.00 mL) at ambient temperature was added K$_2$CO$_3$ (441 mg, 3.19 mmol). The reaction was stirred for 15 h, diluted with water (20 mL) and extracted with EtOAc (2×20 mL). The combined organic layer was washed with brine solution (20 mL) and dried over anhydrous Na$_2$SO$_4$, filtered and concentrated. The crude residue was concentrated and purified with silica gel chromatography to give the title compound (400 mg, 0.900 mmol, 42.3% yield) as a white solid. LCMS: m/z=337.9 (M+H)+, 3.699 min (ret. time)

Intermediate 83

8-Bromo-2-ethyl-2,3,4,5-tetrahydrobenzo[f][1,4]oxazepine

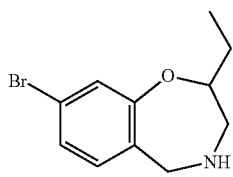

To a solution of 1-((2,4-dibromobenzyl)amino)butan-2-ol (400 mg, 1.187 mmol) in N,N-dimethylformamide (DMF) (5 mL) in a sealed tube at ambient temperature were added Cs$_2$CO$_3$ (773 mg, 2.374 mmol) and copper(I) iodide (45.2 mg, 0.237 mmol). It was heated at 100° C. for 30 h. The reaction mixture was cooled and diluted with ice water (30 mL). It was extracted with EtOAc (2×30 mL). The combined organic layer was washed with brine solution (30 mL), dried over anhydrous Na$_2$SO$_4$, filtered and concentrated. The crude residue was concentrated and purified with silica gel chromatography to give the title compound (150 mg, 0.471 mmol, 39.7% yield). LC-MS: m/z 255.9 (M+H)$^+$, 3.585 min (ret. time).

The compounds in Table 2 were prepared by a method similar to the one described for the preparation of 8-bromo-2-ethyl-2,3,4,5-tetrahydrobenzo[f][1,4]oxazepine. As is appreciated by those skilled in the art, these analogous examples may involve variations in general reaction conditions.

To 2-hydroxybenzamide (500 mg, 3.65 mmol) in tetrahydrofuran (THF) was added methyl 2-bromopentanoate (1067 mg, 5.47 mmol) and potassium carbonate (504 mg, 3.65 mmol). The resulting reaction mixture was heated in a Biotage microwave at high absorption for 1.5 h at 120° C. The reaction was stirred at ambient temperature for 2 days and then filtered. It was washed with ethyl acetate. The filtrate was concentrated. The crude product was purified by silica gel chromatography. The desired fractions were concentrated to give the title compound (750 mg, 2.98 mmol, 82% yield) as white solid. LC-MS m/z 251.9 (M+H)$^+$, 0.78 min (ret. time).

Intermediate 85

2-Propylbenzo[f][1,4]oxazepine-3,5(2H,4H)-dione

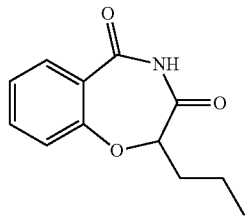

To methyl 2-(2-carbamoylphenoxy)pentanoate (300 mg, 1.194 mmol) in N,N-dimethylformamide (DMF) (3 mL) was added sodium methoxide (2.388 mL, 1.194 mmol) slowly. The resulting reaction mixture was stirred at ambient temperature for 23 h. The solvent was removed under reduced

TABLE 2

| Reagent | Product Name | Product Structure | (M + H)$^+$ | Ret. Time (min) |
|---|---|---|---|---|
| ![Br, Br, F structure] | 2-Ethyl-7-fluoro-2,3,4,5-tetrahydrobenzo[f][1,4]oxazepine | ![product structure] | 196.01 | 3.37 |
| ![Br, Br, Cl structure] | 6-Chloro-2-ethyl-2,3,4,5-tetrahydrobenzo[f][1,4]oxazepine | ![product structure] | 212.0 | 1.57 |

Intermediate 84

Methyl 2-(2-carbamoylphenoxy)pentanoate

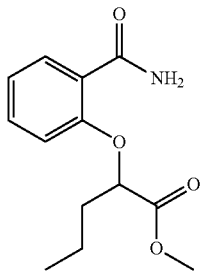 [SMILES: CCCC(Oc1ccccc1C(N)=O)C(=O)OC]

pressure and the residue was purified by silica gel chromatography to give the title compound (116 mg, 0.529 mmol, 44.3% yield) as white solid. LC-MS m/z 220.0 (M+H)$^+$, 0.87 min (ret. time).

Intermediate 86

2-Propyl-2,3,4,5-tetrahydrobenzo[f][1,4]oxazepine

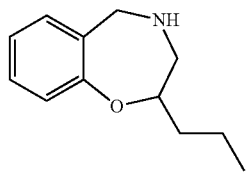

To a suspension of LAH (60.2 mg, 1.587 mmol) in tetrahydrofuran (THF) (2 mL) was added a solution of 2-propylbenzo[f][1,4]oxazepine-3,5(2H,4H)-dione (116 mg, 0.529 mmol) in tetrahydrofuran (THF) (2 mL). The mixture was heated in a Biotage microwave at high absorption for 1.5 h at 100° C. Saturated $Na_2SO_4$ (0.26 mL) was added dropwise. The mixture was stirred for 30 min. The reaction mixture turned from grey to white solution. The solid was filtered and washed with ethyl acetate. The filtrate was concentrated to give the title compound (100 mg, 0.523 mmol, 99% yield). LC-MS m/z 192.0 $(M+H)^+$, 0.54 min (ret. time).

The compounds in Table 3 were prepared by a method similar to the one described for the preparation of 2-propyl-2,3,4,5-tetrahydrobenzo[f][1,4]oxazepine. As is appreciated by those skilled in the art, these analogous examples may involve variations in general reaction conditions.

TABLE 3

| Structure | Name | LCMS [M + H]$^+$ | Retention Time (min) |
|---|---|---|---|
| 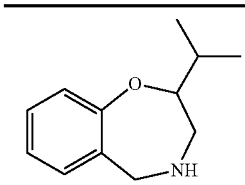 | 2-isopropyl-2,3,4,5-tetrahydro-benzo[f][1,4]oxazepine | 192.1 | 0.61 |
| 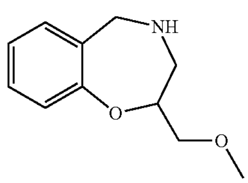 | 2-(Methoxymethyl)-2,3,4,5-tetrahydro-benzo[f][1,4]oxazepine | 194.0 | 0.43 |
| 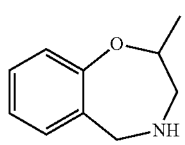 | 2-Methyl-2,3,4,5-tetrahydro-benzo[f][1,4]oxazepine | 163.9 | 0.42 |

Intermediate 87

Bromo-2-(chloromethyl)-1-methylbenzene

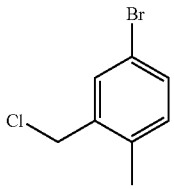

To a solution of (5-bromo-2-methylphenyl)methanol (5 g, 24.87 mmol) in dichloromethane (DCM) (50 mL) at 10° C. was added $SOCl_2$ (2.72 mL, 37.3 mmol). The reaction was stirred for 3 h. It was concentrated and then diluted with $NaHCO_3$ solution and extracted with EtOAc (2×20 mL). The combined organic layer was washed with brine solution (20 mL), dried over anhydrous $Na_2SO_4$, filtered and concentrated to give the title compound (5 g, 22.78 mmol, 92% yield) as color less liquid. 1H NMR (400 MHz, dmso) δ=7.62 (d, J=2.0 Hz, 1H), 7.44 (dd, J=2.2, 8.1 Hz, 1H), 7.20 (d, J=8.1 Hz, 1H), 4.77 (s, 2H), 3.30 (s, 1H).

Intermediate 88

(R)-4-(5-Bromo-2-methylbenzyl)-2-ethyl-2,3,4,5-tetrahydrobenzo[f][1,4]oxazepine

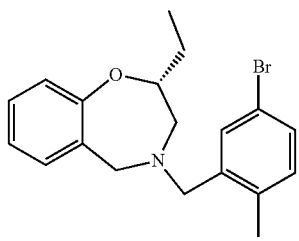 [SMILES: CC[C@@H]1CN(Cc2cc(Br)ccc2C)Cc2ccccc2O1]

To a solution of (R)-2-ethyl-2,3,4,5-tetrahydrobenzo[f][1,4]oxazepine (2.261 g, 12.76 mmol) in acetonitrile (20 mL) was added 4-bromo-2-(chloromethyl)-1-methylbenzene (2 g, 9.11 mmol) followed by addition of DIPEA (4.77 mL, 27.3 mmol). The reaction mixture was stirred at 120° C. in a microwave reactor for 1 h. It was cooled, diluted with ice water and extracted with EtOAc (2×20 mL). The combined organic layer was washed with brine solution (30 mL), dried over anhydrous $Na_2SO_4$, filtered and concentrated. The crude residue was concentrated and purified with silica gel chromatography to give the title compound (6 g, 12.43 mmol, 136% yield) as a color less liquid. LCMS: m/z: 360.22 $(M+H)^+$, 2.17 min. (ret. time)

Intermediate 89

(R)-2-Ethyl-4-(2-methyl-5-(4,4,5,5-tetramethyl-1,3,2-dioxaborolan-2-yl)benzyl)-2,3,4,5-tetrahydrobenzo[f][1,4]oxazepine

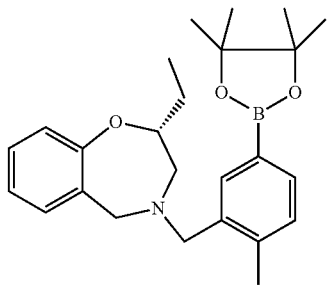 [SMILES: CC[C@@H]1CN(Cc2cc(B3OC(C)(C)C(C)(C)O3)ccc2C)Cc2ccccc2O1]

To a solution of (R)-4-(5-bromo-2-methylbenzyl)-2-ethyl-2,3,4,5-tetrahydrobenzo[f][1,4]oxazepine (3 g, 8.33 mmol) in 1,4-dioxane (10 mL) were added bis(pinacolato)diboron (2.54 g, 9.99 mmol) and potassium acetate (1.634 g, 16.65 mmol). The reaction mixture was degassed with argon for 10 min after which $PdCl_2$(dppf)-$CH_2Cl_2$ adduct (0.680 g, 0.833 mmol) was added. The reaction mixture was heated at 90° C. for 16 h. The reaction mixture was filtered though celite and washed with ethyl acetate (100 mL). The filtrate was concentrated. The crude product was purified with silica gel chromatography to give the title compound (2.8 g, 5.31 mmol, 63.8% yield) as a gum. LCMS: m/z: 408.42 $(M+H)^+$, 2.17 min (ret. time) The compounds in Table 4 were prepared by a method similar to the one described for the preparation of 9-Fluoro-2,2-dimethyl-2,3,4,5-tetrahydrobenzo[f][1,4]oxazepine hydrochloride. As is appreciated by those skilled in the art, these analogous examples may involve variations in general reaction conditions.

TABLE 4

| Reagent | Product Name | Product Structure | (M + H)+ | Ret. Time (min) |
|---|---|---|---|---|
| | 2,2-Dimethyl-2,3,4,5-tetrahydropyrido[2,3-f][1,4]oxazepine hydrochloride | | 178.92 | 1.057 |
| | (R)-2-Ethyl-9-fluoro-2,3,4,5-tetrahydropyrido[3,4-f][1,4]oxazepine, Hydrochloride | | 197.0 | 4.11 |
| | 8-Fluoro-2,2-dimethyl-2,3,4,5-tetrahydrobenzo[f][1,4]oxazepine hydrochloride | | 196.06 | 3.796 |
| | 2,2,7-trimethyl-2,3,4,5-tetrahydrobenzo[f][1,4]oxazepine hydrochloride | | 192.27 | 1.32 |

Intermediate 90

(R)-8-Chloro-2-ethyl-2,3,4,5-tetrahydropyrido[3,4-f][1,4]oxazepine hydrochloride

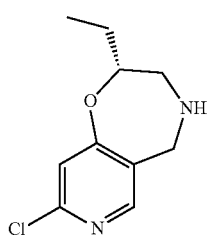

5-(Bromomethyl)-2,4-dichloropyridine

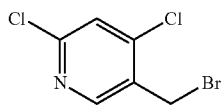

To a solution of (4,6-dichloropyridin-3-yl)methanol (7 g, 39.3 mmol) in dichloromethane (100 mL) was added PBr₃ (7.42 mL, 79 mmol) at 0° C. and the reaction stirred at ambient temperature for 2 h. The reaction mixture was evaporated under reduced pressure, quenched with saturated NaHCO₃ solution (50 mL) and extracted with DCM (2×50 mL). The combined organic layer was washed with brine solution (40 mL) and dried over Na₂SO₄, filtered and concentrated to give the title compound (7 g, 22.54 mmol, 57.3% yield). LCMS: m/z: 240.2 (M+2H)+, 2.43 min (ret. time)

(R)-1-(((4,6-Dichloropyridin-3-yl)methyl)amino)butan-2-ol

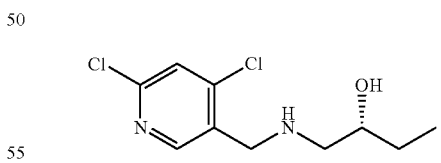

To a solution of (R)-1-aminobutan-2-ol (5.18 g, 58.1 mmol) in dichloromethane (80 mL) was added 5-(bromomethyl)-2,4-dichloropyridine (7 g, 29.1 mmol) and TEA (8.10 mL, 58.1 mmol) and the reaction stirred for 16 h at 25° C. The reaction mixture was diluted with water (40 mL) and extracted with DCM (3×30 mL). The combined organic layer was washed with brine solution (30 mL), dried over anhydrous Na₂SO₄, filtered and concentrated. The crude product was purified by silica gel chromatography to give the title compound (5 g, 17.64 mmol, 60.7% yield). LC-MS: m/z 249.23 (M+H)+, 3.55 min (ret. time)

(R)-8-Chloro-2-ethyl-2,3,4,5-tetrahydropyrido[3,4-f][1,4]oxazepine

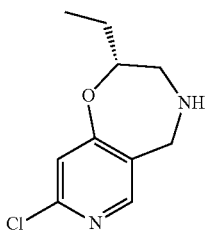

To a solution of (R)-1-(((4,6-dichloropyridin-3-yl)methyl)amino)butan-2-ol (5 g, 20.07 mmol) in dimethyl sulfoxide (50 mL) at 0° C. was added potassium tert-butoxide (5.63 g, 50.2 mmol). The reaction mixture was heated to 65° C. for 30 min. The reaction was quenched with ice water and extracted with ethyl acetate (3×50 mL). The combined organic layer was washed with ice cold water (4×50 mL) then washed with brine (50 mL). The organic layer was dried over anhydrous $Na_2SO_4$, filtered and concentrated. The crude product was purified by silica gel chromatography to give the title compound (2 g, 8.52 mmol, 42.5% yield). LC-MS: m/z: 212.97 $(M+H)^+$, 1.834 min (ret. time)

(R)-tert-Butyl 8-chloro-2-ethyl-2,3-dihydropyrido[3,4-f][1,4]oxazepine-4(5H)-carboxylate

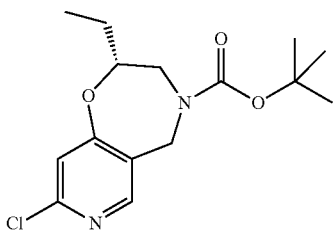 [SMILES: CC[C@@H]1CN(C(=O)OC(C)(C)C)Cc2cnc(Cl)cc2O1]

To a solution of (R)-8-chloro-2-ethyl-2,3,4,5-tetrahydropyrido[3,4-f][1,4]oxazepine (2 g, 9.40 mmol) in dichloromethane (20 mL) was added TEA (1.966 mL, 14.11 mmol) and $Boc_2O$ (2.183 mL, 9.40 mmol) and the reaction stirred for 1 h. The reaction mixture was concentrated under reduced pressure. The reaction was quenched with ice water and extracted with ethyl acetate (2×5 mL). The combined organic layer was washed with brine (5 mL). The organic layer was dried over anhydrous $Na_2SO_4$, filtered and concentrated under reduced pressure to give the crude residue. The crude product was purified by silica gel chromatography to give the title compound (2 g, 6.22 mmol, 66.1% yield). LC-MS: m/z: 313.04 $(M+H)^+$, 5.76 min (ret. time)

(R)-8-Chloro-2-ethyl-2,3,4,5-tetrahydropyrido[3,4-f][1,4]oxazepine hydrochloride

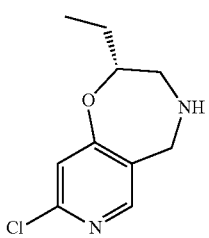

To a solution of (R)-tert-butyl 8-chloro-2-ethyl-2,3-dihydropyrido[3,4-f][1,4]oxazepine-4(5H)-carboxylate (1.7 g, 5.43 mmol) in dioxane (20 mL) at 0° C. was added 4M HCl in 1,4-Dioxane (4.08 mL, 16.30 mmol). It was allowed to warm to 25° C. and the reaction stirred for 3 h. The reaction mixture was concentrated. To the residue was added diethyl ether (20 mL) and the reaction stirred for 30 min. The resulting solid was filtered and dried to give the title compound (1.4 g, 5.50 mmol, 101% yield) as white solid. LC-MS: 213.1 $(M-HCl)^+$, 3.877 min (ret. time)

Intermediate 91

4-Ethyl-6-fluoro-2,3,4,5-tetrahydro-1Hbenzo[c]azepine hydrochloride

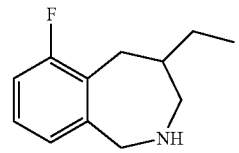

2-(Bromomethyl)-3-fluorobenzonitrile

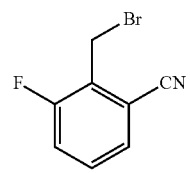

To a solution of 3-fluoro-2-methylbenzonitrile (1 g, 7.40 mmol) in $CCl_4$ (10 ml, 104 mmol) was added AIBN (0.243 g, 1.480 mmol) and NBS (1.580 g, 8.88 mmol). The reaction mixture was heated to reflux for 16 h. The reaction mixture was quenched with water (20 mL), and extracted with ethyl acetate (2×20 mL). The combined organic layer was washed with brine (80 mL), dried over anhydrous $Na_2SO_4$, filtered and concentrated. The crude product was purified by silica gel chromatography using 5% ethyl acetate in n-hexane to give the title compound (500 mg, 2.336 mmol, 31.6% yield). GC-MS m/z 213.0, 8.036 min (ret. time)

Ethyl 2-(2-cyano-6-fluorobenzyl)butanoate

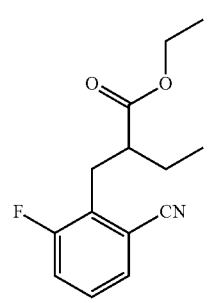 [SMILES: CCOC(=O)C(CC)Cc1c(F)cccc1C#N]

To a solution of ethyl butyrate (271 mg, 2.336 mmol) in tetrahydrofuran (10 mL) at −78° C. was added LDA (500 mg, 4.67 mmol) and the reaction stirred for 45 min. Then a solution of 2-(bromomethyl)-3-fluorobenzonitrile (500 mg, 2.336 mmol) in tetrahydrofuran (4 mL) was added at same the temperature and the reaction stirred for 30 min. It was allowed to warm to 25° C. and the reaction stirred for 2 h. The reaction mixture was quenched with water (20 mL), and extracted with ethyl acetate (2×20 mL). The combined organic layer was washed with brine solution (80 mL), dried over anhydrous Na$_2$SO$_4$, filtered and concentrated. The crude product was purified by silica gel chromatography using 5% ethyl acetate in n-Hexane to give the title compound (400 mg, 0.742 mmol, 31.8% yield. LC-MS: m/z 250.02 (M+H)$^+$, 2.49 min (ret. time)

2-(2-(Aminomethyl)-6-fluorobenzyl)butan-1-ol

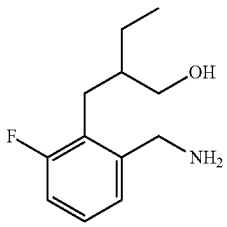

To a solution of ethyl 2-(2-cyano-6-fluorobenzyl)butanoate (400 mg, 1.605 mmol) in tetrahydrofuran (5 mL) at 0° C. was added LAH (1.605 mL, 1.605 mmol). The reaction was allowed to stir at 25° C. for 16 h. The reaction mixture was quenched with saturated Na$_2$SO$_4$ solution (20 mL), and extracted with ethyl acetate (3×10 mL). The combined organic layer was washed with brine solution (15 mL), dried over anhydrous Na$_2$SO$_4$, filtered and concentrated to give the title compound (320 mg, 0.905 mmol, 56.4% yield). LC-MS: m/z 212.28 (M+H)$^+$, 2.99 min (ret. time)

tert-Butyl 3-fluoro-2-(2-(hydroxymethyl)butyl)benzylcarbamate

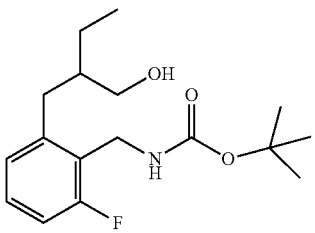 [SMILES: CCC(CO)Cc1cccc(F)c1CNC(=O)OC(C)(C)C]

To a solution of 2-(2-(aminomethyl)-6-fluorobenzyl)butan-1-ol (320 mg, 1.515 mmol) in dichloromethane (10 mL) was added Boc$_2$O (0.352 mL, 1.515 mmol) and the reaction stirred for 2 h at 25° C. The reaction mixture was quenched with ice cold water and extracted with DCM (3×10 mL). The combined organic layer was washed with brine solution (15 mL), dried over anhydrous Na$_2$SO$_4$, filtered and concentrated. The crude residue was purified by silica gel chromatography using 20% ethyl acetate in n-Hexane to give the title compound (300 mg, 0.809 mmol, 53.4% yield). GC-MS m/z 312.37 (M+H)$^+$, 5.50 min (ret. time)

2-(2-(((tert-Butoxycarbonyl)amino)methyl)-3-fluorobenzyl)butyl methanesulfonate

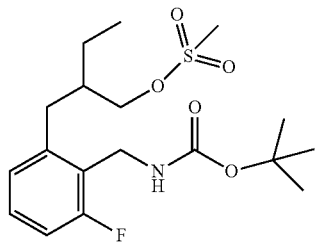 [SMILES: CCC(COS(C)(=O)=O)Cc1cccc(F)c1CNC(=O)OC(C)(C)C]

To a solution of tert-butyl 2-fluoro-6-(2-(hydroxymethyl)butyl)benzylcarbamate (300 mg, 0.963 mmol) in dichloromethane (10 mL) was added TEA (0.269 mL, 1.927 mmol). The reaction mixture was cooled to 0° C. then mesyl chloride (0.188 mL, 2.409 mmol) was added and the reaction stirred for 1 h. The reaction mixture was quenched with ice cold water and extracted with DCM (3×20 mL). The combined organic layer was washed with brine solution (20 mL), dried over anhydrous Na$_2$SO$_4$, filtered and concentrated. The crude residue was purified by silica gel chromatography using 15% ethyl acetate in n-Hexane to give the title compound (280 mg, 0.591 mmol, 61.3% yield). LC-MS: m/z 390.06 (M+H)$^+$, 2.56 min (ret. time)

tert-Butyl 4-ethyl-6-fluoro-4,5-dihydro-1Hbenzo[c]azepine-2(3H)-carboxylate

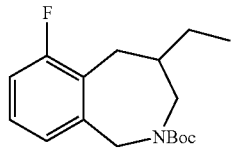 [SMILES: CCC1Cc2c(F)cccc2CN(C(=O)OC(C)(C)C)C1]

To a solution of 2-(2-(((tert-butoxycarbonyl)amino)methyl)-6-fluorobenzyl)butyl methanesulfonate (3.98 g, 10.22 mmol) in isopropanol (40 mL) was added Cs$_2$CO$_3$ (8.32 g, 25.5 mmol) and copper(I) iodide (0.195 g, 1.022 mmol). The reaction mixture was heated to 95° C. in a sealed tube for 16 h. The reaction mixture was filtered through a celite pad, washed with ethyl acetate (50 mL) and the filtrate was concentrated to give the crude residue. The crude product was purified by silica gel chromatography using 2% ethyl acetate in n-Hexane to give the title compound (2.5 g, 7.96 mmol, 78% yield). LC-MS: m/z 294.29 (M+H)$^+$, 6.98 min (ret. time)

4-Ethyl-6-fluoro-2,3,4,5-tetrahydro-1Hbenzo[c]azepine hydrochloride

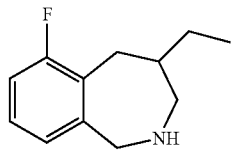

To a solution of tert-butyl 4-ethyl-6-fluoro-4,5-dihydro-1H-benzo[c]azepine-2(3H)-carboxylate (2.5 g, 8.52 mmol) in 1,4-dioxane (5 mL) at 0° C. was added HCl in dioxane (4 mL, 16.00 mmol, 4M). The reaction was stirred at 25° C. for 2 h. The reaction mixture was concentrated to give the crude residue. Diethyl ether (20 ml) was added to the residue and the reaction stirred for 30 min then filtered. The solid was dried under vacuum to give the title compound (1.5 g, 6.28 mmol, 73.7% yield) LC-MS m/z 194.0 (M+H)$^+$, 3.54 min (ret. time)

Intermediate 92

Methyl 3-(1,4-dimethyl-1H-benzo[d][1,2,3]triazol-5-yl)-2,2-dimethyl-3-(3-oxo-2,3-dihydro-1H-inden-5-yl)propanoate

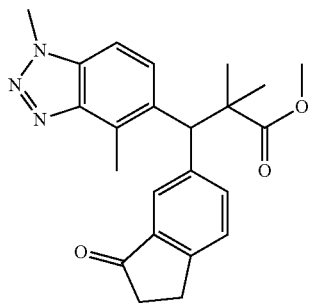 [SMILES: COC(=O)C(C)(C)C(c1ccc2c(c1)C(=O)CC2)c1ccc2c(nnn2C)c1C]

(3-((tert-Butyldimethylsilyl)oxy)-2,3-dihydro-1H-inden-5-yl)(1,4-dimethyl-1H-benzo[d][1,2,3]triazol-5-yl)methanol

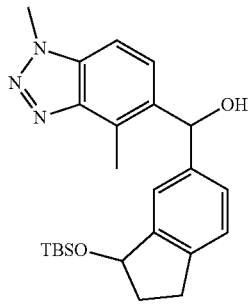 [SMILES: Cc1c(C(O)c2ccc3c(c2)C(O[Si](C)(C)C(C)(C)C)CC3)ccc2c1nnn2C]

To a solution of 5-bromo-1,4-dimethyl-1H-benzo[d][1,2,3]triazole (3.60 g, 15.92 mmol) in tetrahydrofuran (THF) (100 mL) was added tert-butyllithium (13.47 mL, 17.51 mmol) at −78° C. under nitrogen. The reaction mixture was stirred at −78° C. for 1 h, then 3-((tert-butyldimethylsilyl)oxy)-2,3-dihydro-1H-indene-5-carbaldehyde (4.40 g, 15.92 mmol) in THF (20 mL) was slowly added. The reaction mixture was stirred at −78° C. for 2 h and ambient temperature for 8 h. The reaction mixture was quenched with saturated NH$_4$Cl solution and extracted with ethyl acetate (3×). The combined organic layer was washed with brine, dried over anhydrous Na$_2$SO$_4$ and concentrated. The residue was purified silica gel chromatography (petroleum ether:ethyl acetate=1:1) to provide the title compound (3-((tert-Butyldimethylsilyl)oxy)-2,3-dihydro-1H-inden-5-yl)(1,4-dimethyl-1H-benzo[d][1,2,3]triazol-5-yl)methanol (2.24 g, 11.76 mmol, 11.08% yield). LC/MS m/z 424.1 (M+H)$^+$, 1.97 (ret. time).

Methyl 3-(3-((tert-butyldimethylsilyl)oxy)-2,3-dihydro-1H-inden-5-yl)-3-(1,4-dimethyl-1H-benzo[d][1,2,3]triazol-5-yl)-2,2-dimethylpropanoate

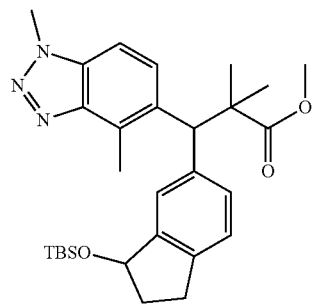 [SMILES: COC(=O)C(C)(C)C(c1ccc2c(c1)C(O[Si](C)(C)C(C)(C)C)CC2)c1ccc2c(nnn2C)c1C]

To a solution of (3-((tert-butyldimethylsilyl)oxy)-2,3-dihydro-1H-inden-5-yl)(1,4-dimethyl-1H-benzo[d][1,2,3]triazol-5-yl)methanol (2 g, 4.72 mmol) in dry acetonitrile (40 mL), DBU (0.014 mL, 0.094 mmol) and 2,2,2-trichloroacetonitrile (0.818 g, 5.67 mmol) were added slowly under nitrogen at 25° C. The reaction mixture was stirred at 25° C. for half an hour after which ((1-methoxy-2-methylprop-1-en-1-yl)oxy)trimethylsilane (2.057 g, 11.80 mmol) was added, followed by 1,1,1-trifluoro-N-((trifluoromethyl)sulfonyl)methanesulfonamide (0.066 g, 0.236 mmol). The reaction mixture was stirred at 25° C. for 2 h after which 40 mL of H$_2$O was added to quench the reaction and extracted with ethyl acetate (3×). The combined organic layer was washed with brine and concentrated. The residue was purified by silica gel chromatography (petroleum ether:ethyl acetate=4:1) to give the title compound methyl 3-(3-((tert-butyldimethylsilyl)oxy)-2,3-dihydro-1H-inden-5-yl)-3-(1,4-dimethyl-1H-benzo[d][1,2,3]triazol-5-yl)-2,2-dimethylpropanoate as a yellow solid. LC/MS m/z 508.2 (M+H)$^+$, 2.52 (ret. time).

Methyl 3-(1,4-dimethyl-1H-benzo[d][1,2,3]triazol-5-yl)-3-(3-hydroxy-2,3-dihydro-1H-inden-5-yl)-2,2-dimethylpropanoate

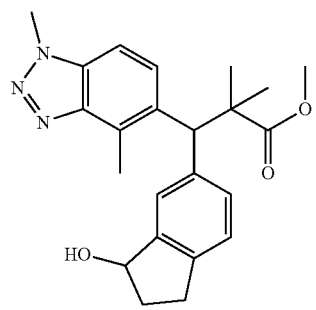 [SMILES: COC(=O)C(C)(C)C(c1ccc2c(c1)C(O)CC2)c1ccc2c(nnn2C)c1C]

To a solution of methyl 3-(3-((tert-butyldimethylsilyl)oxy)-2,3-dihydro-1H-inden-5-yl)-3-(1,4-dimethyl-1H-benzo[d][1,2,3]triazol-5-yl)-2,2-dimethylpropanoate (1.1 g, 2.166 mmol) in tetrahydrofuran (THF) (15 mL) at 0° C., TBAF (0.623 g, 2.383 mmol) was added. The reaction mixture was stirred at 0° C. for 1 h after which the mixture was quenched with saturated NH₄Cl solution (20 mL) and extracted with ethyl acetate (3×). The combined organic layer was washed with water, brine, dried over Na₂SO₄ and concentrated. The residue was purified by silica gel chromatography (petroleum ether:ethyl acetate=1:1) to provide the title compound methyl 3-(1,4-dimethyl-1H-benzo[d][1,2,3]triazol-5-yl)-3-(3-hydroxy-2,3-dihydro-1H-inden-5-yl)-2,2-dimethylpropanoate (650 mg, 1.487 mmol, 68.6% yield) as a yellow oil. LC/MS m/z 394.1 (M+H)⁺, 1.88 (ret. time).

Methyl 3-(1,4-dimethyl-1H-benzo[d][1,2,3]triazol-5-yl)-2,2-dimethyl-3-(3-oxo-2,3-dihydro-1H-inden-5-yl)propanoate

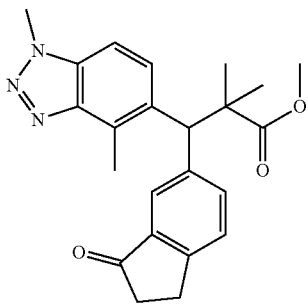

To a solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (650 mg, 1.652 mmol) in dichloromethane (DCM) (50 mL) was added Dess-Martin periodinane (1401 mg, 3.30 mmol) and one drop of water. The reaction mixture was stirred at 25° C. for 8 h after which the mixture was filtered and the filtrate was concentrated. The crude product was purified by silica gel chromatography (petroleum ether:ethyl acetate=1:1) to provide the title compound methyl 3-(1,4-dimethyl-1H-benzo[d][1,2,3]triazol-5-yl)-2,2-dimethyl-3-(3-oxo-2,3-dihydro-1H-inden-5-yl)propanoate (570 mg) as a yellow oil. LC/MS m/z 392.2 (M+H)⁺, 1.65 (ret. time).

Intermediate 93

(E)-Benzyl 5-(1-ethyl-1H-1,2,3-triazol-4-yl)pent-2-enoate

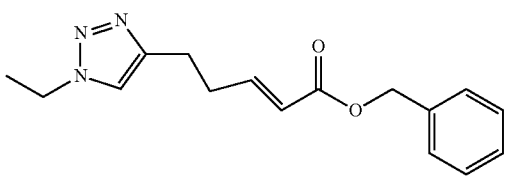 [SMILES: CCn1cc(CC/C=C/C(=O)OCc2ccccc2)nn1]

(E)-Benzyl hept-2-en-6-ynoate

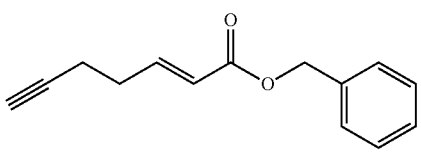 [SMILES: C#CCC/C=C/C(=O)OCc1ccccc1]

To a solution of 3-((2-(dimethoxyphosphoryl)acetoxy)methyl)benzene-1-ylium (51.7 g, 201 mmol) in tetrahydrofuran (THF) (150 mL) was added sodium hydride (8.04 g, 201 mmol)) in small portions at 0° C. After it was stirred for 35 min, pent-4-ynal (15.0 g, 183 mmol) was added slowly. The reaction mixture was stirred at 0° C. for 50 min. 100 mL of saturated NH₄Cl was added and the solution was extracted with DCM (2×). The combined organic layer was washed with brine, dried over Na₂SO₄ and concentrated. The residue was purified by silica gel chromatography (petroleum ether:ethyl acetate=50:1) to give the desired product (E)-benzyl hept-2-en-6-ynoate (12.0 g, 56.0 mmol, 30.7% yield) as an oil. LC/MS m/z 215.1 (M+H)⁺, 2.00 (ret. time).

(E)-Benzyl 5-(1-ethyl-1H-1,2,3-triazol-4-yl)pent-2-enoate

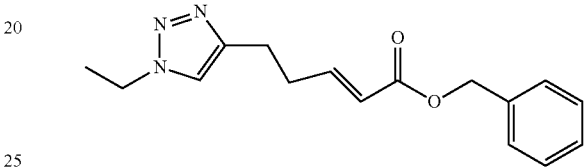

To a solution of (E)-benzyl hept-2-en-6-ynoate (10.0 g, 46.7 mmol) in tetrahydrofuran (THF) (200.0 mL) and water (200.0 mL), sodium azide (9.10 g, 140 mmol), iodoethane (21.84 g, 140 mmol), copper(I) iodide (1.778 g, 9.33 mmol) and NaHCO₃ (11.76 g, 140 mmol) were added slowly under nitrogen. The reaction mixture was stirred at 70° C. for 16 h. The reaction mixture was extracted with ethyl acetate (3×). The combined organic layer was concentrated. The residue was purified by silica gel chromatography (petroleum ether:ethyl acetate=10:1) to provide the title compound (E)-benzyl 5-(1-ethyl-1H-1,2,3-triazol-4-yl)pent-2-enoate (7.5 g, 24.97 mmol, 53.5% yield). LC/MS m/z 286.2 (M+H)⁺, 1.78 (ret. time).

Intermediate 94

(S)-Benzyl 3-(3-(((tert-butyldimethylsilyl)oxy)methyl)-4-methylphenyl)-3-(4-chloro-1-ethyl-1H-benzo[d][1,2,3]triazol-5-yl)propanoate (R)-Benzyl 3-(3-(((tert-butyldimethylsilyl)oxy)methyl)-4-methylphenyl)-3-(4-chloro-1-ethyl-1H-benzo[d][1,2,3]triazol-5-yl)propanoate

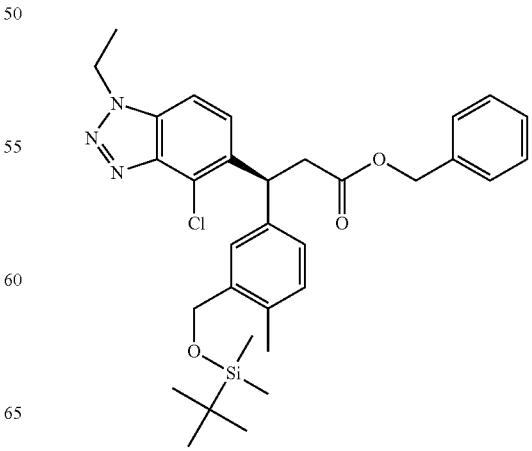

-continued

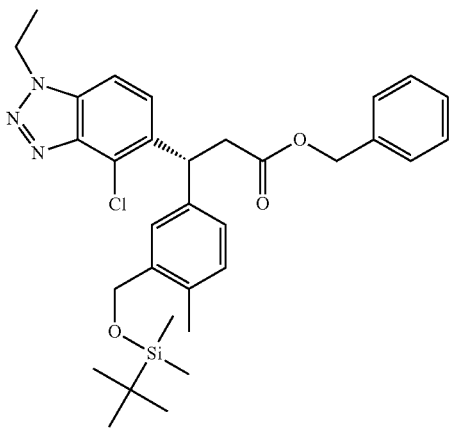

3-Chloro-N-ethyl-2-nitroaniline

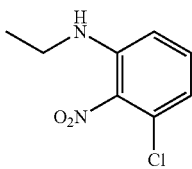

1-Chloro-3-fluoro-2-nitrobenzene (25 g, 142 mmol) in ethanamine (200 ml, 1198 mmol) was stirred at 40° C. for 16 h after which 300 mL of water was added and the mixture extracted with ethyl acetate (3×). The combined organic layer was dried over $Na_2SO_4$ and concentrated to provide the title compound 3-chloro-N-ethyl-2-nitroaniline (30 g, 139 mmol, 98% yield) which was carried to the next step without further purification. LC/MS m/z 201.1 (M+H)$^+$, 2.06 (ret. time).

4-Bromo-3-chloro-N-ethyl-2-nitroaniline

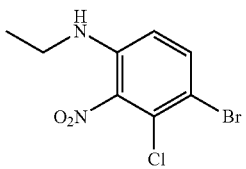

To a solution of 3-chloro-N-ethyl-2-nitroaniline (30 g, 150 mmol) in N,N-dimethylformamide (DMF) (200 mL), NBS (26.6 g, 150 mmol) in N,N-dimethylformamide (DMF) (200 mL) was added at 0° C. under nitrogen. The reaction mixture was stirred at 0° C. for 1 h and quenched with ice water under vigorous stirring. The solid was filtered to provide the title compound 4-bromo-3-chloro-N-ethyl-2-nitroaniline (40 g, 139 mmol, 93% yield). LC/MS m/z 278.9 (M+H)$^+$, 1.91 (ret. time).

4-Bromo-3-chloro-N1-ethylbenzene-1,2-diamine

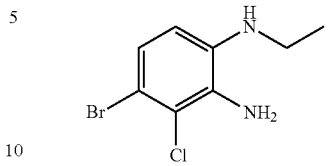

To a solution of 4-bromo-3-chloro-N-ethyl-2-nitroaniline (40 g, 143 mmol) in ethanol (200 mL), 1,2-Dichloroethane (DCE) (200 mL) and nickel (8.40 g, 143 mmol) were added slowly under nitrogen at 0° C. after which hydrazine (8.42 mL, 172 mmol) was added dropwise. The reaction mixture was stirred at 0° C. for 0.5 h. The solid was filtered, 200 mL of water was added to the solid and extracted with ethyl acetate (3×). The combined organic phase was concentrated to provide the title compound 4-bromo-3-chloro-N1-ethylbenzene-1,2-diamine (35 g, 126 mmol, 88% yield) which was carried to the next step without further purification. LC/MS m/z 249.0 (M+H)$^+$, 1.97 (ret. time).

5-Bromo-4-chloro-1-ethyl-1H-benzo[d][1,2,3]triazole

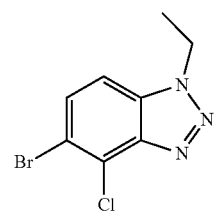

A stirred suspension of 4-bromo-3-chloro-N1-ethylbenzene-1,2-diamine (35 g, 140 mmol) in a solution of sulfuric acid (29.9 ml, 561 mmol) in water (300 mL) was treated with a solution of sodium nitrite (14.52 g, 210 mmol) in water (300 mL). The reaction mixture was stirred at 0° C. for 1 h after which the solid was filtered to provide the title compound 5-bromo-4-chloro-1-ethyl-1H-benzo[d][1,2,3]triazole (30 g, 104 mmol, 73.9% yield). LC/MS m/z 260.0 (M+H)$^+$, 1.89 (ret. time).

(E)-Benzyl 3-(4-chloro-1-ethyl-1H-benzo[d][1,2,3]triazol-5-yl)acrylate

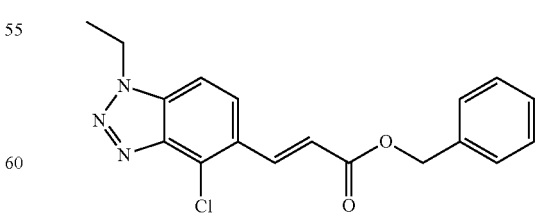

A mixture of 5-bromo-4-chloro-1-ethyl-1H-benzo[d][1,2,3]triazole (10 g, 38.4 mmol), benzyl acrylate (8.09 g, 49.9 mmol), 1,1'-Bis(diphenylphosphino)ferrocene-palladium(II) dichloride dichloromethane complex (3.13 g, 3.84 mmol)

and triethylamine (16.05 mL, 115.0 mmol) in N,N-dimethylformamide (DMF) (100 mL) was stirred at 115° C. for 12 h. Water (100 mL) was added and the mixture extracted with ethyl acetate (3×). The combined organic layer was concentrated and the residue was purified by silica gel chromatography (petroleum ether:ethyl acetate=3:1) to provide the title compound (E)-benzyl 3-(4-chloro-1-ethyl-1H-benzo[d][1,2,3]triazol-5-yl)acrylate (7.0 g, 18.43 mmol, 48.0% yield). LC/MS m/z 342.1 (M+H)+, 2.01 (ret. time).

Benzyl 3-(4-chloro-1-ethyl-1H-benzo[d][1,2,3]triazol-5-yl)-3-(3-(hydroxymethyl)-4-methylphenyl)propanoate

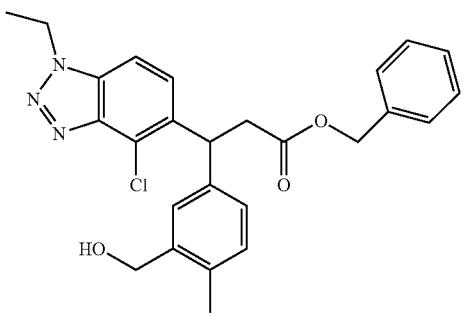 [SMILES: CCn1nnc2c(Cl)c(C(CC(=O)OCc3ccccc3)c3ccc(C)c(CO)c3)ccc21]

To a solution of (E)-benzyl 3-(4-chloro-1-ethyl-1H-benzo[d][1,2,3]triazol-5-yl)acrylate (7 g, 20.48 mmol) in 1,4-dioxane (80 mL) and water (40 mL) was added (2-methyl-5-(4,4,5,5-tetramethyl-1,3,2-dioxaborolan-2-yl)phenyl)methanol (12.70 g, 51.2 mmol) and TEA (7.14 mL, 51.2 mmol). After it was stirred for 5 min, chloro(1,5-cyclooctadiene)rhodium(I) dimer (0.505 g, 1.024 mmol) was added. The reaction mixture was stirred at 90° C. for 16 h. After it was cooled to ambient temperature, it was extracted with EtOAc (3×). The combined organic layer was concentrated and purified by silica gel chromatography (petroleum ether:ethyl acetate=5:4) to provide the title compound benzyl 3-(4-chloro-1-ethyl-1H-benzo[d][1,2,3]triazol-5-yl)-3-(3-(hydroxymethyl)-4-methylphenyl)propanoate (10 g, 18.32 mmol, 89% yield). LC/MS m/z 464.1 (M+H)+, 1.72 (ret. time).

(S)-Benzyl 3-(4-chloro-1-ethyl-1H-benzo[d][1,2,3]triazol-5-yl)-3-(3-(hydroxymethyl)-4-methylphenyl)propanoate and (R)-Benzyl 3-(4-chloro-1-ethyl-1H-benzo[d][1,2,3]triazol-5-yl)-3-(3-(hydroxymethyl)-4-methylphenyl)propanoate

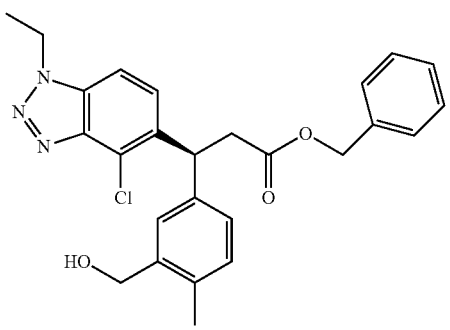

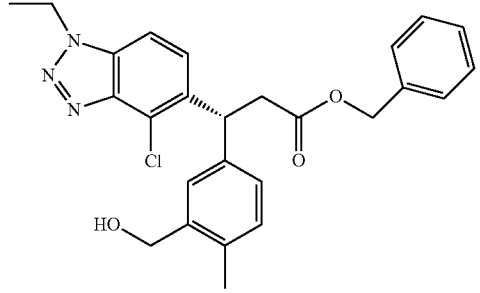

Benzyl 3-(4-chloro-1-ethyl-1H-benzo[d][1,2,3]triazol-5-yl)-3-(3-(hydroxymethyl)-4-methylphenyl)propanoate (10 g, 21.55 mmol) was separated by Chiral SFC (Column: AD IC 20×250 mm; Co-solvent: CO2/MEOH (0.2% methanol amina)=50/50; Flowrate: 130 g/min; Back pressure: 100 Bar) to give single enantiomerically pure (S)-benzyl 3-(4-chloro-1-ethyl-1H-benzo[d][1,2,3]triazol-5-yl)-3-(3-(hydroxymethyl)-4-methylphenyl)propanoate (3.6 g, 7.45 mmol, 34.6% yield) (chiral SFC ret. time: 1.97 min) and enantiomerically pure (R)-benzyl 3-(4-chloro-1-ethyl-1H-benzo[d][1,2,3]triazol-5-yl)-3-(3-(hydroxymethyl)-4-methylphenyl)propanoate (3.5 g, 7.39 mmol, 34.3% yield) (chiral SFC ret. time: 8.13 min).

(S)-Benzyl 3-(3-(((tert-butyldimethylsilyl)oxy)methyl)-4-methylphenyl)-3-(4-chloro-1-ethyl-1H-benzo[d][1,2,3]triazol-5-yl)propanoate

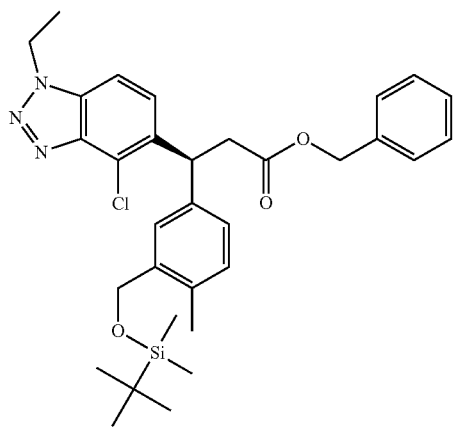 [SMILES: CCn1nnc2c(Cl)c([C@@H](CC(=O)OCc3ccccc3)c3ccc(C)c(CO[Si](C)(C)C(C)(C)C)c3)ccc21]

To a solution of (S)-benzyl 3-(4-chloro-1-ethyl-1H-benzo[d][1,2,3]triazol-5-yl)-3-(3-(hydroxymethyl)-4-methylphenyl)propanoate (3.6 g, 7.76 mmol) in dichloromethane (DCM) (50 mL), imidazole (0.792 g, 11.64 mmol) and tert-butylchlorodimethylsilane (1.754 g, 11.64 mmol) were added at 0° C. The reaction mixture was stirred at 10° C. for 2 h. The solvent was removed and the residue was purified by silica gel chromatography (petroleum ether:ethyl acetate=3:1) to provide the title compound (S)-benzyl 3-(3-(((tert-butyldimethylsilyl)oxy)methyl)-4-methylphenyl)-3-(4-chloro-1-ethyl-1H-benzo[d][1,2,3]triazol-5-yl)propanoate (3.5 g, 5.93 mmol, 76% yield) as a yellow oil. LC/MS m/z 578.3 (M+H)+, 2.488 (ret. time).

(R)-Benzyl 3-(3-(((tert-butyldimethylsilyl)oxy)methyl)-4-methylphenyl)-3-(4-chloro-1-ethyl-1H-benzo[d][1,2,3]triazol-5-yl)propanoate

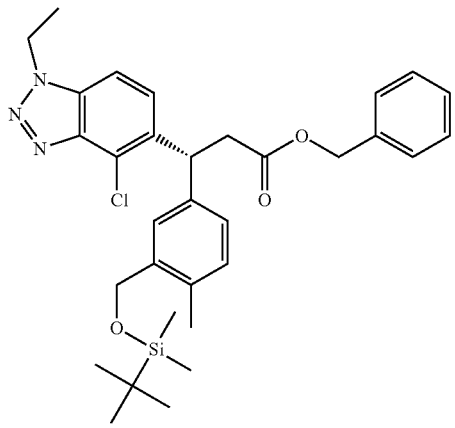 [SMILES: CCn1nnc2c(Cl)c([C@H](CC(=O)OCc3ccccc3)c3ccc(C)c(CO[Si](C)(C)C(C)(C)C)c3)ccc21]

To a solution of (R)-benzyl 3-(4-chloro-1-ethyl-1H-benzo[d][1,2,3]triazol-5-yl)-3-(3-(hydroxymethyl)-4-methylphenyl)propanoate (3.5 g, 7.54 mmol) in dichloromethane (DCM) (50 mL), imidazole (0.565 g, 8.30 mmol) and tert-butylchlorodimethylsilane (1.364 g, 9.05 mmol) were added at 00° C. The reaction mixture was stirred at 0° C. to 10° C. for 2 h after which the solvent was removed and the residue was purified silica gel chromatography (petroleum ether:ethyl acetate=3:1) provide the title compound (R)-benzyl 3-(3-(((tert-butyldimethylsilyl)oxy)methyl)-4-methylphenyl)-3-(4-chloro-1-ethyl-1H-benzo[d][1,2,3]triazol-5-yl)propanoate (3.3 g, 5.59 mmol, 74.1% yield) as a yellow oil. LC/MS m/z 578.3 (M+H)$^+$, 2.47 (ret. time).

Intermediate 95

1-((1H-imidazol-2-yl)methyl)azepane

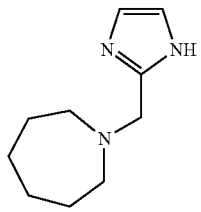 [SMILES: c1c[nH]c(CN2CCCCCC2)n1]

Azepane N33442-33-A1

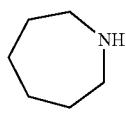

The mixture of azepan-2-one (8.0 g, 70.7 mmol) and LiAlH$_4$ (5.37 g, 141 mmol) in tetrahydrofuran (THF) (50 mL) was stirred at ice bath for 8 h under nitrogen after which 5.3 mL of water, 5.3 mL of 10% NaOH aqueous solution and 16 mL of water were added dropwise, respectively. The solid was filtered. The filtrate was concentrated to provide the title compound azepane (3.0 g, 30.2 mmol, 42.8% yield) as an oil which was carried to the next step without further purification. LC/MS m/z 100.2 (M+H)$^+$, 0.48 (ret. time).

1-((1H-imidazol-2-yl)methyl)azepane

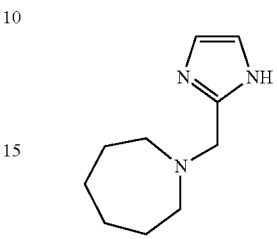

To a solution of azepane (2.0 g, 20.17 mmol) in 1,2-dichloroethane (DCE) (120 mL), acetic acid (1 mL, 17.47 mmol), 1H-imidazole-2-carbaldehyde (1.938 g, 20.17 mmol) and NaBH(OAc)$_3$ (17.10 g, 81 mmol) were added at 0° C. The reaction mixture was stirred at 25° C. for 16 h. The mixture was quenched with aqueous NaHCO$_3$ (100 mL) and extracted with DCM (2×), the organic layer was washed with water (2×), brine, dried over Na$_2$SO$_4$ and concentrated. The residue was purified by reverse phase preparative HPLC (MeOH/0.05% NH$_3$H$_2$O/H$_2$O=50%) to provide the title compound 1-((1H-imidazol-2-yl)methyl)azepane (1.5 g, 7.95 mmol, 39.4% yield) as a solid. LC/MS m/z 180.2 (M+H)$^+$, 1.37 (ret. time).

Intermediate 96

1-((1H-Imidazol-2-yl)methyl)-4-ethylpiperidine

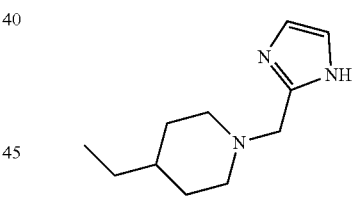

tert-Butyl 4-ethylidenepiperidine-1-carboxylate

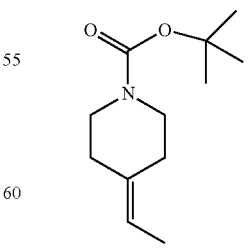

Ethyltriphenylphosphonium bromide (27.9 g, 75 mmol) was added to the LiHMDS (75 mL, 75 mmol) in THF (60 mL) at 0° C. After the reaction mixture was stirred at 00° C. for 1 h, a solution of tert-butyl 4-oxopiperidine-1-carboxylate (10.0 g, 50.2 mmol) in tetrahydrofuran (THF) (60 mL) was added and stirred for a further 2 h at ambient temperature. Brine was added to quench the reaction and extracted with ethyl acetate (2×). The combined organic layer was washed with brine and concentrated. The residue was purified by silica gel chromatography (petroleum ether:ethyl acetate=10:1) to give the title compound tert-butyl 4-ethylidenepiperidine-1-carboxylate (6.2 g, 29.3 mmol, 58.5% yield) as an oil. LC/MS m/z 156.2 (M+H-56)*, 2.21 min (ret. time)

tert-Butyl-4-ethylpiperidine-1-carboxylate

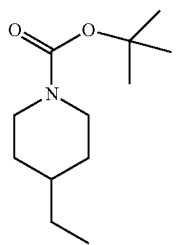

The mixture of tert-butyl 4-ethylidenepiperidine-1-carboxylate (6200 mg, 29.3 mmol) and Pd/C (10%, 1561 mg, 14.67 mmol) in methanol (100 mL) was hydrogenated with $H_2$ balloon for 5 h. The mixture was filtered through celite and the organic layer was concentrated to give the title compound tert-butyl 4-ethylpiperidine-1-carboxylate (6200 mg, 29.1 mmol, 99% yield) as an oil. LC-MS m/z 158.1 (M+H)$^+$, 2.28 min (ret. time)

4-Ethylpiperidine

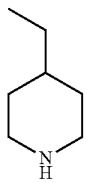

The mixture of tert-butyl 4-ethylpiperidine-1-carboxylate (6200 mg, 29.1 mmol), trifluoroacetic acid (2.239 mL, 29.1 mmol) in dichloromethane (DCM) (50 mL) was stirred at ambient temperature for 5 h. The solvent was concentrated to give the title compound 4-ethylpiperidine (2500 mg, 22.08 mmol, 76% yield) as an oil which was carried to the next step without further purification. LC/MS m/z 114.2 (M+H)$^+$, 1.03 min (ret. time)

1-((1H-Imidazol-2-yl)methyl)-4-ethylpiperidine

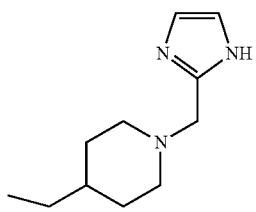

To a mixture of 4-ethylpiperidine (1200 mg, 10.60 mmol) and 1H-imidazole-2-carbaldehyde (1019 mg, 10.60 mmol) was added titanium(IV) isopropoxide (3.73 mL, 12.72 mmol) dropwise. After it was stirred at 25° C. for 2 h, ethanol (120 mL) and NaCNBH$_3$ (666 mg, 10.60 mmol) were added and stirred for another 8 h. Water (2 mL) was added and the solvent was concentrated. The residue was purified by reverse-phase HPLC (MeOH/0.05% NH$_3$H$_2$O/ H$_2$O=50%) to give the title compound 1-((1H-imidazol-2-yl)methyl)-4-ethylpiperidine (850 mg, 4.18 mmol, 39.4% yield) as a solid. LC-MS m/z 194.2 (M+H)$^+$, 1.53 min (ret. time)

Intermediate 97

4-Fluoro-3-(((4-methoxybenzyl)oxy)methyl)benzaldehyde

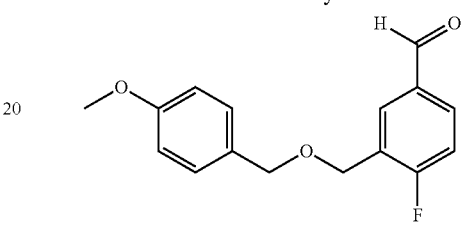

(5-Bromo-2-fluorophenyl)methanol

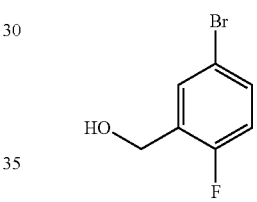

Trimethyl borate (2.55 mL, 22.83 mmol) was added to a stirred solution of 5-bromo-2-fluorobenzoic acid (5.0 g, 22.83 mmol) in tetrahydrofuran (THF) (60 mL) under argon and the mixture was stirred at ambient temperature. After 15 minutes, a solution of DMS (21.69 mL, 43.4 mmol) was added to the reaction mixture at 0° C. and stirred at ambient temperature for 16 h. Methanol (10 mL) was added slowly to the reaction mixture. After 30 min, the solvent was evaporated and ethyl acetate was added to the residue. The organic layer was washed with aqueous sodium bicarbonate solution and water, dried over Na$_2$SO$_4$ and concentrated. The residue was purified by silica gel chromatography (petroleum ether:ethyl acetate=4:1) to give title compound (5-bromo-2-fluorophenyl)methanol (4.65 g, 19.07 mmol, 84% yield) as a white solid. LC/MS m/z 189.1 (M+H)$^+$, 1.52 (ret. time).

4-Bromo-1-fluoro-2-(((4-methoxybenzyl)oxy)methyl)benzene

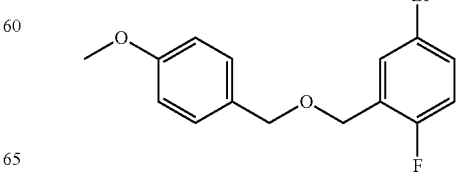

To a solution of (5-bromo-2-fluorophenyl)methanol (9.25 g, 45.1 mmol) in N,N-dimethylformamide (DMF) (80 mL) at 0° C. under nitrogen, sodium hydride (2.165 g, 54.1 mmol) was added in two portions. The reaction mixture was stirred at 0° C. for 20 min after which 1-(chloromethyl)-4-methoxybenzene (8.48 g, 54.1 mmol) was added to the mixture and it was stirred at 0° C. to 25° C. for 1 hr. Then ice water was added to the reaction mixture under 0° C. The reaction mixture was extracted with ethyl acetate (3×). The combined organic layer was washed with brine and dried over anhydrous $Na_2SO_4$ and concentrated. The residue was purified with silica gel chromatography (petroleum ether:ethyl acetate=5:1) to give the title compound 4-bromo-1-fluoro-2-(((4-methoxybenzyl)oxy)methyl)benzene (13.25 g, 40.7 mmol, 90% yield) as an oil. LC/MS m/z 325.1/326.1 $(M+H)^+$, 1.46 (ret. time).

4-Fluoro-3-(((4-methoxybenzyl)oxy)methyl)benzaldehyde

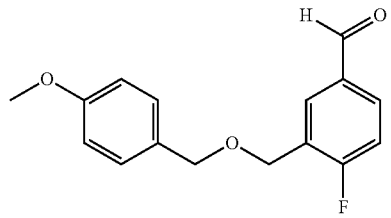 [SMILES: COc1ccc(COCc2cc(C=O)ccc2F)cc1]

To a solution of 4-bromo-1-fluoro-2-(((4-methoxybenzyl)oxy)methyl)benzene (13.25 g, 40.7 mmol) in tetrahydrofuran (THF) (100 mL) at −78° C. under $N_2$, n-butyllithium (19.56 mL, 48.9 mmol) was carefully added. The reaction mixture was stirred at −78° C. for 45 min. DMF (15.78 mL, 204 mmol) was added. The reaction mixture was stirred at −78° C. to 25° C. for another 30 min. The reaction mixture was quenched with saturated $NH_4Cl$ and extracted with ethyl acetate (3×). The organic layer was washed with water (2×), brine (2×), dried over $Na_2SO_4$ and concentrated. The residue was purified with silica gel chromatography (petroleum ether:ethyl acetate=1:10) to give the title compound 4-fluoro-3-(((4-methoxybenzyl)oxy)methyl)benzaldehyde (10.5 g, 37.8 mmol, 93% yield) as an oil. LC/MS m/z 296.9 $(M+Na)^+$, 2.03 (ret. time).

Example 1

3-(3-((2,3-Dihydrobenzo[f][1,4]oxazepin-4(5H)-yl)methyl)-4-methylphenyl)-3-(1,4-dimethyl-1H-benzo[d][1,2,3]triazol-5-yl)propanoic Acid, Trifluoroacetic Acid Salt

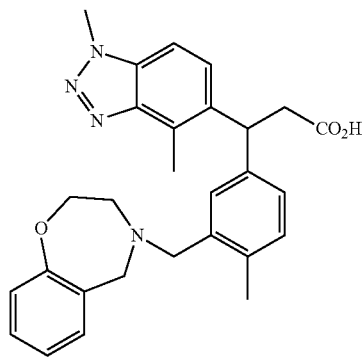 [SMILES: Cc1ccc(C(CC(=O)O)c2ccc3c(nnn3C)c2C)cc1CN1CCOc2ccccc2C1]

A mixture of ethyl 3-(3-(chloromethyl)-4-methylphenyl)-3-(1,4-dimethyl-1H-benzo[d][1,2,3]triazol-5-yl)propanoate (80 mg, 0.207 mmol), 2,3,4,5-tetrahydrobenzo[f][1,4]oxazepine (55.7 mg, 0.373 mmol) and DIEA (0.109 mL, 0.622 mmol) in tetrahydrofuran (THF) (1.5 mL) was heated in a Biotage microwave at high absorption for 2 h at 120° C. The reaction mixture was concentrated and the resulting mixture re-dissolved in methanol (2 mL), 2 M LiOH (0.622 mL, 1.244 mmol) was added. It was heated at 85° C. for 30 min. 0.8 mL of 1N HCl and 1.5 mL of DMSO were added, solvents removed, and the sample was purified by reverse-phase HPLC (with 0.1% TFA condition) to give the title compound (107 mg, 0.227 mmol, 110% yield) as white solid. LC-MS: m/z 471.5 $(M+H)^+$, 0.66 min (ret. time).

Example 2

3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic Acid, Trifluoroacetic Acid Salt

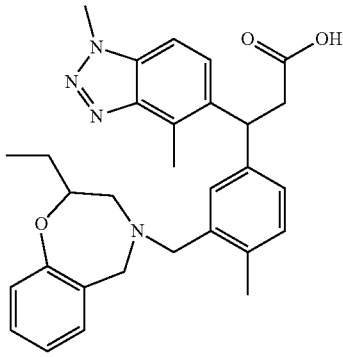 [SMILES: CCC1CN(Cc2cc(C(CC(=O)O)c3ccc4c(nnn4C)c3C)ccc2C)Cc2ccccc2O1]

A mixture of ethyl 3-(3-(chloromethyl)-4-methylphenyl)-3-(1,4-dimethyl-1H-benzo[d][1,2,3]triazol-5-yl)propanoate (70 mg, 0.181 mmol), 2-ethyl-2,3,4,5-tetrahydrobenzo[f][1,4]oxazepine (57.9 mg, 0.327 mmol), and DIEA (0.095 mL, 0.544 mmol) in tetrahydrofuran (THF) (3 mL) was heated in a Biotage microwave at high absorption for 2 h at 120° C. The reaction mixture was concentrated and re-dissolved in methanol (2 mL). It was heated at 85° C. for 30 min. 0.8 mL of 1N HCl and 1.5 mL of DMSO were added, solvents removed, and the sample was purified by reverse-phase HPLC (with 0.1% TFA condition) to give the title compound (86.68 mg, 0.174 mmol, 96% yield) as white solid. LC-MS m/z 499.5 $(M+H)^+$, 0.85 min (ret. time).

Example 3

Ethyl 3-(1,4-dimethyl-1H-benzo[d][1,2,3]triazol-5-yl)-3-(4-methyl-3-((2-methyl-2,3-dihydrobenzo[f][1,4]oxazepin-4(5H)-yl)methyl)phenyl)propanoate, trifluoroacetic Acid Salt

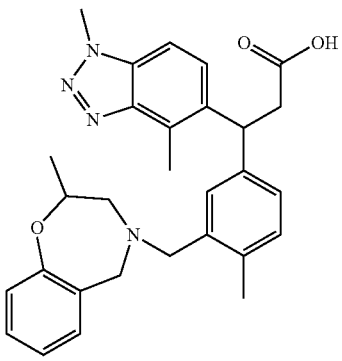 [SMILES: Cc1ccc(C(CC(=O)O)c2ccc3c(nnn3C)c2C)cc1CN1Cc2ccccc2OC(C)C1]

2-methyl-2,3,4,5-tetrahydrobenzo[f][1,4]oxazepine

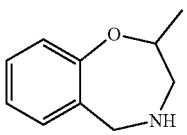

To a solution of LAH (119 mg, 3.14 mmol) in tetrahydrofuran (THF) (2 mL) was added a solution of 2-methylbenzo[f][1,4]oxazepine-3,5(2H,4H)-dione (200 mg, 1.046 mmol) in tetrahydrofuran (THF) (2 mL). The mixture was heated in a Biotage microwave at high absorption for 2 h at 120° C. To the reaction mixture was added 0.52 mL saturated Na₂SO₄. The mixture was stirred for 30 min. The reaction mixture turns from grey to white solution. Solid was filtered and washed with ethyl acetate. The filtrate was concentrated to give the title compound (179.5 mg, 1.100 mmol, 105% yield) as oil. LC-MS m/z 163.9 (M+H)⁺, 0.42 min (ret. time).

Ethyl 3-(1,4-dimethyl-1H-benzo[d][1,2,3]triazol-5-yl)-3-(4-methyl-3-((2-methyl-2,3-dihydrobenzo[f][1,4]oxazepin-4(5H)-yl)methyl)phenyl)propanoate, trifluoroacetic Acid Salt

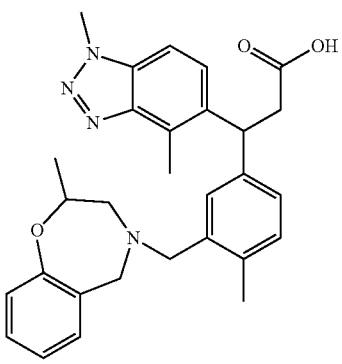 [SMILES: Cc1ccc(C(CC(=O)O)c2ccc3c(nnn3C)c2C)cc1CN1Cc2ccccc2OC(C)C1]

To a solution of 3-(3-(chloromethyl)-4-methylphenyl)-3-(1,4-dimethyl-1H-benzo[d][1,2,3]triazol-5-yl)propanoate (0.130 mL, 0.302 mmol) and 2-methyl-2,3,4,5-tetrahydrobenzo[f][1,4]oxazepine (89 mg, 0.544 mmol) in tetrahydrofuran (THF) (3 mL) at ambient temperature was added N,N-diisopropylethylamine (DIEA) (0.158 mL, 0.906 mmol). The reaction mixture was heated in a Biotage microwave at high absorption for 2 hr at 180° C. After cooling, the reaction mixture was concentrated to remove solvent. The crude product was redissolved in methanol (3 mL). To the reaction mixture was added 2 M lithium hydroxide (0.453 mL, 0.906 mmol). The reaction mixture was heated in a Biotage microwave at high absorption for 30 min at 80° C. After cooling, 1 N HCl (0.8 mL) and DMSO (2 mL) was added and the volatiles removed. The crude product was purified via reverse-phase HPLC under acidic conditions to give the title compound 3-(1,4-dimethyl-1H-benzo[d][1,2,3]triazol-5-yl)-3-(4-methyl-3-((2-methyl-2,3-dihydrobenzo[f][1,4]oxazepin-4(5H)-yl)methyl)phenyl)propanoic acid, trifluoroacetic acid salt (41.3 mg, 0.085 mmol, 28.2% yield). LC-MS m/z 485.5 (M+H)⁺, 0.72 min (ret. time). ¹H NMR (400 MHz, DMSO-d₆) δ ppm 1.30 (d, J=6.27 Hz, 3H) 2.27 (br. s., 1H) 2.36 (br. s., 2H) 2.79 (s, 3H) 3.01-3.21 (m, 2H) 3.27-3.46 (m, 1H) 3.53 (br. s., 1H) 4.12 (br. s., 1H) 4.25 (s, 3H) 4.34-4.64 (m, 4H) 4.82-4.91 (m, 1H) 7.07-7.63 (m, 9H) 9.93 (br. s., 1H)

Example 4

5-(1-Ethyl-1H-1,2,3-triazol-4-yl)-3-(3-((2-ethyl-2,3-dihydrobenzo[f][1,4]oxazepin-4(5H)-yl)methyl)-4-methylphenyl)pentanoic Acid, Trifluoroacetic Acid Salt

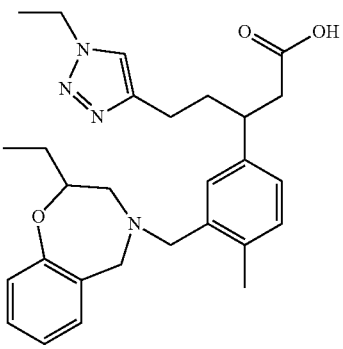 [SMILES: CCC1CN(Cc2cc(C(CCc3cn(CC)nn3)CC(=O)O)ccc2C)Cc2ccccc2O1]

(2-Methyl-5-(4,4,5,5-tetramethyl-1,3,2-dioxaborolan-2-yl)phenyl)methanol

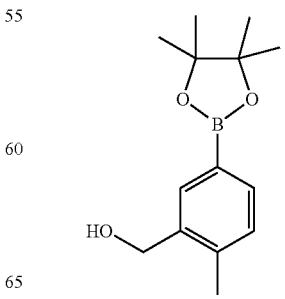

To a solution of (5-bromo-2-methylphenyl)methanol (49 g, 244 mmol) in 1,4-dioxane (600 mL) was added potassium acetate (59.8 g, 609 mmol) and bis(pinacolato)diboron (80 g, 317 mmol). The reaction mixture was degassed with Argon for 30 min after which PdCl$_2$(dppf)-CH$_2$Cl$_2$ adduct (19.90 g, 24.37 mmol) was added to reaction mixture and stirred at 100° C. for 16 h. After completion, the reaction mixture was cooled and filtered through celite. The filtrate was concentrated and the crude residue was purified via silica gel chromatography to give the title compound (40 g, 159 mmol, 65.2% yield) as white solid. LC-MS m/z 248.1 (M+H)$^+$, 3.71 min (ret. time).

Ethyl 5-(1-ethyl-1H-1,2,3-triazol-4-yl)-3-(3-(hydroxymethyl)-4-methylphenyl)pentanoate

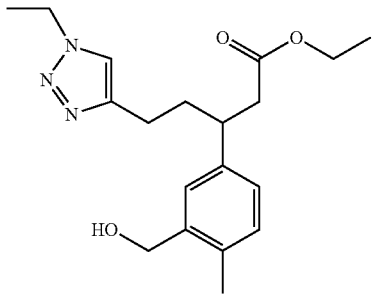 [SMILES: CCOC(=O)CC(CCc1cn(CC)nn1)c1ccc(C)c(CCl)c1]

To a suspension of (E)-ethyl 5-(1-ethyl-1H-1,2,3-triazol-4-yl)pent-2-enoate (500 mg, 2.239 mmol), (2-methyl-5-(4,4,5,5-tetramethyl-1,3,2-dioxaborolan-2-yl)phenyl)methanol (667 mg, 2.69 mmol), and [RhCl(cod)]$_2$ (110 mg, 0.224 mmol) in 1,4-dioxane (2 mL) and water (1 mL) at ambient temperature was added triethylamine (0.936 mL, 6.72 mmol). The resulting suspension was heated at 90° C. for 1 h. The reaction mixture was passed through celite and washed with EtOAc. The organic layer was collected and concentrated to give the crude product which was purified via silica gel chromatography to give the title compound (685 mg, 1.983 mmol, 89% yield) as oil. LC/MS: m/z 346.1 (M+H)$^+$, Rt 0.83 min.

Ethyl 3-(3-(chloromethyl)-4-methylphenyl)-5-(1-ethyl-1H-1,2,3-triazol-4-yl)pentanoate

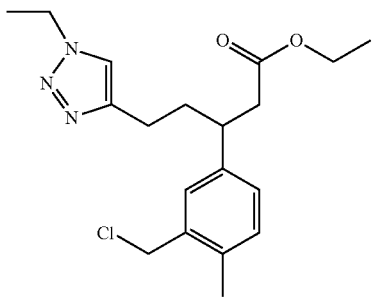

To a solution of ethyl 5-(1-ethyl-1H-1,2,3-triazol-4-yl)-3-(3-(hydroxymethyl)-4-methylphenyl)pentanoate (95 mg, 0.275 mmol) in dichloromethane (DCM) (2 mL) was added SOCl$_2$ (0.040 mL, 0.550 mmol). The result reaction mixture was stirred at ambient temperature for 40 min. Solvent was evaporated to afford the title compound (95 mg, 0.261 mmol, 95% yield). LC/MS: m/z 364.4 (M+H)$^+$, Rt 1.01 min.

5-(1-Ethyl-1H-1,2,3-triazol-4-yl)-3-(3-((2-ethyl-2,3-dihydrobenzo[f][1,4]oxazepin-4(5H)-yl)methyl)-4-methylphenyl)pentanoic Acid, Trifluoroacetic Acid Salt

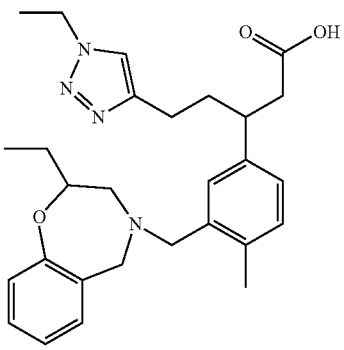 [SMILES: CCC1CN(Cc2cc(C(CCc3cn(CC)nn3)CC(=O)O)ccc2C)Cc2ccccc2O1]

A mixture of ethyl 3-(3-(chloromethyl)-4-methylphenyl)-5-(1-ethyl-1H-1,2,3-triazol-4-yl)pentanoate (95 mg, 0.261 mmol), 2-ethyl-2,3,4,5-tetrahydrobenzo[f][1,4]oxazepine (83 mg, 0.470 mmol) and DIEA (0.137 mL, 0.783 mmol) in tetrahydrofuran (THF) (3 mL) was heated via microwave for 2 h at 120° C. The solvent was removed and the crude residue re-dissolved in methanol (2 mL). It was heated in a Biotage microwave at high absorption at 80° C. for 35 min. LC-MS showed the reaction was not complete. It was heated in a Biotage microwave at high absorption at 80° C. for 30 min. 0.8 mL of 1 N HCl and 1.5 mL of DMSO were added. The mixture was concentrated and purified with reverse-phase HPLC to give title compound (132 mg, 0.277 mmol, 106% yield). LC-MS m/z 477.1 (M+H)$^+$, 0.79 min (ret. time).

Example 5

(3S)-3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic Acid, Trifluoroacetic Acid Salt

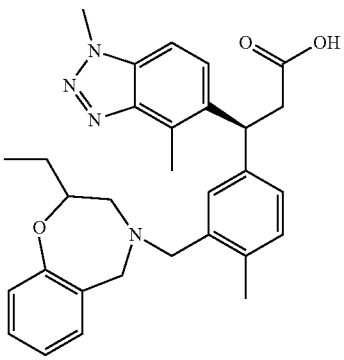 [SMILES: CCC1CN(Cc2cc([C@H](CC(=O)O)c3ccc4c(nnn4C)c3C)ccc2C)Cc2ccccc2O1]

2-Ethyl-2,3,4,5-tetrahydrobenzo[f][1,4]oxazepine

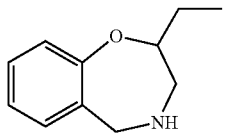

To a suspension of LAH (294 mg, 7.75 mmol) in tetrahydrofuran (THF) (2 mL) was added a solution of 2-ethylbenzo[f][1,4]oxazepine-3,5(2H,4H)-dione (530 mg, 2.58 mmol) in tetrahydrofuran (THF) (2 mL). The mixture was heated via microwave for 2 h at 120° C. after which time 4.8 mL saturated Na$_2$SO$_4$ was added drop wise. The mixture was stirred for 30 min, the solid was filtered and washed with ethyl acetate. The filtrate was concentrated to give the title compound (450 mg, 98%) as an oil. LC-MS m/z 178.1 (M+H)$^+$, 0.58 min (ret. time).

(3S)-3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic Acid, Trifluoroacetic Acid Salt

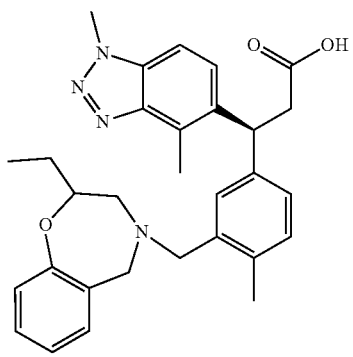 [SMILES: CCC1CN(Cc2cc([C@H](CC(=O)O)c3ccc4c(nnn4C)c3C)ccc2C)Cc2ccccc2O1]

A mixture of (S)-ethyl 3-(3-(chloromethyl)-4-methylphenyl)-3-(1,4-dimethyl-1H-benzo[d][1,2,3]triazol-5-yl)propanoate (80 mg, 0.207 mmol), 2-ethyl-2,3,4,5-tetrahydrobenzo[f][1,4]oxazepine (55.1 mg, 0.311 mmol), and DIEA (0.109 mL, 0.622 mmol) in tetrahydrofuran (THF) (3 mL) was heated via microwave for 2 h at 120° C. The solvent was removed and the resulting residue re-dissolved in methanol (2 mL). The reaction mixture was heated at 85° C. for 30 min after which 0.8 mL of 1 N HCl and 1.5 mL of DMSO were added. Most solvents were dried and purified with reverse-phase HPLC to give the title compound (78.8 mg, 0.129 mmol, 62.0% yield) as white solid. LC-MS m/z 499.5 (M+H)$^+$, 0.85 min (ret. time).

Example 6

(3R)-3-(1,4-Dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoic Acid, Trifluoroacetic Acid Salt

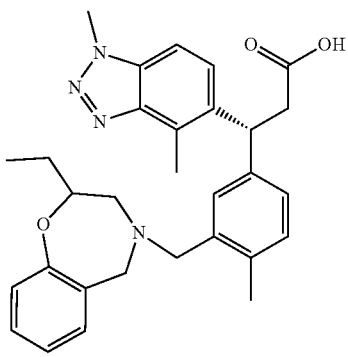 [SMILES: CCC1CN(Cc2cc([C@@H](CC(=O)O)c3ccc4c(nnn4C)c3C)ccc2C)Cc2ccccc2O1]

A mixture of (R)-ethyl 3-(3-(chloromethyl)-4-methylphenyl)-3-(1,4-dimethyl-1H-benzo[d][1,2,3]triazol-5-yl)propanoate (90 mg, 0.233 mmol), 2-ethyl-2,3,4,5-tetrahydrobenzo[f][1,4]oxazepine (62.0 mg, 0.350 mmol), and DIEA (0.122 mL, 0.700 mmol) in tetrahydrofuran (THF) (3 mL) was heated via microwave for 2 h at 120° C. The solvent was removed and the residue re-dissolved in methanol (2 mL). The reaction mixture was heated at 85° C. for 30 min. after which time 0.8 mL of 1 N HCl and 1.5 mL of DMSO were added. Volatile solvents were removed and the crude product purified with reverse-phase HPLC to give the title compound (67.9 mg, 0.111 mmol, 47.5% yield) as white solid. LC-MS m/z 499.5 (M+H)$^+$, 0.85 min (ret. time).

Example 7

3-(1,4-dimethyl-1H-benzo[d][1,2,3]triazol-5-yl)-3-(3-((8-methoxy-4-methyl-4,5-dihydro-1H-benzo[c]azepin-2(3H)-yl)methyl)-4-methylphenyl)propanoic Acid

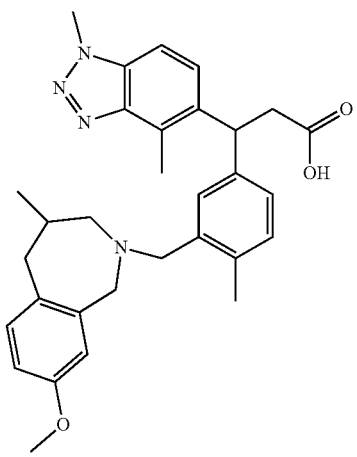 [SMILES: COc1ccc2c(c1)CN(Cc1cc(C(CC(=O)O)c3ccc4c(nnn4C)c3C)ccc1C)CC(C)C2]

173

Methyl 3-(3-methoxyphenyl)propanoate

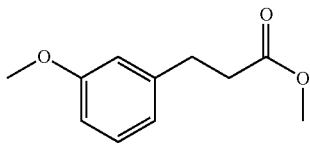

To a solution of 3-(3-methoxyphenyl)propanoic acid (5000 mg, 27.7 mmol) in methanol (50 mL), SOCl₂ (2.025 mL, 27.7 mmol) was added slowly under nitrogen at ambient temperature. The reaction mixture was stirred at 65° C. for 12 hrs then concentrated under a stream of nitrogen at 50° C. Ethyl acetate (100 mL) was added and the organic phase washed with aqueous NaHCO₃, dried with MgSO₄ and concentrated to afford the title compound methyl 3-(3-methoxyphenyl)propanoate (5.4 g, 26.7 mmol, 96% yield). LC-MS m/z 195.1 (M+H)⁺, 1.67 (ret. time).

3-(3-Methoxyphenyl)propan-1-ol

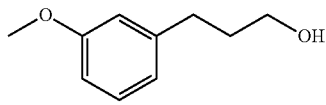

To a solution of methyl 3-(3-methoxyphenyl)propanoate (5 g, 25.7 mmol) in tetrahydrofuran (50 mL), was added LiAlH₄ (1.172 g, 30.9 mmol) slowly under nitrogen at 25° C. The reaction mixture was stirred at 25° C. for 16 hrs and was cooled to 0° C. after which 1.17 mL of water was added, followed by 1.17 mL of 10% NaOH, and 3.5 mL of water. The solid was filtered and the filtrate was concentrated under a stream of nitrogen at 50° C. to afford the title compound 3-(3-methoxyphenyl)propan-1-ol (4.1 g, 23.19 mmol, 90% yield). LC-MS m/z 167.2 (M+H)⁺, 1.45 (ret. time).

3-(3-Methoxyphenyl)propanal

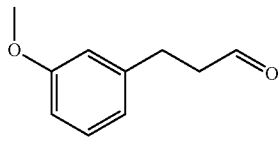

To a solution of 3-(3-methoxyphenyl)propan-1-ol (3500 mg, 21.06 mmol) in dichloromethane (DCM) (50 mL) at 30° C. was added PCC (19.500 g, 90 mmol) slowly under nitrogen. The reaction mixture was stirred at 30° C. for 12 h. Water (50 mL) was added to reaction mixture and the mixture extracted with ethyl acetate (3×60 mL) The combined organic layer was dried with MgSO₄, filtered and concentrated. The crude product was purified by silica gel column (hexane:ethyl acetate=20:1) to afford the title compound 3-(3-methoxyphenyl)propanal (2000 mg, 10.35 mmol, 49.2% yield). LC-MS m/z 165.0 (M+H)+1.09 (ret. time).

174

(S,E)-2-(Methoxymethyl)-N-(3-(3-methoxyphenyl)propylidene)pyrrolidin-1-amine

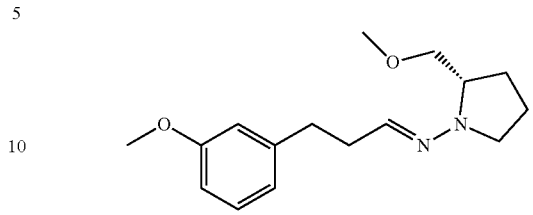

To a solution of 3-(3-methoxyphenyl)propanal (1187 mg, 6.14 mmol) in dichloromethane (DCM) (20 mL) at 30° C. was added (S)-2-(methoxymethyl)pyrrolidin-1-amine (800 mg, 6.14 mmol) and MgSO₄ (740 mg, 6.14 mmol) slowly under nitrogen. The reaction mixture was stirred at 30° C. for 12 h. The mixture was filtered and the filtrate was concentrated. The crude product was purified by silica gel column (hexane:ethyl acetate=4:1) to afford the title compound (S,E)-2-(methoxymethyl)-N-(3-(3-methoxyphenyl)propylidene)pyrrolidin-1-amine (1700 mg, 5.54 mmol, 90% yield). LC-MS m/z 277.2 (M+H)⁺, 1.50 (ret. time).

(2S,E)-2-(Methoxymethyl)-N-(3-(3-methoxyphenyl)-2-methylpropylidene)pyrrol din-1-amine

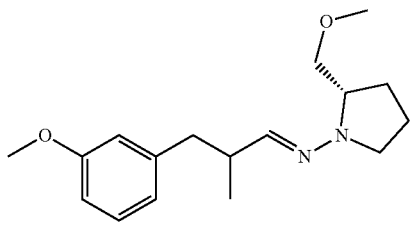 [SMILES: COC[C@@H]1CCCN1/N=C/C(C)Cc1cccc(OC)c1]

To a solution of (S,E)-2-(methoxymethyl)-N-(3-(3-methoxyphenyl)propylidene)pyrrolidin-1-amine (800 mg, 2.89 mmol) in tetrahydrofuran (THF) (20 mL) at −78° C. was added 2 M LDA in THF (7.24 mL, 14.47 mmol) slowly under nitrogen. The reaction mixture was stirred at −78° C. for 30 mins then warmed to 0° C. and stirred at 0° C. for 1 h. It was cooled to −78° C., a solution of iodomethane (1.086 mL, 17.37 mmol) in 5 mL THF was added dropwise. The reaction mixture was stirred at −78° C. for 1 h, then it was slowly warmed to ambient temperature and stirred for 12 h. Water (50 mL) was added and the mixture extracted with ethyl acetate (3×50 mL). The combined organic layer was dried with MgSO₄, filtered and concentrated. The crude product was purified by preparative HPLC to afford the title compound (2S,E)-2-(methoxymethyl)-N-(3-(3-methoxyphenyl)-2-methylpropylidene)pyrrolidin-1-amine (650 mg, 2.126 mmol, 73.5% yield). LC-MS m/z 291.2 (M+H)⁺, 1.54 (ret. time).

(2S)-2-(Methoxymethyl)-N-(3-(3-methoxyphenyl)-2-methylpropyl)pyrrolidin-1-amine

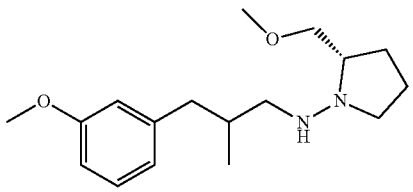 [SMILES: COC[C@@H]1CCCN1NCC(C)Cc1cccc(OC)c1]

To a solution of (2S,E)-2-(methoxymethyl)-N-(3-(3-methoxyphenyl)-2-methylpropylidene)pyrrolidin-1-amine (1.5 g, 5.17 mmol) in tetrahydrofuran (THF) (10 mL) at ambient temperature was added 1M LiAlH$_4$ in THF (12.91 mL, 12.91 mmol) slowly under nitrogen. The reaction mixture was stirred at 65° C. for 10 h. 1 N NaOH (5 mL) was added and the mixture was extracted with ethyl acetate (3×10 mL). The combined organic layer was washed with brine, dried with MgSO$_4$, filtered and concentrated to afford the title compound (2S)-2-(methoxymethyl)-N-(3-(3-methoxyphenyl)-2-methylpropyl)pyrrolidin-1-amine (1.5 g, 4.10 mmol, 79% yield). LC-MS m/z 293.2 (M+H)$^+$, 1.63 (ret. time).

7-Methoxy-4-methyl-2,3,4,5-tetrahydro-1H-benzo[c]azepine

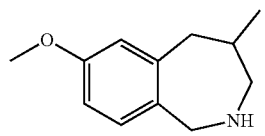

To a solution of 7-methoxy-2-((S)-2-(methoxymethyl)pyrrolidin-1-yl)-4-methyl-2,3,4,5-tetrahydro-1H-benzo[c]azepine (670 mg, 2.201 mmol) in tetrahydrofuran (THF) (10 mL) at ambient temperature was added 1 M BH$_3$ in THF (1.642 ml, 1.642 mmol) slowly under nitrogen. The reaction mixture was stirred at 60° C. for 48 h. After it was cooled to ambient temperature, 20 mL of 4 N NaOH was added slowly. It was heated at 60° C. for 4 h, 10 mL of water was added and the mixture extracted with ethyl acetate (3×50 mL). The combined organic layers were dried with MgSO$_4$, filtered and concentrated to afford the title compound 7-methoxy-4-methyl-2,3,4,5-tetrahydro-1H-benzo[c]azepine (340 mg, 0.729 mmol, 33.1% yield). LC-MS m/z 192.1 (M+H)$^+$, 0.88 (ret. time).

Ethyl 3-(3-(bromomethyl)-4-methylphenyl)-3-(1,4-dimethyl-1H-benzo[d][1,2,3]triazol-5-yl)propanoate

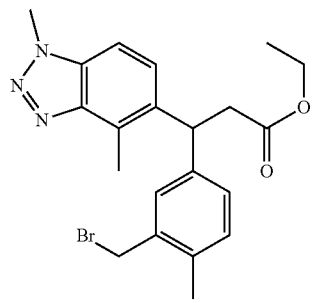 [SMILES: CCOC(=O)CC(c1ccc(C)c(CBr)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (500 mg, 1.361 mmol) in dichloromethane (DCM) (5 mL) at 0° C. under nitrogen was added a solution of PBr$_3$ (0.513 ml, 5.44 mmol) in dichloromethane (DCM) (5 mL) slowly. The reaction mixture was stirred at 0° C. for 30 mins after which 10 mL of water was added and the mixture extracted with ethyl acetate (3×10 mL). The combined organic layers were dried with MgSO$_4$, filtered and concentrated. The crude product was purified by preparative HPLC to afford ethyl 3-(3-(bromomethyl)-4-methylphenyl)-3-(1,4-dimethyl-1H-benzo[d][1,2,3]triazol-5-yl)propanoate (320 mg, 0.639 mmol, 47.0% yield). LC-MS m/z 432.0 (M+H)$^+$, 1.26 (ret. time).

Ethyl 3-(1,4-dimethyl-1H-benzo[d][1,2,3]triazol-5-yl)-3-(3-((7-methoxy-4-methyl-4,5-dihydro-1H-benzo[c]azepin-2(3H)-yl)methyl)-4-methylphenyl)propanoate

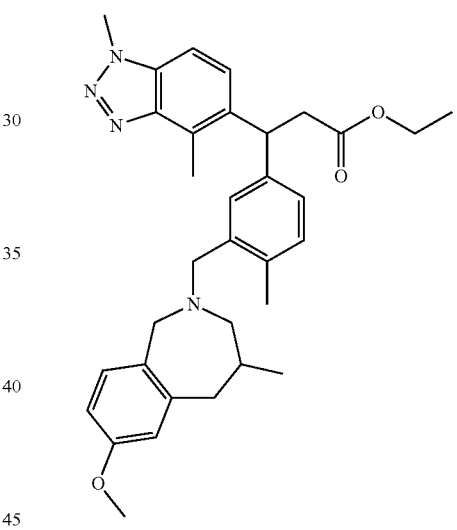

To a mixture of 7-methoxy-4-methyl-2,3,4,5-tetrahydro-1H-benzo[c]azepine (340 mg, 0.711 mmol) and ethyl 3-(3-(bromomethyl)-4-methylphenyl)-3-(1,4-dimethyl-1H-benzo[d][1,2,3]triazol-5-yl)propanoate (200 mg, 0.465 mmol) in dichloromethane (DCM) (10 mL) was added DIPEA (0.081 mL, 0.465 mmol) under nitrogen at ambient temperature. The reaction mixture was stirred at ambient temperature for 16 hrs after which the reaction mixture was concentrated and purified by preparative HPLC to afford the title compound ethyl 3-(1,4-dimethyl-1H-benzo[d][1,2,3]triazol-5-yl)-3-(3-((7-methoxy-4-methyl-4,5-dihydro-1H-benzo[c]azepin-2(3H)-yl)methyl)-4-methylphenyl)propanoate (230 mg, 0.408 mmol, 88% yield). LC-MS m/z 541.3 (M+H)$^+$, 1.07 (ret. time).

3-(1,4-dimethyl-1H-benzo[d][1,2,3]triazol-5-yl)-3-(3-((7-methoxy-4-methyl-4,5-dihydro-1H-benzo[c]azepin-2(3H)-yl)methyl)-4-methylphenyl)propanoic Acid

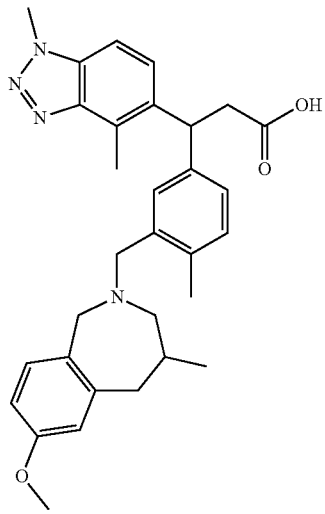 [SMILES: COc1ccc2c(c1)CC(C)CN(Cc1cc(C(CC(=O)O)c3ccc4c(nnn4C)c3C)ccc1C)C2]

To a solution of ethyl 3-(1,4-dimethyl-1H-benzo[d][1,2,3]triazol-5-yl)-3-(3-((7-methoxy-4-methyl-4,5-dihydro-1H-benzo[c]azepin-2(3H)-yl)methyl)-4-methylphenyl)propanoate (230 mg, 0.425 mmol) in tetrahydrofuran (THF) (5 mL) at 25° C. under nitrogen was added a solution of lithium hydroxide (40.7 mg, 1.702 mmol) in water (5.00 mL) slowly. The reaction mixture was stirred at 25° C. for 16 h. 1N HCl was added to pH=3. The mixture was extracted with ethyl acetate (3×20 mL) and the combined organic layers were dried with MgSO$_4$, filtered and concentrated. The crude product was recrystallized from ethyl acetate and hexane to afford the title compound 3-(1,4-dimethyl-1H-benzo[d][1,2,3]triazol-5-yl)-3-(3-((7-methoxy-4-methyl-4,5-dihydro-1H-benzo[c]azepin-2(3H)-yl)methyl)-4-methylphenyl)propanoic acid (100 mg, 0.195 mmol, 45.9% yield). LC-MS m/z 513.1 (M+H)$^+$, 1.67 (ret. time).

Example 8

3-(1,4-Dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)-2,2-dimethylpropanoic Acid, Formic Acid Salt

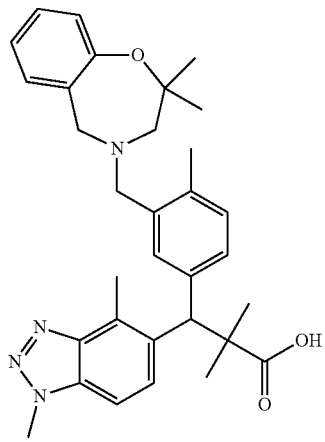 [SMILES: Cc1ccc(C(c2ccc3c(nnn3C)c2C)C(C)(C)C(=O)O)cc1CN1Cc2ccccc2OC(C)(C)C1]

To a solution of methyl 3-(1,4-dimethyl-1H-benzo[d][1,2,3]triazol-5-yl)-3-(3-(hydroxymethyl)-4-methylphenyl)-2,2-dimethylpropanoate (50 mg, 0.131 mmol) in dichloromethane (0.2 mL) was added thionyl chloride (0.019 mL, 0.262 mmol). The resulting reaction mixture was stirred at ambient temperature for 100 min after which time it was evaporated under vacuum then dissolved in acetonitrile (1.5 mL). 2,2-Dimethyl-2,3,4,5-tetrahydrobenzo[f][1,4]oxazepine, hydrochloride (42.0 mg, 0.197 mmol), K$_2$CO$_3$ (54.3 mg, 0.393 mmol) and sodium iodide (3.93 mg, 0.026 mmol) were added. The resulting reaction mixture was stirred at 40° C. for 18 h. This reaction mixture was concentrated. It was dissolved in methanol (1.5 mL) and NaOH (3 N) (0.218 mL, 0.655 mmol) was added. The resulting reaction mixture was heated with microwave at 80° C. for 20 min. It was heated again with microwave at 100° C. for 20 min; heated again with microwave at 120° C. for 30 min; heated again with microwave at 130° C. for 90 min. The reaction mixture was acidified with HCl (3 N) to pH~6, evaporated under vacuum, purified by reverse phase HPLC to afford desired product 3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)-2,2-dimethylpropanoic acid, formic acid salt (50.9 mg, 0.091 mmol, 69.5% yield). LC-MS m/z 527.4 (M+H)$^+$, 0.83 min (ret. time).

Example 9

Ammonium 3-(3-((3-(1H-pyrazol-1-yl)piperidin-1-yl)methyl)-4-methylphenyl)-3-(1,4-dimethyl-1H-benzo[d][1,2,3]triazol-5-yl)propanoate

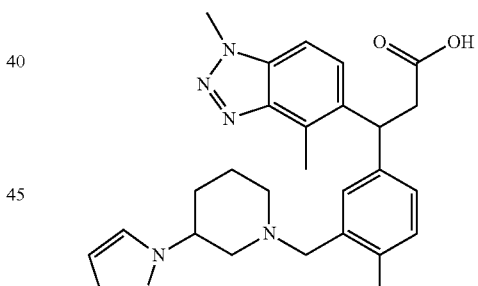

A mixture of ethyl 3-(3-(chloromethyl)-4-methylphenyl)-3-(1,4-dimethyl-1H-benzo[d][1,2,3]triazol-5-yl)propanoate (0.039 g, 0.1 mmol), 3-(1H-pyrazol-1-yl)piperidine (0.023 g, 0.15 mmol) and N,N-diisopropylethylamine (0.07 mL, 0.4 mmol) in N,N-dimethylformamide (DMF) (0.6 mL) was heated to 70° C. for 18 h. The cooled reaction mixture was evaporated, redissolved in acetonitrile (0.5 mL) and ethanol (0.15 mL). Sodium hydroxide (10 M, 0.1 mL) added. The solution was stirred at 40° C. for 18 h. The cooled reaction mixture was evaporated, redissolved in DMSO:MeOH (1:1, 1 mL) and the residue purified by MDAP using a high pH ammonium carbonate buffer (pH 10) to give the title compound ammonium 3-(3-((3-(1H-pyrazol-1-yl)piperidin-1-yl)methyl)-4-methylphenyl)-3-(1,4-dimethyl-1H-benzo[d][1,2,3]triazol-5-yl)propanoate (36.6 mg, 69.7% yield). LC-MS m/z 473.2 (M+H)$^+$, 0.67 min (ret. Time)

Example 10

Ammonium 3-(1,4-dimethyl-1H-benzo[d][1,2,3]triazol-5-yl)-3-(3-((2-(5-isopropyl-4H-1,2,4-triazol-3-yl)pyrrolidin-1-yl)methyl)-4-methylphenyl)propanoate

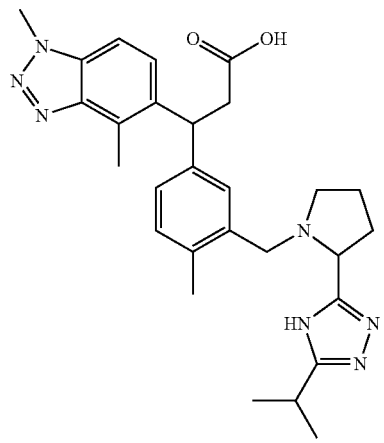 [SMILES: Cc1ccc(C(CC(=O)O)c2ccc3c(nnn3C)c2C)cc1CN1CCCC1c1nnc(C(C)C)[nH]1]

A mixture of ethyl 3-(3-(chloromethyl)-4-methylphenyl)-3-(1,4-dimethyl-1H-benzo[d][1,2,3]triazol-5-yl)propanoate (0.0347 g, 0.09 mmol), 3-isopropyl-5-(pyrrolidin-2-yl)-4H-1,2,4-triazole (0.0258 g, 0.135 mmol) and N,N-diisopropylethylamine (0.063 mL, 0.36 mmol) in N,N-dimethylformamide (DMF) (0.6 mL) was heated to 70° C. for 18 h. The cooled reaction mixture was evaporated, redissolved in acetonitrile (0.5 mL) and ethanol (0.15 mL) and sodium hydroxide (10 M, 0.1 mL) was added. The solution was stirred at 40° C. for 18 h. The cooled reaction mixture was evaporated, redissolved in DMSO: MeOH (1:1, 1 mL) and water (0.1 mL). The residue purified by MDAP using a high pH ammonium carbonate buffer (pH 10) to give the title compound ammonium 3-(1,4-dimethyl-1H-benzo[d][1,2,3]triazol-5-yl)-3-(3-((2-(5-isopropyl-4H-1,2,4-triazol-3-yl)pyrrolidin-1-yl)methyl)-4-methylphenyl)propanoate (17.0 mg, 33.9% yield). LC-MS m/z 502.24 (M+H)$^+$, 0.67 min (ret. time).

The compounds in Table 5 were prepared by a method similar to the one described for the preparation of ammonium 3-(1,4-Dimethyl-1H-benzo[d][1,2,3]triazol-5-yl)-3-(3-((2-(5-isopropyl-4H-1,2,4-triazol-3-yl)pyrrolidin-1-yl)methyl)-4-methyl phenyl)propanoate. As is appreciated by those skilled in the art, these analogous examples may involve variations in general reaction conditions.

TABLE 5

| Ex # | Structure | Name | LCMS [M + H]$^+$ | Retention Time (min) |
|---|---|---|---|---|
| Example 11 | 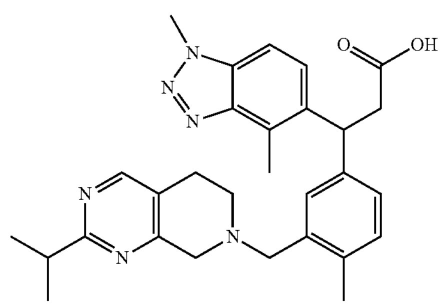 [SMILES: Cc1ccc(C(CC(=O)O)c2ccc3c(nnn3C)c2C)cc1CN1CCc2cnc(C(C)C)nc2C1] | Ammonium 3-(1,4-dimethyl-1H-benzo[d][1,2,3]triazol-5-yl)-3-(3-((2-isopropyl-5,6-dihydropyrido[3,4-d]pyrimidin-7(8H)-yl)methyl)-4-methylphenyl)propanoate | 499.21 | 0.73 |
| Example 12 | 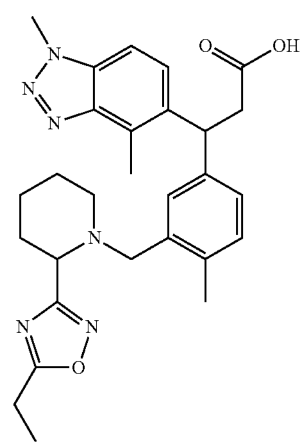 [SMILES: CCc1nc(C2CCCCN2Cc2cc(C(CC(=O)O)c3ccc4c(nnn4C)c3C)ccc2C)no1] | Ammonium 3-(1,4-dimethyl-1H-benzo[d][1,2,3]triazol-5-yl)-3-(3-((2-(5-ethyl-1,2,4-oxadiazol-3-yl)piperidin-1-yl)methyl)-4-methylphenyl)propanoate | 503.26 | 0.78 |

TABLE 5-continued

| Ex # | Structure | Name | LCMS [M + H]+ | Retention Time (min) |
|---|---|---|---|---|
| Example 13 | 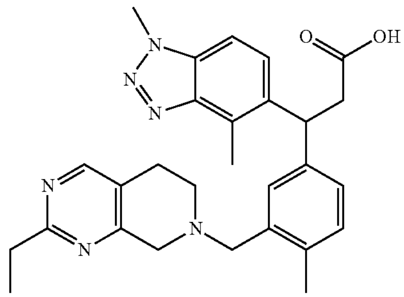 [SMILES: CCc1ncc2c(n1)CN(Cc1cc(C(CC(=O)O)c3ccc4c(nnn4C)c3C)ccc1C)CC2] | Ammonium 3-(1,4-dimethyl-1H-benzo[d][1,2,3]triazol-5-yl)-3-(3-((2-ethyl-5,6-dihydropyrido[3,4-d]pyrimidin-7(8H)-yl)methyl)-4-methylphenyl)propanoate | 485.23 | 0.65 |
| Example 14 | 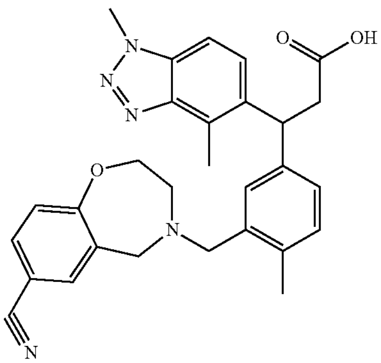 [SMILES: Cc1ccc(C(CC(=O)O)c2ccc3c(nnn3C)c2C)cc1CN1CCOc2ccc(C#N)cc2C1] | Ammonium 3-(3-((7-cyano-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoate | 496.24 | 0.71 |
| Example 15 | 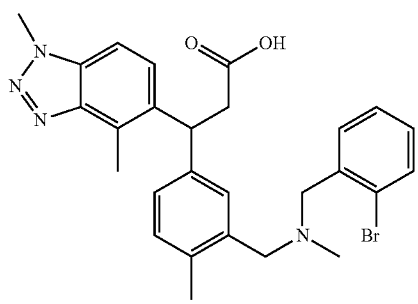 [SMILES: Cc1ccc(C(CC(=O)O)c2ccc3c(nnn3C)c2C)cc1CN(C)Cc1ccccc1Br] | Ammonium 3-(3-(((2-bromobenzyl)(methyl)amino)methyl)-4-methylphenyl)-3-(1,4-dimethyl-1H-benzo[d][1,2,3]triazol-5-yl)propanoate | 521.15 | 0.65 |
| Example 16 | 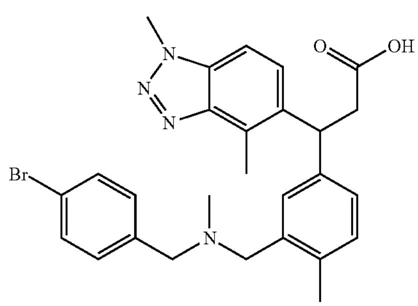 [SMILES: Cc1ccc(C(CC(=O)O)c2ccc3c(nnn3C)c2C)cc1CN(C)Cc1ccc(Br)cc1] | Ammonium 3-(3-(((4-bromobenzyl)(methyl)amino)methyl)-4-methylphenyl)-3-(1,4-dimethyl-1H-benzo[d][1,2,3]triazol-5-yl)propanoate | 521.15 | 0.68 |
| Example 17 | 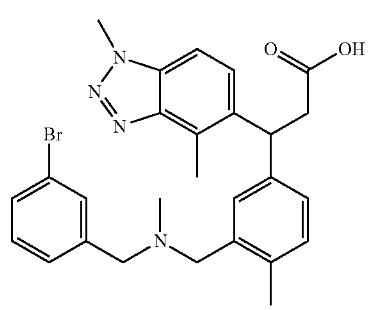 [SMILES: Cc1ccc(C(CC(=O)O)c2ccc3c(nnn3C)c2C)cc1CN(C)Cc1cccc(Br)c1] | Ammonium 3-(3-(((3-bromobenzyl)(methyl)amino)methyl)-4-methylphenyl)-3-(1,4-dimethyl-1H-benzo[d][1,2,3]triazol-5-yl)propanoate | 521.19 | 0.68 |

Example 18

3-(1,4-Dimethyl-1H-benzo[d][1,2,3]triazol-5-yl)-3-(4-methyl-3-((2-methyl-2-(p-tolyl)morpholino)methyl)phenyl)propanoic Acid, Formic Acid Salt

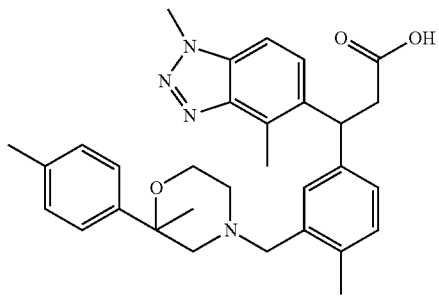

A mixture of ethyl 3-(3-(chloromethyl)-4-methylphenyl)-3-(1,4-dimethyl-1H-benzo[d][1,2,3]triazol-5-yl)propanoate (0.0347 g, 0.09 mmol), 2-methyl-2-(p-tolyl)morpholine (0.0258 g, 0.135 mmol) and N,N-diisopropylethylamine (0.063 mL, 0.36 mmol) in N,N-dimethylformamide (DMF) (0.6 mL) was heated to 70° C. for 18 h. The cooled reaction mixture was evaporated, redissolved in acetonitrile (0.5 mL) and ethanol (0.15 mL). Sodium hydroxide (10 M, 0.1 m L) was added. The solution was stirred at 40° C. for 18 h. The cooled reaction mixture was evaporated, redissolved in DMSO: MeOH (1:1, 1 mL) and water (0.1 mL). The residue was purified by MDAP using a high pH ammonium carbonate buffer (pH 10). Impure compound was redissolved in DMSO (1 mL) and the residue was purified by MDAP using a formic acid modifier to give the title compound 3-(1,4-dimethyl-1H-benzo[d][1,2,3]triazol-5-yl)-3-(4-methyl-3-((2-methyl-2-(p-tolyl)morpholino)methyl)phenyl)propanoic acid, formic acid salt (20.8 mg, 40.6% yield). LC-MS m/z 513.25 (M+H)+, 0.82 min (ret. time).

The compounds in Table 6 were prepared by a method similar to the one described for the preparation of 3-(1,4-Dimethyl-1H-benzo[d][1,2,3]triazol-5-yl)-3-(3-((2-(5-isopropyl-4H-1,2,4-triazol-3-yl)pyrrolidin-1-yl)methyl)-4-methylphenyl)propanoic acid, formic acid salt. As is appreciated by those skilled in the art, these analogous examples may involve variations in general reaction conditions.

TABLE 6

| Ex # | Structure | Name | LCMS [M + H]+ | Retention Time (min) |
|---|---|---|---|---|
| Example 19 | 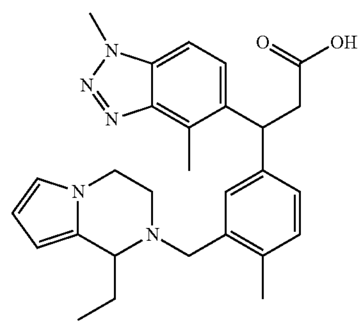 [SMILES: CCC1c2cccn2CCN1Cc1cc(C(CC(=O)O)c2ccc3c(nnn3C)c2C)ccc1C] | 3-(1,4-dimethyl-1H-benzo[d][1,2,3]triazol-5-yl)-3-(3-((1-ethyl-3,4-dihdyropyrrolo[1,2-a]pyrazin-2(1H)-yl)methyl)-4-methylphenyl)propanoic acid, formic acid salt | 472.26 | 0.70 |
| Example 20 | 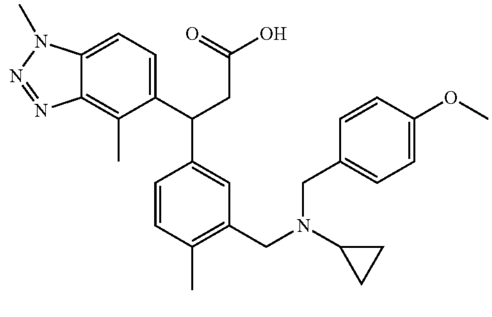 [SMILES: COc1ccc(CN(Cc2cc(C(CC(=O)O)c3ccc4c(nnn4C)c3C)ccc2C)C2CC2)cc1] | 3-(3-((cyclopropyl(4-methoxybenzyl)amino)methyl)-4-methylphenyl)-3-(1,4-dimethyl-1H-benzo[d][1,2,3]triazol-5-yl)propanoic acid, formic acid salt | 499.22 | 0.73 |

TABLE 6-continued

| Ex # | Structure | Name | LCMS [M + H]+ | Retention Time (min) |
|---|---|---|---|---|
| Example 21 | 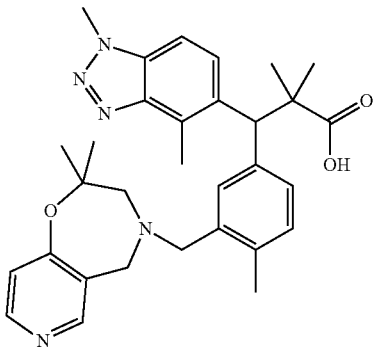 [SMILES: Cc1ccc(C(c2ccc3c(nnn3C)c2C)C(C)(C)C(=O)O)cc1CN1Cc2cnccc2OC(C)(C)C1] | 3-(1,4-dimethyl-1H-benzo[d][1,2,3]triazol-5-yl)-3-(3-((3-(4-methoxyphenyl)morpholino)methyl)-4-methylphenyl)propanoic acid, formic acid salt | 515.20 | 0.78 |

Example 22

3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2,2-dimethylpropanoic Acid, Trifluoroacetic Acid

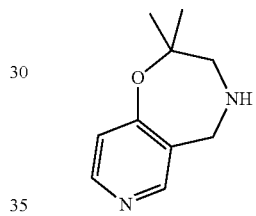

1-(((4-Chloropyridin-3-yl)methyl)amino)-2-methylpropan-2-ol

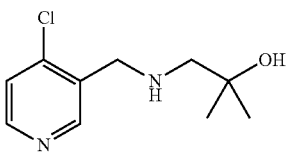

To a solution of 4-chloronicotinaldehyde (0.425 g, 3 mmol) in methanol (10 mL) was added 1-amino-2-methylpropan-2-ol (0.281 g, 3.15 mmol). The reaction mixture was stirred at ambient temperature for 3 h after which time NaBH$_4$ (0.057 g, 1.500 mmol) was added. The resulting reaction mixture was stirred at ambient temperature for 1 h. The reaction mixture was concentrated and redissolved in DCM (15 mL), dried over MgSO$_4$, filtered, then evaporated under vacuum to afford product 1-(((4-chloropyridin-3-yl)methyl)amino)-2-methylpropan-2-ol (0.657 g, 3.06 mmol, 102% yield). LC-MS m/z 215.1 (M+H)+, 0.19 min (ret. time).

2,2-Dimethyl-2,3,4,5-tetrahydropyrido[3,4-f][1,4]oxazepine

To a solution of 1-(((4-chloropyridin-3-yl)methyl)amino)-2-methylpropan-2-ol (0.656 g, 3.06 mmol) in dimethyl sulfoxide (8 mL) was added KOtBu (0.686 g, 6.11 mmol). The resulting reaction mixture was stirred at 80° C. for 20 h. To the reaction mixture was added sodium bicarbonate (0.513 g, 6.11 mmol) and stirred at 80° C. for 2 h. The reaction mixture was filtered then evaporated down after which time it was redissolved in DCM (20 mL), dried over K$_2$CO$_3$, filtered, concentrated to afford desired product 2,2-dimethyl-2,3,4,5-tetrahydropyrido[3,4-f][1,4]oxazepine (0.432 g, 2.424 mmol, 79% yield). LC-MS m/z 178.9 (M+H)+, 0.25 min (ret. time).

3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2,2-dimethylpropanoic Acid, Trifluoroacetic Acid

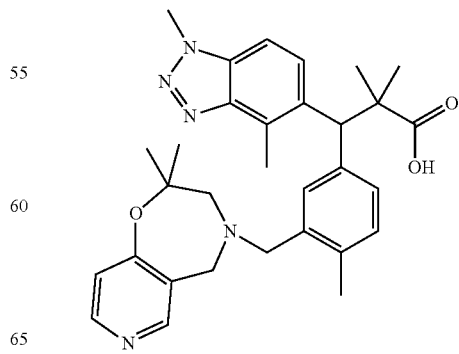

To a solution of methyl 3-(1,4-dimethyl-1H-benzo[d][1,2,3]triazol-5-yl)-3-(3-(hydroxymethyl)-4-methylphenyl)-2,2-dimethylpropanoate (76 mg, 0.2 mmol) in dichloromethane (1 mL) was added SOCl$_2$ (0.029 mL, 0.400 mmol). The resulting reaction mixture was stirred at ambient temperature for 10 min and then concentrated. To this crude was added the solution of 2,2-dimethyl-2,3,4,5-tetrahydropyrido[3,4-f][1,4]oxazepine (178 mg, 1.000 mmol) and DIEA (0.140 mL, 0.800 mmol) in tetrahydrofuran (1 mL) and acetonitrile (2 mL). The resulting reaction mixture was heated with microwave at 100° C. for 1 h. The reaction mixture was evaporated under vacuum, redissolved in methanol (3 mL) then NaOH (3.0 N) (0.533 mL, 1.600 mmol) was added. The resulting reaction mixture was heated with microwave at 130° C. for 60 min. The reaction mixture was then acidified with HCl (2 N) to pH~6, evaporated under vacuum, purified by reverse phase HPLC to afford desired product 3-(1,4-dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2,2-dimethylpropanoic acid, trifluoroacetic acid (18.0 mg, 0.034 mmol, 17.06% yield). LC-MS m/z 528.2 (M+H)$^+$, 0.88 min (ret. time).

Example 23

3-(1,4-Dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2,2-dimethylpropanoic Acid, Trifluoroacetic Acid

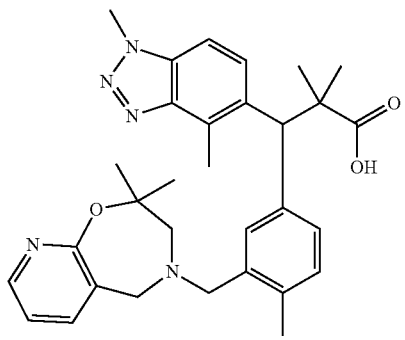 [SMILES: Cc1ccc(C(c2ccc3c(nnn3C)c2C)C(C)(C)C(=O)O)cc1CN1Cc2cccnc2OC(C)(C)C1]

1-(((2-Chloropyridin-3-yl)methyl)amino)-2-methylpropan-2-ol

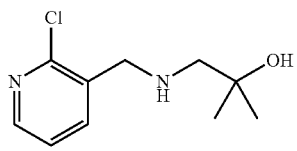

To a solution of 2-chloronicotinaldehyde (1.44 g, 10.17 mmol) in methanol (30 mL) was added 1-amino-2-methylpropan-2-ol (0.952 g, 10.68 mmol). The reaction mixture was stirred at ambient temperature for 30 min, then NaBH$_4$ (0.192 g, 5.09 mmol) was added. The resulting reaction mixture was stirred at ambient temperature for 1 h. More NaBH$_4$ (0.077 g, 2.035 mmol) was added. The resulting reaction mixture was stirred at ambient temperature for 17 h and then concentrated. It was redissolved in DCM (50 mL), dried over MgSO$_4$, filtered then evaporated under vacuum to afford product 1-(((2-chloropyridin-3-yl)methyl)amino)-2-methylpropan-2-ol (2.6017 g, 12.12 mmol, 119% yield). LC-MS m/z 215.2 (M+H)$^+$, 0.33 min (ret. time).

2,2-Dimethyl-2,3,4,5-tetrahydropyrido[3,2-f][1,4]oxazepine

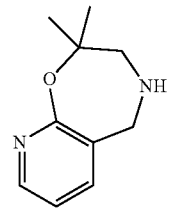

To a solution of 1-(((2-chloropyridin-3-yl)methyl)amino)-2-methylpropan-2-ol (0.859 g, 4.0 mmol) in dimethyl sulfoxide (10 mL) was added KOtBu (0.898 g, 8.00 mmol). The resulting reaction mixture was stirred at 80° C. for 65 h. To the reaction mixture was added sodium bicarbonate (0.672 g, 8.00 mmol) then stirred at 80° C. for 1 h. The reaction mixture was filtered, evaporated down, redissolved in DCM (20 mL), dried over K$_2$CO$_3$, filtered, evaporated under vacuum to afford desired product 2,2-dimethyl-2,3,4,5-tetrahydropyrido[3,2-f][1,4]oxazepine (0.6151 g, 3.45 mmol, 86% yield). LC-MS m/z 178.9 (M+H)$^+$, 0.20 min (ret. time).

3-(1,4-Dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2,2-dimethylpropanoic Acid, Trifluoroacetic Acid
GSK3377037A N34297-62-A1

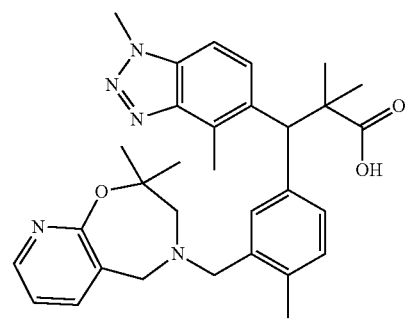 [SMILES: Cc1ccc(C(c2ccc3c(nnn3C)c2C)C(C)(C)C(=O)O)cc1CN1Cc2cccnc2OC(C)(C)C1]

To a solution of methyl 3-(1,4-dimethyl-1H-benzo[d][1,2,3]triazol-5-yl)-3-(3-(hydroxymethyl)-4-methylphenyl)-2,2-dimethylpropanoate (76 mg, 0.2 mmol) in dichloromethane (1 mL) was added SOCl$_2$ (0.029 mL, 0.400 mmol). The resulting reaction mixture was stirred at ambient temperature for 10 min and then concentrated. A solution of 2,2-dimethyl-2,3,4,5-tetrahydropyrido[3,2-f][1,4]oxazepine (71.3 mg, 0.400 mmol), DIEA (0.140 mL, 0.800 mmol) in tetrahydrofuran (1 mL) and acetonitrile (2 mL) was added. The resulting reaction mixture was heated with microwave at 100° C. for 1 h. To the reaction mixture was added more DIEA (0.070 mL, 0.400 mmol) then heated with microwave at 100° C. for 1 h. The reaction mixture was evaporated under vacuum then redissolved in methanol (3 mL) and NaOH (3.0 N) (0.533 mL, 1.600 mmol) was added. The resulting reaction mixture was heated with microwave at 140° C. for 1 h. The reaction mixture was acidified with HCl (2 N) to pH~6, evaporated under vacuum, purified by reverse phase HPLC to afford desired product 3-(1,4-dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2,2-dimethylpropanoic acid, trifluoroacetic acid (65.1 mg, 0.123 mmol, 61.7% yield). LC-MS m/z 528.3 (M+H)$^+$, 0.73 min (ret. time).

Example 24

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic Acid, Formic Acid Salt

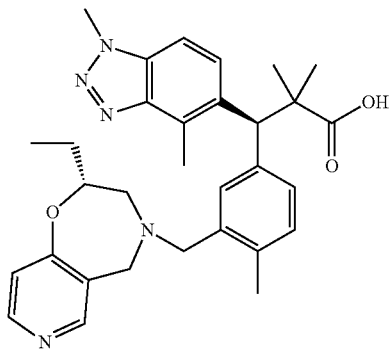 [SMILES: CC[C@@H]1CN(Cc2cc([C@@H](c3ccc4c(nnn4C)c3C)C(C)(C)C(=O)O)ccc2C)Cc2cnccc2O1]

(R)-1-Aminobutan-2-ol

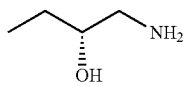

To a solution of NH$_4$OH (~28% solution in H$_2$O) (36.3 mL, 261 mmol) was added (R)-2-ethyloxirane (2.246 mL, 26.1 mmol). The resulting reaction mixture was stirred at ambient temperature for 18 h. The reaction mixture was concentrated under reduced pressure to afford the desired product (R)-1-aminobutan-2-ol (2.488 g, 19.54 mmol, 74.9% yield). $^1$H NMR (400 MHz, CHLOROFORM-d) δ ppm 0.97 (t, J=7.53 Hz, 3H) 1.42-1.53 (m, 2H) 1.71 (br. s., 3H) 2.47-2.59 (m, 1H) 2.85 (dd, J=12.80, 3.26 Hz, 1H) 3.39-3.49 (m, 1H).

4-Bromonicotinaldehyde

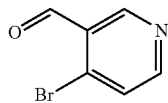

To a solution of 4-bromopyridine hydrochloride (50 g, 257 mmol) in tetrahydrofuran (THF) (250 mL) was added LDA 2M solution in THF (250 mL, 500 mmol) at −78° C. and stirred for 1 h. DMF (19.91 mL, 257 mmol) was added at −78° C. It was stirred for 1 h at this same temperature. The reaction mixture was warmed to ambient temperature and stirred for 16 h. The reaction mixture was cooled to 0° C., quenched with 2 N HCl and extracted twice with EtOAc. The organic layer was dried over anhydrous Na$_2$SO$_4$ and filtered. The filtrate was concentrated to give the title compound (13 g, 69.9 mmol, 27.2% yield) as brown colored liquid. GCMS: rt=6.59 mins, M$^+$=185.0

(R)-1-(((4-Bromopyridin-3-yl)methyl)amino)butan-2-ol

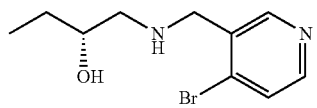

To a solution of (R)-1-aminobutan-2-ol (1.677 g, 18.82 mmol) in methanol (30 mL) and was added 4-bromonicotinaldehyde (3.5 g, 18.82 mmol) at ambient temperature. Then NaOH (18.82 mL, 18.82 mmol) was added at 0° C. The reaction mixture was stirred at ambient temperature for 1 h after which time NaBH$_4$ (0.712 g, 18.82 mmol) was added portionwise at 0° C. The reaction mixture was stirred for 48 h at ambient temperature. The reaction mixture was concentrated and then quenched with cold water, extracted with EtOAc and washed with brine solution. The organic layer was dried over Na$_2$SO$_4$, filtered and then concentrated. The crude product was purified with silica gel chromatography to give the title compound (5 g, 15.58 mmol, 83% yield) as liquid. LC-MS m/z 261.12 (M+H)$^+$, 2.49 min (ret. time).

(R)-2-Ethyl-2,3,4,5-tetrahydropyrido[3,4-f][1,4]oxazepine

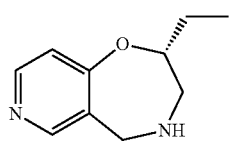

To a solution of (R)-1-(((4-bromopyridin-3-yl)methyl)amino)butan-2-ol (800 mg, 3.09 mmol) in isopropanol (30 mL) was added Cs$_2$CO$_3$ (2012 mg, 6.17 mmol) at ambient temperature, followed by copper(I) iodide (588 mg, 3.09 mmol). The reaction mixture was heated in a microwave reactor for 1 h at 95° C. The reaction mixture was filtered though celite and washed with ethyl acetate. The filtrate was concentrated and was purified with silica gel chromatography to give the title compound (590 mg, 2.70 mmol, 87% yield) as liquid. LC-MS m/z 179.26 (M+H)$^+$, 2.58 min (ret. time).

(R)-tert-Butyl 2-ethyl-2,3-dihydropyrido[3,4-f][1,4]oxazepine-4(5H)-carboxylate

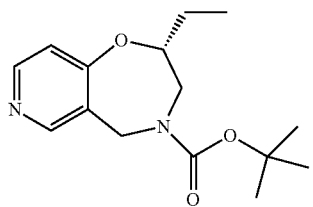 [SMILES: CC[C@@H]1CN(C(=O)OC(C)(C)C)Cc2cnccc2O1]

To a solution of (R)-2-ethyl-2,3,4,5-tetrahydropyrido[3,4-f][1,4]oxazepine (2.5 g, 14.03 mmol) in THF (20 mL) was added TEA (0.313 mL, 2.244 mmol) at ambient temperature. Di-tert-butyl dicarbonate (6.51 mL, 28.1 mmol) was added at 0° C. The reaction mixture was stirred at ambient temperature for 2 h. The reaction mixture was quenched with water and extracted with ethyl acetate, washed with brine solution, dried over $Na_2SO_4$, filtered and concentrated. It was purified with silica gel chromatography to give the title compound (3.5 g, 11.53 mmol, 82% yield) as liquid. LC-MS m/z 279.24 (M+H)$^+$, 1.60 min (ret. time).

(R)-2-Ethyl-2,3,4,5-tetrahydropyrido[3,4-f][1,4]oxazepine hydrochloride

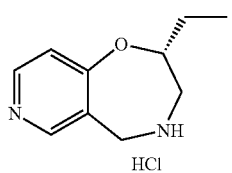

To a solution of (R)-tert-butyl 2-ethyl-2,3-dihydropyrido[3,4-f][1,4]oxazepine-4(5H)-carboxylate (3.5 g, 12.57 mmol) in 1,4-dioxane (20 mL) was added 4 M HCl in dioxane (3 mL, 12.00 mmol) at 0° C. The reaction mixture was stirred at ambient temperature for 1 h. The reaction mixture was concentrated to obtain a solid. The solid was washed with diethyl ether and hexane to give the title compound (2.1 g, 9.43 mmol, 75% yield). LC-MS m/z 179.0 (M+H)$^+$, 2.78 min (ret. time).

(1,4-Dimethyl-1H-benzo[d][1,2,3]triazol-5-yl)(3-(((4-methoxybenzyl)oxy)methyl)-4-methylphenyl)methanol

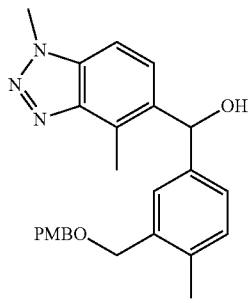

tert-Butyllithium (19.52 mL, 33.2 mmol) was added dropwise to a solution of 5-bromo-1,4-dimethyl-1H-benzo[d][1,2,3]triazole (3.91 g, 17.31 mmol) in tetrahydrofuran (THF) (108 ml) at −78° C. under a nitrogen atmosphere and stirred for 30 minutes. A solution of 3-(((4-methoxybenzyl)oxy)methyl)-4-methylbenzaldehyde (3.9 g, 14.43 mmol) in tetrahydrofuran (THF) (36.1 ml) was then added dropwise and stirred at −78° C. for 1.5 hours followed by warming to room temperature and stirring for an additional hour. Saturated aqueous ammonium chloride (100 mL) was added to the solution. Same scale reaction was runned side by side. The 2 batches were combined and the mixture was extracted with ethyl acetate (3×100 mL). The combined organic fractions were washed (brine), dried (sodium sulfate), filtered and the solvent was concentrated. The crude product was purified by silica gel chromatography to give title compound (8.8 g, 21.08 mmol, 73.0% yield). LC/MS: m/z 418.0 (M+H)$^+$, 1.11 min (ret. time). 1H NMR (400 MHz, CHLOROFORM-d) δ=7.76-7.69 (m, 1H), 7.34 (s, 2H), 7.24 (d, J=8.3 Hz, 2H), 7.21-7.12 (m, 2H), 6.87 (d, J=8.3 Hz, 2H), 6.27 (s, 1H), 4.49 (d, J=5.0 Hz, 4H), 4.29 (s, 3H), 3.83 (s, 3H), 2.81 (s, 3H), 2.31 (s, 3H), 2.07 (s, 1H)

Methyl 3-(1,4-dimethyl-1H-benzo[d][1,2,3]triazol-5-yl)-3-(3-(hydroxymethyl)-4-methylphenyl)-2,2-dimethylpropanoate

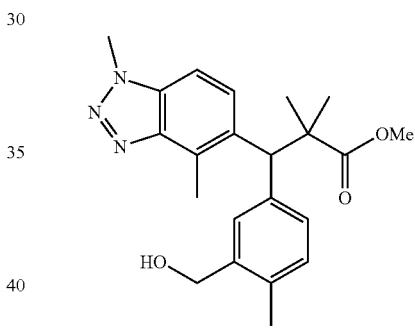

2,2,2-trichloroacetonitrile (4.23 ml, 42.2 mmol) and DBU (0.146 ml, 1.054 mmol) were added sequentially to a solution of (1,4-dimethyl-1H-benzo[d][1,2,3]triazol-5-yl)(3-(((4-methoxybenzyl)oxy)methyl)-4-methylphenyl)methanol (8.8 g, 21.08 mmol) in acetonitrile (263 ml) at ambient temperature and stirred for 45 minutes. ((1-Methoxy-2-methylprop-1-en-1-yl)oxy)trimethylsilane (9.19 g, 52.7 mmol) followed by 1,1,1-trifluoro-N-((trifluoromethyl)sulfonyl)methanesulfonamide (0.593 g, 2.108 mmol) were then added and the solution stirred at ambient temperature for 2 h. The reaction was quenched with saturated sodium bicarbonate (10 mL) and extracted with DCM (3×15 mL), dried over sodium sulfate, filtered and concentrated. The residue was redissolved in dichloromethane (DCM) (263 mL). Water (15.19 mL, 843 mmol) was added and the solution was cooled to 0° C., 4,5-dichloro-3,6-dioxocyclohexa-1,4-diene-1,2-dicarbonitrile (9.57 g, 42.2 mmol) was added. The solution was stirred at 0° C. for 1 h. The reaction was quenched with saturated sodium bicarbonate (10 mL) and extracted with DCM (3×15 mL) and dried over sodium sulfate. The crude product was purified by flash chromatography on a silica gel chromatography to give the title compound (6.9 g, 18.09 mmol, 86% yield). LC/MS: m/z 382.0 (M+H)$^+$, 1.00 min (ret. time).

193

Methyl 3-(3-(chloromethyl)-4-methylphenyl)-3-(1,4-dimethyl-1H-benzo[d][1,2,3]triazol-5-yl)-2,2-dimethylpropanoate

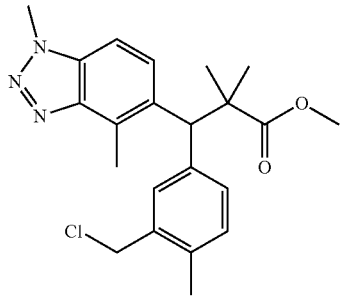 [SMILES: COC(=O)C(C)(C)C(c1ccc(C)c(CCl)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate (2200 mg, 5.77 mmol) in dichloromethane (DCM) (10 mL) at 25° C. was added thionyl chloride (0.842 mL, 11.53 mmol). The mixture was stirred at 25° C. for 40 min. The reaction mixture was concentrated to give the title compound (2200 mg, 5.50 mmol, 95% yield). LC-MS m/z 399.9 (M)$^+$, 1.14 min (ret. time).

Methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

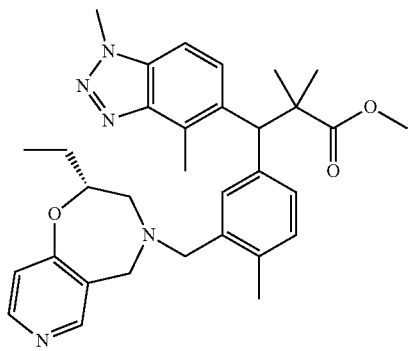 [SMILES: CC[C@@H]1CN(Cc2cc(C(c3ccc4c(nnn4C)c3C)C(C)(C)C(=O)OC)ccc2C)Cc2cnccc2O1]

To a solution of methyl 3-(3-(chloromethyl)-4-methylphenyl)-3-(1,4-dimethyl-1H-benzo[d][1,2,3]triazol-5-yl)-2,2-dimethylpropanoate (1380 mg, 3.45 mmol) in acetonitrile (8 mL) at 25° C. was added (R)-2-ethyl-2,3,4,5-tetrahydropyrido[3,4-f][1,4]oxazepine, hydrochloride (889 mg, 4.14 mmol) and DIEA (2.411 mL, 13.80 mmol). The reaction mixture was heated in a Biotage microwave at high absorption for 1 h at 120° C. The solvent was removed under reduced pressure and the residue then purified by silica gel chromatography. The desired fractions were concentrated under reduced pressure to give the title compound (1000 mg, 1.846 mmol, 53.5% yield). LC-MS m/z 542.4 (M+H)$^+$, 0.82 min (ret. time).

194

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic Acid

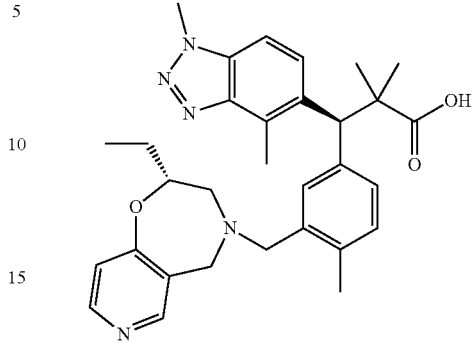

To a solution of methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate (1000 mg, 1.846 mmol) in methanol (8 mL) at 25° C. was added LiOH (5.54 mL, 11.08 mmol). The reaction mixture was heated in a Biotage microwave at high absorption for 2 h at 120° C. This reaction was repeated with 1.5 g of methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate and 8.3 mL LiOH in 10 mL MeOH. Both batches were combined and then acidified with 6H HCl to pH~1 and extracted with ethyl acetate twice. The aqueous layer was basified with 2M LiOH to pH 5. It was extracted with ethyl acetate twice. The combined organic layer was washed with water twice and then brine and concentrated to give the crude product (1350 mg). The water layer was extracted with 4:1 DCM and IPA to obtain another impure batch (900 mg crude). The impure batch was purified with preparative HPLC under acidic conditions. Fractions were concentrated and combined with the 1.35 g batch. The combined batch was purified with chiral SFC (Column: Chiralpak AD 20×250 mm; Co-solvent: 20% EtOH; Flowrate: 50 g/min; Back pressure: 100 Bar). (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (654 mg, 1.239 mmol) was obtained as solid. LC-MS m/z 528.3 (M+H)$^+$, 0.83 min (ret. time). (chiral SFC ret. time: 7.52 min)

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic Acid, Formic Acid Salt

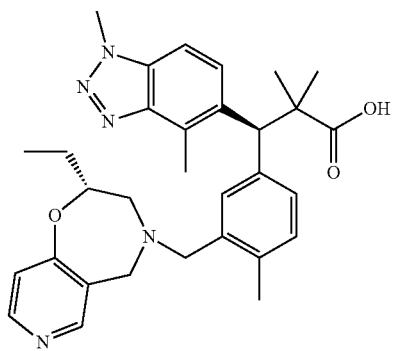 [SMILES: CC[C@@H]1CN(Cc2cc([C@@H](c3ccc4c(nnn4C)c3C)C(C)(C)C(=O)O)ccc2C)Cc2cnccc2O1]

To a suspension of (S)-methyl 3-(1,4-dimethyl-1H-benzo[d][1,2,3]triazol-5-yl)-3-(3-(hydroxymethyl)-4-methylphenyl)-2,2-dimethylpropanoate (100 mg, 0.262 mmol) in dichloromethane (DCM) (2 mL) was added thionyl chloride (0.038 mL, 0.524 mmol). The mixture was stirred at ambient temperature for 30 min and the solvent removed. The residue was re-dissolved in acetonitrile (2 mL), DIEA (0.183 mL, 1.049 mmol) and (R)-2-ethyl-2,3,4,5-tetrahydropyrido[3,4-f][1,4]oxazepine hydrochloride (56.3 mg, 0.262 mmol) were added. The resulting reaction mixture was heated in a Biotage microwave at high absorption for 1 h at 120° C., the solvent was removed and the residue was purified by silica gel chromatography to give the intermediate. It was re-dissolved in MeOH (2 mL) and 2M LiOH (0.786 mL, 1.573 mmol) was added and the reaction mixture was heated in a Biotage microwave at high absorption for 2 h at 120° C. It was acidified with 6N HCl and 0.5 mL DMSO was added. It was concentrated to give the crude material. The crude product was purified by reverse-phase HPLC (with 0.1% formic acid condition) to give the title compound (61 mg, 0.106 mmol, 40.6% yield). LC-MS m/z 528.3 (M+H)$^+$, 0.77 min (ret. time).

The compounds in Table 7 were prepared by a method similar to the one described for the preparation of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid. As is appreciated by those skilled in the art, these analogous examples may involve variations in general reaction conditions.

TABLE 7

| Ex # | Structure | Name | LCMS [M + H]$^+$ | Retention Time (min) |
|---|---|---|---|---|
| Example 25 | 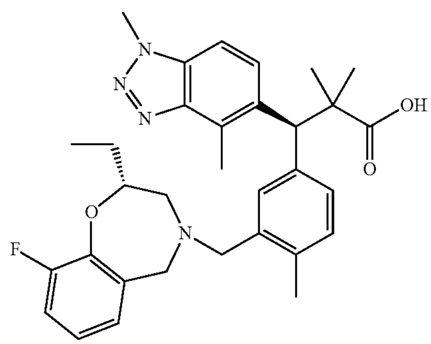 [SMILES: CC[C@@H]1CN(Cc2cc([C@@H](c3ccc4c(nnn4C)c3C)C(C)(C)C(=O)O)ccc2C)Cc2cccc(F)c2O1] | (S)-3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)-2,2-dimethylpropanoic acid, trifluoroacetic acid salt | 527.4 | 0.81 |
| Example 26 | 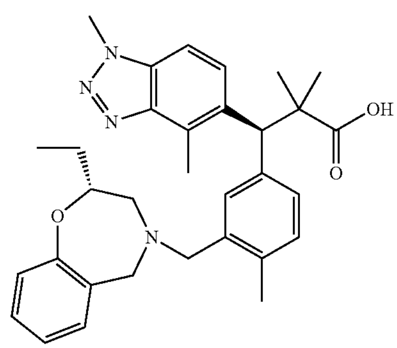 [SMILES: CC[C@@H]1CN(Cc2cc([C@@H](c3ccc4c(nnn4C)c3C)C(C)(C)C(=O)O)ccc2C)Cc2ccccc2O1] | (S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoic acid, trifluoroacetic acid salt | 527.4 | 0.81 |
| Example 27 | 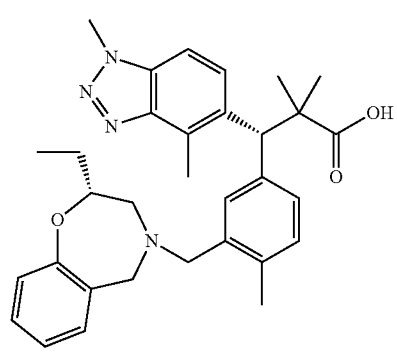 [SMILES: CC[C@@H]1CN(Cc2cc([C@H](c3ccc4c(nnn4C)c3C)C(C)(C)C(=O)O)ccc2C)Cc2ccccc2O1] | (R)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoic acid | 527.6 | 0.81 |

TABLE 7-continued

| Ex # | Structure | Name | LCMS [M + H]+ | Retention Time (min) |
|---|---|---|---|---|
| Example 28 | 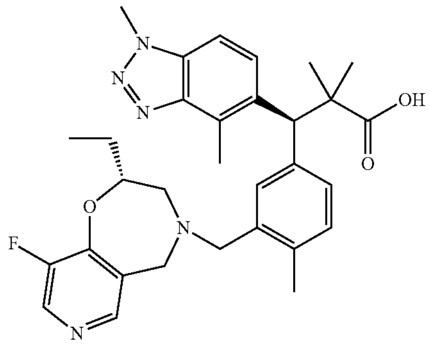 [SMILES: CC[C@@H]1CN(Cc2cc([C@@H](c3ccc4c(nnn4C)c3C)C(C)(C)C(=O)O)ccc2C)Cc2cncc(F)c2O1] | (S)-3-(1,4-Dimethyl-1H-benzo[d][1,2,3]triazol-5-yl)-3-(3-(((R)-2-ethyl-9-fluoro-2,3-dihydropyrido[3,4-f][1,4]oxazepin-4(5H)-yl)methyl)-4-methylphenyl)-2,2-dimethylpropanoic acid | 546.5 | 0.90 |
| Example 29 | 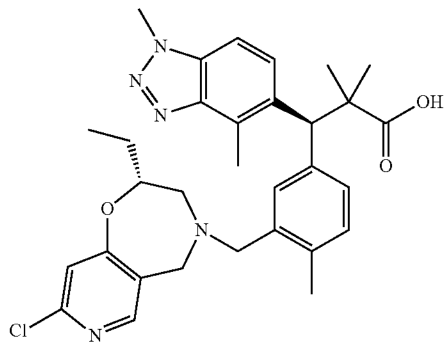 [SMILES: CC[C@@H]1CN(Cc2cc([C@@H](c3ccc4c(nnn4C)c3C)C(C)(C)C(=O)O)ccc2C)Cc2cnc(Cl)cc2O1] | (S)-3-(3-(((R)-8-Chloro-2-methyl-2,3-dihdyropyrido[3,4-f][1,4]oxazepin-4(5H)-yl)methyl)-4-methylphenyl)-3-(1,4-dimethyl-1H-benzo[d][1,2,3]triazol-5-yl)-2,2-dimethylpropanoic acid | 562.5 | 0.93 |
| Example 30 | 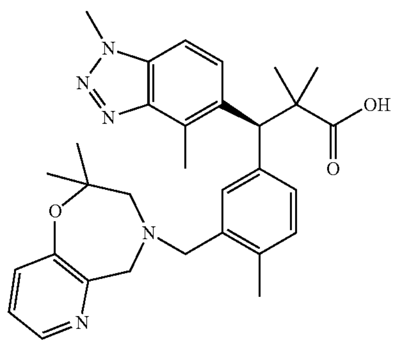 [SMILES: Cc1ccc([C@@H](c2ccc3c(nnn3C)c2C)C(C)(C)C(=O)O)cc1CN1Cc2ncccc2OC(C)(C)C1] | (S)-Methyl 3-(1,4-dimethyl-1H-benzo[d][1,2,3]triazol-5-yl)-3-(3-((2,2-dimethyl-2,3-dihydropyrido[2,3-f][1,4]oxazepin-4(5H)-yl)methyl)-4-methylphenyl)-2,2-dimethylpropanoate, formic acid salt | 528.5 | 0.93 |

Example 31

3-(1,4-Dimethyl-1H-benzo[d][1,2,3]triazol-5-yl)-3-(3-(((R)-2-ethyl-6-fluoro-2,3-dihydrobenzo[f][1,4]oxazepin-4(5H)-yl)methyl)-4-methylphenyl)-2,2-dimethylpropanoic Acid, Formic Acid Salt

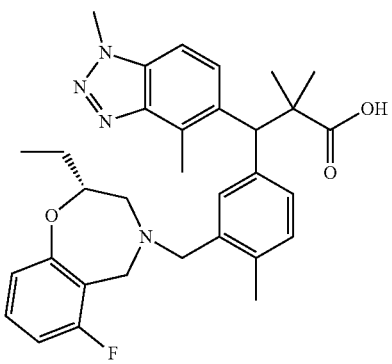 [SMILES: CC[C@@H]1CN(Cc2cc(C(c3ccc4c(nnn4C)c3C)C(C)(C)C(=O)O)ccc2C)Cc2c(F)cccc2O1]

Methyl 3-(3-(chloromethyl)-4-methylphenyl)-3-(1,4-dimethyl-1H-benzo[d][1,2,3]triazol-5-yl)-2,2-dimethylpropanoate

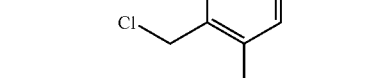

To a solution of methyl 3-(1,4-dimethyl-1H-benzo[d][1,2,3]triazol-5-yl)-3-(3-(hydroxymethyl)-4-methylphenyl)-2, 2-dimethylpropanoate (500 mg, 1.311 mmol) in dichloromethane (DCM) (5 mL) was added thionyl chloride (0.191 mL, 2.62 mmol). The mixture was stirred at ambient temperature for 40 min. The reaction mixture was concentrated to give the title compound (515 mg, 1.288 mmol, 98% yield) as solid. LC-MS m/z 400.1 (M+H)+, 1.13 min (ret. time).

3-(1,4-Dimethyl-1H-benzo[d][1,2,3]triazol-5-yl)-3-(3-(((R)-2-ethyl-6-fluoro-2,3-dihydrobenzo[f][1,4]oxazepin-4(5H)-yl)methyl)-4-methylphenyl)-2,2-dimethylpropanoic Acid, Formic Acid Salt

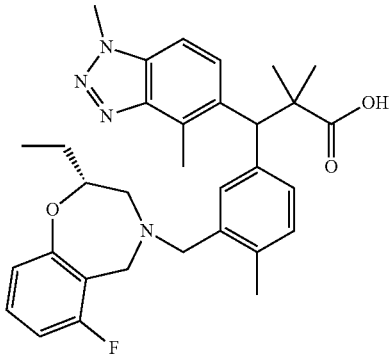 [SMILES: CC[C@@H]1CN(Cc2cc(C(c3ccc4c(nnn4C)c3C)C(C)(C)C(=O)O)ccc2C)Cc2c(F)cccc2O1]

To a suspension of methyl 3-(3-(chloromethyl)-4-methylphenyl)-3-(1,4-dimethyl-1H-benzo[d][1,2,3]triazol-5-yl)-2,2-dimethylpropanoate (50 mg, 0.125 mmol) in acetonitrile (2 mL) was added (R)-2-ethyl-6-fluoro-2,3,4,5-tetrahydrobenzo[f][1,4]oxazepine hydrochloride (29.0 mg, 0.125 mmol) and DIEA (0.066 mL, 0.375 mmol). The resulting reaction mixture was heated with microwave at 120° C. for 1 h. The reaction mixture was concentrated and the resulting residue was re-dissolved in MeOH (2 mL) and 2M LiOH (0.063 mL, 0.125 mmol) was added and the reaction mixture was heated in a Biotage microwave at high absorption for 3 h at 120° C. It was acidified with 6N HCl and 0.5 mL DMSO was added. It was concentrated and purified by reverse-phase HPLC (with 0.1% formic acid condition) to give the title compound (25.6 mg, 0.046 mmol, 36.7% yield). LC-MS m/z 545.3 (M+H)+, 0.85 min (ret. time).

The compounds in Table 8 were prepared by a method similar to the one described for the preparation of 3-(1,4-Dimethyl-1H-benzo[d][1,2,3]triazol-5-yl)-3-(3-(((R)-2-ethyl-6-fluoro-2,3-dihydrobenzo[f][1,4]oxazepin-4(5H)-yl)methyl)-4-methylphenyl)-2,2-dimethylpropanoic acid, formic acid salt. As is appreciated by those skilled in the art, these analogous examples may involve variations in general reaction conditions.

TABLE 8

| Ex # | Structure | Name | LCMS [M + H]+ | Retention Time (min) |
|---|---|---|---|---|
| Example 32 | 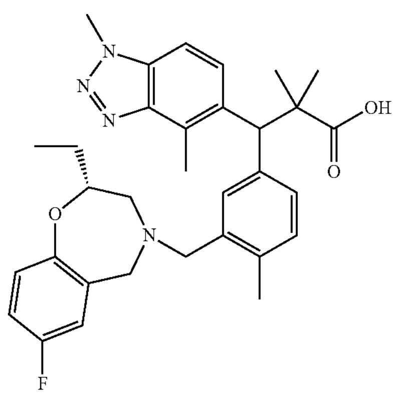 [SMILES: CC[C@@H]1CN(Cc2cc(C(c3ccc4c(nnn4C)c3C)C(C)(C)C(=O)O)ccc2C)Cc2cc(F)ccc2O1] | 3-(1,4-Dimethyl-1H-benzo[d][1,2,3]triazol-5-yl)-3-(3-(((R)-2-ethyl-7-fluoro-2,3-dihdyrobenzo[f][1,4]oxazepin-4(5H)-yl)methyl)-4-methylphenyl)-2,2-dimethylpropanoic acid, formic acid salt | 545.4 | 0.84 |
| Example 33 | 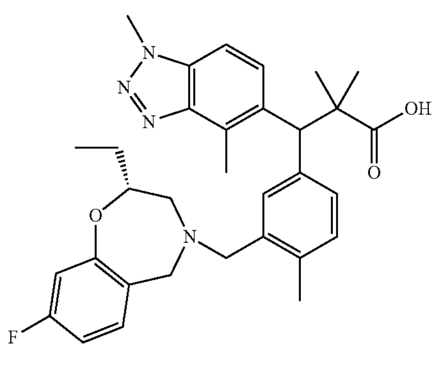 [SMILES: CC[C@@H]1CN(Cc2cc(C(c3ccc4c(nnn4C)c3C)C(C)(C)C(=O)O)ccc2C)Cc2ccc(F)cc2O1] | 3-(1,4-Dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)-2,2-dimethylpropanoic acid, formic acid salt | 545.3 | 0.86 |

TABLE 8-continued

| Ex # | Structure | Name | LCMS [M + H]+ | Retention Time (min) |
|---|---|---|---|---|
| Example 34 | 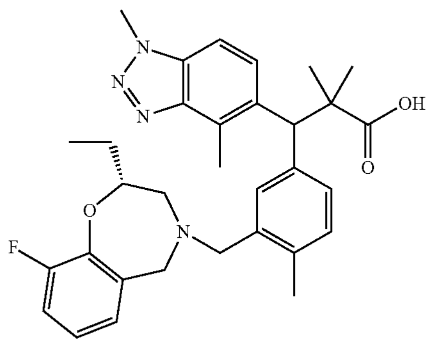 [SMILES: CC[C@@H]1CN(Cc2cc(C(c3ccc4c(nnn4C)c3C)C(C)(C)C(=O)O)ccc2C)Cc2cccc(F)c2O1] | 3-(1,4-Dimethyl-1H-benzo[d][1,2,3]triazol-5-yl)-3-(3-(((R)-2-ethyl-9-fluoro-2,3-dihydrobenzo[f][1,4]oxaz-epin-4(5H)-yl)methyl)-4-methylphenyl)-2,2-dimethylpropanoic acid, formic acid salt | 545.3 | 0.84 |
| Example 35 | 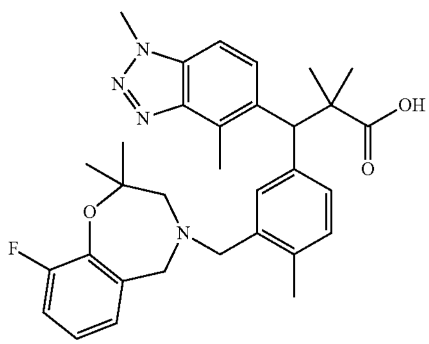 [SMILES: Cc1ccc(C(c2ccc3c(nnn3C)c2C)C(C)(C)C(=O)O)cc1CN1Cc2cccc(F)c2OC(C)(C)C1] | 3-(1,4-Dimethyl-1H-benzo[d][1,2,3]triazol-5-yl)-3-(3-((9-fluoro-2,2-dimethyl-2,3-dihydrobenzo[f][1,4]oxaz-epin-4(5H)-yl)methyl)-4-methylphenyl)-2,2-dimethylpropanoic acid | 545.4 | 0.94 |
| Example 36 | 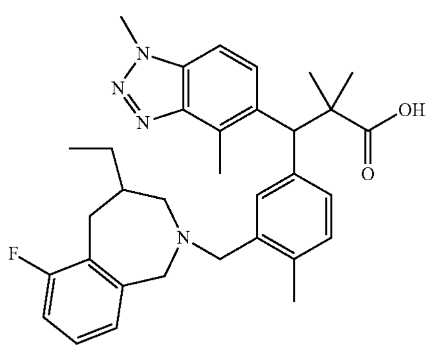 [SMILES: CCC1Cc2c(F)cccc2CN(Cc2cc(C(c3ccc4c(nnn4C)c3C)C(C)(C)C(=O)O)ccc2C)C1] | 3-(1,4-Dimethyl-1H-benzo[d][1,2,3]triazol-5-yl)-3-(3-((4-ethyl-6-fluoro-4,5-dihydro-1H-benzo[c]azepin-2(3H)-yl)methyl)-4-methylphenyl)-2,2-dimethylpropanoic acid | 543.5 | 0.94 |
| Example 37 | 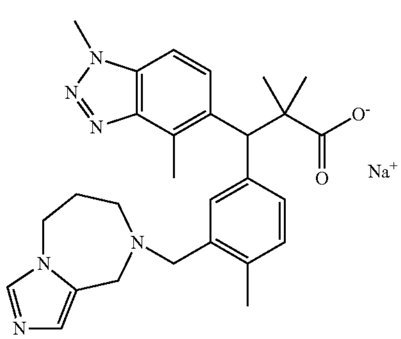 [SMILES: Cc1ccc(C(c2ccc3c(nnn3C)c2C)C(C)(C)C(=O)[O-])cc1CN1CCCn2cncc2C1 ; [Na+]] | 3-(3-((6,7-Dihydro-5H-imidazo[1,5-a][1,4]diazepin-8(9H)-yl)methyl)-4-methylphenyl)-3-(1,4-dimethyl-1H-benzo[d][1,2,3]triazol-5-yl)-2,2-dimethylpropanoate, Sodium salt | 487.3 | 0.64 |

Example 38

(2R,3S)-3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic Acid, Formic Acid Salt

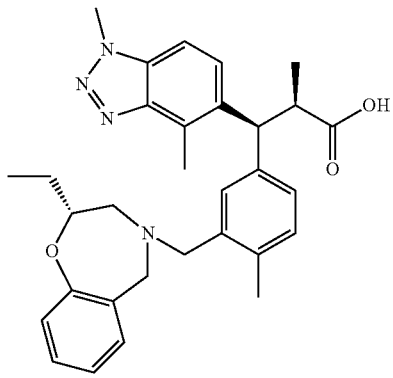 [SMILES: CC[C@@H]1CN(Cc2cc([C@@H](c3ccc4c(nnn4C)c3C)[C@@H](C)C(=O)O)ccc2C)Cc2ccccc2O1]

1,4-Dimethyl-1H-benzo[d][1,2,3]triazole-5-carbaldehyde

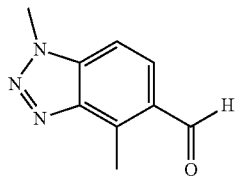

A solution of BuLi (1.6 M in Hexanes) (9.12 mL, 14.60 mmol) and ethylmagnesium bromide (1.0 M in THF) (6.64 mL, 6.64 mmol) in toluene (40 mL) was prepared at −40° C. The resulting solution was stirred at −40° C. for 40 minutes after which time a solution of 5-bromo-1,4-dimethyl-1H-benzo[d][1,2,3]triazole (3000 mg, 13.27 mmol) in tetrahydrofuran (THF) (15 mL) was added. The resulting dark colored solution was allowed to stir for 1 h during which time the cooling bath warmed to −15° C. To the resulting solution was added DMF (6.16 mL, 80 mmol). During the addition a heavy, viscous precipitate formed. The resulting suspension was stirred at −15° C.-−10° C. for 1 h then removed from the cooling bath. After a further 2 h, the reaction was quenched with saturated ammonium chloride solution and diluted with water and ethyl acetate. The bilayer was separated and the aqueous phase extracted with ethyl acetate (1×). The combined organics were washed with brine (1×), and concentrated. It was purified by silica gel chromatography to give the title compound (1.59 g, 9.08 mmol, 68.4% yield) as yellow solid. LC-MS m/z 176.2 (M+H)$^+$, 0.56 min (ret. time).

(1,4-Dimethyl-1H-benzo[d][1,2,3]triazol-5-yl)(3-(((4-methoxybenzyl)oxy)methyl)-4-methylphenyl)methanol

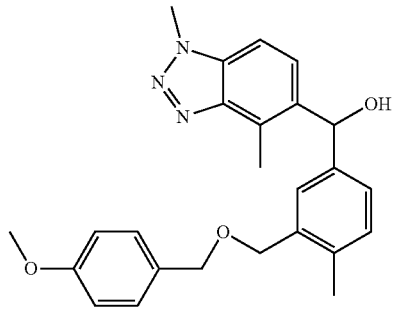 [SMILES: COc1ccc(COCc2cc(C(O)c3ccc4c(nnn4C)c3C)ccc2C)cc1]

To a solution of 4-bromo-2-(((4-methoxybenzyl)oxy)methyl)-1-methylbenzene (2244 mg, 6.99 mmol) in tetrahydrofuran (THF) (30 mL) at −78° C. was added n-butyllithium (4.37 mL, 6.99 mmol) slowly. The reaction mixture was stirred for 30 min at −78° C. and then a solution of 1,4-dimethyl-1H-benzo[d][1,2,3]triazole-5-carbaldehyde (1020 mg, 5.82 mmol) in THF (5 mL) was added slowly. The reaction mixture was stirred at −78° C. for 1 h. The reaction was quenched with saturated ammonium chloride. The organic layer was concentrated to give the crude product. It was purified by silica gel chromatography to give the title compound (1.5 g, 3.59 mmol, 61.7% yield). LC-MS m/z 418.1 (M+H)$^+$, 1.05 min (ret. time).

Methyl 3-(1,4-dimethyl-1H-benzo[d][1,2,3]triazol-5-yl)-3-(3-(((4-methoxybenzyl)oxy)methyl)-4-methylphenyl)-2-methylpropanoate

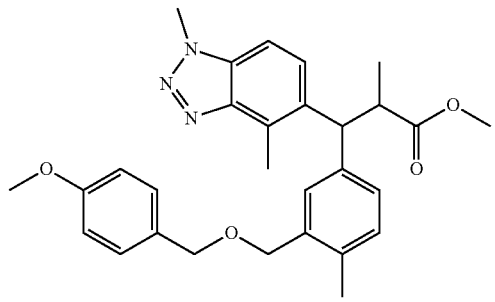

To a solution of (1,4-dimethyl-1H-benzo[d][1,2,3]triazol-5-yl)(3-(((4-methoxybenzyl)oxy)methyl)-4-methylphenyl)methanol (1.5 g, 3.59 mmol) in acetonitrile (20 mL) was added DBU (0.016 mL, 0.108 mmol) slowly followed by addition of 2,2,2-trichloroacetonitrile (0.540 mL, 5.39 mmol). The reaction mixture was stirred for 30 min at ambient temperature. Then (E)-((1-methoxyprop-1-en-1-yl)oxy)trimethylsilane (1.655 mL, 8.98 mmol) was added followed by 1,1,1-trifluoro-N-((trifluoromethyl)sulfonyl)methanesulfonamide (0.071 g, 0.251 mmol). The mixture was stirred at ambient temperature for 3 h. 1,1,1-trifluoro-N-((trifluoromethyl)sulfonyl)methanesulfonamide (0.071 g, 0.251 mmol) and (E)-((1-methoxyprop-1-en-1-yl)oxy)trimethylsilane (1.655 mL, 8.98 mmol) were added and stirred for another 19 h. It was quenched with saturated NH$_4$Cl, extracted with ethyl acetate twice. The combined organic layer was concentrated to give the crude residue. It was purified by silica gel chromatography to give the title compound (766 mg, 1.571 mmol, 43.7% yield) LC-MS m/z 488.4 (M+H)+, 1.19, 1.22 min (ret. time).

(2R,3S)-Methyl 3-(1,4-dimethyl-1H-benzo[d][1,2,3]triazol-5-yl)-3-(3-(((4-methoxybenzyl)oxy)methyl)-4-methylphenyl)-2-methylpropanoate and (2S,3R)-methyl 3-(1,4-dimethyl-1H-benzo[d][1,2,3]triazol-5-yl)-3-(3-(((4-methoxybenzyl)oxy)methyl)-4-methylphenyl)-2-methylpropanoate

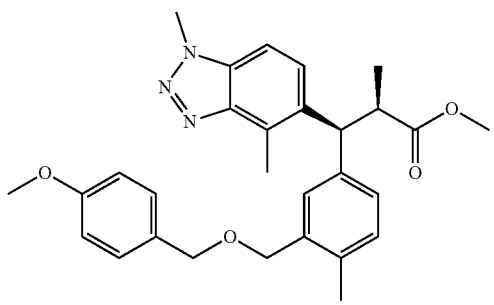

Methyl 3-(1,4-dimethyl-1H-benzo[d][1,2,3]triazol-5-yl)-3-(3-(((4-methoxybenzyl)oxy)methyl)-4-methylphenyl)-2-methylpropanoate (766 mg, 1.571 mmol, 43.7% yield) was separated by preparative HPLC under acidic conditions to give isomer 1 (300 mg) and isomer 2 (280 mg).

Isomer 2 (280 mg, 0.574 mmol) from above was separated by chiral SFC (Column: Chiral pack AD 20×250 mm 5 u; Co-solvent: 25% EtOH; Flow rate: 50 g/min; Back pressure: 100 Bar) to give (2R,3S)-methyl 3-(1,4-dimethyl-1H-benzo[d][1,2,3]triazol-5-yl)-3-(3-(((4-methoxybenzyl)oxy)methyl)-4-methylphenyl)-2-methylpropanoate (93 mg, 0.191 mmol, 33.2% yield) (chiral SFC ret. time: 3.71 min) and (2S,3R)-methyl 3-(1,4-dimethyl-1H-benzo[d][1,2,3]triazol-5-yl)-3-(3-(((4-methoxybenzyl)oxy)methyl)-4-methylphenyl)-2-methylpropanoate (93 mg, 0.191 mmol, 33.2% yield). (chiral SFC ret. time: 6.42)

(2R,3S)-Methyl 3-(1,4-dimethyl-1H-benzo[d][1,2,3]triazol-5-yl)-3-(3-(hydroxymethyl)-4-methylphenyl)-2-methylpropanoate

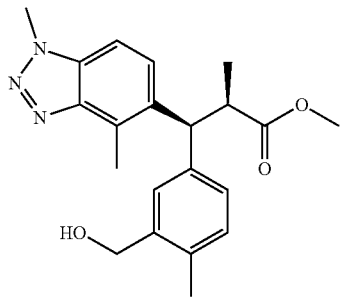 [SMILES: COC(=O)[C@H](C)[C@@H](c1ccc(C)c(CO)c1)c1ccc2c(nnn2C)c1C]

DDQ (47.6 mg, 0.210 mmol) was added to a vigorously stirring, biphasic solution of (2R,3S)-methyl 3-(1,4-dimethyl-1H-benzo[d][1,2,3]triazol-5-yl)-3-(3-(((4-methoxybenzyl)oxy)methyl)-4-methylphenyl)-2-methylpropanoate (93 mg, 0.191 mmol) in dichloromethane (DCM) (2 mL) and water (0.200 mL) at ambient temperature. The reaction flask was covered with aluminum foil. Over the course of 2 h, the reaction mixture turned from deep green color to light grey. It was quenched with water and extracted with DCM twice (2×5 mL). The organic layer was dried over sodium sulfate, filtered and concentrated to give the title compound (71 mg, 0.193 mmol, 101% yield). LC-MS m/z 368.2 (M+H)+, 0.89 min (ret. time).

(2R,3S)-Methyl 3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoate

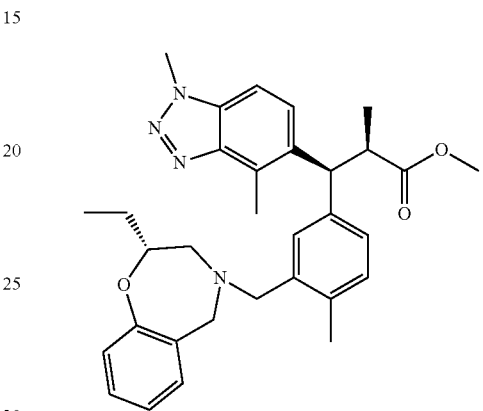

To a suspension of (2R,3S)-methyl 3-(1,4-dimethyl-1H-benzo[d][1,2,3]triazol-5-yl)-3-(3-(hydroxymethyl)-4-methylphenyl)-2-methylpropanoate (70 mg, 0.191 mmol) in dichloromethane (DCM) (2 mL) was added thionyl chloride (0.028 mL, 0.381 mmol). The mixture was stirred for 30 min. The solvent was removed under reduced pressure and the resulting residue was re-dissolved in dichloromethane (DCM) (2 mL). DIEA (0.133 mL, 0.762 mmol) and (R)-2-ethyl-2,3,4,5-tetrahydrobenzo[f][1,4]oxazepine hydrochloride (48.9 mg, 0.229 mmol) were added. The resulting reaction mixture was heated with microwave at 120° C. for 1 h. It was concentrated to give the title compound (65 mg, 0.123 mmol, 64.8% yield). LC-MS m/z 527.6 (M+H)+, 0.87 min (ret. time).

(2R,3S)-3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic Acid, Formic Acid Salt

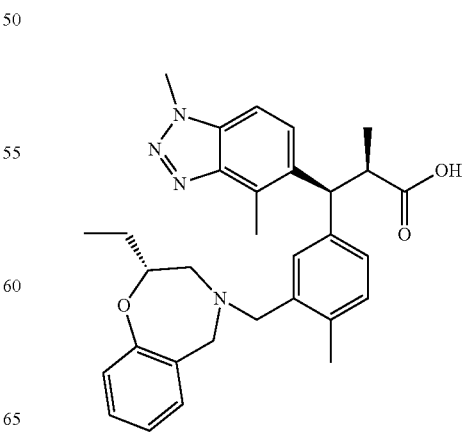

To a solution of (3S)-methyl 3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoate (30 mg, 0.057 mmol) in methanol (2 mL) was added 2 M LiOH (0.171 mL, 0.342 mmol). The mixture was stirred at ambient temperature for 3 days. More 2 M LiOH (0.171 mL, 0.342 mmol) was added and stirred at ambient temperature for 8 days. It was acidified with 6 N HCl and 0.5 mL DMSO was added. It was concentrated and purified by reverse-phase HPLC (with 0.1% formic acid condition) to give the title compound (15 mg, 0.029 mmol, 51.4% yield). LC-MS m/z 513.6 (M+H)$^+$, 0.81 min (ret. time).

Example 39

(2S,3R)-3-(1,4-Di methyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic Acid

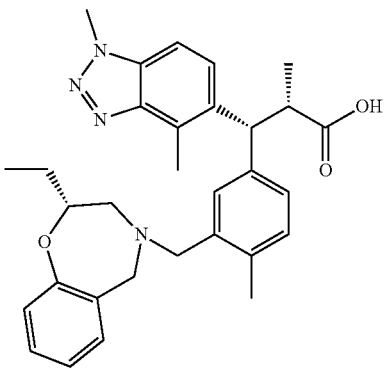 [SMILES: CC[C@@H]1CN(Cc2cc([C@H](c3ccc4c(nnn4C)c3C)[C@H](C)C(=O)O)ccc2C)Cc2ccccc2O1]

(2R,3S)-Benzyl 3-(1,4-dimethyl-1H-benzo[d][1,2,3]triazol-5-yl)-3-(3-(hydroxymethyl)-4-methylphenyl)-2-methylpropanoate and (2S,3R)-benzyl 3-(1,4-dimethyl-1H-benzo[d][1,2,3]triazol-5-yl)-3-(3-(hydroxymethyl)-4-methylphenyl)-2-methylpropanoate

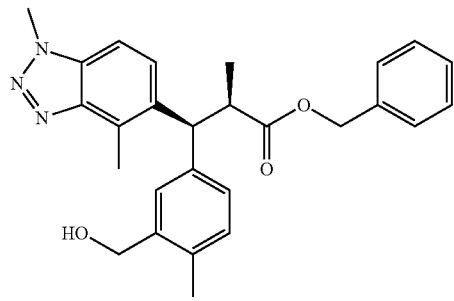

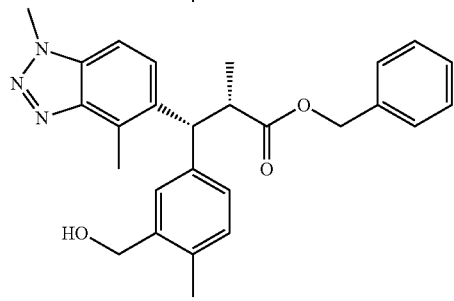

DDQ (443 mg, 1.951 mmol) was added to a vigorously stirring, biphasic solution of racemic benzyl 3-(1,4-dimethyl-1H-benzo[d][1,2,3]triazol-5-yl)-3-(3-(((4-methoxybenzyl)oxy)methyl)-4-methylphenyl)-2-methylpropanoate (1000 mg, 1.774 mmol) in dichloromethane (DCM) (20 mL) and water (2.000 mL) at ambient temperature. The reaction flask was covered with aluminum foil. Over the course of 2 h, the reaction mixture turned from deep green color to light grey. It was quenched with water and extracted with DCM twice (2×10 mL). The organic layer was washed with water (3×4 mL) and concentrated to give the title compound. It was purified by reverse-phase HPLC (with 0.1% TFA condition) to separate two diastereomers to obtain Peak 1 (337.5 mg) and peak 2 (385.2 mg). Since the reverse phase HPLC with acidic modifier, by-product benzyl 3-(1,4-dimethyl-1H-benzo[d][1,2,3]triazol-5-yl)-2-methyl-3-(4-methyl-3-((2,2,2-trifluoroacetoxy)methyl)phenyl)propanoate was also observed with both batches of peak 1 and peak 2.

To a solution of peak 1 (benzyl 3-(1,4-dimethyl-1H-benzo[d][1,2,3]triazol-5-yl)-3-(3-(hydroxymethyl)-4-methylphenyl)-2-methylpropanoate and benzyl 3-(1,4-dimethyl-1H-benzo[d][1,2,3]triazol-5-yl)-2-methyl-3-(4-methyl-3-((2,2,2-trifluoroacetoxy)methyl)phenyl)propanoate (337 mg, 0.760 mmol) in dichloromethane (DCM) (8 mL) was added Et$_3$N (0.106 mL, 0.760 mmol). The mixture was stirred at ambient temperature for 1 h. Solvent was removed under reduced pressure and the residue the sample was separated by Chiral SFC (Column: Chiralpak IC 20×150 mm; Co-solvent: 25% IPA; Flowrate: 50 g/min; Back pressure: 100 Bar) to give single enantiomerically pure (2R,3S)-benzyl 3-(1,4-dimethyl-1H-benzo[d][1,2,3]triazol-5-yl)-3-(3-(hydroxymethyl)-4-methylphenyl)-2-methylpropanoate (144 mg, 0.325 mmol, 42.7% yield) (chiral SFC ret. time: 8.93 min) and single enantiomerically pure (2S,3R)-benzyl 3-(1,4-dimethyl-1H-benzo[d][1,2,3]triazol-5-yl)-3-(3-(hydroxymethyl)-4-methylphenyl)-2-methylpropanoate (99.3 mg, 0.224 mmol, 29.5% yield) (chiral SFC ret. time: 11.2 min).

(2R,3R)-Benzyl 3-(1,4-dimethyl-1H-benzo[d][1,2,3]triazol-5-yl)-3-(3-(hydroxymethyl)-4-methylphenyl)-2-methylpropanoate and (2S,3S)-benzyl 3-(1,4-dimethyl-1H-benzo[d][1,2,3]triazol-5-yl)-3-(3-(hydroxymethyl)-4-methylphenyl)-2-methylpropanoate

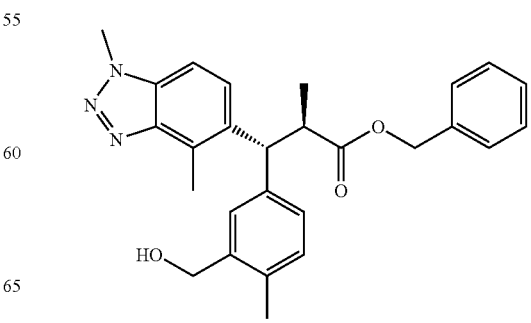

209

-continued

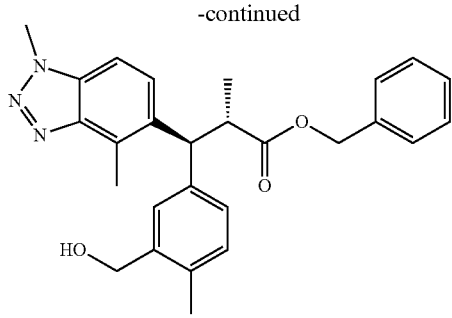

To a solution of peak 2 (benzyl 3-(1,4-dimethyl-1H-benzo[d][1,2,3]triazol-5-yl)-3-(3-(hydroxymethyl)-4-methylphenyl)-2-methylpropanoate and benzyl 3-(1,4-dimethyl-1H-benzo[d][1,2,3]triazol-5-yl)-2-methyl-3-(4-methyl-3-((2,2,2-trifluoroacetoxy)methyl)phenyl)propanoate (410 mg, 0.920 mmol) in dichloromethane (DCM) (8 mL) was added Et₃N (0.128 mL, 0.920 mmol). The mixture was stirred at ambient temperature for 1 h. Solvent was concentrated. It was separated by Chiral SFC (Column: Chiralpak IC 20×150 mm; Co-solvent: 20% MeOH; Flowrate: 50 mg/min; Back pressure: 100 Bar) to give single enantiomerically pure diastereomer (2R,3R)-benzyl 3-(1,4-dimethyl-1H-benzo[d][1,2,3]triazol-5-yl)-3-(3-(hydroxymethyl)-4-methylphenyl)-2-methylpropanoate (117 mg, 0.264 mmol, 34.7% yield) (chiral SFC ret. time: 10.08 min) and single enantiomerically pure diastereomer (2S,3S)-benzyl 3-(1,4-dimethyl-1H-benzo[d][1,2,3]triazol-5-yl)-3-(3-(hydroxymethyl)-4-methylphenyl)-2-methylpropanoate (199 mg, 0.449 mmol, 59.1% yield) (chiral SFC ret. time: 11.32 min).

(2S,3R)-3-(1,4-Di methyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic Acid

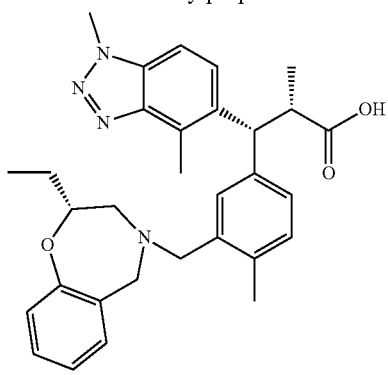

To a solution of (2S,3R)-benzyl 3-(1,4-dimethyl-1H-benzo[d][1,2,3]triazol-5-yl)-3-(3-(hydroxymethyl)-4-methylphenyl)-2-methylpropanoate (30 mg, 0.068 mmol) in dichloromethane (DCM) (1 mL) was added thionyl chloride (9.87 μL, 0.135 mmol). The mixture was stirred at ambient temperature for 40 min. The solvent was concentrated and the resulting residue was re-dissolved in acetonitrile (1.000 mL), (R)-2-ethyl-2,3,4,5-tetrahydrobenzo[f][1,4]oxazepine hydrochloride (21.68 mg, 0.101 mmol) and DIEA (0.047 mL, 0.271 mmol) was added. The reaction mixture was heated in a Biotage microwave at high absorption for 1 h at 120° C. The solvent was concentrated and the resulting residue was re-dissolved in EtOAc (2 mL). It was passed though H-Cube (1 mL/min, Pd/C cartridge, 25° C.) for 3 h. The solvent was removed under reduced pressure and the residue was purified by reverse-phase HPLC to give the title compound (23.4 mg, 0.046 mmol, 67.5% yield). LC-MS m/z 513.6 (M+H)⁺, 0.83 min (ret. time).

Example 40

(2R,3R)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic Acid

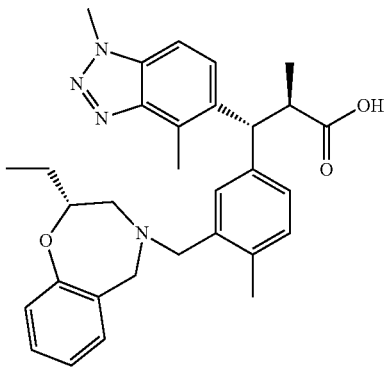 [SMILES: CC[C@@H]1CN(Cc2cc([C@H](c3ccc4c(nnn4C)c3C)[C@@H](C)C(=O)O)ccc2C)Cc2ccccc2O1]

To a solution of (2R,3R)-benzyl 3-(1,4-dimethyl-1H-benzo[d][1,2,3]triazol-5-yl)-3-(3-(hydroxymethyl)-4-methylphenyl)-2-methylpropanoate (30 mg, 0.068 mmol) in dichloromethane (DCM) (1 mL) was added thionyl chloride (9.87 μl, 0.135 mmol). The mixture was stirred at ambient temperature for 40 min. The solvent was concentrated and the resulting residue was re-dissolved in acetonitrile (1 mL), (R)-2-ethyl-2,3,4,5-tetrahydrobenzo[f][1,4]oxazepine hydrochloride (21.68 mg, 0.101 mmol) and DIEA (0.047 mL, 0.271 mmol) was added. The reaction mixture was heated in a Biotage microwave at high absorption for 1 h at 120° C. The solvent was concentrated and the resulting residue was re-dissolved in EtOAc (2 mL). It was passed though H-Cube (1 mL/min, cartridge Pd/C, 25° C.) for 3 h. The solvent was removed under reduced pressure and the residue was purified by reverse-phase HPLC to give the title compound (22.5 mg, 0.044 mmol, 64.9% yield). LC-MS m/z 513.5 (M+H)⁺, 0.83 min (ret. time).

Example 41

(2S,3S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2-methylpropanoic Acid

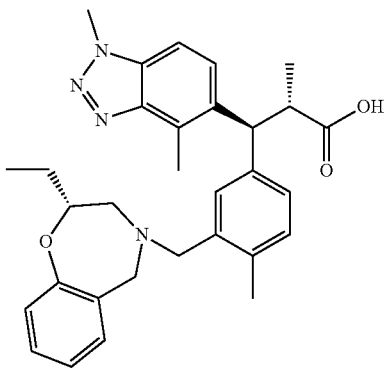 [SMILES: CC[C@@H]1CN(Cc2cc([C@@H](c3ccc4c(nnn4C)c3C)[C@H](C)C(=O)O)ccc2C)Cc2ccccc2O1]

To a solution of (2S,3S)-benzyl 3-(1,4-dimethyl-1H-benzo[d][1,2,3]triazol-5-yl)-3-(3-(hydroxymethyl)-4-methylphenyl)-2-methylpropanoate (30 mg, 0.068 mmol) in dichloromethane (DCM) (1 mL) was added thionyl chloride (9.87 µL, 0.135 mmol). The mixture was stirred at ambient temperature for 40 min. The solvent was concentrated and the resulting residue was re-dissolved in acetonitrile (1.000 mL), (R)-2-ethyl-2,3,4,5-tetrahydrobenzo[f][1,4]oxazepine hydrochloride (21.68 mg, 0.101 mmol) and DIEA (0.047 mL, 0.271 mmol) was added. The reaction mixture was heated in a Biotage microwave at high absorption for 1 h at 120° C. The solvent was concentrated and the resulting residue was re-dissolved in EtOAc (2 mL). It was passed though H-Cube (1 mL/min, cartridge Pd/C, 25° C.) for 3 h. The solvent was removed under reduced pressure and the residue was purified by reverse-phase HPLC to give the title compound (18 mg, 0.035 mmol, 51.9% yield). LC-MS m/z 513.5 (M+H)$^+$, 0.83 min (ret. time).

Example 42

(3R)-3-(1,4-Dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)-2-methylpropanoic Acid, Trifluoroacetic Acid Salt

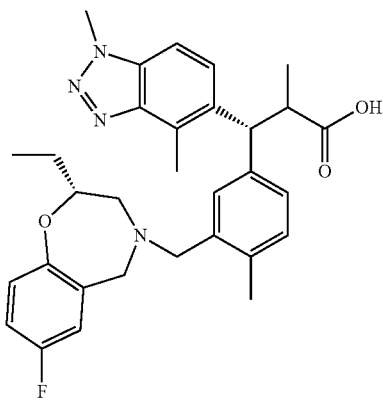 [SMILES: CC[C@@H]1CN(Cc2cc([C@H](c3ccc4c(nnn4C)c3C)C(C)C(=O)O)ccc2C)Cc2cc(F)ccc2O1]

(3R)-Benzyl 3-(3-(chloromethyl)-4-methylphenyl)-3-(1,4-dimethyl-1H-benzo[d][1,2,3]triazol-5-yl)-2-methylpropanoate

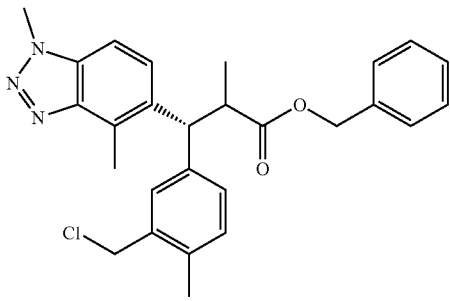 [SMILES: Cc1ccc([C@H](c2ccc3c(nnn3C)c2C)C(C)C(=O)OCc2ccccc2)cc1CCl]

To a solution of (3R)-Benzyl 3-(1,4-dimethyl-1H-benzo[d][1,2,3]triazol-5-yl)-3-(3-(hydroxymethyl)-4-methylphenyl)-2-methylpropanoate (150 mg, 0.338 mmol) in dichloromethane (DCM) (2 mL) was added thionyl chloride (0.049 mL, 0.676 mmol). The mixture was stirred at ambient temperature for 40 min. The reaction mixture was concentrated to give the title compound (153 mg, 0.331 mmol, 98% yield) as a white solid. LC-MS m/z 462.2 (M+H)$^+$, 1.23 min (ret. time).

(3R)-3-(1,4-Dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)-2-methylpropanoic Acid, Trifluoroacetic Acid Salt

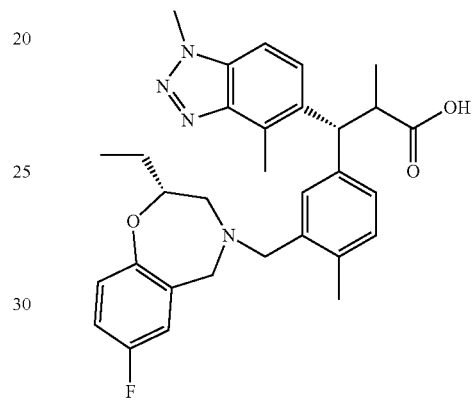

To a mixture of (3R)-benzyl 3-(3-(chloromethyl)-4-methylphenyl)-3-(1,4-dimethyl-1H-benzo[d][1,2,3]triazol-5-yl)-2-methylpropanoate (32 mg, 0.069 mmol) in acetonitrile (4 mL) was added (R)-2-ethyl-7-fluoro-2,3,4,5-tetrahydrobenzo[f][1,4]oxazepine (20.28 mg, 0.104 mmol) and DIEA (0.048 mL, 0.277 mmol). The resulting reaction mixture was heated with microwave at 120° C. for 1 h. The reaction mixture was concentrated to give (3R)-benzyl 3-(1,4-dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)-2-methylpropanoate. The crude material was re-dissolved in ethyl acetate (4 mL). The solution was passed though H-Cube (flow rate: 1 mL/min, 25° C., cartridge: 10% Pd/C) for 1.5 h. It was concentrated and purified by reverse-phase HPLC to give the title compound (30.9 mg, 0.058 mmol, 84% yield) was obtained. LC-MS m/z 531.4 (M+H)$^+$, 0.87 min (ret. time). 1H NMR (400 MHz, METHANOL-d4) δ=7.81 (d, J=8.8 Hz, 1H), 7.62-7.47 (m, 3H), 7.37 (d, J=7.8 Hz, 1H), 7.17 (d, J=3.8 Hz, 2H), 6.89 (d, J=8.0 Hz, 1H), 4.68-4.45 (m, 3H), 4.41-4.26 (m, 4H), 4.00-3081 (m, 1H), 3.60-3.45 (m, 2H), 3.42-3.22 (m, 1H), 2.82 (s, 3H), 2.43 (s, 3H), 1.64 (td, J=7.4, 14.6 Hz, 1H), 1.46-1.36 (m, 1H), 1.24 (d, J=6.8 Hz, 3H), 1.13-0.99 (m, 3H)

Example 43

(R)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)propanoic Acid, Formic Acid Salt

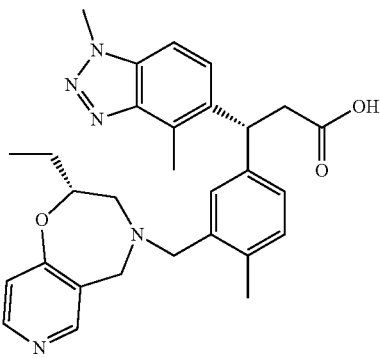 [SMILES: CC[C@@H]1CN(Cc2cc([C@@H](CC(=O)O)c3ccc4c(nnn4C)c3C)ccc2C)Cc2cnccc2O1]

A mixture of (R)-ethyl 3-(3-(chloromethyl)-4-methylphenyl)-3-(1,4-dimethyl-1H-benzo[d][1,2,3]triazol-5-yl)propanoate (200 mg, 0.518 mmol) in acetonitrile (3 mL), DIEA (0.272 mL, 1.555 mmol) and (R)-2-ethyl-2,3,4,5-tetrahydropyrido[3,4-f][1,4]oxazepine hydrochloride (134 mg, 0.622 mmol) was heated with μwave at 120° C. for 1 h. The solvent was concentrated and the resulting residue was purified by silica gel chromatography. Desired fractions were concentrated and the resulting intermediate was re-dissolved in MeOH (3 mL). 2 M LiOH (1.555 mL, 3.11 mmol) was added and the reaction mixture was stirred at ambient temperature for 20 h. It was acidified with 6N HCl and 0.5 mL DMSO was added. It was concentrated and purified by reverse-phase HPLC to give the title compound (135 mg, 0.270 mmol, 52.1% yield) as solid. LC-MS m/z 500.3 (M+H)$^+$, 0.78 min (ret. time).

Example 44

3-(3-((2,3-Dihydrobenzo[f][1,4]oxazepin-4(5H)-yl)methyl)-4-methylphenyl)-3-(1,4-dimethyl-1H-benzo[d][1,2,3]triazol-5-yl)-2,2-dimethylpropanoic Acid, Formic Acid Salt

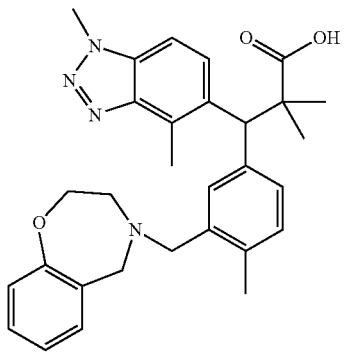 [SMILES: Cc1ccc(C(c2ccc3c(nnn3C)c2C)C(C)(C)C(=O)O)cc1CN1CCOc2ccccc2C1]

To a solution of methyl 3-(1,4-dimethyl-1H-benzo[d][1,2,3]triazol-5-yl)-3-(3-(hydroxymethyl)-4-methylphenyl)-2,2-dimethylpropanoate (70 mg, 0.184 mmol) in Dichloromethane (DCM) (2 mL) was added thionyl chloride (0.027 mL, 0.367 mmol). The mixture was stirred at ambient temperature for 40 min. The solvent was concentrated and the resulting residue was re-dissolved in acetonitrile (2 mL) after which 2,3,4,5-tetrahydrobenzo[f][1,4]oxazepine (36.7 mg, 0.246 mmol) and DIEA (0.095 mL, 0.543 mmol) were added. The resulting reaction mixture was heated with microwave at 120° C. for 1 h. The resulting mixture was concentrated and the resulting residue was re-dissolved in MeOH (2 mL), 2 M LiOH (0.551 mL, 1.101 mmol) was added and the reaction mixture was heated with μwave at 80° C. for 30 min. It was acidified with 6N HCl and 0.5 mL DMSO was added. It was concentrated and purified by reverse-phase HPLC to give the title compound (21.8 mg, 0.044 mmol, 23.83% yield) as solid. LC-MS m/z 500.4 (M+H)$^+$, 0.75 min (ret. time).

Example 45

3-(3-(((R)-2-Ethyl-2,3-dihydrobenzo[f][1,4]oxazepin-4(5H)-yl)methyl)-4-methylphenyl)-3-(7-methoxy-1,4-dimethyl-1H-benzo[d][1,2,3]triazol-5-yl)propanoic Acid, Formic Acid Salt

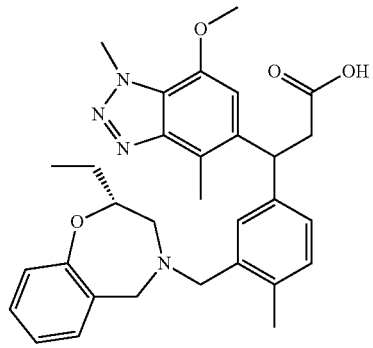 [SMILES: CC[C@@H]1CN(Cc2cc(C(CC(=O)O)c3cc(OC)c4c(nnn4C)c3C)ccc2C)Cc2ccccc2O1]

Methyl 3-(3-(hydroxymethyl)-4-methylphenyl)-3-(7-methoxy-1,4-dimethyl-1H-benzo[d][1,2,3]triazol-5-yl)propanoate

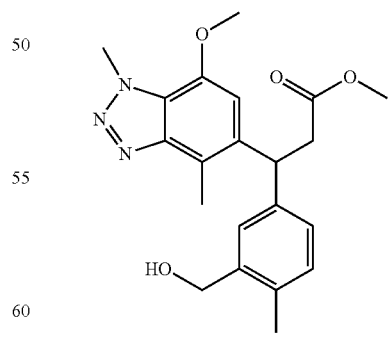

To a suspension of (3-(hydroxymethyl)-4-methylphenyl)boronic acid (152 mg, 0.919 mmol), (E)-methyl 3-(7-methoxy-1,4-dimethyl-1H-benzo[d][1,2,3]triazol-5-yl)acrylate (200 mg, 0.765 mmol), and chloro(1,5-cyclooctadiene)rhodium(I) dimer (37.7 mg, 0.077 mmol) in water (1 mL)

and 1,4-dioxane (3 mL) at ambient temperature was added triethylamine (0.320 mL, 2.296 mmol). The resulting suspension was heated to 95° C. for 2 h. It was filtered through celite and washed with ethyl acetate. The filtrate was concentrated. The crude product was purified by reverse-phase HPLC to give the title compound (109 mg, 0.284 mmol, 37.1% yield). LC-MS m/z 384.2 (M+H)$^+$, 0.85 min (ret. time).

Methyl 3-(3-(chloromethyl)-4-methylphenyl)-3-(7-methoxy-1,4-dimethyl-1H-benzo[d][1,2,3]triazol-5-yl)propanoate

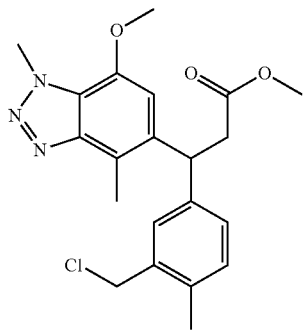 [SMILES: COC(=O)CC(c1ccc(C)c(CCl)c1)c1cc(OC)c2c(nnn2C)c1C]

To a solution of methyl 3-(3-(hydroxymethyl)-4-methylphenyl)-3-(7-methoxy-1,4-dimethyl-1H-benzo[d][1,2,3]triazol-5-yl)propanoate (109 mg, 0.284 mmol) in dichloromethane (DCM) (2 mL) was added SOCl$_2$ (0.041 mL, 0.569 mmol). The resulting reaction mixture was stirred at ambient temperature for 1 h. The solvent was removed to afford desired product (98 mg, 0.244 mmol, 86% yield). LC/MS: m/z 402.0 (M+H)$^+$, 1.15 min (ret. time).

3-(3-(((R)-2-Ethyl-2,3-dihydrobenzo[f][1,4]oxazepin-4(5H)-yl)methyl)-4-methylphenyl)-3-(7-methoxy-1,4-dimethyl-1H-benzo[d][1,2,3]triazol-5-yl)propanoic Acid, Formic Acid Salt

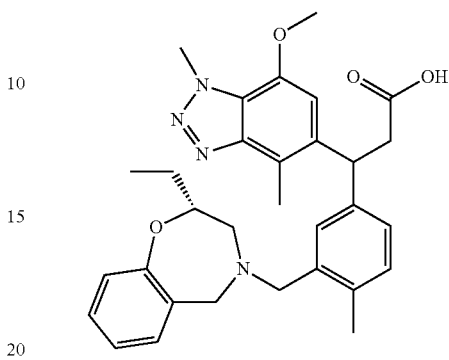

A mixture of methyl 3-(3-(chloromethyl)-4-methylphenyl)-3-(7-methoxy-1,4-dimethyl-1H-benzo[d][1,2,3]triazol-5-yl)propanoate (52 mg, 0.129 mmol), (R)-2-ethyl-2,3,4,5-tetrahydrobenzo[f][1,4]oxazepine (27.5 mg, 0.155 mmol), and DIEA (0.068 mL, 0.388 mmol) in acetonitrile (2 mL) was heated in a Biotage microwave at high absorption for 1 h at 120° C. The solvent was removed under reduced pressure and the crude material was re-dissolved in MeOH (2 mL) and 2M LiOH (0.388 mL, 0.776 mmol) was added and the reaction mixture was heated with microwave at 80° C. for 30 min. It was acidified with 6N HCl and 0.5 mL DMSO was added. It was concentrated and purified by reverse-phase HPLC (with 0.1% formic acid condition) to give the title compound (55 mg, 0.096 mmol, 74.0% yield) as solid. LC-MS m/z 529.2 (M+H)$^+$, 0.86 min (ret. time).

The compounds in Table 9 were prepared by a method similar to the one described for the preparation of 3-(3-(((R)-2-ethyl-2,3-dihydrobenzo[f][1,4]oxazepin-4(5H)-yl)methyl)-4-methylphenyl)-3-(7-methoxy-1,4-dimethyl-1H-benzo[d][1,2,3]triazol-5-yl)propanoic acid, Formic acid salt. As is appreciated by those skilled in the art, these analogous examples may involve variations in general reaction conditions.

TABLE 9

| Ex # | Structure | Name | LCMS [M + H]$^+$ | Retention Time (min) |
|---|---|---|---|---|
| Example 46 | 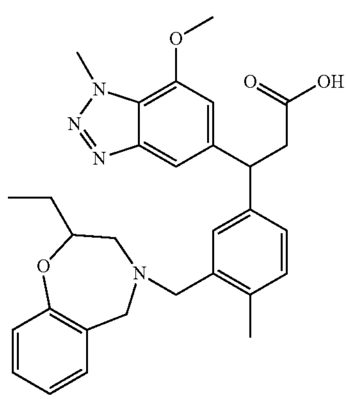 [SMILES: CCC1CN(Cc2cc(C(CC(=O)O)c3cc(OC)c4c(c3)nnn4C)ccc2C)Cc2ccccc2O1] | 3-(3-((2-Ethyl-2,3-dihydrobenzo[f][1,4]oxazepin-4(5H)-yl)methyl)-4-methylphenyl)-3-(7-methoxy-1-methyl-1H-benzo[d][1,2,3]triazol-5-yl)propanoic acid, trifluoroacetic acid salt | 515.3 | 0.81 |

Example 47

3-(3,7-Dimethyl-3H-[1,2,3]triazolo[4,5-b]pyridin-6-yl)-3-(3-(((R)-2-ethyl-2,3-dihydrobenzo[f][1,4]oxazepin-4(5H)-yl)methyl)-4-methylphenyl)propanoic Acid, Trifluoroacetic Acid Salt

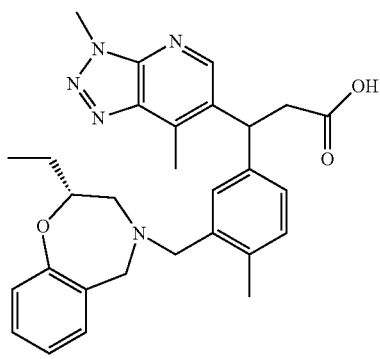 [SMILES: CC[C@@H]1CN(Cc2cc(C(CC(=O)O)c3cnc4c(nnn4C)c3C)ccc2C)Cc2ccccc2O1]

5-Bromo-N2,4-dimethylpyridine-2,3-diamine

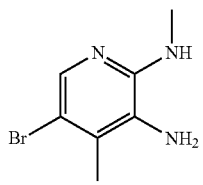

To a solution of 5-bromo-N,4-dimethyl-3-nitropyridin-2-amine (2000 mg, 8.13 mmol) in ethanol (20 mL) at ambient temperature was added tin(II) chloride dihydrate (7336 mg, 32.5 mmol). The reaction mixture was heated at 70° C. for the 2 h. Solvent was evaporated and NaHCO$_3$ (sat.) solution was added to pH 7. It was extracted with EtOAc (3×40 mL). The combined organic phase was dried with Na$_2$SO$_4$, filtered and concentrated to give the title compound (1.53 g, 7.08 mmol, 87% yield) as brown solid. LC-MS m/z 215.9 (M+H)$^+$, 0.41 min (ret. time).

6-Bromo-3,7-dimethyl-3H-[1,2,3]triazolo[4,5-b]pyridine

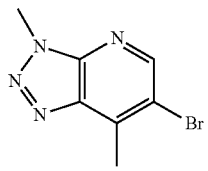

To a solution of 5-bromo-N2,4-dimethylpyridine-2,3-diamine (1500 mg, 6.94 mmol) in sulfuric acid (18.500 mL, 34.7 mmol) at ambient temperature, sodium nitrite (479 mg, 6.94 mmol) was added. The reaction mixture was heated at 70° C. for 1 h. The reaction mixture was cooled and extracted with EtOAc and water. The water layer was extracted with EtOAc (2×30 mL). The combined organic phase was dried and concentrated to afford the title compound (1500 mg, 6.61 mmol, 95% yield) as brown solid. LC-MS m/z 226.9 (M)$^+$, 0.71 min (ret. time).

(E)-Methyl 3-(3,7-dimethyl-3H-[1,2,3]triazolo[4,5-b]pyridin-6-yl)acrylate

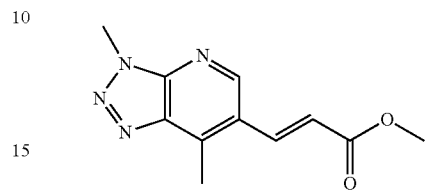

To a solution of 6-bromo-3,7-dimethyl-3H-[1,2,3]triazolo[4,5-b]pyridine (800 mg, 3.52 mmol) in N,N-dimethylformamide (DMF) (5 mL) at ambient temperature was added methyl acrylate (1.612 mL, 17.62 mmol) and N-ethyl-N-isopropylpropan-2-amine (2.154 mL, 12.33 mmol), tri-o-tolylphosphine (322 mg, 1.057 mmol), followed by palladium(II) acetate (103 mg, 0.458 mmol). The reaction mixture was heated in microwave under high absorption at 150° C. for 1 h. It was concentrated and the crude material was purified by silica gel chromatography. The desired fractions were concentrated under reduced pressure to give the title compound (279 mg, 1.201 mmol, 34.1% yield) and less pure batch (250 mg, 1.076 mmol, 30.6% yield). LC-MS m/z 233.0 (M+H)$^+$, 0.68 min (ret. time).

Methyl 3-(3,7-dimethyl-3H-[1,2,3]triazolo[4,5-b]pyridin-6-yl)-3-(3-(hydroxymethyl)-4-methylphenyl)propanoate

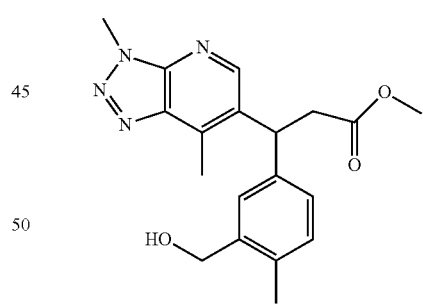

To a suspension of (3-(hydroxymethyl)-4-methylphenyl)boronic acid (214 mg, 1.292 mmol), (E)-methyl 3-(3,7-dimethyl-3H-[1,2,3]triazolo[4,5-b]pyridin-6-yl)acrylate (250 mg, 1.076 mmol), and chloro(1,5-cyclooctadiene)rhodium(I) dimer (53.1 mg, 0.108 mmol) in water (1 mL) and 1,4-dioxane (3 mL) at ambient temperature was added triethylamine (0.450 mL, 3.23 mmol). The resulting suspension was heated to 95° C. for 1 h. It was concentrated and the crude product was purified by silica gel chromatography. The desired fractions were concentrated to give the title compound (353 mg, 0.996 mmol, 93% yield) as oil. LC-MS m/z 355.3 (M+H)$^+$, 0.74 min (ret. time).

219

3-(3,7-Dimethyl-3H-[1,2,3]triazolo[4,5-b]pyridin-6-yl)-3-(3-(((R)-2-ethyl-2,3-dihydrobenzo[f][1,4]oxazepin-4(5H)-yl)methyl)-4-methylphenyl)propanoic Acid, Trifluoroacetic Acid Salt

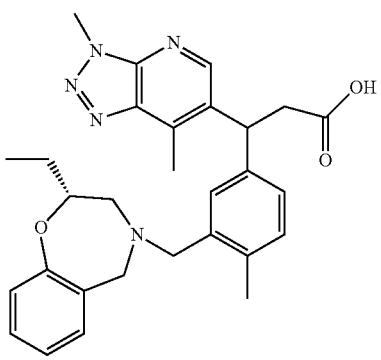 [SMILES: CC[C@@H]1CN(Cc2cc(C(CC(=O)O)c3cnc4c(nnn4C)c3C)ccc2C)Cc2ccccc2O1]

To a solution of methyl 3-(3-ethyl-7-methyl-3H-[1,2,3]triazolo[4,5-b]pyridin-6-yl)-3-(3-(hydroxymethyl)-4-methylphenyl)propanoate (80 mg, 0.226 mmol) in dichloromethane (DCM) (2.000 mL) was added thionyl chloride (0.033 mL, 0.451 mmol). The reaction mixture was stirred at ambient temperature for 1 h. It was concentrated and re-dissolved in acetonitrile (2 mL). (R)-2-ethyl-2,3,4,5-tetrahydrobenzo[f][1,4]oxazepine, hydrochloride (55.89 mg, 0.271 mmol) and DIEA (0.118 mL, 0.677 mmol) were added. The reaction mixture was heated in a Biotage microwave at high absorption for 1 h at 120° C. It was concentrated and re-dissolved in 1 mL MeOH. 2M LiOH (0.651 mL, 1.303 mmol) was added and heated in a Biotage microwave at high absorption for 30 min at 80° C. It was acidified with 6N HCl and 0.5 mL DMSO was added. It was concentrated and purified by reverse-phase HPLC (with 0.1% TFA condition) to give the title compound (79.6 mg, 71.1%) as clear oil. LC-MS m/z 500.3 (M+H)$^+$, 0.77 min (ret. time).

Example 48

3-(3,7-Dimethyl-3H-[1,2,3]triazolo[4,5-c]pyridin-6-yl)-3-(3-(((R)-2-ethyl-2,3-dihydrobenzo[f][1,4]oxazepin-4(5H)-yl)methyl)-4-methylphenyl)propanoic Acid, Trifluoroacetic Acid Salt

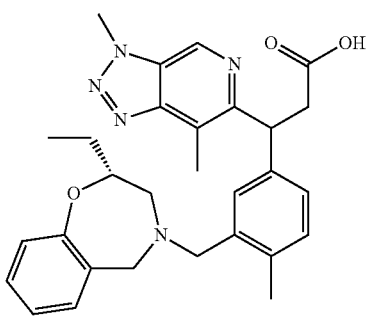 [SMILES: CC[C@@H]1CN(Cc2cc(C(CC(=O)O)c3ncc4c(nnn4C)c3C)ccc2C)Cc2ccccc2O1]

220

Ethyl 3-(3,7-dimethyl-3H-[1,2,3]triazolo[4,5-c]pyridin-6-yl)-3-(3-(hydroxymethyl)-4-methylphenyl)propanoate

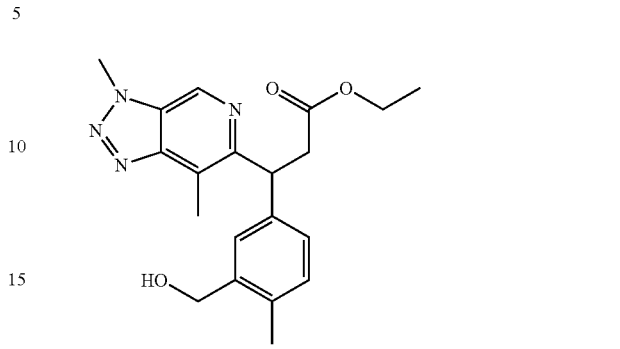

To a suspension of (3-(hydroxymethyl)-4-methylphenyl)boronic acid (8.09 mg, 0.049 mmol), (E)-ethyl 3-(3,7-dimethyl-3H-[1,2,3]triazolo[4,5-c]pyridin-6-yl)acrylate (10 mg, 0.041 mmol), and chloro(1,5-cyclooctadiene)rhodium (I) dimer (2.002 mg, 4.06 µmol) in water (1 mL) and 1,4-dioxane (3 mL) at ambient temperature was added triethylamine (0.017 mL, 0.122 mmol). The resulting suspension was heated to 95° C. for 2 h. It was filtered though celite and washed with ethyl acetate. The filtrate was concentrated. The crude product was purified by reverse-phase HPLC to give the title compound (3 mg, 8.14 µmol, 20.05% yield). LC-MS m/z 369.2 (M+H)$^+$, 0.85 min (ret. time).

3-(3,7-Dimethyl-3H-[1,2,3]triazolo[4,5-c]pyridin-6-yl)-3-(3-(((R)-2-ethyl-2,3-dihydrobenzo[f][1,4]oxazepin-4(5H)-yl)methyl)-4-methylphenyl)propanoic Acid, Trifluoroacetic Acid Salt

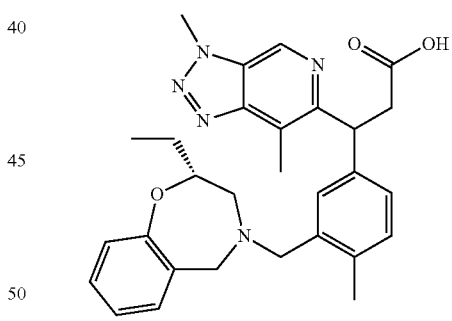

To a solution of ethyl 3-(3,7-dimethyl-3H-[1,2,3]triazolo[4,5-c]pyridin-6-yl)-3-(3-(hydroxymethyl)-4-methylphenyl)propanoate (3 mg, 8.14 µmol) in dichloromethane (DCM) (1.000 mL) was added thionyl chloride (0.594 µL, 8.14 µmol). The mixture was stirred for 1 h at ambient temperature. It was concentrated and re-dissolved in acetonitrile (1 mL). (R)-2-ethyl-2,3,4,5-tetrahydrobenzo[f][1,4]oxazepine, hydrochloride (2.088 mg, 9.77 µmol) and DIEA (4.27 µL, 0.024 mmol) were added. The reaction mixture was heated in a Biotage microwave at high absorption for 1 h at 120° C. It was concentrated and re-dissolved in 1 mL MeOH. 2M LiOH (0.024 mL, 0.049 mmol) was added and heated in a Biotage microwave at high absorption for 30 min at 80° C. It was acidified with 6N HCl and 0.5 mL DMSO was added. It was concentrated and purified by reverse-phase HPLC to give the title compound (2.6 mg, 0.052 mmol, 55%) as solid. LC-MS m/z 500.4 (M+H)+, 0.76 min (ret. time).

Example 49

(S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic Acid, Formic Acid Salt

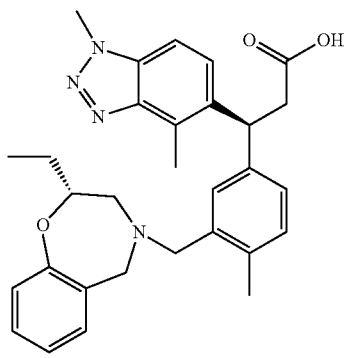 [SMILES: CC[C@@H]1CN(Cc2cc([C@H](CC(=O)O)c3ccc4c(nnn4C)c3C)ccc2C)Cc2ccccc2O1]

(S)-Ethyl 3-(1,4-dimethyl-1H-benzo[d][1,2,3]triazol-5-yl)-3-(3-(hydroxymethyl)-4-methylphenyl)propanoate and (R)-ethyl 3-(1,4-dimethyl-1H-benzo[d][1,2,3]triazol-5-yl)-3-(3-(hydroxymethyl)-4-methylphenyl)propanoate

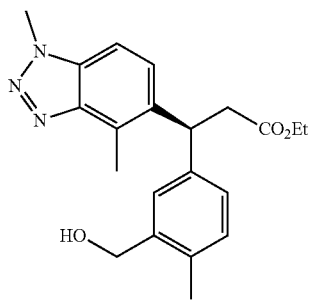

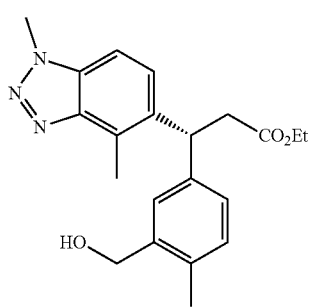

Ethyl 3-(1,4-dimethyl-1H-benzo[d][1,2,3]triazol-5-yl)-3-(3-(hydroxymethyl)-4-methylphen yl)propanoate (950 mg, 2.59 mmol) was purified with chiral SFC (Column: Chiralpak AD, 20×250 mm, 5 u; Co-solvent: 30% MeOH; Flow rate: 50 g/min; Back Pressure: 100 bar to give single enantiomerically pure (S)-ethyl 3-(1,4-dimethyl-1H-benzo[d][1,2,3]triazol-5-yl)-3-(3-(hydroxymethyl)-4-methylphenyl)propanoate (475 mg, 1.293 mmol, 50.0% yield) (chiral SFC ret. time: 2.7 min) and single enantiomerically pure (R)-ethyl 3-(1,4-dimethyl-1H-benzo[d][1,2,3]triazol-5-yl)-3-(3-(hydroxymethyl)-4-methylphenyl)propanoate (481 mg, 1.309 mmol, 50.6% yield) (chiral SFC ret. time: 3.41 min) as oil.

(S)-3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic Acid, Formic Acid Salt

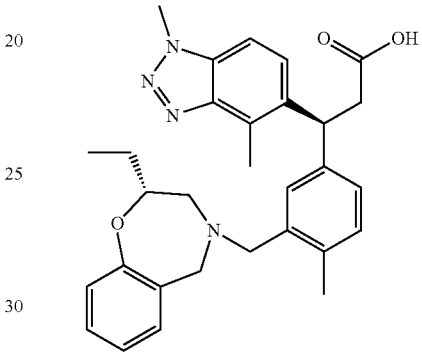

To a solution of (S)-ethyl 3-(1,4-dimethyl-1H-benzo[d][1,2,3]triazol-5-yl)-3-(3-(hydroxymethyl)-4-methylphenyl)propanoate (60 mg, 0.163 mmol) in dichloromethane (DCM) (2 mL) was added thionyl chloride (0.024 mL, 0.327 mmol). The mixture was stirred at ambient temperature for 1 h. The solvent was removed under reduced pressure and the residue re-dissolved in acetonitrile (2 mL). (R)-2-ethyl-2,3,4,5-tetrahydrobenzo[f][1,4]oxazepine, hydrochloride (52.3 mg, 0.245 mmol) and DIEA (0.114 mL, 0.653 mmol) were added. The resulting reaction mixture was heated with microwave at 120° C. for 1 h. The reaction mixture was concentrated to give (S)-ethyl 3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate. It was re-dissolved in methanol (2 mL) and 2M LiOH (0.490 mL, 0.980 mmol) was added. The resulting reaction mixture was heated with microwave at 80° C. for 30 min. It was quenched with 6N HCl and 0.5 mL DMSO was added. The solvent was removed under reduced pressure and the residue purified by reverse-phase HPLC (with 0.1% formic acid condition) to give the title compound (66.7 mg, 0.128 mmol, 78% yield). LC-MS m/z 499.5 (M+H)+, 0.79 min (ret. time).

The compounds in Table 10 were prepared by a method similar to the one described for the preparation of (S)-3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid. As is appreciated by those skilled in the art, these analogous examples may involve variations in general reaction conditions.

TABLE 10

| Ex # | Structure | Name | LCMS [M + H]+ | Retention Time (min) |
|---|---|---|---|---|
| Example 50 | 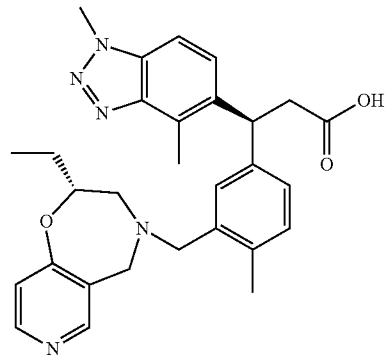 [SMILES: CC[C@@H]1CN(Cc2cc([C@H](CC(=O)O)c3ccc4c(nnn4C)c3C)ccc2C)Cc2cnccc2O1] | (S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)propanoic acid, formic acid salt | 500.4 | 0.72 |
| Example 51 | 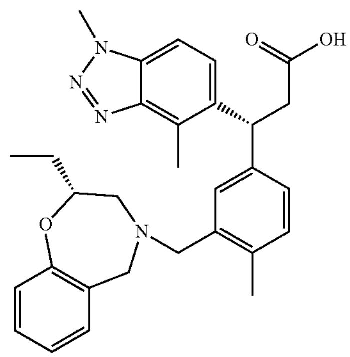 [SMILES: CC[C@@H]1CN(Cc2cc([C@@H](CC(=O)O)c3ccc4c(nnn4C)c3C)ccc2C)Cc2ccccc2O1] | (R)-3-(1,4-Dimethyl-1H-benzo[d][1,2,3]triazol-5-yl)-3-(3-(((R)-2-ethyl-2,3-dihydyrobenzo[f][1,4]oxazepin-4(5H)-yl)methyl)-4-methylphenyl)propanoic acid, formic acid salt | 499.4 | 0.79 |
| Example 52 | 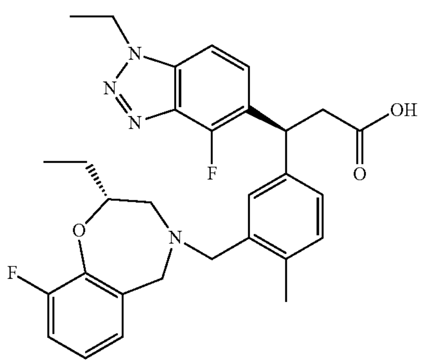 [SMILES: CC[C@@H]1CN(Cc2cc([C@H](CC(=O)O)c3ccc4c(nnn4CC)c3F)ccc2C)Cc2cccc(F)c2O1] | (S)-3-(1-Ethyl-4-fluoro-1H-benzo[d][1,2,3]triazol-5-yl)-3-(3-(((R)-2-ethyl-9-fluoro-2,3-dihydyrobenzo[f][1,4]oxazepin-4(5H)-yl)methyl)-4-methylphenyl)propanoic acid, 0.5formic acid salt | 535.6 | 0.86 |
| Example 53 | 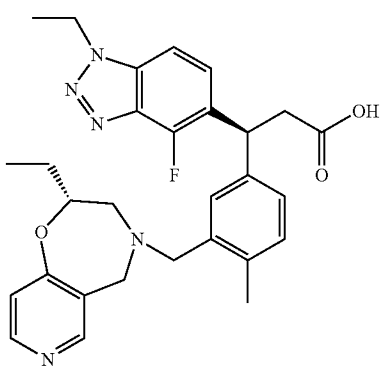 [SMILES: CC[C@@H]1CN(Cc2cc([C@H](CC(=O)O)c3ccc4c(nnn4CC)c3F)ccc2C)Cc2cnccc2O1] | (S)-3-(3-(((R)-2-Ethyl-2,3-dihydropyrido[3,4-f][1,4]oxazepin-4(5H)-yl)methyl)-4-methylphenyl)-3-(1-ethyl-4-fluoro-1H-benzo[d][1,2,3]triazol-5-yl)propanoic acid | 518.3 | 0.89 |

TABLE 10-continued

| Ex # | Structure | Name | LCMS [M + H]+ | Retention Time (min) |
|---|---|---|---|---|
| Example 54 | 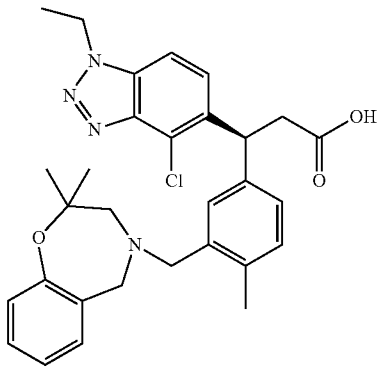 [SMILES: CCn1nnc2c(Cl)c([C@@H](CC(=O)O)c3ccc(C)c(CN4Cc5ccccc5OC(C)(C)C4)c3)ccc21] | (S)-3-(4-Chloro-1-ethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic acid, hydrochloride | 533.2 | 0.86 |
| Example 55 | 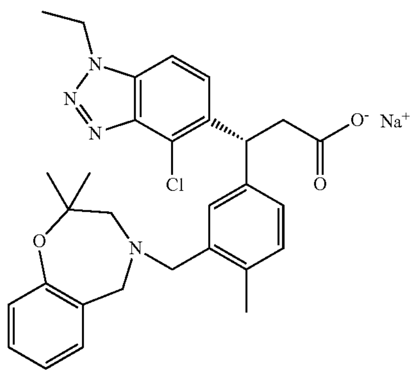 [SMILES: CCn1nnc2c(Cl)c([C@H](CC(=O)[O-])c3ccc(C)c(CN4Cc5ccccc5OC(C)(C)C4)c3)ccc21 ; [Na+]] | (R)-3-(4-Chloro-1-ethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoate, Sodium salt | 533.2 | 0.87 |
| Example 56 | 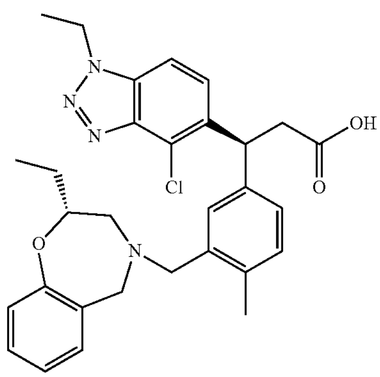 [SMILES: CC[C@@H]1CN(Cc2cc([C@H](CC(=O)O)c3ccc4c(nnn4CC)c3Cl)ccc2C)Cc2ccccc2O1] | (S)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid | 533.3 | 0.84 |
| Example 57 | 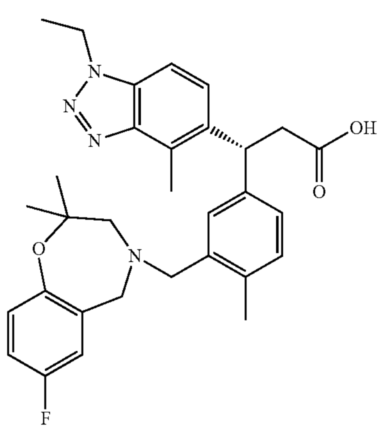 [SMILES: CCn1nnc2c(C)c([C@H](CC(=O)O)c3ccc(C)c(CN4Cc5cc(F)ccc5OC(C)(C)C4)c3)ccc21] | (R)-3-(1,4-Dimethyl-1H-benzo[d][1,2,3]triazol-5-yl)-3-(3-((7-fluoro-2,2-dimethyl-2,3-dihydrobenzo[f][1,4]oxazepin-4(5H)-yl)methyl)-4-methylphenyl)propanoic acid, 0.7formic acid salt | 517.4 | 0.90 |

TABLE 10-continued

| Ex # | Structure | Name | LCMS [M + H]+ | Retention Time (min) |
|---|---|---|---|---|
| Example 58 | 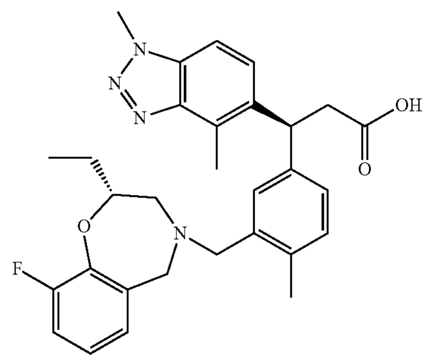 [SMILES: CC[C@@H]1CN(Cc2cc([C@H](CC(=O)O)c3ccc4c(nnn4C)c3C)ccc2C)Cc2cccc(F)c2O1] | (S)-3-(1,4-Dimethyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)propanoic acid, Sodium salt | 517.2 | 0.86 |
| Example 59 | 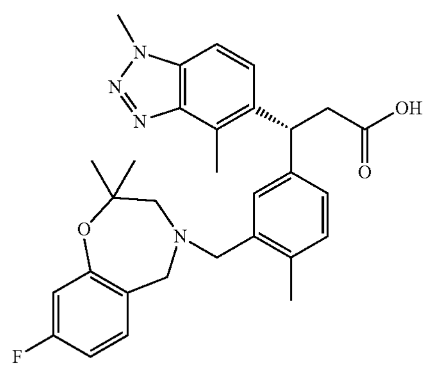 [SMILES: Cc1ccc([C@@H](CC(=O)O)c2ccc3c(nnn3C)c2C)cc1CN1Cc2ccc(F)cc2OC(C)(C)C1] | (R)-3-(1,4-Dimethyl-1H-benzo[d][1,2,3]triazol-5-yl)-3-(3-((8-fluoro-2,2-dimethyl-2,3-dihydrobenzo[f][1,4]oxazepin-4(5H)-yl)methyl)-4-methylphenyl)propanoic acid | 517.4 | 0.96 |
| Example 60 | 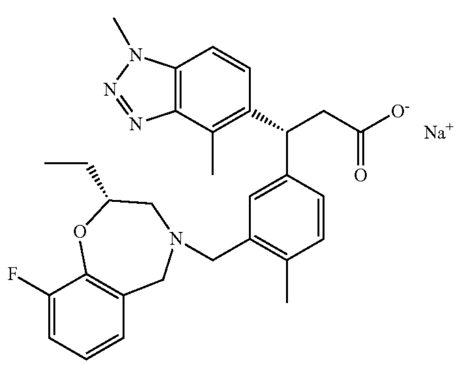 [SMILES: CC[C@@H]1CN(Cc2cc([C@@H](CC(=O)[O-])c3ccc4c(nnn4C)c3C)ccc2C)Cc2cccc(F)c2O1 ; [Na+]] | (R)-3-(1,4-Dimethyl-1H-benzo[d][1,2,3]triazol-5-yl)-3-(3-(((R)-2-ethyl-9-fluoro-2,3-dihydrobenzo-[f][1,4]oxazepin-4(5H)-yl)methyl)-4-methyl-phenyl)propanoic acid, Sodium salt | 517.5 | 0.83 |
| Example 61 | 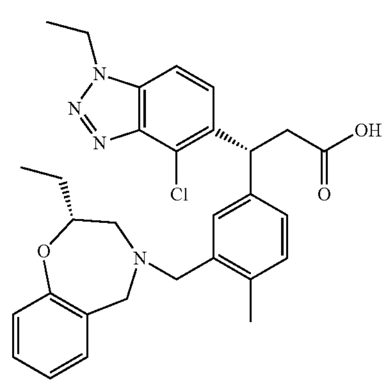 [SMILES: CC[C@@H]1CN(Cc2cc([C@@H](CC(=O)O)c3ccc4c(nnn4CC)c3Cl)ccc2C)Cc2ccccc2O1] | (R)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoic acid | 533.2 | 0.88 |

TABLE 10-continued

| Ex # | Structure | Name | LCMS [M + H]+ | Retention Time (min) |
|---|---|---|---|---|
| Example 62 | 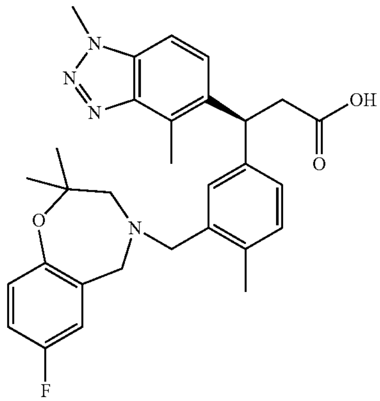 [SMILES: Cc1ccc([C@H](CC(=O)O)c2ccc3c(nnn3C)c2C)cc1CN1Cc2cc(F)ccc2OC(C)(C)C1] | (S)-3-(1,4-Dimethyl-1H-benzo[d][1,2,3]triazol-5-yl)-3-(3-((7-fluoro-2,2-dimethyl-2,3-dihydrobenzo[f][1,4]oxazepin-4(5H)-yl)methyl)-4-methylphenyl)propanoic acid, 1.5formic acid salt | 517.5 | 0.89 |
| Example 63 | 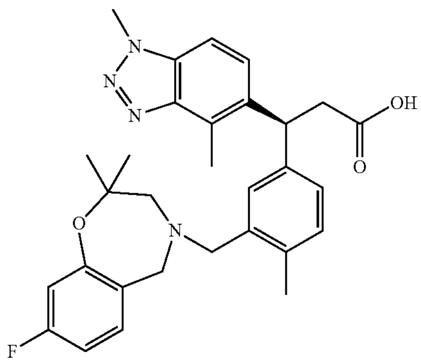 [SMILES: Cc1ccc([C@H](CC(=O)O)c2ccc3c(nnn3C)c2C)cc1CN1Cc2ccc(F)cc2OC(C)(C)C1] | (S)-3-(1,4-Dimethyl-1H-benzo[d][1,2,3]triazol-5-yl)-3-(3-((8-fluoro-2,2-dimethyl-2,3-dihydrobenzo[f][1,4]oxazepin-4(5H)-yl)methyl)-4-methylphenyl)propanoic acid | 517.4 | 0.93 |

Example 64

(S)-3-(3-((2,2-Dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic Acid

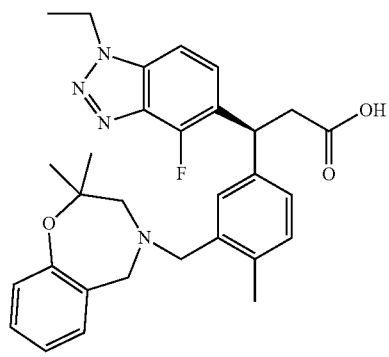 [SMILES: CCn1nnc2c(F)c([C@@H](CC(=O)O)c3ccc(C)c(CN4Cc5ccccc5OC(C)(C)C4)c3)ccc21]

To a solution of benzyl 3-(1-ethyl-4-fluoro-1H-benzo[d][1,2,3]triazol-5-yl)-3-(3-(hydroxymethyl)-4-methylphenyl)propanoate (460 mg, 1.028 mmol) in dichloromethane (5 mL) was added thionyl chloride (0.150 mL, 2.056 mmol). The mixture was stirred for 40 min then concentrated and the residue re-dissolved in acetonitrile (5 mL). 2,2-Dimethyl-2,3,4,5-tetrahydrobenzo[f][1,4]oxazepine hydrochloride (264 mg, 1.234 mmol) was added. The mixture was heated via microwave at 120° C. for 1 h. The resulting mixture was concentrated then re-dissolved in MeOH (3 mL). 2 M LiOH (3.60 mL, 7.20 mmol) was added and the reaction stirred at 60° C. for 4 h. The reaction was acidified with 6N HCl and 0.5 mL DMSO was added. The resulting mixture was concentrated, filtered and purified with preparative HPLC under acidic conditions (with 0.1% TFA as modifier) to give racemic compound. This was resolved by Chiral SFC (Column: Chiralpak OJ 20×250 mm, 5 u; Co-solvent: 20% IPA; Flowrate: 50 g/min; Back pressure: 100 Bar) to give single enantiomerically pure (S)-3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid (229.8 mg) (chiral SFC ret. time: 6.11 min) LC-MS m/z 517.4 (M+H)+, 0.86 min (ret. time) and single enantiomerically pure (R)-3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid (250 mg) (chiral SFC ret. time: 7.22 min). However, a little methanol was used after chiral separation for (R)-3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid which resulted to form a mixture of (R)-methyl 3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoate and (R)-3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]

triazol-5-yl)propanoic acid (250 mg). LC-MS m/z 517.3 (M+H)+, 0.85 min (ret. time). LC-MS m/z 531.1 (M+H)+, 0.96 min (ret. time)

Example 65

(R)-3-(3-((2,2-Dimethyl-2,3-dihydrobenzo[f][1,4] oxazepin-4(5H)-yl)methyl)-4-methylphenyl)-3-(1-ethyl-4-fluoro-1H-benzo[d][1,2,3]triazol-5-yl)propanoic Acid, Hydrochloride

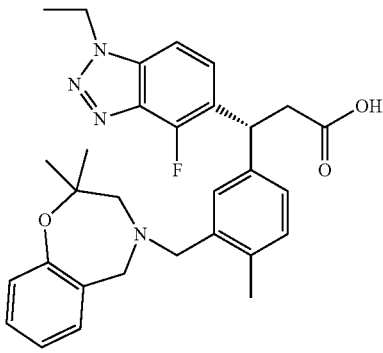 [SMILES: CCn1nnc2c(F)c([C@H](CC(=O)O)c3ccc(C)c(CN4Cc5ccccc5OC(C)(C)C4)c3)ccc21]

To a solution of (R)-methyl 3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl) propanoate and (R)-3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid (250 mg, 0.471 mmol) in methanol (5 mL) was added 2 M LiOH (1.413 mL, 2.83 mmol). The mixture was stirred at ambient temperature for 18 h. The resulting mixture was concentrated then acidified with 6N HCl to pH-, and then extracted with ethyl acetate twice. The organic layer was dried with sodium sulfate, filtered and concentrated to give the title compound (193 mg, 0.349 mmol, 74.1% yield). LC-MS m/z 517.4 (M+H)+, 0.89 min (ret. time)

(S)-Benzyl 3-(4-chloro-1-ethyl-1H-benzo[d][1,2,3] triazol-5-yl)-3-(3-(((R)-2-ethyl-2,3-dihydrobenzo[f] [1,4]oxazepin-4(5H)-yl)methyl)-4-methylphenyl) propanoate and (R)-benzyl 3-(4-chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate

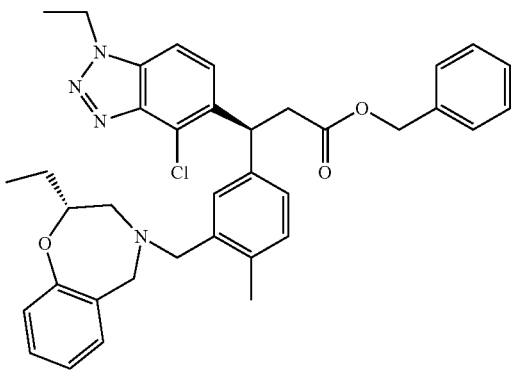

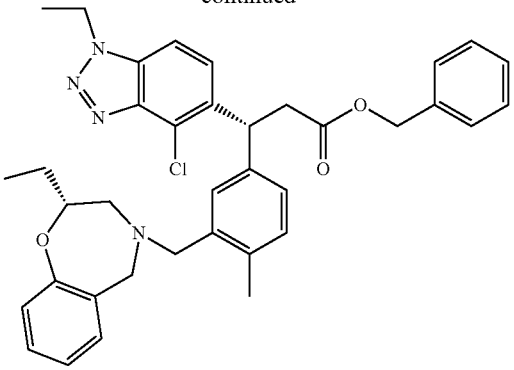

To a suspension of (R)-2-ethyl-4-(2-methyl-5-(4,4,5,5-tetramethyl-1,3,2-dioxaborolan-2-yl)benzyl)-2,3,4,5-tetrahydrobenzo[f][1,4]oxazepine (626 mg, 1.536 mmol), (E)-benzyl 3-(4-chloro-1-ethyl-1H-benzo[d][1,2,3]triazol-5-yl) acrylate (500 mg, 1.463 mmol), and [RhCl(cod)]₂ (72.1 mg, 0.146 mmol) in dioxane (8 mL) and water (2 mL) at ambient temperature was added triethylamine (0.612 mL, 4.39 mmol). The resulting suspension was heated at 90° C. for 1 h. The reaction mixture was passed through celite and washed with EtOAc. The organic layer was collected and concentrated to give the crude product. The crude product was purified by silica gel chromatography the title intermediate benzyl 3-(4-chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate (300 mg, 0.481 mmol, 32.9% yield) and a less pure batch (210 mg). Both batches were resolved by Chiral SFC (Chiralpak IF 20×250 mm, 5 u; Co-solvent: 30% EtOH; Flowrate: 50 g/min; Back pressure: 100 Bar) to give single enantiomerically pure (S)-benzyl 3-(4-chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate (190 mg, 0.305 mmol, 20.84% yield) (chiral SFC ret. time: 6.37 min) LC-MS m/z 623.4 (M+H)+, 1.06 min (ret. time) and single enantiomerically pure (R)-benzyl 3-(4-chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate (204 mg, 0.327 mmol, 22.38% yield) (chiral SFC ret. time: 7.62 min) LC-MS m/z 623.4 (M+H)+, 1.06 min (ret. time)

Example 66

(S)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate, Sodium Salt

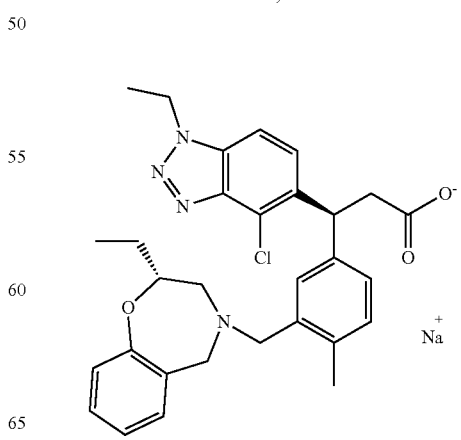

To a solution of (S)-benzyl 3-(4-chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate (190 mg, 0.305 mmol) in methanol (8 mL) at 25° C. was added 2 M LiOH (0.915 mL, 1.829 mmol). The reaction mixture was stirred at ambient temperature for 20 h. The reaction was acidified with 6N HCl to pH~1, 1 mL DMSO was added and the mixture concentrated. The crude material was purified by reverse phase preparative HPLC using 0.1% TFA as a solvent modifier. Desired product fractions were concentrated then re-dissolved in ethyl acetate, extracted with saturated sodium bicarbonate. The organic layer was washed with brine, dried over sodium sulfate, filtered and concentrated to give the title compound (80 mg, 0.144 mmol, 47.3% yield) as solid. LC-MS m/z 533.2 (M+H)$^+$, 0.88 min (ret. time)

Example 67

(R)-3-(4-Chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate, Sodium Salt

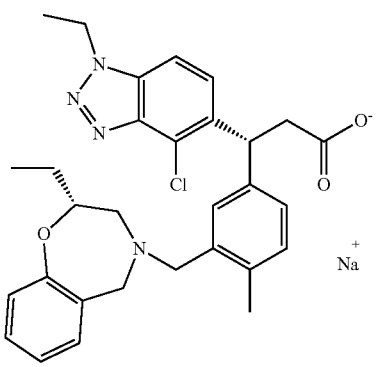

To a solution of (R)-benzyl 3-(4-chloro-1-ethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanoate (204 mg, 0.327 mmol) in methanol (8 mL) at 25° C. was added 2 M LiOH (0.982 mL, 1.964 mmol). The reaction mixture was stirred at ambient temperature for 20 h. The reaction was acidified with 6N HCl to pH~1, 1 mL DMSO was added and the mixture concentrated. The crude material was purified by reverse phase preparative HPLC using 0.1% TFA as a solvent modifier. The desired product was re-dissolved in ethyl acetate and extracted with saturated sodium bicarbonate. The organic layer was washed with brine, dried over sodium sulfate, filtered and concentrated to give the title compound (106 mg, 0.191 mmol, 58.3% yield) as solid. LC-MS m/z 533.2 (M+H)$^+$, 0.90 min (ret. time)

Example 68

(S)-3-(3-(((R)-2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)propanoic Acid, Formic Acid Salt

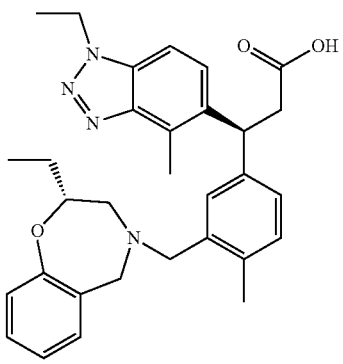 [SMILES: CC[C@@H]1CN(Cc2cc([C@H](CC(=O)O)c3ccc4c(nnn4CC)c3C)ccc2C)Cc2ccccc2O1]

(S)-Ethyl 3-(1-ethyl-4-methyl-1H-benzo[d][1,2,3]triazol-5-yl)-3-(3-(hydroxymethyl)-4-methylphenyl)propanoate and (R)-ethyl 3-(1-ethyl-4-methyl-1H-benzo[d][1,2,3]triazol-5-yl)-3-(3-(hydroxymethyl)-4-methylphenyl)propanoate

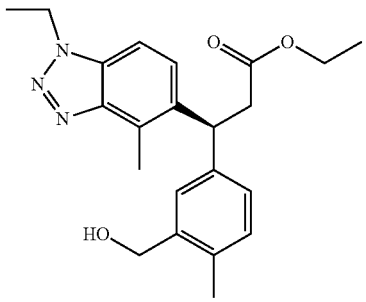

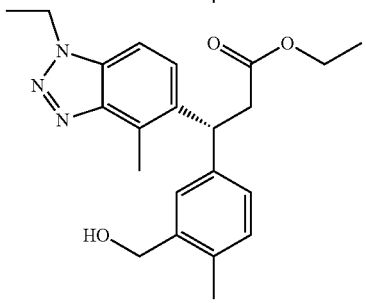

Ethyl 3-(1-ethyl-4-methyl-1H-benzo[d][1,2,3]triazol-5-yl)-3-(3-(hydroxymethyl)-4-methylphenyl) propanoate (390 mg, 1.022 mmol) was separated by Chiral SFC method (Column: Chiralpak AY, 20×250 mm, 5 u; Co-solvent: 20% EtOH; Flow rate: 55 g/min; Back Pressure: 100 bar) to give single enantiomerically pure (S)-ethyl 3-(1-ethyl-4-methyl-1H-benzo[d][1,2,3]triazol-5-yl)-3-(3-(hydroxymethyl)-4-methylphenyl)propanoate (139 mg) (chiral SFC ret. time: 2.71 min) LC-MS m/z 382.2 (M+H)$^+$, 0.91 min (ret. time) and single enantiomerically pure (R)-ethyl 3-(1-ethyl-4- methyl-1H-benzo[d][1,2,3]triazol-5-yl)-3-(3-(hydroxymethyl)-4-methylphenyl)propanoate (151 mg) (chiral SFC ret. time: 4.18 min) LC-MS m/z 382.3 (M+H)⁺, 0.92 min (ret. time).

(S)-3-(3-(((R)-2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)propanoic Acid, Formic Acid Salt

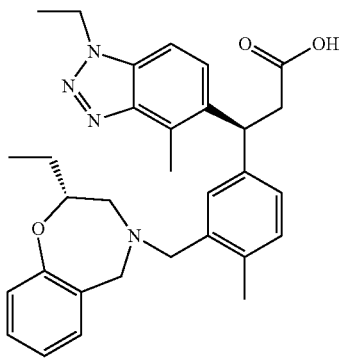 [SMILES: CC[C@@H]1CN(Cc2cc([C@H](CC(=O)O)c3ccc4c(nnn4CC)c3C)ccc2C)Cc2ccccc2O1]

A mixture of (S)-ethyl 3-(1-ethyl-4-methyl-1H-benzo[d][1,2,3]triazol-5-yl)-3-(3-(hydroxymethyl)-4-methylphenyl)propanoate (50 mg, 0.131 mmol), (R)-2-ethyl-2,3,4,5-tetrahydrobenzo[f][1,4]oxazepine (27.9 mg, 0.157 mmol), and DIEA (0.069 mL, 0.393 mmol) in acetonitrile (2 mL) was heated in a Biotage microwave at high absorption for 1 h at 120° C. The solvent was removed under reduced pressure and the crude material was re-dissolved in MeOH (2 mL) and 2M LiOH (0.393 mL, 0.786 mmol) was added and the reaction mixture was heated with microwave at 80° C. for 30 min. It was acidified with 6N HCl and 0.5 mL DMSO was added. It was concentrated and purified by reverse-phase HPLC to give the title compound (40.3 mg, 0.079 mmol, 60.0% yield) as solid. LC-MS m/z 513.4 (M+H)⁺, 0.83 min (ret. time).

Example 69

3-(3-((2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)propanoic Acid, Formic Acid Salt

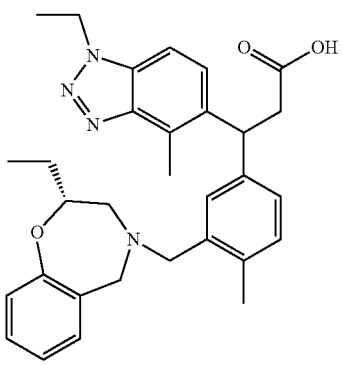 [SMILES: CC[C@@H]1CN(Cc2cc(C(CC(=O)O)c3ccc4c(nnn4CC)c3C)ccc2C)Cc2ccccc2O1]

Ethyl 3-(3-(chloromethyl)-4-methylphenyl)-3-(1-ethyl-4-methyl-1H-benzo[d][1,2,3]triazol-5-yl)propanoate

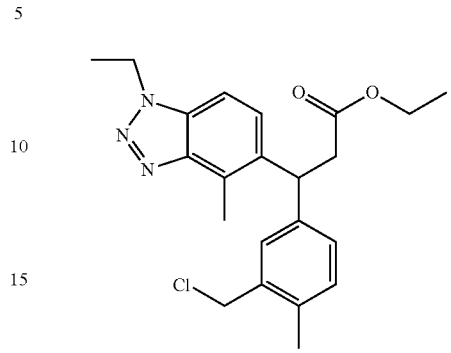

To ethyl 3-(1-ethyl-4-methyl-1H-benzo[d][1,2,3]triazol-5-yl)-3-(3-(hydroxymethyl)-4-methylphenyl) propanoate (120 mg, 0.315 mmol) in dichloromethane (DCM) (2 mL) was added SOCl₂ (0.046 mL, 0.629 mmol). The resulting reaction mixture was stirred at ambient temperature for 1 h. The solvent was removed to give the title compound (126 mg, 0.315 mmol, 100% yield). LC/MS m/z 399.9 (M+H)⁺, 1.14 min (ret. time).

3-(3-((2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)propanoic Acid, Formic Acid Salt

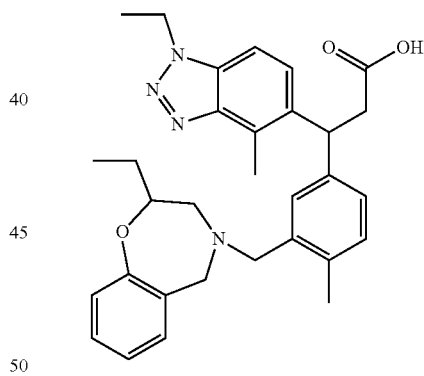

To methyl 3-(3-(chloromethyl)-4-methylphenyl)-3-(1-ethyl-4-methyl-1H-benzo[d][1,2,3]triazol-5-yl)propanoate (70 mg, 0.181 mmol) in acetonitrile (2 mL) was added 2-ethyl-2,3,4,5-tetrahydrobenzo[f][1,4]oxazepine (0.056 mL, 0.272 mmol) and DIEA (0.095 mL, 0.544 mmol). The resulting reaction mixture was heated with μwave at 120° C. for 1 h. The solvent was removed under reduced pressure and the residue re-dissolved in MeOH (2 mL). 2M LiOH (0.544 mL, 1.088 mmol) was added. It was heated with microwave at 80° C. for 60 min. It was quenched with 6N HCl and 0.5 mL DMSO was added. The solvent was removed under reduced pressure and the residue purified by reverse-phase HPLC (with 0.1% formic acid condition) to give the title compound (52 mg, 0.093 mmol, 51.3% yield) as solid. LC-MS m/z 513.5 (M+H)⁺, 0.83 min (ret. time).

Example 70

3-(3-((2-Ethyl-2,3-dihydrobenzo[f][1,4]oxazepin-4 (5H)-yl)methyl)-4-methylphenyl)-3-(7-methoxy-1,4-dimethyl-1H-benzo[d][1,2,3]triazol-5-yl)propanoic Acid, Formic Acid Salt

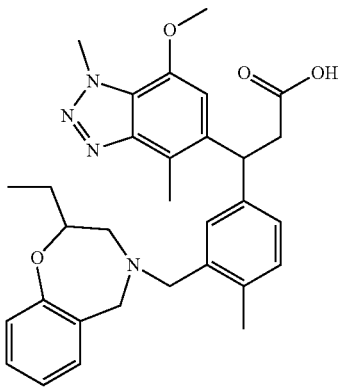 [SMILES: CCC1CN(Cc2cc(C(CC(=O)O)c3cc(OC)c4c(nnn4C)c3C)ccc2C)Cc2ccccc2O1]

To methyl 3-(3-(chloromethyl)-4-methylphenyl)-3-(7-methoxy-1,4-dimethyl-1H-benzo[d][1,2,3]triazol-5-yl)propanoate (70 mg, 0.174 mmol) in acetonitrile (6 mL) were added 2-ethyl-2,3,4,5-tetrahydrobenzo[f][1,4]oxazepine (0.054 mL, 0.261 mmol) and DIEA (0.091 mL, 0.523 mmol). The resulting reaction mixture was heated with microwave at 120° C. for 1 h. The reaction mixture was concentrated to give methyl 3-(3-((2-ethyl-2,3-dihydrobenzo[f][1,4]oxazepin-4(5H)-yl)methyl)-4-methylphenyl)-3-(7-methoxy-1,4-dimethyl-1H-benzo[d][1,2,3]triazol-5-yl)propanoate. It was re-dissolved in methanol (2 mL) and 2M LiOH (0.523 mL, 1.045 mmol) was added. The resulting reaction mixture was heated with microwave at 80° C. for 60 min. It was quenched with 6N HCl and 0.5 mL DMSO was added. The solvent was removed under reduced pressure and the residue purified by reverse-phase HPLC (with 0.1% formic acid condition) to give the title compound (65 mg, 0.113 mmol, 64.9% yield) was obtained. LC-MS m/z 529.2 (M+H)+, 0.82 min (ret. time).

Example 71

3-(1,4-dimethyl-1H-benzo[d][1,2,3]triazol-5-yl)-3-(4-methyl-3-((2-propyl-2,3-dihydrobenzo[f][1,4] oxazepin-4(5H)-yl)methyl)phenyl)propanoic Acid, Formic Acid Salt

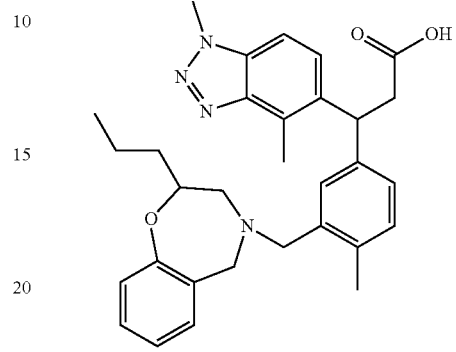

To ethyl 3-(3-(chloromethyl)-4-methylphenyl)-3-(1,4-dimethyl-1H-benzo[d][1,2,3]triazol-5-yl)propanoate (80 mg, 0.207 mmol) in acetonitrile (2 mL) were added 2-propyl-2,3,4,5-tetrahydrobenzo[f][1,4]oxazepine (59.5 mg, 0.311 mmol) and DIEA (0.109 mL, 0.622 mmol). The resulting reaction mixture was heated with microwave at 120° C. for 1.5 h. The solvent was removed under reduced pressure and the crude material was re-dissolved in MeOH (2 mL) and 2M LiOH (0.622 mL, 1.244 mmol) was added and the reaction mixture was heated with microwave at 80° C. for 30 min. It was acidified with 6N HCl and 0.5 mL DMSO was added. It was concentrated and purified by reverse-phase HPLC to give the title compound (55.7 mg, 0.100 mmol, 48.1% yield) as solid. LC-MS m/z 513.3 (M+H)+, 0.87 min (ret. time).

The compounds in Table 11 were prepared by a method similar to the one described for the preparation of 3-(1,4-dimethyl-1H-benzo[d][1,2,3]triazol-5-yl)-3-(4-methyl-3-((2-propyl-2,3-dihydrobenzo[f][1,4]oxazepin-4(5H)-yl)methyl)phenyl)propanoic acid, formic acid salt. As is appreciated by those skilled in the art, these analogous examples may involve variations in general reaction conditions.

TABLE 11

| Ex # | Structure | Name | LCMS [M + H]+ | Retention Time (min) |
|---|---|---|---|---|
| Example 72 | 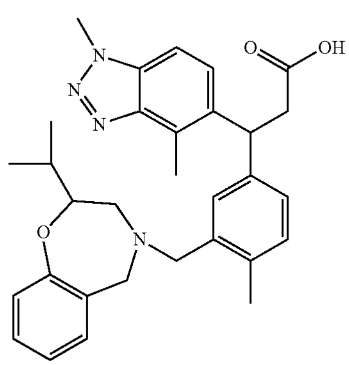 [SMILES: Cc1ccc(C(CC(=O)O)c2ccc3c(nnn3C)c2C)cc1CN1Cc2ccccc2OC(C(C)C)C1] | 3-(1,4-dimethyl-1H-benzo[d][1,2,3]triazol-5-yl)-3-(3-((2-isopropyl-2,3-dihydrobenzo[f][1,4]oxazepin-4(5H)-yl)methyl)-4-methylphenyl)propanoic acid, formic acid salt | 513.6 | 0.84 |

TABLE 11-continued

| Ex # | Structure | Name | LCMS [M + H]+ | Retention Time (min) |
|---|---|---|---|---|
| Example 73 | 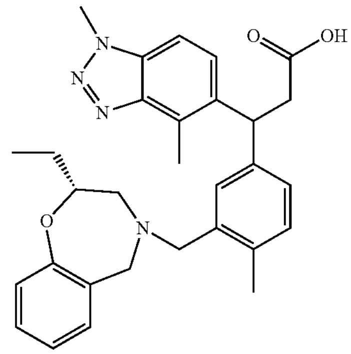 [SMILES: CC[C@@H]1CN(Cc2cc(C(CC(=O)O)c3ccc4c(nnn4C)c3C)ccc2C)Cc2ccccc2O1] | 3-(1,4-Diemthyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanonic acid, formic acid salt | 499.2 | 0.81 |
| Example 74 | 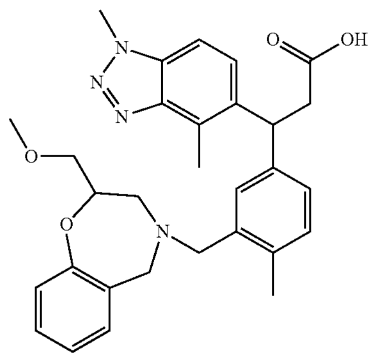 [SMILES: COCC1CN(Cc2cc(C(CC(=O)O)c3ccc4c(nnn4C)c3C)ccc2C)Cc2ccccc2O1] | 3-(1,4-Dimethyl-1H-benzo[d][1,2,3]triazol-5-yl)-3-(3-((2-(methoxymethyl)-2,3-dihydrobenzo[f][1,4]oxazepin-4(5H)-yl)methyl)-4-methylphenyl)propanoic acid, formic acid salt | 515.2 | 0.74 |

Example 75

3-(1,4-Dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)propanoic Acid, Formic Acid Salt

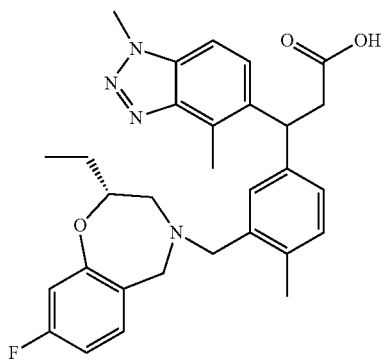 [SMILES: CC[C@@H]1CN(Cc2cc(C(CC(=O)O)c3ccc4c(nnn4C)c3C)ccc2C)Cc2ccc(F)cc2O1]

Ethyl 3-(1,4-dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methy)-4-methylphenyl) propanoate

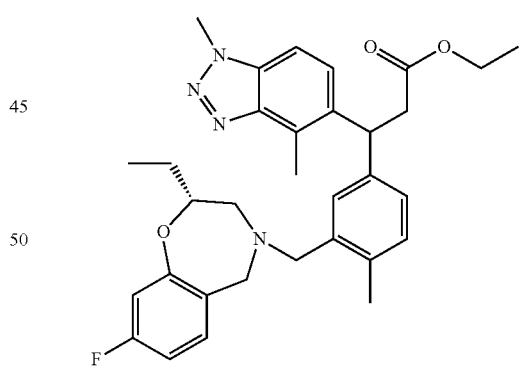

To a solution of (R)-2-ethyl-8-fluoro-2,3,4,5-tetrahydrobenzo[f][1,4]oxazepine (152 mg, 0.777 mmol) and ethyl 3-(3-(chloromethyl)-4-methylphenyl)-3-(1,4-dimethyl-1Hbenzo[d][1,2,3]triazol-5-yl)propanoate (150 mg, 0.389 mmol) in acetonitrile (6 mL) was added DIPEA (0.136 mL, 0.777 mmol) at ambient temperature. The reaction mixture was stirred in microwave reactor at 90° C. for 1 h. The reaction mixture was cooled to 0° C., quenched with cold water, extracted twice with EtOAc followed by brine solution. The organic layer was dried over anhydrous $Na_2SO_4$, filtered and concentrated. It was purified by silica gel chromatography to give the title compound (180 mg, 0.330 mmol, 85% yield) as liquid. LC-MS m/z 545.42 (M+H)⁺, 2.16 min (ret. time).

3-(1,4-Dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)propanoic Acid, Formic Acid Salt

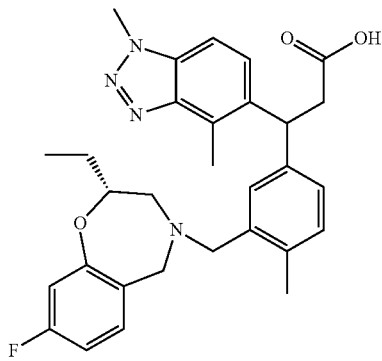 [SMILES: CC[C@@H]1CN(Cc2cc(C(CC(=O)O)c3ccc4c(nnn4C)c3C)ccc2C)Cc2ccc(F)cc2O1]

To a solution of ethyl 3-(1,4-dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)propanoate (180 mg, 0.330 mmol) in ethanol (10 mL) was added 10% NaOH (10 mL, 0.330 mmol) at 0° C. The reaction was stirred at ambient temperature for 16 h. The reaction mixture was evaporated under reduced pressure, neutralized with 2N HCl, extracted with twice DCM followed by brine solution. The organic layer was dried (Na₂SO₄), filtered and purified by reverse-phase HPLC to give the title compound (80 mg, 0.154 mmol, 46.7% yield) as white solid. LC-MS m/z 517.36 (M+H)⁺, 1.90 min (ret. time).

The compounds in Table 12 were prepared by a method similar to the one described for the preparation of 3-(1,4-dimethyl-1H-benzo[d][1,2,3]triazol-5-yl)-3-(3-(((R)-2-ethyl-8-fluoro-2,3-dihydrobenzo[f][1,4]oxazepin-4(5H)-yl)methyl)-4-methylphenyl)propanoic acid, formic acid salt. As is appreciated by those skilled in the art, these analogous examples may involve variations in general reaction conditions.

TABLE 12

| Ex # | Structure | Name | LCMS [M + H]⁺ | Retention Time (min) |
|---|---|---|---|---|
| Example 76 | 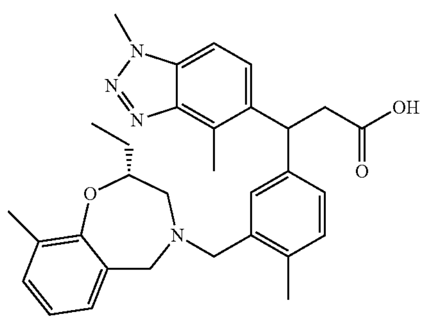 [SMILES: CC[C@@H]1CN(Cc2cc(C(CC(=O)O)c3ccc4c(nnn4C)c3C)ccc2C)Cc2cccc(C)c2O1] | Ammonium 3-(1,4-Dimethyl-1H-benzo[d][1,2,3]triazol-5-yl)-3-(3-(((R)-2-ethyl-9-methyl-2,3-dihydrobenzo[f][1,4]oxazepin-4(5H)-yl)methyl)-4-methylphenyl)propanate | 513.42 | 1.90 |
| Example 77 | 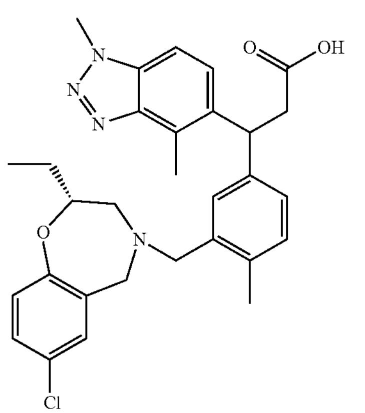 | Ammonium 3-(3-(((R)-7-Chloro-2-ethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanate | 553.36 | 2.03 |

TABLE 12-continued

| Ex # | Structure | Name | LCMS [M + H]+ | Retention Time (min) |
|---|---|---|---|---|
| Example 78 | 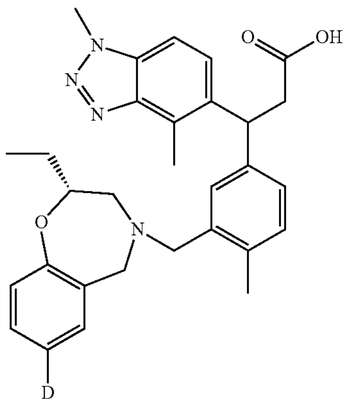 [SMILES: CC[C@@H]1CN(Cc2cc(C(CC(=O)O)c3ccc4c(nnn4C)c3C)ccc2C)Cc2cc(Cl)ccc2O1] | 3-(1,4-Dimethyl-1H-benzo[d][1,2,3]triazol-5-yl)-3-(3-(((R)-2-ethyl-7-fluoro-2,3-dihydrobenzo[f][1,4]oxazepin-4(5H)-yl)methyl)-4-methylphenyl)propanoic acid, formic acid salt | 517.36 | 1.91 |
| Example 79 | 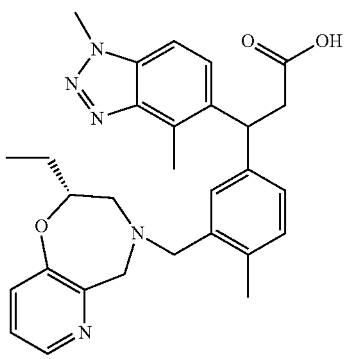 [SMILES: CC[C@@H]1CN(Cc2cc(C(CC(=O)O)c3ccc4c(nnn4C)c3C)ccc2C)Cc2ncccc2O1] | 3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid | 500.19 | 1.70 |
| Example 80 | 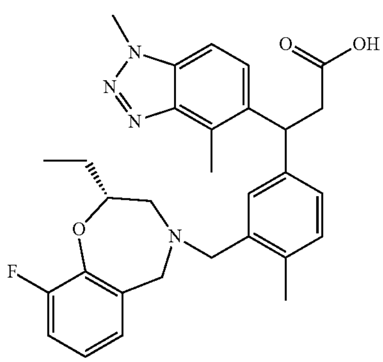 [SMILES: CC[C@@H]1CN(Cc2cc(C(CC(=O)O)c3ccc4c(nnn4C)c3C)ccc2C)Cc2cccc(F)c2O1] | 3-(1,4-Diemthyl-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)propanoic acid, formic acid salt | 517.36 | 1.93 |
| Example 81 | 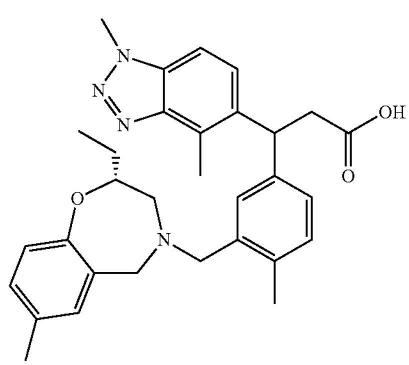 [SMILES: CC[C@@H]1CN(Cc2cc(C(CC(=O)O)c3ccc4c(nnn4C)c3C)ccc2C)Cc2cc(C)ccc2O1] | Ammonium 3-(1,4-dimethyl-1H-benzo[d][1,2,3]triazol-5-yl)-3-(3-(((R)-2-ethyl-7-methyl-2,3-dihydrobenzo[f][1,4]oxazepin-4(5H)-yl)methyl)-4-methylphenyl)propanate | 513.42 | 1.88 |

TABLE 12-continued

| Ex # | Structure | Name | LCMS [M + H]+ | Retention Time (min) |
|---|---|---|---|---|
| Example 82 | 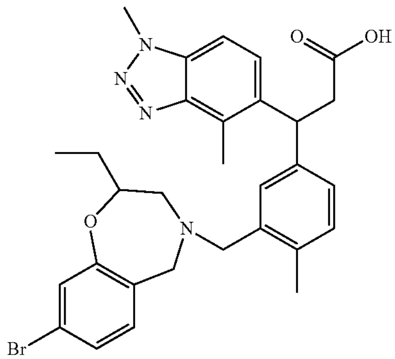 [SMILES: CCC1CN(Cc2cc(C(CC(=O)O)c3ccc4c(nnn4C)c3C)ccc2C)Cc2ccc(Br)cc2O1] | 3-(3-((8-Bromo-2-ethyl-2,3-dihydrobenzo-[f][1,4]oxazepin-4(5H)-yl)methyl)-4-methyl-phenyl)-3-(1,4-dimethyl-1H-benzo[d]-[1,2,3]triazol-5-yl)propanoic acid | 577.0 | 3.30 |
| Example 83 | 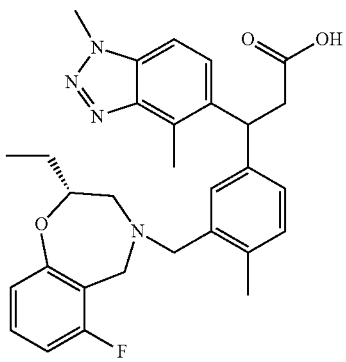 [SMILES: CC[C@@H]1CN(Cc2cc(C(CC(=O)O)c3ccc4c(nnn4C)c3C)ccc2C)Cc2c(F)cccc2O1] | 3-(1,4-Dimethyl-1H-benzo[d][1,2,3]triazol-5-yl)-3-(3-(((R)-2-ethyl-6-fluoro-2,3-dihydrobenzo[f][1,4]oxaze-pin-4(5H)-yl)methyl)-4-methylphenyl)propanoic acid | 517.32 | 1.95 |
| Example 84 | 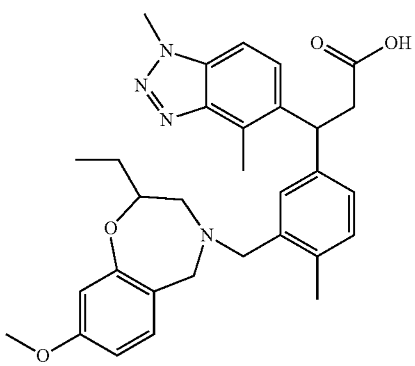 [SMILES: CCC1CN(Cc2cc(C(CC(=O)O)c3ccc4c(nnn4C)c3C)ccc2C)Cc2ccc(OC)cc2O1] | 3-(1,4-Dimethyl-1H-benzo[d][1,2,3]triazol-5-yl)-3-(3-((2-ethyl-8-methoxy-2,3-dihdyrobenzo[f][1,4]oxaze-pin-4(5H)-yl)methyl)-4-methylphenyl)propanoic acid, form acid salt | 529.35 | 1.83 |
| Example 85 | 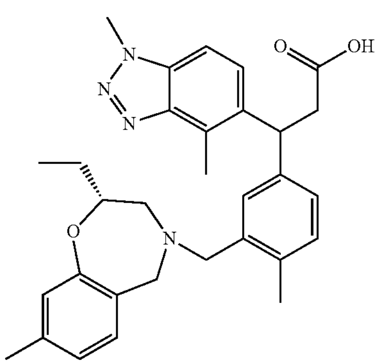 [SMILES: CC[C@@H]1CN(Cc2cc(C(CC(=O)O)c3ccc4c(nnn4C)c3C)ccc2C)Cc2ccc(C)cc2O1] | Ammoniumn 3-(1,4-Dimethyl-1H-benzo[d][1,2,3]triazol-5-yl)-3-(3-(((R)-2-ethyl-8-methyl-2,3-dihydrobenzo[f][1,4]oxaze-pin-4(5H)-yl)methyl)-4-methyphenyl)propanoate | 513.42 | 1.92 |

TABLE 12-continued

| Ex # | Structure | Name | LCMS [M + H]+ | Retention Time (min) |
|---|---|---|---|---|
| Example 86 | 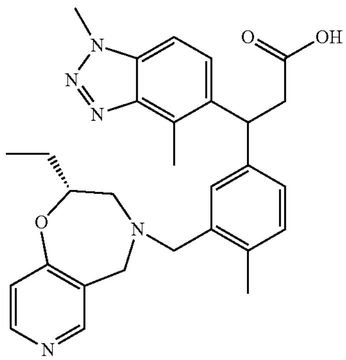 [SMILES: CC[C@@H]1CN(Cc2cc(C(CC(=O)O)c3ccc4c(nnn4C)c3C)ccc2C)Cc2cnccc2O1] | 3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)propanoic acid | 500.41 | 1.66 |
| Example 87 | 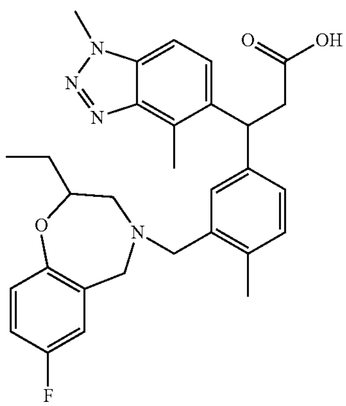 [SMILES: CCC1CN(Cc2cc(C(CC(=O)O)c3ccc4c(nnn4C)c3C)ccc2C)Cc2cc(F)ccc2O1] | 3-(1,4-Dimethyl-1H-benzo[d][1,2,3]triazol-5-yl)-3-(3-((2-ehtyl-7-fluoro-2,3-dihydrobenzo[f][1,4]oxazepin-4(5H)-yl)methyl)-4-methylphenyl)propanoic acid | 517.39 | 3.37 |
| Example 88 | 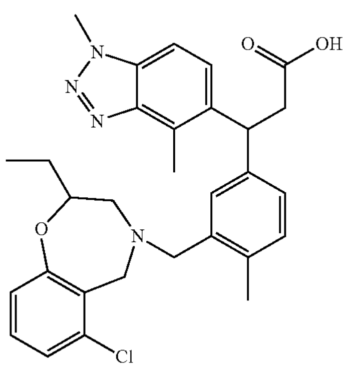 [SMILES: CCC1CN(Cc2cc(C(CC(=O)O)c3ccc4c(nnn4C)c3C)ccc2C)Cc2c(Cl)cccc2O1] | 3-(3-((6-Chloro-2-ethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid | 533.23 | 3.48 |
| Example 89 | 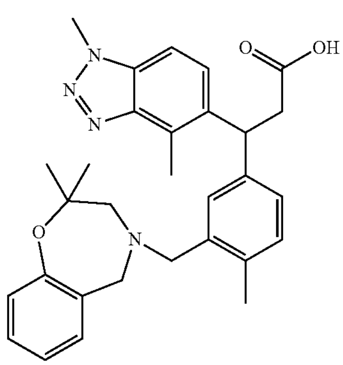 [SMILES: Cc1ccc(C(CC(=O)O)c2ccc3c(nnn3C)c2C)cc1CN1Cc2ccccc2OC(C)(C)C1] | 3-(1,4-Diemthyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic acid | 499.25 | 1.85 |

TABLE 12-continued

| Ex # | Structure | Name | LCMS [M + H]+ | Retention Time (min) |
|---|---|---|---|---|
| Example 90 | 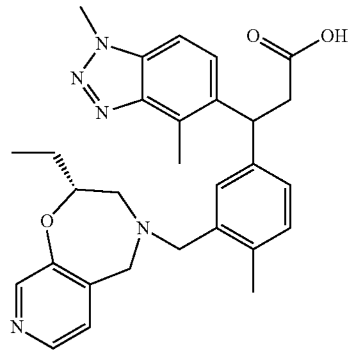 [SMILES: CC[C@@H]1CN(Cc2cc(C(CC(=O)O)c3ccc4c(nnn4C)c3C)ccc2C)Cc2ccncc2O1] | 3-(1,4-Dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)propanoic acid | 500.1 | 3.10 |
| Example 91 | 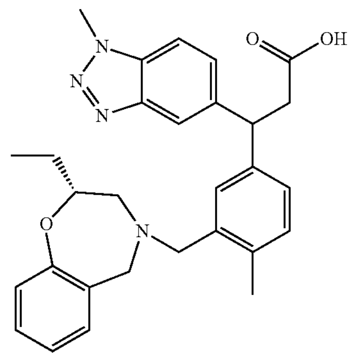 [SMILES: CC[C@@H]1CN(Cc2cc(C(CC(=O)O)c3ccc4c(c3)nnn4C)ccc2C)Cc2ccccc2O1] | 3-(3-(((R)-2-Ethyl-2,3-dihydrobenzo[f][1,4]oxazepin-4(5H)-yl)methyl)-4-methylphenyl)-3-(1-methyl-1H-benzo[d][1,2,3]triazol-5-yl)propanoic acid | 485.32 | 1.77 |
| Example 92 | 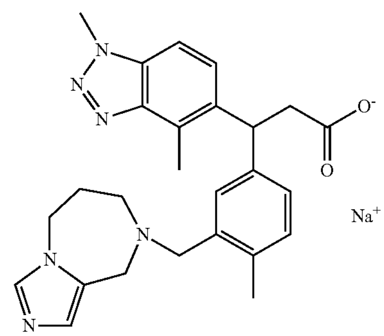 [SMILES: Cc1ccc(C(CC(=O)[O-])c2ccc3c(nnn3C)c2C)cc1CN1CCCn2cncc2C1 ; [Na+]] | 3-(3-((6,7-Dihydro-5H-imidazo[1,5-a][1,4]diazepin-8(9H)-yl)methyl)-4-methylphenyl)-3-(1,4-dimethyl-1H-benzo[d][1,2,3]triazol-5-yl)propanoic acid, Sodium salt | 459.3 | 0.68 |

Example 93

3-(3-(((S)-8-bromo-2-methyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic Acid, Formic Acid Salt

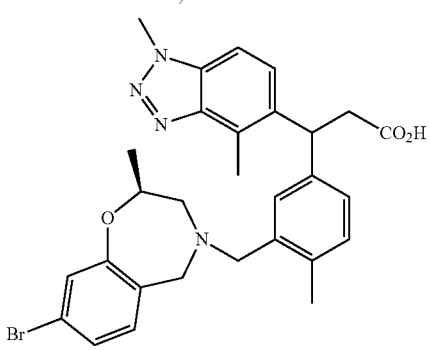

(S)-8-bromo-2-methyl-2,3,4,5-tetrahydrobenzo[f][1,4]oxazepine

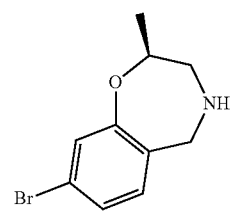

To a solution of (S)-1-aminopropan-2-ol (0.079 mL, 1.000 mmol) in methanol (5 mL) was added 2,4-dibromobenzaldehyde (0.167 mL, 1 mmol). The resulting reaction mixture was stirred at ambient temperature for 20 min. NaBH$_4$ (15.13 mg, 0.400 mmol) was added slowly. The resulting reaction mixture was stirred at ambient temperature for 20 min. after which time it was evaporated under vacuum then was redissolved in DCM (5 mL), dried over MgSO₄, filtered, and concentrated. This result intermediate was dissolved in isopropanol (5.00 mL), copper(I) iodide (19.05 mg, 0.100 mmol) and K₂CO₃ (276 mg, 2.000 mmol) were added. The resulting reaction mixture was heated with microwave at 100° C. for 30 min. This reaction mixture was evaporated under vacuum, redissolved in DCM (5 mL), dried over MgSO₄, filtered, evaporated under vacuum to afford the product (S)-8-bromo-2-methyl-2,3,4,5-tetrahydrobenzo[f][1,4]oxazepine (258.9 mg, 1.069 mmol, 107% yield). LC-MS m/z 242.0 (M+H)⁺, 0.57 min (ret. time).

3-(3-(((S)-8-bromo-2-methyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic Acid, Formic Acid Salt

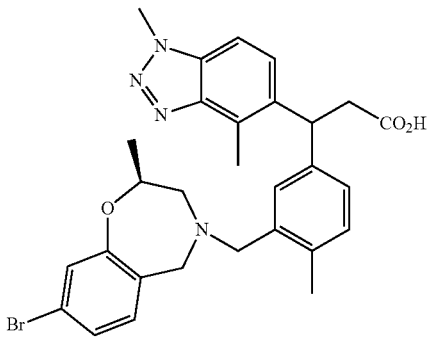 [SMILES: Cc1ccc(C(CC(=O)O)c2ccc3c(nnn3C)c2C)cc1CN1Cc2ccc(Br)cc2O[C@@H](C)C1]

To a solution of (S)-8-bromo-2-methyl-2,3,4,5-tetrahydrobenzo[f][1,4]oxazepine (47.1 mg, 0.194 mmol) in tetrahydrofuran (0.5 mL) and acetonitrile (1 mL) were added DIEA (0.091 mL, 0.518 mmol) and then a solution of ethyl 3-(3-(chloromethyl)-4-methylphenyl)-3-(1,4-dimethyl-1H-benzo[d][1,2,3]triazol-5-yl)propanoate (50 mg, 0.130 mmol) in acetonitrile (1 mL). The resulting reaction mixture was heated with microwave at 100° C. for 1 h. It was concentrated and redissolved in methanol (2 mL). NaOH (3.0 N) (0.346 mL, 1.037 mmol) was added. The resulting reaction mixture was heated with microwave at 80° C. for 20 min. The reaction mixture was then neutralized with HCl (2 N) to pH~6, evaporated under vacuum, purified by reverse phase HPLC to afford the desired product 3-(3-(((S)-8-bromo-2-methyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid, formic acid salt (12.1 mg, 0.021 mmol, 16.57% yield). LC-MS m/z 563.2 (M+H)⁺, 0.85 min (ret. time).

Example 94

3-(1,4-Dimethyl-1H-benzo[d][1,2,3]triazol-5-yl)-3-(4-methyl-3-(((R)-2-methyl-2,3-dihydrobenzo[f][1,4]oxazepin-4(5H)-yl)methyl)phenyl)propanoic Acid, Formic Acid Salt

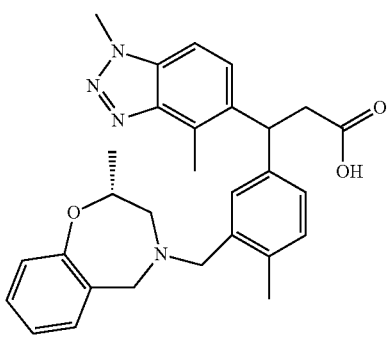 [SMILES: Cc1ccc(C(CC(=O)O)c2ccc3c(nnn3C)c2C)cc1CN1Cc2ccccc2O[C@H](C)C1]

To a solution of ethyl 3-(3-(chloromethyl)-4-methylphenyl)-3-(1,4-dimethyl-1H-benzo[d][1,2,3]triazol-5-yl)propanoate (50 mg, 0.130 mmol) in acetonitrile (1.5 mL) were added (R)-2-methyl-2,3,4,5-tetrahydrobenzo[f][1,4]oxazepine, hydrochloride (38.8 mg, 0.194 mmol), K₂CO₃ (53.7 mg, 0.389 mmol) and sodium iodide (3.88 mg, 0.026 mmol). The resulting reaction mixture was stirred at 40° C. for 67 h. The reaction mixture was filtered. The filter cake was washed with MeCN (1 mL). The filtrate was concentrated. This intermediate was dissolved in methanol (1.5 mL), NaOH (3 N) (0.216 mL, 0.648 mmol) was added. The resulting reaction mixture was heated with microwave at 80° C. for 20 min. The reaction mixture was acidified with HCl (3 N) to pH~6, evaporated under vacuum, purified by reverse phase HPLC to afford desired product 3-(1,4-dimethyl-1H-benzo[d][1,2,3]triazol-5-yl)-3-(4-methyl-3-(((R)-2-methyl-2,3-dihydrobenzo[f][1,4]oxazepin-4(5H)-yl)methyl)phenyl)propanoic acid, formic acid salt (47.0 mg, 0.091 mmol, 70.2% yield). LC-MS m/z 485.5 (M+H)⁺, 0.70 min (ret. time).

Example 95

3-(1,4-Dimethyl-1H-benzo[d][1,2,3]triazol-5-yl)-3-(4-fluoro-3-(((S)-2-methyl-2,3-dihydrobenzo[f][1,4]oxazepin-4(5H)-yl)methyl)phenyl)propanoic Acid, Formic Acid Salt

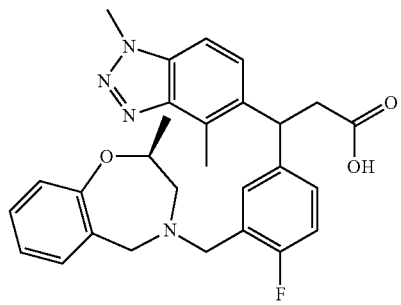 [SMILES: Cc1c(C(CC(=O)O)c2ccc(F)c(CN3Cc4ccccc4O[C@@H](C)C3)c2)ccc2c1nnn2C]

(S)-1-((2-bromobenzyl)amino)propan-2-ol

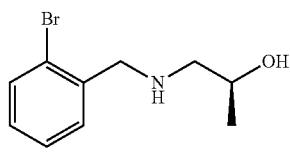

To a solution of (S)-1-aminopropan-2-ol (0.236 mL, 3.00 mmol) in methanol (10 mL) was added 2-bromobenzaldehyde (0.350 mL, 3 mmol). The resulting reaction mixture was stirred at ambient temperature for 1 h. Then NaBH₄ (45.4 mg, 1.200 mmol) was added slowly. The resulting reaction mixture was stirred at ambient temperature for 66 h. Solvent was evaporated under vacuum. It was redissolved in DCM (5 mL), dried over MgSO₄, filtered, evaporated under vacuum to afford product (S)-1-((2-bromobenzyl)amino)propan-2-ol (710.7 mg, 2.91 mmol, 97% yield). LC-MS m/z 244.1 (M+H)⁺, 0.49 min (ret. time).

253

(S)-2-methyl-2,3,4,5-tetrahydrobenzo[f][1,4]ox-
azepine

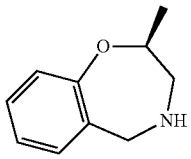

To a solution of (S)-1-((2-bromobenzyl)amino)propan-2-ol (580 mg, 2.376 mmol) in isopropanol (10 mL) was added copper(I) iodide (45.2 mg, 0.238 mmol) and K$_2$CO$_3$ (657 mg, 4.75 mmol). The result reaction mixture was heated with microwave at 130° C. under N$_2$ atmosphere for 1 h. The reaction mixture was filtered. The filter cake was washed with i-PrOH (1 mL). The combined filtrate was evaporated down under vacuum before was redissolved in DCM (5 mL), dried over MgSO$_4$, filtered, evaporated down under vacuum to afford product (S)-2-methyl-2,3,4,5-tetrahydrobenzo[f][1,4]oxazepine (393.3 mg, 2.410 mmol, 101% yield). LC-MS m/z 164.1 (M+H)$^+$, 0.49 min (ret. time).

Ethyl 3-(1,4-dimethyl-1H-benzo[d][1,2,3]triazol-5-yl)-3-(4-fluoro-3-(hydroxymethyl)phenyl)propanoate

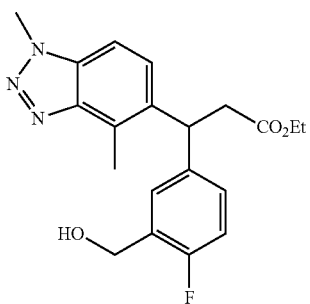 [SMILES: CCOC(=O)CC(c1ccc(F)c(CO)c1)c1ccc2c(nnn2C)c1C]

To a solution of (E)-ethyl 3-(1,4-dimethyl-1H-benzo[d][1,2,3]triazol-5-yl)acrylate (490 mg, 1.998 mmol) and (2-fluoro-5-(4,4,5,5-tetramethyl-1,3,2-dioxaborolan-2-yl)phenyl)methanol (762 mg, 3.02 mmol) in 1,4-dioxane (9 mL) and water (6 mL) was added chloro(1,5-cyclooctadiene)rhodium(I) dimer (65 mg, 0.132 mmol) and TEA (0.557 mL, 4.00 mmol). The mixture was heated in microwave at 100° C. for 1 h. The resulting mixture was filtered, water (10 mL) and ethyl acetate were added. The layers were separated. The aqueous layer was extracted with ethyl acetate twice. The combined organic layer was dried over MgSO$_4$, filtered, concentrated and purified by silica gel chromatography to get 400 mg of ethyl 3-(1,4-dimethyl-1H-benzo[d][1,2,3]triazol-5-yl)-3-(4-fluoro-3-(hydroxymethyl)phenyl)propanoate (53.9%). LC-MS m/z 372.2 (M+1)$^+$, 0.84 (ret. time).

254

Ethyl 3-(3-(chloromethyl)-4-fluorophenyl)-3-(1,4-dimethyl-1H-benzo[d][1,2,3]triazol-5-yl)propanoate

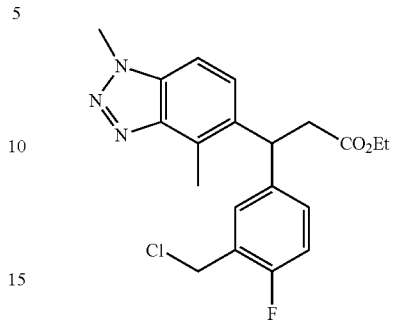

To a solution of ethyl 3-(1,4-dimethyl-1H-benzo[d][1,2,3]triazol-5-yl)-3-(4-fluoro-3-(hydroxymethyl)phenyl)propanoate (100 mg, 0.269 mmol) in dichloromethane (1 mL) was added SOCl$_2$ (0.039 mL, 0.538 mmol). The resulting reaction mixture was stirred at ambient temperature for 1 h. Solvent was evaporated under vacuum to afford product ethyl 3-(3-(chloromethyl)-4-fluorophenyl)-3-(1,4-dimethyl-1H-benzo[d][1,2,3]triazol-5-yl)propanoate (104 mg, 0.267 mmol, 99% yield). LC-MS m/z 390.0 (M+H)$^+$, 1.70 min (ret. time).

3-(1,4-Dimethyl-1H-benzo[d][1,2,3]triazol-5-yl)-3-(4-fluoro-3-(((S)-2-methyl-2,3-dihydrobenzo[f][1,4]oxazepin-4(5H)-yl)methyl)phenyl)propanoic Acid, Formic Acid Salt

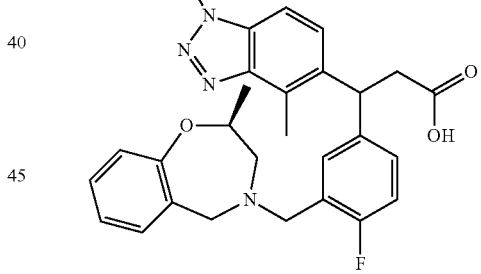

To a solution of ethyl 3-(3-(chloromethyl)-4-fluorophenyl)-3-(1,4-dimethyl-1H-benzo[d][1,2,3]triazol-5-yl)propanoate (52 mg, 0.133 mmol) in acetonitrile (1 mL) were added Et$_3$N (0.037 mL, 0.267 mmol) and (S)-2-methyl-2,3,4,5-tetrahydrobenzo[f][1,4]oxazepine (32.7 mg, 0.200 mmol). The result solution was heated with microwave at 80° C. for 2 h. The solvent was removed and the residue was diluted in methanol (1.5 mL) then was added NaOH (2 N) (26.7 mg, 0.667 mmol). The resulting suspension was heated with microwave at 80° C. for 30 min. The reaction mixture was acidified with AcOH (2 N) to pH~5, evaporated under vacuum, purified by reverse phase HPLC to afford product 3-(1,4-dimethyl-1H-benzo[d][1,2,3]triazol-5-yl)-3-(4-fluoro-3-(((S)-2-methyl-2,3-dihydrobenzo[f][1,4]oxazepin-4(5H)-yl)methyl)phenyl)propanoic acid, formic acid salt (39.2 mg, 0.080 mmol, 60.2% yield). LC-MS m/z 489.3 (M+H)$^+$, 0.74 min (ret. time).

Example 96

3-(1,4-Dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)propanoic Acid

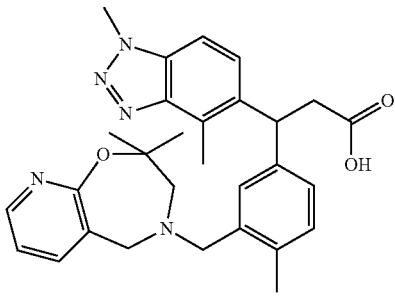 [SMILES: Cc1ccc(C(CC(=O)O)c2ccc3c(nnn3C)c2C)cc1CN1Cc2cccnc2OC(C)(C)C1]

To a solution of ethyl 3-(3-(chloromethyl)-4-methylphenyl)-3-(1,4-dimethyl-1H-benzo[d][1,2,3]triazol-5-yl)propanoate (90 mg, 0.233 mmol) in acetonitrile (1 mL) was added 2,2-dimethyl-2,3,4,5-tetrahydropyrido[3,2-f][1,4]oxazepine (49.9 mg, 0.280 mmol). The resulting solution was heated with microwave at 80° C. for 30 min. The reaction mixture was concentrated. It was diluted with methanol (1.5 mL) then was added NaOH (2 N) (46.6 mg, 1.166 mmol). The resulting solution was heated with microwave at 80° C. for 30 min. The reaction mixture was acidified with AcOH (2 N) to pH~5, evaporated under vacuum, purified by reverse phase HPLC to afford product 3-(1,4-dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)propanoic acid (78.7 mg, 0.158 mmol, 67.5% yield). LC-MS m/z 500.2 (M+H)$^+$, 0.72 min (ret. time).

Example 97

3-(1-Ethyl-4-methyl-1H-benzo[d][1,2,3]triazol-5-yl)-3-(4-methyl-3-(((S)-2-methyl-2,3-dihydrobenzo[f][1,4]oxazepin-4(5H)-yl)methyl)phenyl)propanoic Acid, Formic Acid Salt

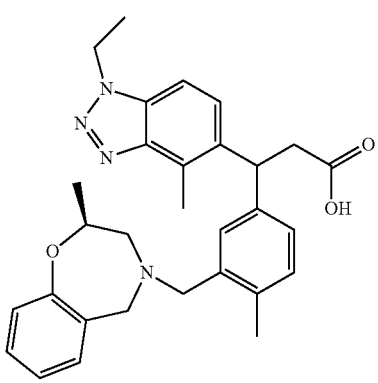 [SMILES: CCn1nnc2c(C)c(C(CC(=O)O)c3ccc(C)c(CN4Cc5ccccc5O[C@@H](C)C4)c3)ccc21]

N-Ethyl-3-methyl-2-nitroaniline

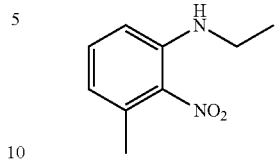

To a solution of 2-fluoro-6-methylaniline (8.5 g, 67.9 mmol) in 1,2-dichloroethane (DCE) (150 mL) at ambient temperature was added m-CPBA (58.6 g, 272 mmol) slowly under nitrogen. The reaction mixture was stirred at 70° C. for 4 h. DCM (500 mL) was added. It was washed with 1N NaOH (200 mL×4). The combined organic layers was dried and concentrated to give the crude product (11.2 g, 72.2 mmol). It was dissolved in ethanol (80 mL), ethanamine (80 mL, 911 mmol) was added slowly under nitrogen at ambient temperature. The reaction mixture was stirred at 60° C. for 16 h. Water (100 mL) was added. It was extracted with ethyl acetate (3×80 mL). The combined organic layers was dried and concentrated. The crude product was purified by silica gel chromatography (hexane:ethyl acetate=100:1) to give 11.9 g (85%) of the title compound. LC-MS m/z 181.2 (M+H)$^+$, 1.81 (ret. time).

4-Bromo-N-ethyl-3-methyl-2-nitroaniline

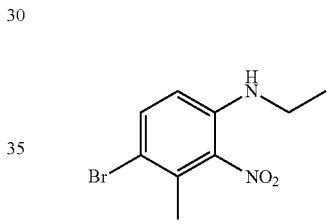

To a solution of N-ethyl-3-methyl-2-nitroaniline (11.9 g, 66.0 mmol) in N,N-dimethylformamide (DMF) (100 mL) was added a solution of NBS (11.75 g, 66.0 mmol) in 100 mL of DMF dropwise. Then the reaction mixture was stirred at ambient temperature for 16 h. Water (800 mL) was added. The solid was filtered and dried to give 16 g (78%) of the title compound. LC-MS m/z 2.02 (M+H)$^+$, 260.9 (ret. time).

4-Bromo-N1-ethyl-3-methylbenzene-1,2-diamine

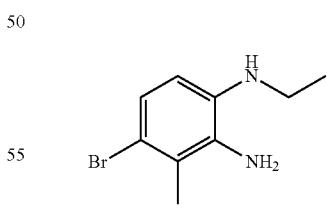

To 4-bromo-N-ethyl-3-methyl-2-nitroaniline (16 g, 61.8 mmol) in acetic acid (100 mL) was added zinc (12.11 g, 185 mmol) in small portions. The reaction mixture was stirred at ambient temperature for 10 h. The reaction mixture was filtered through celite and the solid was washed with EtOAc (3×). The combined organic was concentrated. The crude product was purified by silica gel chromatography (hexane:ethyl acetate=10:1) to give 4.0 g (16.96%) of the title compound. LC-MS m/z 231.0 (M+H)$^+$, 1.51 (ret. time).

5-Bromo-1-ethyl-4-methyl-1H-benzo[d][1,2,3]triazole

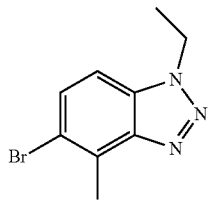

To H$_2$SO$_4$ (1.954 mL, 36.7 mmol) in water (30 mL) was added 4-bromo-N1-ethyl-3-methylbenzene-1,2-diamine (4 g, 10.48 mmol). Then a solution of sodium nitrite (1.445 g, 20.95 mmol) in water (20 mL) was added by dropwise at 0° C. The reaction mixture was stirred at 0° C. for 16 h. Water (200 mL) was added. Solid was filtered. The solid was then dissolved in 500 mL of DCM, washed with aqueous NaCl (2×50 mL). The organic layer was dried with MgSO$_4$, filtered and concentrated to give 2.4 g (76%) of the title compound. LC-MS m/z 242.0 (M+H)$^+$, 1.80 (ret. time).

(E)-Ethyl 3-(1-ethyl-4-methyl-1H-benzo[d][1,2,3]triazol-5-yl)acrylate

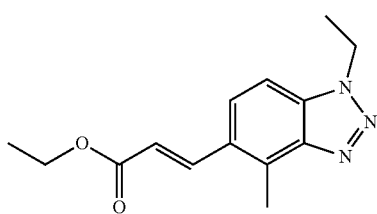 [SMILES: CCOC(=O)/C=C/c1ccc2c(nnn2CC)c1C]

To a solution of 5-bromo-1-ethyl-4-methyl-1H-benzo[d][1,2,3]triazole (2.4 g, 7.00 mmol) in N,N-dimethylformamide (DMF) (100 mL) were added tri-o-tolylphosphine (0.426 g, 1.399 mmol), ethyl acrylate (1.401 g, 13.99 mmol) and DIPEA (3.67 mL, 20.99 mmol). Then Pd(OAc)$_2$ (0.157 g, 0.700 mmol) was added. The reaction mixture was stirred at 100° C. for 12 h. The reaction mixture was poured into water (30 mL) and extracted with ethyl acetate (3×30 mL). The combined organic layers were dried and concentrated. The crude product was purified by silica gel chromatography (hexane:ethyl acetate=4:1) to give 1.75 g (87%) of the title compound. LC-MS m/z 260.1 (M+H)$^+$, 1.75 (ret. time).

Ethyl 3-(1-ethyl-4-methyl-1H-benzo[d][1,2,3]triazol-5-yl)-3-(3-(hydroxymethyl)-4-methylphenyl)propanoate

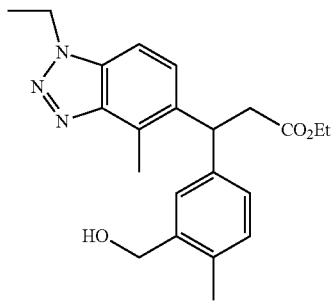 [SMILES: CCOC(=O)CC(c1ccc(C)c(CO)c1)c1ccc2c(nnn2CC)c1C]

To the solution of (E)-ethyl 3-(1-ethyl-4-methyl-1H-benzo[d][1,2,3]triazol-5-yl)acrylate (1 g, 3.86 mmol) in 1,4-dioxane (30 mL) and water (10 ml) were added (3-(hydroxymethyl)-4-methylphenyl)boronic acid (1.280 g, 7.71 mmol), triethylamine (1.613 mL, 11.57 mmol) and then [RhCl(cod)]$_2$ (0.095 g, 0.193 mmol). The resulting reaction mixture was stirred at 90° C. for 2 h. The reaction mixture was extracted with EtOAc (3×30 mL). The combined organic layer was dried over MgSO$_4$, filtered, and concentrated under reduced pressure. It was purified by silica gel chromatography to afford the desired product ethyl 3-(1-ethyl-4-methyl-1H-benzo[d][1,2,3]triazol-5-yl)-3-(3-(hydroxymethyl)-4-methylphenyl)propanoate (1.3764 g, 3.61 mmol, 94% yield). LC-MS m/z 382 (M+H)$^+$, 0.96 (ret. time).

Ethyl 3-(3-(chloromethyl)-4-methylphenyl)-3-(1-ethyl-4-methyl-1H-benzo[d][1,2,3]triazol-5-yl)propanoate

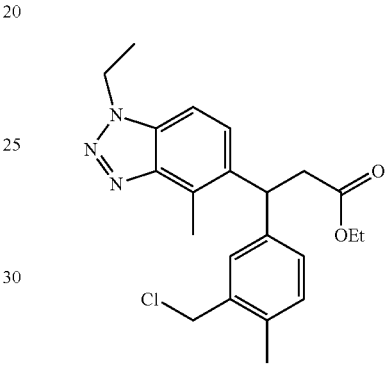

To a solution of ethyl 3-(1-ethyl-4-methyl-1H-benzo[d][1,2,3]triazol-5-yl)-3-(3-(hydroxymethyl)-4-methylphenyl)propanoate (880 mg, 2.307 mmol) in dichloromethane (4 mL) was added SOCl$_2$ (0.337 mL, 4.61 mmol). The resulting reaction mixture was stirred at ambient temperature for 30 min. The reaction was evaporated under vacuum to afford the product ethyl 3-(3-(chloromethyl)-4-methylphenyl)-3-(1-ethyl-4-methyl-1H-benzo[d][1,2,3]triazol-5-yl)propanoate. LC-MS m/z 400.0 (M+H)$^+$, 1.16 min (ret. time).

3-(1-Ethyl-4-methyl-1H-benzo[d][1,2,3]triazol-5-yl)-3-(4-methyl-3-(((S)-2-methyl-2,3-dihydrobenzo[f][1,4]oxazepin-4(5H)-yl)methyl)phenyl)propanoic Acid, Formic Acid Salt

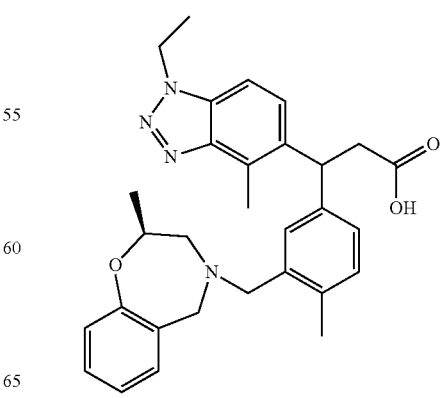

To a solution of (S)-2-methyl-2,3,4,5-tetrahydrobenzo[f][1,4]oxazepine (30.6 mg, 0.188 mmol) in tetrahydrofuran (0.5 mL) and acetonitrile (1 mL) was added DIEA (0.087 mL, 0.500 mmol) and then a solution of ethyl 3-(3-(chloromethyl)-4-methylphenyl)-3-(1-ethyl-4-methyl-1H-benzo[d][1,2,3]triazol-5-yl)propanoate (50 mg, 0.125 mmol) in acetonitrile (1 mL). The resulting reaction mixture was heated with microwave at 100° C. for 1 h. The reaction mixture was concentrated. It was redissolved in methanol (2 mL), NaOH (3.0 N) (0.333 mL, 1.000 mmol) was added. The resulting reaction mixture was heated with microwave at 80° C. for 20 min. It was neutralized with HCl (2 N) to pH~6, evaporated under vacuum, purified by reverse phase HPLC to afford the desired product 3-(1-ethyl-4-methyl-1H-benzo[d][1,2,3]triazol-5-yl)-3-(4-methyl-3-(((S)-2-methyl-2,3-dihydrobenzo[f][1,4]oxazepin-4(5H)-yl)methyl)phenyl) propanoic acid, formic acid salt (51.6 mg, 0.103 mmol, 82% yield).

LC-MS m/z 499.5 (M+H)$^+$, 0.76 min (ret. time).

Example 98

3-(1,4-Dimethyl-1H-benzo[d][1,2,3]triazol-5-yl)-3-(4-methyl-3-(((S)-2-methyl-2,3-dihydrobenzo[f][1,4]oxazepin-4(5H)-yl)methyl)phenyl)propanoic Acid, Formic Acid Salt

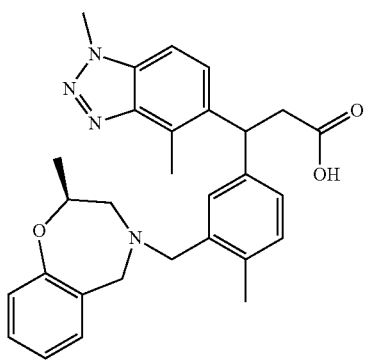 [SMILES: Cc1ccc(C(CC(=O)O)c2ccc3c(nnn3C)c2C)cc1CN1Cc2ccccc2O[C@@H](C)C1]

To a solution of (S)-2-methyl-2,3,4,5-tetrahydrobenzo[f][1,4]oxazepine (31.7 mg, 0.194 mmol) in tetrahydrofuran (0.5 mL) and acetonitrile (1 mL) was added DIEA (0.091 mL, 0.518 mmol) and then a solution of ethyl 3-(3-(chloromethyl)-4-methylphenyl)-3-(1,4-dimethyl-1H-benzo[d][1,2,3]triazol-5-yl)propanoate (50 mg, 0.130 mmol) in acetonitrile (1 mL). The resulting reaction mixture was heated with microwave at 100° C. for 1 h. The reaction mixture was concentrated. It was redissolved in methanol (2 mL), NaOH (3.0 N) (0.346 mL, 1.037 mmol) was added. The resulting reaction mixture was heated with microwave at 80° C. for 20 min then was neutralized with HCl (2 N) to pH~6, evaporated under vacuum, purified by reverse phase HPLC to afford the product 3-(1,4-dimethyl-1H-benzo[d][1,2,3]triazol-5-yl)-3-(4-methyl-3-(((S)-2-methyl-2,3-dihydrobenzo[f][1,4]oxazepin-4(5H)-yl)methyl)phenyl)propanoic acid, formic acid salt (48.2 mg, 0.099 mmol, 76% yield). LC-MS m/z 485.4 (M+H)$^+$, 0.70 min (ret. time).

Example 99

3-(4-Chloro-3-((2,3-dihydrobenzo[f][1,4]oxazepin-4(5H)-yl)methyl)phenyl)-3-(1,4-dimethyl-1H-benzo[d][1,2,3]triazol-5-yl)propanoic Acid, Formic Acid Salt

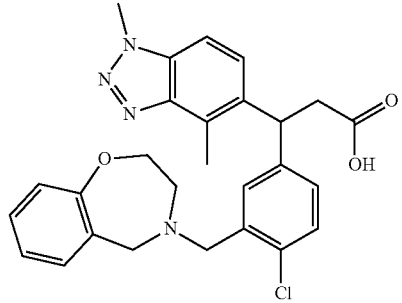 [SMILES: Cc1c(C(CC(=O)O)c2ccc(Cl)c(CN3CCOc4ccccc4C3)c2)ccc2c1nnn2C]

To a solution of ethyl 3-(4-chloro-3-(hydroxymethyl)phenyl)-3-(1,4-dimethyl-1H-benzo[d][1,2,3]triazol-5-yl)propanoate (70 mg, 0.180 mmol) in dichloromethane (0.5 mL) was added SOCl$_2$ (0.026 mL, 0.361 mmol). The resulting reaction mixture was stirred at ambient temperature for 3 h. The reaction mixture was evaporated under vacuum. It was diluted with acetonitrile (1 mL) followed by addition of Et$_3$N (0.050 mL, 0.361 mmol) and 2,3,4,5-tetrahydrobenzo[f][1,4]oxazepine (32.3 mg, 0.217 mmol). The resulting mixture was heated with microwave at 80° C. for 30 min. Solvent was removed and the residue was diluted with methanol (1.5 mL) followed by addition of NaOH (2N) (36.1 mg, 0.902 mmol). The resulting suspension was heated with microwave at 80° C. for 30 min. The reaction mixture was acidified with AcOH (2 N) to pH~5, evaporated under vacuum, purified by reverse phase HPLC to afford the product 3-(4-chloro-3-((2,3-dihydrobenzo[f][1,4]oxazepin-4(5H)-yl)methyl)phenyl)-3-(1,4-dimethyl-1H-benzo[d][1,2,3]triazol-5-yl)propanoic acid, formic acid salt (78.3 mg, 0.159 mmol, 88% yield). LC-MS m/z 500.2 (M+H)$^+$, 0.72 min (ret. time).

Example 100

(3S)-3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoic Acid

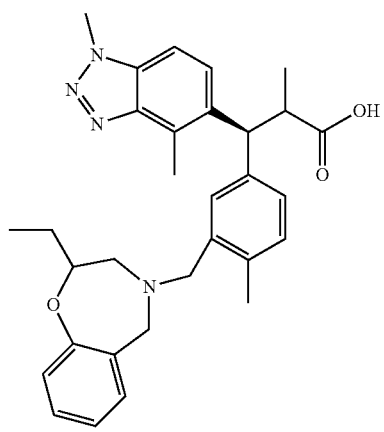 [SMILES: CCC1CN(Cc2cc([C@@H](c3ccc4c(nnn4C)c3C)C(C)C(=O)O)ccc2C)Cc2ccccc2O1]

(S)-Ethyl 3-(3-(chloromethyl)-4-methylphenyl)-3-(1,4-dimethyl-1H-benzo[d][1,2,3]triazol-5-yl)propanoate

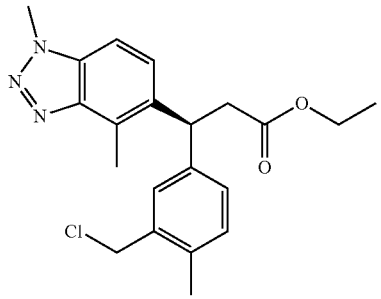 [SMILES: CCOC(=O)C[C@@H](c1ccc(C)c(CCl)c1)c1ccc2c(nnn2C)c1C]

To a solution of (S)-ethyl 3-(1,4-dimethyl-1H-benzo[d][1,2,3]triazol-5-yl)-3-(3-(hydroxymethyl)-4-methylphenyl)propanoate (720 mg, 1.959 mmol) in dichloromethane (DCM) (10 mL) was added thionyl chloride (0.172 mL, 2.351 mmol) and one drop DMF. The reaction mixture was stirred at ambient temperature for 1 h. The solvent was removed under reduced pressure to give the title compound (S)-Ethyl 3-(3-(chloromethyl)-4-methylphenyl)-3-(1,4-dimethyl-1H-benzo[d][1,2,3]triazol-5-yl)propanoate (700 mg, 1.778 mol, 91% yield). LC-MS m/z 386.1 (M+H)$^+$, 2.05 min (ret. time).

(3S)-Ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoate

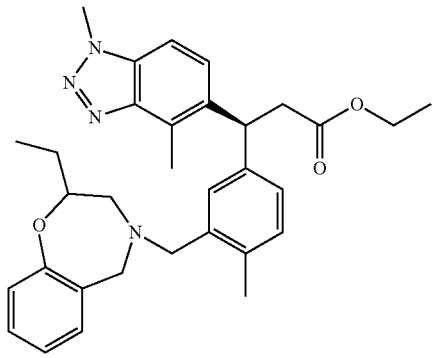 [SMILES: CCOC(=O)C[C@@H](c1ccc(C)c(CN2Cc3ccccc3OC(CC)C2)c1)c1ccc2c(nnn2C)c1C]

To a solution of (S)-ethyl 3-(3-(chloromethyl)-4-methylphenyl)-3-(1,4-dimethyl-1H-benzo[d][1,2,3]triazol-5-yl)propanoate (530 mg, 1.373 mmol) in acetonitrile (20 mL) were added 2-ethyl-2,3,4,5-tetrahydrobenzo[f][1,4]oxazepine (219 mg, 1.236 mmol) and potassium carbonate (380 mg, 2.75 mmol). The reaction mixture was stirred at ambient temperature for 16 h. The reaction mixture was quenched with H$_2$O (15 mL) and extracted with EtOAc (3×50 mL). The organic phase was washed with saturated brine (50 mL), dried over sodium sulfate and concentrated to give the title compound (3S)-ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoate (500 mg, 0.665 mmol, 48.4% yield) as a brown solid. LC-MS m/z 527.3 (M+H)$^+$, 1.44 min (ret. time).

(3S)-ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoate

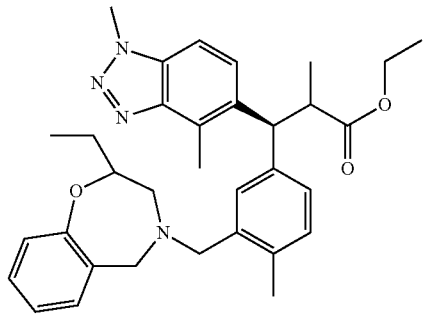 [SMILES: CCOC(=O)C(C)[C@@H](c1ccc(C)c(CN2Cc3ccccc3OC(CC)C2)c1)c1ccc2c(nnn2C)c1C]

To a solution of (3S)-ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoate (200 mg, 0.380 mmol) in tetrahydrofuran (THF) (5 mL) at −78° C., (1.899 mL, 1.899 mmol, 1.0M solution in THF) was added. The wine red solution was stirred at −78° C. (dry-ice acetone) for 45 min and MeI (0.119 mL, 1.899 mmol) was added in one portion. The red wine color was turned to light yellow. The reaction mixture was stirred at −78° C. for a further 45 min. The reaction was diluted with EtOAc (75 mL) and water (25 mL). The aqueous layer was extracted again with EtOAc (25 mL) and the combined organics washed with brine (25 mL), dried over Na$_2$SO$_4$ and concentrated to obtain the title compound (3S)-ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoate (180 mg, 8.58 mmol, 0.280 mmol, 73.6% yield) which was carried to the next step without further purification. LC-MS m/z 541.3 (M+H)$^+$, 1.51 min (ret. time).

(3S)-3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoic Acid

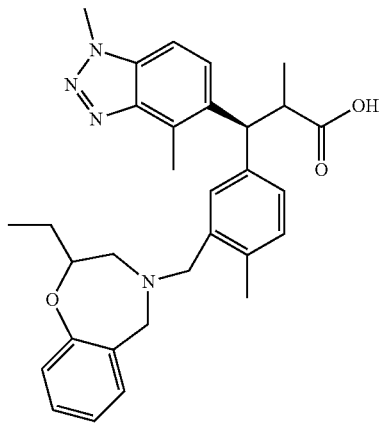 [SMILES: CCC1CN(Cc2cc([C@@H](c3ccc4c(nnn4C)c3C)C(C)C(=O)O)ccc2C)Cc2ccccc2O1]

To a solution of (3S)-ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoate (25 mg, 0.046 mmol) in a mixture of tetrahydrofuran (THF) (5 mL)/methanol (1 mL) was added LiOH (5.54 mg, 0.231 mmol) in water (2.0 mL). The reaction mixture was stirred at 60° C. for 24 h. Then the organic solvent was evaporated and the residue was adjusted to pH 5 with HCl (3M, 1.5 mL). The solid was filtered, washed with H$_2$O (10 mL) and Et$_2$O (10 mL) to give the title compound (3S)-3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoic acid (100 mg, 0.195 mmol, 58.6% yield) as a yellow solid. LC-MS m/z 513.2 (M+H)$^+$, 1.56 min (ret. time).

Example 101

Ammonium (2S,3R)-3-(3-(((R)-2-ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanate

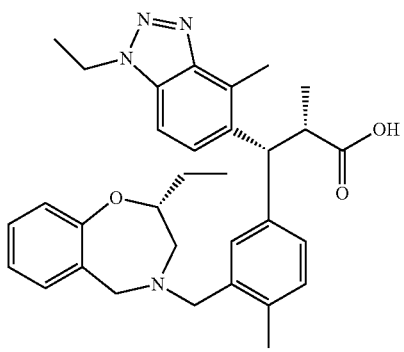 [SMILES: CC[C@@H]1CN(Cc2cc([C@H](c3ccc4c(nnn4CC)c3C)[C@H](C)C(=O)O)ccc2C)Cc2ccccc2O1]

(R)-Ethyl 3-(3-(((tert-butyldimethylsilyl)oxy)methyl)-4-methylphenyl)-3-(1,4-dimethyl-1H-benzo[d][1,2,3]triazol-5-yl)propanoate

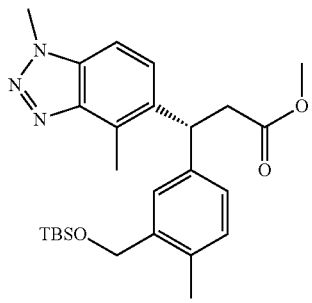 [SMILES: COC(=O)C[C@H](c1ccc(C)c(CO[Si](C)(C)C(C)(C)C)c1)c1ccc2c(nnn2C)c1C]

To a solution of (R)-ethyl 3-(1,4-dimethyl-1H-benzo[d][1,2,3]triazol-5-yl)-3-(3-(hydroxymethyl)-4-methylphenyl)propanoate (800 mg, 2.177 mmol) in dichloromethane (DCM) (15 mL) at 0° C., imidazole (296 mg, 4.35 mmol), DMAP (13.30 mg, 0.109 mmol) and tert-butylchlorodimethylsilane (492 mg, 3.27 mmol) were added. The reaction mixture was stirred at 0° C. to 25° C. for 2 h. The reaction mixture was quenched with water (10 mL), and extracted with DCM (3×20 mL). The combined organic layer was washed with water (2×8 mL) and brine (2×8 mL), dried over Na$_2$SO$_4$ and concentrated. The residue was purified with silica gel chromatography (petroleum ether/ethyl acetate=95:5) to obtain the title compound (R)-ethyl 3-(3-(((tert-butyldimethylsilyl)oxy)methyl)-4-methylphenyl)-3-(1,4-dimethyl-1H-benzo[d][1,2,3]triazol-5-yl)propanoate (1 g, 2.076 mmol, 95% yield) as yellow oil. LC-MS m/z 482.2 (M+H)$^+$, 1.98 (ret. time).

(3R)-Ethyl 3-(3-(((tert-butyldimethylsilyl)oxy)methyl)-4-methylphenyl)-3-(1,4-dimethyl-1H-benzo[d][1,2,3]triazol-5-yl)-2-methylpropanoate and (3R)-ethyl 3-(3-(((tert-butyldimethylsilyl)oxy)methyl)-4-methylphenyl)-3-(1-ethyl-4-methyl-1H-benzo[d][1,2,3]triazol-5-yl)-2-methylpropanoate

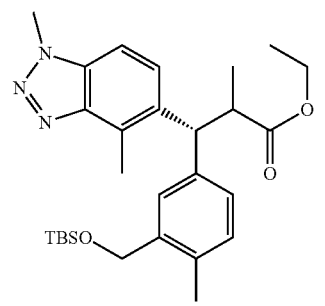

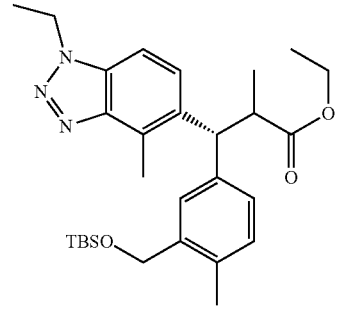

A solution of (R)-ethyl 3-(3-(((tert-butyldimethylsilyl)oxy)methyl)-4-methylphenyl)-3-(1,4-dimethyl-1H-benzo[d][1,2,3]triazol-5-yl)propanoate (1 g, 2.076 mmol) in tetrahydrofuran (THF) (20 mL) was added to a solution of dry-ice acetone bath cooled LDA (4.15 mL, 4.15 mmol, 1.0M solution in THF). The wine red solution was stirred at −78° C. for 45 min and MeI (0.26 mL, 4.15 mmol) was added in one portion and the red wine color was turned to light yellow. The reaction mixture was stirred at −78° C. for an additional 45 min. The residue was diluted with EtOAc (100 mL) and water (25 mL). The aqueous layer was extracted with EtOAc (3×50 mL) and the combined organic layer was washed with brine (25 mL), dried over Na$_2$SO$_4$ and concentrated to give the title compounds—a mixture of (3R)-ethyl 3-(3-(((tert-butyldimethylsilyl)oxy)methyl)-4-methylphenyl)-3-(1,4-dimethyl-1H-benzo[d][1,2,3]triazol-5-yl)-2-methylpropanoate and (3R)-ethyl 3-(3-(((tert-butyldimethylsilyl)oxy)methyl)-4-methylphenyl)-3-(1-ethyl-4-methyl-1H-benzo[d][1,2,3]triazol-5-yl)-2-methylpropanoate (1.0 g, 1.009 mmol, 48.6%) which was carried to the next step without further purification. LC-MS m/z 496.3 (M+H)$^+$, 2.03 (ret. time), 510.2 (M+H)$^+$, 2.06 (ret. time).

265

(3R)-Ethyl 3-(1,4-dimethyl-1H-benzo[d][1,2,3]tri-
azol-5-yl)-3-(3-(hydroxymethyl)-4-methylphenyl)-2-
methylpropanoate

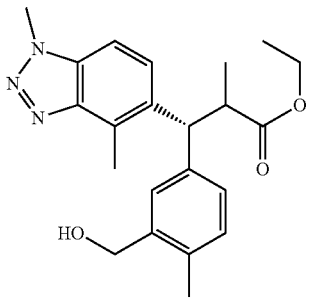

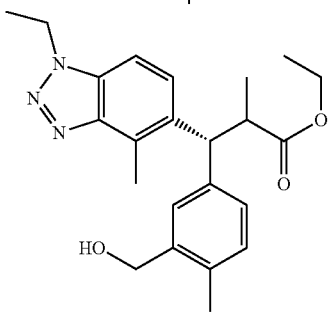

To a solution of a mixture of (3R)-ethyl 3-(3-(((tert-butyldimethylsilyl)oxy)methyl)-4-methylphenyl)-3-(1,4-dimethyl-1H-benzo[d][1,2,3]triazol-5-yl)-2-methylpropanoate and (3R)-ethyl 3-(3-(((tert-butyldimethylsilyl)oxy)methyl)-4-methylphenyl)-3-(1-ethyl-4-methyl-1H-benzo[d][1,2,3]triazol-5-yl)-2-methylpropanoate (980 mg, 1.977 mmol) in tetrahydrofuran (THF) (20 mL) at 0° C., TBAF (569 mg, 2.175 mmol) was added. The reaction mixture was stirred at 0° C. for 1 h. The reaction mixture was quenched with saturated. NH$_4$Cl solution (20 mL), extracted with ethyl acetate (3×50 mL). The organic layer was washed with water (30 mL) and brine (30 mL), dried over Na$_2$SO$_4$ and concentrated to obtain the title compounds—a mixture of (3R)-ethyl 3-(1-ethyl-4-methyl-1H-benzo[d][1,2,3]triazol-5-yl)-3-(3-(hydroxymethyl)-4-methylphenyl)-2-methylpropanoate and (3R)-ethyl 3-(1,4-dimethyl-1H-benzo[d][1,2,3]triazol-5-yl)-3-(3-(hydroxymethyl)-4-methylphenyl)-2-methylpropanoate (800 mg, 0.965 mmol, 48.8%) which was carried to the next step without further purification. LC-MS m/z 382.1 (M+H)$^+$, 1.56 (ret. time), 396.2 (M+H)$^+$, 1.60 (ret. time).

(3R)-Ethyl 3-(3-(chloromethyl)-4-methylphenyl)-3-
(1,4-dimethyl-1H-benzo[d][1,2,3]triazol-5-yl)-2-
methylpropanoate

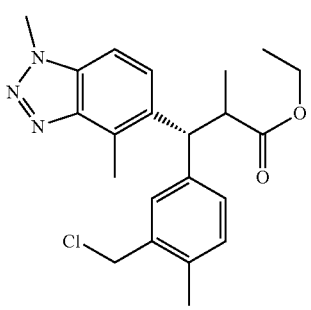

266

-continued

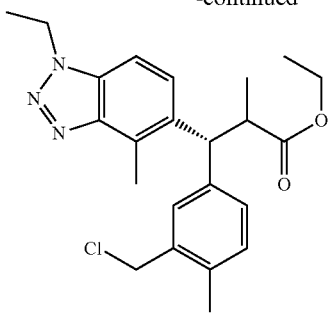

To a solution of a mixture of (3R)-ethyl 3-(1,4-dimethyl-1H-benzo[d][1,2,3]triazol-5-yl)-3-(3-(hydroxymethyl)-4-methylphenyl)-2-methylpropanoate and (3R)-ethyl 3-(1,4-dimethyl-1H-benzo[d][1,2,3]triazol-5-yl)-3-(3-(hydroxymethyl)-4-methylphenyl)-2-methylpropanoate (800 mg, 2.097 mmol) in dichloromethane (DCM) (10 mL) was added thionyl chloride (0.184 mL, 2.52 mmol) and one drop DMF. The reaction mixture was stirred at ambient temperature for 1 h. The solvent was removed under reduced pressure to obtain the title compounds—a mixture of (3R)-ethyl 3-(3-(chloromethyl)-4-methylphenyl)-3-(1,4-dimethyl-1H-benzo[d][1,2,3]triazol-5-yl)-2-methylpropanoate and (3R)-ethyl 3-(3-(chloromethyl)-4-methylphenyl)-3-(1,4-dimethyl-1H-benzo[d][1,2,3]triazol-5-yl)-2-methylpropanoate (780 mg, 0.936 mmol, 44.6%) which was carried to the next step without further purification. LC-MS m/z 400.1 (M+H)$^+$, 2.03 (ret. time), 414.2 (M+H)$^+$, 2.07 (ret. time).

(3R)-Ethyl 3-(3-(((R)-2-ethyl-2,3-dihydrobenzo[f][1,
4]oxazepin-4(5H)-yl)methyl)-4-methylphenyl)-3-(1-
ethyl-4-methyl-1H-benzo[d][1,2,3]triazol-5-yl)-2-
methylpropanoate

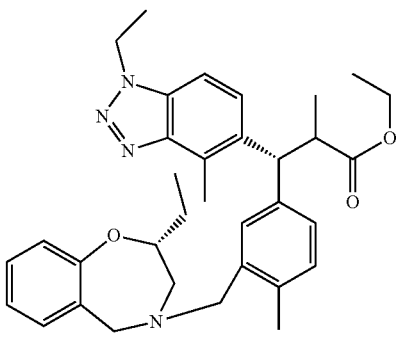 [SMILES: CCOC(=O)C(C)[C@H](c1ccc(C)c(CN2Cc3ccccc3O[C@H](CC)C2)c1)c1ccc2c(nnn2CC)c1C]

To a solution of a mixture of (3R)-ethyl 3-(3-(chloromethyl)-4-methylphenyl)-3-(1,4-dimethyl-1H-benzo[d][1,2,3]triazol-5-yl)-2-methylpropanoate and (3R)-ethyl 3-(3-(chloromethyl)-4-methylphenyl)-3-(1,4-dimethyl-1H-benzo[d][1,2,3]triazol-5-yl)-2-methylpropanoate (780 mg, 1.950 mmol) in acetonitrile (20 mL) was added (R)-2-ethyl-2,3,4,5-tetrahydrobenzo[f][1,4]oxazepine (346 mg, 1.950 mmol) and K$_2$CO$_3$ (539 mg, 3.90 mmol). The reaction mixture was stirred at 25° C. for 24 h. The solvent was removed under reduced pressure. The residue was purified by reverse-phase HPLC (0.05% TFA/H$_2$O:CH$_3$CN=5%-95%) to obtain the title compound (3R)-ethyl 3-(3-(((R)-2-ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2- methylpropanoate (300 mg, 0.514 mmol, 26.3% yield). LC-MS m/z 555.3 (M+H)+, 1.51 (ret. time).

Ammonium (2S,3R)-3-(3-(((R)-2-ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanate

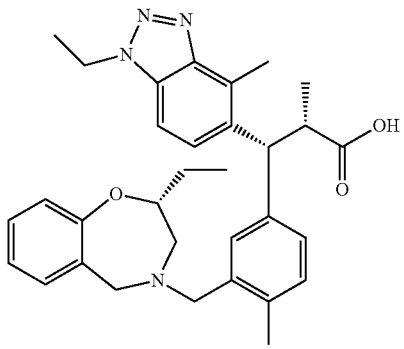 [SMILES: CC[C@@H]1CN(Cc2cc([C@H](c3ccc4c(nnn4CC)c3C)[C@H](C)C(=O)O)ccc2C)Cc2ccccc2O1]

To a solution of (3R)-ethyl 3-(3-(((R)-2-ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoate (300 mg, 0.541 mmol) in methanol (12 mL) was added LiOH (25.9 mg, 1.082 mmol). The reaction was heated via microwave reactor for 2 h at 125° C. at high absorption. Then the organic solvent was removed. The residue was adjusted to pH 6 with 2M HCl (3 mL). After solid was filtered, it was purified by reverse-phase HPLC (0.05% NH4HCO3/H2O:CH3CN=5%-95%) to obtain the title compound ammonium (2R,3R)-3-(3-(((R)-2-ethyl-2,3-dihydrobenzo[f][1,4]oxazepin-4(5H)-yl)methyl)-4-methylphenyl)-3-(1-ethyl-4-methyl-1Hbenzo[d][1,2,3]triazol-5-yl)-2-methylpropanoic acid (39 mg, 0.074 mmol, 13.69% yield) (LC-MS m/z 527.3 (M+H)+, 1.67 (ret. time)) and title compound ammonium (2S,3R)-3-(3-(((R)-2-ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid (40 mg, 0.076 mmol, 14.04% yield). LC-MS m/z 527.3 (M+H)+, 1.74 (ret. time).

Example 102

(3R)-3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)-2-methylpropanoic Acid

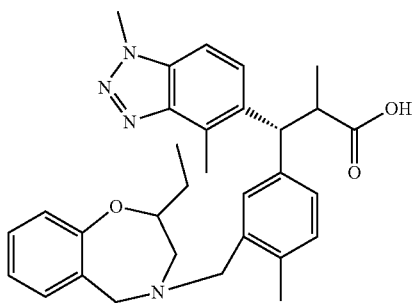 [SMILES: CCC1CN(Cc2cc([C@H](c3ccc4c(nnn4C)c3C)C(C)C(=O)O)ccc2C)Cc2ccccc2O1]

(R)-Ethyl 3-(3-(chloromethyl)-4-methylphenyl)-3-(1,4-dimethyl-1H-benzo[d][1,2,3]triazol-5-yl)propanoate

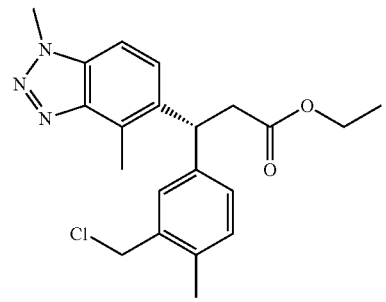 [SMILES: CCOC(=O)C[C@H](c1ccc(C)c(CCl)c1)c1ccc2c(nnn2C)c1C]

To a solution of (R)-ethyl 3-(1,4-dimethyl-1H-benzo[d][1,2,3]triazol-5-yl)-3-(3-(hydroxymethyl)-4-methylphenyl)propanoate (600 mg, 1.633 mmol) in dichloromethane (DCM) (10 mL) was added thionyl chloride (0.143 mL, 1.959 mmol) and one drop DMF. The reaction mixture was stirred at ambient temperature for 1 h. The solvent was removed under reduced pressure to obtain the title compound (R)-ethyl 3-(3-(chloromethyl)-4-methylphenyl)-3-(1,4-dimethyl-1H-benzo[d][1,2,3]triazol-5-yl)propanoate (560 mg, 1.451 mmol, 89%) which was carried over to next step without further purification. LC-MS m/z 384.7 (M−H)+, 2.03 (ret. time).

(3R)-Ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoate

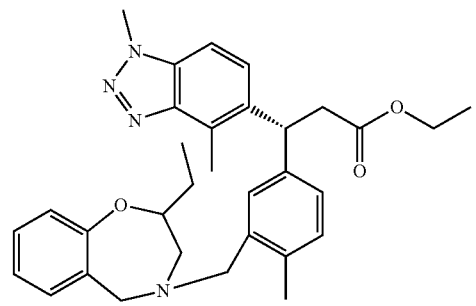 [SMILES: CCOC(=O)C[C@H](c1ccc(C)c(CN2Cc3ccccc3OC(CC)C2)c1)c1ccc2c(nnn2C)c1C]

To a solution of (R)-ethyl 3-(3-(chloromethyl)-4-methylphenyl)-3-(1,4-dimethyl-1H-benzo[d][1,2,3]triazol-5-yl)propanoate (530 mg, 1.373 mmol) in acetonitrile (20 mL) was added 2-ethyl-2,3,4,5-tetrahydrobenzo[f][1,4]oxazepine (219 mg, 1.236 mmol), potassium carbonate (380 mg, 2.75 mmol). The reaction mixture was stirred at ambient temperature for 16 h. The reaction mixture was quenched with H2O (15 mL), extracted with EtOAc (3×50 mL). The organic phase was washed with saturated brine (50 mL), dried over sodium sulfate and concentrated to obtain the title compound (3R)-ethyl 3-(1,4-dimethyl-1H-benzo[d][1,2,3]triazol-5-yl)-3-(3-((2-ethyl-2,3-dihydrobenzo[f][1,4]oxazepin-4(5H)-yl)methyl)-4-methylphenyl)propanoate (480 mg, 0.838 mmol, 61.0% yield) as a brown solid. LCMS m/z 527.3 (M+H)+, 1.70 (ret. time).

(3R)-ethyl 3-(1,4-dimethyl-1H-benzo[d][1,2,3]tri-
azol-5-yl)-3-(3-((2-ethyl-2,3-dihydrobenzo[f][1,4]
oxazepin-4(5H)-yl)methyl)-4-methylphenyl)-2-
methylpropanoate

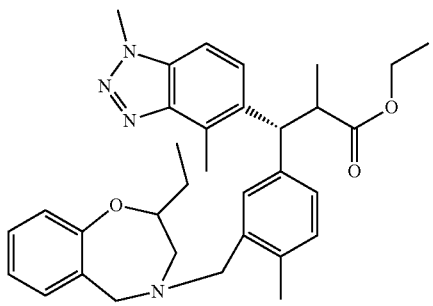 [SMILES: CCOC(=O)C(C)[C@H](c1ccc(C)c(CN2Cc3ccccc3OC(CC)C2)c1)c1ccc2c(nnn2C)c1C]

To a solution of (3R)-ethyl 3-(1,4-dimethyl-1H-benzo[d]
[1,2,3]triazol-5-yl)-3-(3-((2-ethyl-2,3-dihydrobenzo[f][1,4]
oxazepin-4(5H)-yl)methyl)-4-methylphenyl)propanoate
(200 mg, 0.380 mmol) in tetrahydrofuran (THF) (5 mL) at
−78° C. was added lithium diisopropylamide (1.899 mL,
1.899 mmol, 1.0M solution in THF) The wine red solution
was stirred at −78° C. for 45 min and iodomethane (270 mg,
1.899 mmol) was added in one portion and the red wine
color turned to light yellow. The reaction mixture was stirred
for an additional 45 min at −78° C. The residue was diluted
with EtOAc (75 mL) and water (25 mL). The aqueous layer
was extracted with EtOAc (25 mL) and the combined
EtOAc layer was washed with saturated NaCl (25 mL), dried
over $Na_2SO_4$ and concentrated. The residue was purified by
reverse-phase HPLC (0.05% TFA/$H_2O$:$CH_3CN$=5%~95%)
to obtain the title compound (3R)-ethyl 3-(1,4-dimethyl-1H-
benzo[d][1,2,3]triazol-5-yl)-3-(3-((2-ethyl-2,3-dihyd-
robenzo[f][1,4]oxazepin-4(5H)-yl)methyl)-4-methylphe-
nyl)-2-methylpropanoate (150 mg, 0.250 mmol, 65.7%
yield) as yellow oil. LC-MS m/z 541.3 (M+H)$^+$, 1.47 (ret.
time).

(3R)-3-(1,4-dimethyl-1H-benzo[d][1,2,3]triazol-5-
yl)-3-(3-((2-ethyl-2,3-dihydrobenzo[f][1,4]oxazepin-
4(5H)-yl)methyl)-4-methylphenyl)-2-methylpro-
panoic Acid

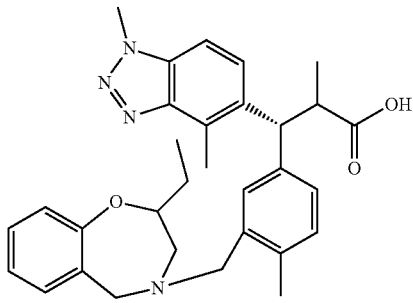 [SMILES: CCC1CN(Cc2cc([C@H](c3ccc4c(nnn4C)c3C)C(C)C(=O)O)ccc2C)Cc2ccccc2O1]

To a solution of (3R)-ethyl 3-(1,4-dimethyl-1H-benzo[d]
[1,2,3]triazol-5-yl)-3-(3-((2-ethyl-2,3-dihydrobenzo[f][1,4]
oxazepin-4(5H)-yl)methyl)-4-methylphenyl)-2-methylpro-
panoate (150 mg, 0.277 mmol) in tetrahydrofuran (THF) (5
mL)/methanol (1 mL) was added LiOH (33.2 mg, 1.387 mmol) in water (2.0 mL). The reaction mixture was stirred
at 60° C. for 24 h. Then the organic solvent was removed.
The residue was adjusted to pH 5 with HCl (3M, 1.0 mL).
Water (10 mL) was added and the reaction mixture was
extracted with EtOAc (3×10 m). The organic phase was
washed with saturated brine (10 mL), dried over sodium
sulfate and concentrated to obtain the title compound (3R)-
3-(1,4-dimethyl-1H-benzo[d][1,2,3]triazol-5-yl)-3-(3-((2-
ethyl-2,3-dihydrobenzo[f][1,4]oxazepin-4(5H)-yl)methyl)-
4-methylphenyl)-2-methylpropanoic acid (70 mg, 0.131
mmol, 47.3% yield) as a white solid. LC-MS m/z 513.2
(M+H)$^+$, 1.57 min (ret. time).

Example 103

Ammonium 3-(3-(((R)-2-Ethyl-2,3-dihydrobenzo[f]
[1,4]oxazepin-4(5H)-yl)methyl)-4-methylphenyl)-2,
2-dimethyl-3-(1-methyl-1H-benzo[d][1,2,3]triazol-5-
yl)propanoate

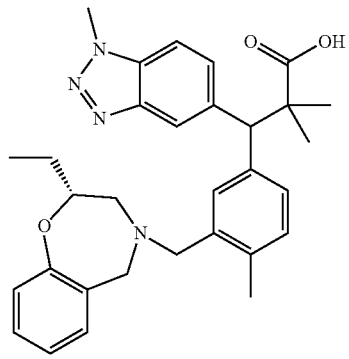 [SMILES: CC[C@@H]1CN(Cc2cc(C(c3ccc4c(c3)nnn4C)C(C)(C)C(=O)O)ccc2C)Cc2ccccc2O1]

4-Bromo-2-(((4-methoxybenzyl)oxy)methyl)-1-
methylbenzene

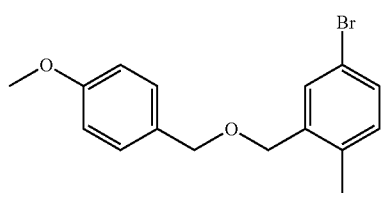 [SMILES: COc1ccc(COCc2cc(Br)ccc2C)cc1]

To a solution of (5-bromo-2-methylphenyl)methanol (20
g, 99 mmol) in N,N-dimethylformamide (DMF) (120 mL) at
0° C. under nitrogen, sodium hydride (4.77 g, 119 mmol)
was added in two portions. The reaction mixture was stirred
at 0° C. for 20 min. Then 1-(chloromethyl)-4-methoxyben-
zene (17.14 g, 109 mmol) was added and the reaction
mixture was stirred at 0° C. to 25° C. for 1 h. The reaction
mixture was quenched with water (200 mL) and extracted
with ethyl acetate (3×200 mL). The organic layer was
washed with water (2×200 mL) and brine (2×200 mL), dried
over $Na_2SO_4$ and concentrated. The residue was purified by
silica gel chromatography (petroleum ether/ethyl acetate=4:
1) to give the title compound 4-bromo-2-(((4-methoxyben-
zyl)oxy)methyl)-1-methylbenzene (25 g, 70.0 mmol, 70.4%
yield) as yellow oil. LC/MS m/z 321.7 (M+H)$^+$, 1.90 min
(ret. time).

(3-(((4-Methoxybenzyl)oxy)methyl)-4-methylphenyl)(1-methyl-1H-benzo[d][1,2,3]triazol-5-yl)methanol

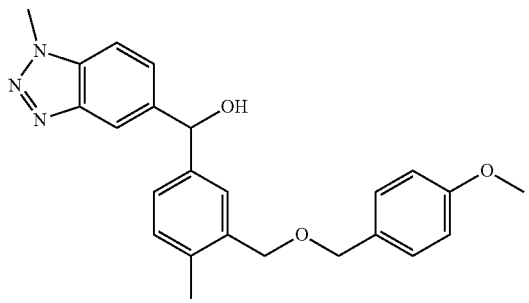 [SMILES: COc1ccc(COCc2cc(C(O)c3ccc4c(c3)nnn4C)ccc2C)cc1]

To a solution of 4-bromo-2-(((4-methoxybenzyl)oxy)methyl)-1-methylbenzene (642 mg, 1.998 mmol) (322 mg, 1.998 mmol) in tetrahydrofuran (THF) (50 mL) was added butyllithium (0.879 mL, 2.198 mmol) at −78° C. The reaction mixture was stirred at −78° C. for 1.5 h under $N_2$. Then 1-methyl-1H-benzo[d][1,2,3]triazole-5-carbaldehyde in THF (10 mL) was slowly added at −78° C. The reaction mixture was stirred at −78° C. for 2 h. Then the reaction mixture was quenched with $NH_4Gl$ saturated aqueous solution (10 mL) and was extracted with ethyl acetate (3×40 mL), the combined organic layer was washed with brine (2×10 mL) and dried over anhydrous $Na_2SO_4$. After filtration and concentration, the crude product was purified by silica gel chromatography (petroleum ether/ethyl acetate=75%) to obtain the title compound (3-(((4-methoxybenzyl)oxy)methyl)-4-methylphenyl)(1-methyl-1H-benzo[d][1,2,3]triazol-5-yl)methanol (285 mg, 0.678 mmol, 33.9% yield) as colorless oil. LCMS m/z 404.2 (M+H)$^+$, 1.87 min (ret. time).

Methyl 3-(3-(((4-methoxybenzyl)oxy)methyl)-4-methylphenyl)-2,2-dimethyl-3-(1-methyl-1H-benzo[d][1,2,3]triazol-5-yl)propanoate

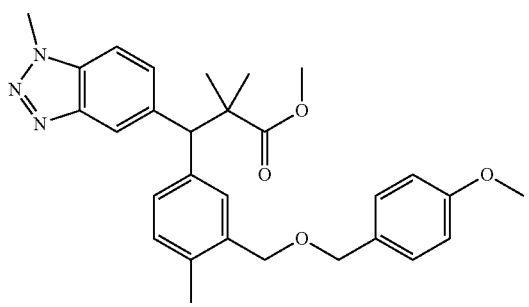 [SMILES: COC(=O)C(C)(C)C(c1ccc(C)c(COCc2ccc(OC)cc2)c1)c1ccc2c(c1)nnn2C]

To a solution of (3-(((4-methoxybenzyl)oxy)methyl)-4-methylphenyl)(1-methyl-1H-benzo[d][1,2,3]triazol-5-yl)methanol (285 mg, 0.706 mmol) in dry acetonitrile (10 mL) was slowly added DBU (2.129 μL, 0.014 mmol) and 2,2,2-trichloroacetonitrile (122 mg, 0.848 mmol) under $N_2$ protection. The reaction mixture was stirred at ambient temperature for 30 min. Then ((1-methoxy-2-methylprop-1-en-1-yl)oxy)trimethylsilane (308 mg, 1.766 mmol) was added followed by 1,1,1-trifluoro-N-((trifluoromethyl)sulfonyl)methanesulfonamide (9.93 mg, 0.035 mmol) under $N_2$ protection. The reaction mixture was stirred at ambient temperature for 2 h. Water (20 mL) was added to quench the reaction. The mixture was extracted with ethyl acetate (3×10 mL) and the organic layer was washed with brine, filtered and concentrated to obtain the title compound methyl 3-(3-(((4-methoxybenzyl)oxy)methyl)-4-methylphenyl)-2,2-dimethyl-3-(1-methyl-1H-benzo[d][1,2,3]triazol-5-yl)propanoate (285 mg, 0.678 mmol, 33.9%) which was carried to the next step without further purification. LC-MS m/z 487.9 (M+H)$^+$, 1.83 (ret. time).

Methyl 3-(3-(hydroxymethyl)-4-methylphenyl)-2,2-dimethyl-3-(1-methyl-1H-benzo[d][1,2,3]triazol-5-yl)propanoate

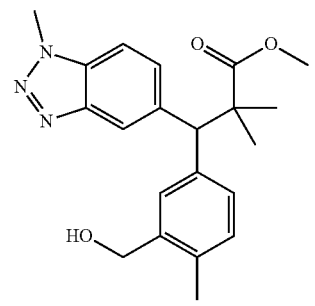 [SMILES: COC(=O)C(C)(C)C(c1ccc(C)c(CO)c1)c1ccc2c(c1)nnn2C]

To a solution of methyl 3-(3-(((4-methoxybenzyl)oxy)methyl)-4-methylphenyl)-2,2-dimethyl-3-(1-methyl-1H-benzo[d][1,2,3]triazol-5-yl)propanoate (320 mg, 0.656 mmol) in dichloromethane (DCM) (19 mL) and water (1 mL) was added DDQ (149 mg, 0.656 mmol) at 0° C. The reaction mixture was stirred at 0° C. for 30 min, then was stirred for an additional 2 h at ambient temperature. The reaction mixture was quenched with water (10 mL), extracted with ethyl acetate (3×30 mL) and the combined organic layer was washed with saturated $NaHCO_3$ (2×10 mL), and brine (2×10 mL), dried over anhydrous $Na_2SO_4$, filtered and concentrated. The crude product was purified by silica gel chromatography (petroleum ether: ethyl acetate=75%) to obtain the title compound methyl 3-(3-(hydroxymethyl)-4-methylphenyl)-2,2-dimethyl-3-(1-methyl-1H-benzo[d][1,2,3]triazol-5-yl)propanoate (110 mg, 0.296 mmol, 45.2% yield) as colorless oil. LCMS m/z 367.9 (M+H)$^+$, 1.54 min (ret. time).

Methyl 3-(3-(chloromethyl)-4-methylphenyl)-2,2-dimethyl-3-(1-methyl-1H-benzo[d][1,2,3]triazol-5-yl)propanoate

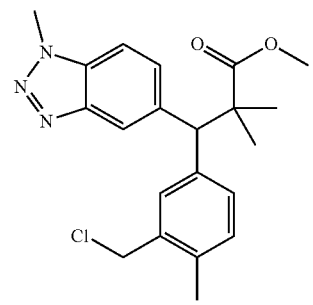 [SMILES: COC(=O)C(C)(C)C(c1ccc(C)c(CCl)c1)c1ccc2c(c1)nnn2C]

To a solution of methyl 3-(3-(hydroxymethyl)-4-methylphenyl)-2,2-dimethyl-3-(1-methyl-1H-benzo[d][1,2,3]triazol-5-yl)propanoate (110 mg, 0.299 mmol) in dichloromethane (DCM) (10.0 mL), SOCl₂ (0.026 mL, 0.359 mmol) was added at 00° C. Then the reaction mixture was stirred for 2 h at 00° C. The reaction mixture was concentrated to obtain the title compound methyl 3-(3-(chloromethyl)-4-methylphenyl)-2,2-dimethyl-3-(1-methyl-1H-benzo[d][1,2,3]triazol-5-yl)propanoate (110 mg, 0.279 mmol, 93% yield) as colorless oil. LCMS m/z 385.8 (M+H)⁺, 1.75 min (ret. time).

Methyl 3-(3-(((R)-2-ethyl-2,3-dihydrobenzo[f][1,4]oxazepin-4(5H)-yl)methyl)-4-methylphenyl)-2,2-dimethyl-3-(1-methyl-1H-benzo[d][1,2,3]triazol-5-yl)propanoate

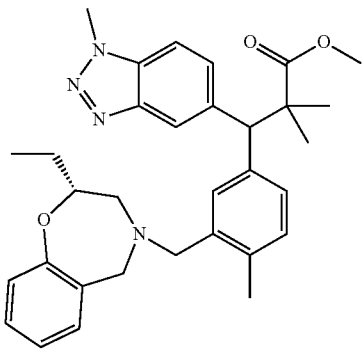 [SMILES: CC[C@@H]1CN(Cc2cc(C(c3ccc4c(c3)nnn4C)C(C)(C)C(=O)OC)ccc2C)Cc2ccccc2O1]

To a solution of (R)-2-ethyl-2,3,4,5-tetrahydrobenzo[f][1,4]oxazepine (50.5 mg, 0.285 mmol) in N,N-dimethylformamide (DMF) (15 mL) at 0° C. under N₂, NaH (12.54 mg, 0.314 mmol) was carefully added. The reaction mixture was stirred at 0° C. for 0.5 h. Then a solution of methyl 3-(3-(chloromethyl)-4-methylphenyl)-2,2-dimethyl-3-(1-methyl-1H-benzo[d][1,2,3]triazol-5-yl)propanoate (110 mg, 0.285 mmol) in N,N-dimethylformamide (DMF) (15 mL) was added and the reaction mixture was stirred at 0° C. to 25° C. for 16 h. The reaction mixture was quenched with saturated NH₄Cl solution (10 mL) and extracted with EtOAc (3×30 mL). The combined organic layer was washed with water (2×8 mL) and brine (2×8 mL), dried over Na₂SO₄ and concentrated. The residue was purified by silica gel chromatography (PE:EA=50%) to obtain the title compound methyl 3-(3-(((R)-2-ethyl-2,3-dihydrobenzo[f][1,4]oxazepin-4(5H)-yl)methyl)-4-methylphenyl)-2,2-dimethyl-3-(1-methyl-1H-benzo[d][1,2,3]triazol-5-yl)propanoate (50 mg, 0.093 mmol, 32.6% yield) as colorless oil. LC/MS m/z 526.8 (M+H)⁺, 1.41 min (ret. time).

Ammonium 3-(3-(((R)-2-ethyl-2,3-dihydrobenzo[f][1,4]oxazepin-4(5H)-yl)methyl)-4-methylphenyl)-2,2-dimethyl-3-(1-methyl-1H-benzo[d][1,2,3]triazol-5-yl)propanoate

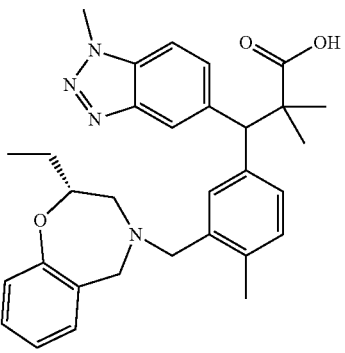 [SMILES: CC[C@@H]1CN(Cc2cc(C(c3ccc4c(c3)nnn4C)C(C)(C)C(=O)O)ccc2C)Cc2ccccc2O1]

To a solution of methyl 3-(3-(((R)-2-ethyl-2,3-dihydrobenzo[f][1,4]oxazepin-4(5H)-yl)methyl)-4-methylphenyl)-2,2-dimethyl-3-(1-methyl-1H-benzo[d][1,2,3]triazol-5-yl)propanoate (50 mg, 0.095 mmol) in tetrahydrofuran (THF) (2.0 mL), ethylene glycol (3.0 mL) and water (1.0 mL) was added lithium hydroxide (6.82 mg, 0.285 mmol). The reaction mixture was heated in a microwave at 125° C. for 3 h. The solvent was removed under vacuum and the residue was dissolved into water (2 mL) and acidified to pH 5 by 1 N HCl with ice bath cooling, then it was purified by reverse-phase HPLC (CH₃CN/0.05% NH₃H₂O/H₂O=55%) to obtain the title compound ammonium 3-(3-(((R)-2-ethyl-2,3-dihydrobenzo[f][1,4]oxazepin-4(5H)-yl)methyl)-4-methylphenyl)-2,2-dimethyl-3-(1-methyl-1H-benzo[d][1,2,3]triazol-5-yl)propanoic acid (15 mg, 0.029 mmol, 30.5% yield) as white solid. LC/MS m/z 513.2 (M+H)⁺, 1.32 min (ret. time).

Example 104

3-(3-((4,5-Dihydro-1H-benzo[c]azepin-2(3H)-yl)methyl)-4-methylphenyl)-3-(1,4-dimethyl-1H-benzo[d][1,2,3]triazol-5-yl)-2,2-dimethylpropanoic acid

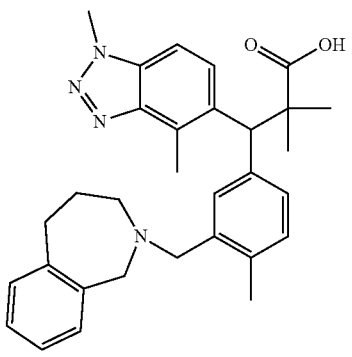 [SMILES: Cc1ccc(C(c2ccc3c(nnn3C)c2C)C(C)(C)C(=O)O)cc1CN1CCCc2ccccc2C1]

To a solution of methyl 3-(1,4-dimethyl-1H-benzo[d][1,2,3]triazol-5-yl)-3-(3-(hydroxymethyl)-4-methylphenyl)-2,2-dimethylpropanoate (70 mg, 0.184 mmol) in dichloromethane (DCM) (2 mL) was added thionyl chloride (0.027 mL, 0.367 mmol). The mixture was stirred at ambient temperature for 40 min. The reaction mixture was concentrated and was redissolved in acetonitrile (2 mL), 2,3,4,5-tetrahydro-1H-benzo[c]azepine (36.7 mg, 0.249 mmol) and DIEA (0.095 mL, 0.543 mmol) were added. The resulting reaction mixture was heated in a Biotage microwave at high absorption for 1 h at 120° C. The reaction mixture was concentrated and the residue redissolved in MeOH (2 mL). 2 M LiOH (0.551 mL, 1.101 mmol) was added and the reaction mixture was heated in a Biotage microwave at high absorption for 3 h at 120° C. It was acidified with 6N HCl and 0.5 mL DMSO was added. It was concentrated and purified with preparative HPLC to give the title compound (53.1 mg, 0.107 mmol, 58.3% yield) as solid. LC-MS m/z 497.6 (M+H)$^+$, 0.79 min (ret. time).

Example 105

Ammonium 3-(1,4-dimethyl-1H-benzo[d][1,2,3]triazol-5-yl)-3-(3-((4,4-dimethyl-4,5-dihydro-1H-benzo[c]azepin-2(3H)-yl)methyl)-4-methylphenyl)propanoate

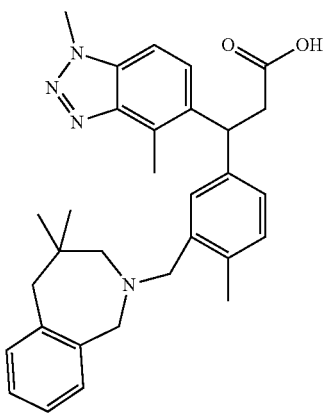 [SMILES: Cc1ccc(C(CC(=O)O)c2ccc3c(nnn3C)c2C)cc1CN1Cc2ccccc2CC(C)(C)C1]

Ethyl 3-(2-cyanophenyl)-2,2-dimethylpropanoate

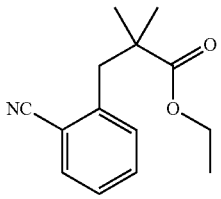 [SMILES: CCOC(=O)C(C)(C)Cc1ccccc1C#N]

To a solution of ethyl isobutyrate (1.185 g, 10.20 mmol) in tetrahydrofuran (THF) (20 mL) at −78° C. was added LDA (7.65 mL, 15.30 mmol). It was stirred for 45 min after which a solution of 2-(bromomethyl)benzonitrile (2 g, 10.20 mmol) in tetrahydrofuran (THF) (10 mL) was added slowly and stirred for 1 h at −78° C. It was warmed to ambient temperature for 3 h. The reaction mixture was quenched with saturated NH$_4$Cl solution and extracted with DCM (2×30 mL). The combined organic layer was washed with brine solution (50 mL). The organic layer was dried over anhydrous Na$_2$SO$_4$, filtered and concentrated. The crude residue was purified by silica gel chromatography to give the title compound (1.6 g, 6.92 mmol, 67.8% yield). LC-MS m/z 232.23 (M+H)$^+$, 3.72 min (ret. time).

3-(2-(Aminomethyl)phenyl)-2,2-dimethylpropan-1-ol

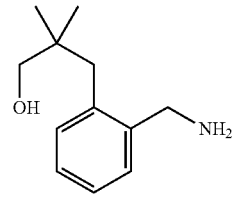

To a solution of ethyl 3-(2-cyanophenyl)-2,2-dimethylpropanoate (1.6 g, 6.92 mmol) in tetrahydrofuran (THF) (20 mL) at −78° C. LAH (20.75 mL, 20.75 mmol) was added. It was stirred for 30 min at −78° C. and then allowed to warm to 25° C. for 1 h. The reaction mixture was quenched with saturated Na$_2$SO$_4$ solution, the solid was filtered and washed with ethyl acetate (40 mL). The organic layer was separated from the filtrate and the aqueous layer was extracted with ethyl acetate (2×30 mL). The combined organic layer washed with brine solution (30 mL), dried over anhydrous Na$_2$SO$_4$, filtered and concentrated. The crude residue was purified by silica gel chromatography to give the title compound (900 mg, 4.48 mmol, 64.7% yield). LC-MS m/z 194.00 (M+H)$^+$, 2.19 min (ret. time).

tert-Butyl 2-(3-hydroxy-2,2-dimethylpropyl)benzylcarbamate

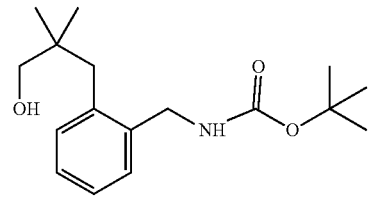 [SMILES: CC(C)(CO)Cc1ccccc1CNC(=O)OC(C)(C)C]

To a solution of 3-(2-(aminomethyl)phenyl)-2,2-dimethylpropan-1-ol (500 mg, 2.59 mmol) in dichloromethane (DCM) (10 mL) was added Boc$_2$O (0.601 mL, 2.59 mmol) and the reaction stirred for 16 h at ambient temperature. The reaction mixture was diluted with water and extracted with DCM (3×20 mL). The combined organic layer dried over anhydrous Na$_2$SO$_4$, filtered and concentrated. The crude residue was purified by silica gel chromatography to give the title compound (400 mg, 1.362 mmol, 52.6% yield). LC-MS m/z 294.23 (M+H)$^+$, 2.29 min (ret. time).

3-(2-(((tert-Butoxycarbonyl)amino)methyl)phenyl)-2,2-dimethylpropyl methanesulfonate

To a solution of tert-butyl 2-(3-hydroxy-2,2-dimethylpropyl)benzylcarbamate (400 mg, 1.363 mmol) in dichloromethane (DCM) (10 mL) was added TEA (0.475 mL, 3.41 mmol) and then cooled to 0° C. Mesyl chloride (0.212 mL, 2.73 mmol) was added and the reaction stirred at ambient temperature for 2 h. The reaction mixture was diluted with water and extracted with DCM (3×20 mL). The combined organic layer was dried over anhydrous Na$_2$SO$_4$, filtered and concentrated. The crude residue was purified by silica gel chromatography to give the title compound (400 mg, 0.996 mmol, 73.1% yield). LC-MS m/z 372.44 (M+H)$^+$, 2.45 min (ret. time).

4,4-Dimethyl-2,3,4,5-tetrahydro-1H-benzo[c]azepine

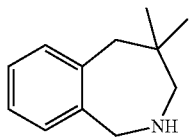

To a solution of 3-(2-(((tert-butoxycarbonyl)amino)methyl)phenyl)-2,2-dimethylpropyl methanesulfonate (400 mg, 1.077 mmol) in isopropanol (10 mL) was added Cs$_2$CO$_3$ (1052 mg, 3.23 mmol) and copper(I) iodide (20.51 mg, 0.108 mmol). The reaction mixture was heated in a microwave for 3 h at 90° C. The reaction mixture was filtered through celite and washed with ethyl acetate (20 mL). The filtrate was concentrated and purified by silica gel chromatography to give the title compound (90 mg, 0.353 mmol, 32.7% yield) LC-MS m/z 176.13 (M+H)$^+$, 1.27 min (ret. time).

Ethyl 3-(1,4-dimethyl-1H-benzo[d][1,2,3]triazol-5-yl)-3-(3-((4,4-dimethyl-4,5-dihydro-1H-benzo[c]azepin-2(3H)-yl)methyl)-4-methylphenyl)propanoate

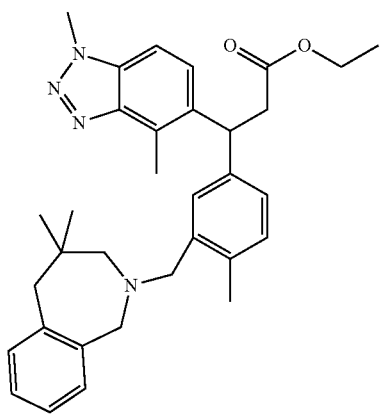 [SMILES: CCOC(=O)CC(c1ccc(C)c(CN2Cc3ccccc3CC(C)(C)C2)c1)c1ccc2c(nnn2C)c1C]

To a solution of ethyl 3-(3-(chloromethyl)-4-methylphenyl)-3-(1,4-dimethyl-1H-benzo[d][1,2,3]triazol-5-yl)propanoate (150 mg, 0.389 mmol) in acetonitrile (3 mL) was added 4,4-dimethyl-2,3,4,5-tetrahydro-1H-benzo[c]azepine (90 mg, 0.513 mmol) and DIPEA (0.170 mL, 0.972 mmol). The reaction mixture was heated in microwave for 30 min at 65° C. The reaction mixture was quenched with saturated NH$_4$Cl solution and extracted with DCM (2×30 mL). The combined organic layer was washed with brine solution (50 mL). The organic layer was dried over anhydrous Na$_2$SO$_4$, filtered and concentrated. The crude residue was purified by silica gel chromatography to give the title compound (120 mg, 0.192 mmol, 83.82% yield) LC-MS m/z 525.0 (M+H)$^+$, 5.736 min (ret. time).

Ammonium 3-(1,4-dimethyl-1H-benzo[d][1,2,3]triazol-5-yl)-3-(3-((4,4-dimethyl-4,5-dihydro-1H-benzo[c]azepin-2(3H)-yl)methyl)-4-methylphenyl)propanoate

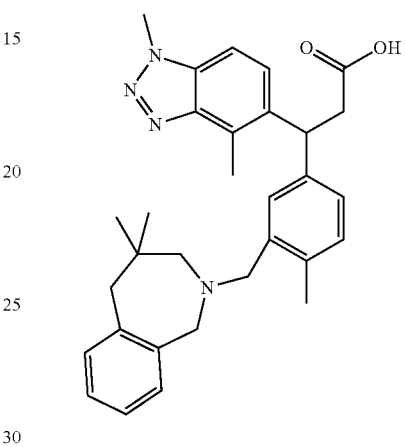

To a solution of ethyl 3-(1,4-dimethyl-1H-benzo[d][1,2,3]triazol-5-yl)-3-(3-((4,4-dimethyl-4,5-dihydro-1H-benzo[c]azepin-2(3H)-yl)methyl)-4-methylphenyl)propanoate (120 mg, 0.229 mmol) in ethanol (5 mL) was added NaOH (0.286 mL, 0.572 mmol). It was stirred for 2 h at ambient temperature. The reaction mixture was concentrated and acidified with 1N HCl solution (6 mL) to pH~2. The resulting suspension was filtered, dried, and purified with preparative HPLC to give the title compound (40 mg, 0.080 mmol, 35.0% yield) LC-MS m/z 497.40 (M+H)$^+$, 1.75 min (ret. time).

Example 106

3-(1,4-Dimethyl-1H-benzo[d][1,2,3]triazol-5-yl)-3-(3-((4-ethyl-4,5-dihydro-1H-benzo[c]azepin-2(3H)-yl)methyl)-4-methylphenyl)propanoic Acid

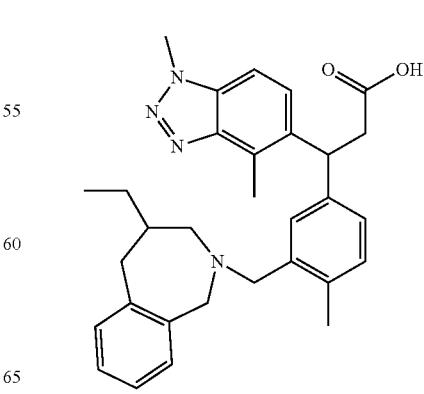

Ethyl 2-(2-cyanobenzyl)butanoate

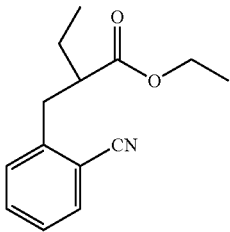 [SMILES: CCOC(=O)C(CC)Cc1ccccc1C#N]

To a solution of ethyl butyrate (0.681 mL, 5.10 mmol) in tetrahydrofuran (THF) (10 mL) at −78° C., was added lithium diisopropylamide (2M in THF) (3.83 mL, 7.65 mmol) slowly. After 30 min, a solution of 2-(bromomethyl)benzonitrile (1 g, 5.10 mmol) in THF (2 mL) was added slowly. It was stirred at −78° C. for 3 h. The reaction mixture was quenched with ammonium chloride solution (50 mL) and extracted with EtOAc (2×20 mL). The combined organic layer was washed with brine solution (20 mL) and dried over Na$_2$SO$_4$, filtered and concentrated. The crude residue was purified by silica gel chromatography to give the title compound (600 mg, 2.360 mmol, 46.3% yield) as a colorless liquid. LCMS m/z: 232.17 (M+H)$^+$, 3.716 min (ret. time)

2-(2-(Aminomethyl)benzyl)butan-1-ol

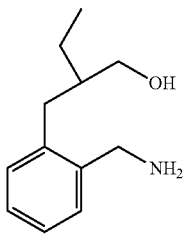

To a solution of ethyl 2-(2-cyanobenzyl)butanoate (600 mg, 2.59 mmol) in tetrahydrofuran (THF) (10 mL) at ambient temperature was added LAH (7.78 mL, 7.78 mmol) slowly. The reaction mixture was stirred for 3 h. The reaction mixture was quenched with ammonium chloride solution and extracted with EtOAc (2×50 mL). The combined organic layer was dried over Na$_2$SO$_4$, filtered and concentrated. The crude residue was purified by silica gel chromatography to give the title compound (400 mg, 2.069 mmol, 80% yield). LCMS m/z: 194 (M+H)$^+$, 3.036 min (ret. time)

(2-(2-(Chloromethyl)butyl)phenyl)methanamine

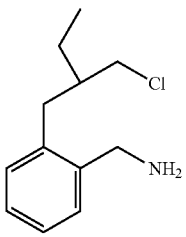

To a solution of 2-(2-(aminomethyl)benzyl)butan-1-ol (400 mg, 2.069 mmol) in 1,2-dichloroethane (DCE) (10 mL) at 5° C. was added sulfurous dichloride (0.302 mL, 4.14 mmol) slowly. The reaction mixture was allowed to stir at ambient temperature for 15 h. It was concentrated and quenched with saturated sodium bicarbonate and extracted with DCM (2×25 mL). The combined organic layer was washed with brine solution (20 mL), dried over Na$_2$SO$_4$, filtered and concentrated. The crude residue was purified by silica gel chromatography to give the title compound (300 mg, 1.417 mmol, 68.5% yield). LCMS m/z: 212 (M+H)$^+$, 1.94 min (ret. time)

4-Ethyl-2,3,4,5-tetrahydro-1H-benzo[c]azepine

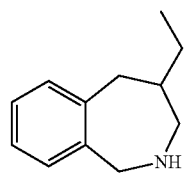

To a solution of (2-(2-(chloromethyl)butyl)phenyl)methanamine (300 mg, 1.417 mmol) in acetonitrile (2 mL) was added DIPEA (1.237 mL, 7.08 mmol). The reaction mixture was stirred at ambient temperature for 16 h. It was concentrated and extracted with DCM (2×50 mL). The organic layer was dried over Na$_2$SO$_4$, filtered, and concentrated. The crude residue was purified by silica gel chromatography to give the title compound (180 mg, 1.027 mmol, 72.5% yield). LCMS m/z: 176.22 (M+H)$^+$, 1.33 min (ret. time)

Ethyl 3-(1,4-dimethyl-1H-benzo[d][1,2,3]triazol-5-yl)-3-(3-((4-ethyl-4,5-dihydro-1H-benzo[c]azepin-2(3H)-yl)methyl)-4-methylphenyl)propanoate

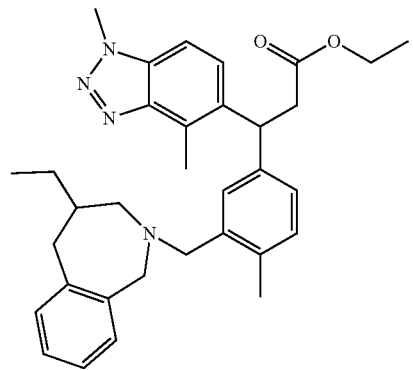 [SMILES: CCOC(=O)CC(c1ccc(C)c(CN2Cc3ccccc3CC(CC)C2)c1)c1ccc2c(nnn2C)c1C]

To a solution of 4-ethyl-2,3,4,5-tetrahydro-1H-benzo[c]azepine (150 mg, 0.856 mmol) in acetonitrile (5 mL) was added DIPEA (0.149 mL, 0.856 mmol) and ethyl 3-(3-(chloromethyl)-4-methylphenyl)-3-(1,4-dimethyl-1H-benzo[d][1,2,3]triazol-5-yl)propanoate (132 mg, 0.342 mmol). The reaction mixture was heated at 80° C. for 1 h. The reaction mixture was quenched with water and extracted with ethyl acetate (3×20 mL). The combined organic layer washed with brine solution (20 mL), dried over anhydrous Na$_2$SO$_4$, filtered and concentrated. The crude residue was purified by silica gel chromatography to give the title compound (100 mg, 0.191 mmol, 22.27% yield) as gum. LCMS m/z: 524.32 (M+H)$^+$, 2.017 min (ret. time)

3-(1,4-Dimethyl-1H-benzo[d][1,2,3]triazol-5-yl)-3-(3-((4-ethyl-4,5-dihydro-1H-benzo[c]azepin-2(3H)-yl)methyl)-4-methylphenyl)propanoic Acid

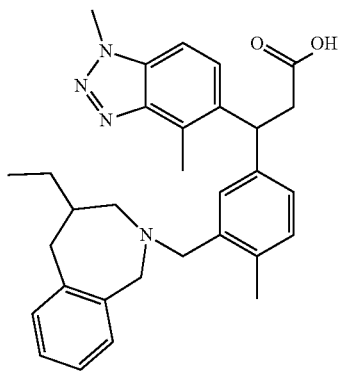 [SMILES: CCC1Cc2ccccc2CN(Cc2cc(C(CC(=O)O)c3ccc4c(nnn4C)c3C)ccc2C)C1]

To a solution of ethyl 3-(1,4-dimethyl-1H-benzo[d][1,2,3]triazol-5-yl)-3-(3-((4-ethyl-4,5-dihydro-1H-benzo[c]azepin-2(3H)-yl)methyl)-4-methylphenyl)propanoate (100 mg, 0.191 mmol) in ethanol (2 mL) at ambient temperature was added 2 M NaOH in water (0.191 mL, 0.381 mmol). The reaction mixture was stirred at ambient temperature for 15 h. The reaction mixture was concentrated and acidified with 1N HCl to pH 1. It was extracted with DCM (2×10 mL). The combined organic layer was washed with brine solution (20 mL), dried over $Na_2SO_4$, filtered and concentrated. The crude residue was purified by silica gel chromatography to give the title compound (42 mg, 0.084 mmol, 44.1% yield) as a pale yellow solid. LCMS: m/z: 497.36 (M+H)$^+$, 1.800 min (ret. time)

The compounds in Table 13 were prepared by a method similar to the one described for the preparation of 3-(1,4-Dimethyl-1H-benzo[d][1,2,3]triazol-5-yl)-3-(3-((4-ethyl-4,5-dihydro-1H-benzo[c]azepin-2(3H)-yl)methyl)-4-methylphenyl)propanoic acid. As is appreciated by those skilled in the art, these analogous examples may involve variations in general reaction conditions.

Example 108

3-(1,4-dimethyl-1H-benzo[d][1,2,3]triazol-5-yl)-3-(4-methyl-3-((2,2,8-trimethyl-2,3-dihydropyrido[3,4-f][1,4]oxazepin-4(5H)-yl)methyl)phenyl)propanoic Acid, Formic Acid Salt

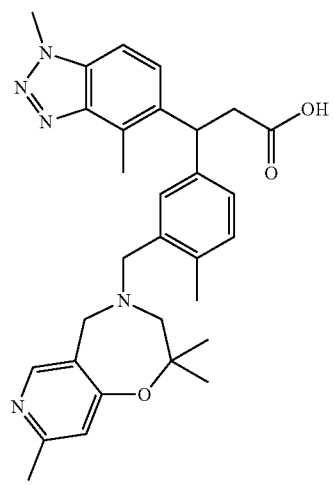 [SMILES: Cc1cc2c(cn1)CN(Cc1cc(C(CC(=O)O)c3ccc4c(nnn4C)c3C)ccc1C)CC(C)(C)O2]

4-chloro-6-methylnicotinoyl chloride

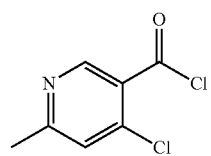

4-hydroxy-6-methylnicotinic acid (5 g, 32.7 mmol) in phosphoryl trichloride (30.4 mL, 327 mmol) was refluxed at 106° C. for 3 hours. The solution was cooled and excess

TABLE 13

| Ex # | Structure | Name | LCMS [M + H]$^+$ | Retention Time (min) |
|---|---|---|---|---|
| Example 107 | | 3-(1,4-dimethyl-1H-benzo[d][1,2,3]triazol-5-yl)-3-(3-((4-ethyl-8-fluoro-4,5-dihydro-1H-benzo[c]azepin-2(3H)-yl)methyl)-4-methylphenyl)propanoic acid | 515.43 | 1.852 | phosphoryl trichloride was removed in vacuo with a rotary evaporator. The crude product was azeotropically dried with toluene (3×25 mL) and dried under high vacuum to give the title compound (6 g, 31.6 mmol, 97% yield), which was taken to the next step without purification. LC/MS: m/z 189.8, 191.8 (M+H)+, 0.89 min (ret. time).

4-chloro-N-(2-hydroxy-2-methylpropyl)-6-methylnicotinamide

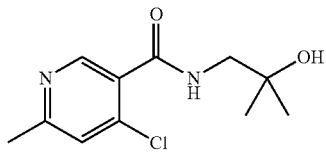 [SMILES: Cc1cc(Cl)c(C(=O)NCC(C)(C)O)cn1]

Sodium hydroxide (52.3 mL, 105 mmol) was added dropwise to a solution of 4-chloro-6-methylnicotinoyl chloride (6.21 g, 32.7 mmol) and 1-amino-2-methylpropan-2-ol (4.37 g, 49.1 mmol) in dichloromethane (DCM) (54.5 mL) at 0° C. and allowed to warm to ambient temperature while stirring vigorously. The reaction was complete after 3 hours. The DCM and aqueous NaOH layers were separated and the aqueous NaOH fraction extracted with DCM (3×50 mL). The combined organic fractions were dried (sodium sulfate) and the solvent removed in vacuo. The product was purified by flash chromatography (combiflash 20-100% Hexanes/EtOAc:EtOH (3:1)) to give the title compound (1.9 g, 7.83 mmol, 23.94% yield) over 2 steps. LC/MS: m/z 242.9, 244.9 (M+H)+, 0.5 min (ret. time).

1-(((4-chloro-6-methylpyridin-3-yl)methyl)amino)-2-methylpropan-2-ol

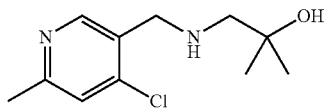

Borane dimethyl sulfide (6.18 mL, 12.36 mmol) was added to a solution of 4-chloro-N-(2-hydroxy-2-methylpropyl)-6-methylnicotinamide (500 mg, 2.060 mmol) in tetrahydrofuran (THF) (41.203 mL) and heated to reflux. The reaction was complete after 5 hours. The reaction was then cooled to 0° C. and methanol (MeOH) (20 mL) was added dropwise. The solvent was then removed under vacuum to give the title compound (471 mg, 2.059 mmol, 100% yield) which was taken to the next step without further purification. LC/MS: m/z 228.9 (M+H)+, 0.49 min (ret. time).

Tert-butyl 2,2,8-trimethyl-2,3-dihydropyrido[3,4-f][1,4]oxazepine-4(5H)-carboxylate

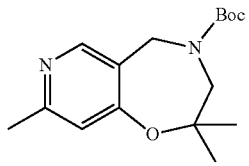

1-(((4-chloro-6-methylpyridin-3-yl)methyl)amino)-2-methylpropan-2-ol (0.471 g, 2.06 mmol) and potassium tert-butoxide (0.462 g, 4.12 mmol) in dimethyl sulfoxide (DMSO) (13.73 mL) were heated to 80° C. in a biotage microwave reactor (high intensity) for 1 hour. Solid sodium bicarbonate was added and the suspension was filtered. The filtrate was concentrated and the crude material redissolved in tetrahydrofuran (THF) (6.87 mL). The solution was cooled to 0° C. and triethylamine (0.417 g, 4.12 mmol) followed by di-tert-butyl dicarbonate (1.349 g, 6.18 mmol) was added. The solution was allowed to warm to ambient temperature and the reaction was complete after 12 hours. The solvent was removed in vacuo and the product purified by flash chromatography on a Combiflash instrument (0-100% EtOAc/Hexanes) to give the title compound (20 mg, 0.068 mmol, 3.32% yield). LC/MS: m/z 293.0 (M+H)+, 0.70 min (ret. time).

2,2,8-trimethyl-2,3,4,5-tetrahydropyrido[3,4-f][1,4]oxazepine hydrochloride

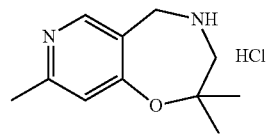

tert-Butyl 2,2,8-trimethyl-2,3-dihydropyrido[3,4-f][1,4]oxazepine-4(5H)-carboxylate (20 mg, 0.068 mmol) in hydrogen chloride (4 M in dioxane) (1026 µl, 4.10 mmol) was stirred at ambient temperature for 3 hours. The solvent was removed under a stream of nitrogen at 50° C. to give the title compound (15.65 mg, 0.068 mmol, 100% yield). LC/MS: m/z 193.0 (M+H)+, 0.28 min (ret. time).

Ethyl 3-(1,4-dimethyl-1H-benzo[d][1,2,3]triazol-5-yl)-3-(4-methyl-3-((2,2,8-trimethyl-2,3-dihydropyrido[3,4-f][1,4]oxazepin-4(5H)-yl)methyl)phenyl)propanoate

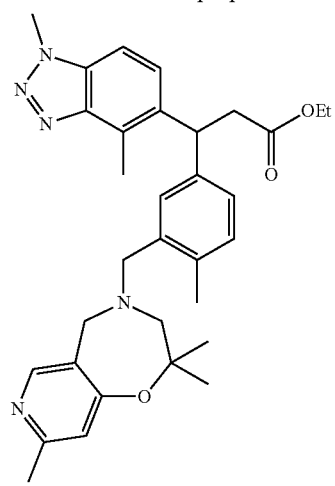

Ethyl 3-(3-(chloromethyl)-4-methylphenyl)-3-(1,4-dimethyl-1H-benzo[d][1,2,3]triazol-5-yl)propanoate (18.98 mg, 0.049 mmol), 2,2,8-trimethyl-2,3,4,5-tetrahydropyrido[3,4-f][1,4]oxazepine hydrochloride (15 mg, 0.066 mmol), and N-ethyl-N-isopropylpropan-2-amine (17.18 µl, 0.098 mmol) in acetonitrile (293 µl) were heated in a Biotage microwave reactor at high absorption for 1 h at 120° C. The solvent was removed to give the title compound (35.5 mg, 0.066 mmol, 100% yield). LC/MS: m/z 542.3 (M+H)+, 0.94 min (ret. time).

3-(1,4-dimethyl-1H-benzo[d][1,2,3]triazol-5-yl)-3-(4-methyl-3-((2,2,8-trimethyl-2,3-dihydropyrido[3,4-f][1,4]oxazepin-4(5H)-yl)methyl)phenyl)propanoic Acid, Formic Acid Salt

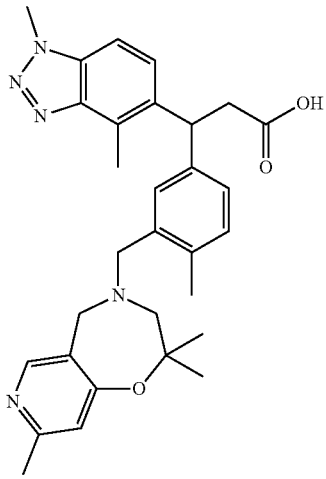 [SMILES: Cc1cc2c(cn1)CN(Cc1cc(C(CC(=O)O)c3ccc4c(nnn4C)c3C)ccc1C)CC(C)(C)O2]

Sodium hydroxide (0.270 mL, 0.539 mmol) was added to a solution of ethyl 3-(1,4-dimethyl-1H-benzo[d][1,2,3]triazol-5-yl)-3-(4-methyl-3-((2,2,8-trimethyl-2,3-dihydropyrido[3,4-f][1,4]oxazepin-4(5H)-yl)methyl)phenyl)propanoate (27 mg, 0.049 mmol) in methanol (0.408 mL) at ambient temperature and stirred for 18 hours. DMSO (3 mL) was added and the methanol was removed in vacuo. The solution was acidified with 1N HCl and the aqueous fraction removed in vacuo. The crude product was purified by reverse-phase HPLC (with 0.1% formic acid) to give the title compound (19 mg, 0.034 mmol, 69.3% yield). LC/MS: m/z 514.4 (M+H)+, 0.75 min (ret. time).

Example 109

(S)-3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic Acid, Formic Acid Salt

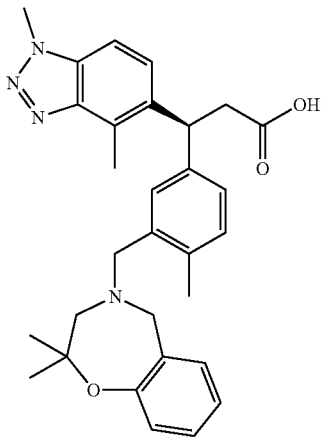 [SMILES: Cc1ccc([C@H](CC(=O)O)c2ccc3c(nnn3C)c2C)cc1CN1Cc2ccccc2OC(C)(C)C1]

(S)-ethyl 3-(3-(chloromethyl)-4-methylphenyl)-3-(1,4-dimethyl-1H-benzo[d][1,2,3]triazol-5-yl)propanoate

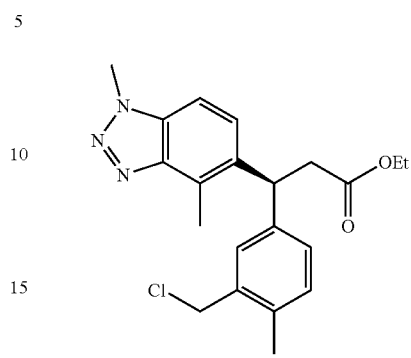

Thionyl chloride (0.397 mL, 5.44 mmol) was added to a solution of (S)-ethyl 3-(1,4-dimethyl-1H-benzo[d][1,2,3]triazol-5-yl)-3-(3-(hydroxymethyl)-4-methylphenyl)propanoate (1 g, 2.72 mmol) in dichloromethane (DCM) (5.44 mL) at ambient temperature and stirred for 1 h. Solvent was concentrated in vacuo to give the title compound (1.050 g, 2.72 mmol, 100% yield) LC/MS: m/z 386.1 (M+H)+, 1.16 min (ret. time).

(S)-ethyl 3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoate

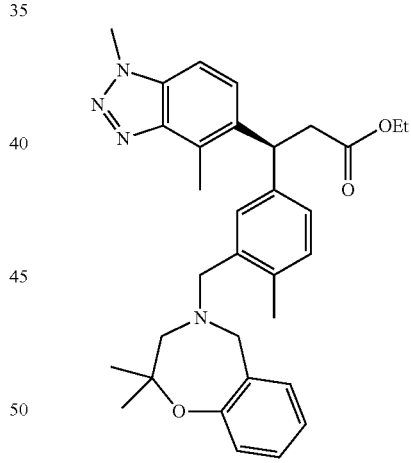

(S)-ethyl 3-(3-(chloromethyl)-4-methylphenyl)-3-(1,4-dimethyl-1H-benzo[d][1,2,3]triazol-5-yl)propanoate (150 mg, 0.389 mmol), 2,2-dimethyl-2,3,4,5-tetrahydrobenzo[f][1,4]oxazepine hydrochloride (166 mg, 0.777 mmol), and N-ethyl-N-isopropylpropan-2-amine (0.204 mL, 1.166 mmol) in acetonitrile (2.718 mL) were heated in a Biotage microwave reactor at high power for 60 minutes at 120° C. The solvent was removed to give the title compound (204.7 mg, 0.389 mmol, 100% yield). LC/MS: m/z 527.4 (M+H)+, 0.97 min (ret. time).

287

(S)-3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic Acid, Formic Acid Salt

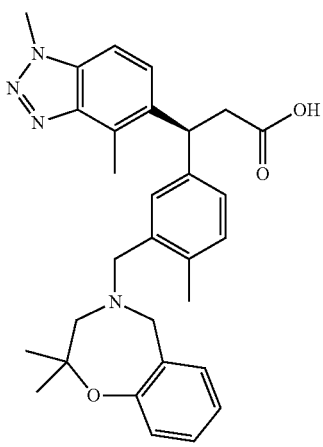 [SMILES: CCOC(=O)C[C@@H](c1ccc(C)c(CN2Cc3ccccc3OC(C)(C)C2)c1)c1ccc2c(nnn2C)c1C]

Sodium hydroxide (2.140 mL, 4.28 mmol) was added to a solution of (S)-ethyl 3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoate (205 mg, 0.389 mmol) in methanol (3.242 mL) at ambient temperature and stirred for 18 hours. The solution was acidified with 1 N HCl and concentrated. The solution was acidified with 1N HCl and the aqueous fraction removed in vacuo. The crude product was purified by reverse-phase HPLC (with 0.1% formic acid) to give the title compound (140.2 mg, 0.257 mmol, 66.2% yield). LC/MS: m/z 499.5 (M+H)$^+$, 0.74 min (ret. time).

Example 110

(R)-3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic Acid, Formic Acid Salt

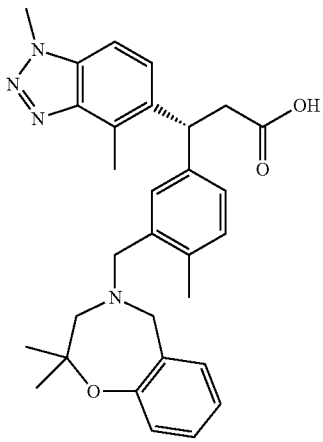 [SMILES: CCOC(=O)C[C@H](c1ccc(C)c(CN2Cc3ccccc3OC(C)(C)C2)c1)c1ccc2c(nnn2C)c1C]

288

(R)-ethyl 3-(3-(chloromethyl)-4-methylphenyl)-3-(1,4-dimethyl-1H-benzo[d][1,2,3]triazol-5-yl)propanoate Thionyl chloride (0.397 mL, 5.44 mmol) was added to a solution of (R)-ethyl 3-(1,4-dimethyl-1H-benzo[d][1,2,3]triazol-5-yl)-3-(3-(hydroxymethyl)-4-methylphenyl)propanoate (1 g, 2.72 mmol) in dichloromethane (DCM) (5.44 mL) at ambient temperature and stirred for 30 min. Solvent was concentrated in vacuo to give the title compound (1.050 g, 2.72 mmol, 100% yield). LC/MS: m/z 386.1 (M+H)$^+$, 1.15 min (ret. time).

(R)-ethyl 3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoate (R)-ethyl 3-(3-(chloromethyl)-4-methylphenyl)-3-(1,4-dimethyl-1H-benzo[d][1,2,3]triazol-5-yl)propanoate (150 mg, 0.389 mmol), 2,2-dimethyl-2,3,4,5-tetrahydrobenzo[f][1,4]oxazepine hydrochloride (166 mg, 0.777 mmol), N-ethyl-N-isopropylpropan-2-amine (0.204 mL, 1.166 mmol) in acetonitrile (2.72 mL) were heated in a Biotage microwave reactor at high power for 1 hour at 120° C. The solvent was removed to give the title compound (204.7 mg, 0.389 mmol, 100% yield). LC/MS: m/z 527.4 (M+H)$^+$, 0.95 min (ret. time).

289

(R)-3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoic Acid, Formic Acid Salt

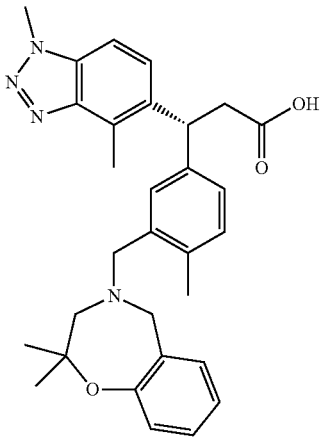

Sodium hydroxide (2.140 mL, 4.28 mmol) was added to a solution of (R)-ethyl 3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoate (205 mg, 0.389 mmol) in methanol (3.242 mL) at ambient temperature and stirred for 18 hours. The solution was acidified with 1N HCl and concentrated. The crude product was purified by reverse-phase HPLC (with 0.1% formic acid) to give the title compound (153.89 mg, 0.283 mmol, 72.6% yield). LC/MS: m/z 499.5 (M+H)$^+$, 0.76 min (ret. time).

Example 111

3-(1,4-dimethyl-1H-benzo[d][1,2,3]triazol-5-yl)-3-(3-((1-ethyl-2,3-dihydro-1H-benzo[e][1,4]diazepin-4(5H)-yl)methyl)-4-methylphenyl)-2,2-dimethylpropanoic Acid, Formic Acid Salt

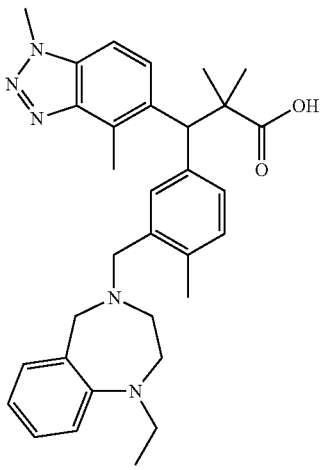 [SMILES: CCN1CCN(Cc2cc(C(c3ccc4c(nnn4C)c3C)C(C)(C)C(=O)O)ccc2C)Cc2ccccc21]

290

Ethyl 2-((2-nitrobenzyl)amino)acetate

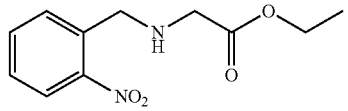 [SMILES: CCOC(=O)CNCc1ccccc1[N+](=O)[O-]]

To 1-(bromomethyl)-2-nitrobenzene (20 g, 93 mmol) in N,N-dimethylformamide (DMF) (200 mL) was added ethyl 2-aminoacetate, hydrochloride (19.38 g, 139 mmol) and DIPEA (48.5 mL, 278 mmol) slowly under nitrogen at 25° C. The reaction mixture was stirred at 25° C. for 6 h after which 500 mL of water was added and the mixture extracted with ethyl acetate (3×200 mL). The combined organic layer was dried over MgSO$_4$ and concentrated. The crude product was purified by silica gel chromatography (hexane:ethyl acetate=10:1) to give the title compound ethyl 2-((2-nitrobenzyl)amino)acetate (16 g, 67.2 mmol, 72.5% yield) which was carried to the next step without further purification. LC-MS m/z 239.1 (M+H)$^+$, 1.20 min (ret. time).

Ethyl 2-((tert-butoxycarbonyl)(2-nitrobenzyl)amino)acetate

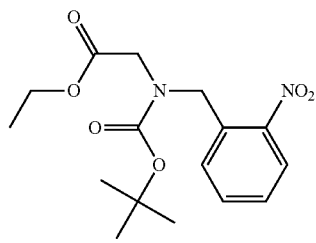 [SMILES: CCOC(=O)CN(Cc1ccccc1[N+](=O)[O-])C(=O)OC(C)(C)C]

To ethyl 2-((2-nitrobenzyl)amino)acetate (16 g, 67.2 mmol) in dichloromethane (DCM) (200 mL) was added Boc$_2$O (23.39 mL, 101 mmol), DMAP (0.410 g, 3.36 mmol) and TEA (18.72 mL, 134 mmol) slowly under nitrogen at 25° C. The reaction mixture was stirred at 25° C. for 16 h. The solvent was evaporated and the crude product was purified by silica gel chromatography (hexane:ethyl acetate=10:1) to give the title compound ethyl 2-((tert-butoxycarbonyl)(2-nitrobenzyl)amino)acetate (16 g, 46.8 mmol, 69.7% yield) which was carried to the next step without further purification. LC-MS m/z 361.1 (M+Na)$^+$, 2.06 min (ret. time).

Ethyl 2-((2-aminobenzyl)(tert-butoxycarbonyl)amino)acetate

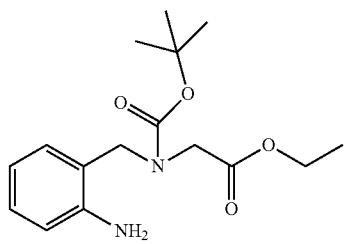 [SMILES: CCOC(=O)CN(Cc1ccccc1N)C(=O)OC(C)(C)C]

A solution of ethyl 2-((tert-butoxycarbonyl)(2-nitrobenzyl)amino)acetate (16 g, 47.3 mmol) in methanol (500 mL) was degassed for 10 min with argon, Pd/C (5 g, 4.70 mmol) was added. Then it was stirred for 22 h under H₂ balloon. The reaction mixture was filtered through celite and the filtrate was concentrated to give the title compound ethyl 2-((2-aminobenzyl)(tert-butoxycarbonyl)amino)acetate (14 g, 45.4 mmol, 96% yield) which was carried to the next step without further purification. LC-MS m/z 309.1 (M+H)⁺, 1.87 min (ret. time).

Tert-butyl 2-oxo-2,3-dihydro-1H-benzo[e][1,4]diazepine-4(5H)-carboxylate

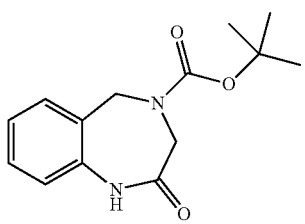 [SMILES: CC(C)(C)OC(=O)N1CC(=O)Nc2ccccc2C1]

To ethyl 2-((2-aminobenzyl)(tert-butoxycarbonyl)amino)acetate (14 g, 45.4 mmol) in toluene (700 mL) was added HOBt (5.56 g, 36.3 mmol) slowly under nitrogen at ambient temperature. The reaction mixture was stirred at 110° C. for 16 h. The solvent was evaporated and the crude product was purified by silica gel chromatography (hexane:ethyl acetate=4:1) to give the title compound tert-butyl 2-oxo-2,3-dihydro-1H-benzo[e][1,4]diazepine-4(5H)-carboxylate (8.6 g, 31.8 mmol, 70.1% yield) which was carried to the next step without further purification. LC-MS m/z 207.1 (M+H-t-tutyl)⁺ 1.74 min (ret. time).

tert-Butyl 1-ethyl-2-oxo-2,3-dihydro-1H-benzo[e][1,4]diazepine-4(5H)-carboxylate

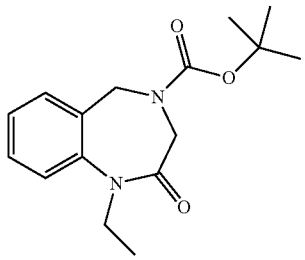 [SMILES: CCN1C(=O)CN(C(=O)OC(C)(C)C)Cc2ccccc21]

To tert-butyl 2-oxo-2,3-dihydro-1H-benzo[e][1,4]diazepine-4(5H)-carboxylate (8.6 g, 32.8 mmol) in N,N-dimethylformamide (DMF) (200 mL) was added NaH (2.229 g, 55.7 mmol) slowly under nitrogen at 25° C. After it was stirred at 25° C. for 30 min, iodoethane (7.67 g, 49.2 mmol) solution in 1 ml of DMF was added. The reaction mixture was stirred at ambient temperature for 2 h, then 50 mL of water was added and the mixture extracted with ethyl acetate (3×100 mL). The combined organic layer was dried over MgSO₄, and concentrated to give the title compound tert-butyl 1-ethyl-2-oxo-2,3-dihydro-1H-benzo[e][1,4]diazepine-4(5H)-carboxylate (9 g, 31.0 mmol, 95% yield) which was carried to the next step without further purification. LC-MS m/z 309.1 (M+23)⁺, 1.91 min (ret. time).\

1-Ethyl-4,5-dihydro-1H-benzo[e][1,4]diazepin-2(3H)-one

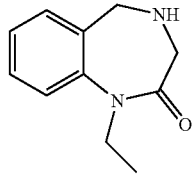

To tert-butyl 1-ethyl-2-oxo-2,3-dihydro-1H-benzo[e][1,4]diazepine-4(5H)-carboxylate (9 g, 31.0 mmol) in dichloromethane (DCM) (150 mL) was added TFA (50 ml, 649 mmol) slowly under nitrogen at 25° C. The reaction mixture was stirred at 25° C. for 16 h. The solvent was evaporated. 100 mL of 20% of Na₂CO₃ was added and extracted with ethyl acetate (3×100 mL). The combined organic layer was dried over MgSO₄ and concentrated to give the title compound 1-ethyl-4,5-dihydro-1H-benzo[e][1,4]diazepin-2(3H)-one (4.2 g, 22.08 mmol, 71.2% yield) which was carried to the next step without further purification. LC-MS m/z 191.1 (M+H)⁺, 1.06 min (ret. time).

1-Ethyl-2,3,4,5-tetrahydro-1H-benzo[e][1,4]diazepine

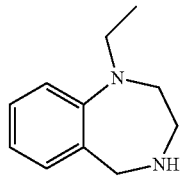

To 1-ethyl-4,5-dihydro-1H-benzo[e][1,4]diazepin-2(3H)-one (4.2 g, 22.08 mmol) in tetrahydrofuran (THF) (50 mL) was added LiAlH₄ (1.006 g, 26.5 mmol) slowly under nitrogen at 0° C. The reaction was stirred at 0° C. for 30 min and stirred at 60° C. for 6 h. It was cooled to 0° C., water (1 mL) and 1 mL of 10% NaOH were added, followed by an additional 3 mL of water. The mixture was filtered and the filtrate was concentrated. The crude product was purified by silica gel chromatography (hexane:ethyl acetate:triethylamine=1:4:0.05) to give the title compound 1-ethyl-2,3,4,5-tetrahydro-1H-benzo[e][1,4]diazepine (1.6 g, 8.17 mmol, 37.0% yield) as oil. LC-MS: m/z 177.2 (M+H)⁺, 1.51 min (ret. time).

Methyl 3-(3-(chloromethyl)-4-methylphenyl)-3-(1,4-dimethyl-1H-benzo[d][1,2,3]triazol-5-yl)-2,2-dimethylpropanoate

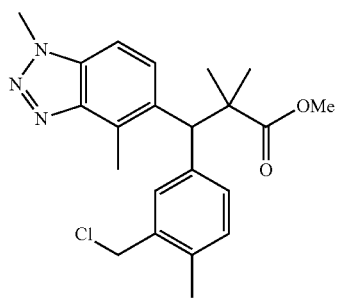 [SMILES: COC(=O)C(C)(C)C(c1ccc(C)c(CCl)c1)c1ccc2c(nnn2C)c1C]

Thionyl chloride (0.727 mL, 9.96 mmol) was added to a solution of methyl 3-(1,4-dimethyl-1H-benzo[d][1,2,3]triazol-5-yl)-3-(3-(hydroxymethyl)-4-methylphenyl)-2,2-dimethylpropanoate (1.9 g, 4.98 mmol) in dichloromethane (DCM) (9.96 mL) at ambient temperature and stirred for 1 hour. The solution was concentrated in vacuo to give the title compound (1.99 g, 4.98 mmol, 100% yield). LC/MS: m/z 400.1 (M+H)$^+$, 1.16 min (ret. time).

Methyl 3-(1,4-dimethyl-1H-benzo[d][1,2,3]triazol-5-yl)-3-(3-((1-ethyl-2,3-dihydro-1H-benzo[e][1,4]diazepin-4(5H)-yl)methyl)-4-methylphenyl)-2,2-dimethylpropanoate

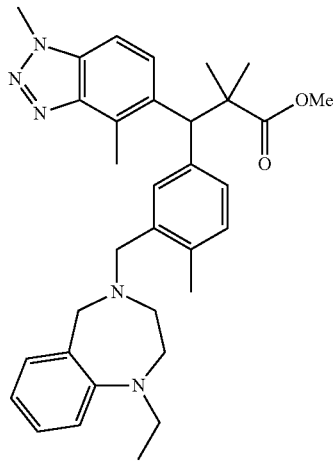 [SMILES: CCN1CCN(Cc2cc(C(c3ccc4c(nnn4C)c3C)C(C)(C)C(=O)OC)ccc2C)Cc2ccccc21]

Methyl 3-(3-(chloromethyl)-4-methylphenyl)-3-(1,4-dimethyl-1H-benzo[d][1,2,3]triazol-5-yl)-2,2-dimethylpropanoate (60 mg, 0.150 mmol), 1-ethyl-2,3,4,5-tetrahydro-1H-benzo[e][1,4]diazepine (34.4 mg, 0.195 mmol), and N-ethyl-N-isopropylpropan-2-amine (0.081 mL, 0.466 mmol) in acetonitrile (0.670 mL) were heated in a Biotage microwave reactor at high power for 1 hour at 120° C. The solvent was removed in vacuo to give the title compound (81 mg, 0.150 mmol, 100% yield). LC/MS: m/z 540.3 (M+H)$^+$, 1.01 min (ret. time).

3-(1,4-dimethyl-1H-benzo[d][1,2,3]triazol-5-yl)-3-(3-((1-ethyl-2,3-dihydro-1H-benzo[e][1,4]diazepin-4(5H)-yl)methyl)-4-methylphenyl)-2,2-dimethylpropanoic Acid, Formic Acid Salt

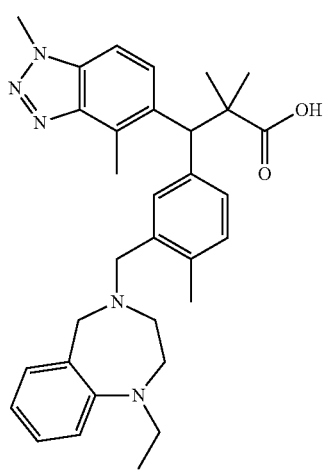 [SMILES: CCN1CCN(Cc2cc(C(c3ccc4c(nnn4C)c3C)C(C)(C)C(=O)O)ccc2C)Cc2ccccc21]

Lithium hydroxide (2.66 mg, 0.111 mmol) was a added to a solution of methyl 3-(1,4-dimethyl-1H-benzo[d][1,2,3]triazol-5-yl)-3-(3-((1-ethyl-2,3-dihydro-1H-benzo[e][1,4]diazepin-4(5H)-yl)methyl)-4-methylphenyl)-2,2-dimethylpropanoate (60 mg, 0.111 mmol) in water (285 µl) and methanol (570 µl) and heated in a Biotage microwave reactor at high power at 130° C. for 2 hours. The crude product was purified by reverse-phase HPLC (with 0.1% formic acid) to give a yellow solid (40 mg, 0.070 mmol, 62.9% yield). LC/MS: m/z 526.5 (M+H)$^+$, 0.79 min (ret. time).

Example 112

(2R)-4-(5-(1-(1,4-dimethyl-1H-benzo[d][1,2,3]triazol-5-yl)-2-(1H-tetrazol-5-yl)ethyl)-2-methylbenzyl)-2-ethyl-2,3,4,5-tetrahydrobenzo[f][1,4]oxazepine, Formic Acid Salt

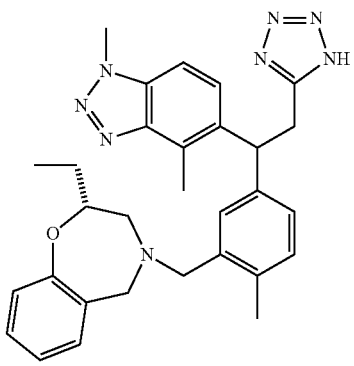 [SMILES: CC[C@@H]1CN(Cc2cc(C(Cc3nnn[nH]3)c3ccc4c(nnn4C)c3C)ccc2C)Cc2ccccc2O1]

(E)-3-(1,4-dimethyl-1H-benzo[d][1,2,3]triazol-5-yl)acrylonitrile

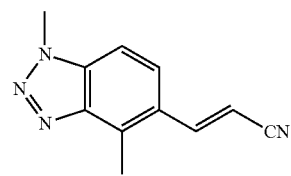

To a solution of 5-bromo-1,4-dimethyl-1H-benzo[d][1,2,3]triazole (1.00 g, 4.42 mmol) in N,N-dimethylformamide (DMF) (11 mL) in a 20 mL microwave reaction vessel was added acrylonitrile (1.747 mL, 26.5 mmol), tri-o-tolylphosphine (0.404 g, 1.327 mmol), and DIEA (3.09 mL, 17.69 mmol). The solution was flushed with nitrogen for 3 min and then palladium(II) acetate (0.149 g, 0.664 mmol) was added. The reaction was heated via microwave at 150° C. for 2 h. Additional palladium(II) acetate (0.149 g, 0.664 mmol) was added and the reaction was heated via microwave at 150° C. for 1.5 h. The reaction was filtered through Celite and washed with EtOAc. The filtrate was washed with water (3×). The combined organics were washed with brine, dried with MgSO$_4$, and solvents were concentrated. The residue was purified by flash chromatography eluting with 0-10% EtOAc/DCM and repurified by flash chromatography eluting with 0-40% EtOAc/Hexane to provide the title compound as a mixture of cis and trans isomers. (0.583 g, 66% yield) LC-MS m/z 199 (M+H)⁺, 0.67 min (ret. time).

3-(1,4-Dimethyl-1H-benzo[d][1,2,3]triazol-5-yl)-3-(3-(hydroxymethyl)-4-methylphenyl)propanenitrile

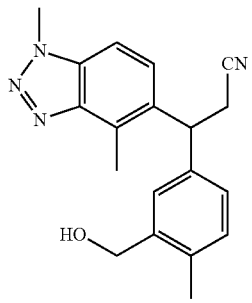 [SMILES: Cc1ccc(C(CC#N)c2ccc3c(nnn3C)c2C)cc1CO]

To a solution of (E)-3-(1,4-dimethyl-1H-benzo[d][1,2,3]triazol-5-yl)acrylonitrile (0.583 g, 2.94 mmol) and (3-(hydroxymethyl)-4-methylphenyl)boronic acid (0.586 g, 3.53 mmol) in 1,4-dioxane (25 mL) and water (15 mL) was added triethylamine (0.615 mL, 4.41 mmol) and, chloro(1,5-cyclooctadiene)rhodium(I) dimer (0.145 g, 0.294 mmol). The reaction was heated at 95° C. for 3.5 h. The reaction was cooled and the solvents were concentrated. The residue was diluted with water and extracted with EtOAc. The combined organics were washed with water (2×) and the aqueous layers were back extracted with EtOAc. The combined organics were washed with water, brine, and dried with MgSO₄, and the solvent was concentrated. The residue was purified by flash chromatography eluting with 0-30% EtOAc/hexane to provide the title compound. (0.62 g, 65% yield) LC-MS m/z 320.0 (M+H)⁺, 0.74 min (ret. time).

3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanenitrile

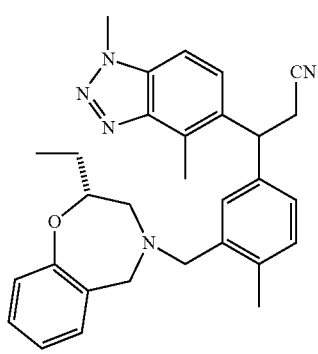 [SMILES: CC[C@@H]1CN(Cc2cc(C(CC#N)c3ccc4c(nnn4C)c3C)ccc2C)Cc2ccccc2O1]

To a solution of 3-(1,4-dimethyl-1H-benzo[d][1,2,3]triazol-5-yl)-3-(3-(hydroxymethyl)-4-methylphenyl)propanenitrile (0.275 g, 0.858 mmol) in dichloromethane (DCM) (8 mL) was added thionyl chloride (0.125 mL, 1.717 mmol) and stirred at ambient temperature for 1 h. The reaction was evaporated and the residue was suspended in acetonitrile (8.00 mL). DIEA (0.450 mL, 2.58 mmol) and (R)-2-ethyl-2,3,4,5-tetrahydrobenzo[f][1,4]oxazepine, hydrochloride (0.202 g, 0.944 mmol) was added to the suspension and the reaction was stirred at ambient temperature for 3 h. The solvents were concentrated and the residue was purified by flash chromatography, eluting with 0-40% EtOAc/Hexane to provide the title compound. (0.087 g, 18% yield) LC-MS m/z 480 (M+H)⁺, 0.88 min (ret. time).

(2R)-4-(5-(1-(1,4-dimethyl-1H-benzo[d][1,2,3]triazol-5-yl)-2-(1H-tetrazol-5-yl)ethyl)-2-methylbenzyl)-2-ethyl-2,3,4,5-tetrahydrobenzo[f][1,4]oxazepine, Formic Acid Salt

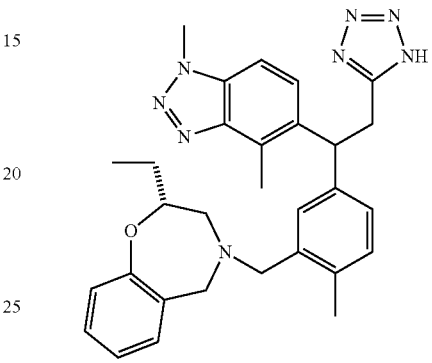

A mixture of 3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)propanenitrile (0.087 g, 0.181 mmol), TMS-N₃ (0.072 mL, 0.544 mmol) and TBAF (0.253 g, 0.907 mmol) were heated in a 20 mL vial at 85° C. for 1 h. After which, additional TMS-N₃ (0.072 mL, 0.544 mmol was added and heated at 85° C. for 18.5 h. Additional TMS-N₃ (0.072 mL, 0.544 mmol) was then added and continued heating for 18 h. The residue was purified by reverse phase preparative HPLC under neutral conditions and then acidic conditions to provide the title compound. (0.025 g, 24% yield) LC-MS m/z 523 (M+H)⁺, 0.71 min (ret. time).

Example 113

3-(1,4-Dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)-2,2-dimethylpropanoic Acid

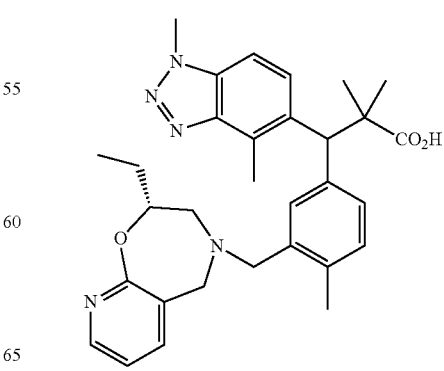

(2-Bromopyridin-3-yl)methanamine

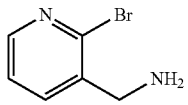

To a solution of 2-bromo-3-(bromomethyl)pyridine, hydrochloride (1.81 g, 6.30 mmol) in ethanol (4 mL) was added ammonium hydroxide (50 mL, 1284 mmol) and stirred at 50° C. for 30 min. The reaction was diluted with water and aqueous layer was extracted with EtOAc (12×, 600 mL total). The combined organics were washed with brine and dried with MgSO$_4$. The solvent was concentrated and the residue was purified by flash chromatography eluting with 0-5% MeOH/DCM to provide the title compound. (0.750 g, 63% yield) LC-MS m/z 187 (M+H)$^+$, 0.10 min (ret. time).

(R)-1-(((2-bromopyridin-3-yl)methyl)amino)butan-2-ol

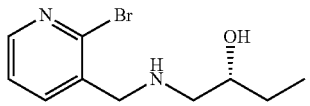

A solution of (2-bromopyridin-3-yl)methanamine (1.27 g, 6.79 mmol) and (R)-2-ethyloxirane (0.490 g, 6.79 mmol) in ethanol (10 mL) in a 20 mL microwave reaction vessel was heated via microwave at 150° C. for 2 h. The solvent was concentrated and the residue was purified by flash chromatography eluting with 0-50-90% (3:1 EtOAc:ethanol)/hexane to provide the title compound. (0.934 g, 53% yield) LC-MS m/z 542 (M+H)$^+$, 0.83 min (ret. time).

(R)-2-ethyl-2,3,4,5-tetrahydropyrido[3,2-f][1,4]oxazepine

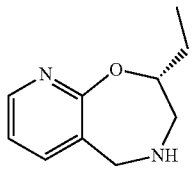

To a solution of (R)-1-(((2-bromopyridin-3-yl)methyl)amino)butan-2-ol (1.365 g, 5.27 mmol) in N,N-Dimethylformamide (DMF) (20 mL) was added potassium tert-butoxide (1.773 g, 15.80 mmol) and heated to 80° C. for 1.5 h. The reaction was cooled, filtered and washed with DMF. The solvent was concentrated under vacuum and the residue was purified by flash chromatography eluting with 0-5% MeOH/DCM to provide the title compound. (0.890 g, 95% yield) LC-MS m/z 179 (M+H)$^+$, 0.23 min (ret. time).

Methyl 3-(1,4-dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)-2,2-dimethylpropanoate

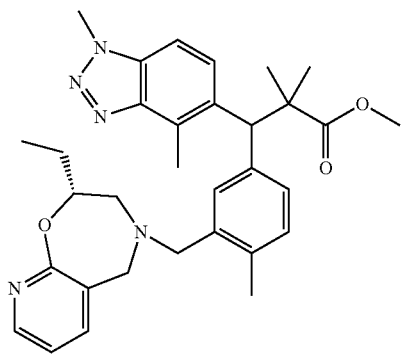 [SMILES: CC[C@@H]1CN(Cc2cc(C(c3ccc4c(nnn4C)c3C)C(C)(C)C(=O)OC)ccc2C)Cc2cccnc2O1]

To a solution of methyl 3-(1,4-dimethyl-1H-benzo[d][1,2,3]triazol-5-yl)-3-(3-(hydroxymethyl)-4-methylphenyl)-2,2-dimethylpropanoate (0.075 g, 0.197 mmol) in dichloromethane (DCM) (2 mL) was added thionyl chloride (0.042 mL, 0.575 mmol) and stirred at ambient temperature for 2 h. The solvents were concentrated. The residue, (R)-2-ethyl-2,3,4,5-tetrahydropyrido[3,2-f][1,4]oxazepine (0.035 g, 0.197 mmol) and DIEA (0.137 mL, 0.786 mmol) were dissolved in acetonitrile (4 mL) in a 10 mL microwave reaction vessel and heated to 120° C. for 30 min. The solvent was concentrated and the residue was purified by flash chromatography eluting with 0-60% (3:1 EtOAc:Ethanol)/Hexane to provide the title compound. (0.075 g, 64% yield) LC-MS m/z 542 (M+H)$^+$, 0.83 min (ret. time).

3-(1,4-Dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)-2,2-dimethylpropanoic Acid

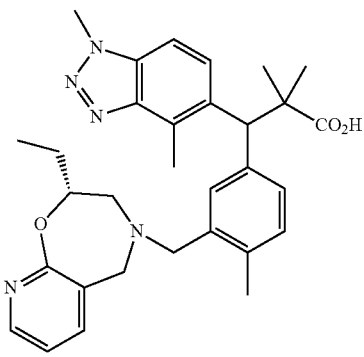 [SMILES: CC[C@@H]1CN(Cc2cc(C(c3ccc4c(nnn4C)c3C)C(C)(C)C(=O)O)ccc2C)Cc2cccnc2O1]

To a solution of methyl 3-(1,4-dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)-2,2-dimethylpropanoate (75 mg, 0.138 mmol) dissolved in tetrahydrofuran (THF) (2 mL), water (1 mL). and methanol (0.5 mL) in a 10 mL microwave reaction vessel was added lithium hydroxide (16.58 mg, 0.692 mmol) and heated via microwave at 125° C. for 8 h. The solvent was concentrated and the residue was acidified with formic acid. The residue was purified by reverse phase preparative HPLC under acidic conditions to provide the title compound. (0.037 g, 50% yield) LC-MS m/z 528 (M+H)$^+$, 0.72 min (ret. time).

Example 114

3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoic Acid, Lithium Salt

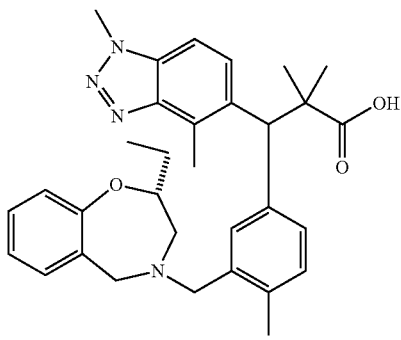 [SMILES: CC[C@@H]1CN(Cc2cc(C(c3ccc4c(nnn4C)c3C)C(C)(C)C(=O)O)ccc2C)Cc2ccccc2O1]

Methyl 3-(1,4-dimethyl-1H-benzo[d][1,2,3]triazol-5-yl)-3-(3-formyl-4-methylphenyl)-2,2-dimethylpropanoate

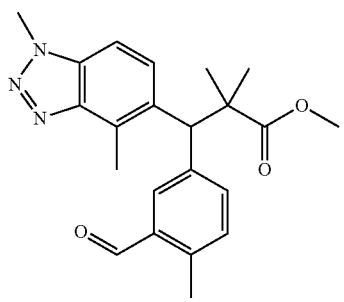 [SMILES: COC(=O)C(C)(C)C(c1ccc(C)c(C=O)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate (75 mg, 0.197 mmol) in dichloromethane (DCM) (5 mL) was added Dess-Martin periodinane (100 mg, 0.236 mmol) at 0° C. and was stirred for 2 h. The reaction mixture was purified via by flash chromatography eluting 0-100% EtOAc/Hexanes to provide the title compound (70 mg, 75% yield) as a white foam. LC-MS m/z 380 (M+H)+, 1.01 min (ret. time).

Methyl 3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoate

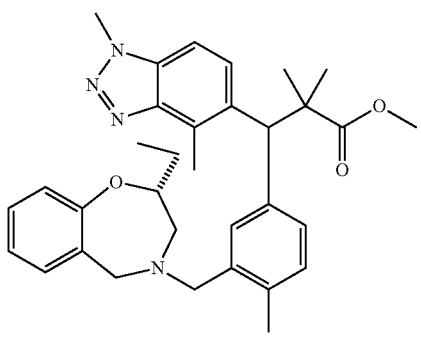 [SMILES: CC[C@@H]1CN(Cc2cc(C(c3ccc4c(nnn4C)c3C)C(C)(C)C(=O)OC)ccc2C)Cc2ccccc2O1]

To a solution of methyl 3-(1,4-dimethyl-1H-benzo[d][1,2,3]triazol-5-yl)-3-(3-formyl-4-methylphenyl)-2,2-dimethylpropanoate (70 mg, 0.184 mmol) in dichloromethane (DCM) (3 mL) was added (R)-2-ethyl-2,3,4,5-tetrahydrobenzo[f][1,4]oxazepine hydrochloride (59.1 mg, 0.277 mmol) under an argon atmosphere. The two reagents were stirred together for 1.5 h and then sodium triacetoxyborohydride (78 mg, 0.369 mmol) was added as the solid in one portion. The reaction was stirred for 30 min and was quenched with water (5 mL), diluted with CH$_2$Cl$_2$ (15 mL) and the layers separated. The organic layer was dried with sodium sulfate and concentrated. The residue was purified by flash chromatography eluting 0-100% EtOAc/Hexanes to provide the title compound. (0.040 g, 36% yield) LC-MS m/z 541 (M+H)+, 0.90 min (ret. time).

3-(1,4-Dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoic Acid, Lithium Salt

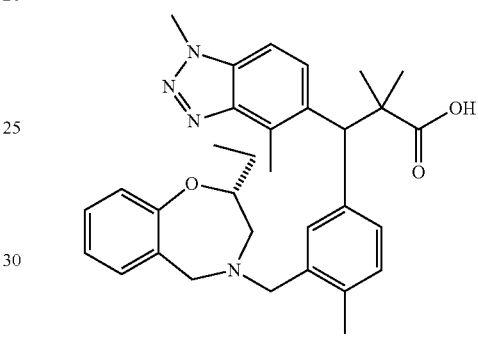

To a solution of methyl 3-(1,4-dimethyl-1H-benzo[d][1,2,3]triazol-5-yl)-3-(3-(((R)-2-ethyl-2,3-dihydrobenzo[f][1,4]oxazepin-4(5H)-yl)methyl)-4-methylphenyl)-2,2-dimethylpropanoate (80 mg, 0.148 mmol) in water (2.000 mL) and methanol (2.000 mL) was added lithium hydroxide (3.54 mg, 0.148 mmol) in a 5 mL microwave vial. The reaction was stirred at ambient temperature for 10 min to make a homogenous solution and then heated on the microwave for 90 min at 125° C. The reaction was purified by reverse phase preparative HPLC under neutral conditions to provide the title compound. (0.028 g, 36% yield) LC-MS m/z 527 (M+H)+, 0.86 min (ret. time).

Example 115

3-(3-(((R)-2-ethyl-2,3-dihydrobenzo[f][1,4]oxazepin-4(5H)-yl)methyl)-4-methylphenyl)-3-(4-fluoro-2-methylphenyl)-2,2-dimethylpropanoic Acid, Formic Acid Salt

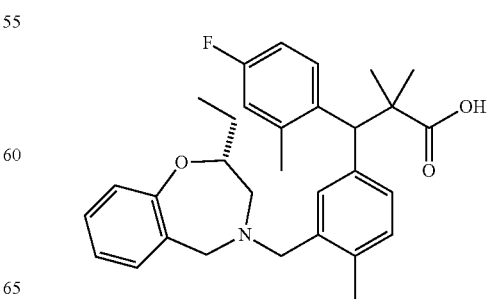

To a solution of methyl 3-(4-fluoro-2-methylphenyl)-3-(3-(hydroxymethyl)-4-methylphenyl)-2,2-dimethylpropanoate (110 mg, 0.319 mmol) in dichloromethane (DCM) (5 mL) was added thionyl chloride (0.047 mL, 0.639 mmol). The resulting mixture was stirred at room temperature for 1 h. The solvent was then removed by evaporation and the residue was redissolved in N,N-dimethylformamide (DMF) (5 mL). To that solution was added DIEA (0.223 mL, 1.278 mmol) and (R)-2-ethyl-2,3,4,5-tetrahydrobenzo[f][1,4]oxazepine hydrochloride (102 mg, 0.479 mmol). The reaction mixture was heated to 75° C. and stirred for 18 h. To the reaction mixture was added LiOH (38.2 mg, 1.597 mmol) and Water (5.00 mL) and heated to 60° C. for 18 h. The reaction has not progressed so the sample was heated in the Biotage microwave reactor at 120° C. for 3 h. The reaction mixture was acidified with formic acid and concentrated. The sample was purified by reverse phase preparative HPLC under acidic conditions to obtain mainly methyl 3-(3-(((R)-2-ethyl-2,3-dihydrobenzo[f][1,4]oxazepin-4(5H)-yl)methyl)-4-methylphenyl)-3-(4-fluoro-2-methylphenyl)-2,2-dimethylpropanoate. The ester was redissolved in water (5.00 mL) and N,N-dimethylformamide (DMF) (5 mL) and reexposed to LiOH (38.2 mg, 1.595 mmol) under the same microwave conditions as previously. The residue was concentrated and redissolved in minimal DMSO and purified by reverse phase preparative HPLC under acidic conditions to yield 3-(3-(((R)-2-ethyl-2,3-dihydrobenzo[f][1,4]oxazepin-4(5H)-yl)methyl)-4-methylphenyl)-3-(4-fluoro-2-methylphenyl)-2,2-dimethylpropanoic acid, formic acid salt (45 mg, 0.083 mmol, 26.0% yield) as a auburn oil. LC-MS m/z 490 (M+H)+, 0.99 min (ret. time).

Example 116

3-(1,4-Dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)propanoic Acid, Formic Acid Salt

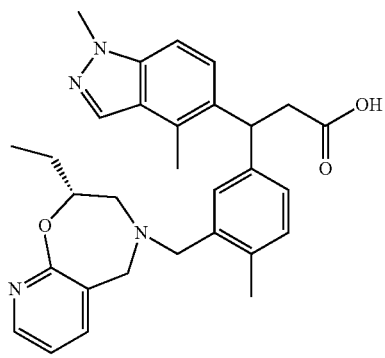 [SMILES: CC[C@@H]1CN(Cc2cc(C(CC(=O)O)c3ccc4c(cnn4C)c3C)ccc2C)Cc2cccnc2O1]

Ethyl 3-(1,4-dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)propanoate

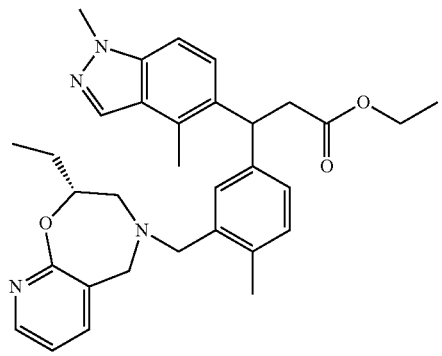 [SMILES: CCOC(=O)CC(c1ccc(C)c(CN2Cc3cccnc3O[C@H](CC)C2)c1)c1ccc2c(cnn2C)c1C]

To a solution of ethyl 3-(1,4-dimethyl-1H-benzo[d][1,2,3]triazol-5-yl)-3-(3-(hydroxymethyl)phenyl)propanoate (100 mg, 0.272 mmol) in DCM (2 mL) was added thionyl chloride (65 mg, 0.544 mmol) and stirred for 1 h. The solvent was concentrated and residue was redissolved in acetonitrile (4 mL) and (R)-2-ethyl-2,3,4,5-tetrahydropyrido[3,2-f][1,4]oxazepine (58 mg, 0.327 mmol) and DIEA (141 mg, 1.089 mmol) were added and heated via microwave at 120° C. The solvent was concentrated and the residue was purified via by flash chromatography eluting 0-50-70% (3:1 EtOAc:Ethanol)/Hexane to provide the title compound (15 mg, 10% yield). LC-MS m/z 528 (M+H)+, 0.82 min (ret. time).

3-(1,4-Dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)propanoic Acid, Formic Acid Salt

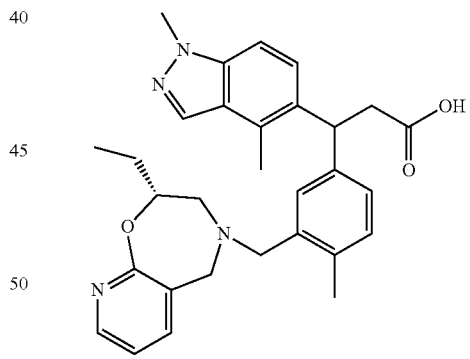

To a solution of ethyl 3-(1,4-dimethyl-1H-benzo[d][1,2,3]triazol-5-yl)-3-(3-(((R)-2-ethyl-2,3-dihydropyrido[3,2-f][1,4]oxazepin-4(5H)-yl)methyl)-4-methylphenyl)propanoate (15 mg, 0.028 mmol) in THF (2 mL)/water (1 mL) was added lithium hydroxide (3 mg, 0.125 mmol) and stirred at ambient temperature for 18 h. The reaction was then heated at 50° C. for 2 h. Additional lithium hydroxide (3 mg, 0.125 mmol) was added and the reaction was heated for 6 h and then for 18 h at ambient temperature. The reaction was then acidified with formic acid and the solvents were concentrated. The residue was purified by reverse phase preparative HPLC under acidic conditions to provide the title compound. (0.006 g, 42% yield) LC-MS m/z 500 (M+H)+, 0.69 min (ret. time).

Example 117

3-(2,4-Difluorophenyl)-3-(3-(((R)-2-ethyl-2,3-dihydrobenzo[f][1,4]oxazepin-4(5H)-yl)methyl)-4-methylphenyl)propanoic Acid, Formic Acid Salt

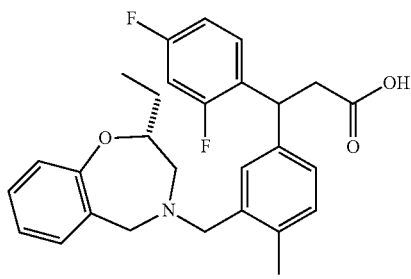 [SMILES: CC[C@@H]1CN(Cc2cc(C(CC(=O)O)c3ccc(F)cc3F)ccc2C)Cc2ccccc2O1]

(E)-Methyl 3-(2,4-difluorophenyl)acrylate

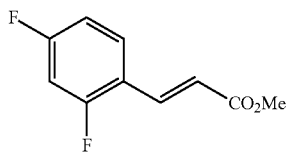

Trimethyl phosphonoacetate (1.425 mL, 8.80 mmol) in tetrahydrofuran (THF) (30 mL) was added KOtBu (0.987 g, 8.80 mmol) and stirred at room temperature for 10 min before adding 2,4-difluorobenzaldehyde (0.875 mL, 8 mmol) in tetrahydrofuran (THF) (5 mL). The resulting reaction mixture was stirred at room temperature for 160 min. To the reaction mixture was added more trimethyl phosphonoacetate (0.648 mL, 4.00 mmol) then KOtBu (0.449 g, 4.00 mmol). The resulting reaction mixture was stirred at room temperature for 30 min. The reaction mixture was added H$_2$O (20 mL), extracted with EtOAc (3×30 mL). The combined organic layer was washed with brine (20 mL), dried over MgSO$_4$, filtered and concentrated to give the title compound (1.5710 g, 7.93 mmol, 99% yield). LCMS: m/z: 199.1 (M-17)$^+$, 0.94 min (ret. time)

Methyl 3-(2,4-difluorophenyl)-3-(3-(hydroxymethyl)-4-methylphenyl)propanoate

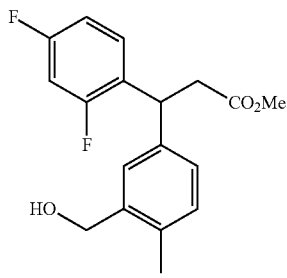 [SMILES: COC(=O)CC(c1ccc(C)c(CO)c1)c1ccc(F)cc1F]

(E)-methyl 3-(2,4-difluorophenyl)acrylate (396 mg, 2 mmol) in 1,4-dioxane (10 mL) and water (3 ml) was treated with (3-(hydroxymethyl)-4-methylphenyl)boronic acid (664 mg, 4.00 mmol), triethylamine (1.115 mL, 8.00 mmol) and [RhCl(cod)]$_2$ (49.3 mg, 0.100 mmol). The resulting reaction mixture was stirred at 90° C. for 19 h. The reaction mixture was extracted with EtOAc (3×15 mL). The combined organic layer was dried over MgSO$_4$, filtered and concentrated. The crude product was purified with silica gel chromatography to give the title compound (522.3 mg, 1.631 mmol, 82% yield). LCMS: m/z: 303.1 (M-17)$^+$, 0.98 min (ret. time)

3-(2,4-Difluorophenyl)-3-(3-(((R)-2-ethyl-2,3-dihydrobenzo[f][1,4]oxazepin-4(5H)-yl)methyl)-4-methylphenyl)propanoic Acid, Formic Acid Salt

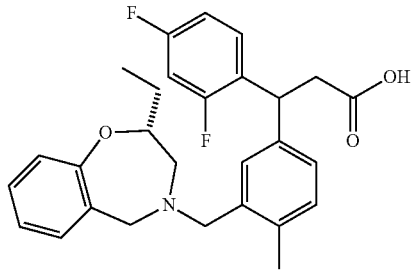 [SMILES: CC[C@@H]1CN(Cc2cc(C(CC(=O)O)c3ccc(F)cc3F)ccc2C)Cc2ccccc2O1]

To a solution of methyl 3-(2,4-difluorophenyl)-3-(3-(hydroxymethyl)-4-methylphenyl)propanoate (110 mg, 0.223 mmol) in dichloromethane (DCM) (5 mL) was added thionyl chloride (0.033 mL, 0.446 mmol). The resulting mixture was stirred at ambient temperature for 1 h. The solvent was then removed by evaporation and the residue was redissolved in N,N-dimethylformamide (DMF) (5 mL). To that solution was added DIEA (0.156 mL, 0.893 mmol) and (R)-2-ethyl-2,3,4,5-tetrahydrobenzo[f][1,4]oxazepine hydrochloride (71.6 mg, 0.335 mmol). The reaction mixture was heated to 75° C. and stirred for 18 h. Afterwards, LiOH (26.7 mg, 1.116 mmol) and water (5.00 mL) was added to the reaction mixture and heated to 60° C. for 18 h. The reaction mixture was acidified with formic acid and concentrated. The residue was purified by reverse phase preparative HPLC under acidic conditions to provide the title compound. (34.7 mg, 31.9% yield) LC-MS m/z 466 (M+H)$^+$, 0.96 min (ret. time) as a brown oil.

Example 118

5-(1-Ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid ISOMER 1

ISOMER 1

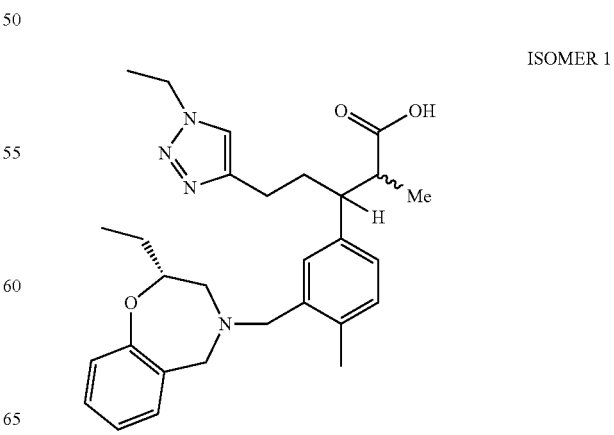

305

Pent-4-ynal

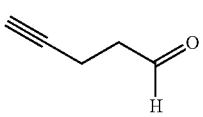

DMSO (5.58 g, 71.4 mmol) was added dropwise to a solution of oxalyl chloride (4.53 g, 35.7 mmol) in dichloromethane (DCM) (80 mL) at −78° C. The mixture was stirred at −78° C. for 15 min, pent-4-yn-1-ol (2.0 g, 23.8 mmol) in DCM (20 mL) was added dropwise to the reaction mixture and the mixture was stirred 15 min. Et$_3$N (10.84 g, 107.1 mmol) was added and the reaction mixture was stirred an additional 15 min, then the reaction mixture was warmed to 0° C. and quenched with water. The aqueous layer was extracted with DCM. The combined organic phase was washed with water, brine and dried over Na$_2$SO$_4$. The organic layer was concentrated, giving 0.6 g (31%) of the title compound. $^1$H NMR (400 MHz, CHLOROFORM-d) δ ppm 2.54 (td, J=7.03, 2.51 Hz, 2H); 2.68-2.76 (m, 2H); 4.72 (s, 1H); 9.83 (s, 1H).

(E)-Ethyl hept-2-en-6-ynoate

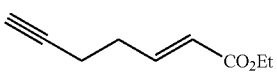

NaH (1.056 g, 26.4 mmol) was added in small portions to a solution of ethyl 2-(diethoxyphosphoryl)acetate (3.03 mL, 14.4 mmol) in DCM (15 mL). The mixture was stirred at 23° C. for 5 min, crude pent-4-ynal (0.985 g, ~1 mL, 12 mmol) in DCM (10 mL) was added slowly, and the mixture was stirred at 23° C. for 30 min. NH$_4$Cl (saturated aqueous) was added and the solution was extracted with DCM. The crude product was purified by silica gel chromatography to give the title compound (1.32 g, 72%). LC-MS m/z 153.0 (M+H)$^+$, 0.82 (ret. time).

(E)-ethyl 5-(1-ethyl-1H-1,2,3-triazol-4-yl)pent-2-enoate

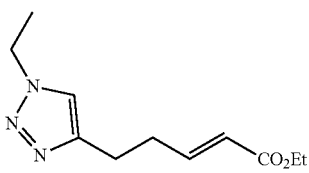

NaN$_3$ (0.085 g, 1.31 mmol), CuI (0.25 mg, 1.31 umol) and iodoethane (0.090 mL, 1.31 mmol) was added to a solution of (E)-ethyl hept-2-en-6-ynoate (0.2 g, 1.31 mmol) in water (5 mL), the mixture was stirred at 70° C. for 14 h. The mixture was concentrated and was purified by silica gel chromatography to give the title compound (100 mg, 34%). LC-MS m/z 224.1 (M+H)$^+$, 0.65 (ret. time).

306

Ethyl 5-(1-ethyl-1H-1,2,3-triazol-4-yl)-3-(3-(hydroxymethyl)-4-methylphenyl)pentanoate

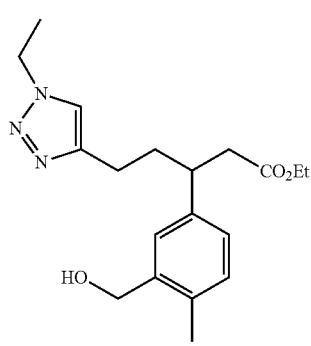 [SMILES: CCOC(=O)CC(CCc1cn(CC)nn1)c1ccc(C)c(CO)c1]

(3-(Hydroxymethyl)-4-methylphenyl)boronic acid (0.11 g, 0.67 mmol), Et$_3$N (0.094 mL, 0.67 mmol) and [RhCl (cod)]$_2$ (11 mg, 0.022 mmol) were added to a solution of (E)-ethyl 5-(1-ethyl-1H-1,2,3-triazol-4-yl)pent-2-enoate (0.1 g, 0.45 mmol) in 1,4-Dioxane (1 mL) and Water (0.5 mL). The reaction was heated in a microwave at 140° C. (high absorption) for 4 h. The mixture was concentrated and purified by silica gel chromatography to give the title compound (64 mg, 41%) Ethyl 5-(1-ethyl-1H-1,2,3-triazol-4-yl)-3-(3-(hydroxymethyl)-4-methylphenyl)pentanoate and 50 mg recovered (E)-ethyl 5-(1-ethyl-1H-1,2,3-triazol-4-yl)pent-2-enoate. LC-MS m/z 346.2 (M+H)$^+$, 0.81 (ret. time).

Ethyl 3-(3-(((tert-butyldimethylsilyl)oxy)methyl)-4-methylphenyl)-5-(1-ethyl-1H-1,2,3-triazol-4-yl)pentanoate

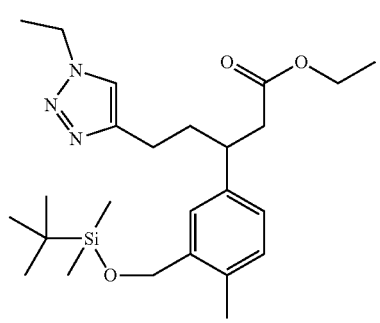 [SMILES: CCOC(=O)CC(CCc1cn(CC)nn1)c1ccc(C)c(CO[Si](C)(C)C(C)(C)C)c1]

To a solution of ethyl 5-(1-ethyl-1H-1,2,3-triazol-4-yl)-3-(3-(hydroxymethyl)-4-methylphenyl)pentanoate (4.2 g, 7.78 mmol) in N,N-Dimethylformamide (DMF) (30 mL) at 4° C. was added imidazole (2.483 g, 36.5 mmol) followed by tert-butyldimethylchlorosilane (3.21 g, 21.30 mmol). The reaction was allowed to stir for 2 h while warming from 4° C. to 23° C. slowly. The reaction was poured over ice water and extracted with DCM. Combined organic layers were washed with water before being concentrated. Crude residue was purified by silica gel chromatography to give the title compound (3.07 g, 6.68 mmol, 86% yield). LCMS m/z 460.2 [M+H]$^+$, 1.45 min (ret. time).

Ethyl 5-(1-ethyl-1H-1,2,3-triazol-4-yl)-3-(3-(hydroxymethyl)-4-methylphenyl)-2-methylpentanoate Major Diastereomer

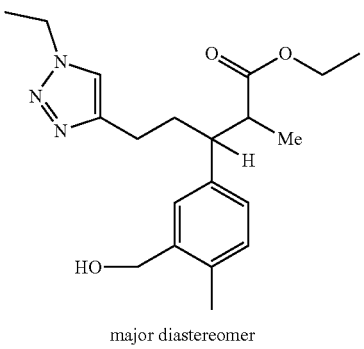 [SMILES: CCOC(=O)C(C)C(CCc1cn(CC)nn1)c1ccc(C)c(CO)c1]

major diastereomer

Diisopropylamine (0.341 mL, 2.393 mmol) in tetrahydrofuran (THF) (18 mL) was cooled to −78° C. and then 2M n-butyllithium (1.03 mL, 2.060 mmol) was added and the mixture was stirred at −78° C. for 45 min. Ethyl 3-(3-(((tert-butyldimethylsilyl)oxy)methyl)-4-methylphenyl)-5-(1-ethyl-1H-1,2,3-triazol-4-yl)pentanoate (1.0 g, 2.175 mmol) in tetrahydrofuran (THF) (18 mL) was added dropwise (T<−70° C.) and the resulting mix was kept at −70° C. for 45 min and then iodomethane (2.72 mL, 43.5 mmol) was added. The reaction was warmed slowly to 23° C. and stirred 30 min. The reaction was diluted with water (150 mL) and ethyl acetate (EtOAc) (3×75 mL). The combined EtOAc was washed with saturated aq NaCl (50 mL), dried (Na$_2$SO$_4$) and concentrated. The crude product was dissolved in THF (16 mL) and 1 M TBAF in THF (4 mL, 4.00 mmol) was added and stirred 16 h. The reaction was diluted with EtOAc (200 mL) and washed with water (75 mL) and saturated aqueous NaCl (50 mL), dried (Na$_2$SO$_4$) and concentrated to afford a yellow oil as a diastereomeric mixture of monomethyl alcohols and recovered starting materials. The crude product was dissolved in acetonitrile (4 mL), filtered and was purified by reverse-phase HPLC (with 0.1% TFA condition) to give the title compound as predominantly the major diastereomer ethyl 5-(1-ethyl-1H-1,2,3-triazol-4-yl)-3-(3-(hydroxymethyl)-4-methylphenyl)-2-methylpentanoate as an oil. This was resubmitted to reverse phase chromatography to afford pure major diastereomer (96 mg). LC-MS m/z=360.3 (M+H)$^+$ 0.87 (ret. time).

Enantiomer A (first to elute from SFC), Ethyl 5-(1-ethyl-1H-1,2,3-triazol-4-yl)-3-(3-(hydroxymethyl)-4-methylphenyl)-2-methylpentanoate

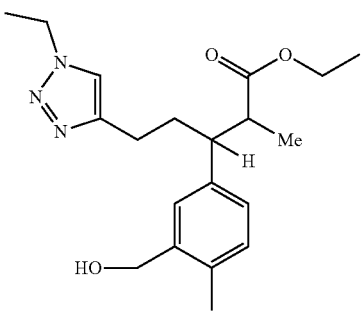

enantiomer A

Combined samples of the major diastereomer from the above separation and 4 methylation reactions run under similar conditions and diastereomer separations of the same substrate were combined to afford 550 mg of the major diastereomer ethyl 5-(1-ethyl-1H-1,2,3-triazol-4-yl)-3-(3-(hydroxymethyl)-4-methylphenyl)-2-methylpentanoate.

These were separated into the pure enantiomers by Chiral SFC (Chiralpak IC, 20×150, 5 u and co-solvent 25% IPA, total flow rate: 50 g/min, back pressure: 100 bar). The first enantiomer to elute was collected and dried. The dried compounds were transferred to pre-weighted 20 mL vial with IPA, and dried under N$_2$ stream at 45° C. to afford: Enantiomer A (first to elute from SFC), Ethyl 5-(1-ethyl-1H-1,2,3-triazol-4-yl)-3-(3-(hydroxymethyl)-4-methylphenyl)-2-methylpentanoate (141 mg). LC-MS m/z=360.2 (M+H+) 0.86 (ret. time). sfc λ=220 (nm), 2.61 (ret. time).

Enantiomer B (second to elute from SFC), Ethyl 5-(1-ethyl-1H-1,2,3-triazol-4-yl)-3-(3-(hydroxymethyl)-4-methylphenyl)-2-methylpentanoate

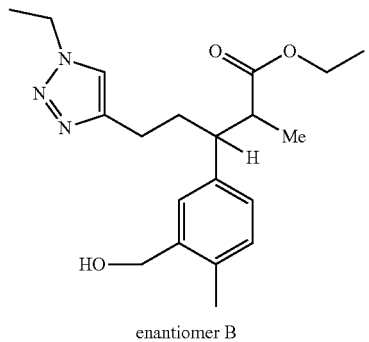 [SMILES: CCOC(=O)C(C)C(CCc1cn(CC)nn1)c1ccc(C)c(CO)c1]

enantiomer B

Enantiomer B (second to elute from SFC), ethyl 5-(1-ethyl-1H-1,2,3-triazol-4-yl)-3-(3-(hydroxymethyl)-4-methylphenyl)-2-methylpentanoate (136 mg). LC-MS m/z=360.2 0.86 (ret. time). SFC λ=220 (nm), 3.04 (ret. time)

Ethyl 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoate Enantiomer A Configuration)

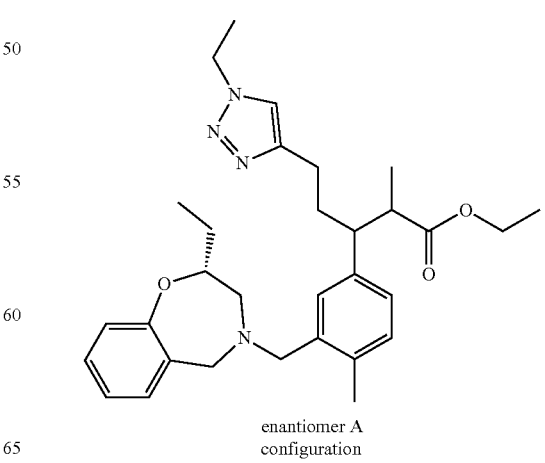

enantiomer A configuration

To a solution of Ethyl 5-(1-ethyl-1H-1,2,3-triazol-4-yl)-3-(3-(hydroxymethyl)-4-methylphenyl)-2-methylpentanoate (141 mg, 0.392 mmol) Enantiomer A (first to elute from sfc) in dichloromethane (DCM) (4 mL) was added thionyl chloride (0.100 mL, 1.373 mmol). The resulting mixture was stirred at 23 C for 1 h. DCM was removed in vacuo and N,N-dimethylformamide (DMF) (4.00 mL) was added. (R)-2-Ethyl-2,3,4,5-tetrahydrobenzo[f][1,4]oxazepine hydrochloride (126 mg, 0.588 mmol) and DIEA (0.274 mL, 1.569 mmol) were added and the mixture was heated to 75° C. for 1.5 h the reaction was cooled to 23° C. The reaction was partly concentrated in vacuo and the residual solution was diluted with EtOAc (75 mL) and ~0.5M aq NaOH (25 mL) shaken and separated. The aqueous phase was extracted again with EtOAc (25 mL) and the combined EtOAc was washed with water (25 mL) and satd aq NaCl (25 mL), dried (Na$_2$SO$_4$) filtered and concentrated. The crude product was dissolved in acetonitrile (~9.5 mL), filtered and then purified by reverse-phase HPLC (with 0.1% TFA condition) to give the title compound to afford ethyl 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoate (225 mg, 0.434 mmol, 111% yield) as a light green oil. LC-MS m/z=519.3 (M+H)$^+$, 0.95 (ret. time).

5-(1-Ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid ISOMER 1

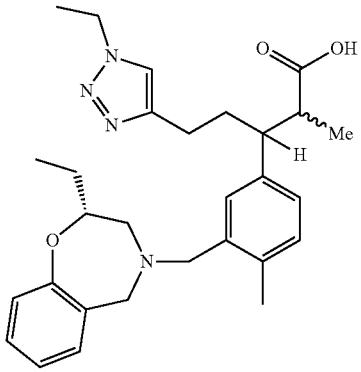

ISOMER 1

Ethyl 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoate (225 mg, 0.434 mmol) was dissolved in tetrahydrofuran (THF) (4. mL) and lithium hydroxide (208 mg, 8.68 mmol) dissolved in Water (4.00 mL) was added and then methanol (2 mL) was added. The resulting mixture was heated in a microwave at high setting at 100° C. for 30 min. Cooled to 23° C., a drop was diluted with water and acetonitrile to afford a clear solution. lcms indicated the desired product but only ~2/3 conversion based on uv214. Run for 90 min at 110° C. Reaction 100% converted. Volatile was partially removed in vacuo and the remaining basic aqueous solution was diluted with water (~10 mL) and washed with EtOAc (10 mL) and hexane (10 mL). The aqueous phase was combined with TFA (~0.5 mL), diluted to a total volume of 15 mL, filtered and then purified by reverse-phase HPLC (with 0.1% TFA condition) to give the title compound 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid (186 mg, 0.379 mmol, 87% yield). The diastereoisomers were separated by chiral SFC (Chiralpak AD, 20×250, 5 u 20% co-solvent: 20% IPA, total flow rate: 50 g/min, back pressure: 100 bar) to afford the first isomer to elute 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid ISOMER 1 (97 mg). LC-MS m/z=491.4 (MH$^+$), 0.82 (ret. time).SFC λ=220 (nm), 3.99 (ret. time)., Area %=100%

Example 119

5-(1-Ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic Acid Isomer 2

The second isomer to elute from the above sfc separation was 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid ISOMER 2 (10 mg). lcms m/z=491.4 (MH$^+$), 0.82 (ret. time). sfc λ=220 (nm), 5.58 (ret. time).

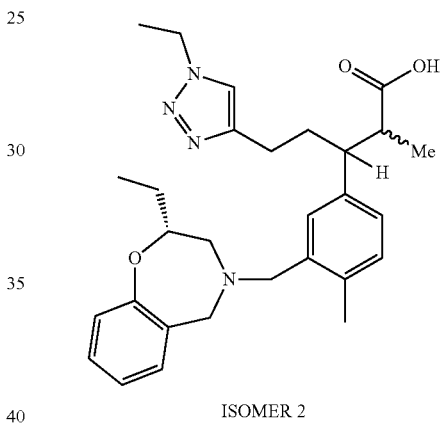

ISOMER 2

Example 120

5-(1-Ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic Acid Isomer 3

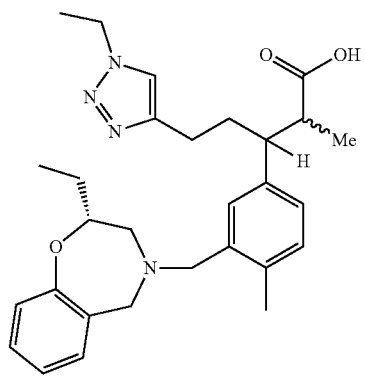

ISOMER 3

Ethyl 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoate Enantiomer B Configuration)

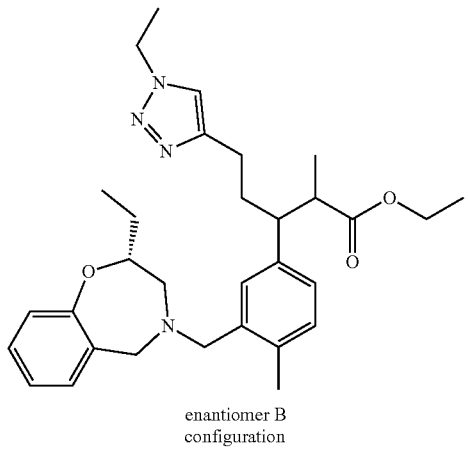 [SMILES: CCOC(=O)C(C)C(CCc1cn(CC)nn1)c1ccc(C)c(CN2Cc3ccccc3O[C@H](CC)C2)c1]

enantiomer B configuration

To a solution of Ethyl 5-(1-ethyl-1H-1,2,3-triazol-4-yl)-3-(3-(hydroxymethyl)-4-methylphenyl)-2-methylpentanoate (136 mg, 0.378 mmol) enantiomer B (second to elute from sfc) prepared as described in ethyl 5-(1-ethyl-1H-4(5H,2,3-triazol-4-yl)-3-(3-(hydroxymethyl)-4-methylphenyl)-2-methylpentanoate, in dichloromethane (DCM) (4 mL) was added thionyl chloride (0.097 mL, 1.324 mmol). The resulting mixture was stirred at 23 C for 2.5 h and the reaction was concentrated and the residue was dissolved in N,N-dimethylformamide (DMF) (4.00 mL) to which was added DIEA (0.26 mL, 1.513 mmol) and (R)-2-ethyl-2,3,4,5-tetrahydrobenzo[f][1,4]oxazepine hydrochloride (121 mg, 0.568 mmol) and the mixture was heated to 75° C. for 1 h. The reaction was partly concentrated in vacuo and the residual solution was diluted with EtOAc (75 mL) and 0.5M aq NaOH (25 mL) shaken and separated. The aq phase was extracted again with EtOAc (25 mL) and the combined EtOAc was washed with water (25 mL) and saturated aqueous NaCl (25 mL), dried (Na$_2$SO$_4$) filtered. The crude product was purified by flash chromatography on a silica gel chromatography to give the title compound (158 mg, 0.305 mmol, 81% yield). LC-MS m/z=519.4 (M+H*), 0.94 (ret. time).

5-(1-Ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic Acid ISOMER 3

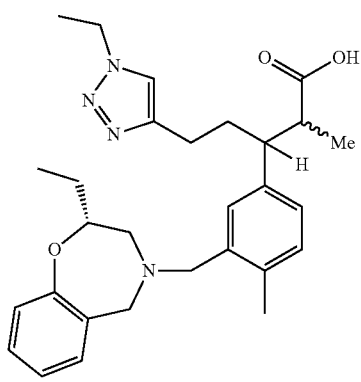

ISOMER 3

Ethyl 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoate (158 mg, 0.305 mmol) was dissolved in tetrahydrofuran (THF) (4.0 mL) and LiOH (146 mg, 6.09 mmol) dissolved in water (4.0 mL) and methanol (2.0 mL) and the resulting mixture was heated in a microwave at high setting at 100° C. for 30 min. Cooled, a drop was diluted with water and acetonitrile to afford a clear solution. lcms indicated the desired product but only 2/3 conversion based on uv-214. Re-run for 1 h at 110 C. Volatile was partially removed in vacuo and the remaining basic aq solution was diluted with water (10 mL) and washed with EtOAc (10 mL) and hexane (10 mL). The aqueous phase was combined with TFA (~0.5 mL), diluted to a total volume of 15 mL, filtered through a 0.45 mm acrodisc, and injected in 4 portions onto Gilson HPLC (Sunfire C18, 5 m 30×250 mm), eluting at 30 mL/min with a linear gradient running from 10% CH3CN/H2O (0.1% TFA) to 90% CH3CN/H2O (0.1% TFA) over 10 min to afford 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid (63 mg, 0.128 mmol, 42.2% yield) The isomers were separated by chiral SFC (Chiralpak AD, 20×250, 5 u 20% co-solvent: 20% IPA, total flow rate: 50 g/min, Back pressure: 100 bar) to afford the first isomer to elute 5-(1-ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid ISOMER 3 (28 mg). LC-MS m/z=491.4 (M+H*), 0.82 (ret. time). sfc λ=220 (nm), 5.17 (ret. time)

Example 121

(S)-3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate, Sodium Salt

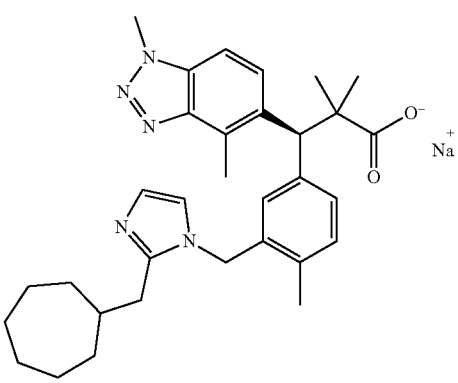

Methyl 2-cycloheptylacetate

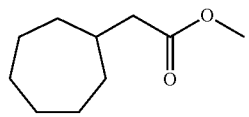

To a solution of 2-cycloheptylacetic acid (4.76 g, 30.5 mmol) in methanol (50 mL) was added sulfuric acid (2.99 g, 30.5 mmol) slowly. Then it was stirred at 70° C. for 16 h. After it was cooled to ambient temperature, the reaction mixture was added to 50 mL of water and extracted with ethyl acetate (3×50 mL), washed with brine, concentrated to obtain the title compound methyl 2-cycloheptylacetate (5.18 g, 28.3 mmol, 92.9% yield). LCMS m/z 171.2 (M+H)$^+$, 1.82 min (Ret. time)

2-Cycloheptylethanol

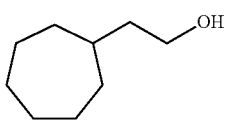

To a solution of methyl 2-cycloheptylacetate (4.33 g, 25.4 mmol) in tetrahydrofuran (THF) (20 mL) was added lithium aluminum hydride (1.931 g, 50.9 mmol) slowly under nitrogen at 0° C. and stirred for 1 hour. Then the reaction mixture was stirred at 25° C. for 16 hours. Then 30 mL of HCl (3 M) was added, extracted with EtOAc (3×30 mL), washed with brine, dried over MgSO$_4$ and concentrated to obtain the title compound 2-cycloheptylethanol (3.28 g, 20.75 mmol, 82% yield) as a white oil. $^1$H NMR (400 MHz, DMSO-d$_6$) L=4.26 (t, J=4.9 Hz, 1H), 3.41 (q, J=5.9 Hz, 2H), 1.73-1.29 (m, 13H), 1.22-1.08 (m, 2H)

2-Cycloheptylacetaldehyde

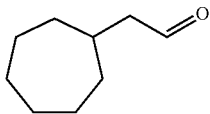

To a solution of 2-cycloheptylethanol (3.28 g, 23.06 mmol) in dichloromethane (DCM) (50 mL) was added PCC (7.46 g, 34.65 mmol) and silica gel (15 g). The reaction mixture was stirred at 25° C. for 16 h. Then it was filtered through a pad of celite. The filtrate was concentrated under vacuum. The crude product was purified by silica gel chromatography (EtOAC:Hexane=1:5) to obtain the title compound 2-cycloheptylacetaldehyde (1.30 g, 8.81 mmol, 38.2% yield) as a yellow oil. $^1$H NMR (400 MHz, CDCl$_3$) δ=9.74 (s, 1H), 2.32-1.28 (m, 15H).

2-(Cycloheptylmethyl)-1H-imidazole

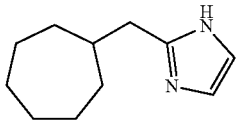 [SMILES: c1c[nH]c(CC2CCCCCC2)n1]

To a solution of 2-cycloheptylacetaldehyde (1.2 g, 8.56 mmol) in methanol (36 mL) and water (36 mL) was added oxaldehyde (0.993 g, 17.12 mmol) and ammonia hydrate (2.189 g, 62.5 mmol). The reaction mixture was stirred at 0° C. for 2 h, then it was stirred at ambient temperature for 18 h. The solid was filtered and dried under vacuum to obtain the title compound 2-(cycloheptylmethyl)-1H-imidazole (680 mg, 3.43 mmol, 40.1% yield) as a white solid. LCMS m/z 179.2 (M+H)$^+$, 1.22 min (ret. time)

(S)-3-(3-((2-(Cycloheptylmethyl)-1H-imidazol-1-yl) methyl)-4-methylphenyl)-3-(1,4-dimethyl-1H-benzo [d][1,2,3]triazol-5-yl)-2,2-dimethylpropanoate, Sodium Salt

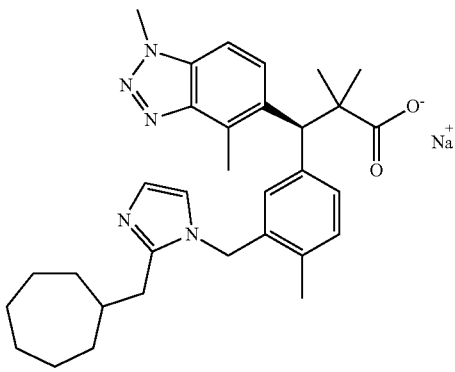

To a solution of 2-(cycloheptylmethyl)-1H-imidazole (145 mg, 0.813 mmol) in N,N-dimethylformamide (DMF) (5 mL) was added NaH (62.5 mg, 1.563 mmol). The mixture was stirred at 25° C. for 40 min. A solution of (S)-methyl 3-(3-(chloromethyl)-4-methylphenyl)-3-(1,4-dimethyl-1H-benzo[d][1,2,3]triazol-5-yl)-2,2-dimethylpropanoate (250 mg, 0.625 mmol) in N,N-dimethylformamide (DMF) (3 mL) was added. The mixture was stirred at ambient temperature for 20 h. It was quenched with saturated NH$_4$Cl, extracted with ethyl acetate twice. The combined organic layer was concentrated to give the crude product. It was purified by silica gel chromatography. Desired fractions were concentrated and re-dissolved in methanol (5.00 mL). LiOH (1.875 mL, 3.75 mmol) was added and the mixture was heated in a Biotage microwave at high absorption for 6 h at 120° C. It was acidified with 1N HCl to pH~1. 5 mL DMSO was added and the solvent was concentrated. The crude product was purified by reverse-phase HPLC (with 0.1% TFA condition) to give the title compound as TFA salt. It was re-dissolved in ethyl acetate (10 mL), extracted with saturated NaHCO$_3$. The aqueous layer was extracted with ethyl acetate. The combined organic layer was dried over sodium sulfate, filtered and then concentrated to give title compound (142 mg, 0.258 mmol, 41.3% yield) as solid. LC-MS m/z 528.3 (M+H)$^+$, 0.87 min (ret. time)

The compounds in Table 14 were prepared by a method similar to the one described for the preparation of (S)-3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate, sodium salt. As is appreciated by those skilled in the art, these analogous examples may involve variations in general reaction conditions.

TABLE 14

| Ex # | Structure | Name | LCMS [M + H]+ | Retention Time (min) |
|---|---|---|---|---|
| Example 122 | 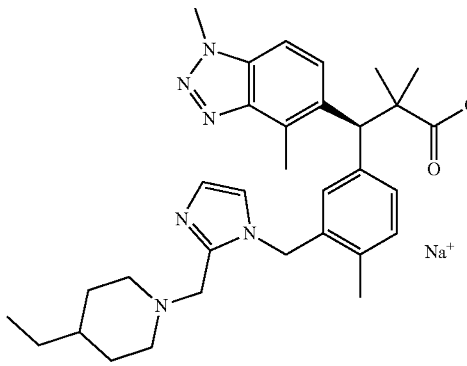 | (S)-3-(1,4-Dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoate, Sodium salt | 543.5 | 0.76 |
| Example 123 | 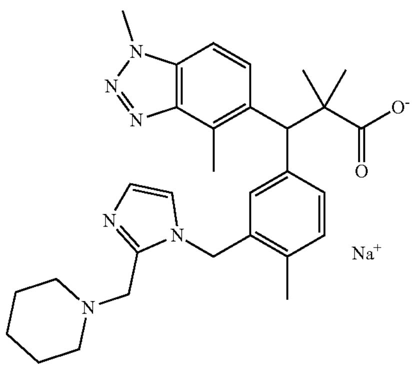 [SMILES: Cc1ccc(C(c2ccc3c(nnn3C)c2C)C(C)(C)C(=O)[O-])cc1Cn1ccnc1CN1CCCCC1 ; [Na+]] | 3-(1,4-Dimethyl-1H-benzo[d][1,2,3]triazol-5-yl)-2,2-dimethyl-3-(4-methyl-3-((2-(piperidin-1-ylmethyl)-1H-imidazol-1-yl)methyl)phenyl) propanoate, Sodium salt | 515.4 | 0.67 |
| Example 124 | 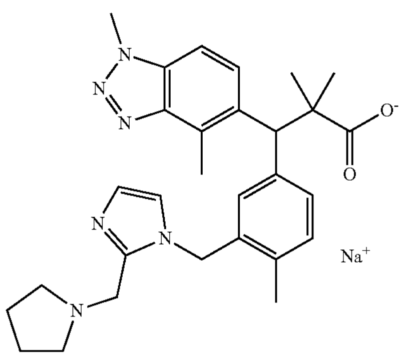 [SMILES: Cc1ccc(C(c2ccc3c(nnn3C)c2C)C(C)(C)C(=O)[O-])cc1Cn1ccnc1CN1CCCC1 ; [Na+]] | 3-(1,4-Dimethyl-1H-benzo[d][1,2,3]triazol-5-yl)-2,2-dimethyl-3-(4-methyl-3-((2-(pyrrolidin-1-ylmethyl)-1H-imidazol-1-yl)methyl)phenyl) propanoate, Sodium salt | 515.5 | 0.81 |
| Example 125 | 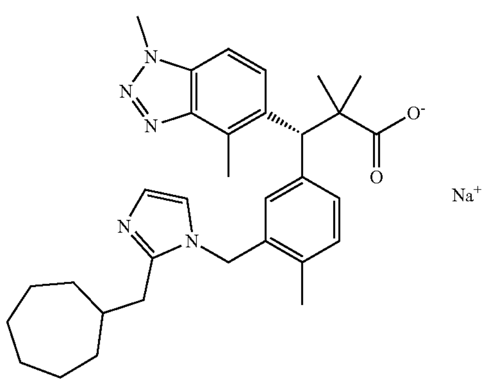 [SMILES: Cc1ccc([C@H](c2ccc3c(nnn3C)c2C)C(C)(C)C(=O)[O-])cc1Cn1ccnc1CC1CCCCCC1 ; [Na+]] | (R)-3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate, Sodium salt | 528.3 | 0.85 |

TABLE 14-continued

| Ex # | Structure | Name | LCMS [M + H]+ | Retention Time (min) |
|---|---|---|---|---|
| Example 126 | 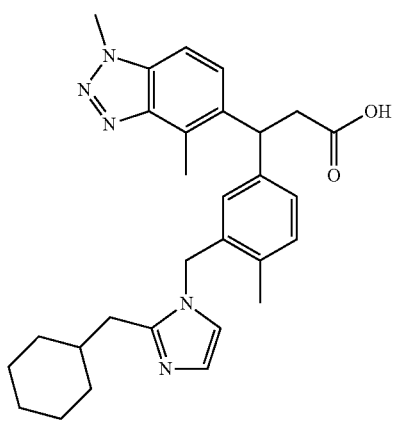 [SMILES: Cc1ccc(C(CC(=O)O)c2ccc3c(nnn3C)c2C)cc1Cn1ccnc1CC1CCCCC1] | (S)-3-(3-((2-(Azepan-1-ylmethyl)-1H-imidazol-1-yl)methyl)-4-methylphenyl)-3-(1,4-dimethyl-1H-benzo[d][1,2,3]triazol-5-yl)-2,2-dimethylpropanoate, Sodium salt | 529.3 | 0.77 |

Example 127

3-(3-((2-(Cyclohexyl methyl)-1H-imidazol-1-yl)methyl)-4-methylphenyl)-3-(1,4-dimethyl1H-benzo[d][1,2,3]triazol-5-yl)propanoic Acid 2-(Cyclohexylmethyl)-1H-imidazole

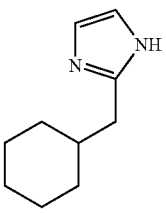

To a solution of oxalaldehyde (3.22 g, 22.19 mmol) in water (30 mL) was added 2-cyclohexylacetaldehyde (2.8 g, 22.19 mmol). After the resultant solution was cooled to 10° C. in an ice/water bath, ammonium hydroxide (0.4 ml, 2.88 mmol) was added and the reaction stirred for 18 hrs. The resulting precipitate was filtered and dried under the vacuum to afford the title compound 2-(cyclohexylmethyl)-1H-imidazole (520 mg, 3.17 mmol, 14.27% yield). LC-MS m/z 165.2 (M+H)+, 1.16 (ret. time).

3-(3-((2-(Cyclohexyl methyl)-1H-imidazol-1-yl)methyl)-4-methylphenyl)-3-(1,4-dimethyl-1H-benzo[d][1,2,3]triazol-5-yl)propanoic Acid 2-Cyclohexylacetaldehyde

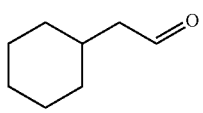

To a solution of 2-cyclohexylethanol (1.0 g, 7.80 mmol) in dichloromethane (DCM) (50 mL), was added PCC (2.52 g, 11.70 mmol). The reaction mixture was stirred at ambient temperature for 2 hrs after which it was diluted with diethyl ether (500 mL) and was stirred at ambient temperature for 1 hr and filtered through a pad of celite and silica gel (1:1). The filtrate was concentrated to give the title compound 2-cyclohexylacetaldehyde (570 mg, 4.52 mmol, 57.9% yield). 1H NMR (400 MHz, CHCL3-d) ∟ ppm 1.15 (m, 2H), 1.28 (m, 3H), 1.73 (m, 5H), 1.91 (m, 1H), 2.30 (d, J=2.0 Hz, 2H), 9.75 (s, 1H).

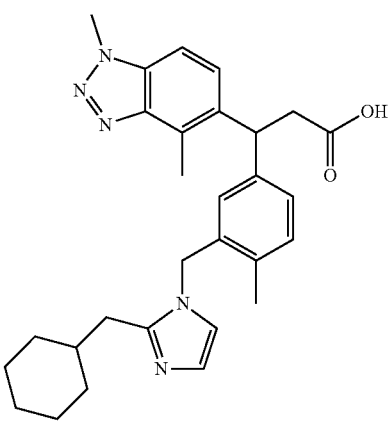 [SMILES: Cc1ccc(C(CC(=O)O)c2ccc3c(nnn3C)c2C)cc1Cn1ccnc1CC1CCCCC1]

To a solution of 2-(cyclohexylmethyl)-1H-imidazole (200 mg, 1.218 mmol) in N,N-dimethylformamide (DMF) (30 mL) was added NaH (73.1 mg, 1.827 mmol) at 00° C. The reaction mixture was stirred at 00° C. for 1 hr after which ethyl 3-(3-(bromomethyl)-4-methylphenyl)-3-(1,4-dimethyl-1H-benzo[d][1,2,3]triazol-5-yl)propanoate (210 mg, 0.487 mmol) was added to the reaction mixture. The reaction mixture was stirred at 00° C. for 4 hrs. Water (20 mL) was added and the reaction extracted with ethyl acetate (3×30 mL). The combined organic layer was washed with water and brine, dried with MgSO$_4$ and concentrated to give a crude product that was purified by preparative HPLC to afford the title compound 3-(3-((2-(cyclohexylmethyl)-1H-imidazol-1-yl)methyl)-4-methylphenyl)-3-(1,4-dimethyl-1H-benzo[d][1,2,3]triazol-5-yl)propanoic acid (75 mg, 0.151 mmol, 12.42% yield). LC-MS m/z 486.4 (M+H)$^+$, 1.43 (ret. time).

Example 128

3-(3-((1-(Cyclohexyl methyl)-1H-1,2,3-triazol-5-yl)methyl)-4-methylphenyl)-3-(1,4-dimethyl-1H-benzo[d][1,2,3]triazol-5-yl)propanoic acid

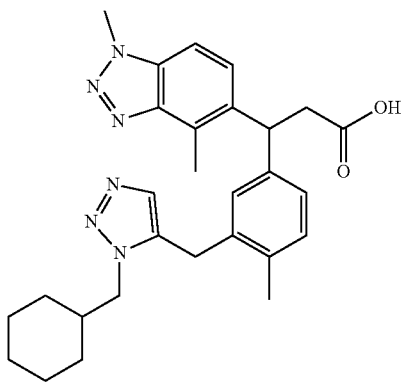 [SMILES: Cc1ccc(C(CC(=O)O)c2ccc3c(nnn3C)c2C)cc1Cc1cnnn1CC1CCCCC1]

1-(Cyclohexylmethyl)-1H-1,2,3-triazole

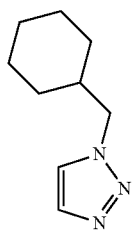 [SMILES: c1cn(CC2CCCCC2)nn1]

To a solution of 1H-1,2,3-triazole (2.5 g, 36.2 mmol) in N,N-dimethylformamide (DMF) (30 mL), (bromomethyl)cyclohexane (7.69 g, 43.4 mmol) was added Cs$_2$CO$_3$ (23.59 g, 72.4 mmol) and sodium iodide (5.43 g, 36.2 mmol). The reaction mixture was stirred at 100° C. for 2 hrs after which the reaction mixture was cooled to ambient temperature and filtered. The filtrate was concentrated and was purified by silica gel chromatography (petroleum ether:ethyl acetate=2:1) to afford the title compound 1-(cyclohexylmethyl)-1H-1,2,3-triazole (1.0 g, 6.05 mmol, 16.72% yield). LC-MS m/z 166.1 (M+H)$^+$, 1.52 (ret. time).

Ethyl 3-(3-((1-(cyclohexylmethyl)-1H-1,2,3-triazol-5-yl)methyl)-4-methylphenyl)-3-(1,4-dimethyl-1H-benzo[d][1,2,3]triazol-5-yl)propanoate

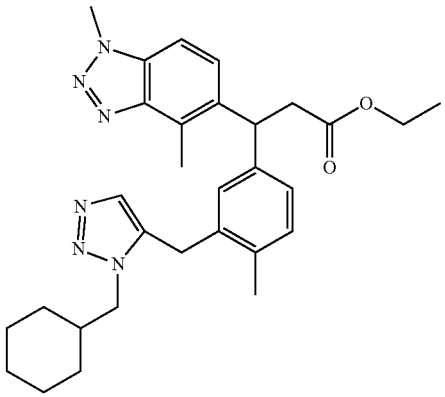 [SMILES: CCOC(=O)CC(c1ccc(C)c(Cc2cnnn2CC2CCCCC2)c1)c1ccc2c(nnn2C)c1C]

To a solution of 1-(cyclohexylmethyl)-1H-1,2,3-triazole (110 mg, 0.666 mmol) in tetrahydrofuran (THF) (20 mL) was added nBuLi (0.250 mL, 0.599 mmol) dropwise at −70° C. The reaction mixture was stirred at that temperature for 30 min after which ethyl 3-(3-(bromomethyl)-4-methylphenyl)-3-(1,4-dimethyl-1H-benzo[d][1,2,3]triazol-5-yl)propanoate (100 mg, 0.232 mmol) in THF (2 ml) was added at −70° C. The reaction mixture was stirred for another 1 hr. After the reaction mixture was warmed to ambient temperature, 20 mL of water was added and the mixture extracted with ethyl acetate (3×30 mL). The combined organic layers were washed with water and brine, dried with MgSO$_4$ and concentrated to give a crude product that was purified by preparative HPLC to afford the title compound ethyl 3-(3-((1-(cyclohexylmethyl)-1H-1,2,3-triazol-5-yl)methyl)-4-methylphenyl)-3-(1,4-dimethyl-1H-benzo[d][1,2,3]triazol-5-yl)propanoate (87 mg, 0.169 mmol, 25.4% yield). LC-MS m/z 515.2 (M+H)$^+$, 2.72 (ret. time).

3-(3-((1-(Cyclohexyl methyl)-1H-1,2,3-triazol-5-yl)methyl)-4-methylphenyl)-3-(1,4-dimethyl-1H-benzo[d][1,2,3]triazol-5-yl)propanoic Acid

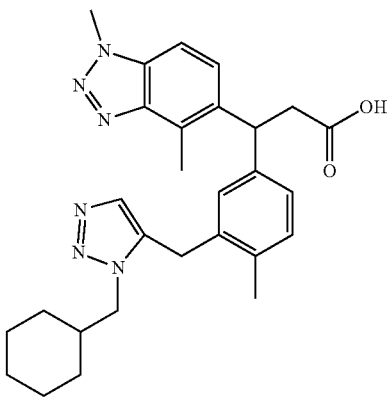 [SMILES: Cc1ccc(C(CC(=O)O)c2ccc3c(nnn3C)c2C)cc1Cc1cnnn1CC1CCCCC1]

To a solution of ethyl 3-(3-((1-(cyclohexylmethyl)-1H-1,2,3-triazol-5-yl)methyl)-4-methylphenyl)-3-(1,4-dimethyl-1H-benzo[d][1,2,3]triazol-5-yl)propanoate (79 mg, 0.153 mmol) in tetrahydrofuran (THF) (10 mL) and water (4 mL) was added LiOH (160 mg, 6.68 mmol). The reaction mixture was stirred at 40° C. for 20 h. The reaction mixture was acidified with HCl (1 N) and the mixture extracted with ethyl acetate (3×20 mL). The combined organic layers were dried with MgSO₄ and concentrated to provide a crude product that was purified by preparative HPLC to afford the title compound 3-(3-((1-(cyclohexylmethyl)-1H-1,2,3-triazol-5-yl)methyl)-4-methylphenyl)-3-(1,4-dimethyl-1H-benzo[d][1,2,3]triazol-5-yl)propanoic acid (32 mg, 0.066 mmol, 42.8% yield). LC-MS m/z 487.3 (M+H)$^+$, 1.62 (ret. time).

Example 129

3-(1,4-Dimethyl-1H-Benzo[d][1,2,3]triazol-5-yl)-3-(4-methyl-3-((2-((tetrahydro-2H-pyran-4-yl)methyl)-1H-imidazol-1-yl)methyl)phenyl)propanoic Acid

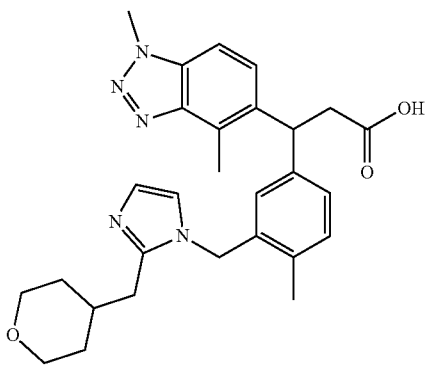 [SMILES: Cc1ccc(C(CC(=O)O)c2ccc3c(nnn3C)c2C)cc1Cn1ccnc1CC1CCOCC1]

2-((Tetrahydro-2H-pyran-4-4yl)methyl)-1H-imidazole

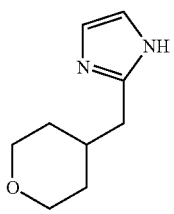 [SMILES: c1c[nH]c(CC2CCOCC2)n1]

To a solution of oxalaldehyde (340 mg, 2.341 mmol) in water (3.6 mL) was added 2-(tetrahydro-2H-pyran-4-yl)acetaldehyde (300 mg, 2.341 mmol). The resulting solution was cooled to 10° C. in an ice/water bath after which ammonium hydroxide (0.4 ml, 2.88 mmol) was added. The reaction mixture was stirred for 18 h and the resulting precipitate was filtered and dried under vacuum to afford the title compound 2-((tetrahydro-2H-pyran-4-yl)methyl)-1H-imidazole (150 mg, 0.902 mmol, 38.6% yield). LC-MS m/z 167.2 (M+H)$^+$, 0.32 (ret. time).

Ethyl 3-(1,4-dimethyl-1H-benzo[d][1,2,3]triazol-5-yl)-3-(4-methyl-3-((2-((tetrahydro-2H-pyran-4-yl)methyl)-1H-imidazol-1-yl)methyl)phenyl)propanoate

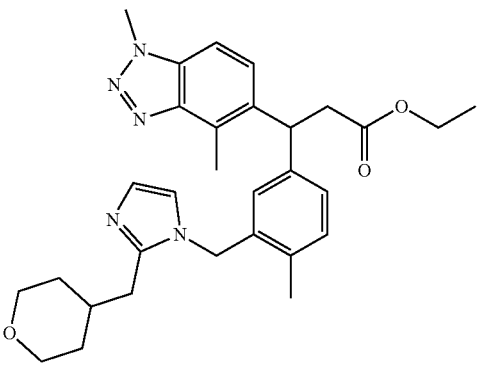 [SMILES: CCOC(=O)CC(c1ccc(C)c(Cn2ccnc2CC2CCOCC2)c1)c1ccc2c(nnn2C)c1C]

To a solution of 2-((tetrahydro-2H-pyran-4-yl)methyl)-1H-imidazole (57.9 mg, 0.349 mmol) in N,N-dimethylformamide (DMF) (3.0 mL) was added DIPEA (0.183 mL, 1.046 mmol) and ethyl 3-(3-(bromomethyl)-4-methylphenyl)-3-(1,4-dimethyl-1H-benzo[d][1,2,3]triazol-5-yl)propanoate (150 mg, 0.349 mmol). The reaction mixture was stirred at 100° C. for 4 hrs after which the reaction mixture was concentrated under reduced pressure and purified by preparative HPLC (50% MeOH/H₂O) to afford the title compound ethyl 3-(1,4-dimethyl-1H-benzo[d][1,2,3]triazol-5-yl)-3-(4-methyl-3-((2-((tetrahydro-2H-pyran-4-yl)methyl)-1H-imidazol-1-yl)methyl)phenyl)propanoate (100 mg, 0.194 mmol, 55.6% yield). LC-MS m/z 516.3 (M+H)$^+$, 1.42 (ret. time).

3-(1,4-Dimethyl-1H-benzo[d][1,2,3]triazol-5-yl)-3-(4-methyl-3-((2-((tetrahydro-2H-pyran-4-yl)methyl)-1H-imidazol-1-yl)methyl)phenyl)propanoic Acid

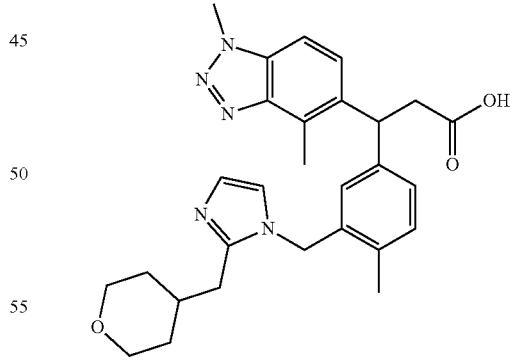

To a solution of ethyl 3-(1,4-dimethyl-1H-benzo[d][1,2,3]triazol-5-yl)-3-(4-methyl-3-((2-((tetrahydro-2H-pyran-4-yl)methyl)-1H-imidazol-1-yl)methyl)phenyl)propanoate (85 mg, 0.165 mmol) in methanol (5 mL) was added a solution of NaOH (19.78 mg, 0.495 mmol) in H₂O (1 mL). The reaction mixture was stirred at 20° C. for 4 hrs. The reaction mixture was concentrated and the residue was acidified with 1N HCl to pH=3. The crude product was purified by preparative HPLC (50% MeOH/H₂O) to afford the title compound 3-(1,4-dimethyl-1H-benzo[d][1,2,3]triazol-5-yl)-3-(4-methyl-3-((2-(((tetrahydro-2H-pyran-4-yl)methyl)-1H-imidazol-1-yl)methyl)phenyl)propanoic acid (45 mg, 0.090 mmol, 54.3% yield). LC-MS m/z 488.3 (M+H)⁺, 1.18 (ret. time).

Example 130

3-(3-((2-(Cyclohexylmethyl)-1H-imidazol-1-yl)methyl)-4-methylphenyl)-5-(1-methyl-1H-1,2,3-triazol-4-yl)pentanoic Acid

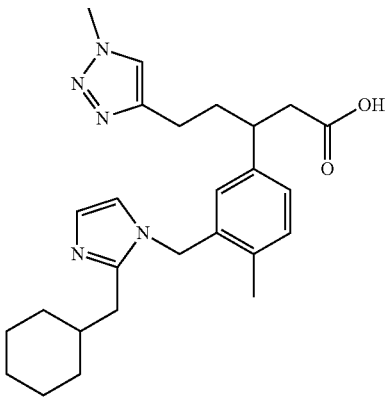 [SMILES: Cc1ccc(C(CCc2cn(C)nn2)CC(=O)O)cc1Cn1ccnc1CC1CCCCC1]

(E)-Ethyl hept-2-en-6-ynoate

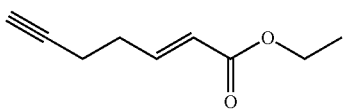

To a solution of ethyl 2-(diethoxyphosphoryl)acetate (24.03 g, 107 mmol) in tetrahydrofuran (THF) (150 mL) was added sodium hydride (4.68 g, 117 mmol)) in small portions. After the reaction mixture was stirred for 5 mins, pent-4-ynal (8.0 g, 97 mmol) was added slowly and the mixture stirred at ambient temperature for 30 mins after which NH₄Cl (sat. aq.) was added and the reaction mixture was extracted with DCM. The organic layer was washed with brine, dried with MgSO₄ and concentrated. The residue was purified via silica gel chromatography with PE/EA=50/1 to give the title compound (E)-ethyl hept-2-en-6-ynoate (12 g, 79 mmol, 81% yield). ¹H NMR (400 MHz, CHCl₃-d) δ ppm 1.29 (t, 3H), 2.01 (s, 1H), 2.41 (m, 4H), 4.21 (q, 2H), 5.87 (d, 1H), 6.96 (m, 1H).

(E)-Ethyl 5-(1-methyl-1H-1,2,3-triazol-4-yl)pent-2-enoate

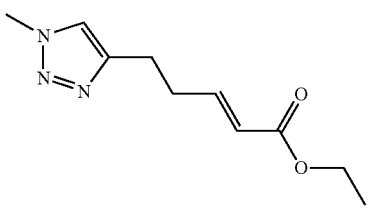

A mixture of methyl iodide (4.93 mL, 79 mmol), (E)-ethyl hept-2-en-6-ynoate (4.0 g, 26.3 mmol), sodium azide (5.13 g, 79 mmol), DIPEA (4.59 mL, 26.3 mmol) and copper(I) iodide (0.050 g, 0.263 mmol) in water (10 mL) and THF (20 mL) were stirred at 70° C. for 2 hrs. The reaction mixture was concentrated and the residue was extracted with ethyl acetate (3×50 mL). The combined organic layer was dried with MgSO₄ and concentrated. The crude product was purified by preparative HPLC to afford the title compound (E)-ethyl 5-(1-methyl-1H-1,2,3-triazol-4-yl)pent-2-enoate (3.0 g, 13.62 mmol, 51.8% yield). LC-MS m/z 210.1 (M+H)⁺, 1.35 (ret. time).

Ethyl 3-(3-(hydroxymethyl)-4-methylphenyl)-5-(1-methyl-1H-1,2,3-triazol-4-yl)pentanoate OH

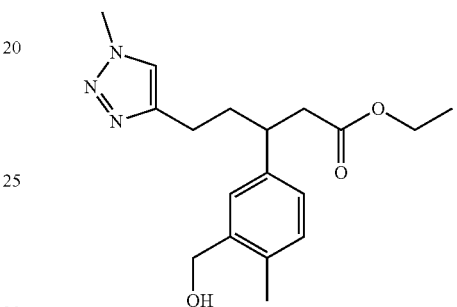

To a suspension of (E)-ethyl 5-(1-methyl-1H-1,2,3-triazol-4-yl)pent-2-enoate (200 mg, 0.956 mmol), (2-methyl-5-(4,4,5,5-tetramethyl-1,3,2-dioxaborolan-2-yl)phenyl)methanol (711 mg, 2.87 mmol) and Et₃N (0.799 mL, 5.73 mmol) in a mixture of 1,4-dioxane (5 mL) and water (2 mL) at ambient temperature was added chloro(1,5-cyclooctadiene)rhodium(I) dimer (23.56 mg, 0.048 mmol). The resulting suspension was heated at 95° C. for 10 hrs. The reaction mixture was diluted with water (30 mL) and the mixture extracted with EtOAc (3×30 mL). The combined organic phases were washed with water, brine, dried over MgSO₄ and concentrated. The crude product was purified by silica gel chromatography (petroleum ether:ethyl acetate=2:1) to afford the title compound ethyl 3-(3-(hydroxymethyl)-4-methylphenyl)-5-(1-methyl-1H-1,2,3-triazol-4-yl)pentanoate (120 mg, 0.362 mmol, 37.9% yield). LC-MS m/z 322.3 (M+H)⁺, 1.13 (ret. time).

Ethyl 3-(3-(chloromethyl)-4-methylphenyl)-5-(1-methyl-1H-1,2,3-triazol-4-yl)pentanoate

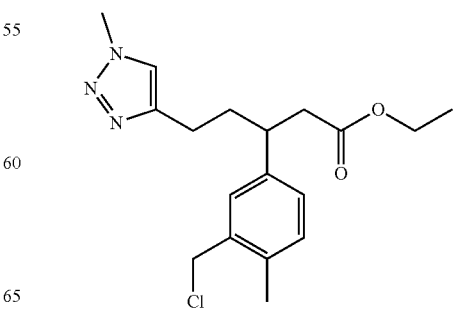

A mixture of ethyl 3-(3-(hydroxymethyl)-4-methylphenyl)-5-(1-methyl-1H-1,2,3-triazol-4-yl)pentanoate (120 mg, 0.362 mmol) and SOCl₂ (0.032 mL, 0.435 mmol) in dichloromethane (DCM) (2.0 mL) was stirred at ice bath for 2 hrs. The reaction mixture was concentrated to afford crude the title compound ethyl 3-(3-(chloromethyl)-4-methylphenyl)-5-(1-methyl-1H-1,2,3-triazol-4-yl)pentanoate (140 mg, 0.400 mmol, 111% yield). LC-MS m/z 350.1 (M+H)⁺, 1.26 (ret. time).

Ethyl 3-(3-((2-(cyclohexylmethyl)-1H-imidazol-1-yl)methyl)-4-methylphenyl)-5-(1-methyl-1H-1,2,3-triazol-4-yl)pentanoate

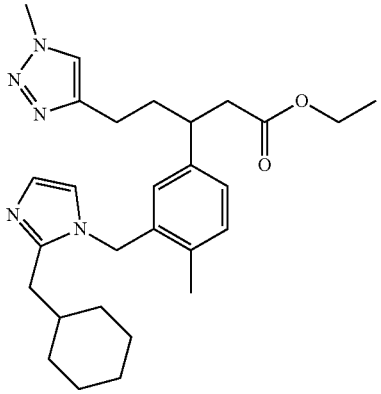 [SMILES: CCOC(=O)CC(CCc1cn(C)nn1)c1ccc(C)c(Cn2ccnc2CC2CCCCC2)c1]

To a solution of 2-(cyclohexylmethyl)-1H-imidazole (46.9 mg, 0.286 mmol) in N,N-dimethylformamide (DMF) (3.0 mL) was added DIPEA (0.150 mL, 0.857 mmol) and ethyl 3-(3-(chloromethyl)-4-methylphenyl)-5-(1-methyl-1H-1,2,3-triazol-4-yl)pentanoate (100 mg, 0.286 mmol). After the reaction mixture was stirred at 100° C. for 4 hrs, it was concentrated. The crude product was purified by preparative HPLC (50% MeOH/H₂O) to afford the title compound ethyl 3-(3-((2-(cyclohexylmethyl)-1H-imidazol-1-yl)methyl)-4-methylphenyl)-5-(1-methyl-1H-1,2,3-triazol-4-yl)pentanoate (110 mg, 0.23 mmol, 81% yield). LC-MS m/z 478.4 (M+H)⁺, 1.48 (ret. time).

3-(3-((2-(Cyclohexylmethyl)-1H-imidazol-1-yl)methyl)-4-methylphenyl)-5-(1-methyl-1H-1,2,3-triazol-4-yl)pentanoic Acid

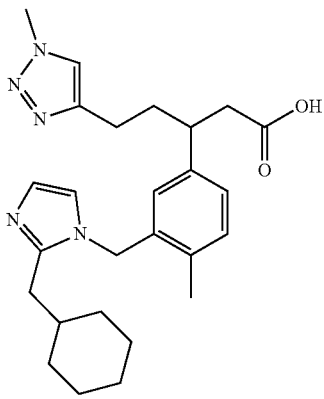 [SMILES: Cc1ccc(C(CCc2cn(C)nn2)CC(=O)O)cc1Cn1ccnc1CC1CCCCC1]

To a solution of ethyl 3-(3-((2-(cyclohexylmethyl)-1H-imidazol-1-yl)methyl)-4-methylphenyl)-5-(1-methyl-1H-1,2,3-triazol-4-yl)pentanoate (110 mg, 0.230 mmol) in methanol (5 mL) was added a solution of NaOH (27.6 mg, 0.691 mmol) in H₂O (1 mL). The reaction mixture was stirred at 20° C. for 4 hrs then concentrated. The residue was acidified with 1N HCl to pH=3 and the crude product was purified by preparative HPLC (50% MeOH/H₂O) to give the title compound 3-(3-((2-(cyclohexylmethyl)-1H-imidazol-1-yl)methyl)-4-methylphenyl)-5-(1-methyl-1H-1,2,3-triazol-4-yl)pentanoic acid (70 mg, 0.148 mmol, 64.2% yield). LC-MS m/z 450.3 (M+H)⁺, 1.44 (ret. time).

Example 131

3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic acid

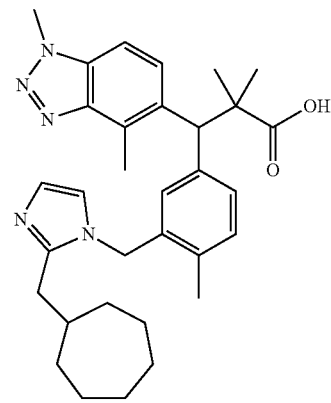 [SMILES: Cc1ccc(C(c2ccc3c(nnn3C)c2C)C(C)(C)C(=O)O)cc1Cn1ccnc1CC1CCCCCC1]

Methyl 3-(3-(chloromethyl)-4-methylphenyl)-3-(1,4-dimethyl-1H-benzo[d][1,2,3]triazol-5-yl)-2,2-dimethylpropanoate

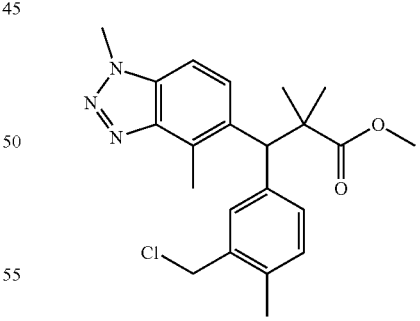

To a solution of methyl 3-(1,4-dimethyl-1H-benzo[d][1,2,3]triazol-5-yl)-3-(3-(hydroxymethyl)-4-methylphenyl)-2,2-dimethylpropanoate (400 mg, 1.049 mmol) in dichloromethane (DCM) (10.0 mL), SOCl₂ (0.092 mL, 1.258 mmol) was added. The reaction mixture was stirred at 0° C. for 2 h. Then the reaction mixture was concentrated to obtain the title compound methyl 3-(3-(chloromethyl)-4-methylphenyl)-3-(1,4-dimethyl-1H-benzo[d][1,2,3]triazol-5-yl)-2,2-dimethylpropanoate (400 mg, 0.960 mmol, 92% yield) as a colorless oil which was carried over to the next step without further purification. LCMS m/z 400.1 (M+H)+, 1.77 min (ret. time)

Methyl 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate

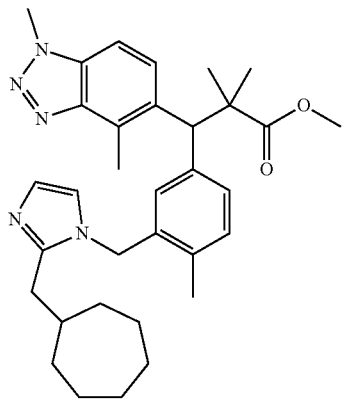 [SMILES: COC(=O)C(C)(C)C(c1ccc(C)c(Cn2ccnc2CC2CCCCCC2)c1)c1ccc2c(nnn2C)c1C]

To a solution of 2-(cycloheptylmethyl)-1H-imidazole (134 g, 0.750 mmol) in N,N-dimethylformamide (DMF) (10 mL) was added sodium hydride (45.0 mg, 1.875 mmol) and stirred for 30 min at 0° C. Methyl 3-(3-(chloromethyl)-4-methylphenyl)-3-(1,4-dimethyl-1H-benzo[d][1,2,3]triazol-5-yl)-2,2-dimethylpropanoate (150 mg, 0.375 mmol) in DMF (10 mL) was added to the reaction mixture slowly and stirred for 1 h at 0° C. Then saturated NH4Cl solution was added and the mixture extracted with EtOAc (3×20 mL). The organic layer was washed with water (2×20 mL) and brine (2×20 mL), dried over Na2SO4 and concentrated to obtain the title compound methyl 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate (190 mg, 0.333 mmol, 89% yield) as a yellow oil. LCMS m/z 542.3 (M+H)+, 1.36 min (ret. time)

3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic Acid

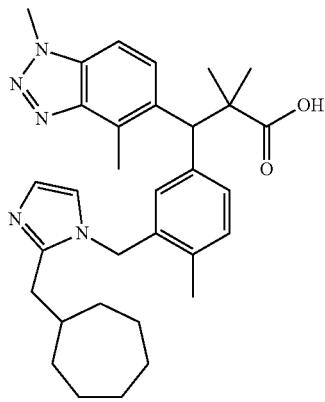 [SMILES: Cc1ccc(C(c2ccc3c(nnn3C)c2C)C(C)(C)C(=O)O)cc1Cn1ccnc1CC1CCCCCC1]

To a solution of methyl 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate (200 mg, 0.369 mmol) in tetrahydrofuran (THF) (3 mL) was added lithium hydroxide (88 mg, 3.69 mmol) in water (1 mL) and ethylene glycol (2 mL). The reaction was heated in a microwave at 125° C. for 4 h. Then the organic solvent was removed. The residue was purified by reverse-phase HPLC (0.05% NH4HCO3/H2O: CH3CN=5-95%) to obtain the title compound 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic acid (12 mg, 0.022 mmol, 5.97% yield) as a white solid. LCMS m/z 528.3 (M+H)+, 1.62 min (ret. time)

Example 132

3-(1,4-Dimethyl-1H-benzo[d][1,2,3]triazol-5-yl)-3-(3-((2-((4-ethylcyclohexyl)methyl)-1H-imidazol-1-yl)methyl)-4-methylphenyl)propanoic Acid

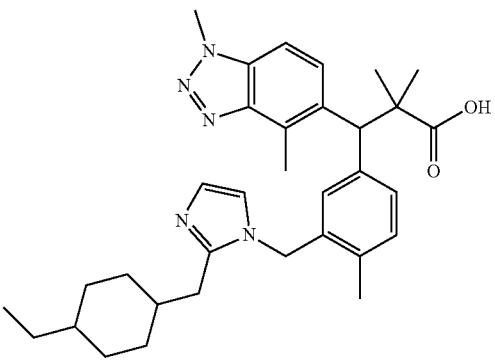 [SMILES: CCC1CCC(Cc2nccn2Cc2cc(C(c3ccc4c(nnn4C)c3C)C(C)(C)C(=O)O)ccc2C)CC1]

Ethyl 2-(4-ethylcyclohexylidene)acetate

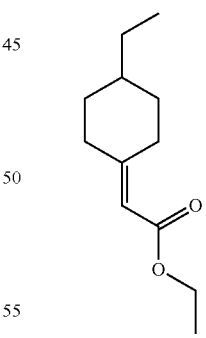

A solution of triethyl phosphonoacetate (9.52 mL, 47.5 mmol) in tetrahydrofuran (THF) (100 mL) at 0° C. was treated with NaH (1.521 g, 38.0 mmol) under nitrogen. The reaction mixture was stirred at 0° C. for 1 h. Then a solution of 4-ethylcyclohexanone (4.0 g, 31.7 mmol) in tetrahydrofuran (THF) (100 mL) was added to the reaction mixture. It was stirred at ambient temperature for 4 h. The reaction mixture was diluted with ethyl acetate (100 mL) and washed with water (2×100 mL). The organic layer was dried over sodium sulfate and concentrated. The crude product was purified by silica gel chromatography (petroleum ether/ethyl acetate=10:1) to give the title compound ethyl 2-(4-ethylcyclohexylidene)acetate (3.8 g, 19.36 mmol, 61.1% yield) as oil. $^1$H NMR (400 MHz, CDCl$_3$) δ=5.61 (s, 1H), 4.16-4.11 (q, 2H), 3.76 (m, 1H), 2.29-2.13 (m, 2H), 1.93-1.89 (m, 3H), 1.41 (m, 1H), 1.28-1.23 (m, 5H), 1.07 (m, 2H), 0.89 (t, 3H).

Ethyl 2-(4-ethylcyclohexyl)acetate

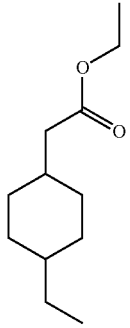

A mixture of ethyl 2-(4-ethylcyclohexylidene)acetate (3.3 g, 16.81 mmol) and Pd/C (10%) (1.789 g, 16.81 mmol) in ethanol (10 mL) was hydrogenated with H$_2$ balloon for 8 h. The reaction mixture was filtered through celite and concentrated to obtain the title compound ethyl 2-(4-ethylcyclohexyl)acetate (2.5 g, 12.61 mmol, 75.0% yield) as an oil. $^1$H NMR (400 MHz, CDCl$_3$) δ=4.13 (q, 2H), 2.17-2.16 (m, 2H), 1.75-1.73 (m, 4H), 1.5 (m, 1H), 1.26-1.20 (m, 6H), 0.93-0.84 (m, 7H).

2-(4-Ethylcyclohexyl)ethanol

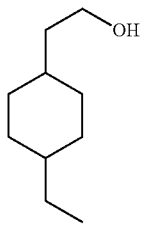

To a solution of ethyl 2-(4-ethylcyclohexyl)acetate (2200 mg, 11.09 mmol) was dissolved in tetrahydrofuran (THF) (8.0 mL) at 0° C. was added LiAlH$_4$ (1053 mg, 27.7 mmol). The reaction mixture was stirred at 0° C. for 8 h. Then 1 M hydrochloric acid was added to the reaction mixture and extracted with ethyl acetate (3×50 mL). The organic layer was washed with saturated sodium chloride solution, dried over magnesium sulfate and concentrated to obtain the title compound 2-(4-ethylcyclohexyl)ethanol (1500 mg, 9.60 mmol, 87% yield) as an oil. $^1$H NMR (400 MHz, CDCl$_3$) δ=3.69 (q, 2H), 1.75 (m, 3H), 1.48-1.40 (m, 4H), 1.32-1.18 (m, 4H), 0.91-0.85 (m, 6H).

2-(4-Ethylcyclohexyl)acetaldehyde

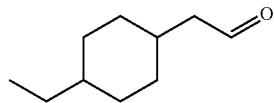

To a solution of 2-(4-ethylcyclohexyl)ethanol (1500 mg, 9.60 mmol) in dichloromethane (DCM) (15.0 mL), PCC (3104 mg, 14.40 mmol) was added. The reaction mixture was stirred at 10° C. for 2 h. The reaction mixture was diluted with diethyl ether (500 mL) and stirred at ambient temperature for 1 h. Then it was filtered through a pad of celite and silica gel (1:1). The filtrate was carefully concentrated to dryness to give the title compound 2-(4-ethylcyclohexyl)acetaldehyde (750 mg, 4.86 mmol, 50.7% yield). $^1$H NMR (400 MHz, CDCl$_3$) δ=9.75 (s, 1H), 2.30-2.28 (m, 2H), 1.77-1.74 (m, 4H), 1.5 (m, 1H), 1.22-1.29 (m, 4H), 1.0-1.85 (m, 6H).

2-((4-Ethylcyclohexyl)methyl)-1H-imidazole

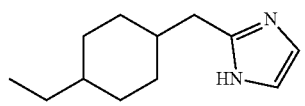

To a solution of 2-(4-ethylcyclohexyl)acetaldehyde (750 mg, 4.86 mmol) in water (2 ml), oxaldehyde (282 mg, 4.86 mmol) and ammonium hydroxide (3.0 mL, 21.57 mmol) were added. The reaction mixture was stirred at 10° C. for 2 h. The solid was filtered and dried to obtain the title compound 2-((4-ethylcyclohexyl)methyl)-1H-imidazole (100 mg, 0.520 mmol, 10.70% yield). LCMS m/z 193.2 (M+H)$^+$, 1.23 min (ret. time).

Ethyl 3-(1,4-Dimethyl-1H-benzo[d][1,2,3]triazol-5-yl)-3-(3-((2-((4-ethylcyclohexyl)methyl)-1H-imidazol-1-yl)methyl)-4-methylphenyl)propanoate

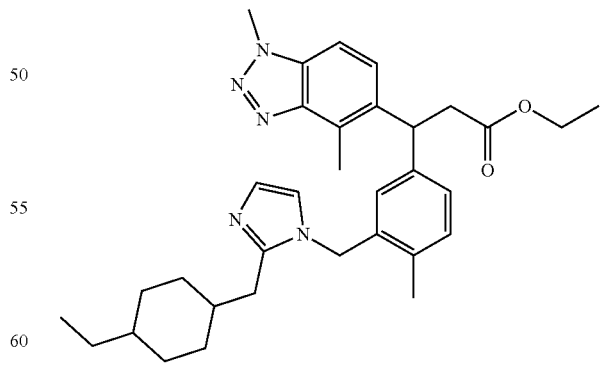

To a solution of 2-((4-ethylcyclohexyl)methyl)-1H-imidazole (50 mg, 0.260 mmol) in N,N-dimethylformamide (DMF) (3.0 mL), DIPEA (0.045 mL, 0.260 mmol) was added. Then ethyl 3-(3-(chloromethyl)-4-methylphenyl)-3-(1,4-dimethyl-1H-benzo[d][1,2,3]triazol-5-yl)propanoate (100 mg, 0.260 mmol) was added to the reaction. The reaction mixture was stirred at 100° C. for 4 h. Then it was purified by reverse-phase HPLC to give the title compound ethyl 3-(1,4-dimethyl-1H-benzo[d][1,2,3]triazol-5-yl)-3-(3-((2-((4-ethylcyclohexyl)methyl)-1H-imidazol-1-yl)methyl)-4-methylphenyl)propanoate (85 mg, 0.157 mmol, 60.3% yield) as a solid. LC-MS m/z 542.2 (M+H)+, 1.48 min (ret. time)

3-(1,4-Dimethyl-1H-benzo[d][1,2,3]triazol-5-yl)-3-(3-((2-((4-ethylcyclohexyl)methyl)-1H-imidazol-1-yl)methyl)-4-methylphenyl)propanoic Acid

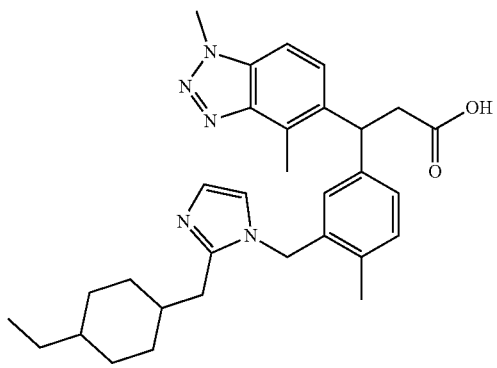 [SMILES: CCC1CCC(Cc2nccn2Cc2cc(C(CC(=O)O)c3ccc4c(nnn4C)c3C)ccc2C)CC1]

To a solution of ethyl 3-(1,4-dimethyl-1H-benzo[d][1,2,3]triazol-5-yl)-3-(3-((2-((4-ethylcyclohexyl)methyl)-1H-imidazol-1-yl)methyl)-4-methylphenyl)propanoate (85 mg, 0.157 mmol) in methanol (5 mL), NaOH (18.83 mg, 0.471 mmol) in H$_2$O (1 mL) was added. The reaction mixture was stirred at 20° C. for 4 h. The solvent was evaporated and the residue was neutralized with 1N HCl to pH 3. The product was purified by reverse-phase HPLC (50% MeOH/H$_2$O) to give the title compound 3-(1,4-dimethyl-1H-benzo[d][1,2,3]triazol-5-yl)-3-(3-((2-((4-ethylcyclohexyl)methyl)-1H-imidazol-1-yl)methyl)-4-methylphenyl)propanoic acid (40 mg, 0.074 mmol, 47.1% yield) as a solid. LC-MS m/z 514.3 (M+H)+, 1.35 min (ret. Time).

Example 133

Ammonium 3-(3-((2-(1-cyclohexylethyl)-1H-imidazol-1-yl)methyl)-4-methylphenyl)-3-(1,4-dimethyl-1H-benzo[d][1,2,3]triazol-5-yl)propanoate

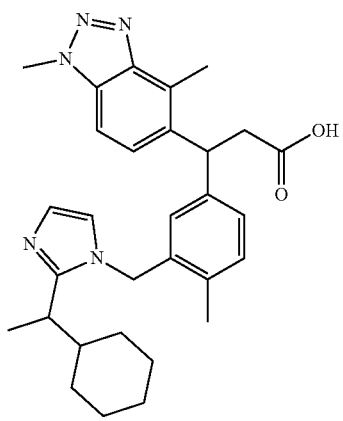 [SMILES: Cc1ccc(C(CC(=O)O)c2ccc3c(nnn3C)c2C)cc1Cn1ccnc1C(C)C1CCCCC1]

Ethyl 2-cyclohexylpropanoate

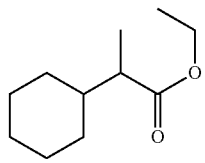

To a solution of ethyl 2-cyclohexylacetate (10 g, 58.7 mmol) in tetrahydrofuran (THF) (100 mL) was added LiHMDS (70.5 mL, 70.5 mmol) slowly under nitrogen at −78° C. The reaction mixture was stirred at −78° C. for 1 h. Iodomethane (10.00 g, 70.5 mmol) solution in 50 ml of THF was added and the reaction stirred at ambient temperature for 1 h. Water (30 mL) was added and the mixture extracted with ethyl acetate (3×30 mL). The combined organic layer was dried over MgSO$_4$ and concentrated under a stream of nitrogen at 50° C. to give the title compound ethyl 2-cyclohexylpropanoate (10 g, 48.8 mmol, 83% yield) which was carried to the next step without further purification. LC-MS m/z 185.1 (M+H)+, 2.28 min (ret. time).

2-Cyclohexylpropan-1-ol

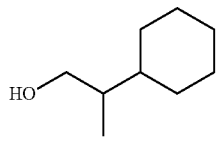

To a solution of ethyl 2-cyclohexylpropanoate (10 g, 54.3 mmol) in tetrahydrofuran (THF) (10 mL) was added LiAlH$_4$ (4.12 g, 109 mmol) slowly under nitrogen at 0° C. The reaction mixture was stirred at 0° C. for 0.5 h and allowed to warm to ambient temperature for 2 h. To the reaction was added 30 mL of water and extracted with ethyl acetate (3×30 mL). The combined organic layer was dried over MgSO$_4$ and concentrated under a stream of nitrogen at 50° C. The crude product was purified by silica gel chromatography (hexane:ethyl acetate=10:1) to give the title compound 2-cyclohexylpropan-1-ol (7.2 g, 45.6 mmol, 84% yield) which was carried to the next step without further purification. $^1$H NMR (400 MHz, CDCl$_3$) δ=3.64-3.63 (m, 1H), 3.61-3.48 (m, 1H), 1.77-1.65 (m, 4H), 1.51 (m, 1H), 1.36-1.13 (m, 10H).

2-Cyclohexylpropanal

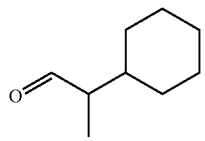

To a solution of 2-cyclohexylpropan-1-ol (1 g, 7.03 mmol) in dichloromethane (DCM) (40 mL), 200 mg silica gel was added, the suspension was stirred at 25° C. for 5 min, then PCC (3.03 g, 14.06 mmol) was added. The reaction mixture was stirred at 25° C. for 4 h. The reaction mixture was filtered through celite and washed with ethyl acetate (3×20 mL). The combined filtrate was concentrated and the residue was purified by silica gel chromatography (petroleum ether/ethyl acetate=22%) to give the title compound 2-cyclohexylpropanal (850 mg, 5.58 mmol, 79% yield) as yellow oil. $^1$H NMR (400 MHz,CDCl$_3$) δ=9.65 (s, 1H), 2.23-2.21 (m, 1H), 2.20-1.60 (m, 6H), 1.30-1.14 (m, 8H).

2-(1-Cyclohexylethyl)-1H-imidazole

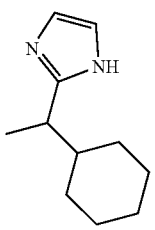

To a solution of 2-cyclohexylpropanal (800 mg, 5.71 mmol) in methanol (12 mL) and water (3.00 mL), oxaldehyde (331 mg, 5.71 mmol) and ammonia hydrate (400 mg, 11.41 mmol) were added. The reaction mixture was stirred at 0° C. to ambient temperature for 16 h. The reaction mixture was concentrated and the residue was purified by silica gel chromatography (petroleum ether/ethyl acetate=48%) to give the title compound 2-(1-cyclohexylethyl)-1H-imidazole (900 mg, 4.75 mmol, 83% yield) as yellow solid. LC-MS m/z 179.1 (M+H)$^+$, 1.15 min (ret. time).

Ethyl 3-(3-(chloromethyl)-4-methylphenyl)-3-(1,4-dimethyl-1H-benzo[d][1,2,3]triazol-5-yl)propanoate

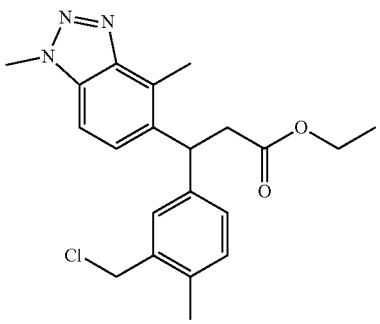 [SMILES: CCOC(=O)CC(c1ccc(C)c(CCl)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (1000 mg, 2.72 mmol) in dichloromethane (DCM) (2.0 mL), SOCl$_2$ (0.238 mL, 3.27 mmol) was added. The reaction mixture was stirred at 00° C. for 2 h. The reaction mixture was concentrated to give the title compound ethyl 3-(3-(chloromethyl)-4-methylphenyl)-3-(1,4-dimethyl-1H-benzo[d][1,2,3]triazol-5-yl)propanoate (1000 mg, 2.59 mmol, 95% yield) as an oil which was carried to the next step without further purification. LC-MS m/z 386.1 (M+H)$^+$, 1.98 min (ret. time)

Ammonium 3-(3-((2-(1-cyclohexylethyl)-1H-imidazol-1-yl)methyl)-4-methylphenyl)-3-(1,4-dimethyl-1H-benzo[d][1,2,3]triazol-5-yl)propanoate

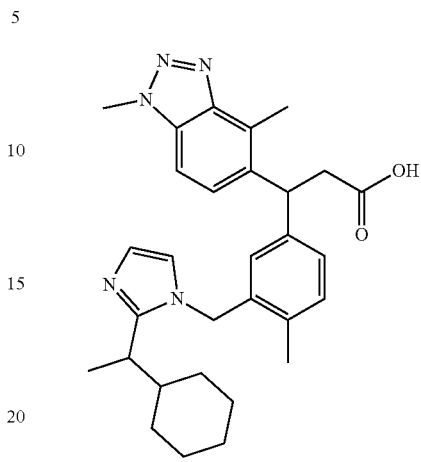

To a solution of 2-(1-cyclohexylethyl)-1H-imidazole (39.3 mg, 0.220 mmol) in N,N-dimethylformamide (DMF) (10 mL) at 0° C. under N$_2$, NaH (10.57 mg, 0.264 mmol) was carefully added. After the reaction mixture was stirred at 0° C. for 0.5 h, a solution of ethyl 3-(3-(chloromethyl)-4-methylphenyl)-3-(1,4-dimethyl-1H-benzo[d][1,2,3]triazol-5-yl)propanoate (85 mg, 0.220 mmol) in N,N-dimethylformamide (DMF) (10 mL) was added and the reaction mixture was stirred at 00° C. to 25° C. for 16 h. The solvent was evaporated and the residue was dissolved into 2 mL of water, acidified to pH 5 by 2N HCl in an ice bath. After part of the water was concentrated, the residue was purified by reverse-phase HPLC (CH$_3$CN/NH$_4$HCO$_3$/H2O=50%) to give the title compound 3-(3-((2-(1-cyclohexylethyl)-1H-imidazol-1-yl)methyl)-4-methylphenyl)-3-(1,4-dimethyl-1H-benzo[d][1,2,3]triazol-5-yl)propanoic acid (38 mg, 0.076 mmol, 34.5% yield) as light yellow solid. LC-MS m/z 500.2 (M+H)$^+$, 1.35 min (ret. time).

Example 134

3-(3-((1-(Cyclohexylmethyl)-1H-tetrazol-5-yl)methyl)-4-methylphenyl)-3-(1,4-dimethyl-1H-benzo[d][1,2,3]triazol-5-yl)propanoic acid, hydrochloride salt

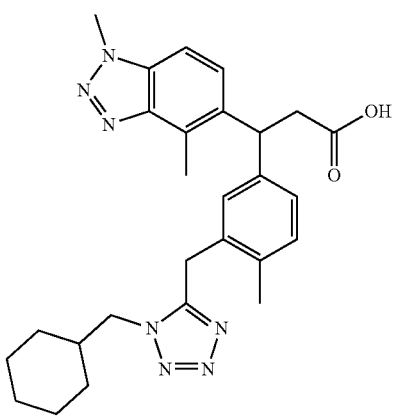 [SMILES: Cc1ccc(C(CC(=O)O)c2ccc3c(nnn3C)c2C)cc1Cc1nnnn1CC1CCCCC1]

4-Bromo-2-(chloromethyl)-1-methylbenzene

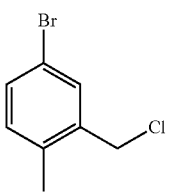

To a solution of (5-bromo-2-methylphenyl)methanol (5.4 g, 26.9 mmol) in dichloromethane (DCM) (50 mL) was added $SOCl_2$ (3.92 mL, 53.7 mmol) slowly under nitrogen at 25° C. The reaction mixture was stirred at 25° C. for 4 h. Then it was concentrated to give the title compound 4-bromo-2-(chloromethyl)-1-methylbenzene (5.45 g, 22.35 mmol, 83% yield) which was carried to the next step without further purification. LC-MS m/z 241.1 $(M+Na)^+$, 1.84 min (ret. time).

2-(5-Bromo-2-methylphenyl)acetonitrile

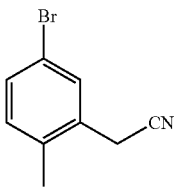

To a solution of 4-bromo-2-(chloromethyl)-1-methylbenzene (4.3 g, 19.59 mmol) in ethanol (20 mL) and water (5 mL) was added potassium cyanide (1.913 g, 29.4 mmol) slowly under nitrogen at ambient temperature. The reaction mixture was stirred at 90° C. for 16 h. Water (10 mL) was added and extracted with ethyl acetate (3×30 mL). The combined organic layer was dried over $MgSO_4$ and concentrated under a stream of nitrogen at 50° C. to give the title compound 2-(5-bromo-2-methylphenyl)acetonitrile (4.3 g, 14.12 mmol, 72.1% yield) which was carried to the next step without further purification. LC-MS m/z 210.0 $(M+H)^+$, 1.66 min (ret. time)

2-(5-Bromo-2-methylphenyl)acetic Acid

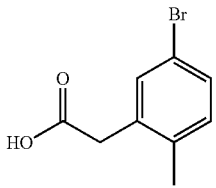

To a solution of 2-(5-bromo-2-methylphenyl)acetonitrile (5 g, 23.80 mmol) in ethanol (50 mL) was added NaOH (23.80 mL, 143 mmol) slowly under nitrogen. The reaction mixture was stirred at ambient temperature for 18 hr. The solvent was evaporated and was acidified to pH 2 with 6 N HCl. The solid was filtered and dried with high vacuum to give the title compound 2-(5-bromo-2-methylphenyl)acetic acid (4.9 g, 19.25 mmol, 81% yield) which was carried to the next step without further purification. LC-MS m/z 230.0 $(M+H)^+$, 1.54 min (ret. time)

2-(5-Bromo-2-methylphenyl)-N-(cyclohexylmethyl)acetamide

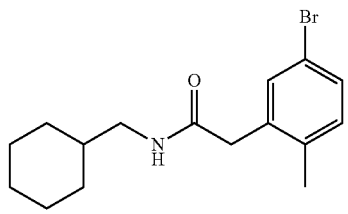 [SMILES: Cc1ccc(Br)cc1CC(=O)NCC1CCCCC1]

To a solution of 2-(5-bromo-2-methylphenyl)acetic acid (4.1 g, 17.90 mmol) in dichloromethane (DCM) (40 mL) was added oxalyl chloride (4.70 mL, 53.7 mmol) slowly under nitrogen at 0° C. The reaction mixture was stirred at ambient temperature for 2 h. Then it was concentrated and dissolved in 10 mL of DCM and added to cyclohexylmethanamine (3.04 g, 26.8 mmol) and TEA (7.48 mL, 53.7 mmol) solution in 20 mL of DCM. The reaction mixture was stirred at ambient temperature for 4 h after which 10 mL of water was added and the mixture extracted with ethyl acetate (3×30 mL). The combined organic layer was washed with 1 N HCl, brine and dried over $MgSO_4$, concentrated under a stream of nitrogen at 50° C. to give the title compound 2-(5-bromo-2-methylphenyl)-N-(cyclohexylmethyl)acetamide (4.1 g, 12.01 mmol, 67.1% yield) which was carried to the next step without further purification. LC-MS m/z 324.1 $(M+H)^+$, 1.79 min (ret. time)

5-(5-Bromo-2-methylbenzyl)-1-(cyclohexylmethyl)-1H-tetrazole

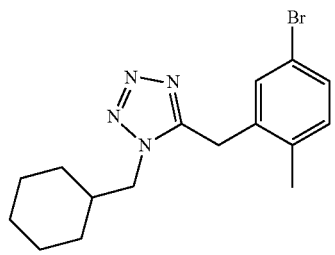 [SMILES: Cc1ccc(Br)cc1Cc1nnnn1CC1CCCCC1]

A solution of 2-(5-bromo-2-methylphenyl)-N-(cyclohexylmethyl)acetamide (3.1 g, 9.56 mmol) in toluene (50 mL) was treated with $PCl_5$ (3.98 g, 19.12 mmol) slowly under nitrogen at 20° C. After the reaction mixture was stirred at 20° C. for 4 h, $TMSN_3$ (3.17 mL, 23.90 mmol) was added and stirred at 20° C. for 16 h. Water (100 mL) was added and the mixture extracted with ethyl acetate (3×100 mL). The combined organic layer was washed with saturated $NaHCO_3$, brine and dried over $MgSO_4$, filtered and concentrated. The crude product was purified by silica gel chromatography (hexane:ethyl acetate=4:1) to give the title compound 5-(5-bromo-2-methylbenzyl)-1-(cyclohexylmethyl)-1H-tetrazole (1.5 g, 4.12 mmol, 43.1% yield) as a white solid. LC-MS m/z 351.1 $(M+H)^+$, 1.83 min (ret. time)

1-(Cyclohexylmethyl)-5-(2-methyl-5-(4,4,5,5-tetramethyl-1,3,2-dioxaborolan-2-yl)benzyl)-1H-tetrazole

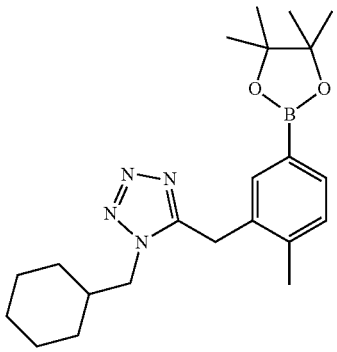 [SMILES: Cc1ccc(B2OC(C)(C)C(C)(C)O2)cc1Cc1nnnn1CC1CCCCC1]

To a solution of 5-(5-bromo-2-methylbenzyl)-1-(cyclohexylmethyl)-1H-tetrazole (1.5 g, 4.29 mmol) in 1,4-dioxane (50 mL) was added 4,4,4',4',5,5,5',5'-octamethyl-2,2'-bi (1,3,2-dioxaborolane) (1.309 g, 5.15 mmol), potassium acetate (0.632 g, 6.44 mmol) and PdCl$_2$(dppf)-CH$_2$Cl$_2$ adduct (0.175 g, 0.215 mmol) slowly under nitrogen at ambient temperature. The reaction mixture was stirred at 90° C. for 16 h. Water (50 mL) was added and the mixture extracted with ethyl acetate (3×50 mL). The combined organic layer was dried over MgSO$_4$, concentrated under a stream of nitrogen at 50° C. The crude product was purified by silica gel chromatography (hexane:ethyl acetate=4:1) to give the title compound 1-(cyclohexylmethyl)-5-(2-methyl-5-(4,4,5,5-tetramethyl-1,3,2-dioxaborolan-2-yl)benzyl)-1H-tetrazole (1.1 g, 2.498 mmol, 58.2% yield). LC-MS m/z 397.3 (M+H)$^+$ 1.90 min (ret. time)

Ethyl 3-(3-((1-(cyclohexyl methyl)-1H-tetrazol-5-yl)methyl)-4-methylphenyl)-3-(1,4-dimethyl-1H-benzo[d][1,2,3]triazol-5-yl)propanoate

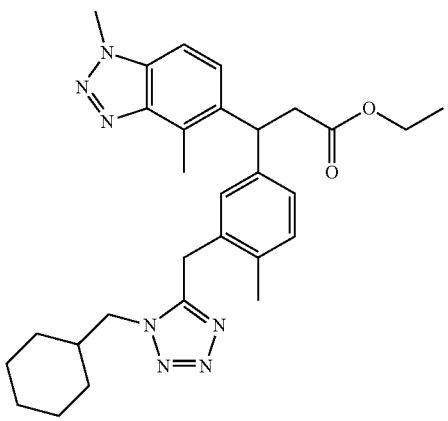 [SMILES: CCOC(=O)CC(c1ccc(C)c(Cc2nnnn2CC2CCCCC2)c1)c1ccc2c(nnn2C)c1C]

To a solution of (E)-ethyl 3-(1,4-dimethyl-1H-benzo[d][1,2,3]triazol-5-yl)acrylate (300 mg, 1.223 mmol) in 1,4-dioxane (30 mL) was added (2R,3R)-butane-2,3-diylbis (diphenylphosphine) (57.4 mg, 0.135 mmol), 1-(cyclohexylmethyl)-5-(2-methyl-5-(4,4,5,5-tetramethyl-1,3,2-dioxaborolan-2-yl)benzyl)-1H-tetrazole (970 mg, 2.446 mmol), (Rh(nbd)Cl)$_2$ (56.4 mg, 0.122 mmol) and KOH (3.67 mL, 3.67 mmol) slowly under nitrogen at 25° C. The reaction mixture was stirred at 25° C. for 16 h. Water (30 mL) was added and the mixture extracted with ethyl acetate (3×60 mL). The combined organic layer was dried over MgSO$_4$ and concentrated under a stream of nitrogen at 50° C. The crude product was purified by silica gel chromatography (hexane:ethyl acetate=1:1) to give the title compound ethyl 3-(3-((1-(cyclohexylmethyl)-1H-tetrazol-5-yl)methyl)-4-methylphenyl)-3-(1,4-dimethyl-1H-benzo[d][1,2,3]triazol-5-yl)propanoate (350 mg, 0.645 mmol, 52.7% yield) as an oil. LC-MS m/z 516.3 (M+H)$^+$, 1.75 min (ret. time)

3-(3-((1-(Cyclohexylmethyl)-1H-tetrazol-5-yl)methyl)-4-methylphenyl)-3-(1,4-dimethyl-1H-benzo[d][1,2,3]triazol-5-yl)propanoic acid, hydrochloride salt

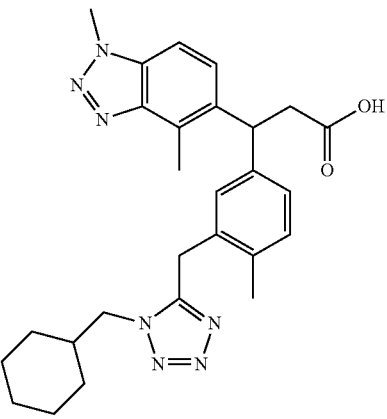 [SMILES: Cc1ccc(C(CC(=O)O)c2ccc3c(nnn3C)c2C)cc1Cc1nnnn1CC1CCCCC1]

To a solution of ethyl 3-(3-((1-(cyclohexylmethyl)-1H-tetrazol-5-yl)methyl)-4-methylphenyl)-3-(1,4-dimethyl-1H-benzo[d][1,2,3]triazol-5-yl)propanoate (350 mg, 0.679 mmol) in tetrahydrofuran (THF) (5 mL) was added LiOH (65.0 mg, 2.72 mmol) in water (5.00 mL) slowly under nitrogen at 50° C. The reaction mixture was stirred at 50° C. for 16 h. Then it was acidified to pH 3 with 1 N HCl and extracted with ethyl acetate (3×10 mL). The combined organic phase was dried over MgSO$_4$ and concentrated. The crude product was purified by silica gel chromatography (hexane:ethyl acetate=4:1) to give the title compound 3-(3-((1-(cyclohexylmethyl)-1H-tetrazol-5-yl)methyl)-4-methylphenyl)-3-(1,4-dimethyl-1H-benzo[d][1,2,3]triazol-5-yl)propanoic acid (150 mg, 0.292 mmol, 43.1% yield) as a white solid. LC-MS m/z 488.3 (M+H)$^+$, 1.60 min (ret. time)

Example 135

3-(3-((2-(Cyclohexyl methyl)-1H-imidazol-1-yl)methyl)-4-methylphenyl)-3-(4-fluoro-2-methylphenyl)propanoic Acid

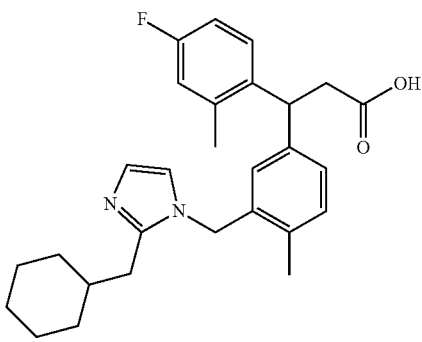 [SMILES: Cc1ccc(C(CC(=O)O)c2ccc(F)cc2C)cc1Cn1ccnc1CC1CCCCC1]

(E)-Ethyl 3-(4-fluoro-2-methylphenyl)acrylate

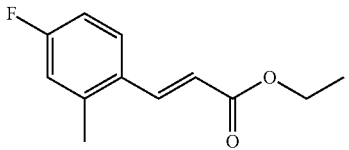

To a solution of ethyl 2-(diethoxyphosphoryl)acetate (19.48 g, 87 mmol) in tetrahydrofuran (THF) (100 mL) at 0° C. was added sodium hydride (3.47 g, 87 mmol)) in small portions. After 15 min, 4-fluoro-2-methylbenzaldehyde (10 g, 72.4 mmol) in THF (20 mL) was added slowly. The mixture stirred at room temperature for 30 min. Then NH$_4$Cl (sat. aq.) was added and the solution was extracted with EtOAc (50 mL×3). The combined organic layer was washed with brine (10 mL×3), dried (Na$_2$SO$_4$), filtered and concentrated. The residue was purified with Combiflash (PE:EA=10%) to give the title compound (E)-ethyl 3-(4-fluoro-2-methylphenyl)acrylate (13 g, 58.7 mmol, 81% yield) as a colorless oil. LCMS m/z: 209 (M+H)$^+$, 1.78 min (ret. time), Ethyl 3-(4-fluoro-2-methylphenyl)-3-(3-(hydroxymethyl)-4-methylphenyl)propanoate

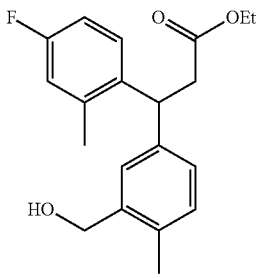 [SMILES: CCOC(=O)CC(c1ccc(C)c(CO)c1)c1ccc(F)cc1C]

To a solution of (E)-ethyl 3-(4-fluoro-2-methylphenyl)acrylate (5.8 g, 27.9 mmol) in 1,4-dioxane (60 mL) and water (30 mL) was added (2-methyl-5-(4,4,5,5-tetramethyl-1,3,2-dioxaborolan-2-yl)phenyl)methanol (13.82 g, 55.7 mmol), TEA (7.76 mL, 55.7 mmol). It was stirred for 5 min and then added chloro(1,5-cyclooctadiene)rhodium(I) dimer (0.687 g, 1.393 mmol) under the protection of nitrogen. The reaction mixture was stirred at 90° C. for 2 h. After cooling to 25° C., the mixture was quenched with water (10 mL), extracted with EtOAc (3×80 mL). The combined organic layer was washed with water (2×5 mL) and brine (2×5 mL), dried (Na$_2$SO$_4$), filtered and concentrated. The residue was purified with Combiflash (sillic gel column, 40 g, PE:EA=15%) to give the title compound (5.9 g, 16.43 mmol, 59.0% yield) as colorless oil. LCMS m/z 353 (M+Na)$^+$ 2.04 min (ret. time)

Ethyl 3-(3-(chloromethyl)-4-methylphenyl)-3-(4-fluoro-2-methylphenyl)propanoate

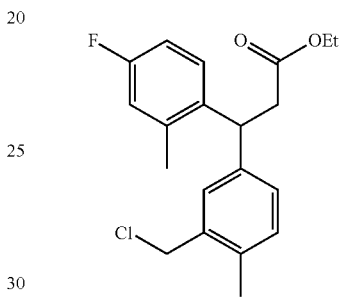

To a solution of ethyl 3-(4-fluoro-2-methylphenyl)-3-(3-(hydroxymethyl)-4-methylphenyl)propanoate (330 mg, 0.999 mmol) in dichloromethane (DCM) (6.0 mL), SOCl$_2$ (0.087 mL, 1.199 mmol) was added at 00° C. The reaction mixture was stirred at for 2 h at 0° C. Then it was concentrated to give the title compound ethyl 3-(3-(chloromethyl)-4-methylphenyl)-3-(4-fluoro-2-methylphenyl)propanoate (300 mg, 0.826 mmol, 83% yield) as colorless oil which was carried to the next step without further purification. LC-MS m/z 371.1 (M+Na)$^+$, 1.88 min (ret. time)

Ethyl 3-(3-((2-(cyclohexylmethyl)-1H-imidazol-1-yl)methyl)-4-methylphenyl)-3-(4-fluoro-2-methylphenyl)propanoate

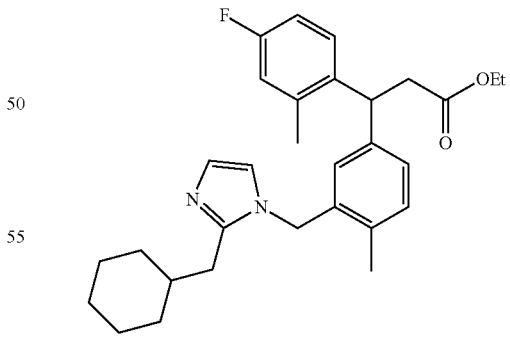

To a solution of 2-(cyclohexylmethyl)-1H-imidazole (141 mg, 0.860 mmol) in tetrahydrofuran (THF) (3 mL) at 0° C. under N$_2$, NaH (34.4 mg, 0.860 mmol) was carefully added. The reaction mixture was stirred at 0° C. for 0.5 h. Then a solution of ethyl 3-(3-(chloromethyl)-4-methylphenyl)-3-(4-fluoro-2-methylphenyl)propanoate (300 mg, 0.860 mmol) in tetrahydrofuran (THF) (3 mL) was added and the mixture was stirred at 0 to 25° C. for 16 h. The reaction mixture was quenched with saturated NH₄Cl solution (10 mL), and extracted with ethyl acetate (3×30 mL). The combined organic layer was washed with water (2×8 mL) and brine (2×8 mL), dried over (Na₂SO₄) and concentrated. The residue was purified with silica gel chromatography (petroleum ether/ethyl acetate=5%) to give the title compound ethyl 3-(3-((1-(cyclohexylmethyl)-1H-imidazol-2-yl)methyl)-4-methylphenyl)-3-(4-fluoro-2-methylphenyl)propanoate (160 mg, 0.302 mmol, 35.1% yield) as colorless oil. LC/MS m/z 477.2 (M+H)⁺ 1.53 min (ret. time)

3-(3-((2-(Cyclohexyl methyl)-1H-imidazol-1-yl)methyl)-4-methylphenyl)-3-(4-fluoro-2-methylphenyl)propanoic Acid

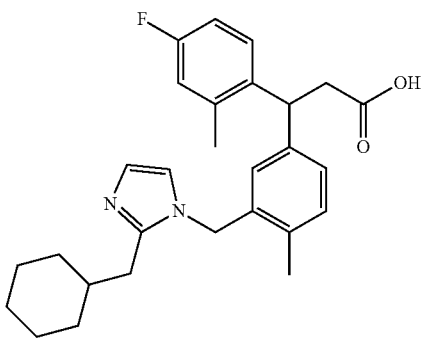 [SMILES: Cc1ccc(C(CC(=O)O)c2ccc(F)cc2C)cc1Cn1ccnc1CC1CCCCC1]

To a solution of ethyl 3-(3-((2-(cyclohexylmethyl)-1H-imidazol-1-yl)methyl)-4-methylphenyl)-3-(4-fluoro-2-methylphenyl)propanoate (160 mg, 0.336 mmol) in methanol (4 mL) and water (1.000 mL) at 25° C., sodium hydroxide (26.9 mg, 0.671 mmol) was added. The reaction mixture was stirred at 25° C. for 1 h. The solvent was removed and the residue was dissolved into 2 mL of water, acidified to pH 4 by 2 N HCl at 0° C. to precipitate a white solid. The crude was purified by reverse-phase HPLC (CH₃CN/H₂O with 0.05% NH₃H₂O) to give the title compound 3-(3-((2-(cyclohexylmethyl)-1H-imidazol-1-yl)methyl)-4-methylphenyl)-3-(4-fluoro-2-methylphenyl)propanoic acid (70 mg, 0.156 mmol, 46.5% yield) as a pale white solid. LC-MS m/z 449.2 (M+H)⁺, 1.44 min (ret. time)

Example 136

3-(3-((4-(Cyclohexyl methyl)-1H-imidazol-1-yl)methyl)-4-methylphenyl)-3-(1,4-dimethyl-1H-benzo[d][1,2,3]triazol-5-yl)propanoic Acid

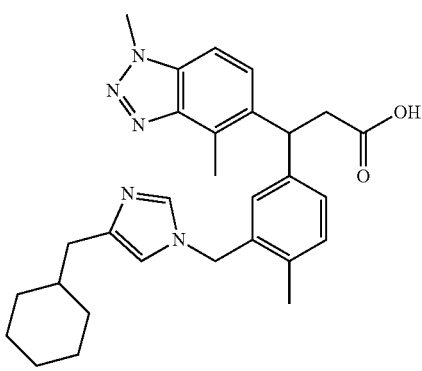 [SMILES: Cc1ccc(C(CC(=O)O)c2ccc3c(nnn3C)c2C)cc1Cn1cnc(CC2CCCCC2)c1]

5-(Cyclohexylmethyl)-1H-imidazole

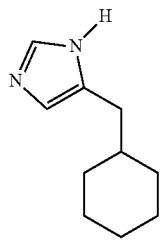 [SMILES: c1ncc(CC2CCCCC2)[nH]1]

TOSMIC (696 mg, 3.57 mmol) was added to a saturated solution of ammonia in methanol (2.0 ml). After stirring at ambient temperature for 1 h, 2-cyclohexylacetaldehyde (300 mg, 2.377 mmol) was added over 2 min. After the reaction mixture was stirred at refluxed temperature for 3 h, it was poured into cold 1 N hydrochloric acid (10 mL) and washed with hexane. The aqueous layer was basified with 1.0 N aqueous sodium hydroxide and extracted with ether (3×50 mL). The combined organic layer was washed with brine (10 mL), dried over magnesium sulfate, filtered and concentrated. The crude product was purified by silica gel chromatography eluting with 5-10% methanol in methylene chloride to give the title compound 5-(cyclohexylmethyl)-1H-imidazole (60 mg, 0.365 mmol, 15.37% yield). LC-MS m/z 165.2 (M+H)⁺, 1.17 min (ret. Time).

Ethyl 3-(3-((4-(cyclohexylmethyl)-1H-imidazol-1-yl)methyl)-4-methylphenyl)-3-(1,4-dimethyl-1H-benzo[d][1,2,3]triazol-5-yl)propanoate

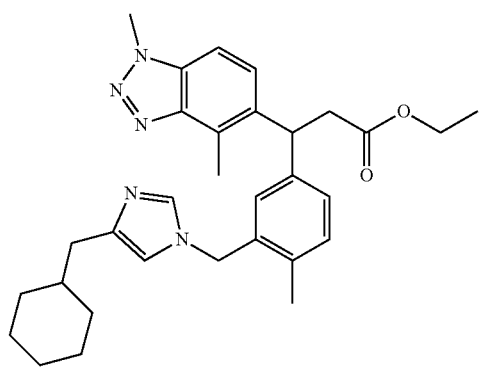 [SMILES: CCOC(=O)CC(c1ccc(C)c(Cn2cnc(CC3CCCCC3)c2)c1)c1ccc2c(nnn2C)c1C]

To a solution of 5-(cyclohexylmethyl)-1H-imidazole (50 mg, 0.304 mmol) in N,N-dimethylformamide (DMF) (3.0 mL), DIPEA (0.053 mL, 0.304 mmol) was added. Then ethyl 3-(3-(chloromethyl)-4-methylphenyl)-3-(1,4-dimethyl-1H-benzo[d][1,2,3]triazol-5-yl)propanoate (117 mg, 0.304 mmol) was added to the reaction. The reaction mixture was stirred at 100° C. for 4 h. Then it was purified by reverse-phase HPLC (50% MeOH/H₂O) to give the title compound ethyl 3-(3-((4-(cyclohexylmethyl)-1H-imidazol-1-yl)methyl)-4-methylphenyl)-3-(1,4-dimethyl-1H-benzo[d][1,2,3]triazol-5-yl)propanoate (85 mg, 0.165 mmol, 54.4% yield) as a solid. LC-MS m/z 514.3 (M+H)⁺, 1.42 min (ret. time)

3-(3-((4-(Cyclohexyl methyl)-1H-imidazol-1-yl)methyl)-4-methylphenyl)-3-(1,4-dimethyl-1H-benzo[d][1,2,3]triazol-5-yl)propanoic Acid

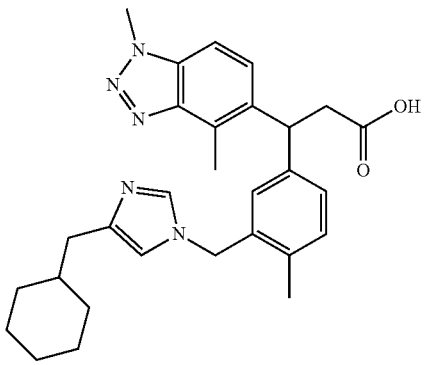 [SMILES: Cc1ccc(C(CC(=O)O)c2ccc3c(nnn3C)c2C)cc1Cn1cnc(CC2CCCCC2)c1]

To a solution of ethyl 3-(3-((4-(cyclohexylmethyl)-1H-imidazol-1-yl)methyl)-4-methylphenyl)-3-(1,4-dimethyl-1H-benzo[d][1,2,3]triazol-5-yl)propanoate (85 mg, 0.165 mmol) in methanol (5 mL), NaOH (19.86 mg, 0.496 mmol) in H₂O (1 ml) was added. The reaction mixture was stirred at 20° C. for 4 h. The solvent was evaporated and the residue was neutralized with 1N HCl to pH 3. The crude product was purified by reverse-phase HPLC (50% MeOH/H₂O) to give the title compound 3-(3-((4-(cyclohexylmethyl)-1H-imidazol-1-yl)methyl)-4-methylphenyl)-3-(1,4-dimethyl-1H-benzo[d][1,2,3]triazol-5-yl)propanoic acid (50 mg, 0.098 mmol, 59.1% yield) as a solid. LCMS m/z 486.2 (M+H)⁺, 1.34 min (ret. Time)

Example 137

3-(3-((3-(Cyclohexyl methyl)-5-methyl-1H-1,2,4-triazol-1-yl)methyl)-4-methylphenyl)-3-(1,4-dimethyl-1H-benzo[d][1,2,3]triazol-5-yl)propanoic Acid

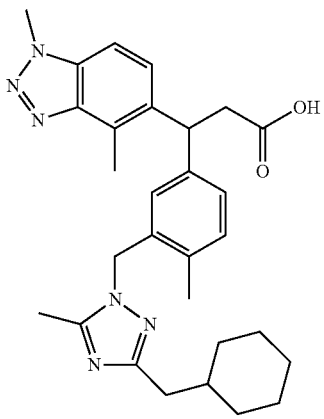 [SMILES: Cc1ccc(C(CC(=O)O)c2ccc3c(nnn3C)c2C)cc1Cn1nc(CC2CCCCC2)nc1C]

2-Cyclohexylacetohydrazide

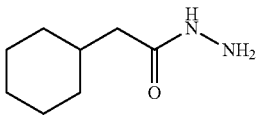 [SMILES: NNC(=O)CC1CCCCC1]

To a solution of methyl 2-cyclohexylacetate (10 g, 64.0 mmol) in methanol (60 mL) was added hydrazine monohydrate (12.44 mL, 256 mmol). The reaction mixture was stirred at 70° C. for 20 h. After it was cooled to ambient temperature, 200 mL of water was added. The solid was filtered to give the title compound 2-cyclohexylacetohydrazide (6.8 g, 42.3 mmol, 66.0% yield) as white solid. LCMS m/z 157.2 (M+H)⁺, 1.47 min (ret. Time)

3-(Cyclohexylmethyl)-5-methyl-1H-1,2,4-triazole

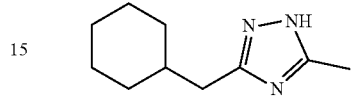

A mixture of 2-cyclohexylacetohydrazide (1 g, 6.40 mmol), ethanethioamide (1.924 g, 25.6 mmol), pyridine (10 mL) and 1-butanol (50.0 mL) were stirred at 130° C. for 20 h. The reaction mixture was concentrated. The crude product was purified by reverse-phase HPLC to give the title compound 3-(cyclohexylmethyl)-5-methyl-4H-1,2,4-triazole (400 mg, 2.072 mmol, 32.4% yield). LC-MS m/z 180.2 (M+H)⁺, 1.43 min (ret. time)

Ethyl 3-(3-((3-(cyclohexylmethyl)-5-methyl-1H-1,2,4-triazol-1-yl)methyl)-4-methylphenyl)-3-(1,4-dimethyl-1H-benzo[d][1,2,3]triazol-5-yl)propanoate

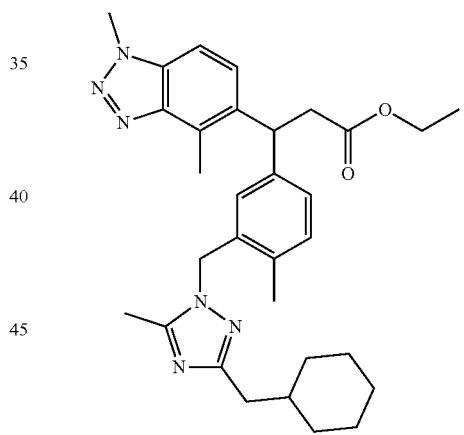

To a solution of 3-(cyclohexylmethyl)-5-methyl-4H-1,2,4-triazole (55.7 mg, 0.311 mmol) in N,N-dimethylformamide (DMF) (2 mL) was added sodium hydride (12.44 mg, 0.311 mmol) under the protection of nitrogen at 0° C. The reaction mixture was stirred for 20 min at 000° C. and ethyl 3-(3-(chloromethyl)-4-methylphenyl)-3-(1,4-dimethyl-1H-benzo[d][1,2,3]triazol-5-yl)propanoate (100 mg, 0.259 mmol) was added to the mixture. Then it was stirred at 10° C. for 1 h. Water (20 mL) was added and the mixture extracted with EtOAc (3×20 mL). The combined organic layer was dried over MgSO₄ and concentrated to give the title compound ethyl 3-(3-((3-(cyclohexylmethyl)-5-methyl-4H-1,2,4-triazol-4-yl)methyl)-4-methylphenyl)-3-(1,4-dimethyl-1H-benzo[d][1,2,3]triazol-5-yl)propanoate (115 mg, 0.183 mmol, 70.6% yield) which was carried to the next step without further purification. LC-MS m/z 529.3 (M+H)⁺, 1.96 (ret. time)

3-(3-((3-(Cyclohexyl methyl)-5-methyl-1H-1,2,4-triazol-1-yl)methyl)-4-methylphenyl)-3-(1,4-dimethyl-1H-benzo[d][1,2,3]triazol-5-yl)propanoic Acid

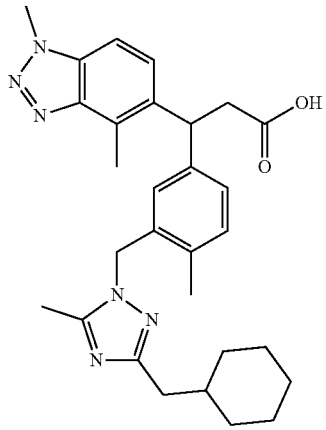 [SMILES: Cc1ccc(C(CC(=O)O)c2ccc3c(nnn3C)c2C)cc1Cn1nc(CC2CCCCC2)nc1C]

To a solution of ethyl 3-(3-((3-(cyclohexylmethyl)-5-methyl-4H-1,2,4-triazol-4-yl)methyl)-4-methylphenyl)-3-(1,4-dimethyl-1H-benzo[d][1,2,3]triazol-5-yl)propanoate (110 mg, 0.208 mmol) in tetrahydrofuran (THF) (2 mL) was added a solution of sodium hydroxide (33.3 mg, 0.832 mmol) in water (2.0 mL). The reaction mixture was stirred at 10° C. for 16 h. 1N HCl was added to pH 3. The crude product was purified by reverse-phase HPLC to give the title compound 3-(3-((3-(cyclohexylmethyl)-5-methyl-1H-1,2,4-triazol-1-yl)methyl)-4-methylphenyl)-3-(1,4-dimethyl-1H-benzo[d][1,2,3]triazol-5-yl)propanoic acid (20 mg, 0.039 mmol, 18.54% yield). LC-MS m/z 501.0 (M+H)+, 1.66 (ret. time)

Example 138

3-(3-((2-((1,4-Oxazepan-4-yl)methyl)-1H-imidazol-1-yl)methyl)-4-methylphenyl)-3-(1,4-dimethyl-1H-benzo[d][1,2,3]triazol-5-yl)-2,2-dimethylpropanoic Acid To a solution of 4-((1H-imidazol-2-yl)methyl)-1,4-oxazepane (43.5 mg, 0.240 mmol) in N,N-dimethylformamide (DMF) (1 mL) at 25° C. was added NaH (16.00 mg, 0.400 mmol). The mixture was stirred at 25° C. for 40 min. Methyl 3-(3-(chloromethyl)-4-methylphenyl)-3-(1,4-dimethyl-1H-benzo[d][1,2,3]triazol-5-yl)-2,2-dimethylpropanoate (80 mg, 0.200 mmol) in N,N-dimethylformamide (DMF) (1 mL) was added and the mixture was stirred for 21 h. It was quenched with saturated NH₄Cl and extracted with ethyl acetate twice. The combined organic layer was concentrated to give the crude product. The reaction mixture was purified by silica gel chromatography (product eluted at 100% ethyl acetate). Desired fractions were concentrated and re-dissolved in MeOH (2 mL). LiOH (0.600 mL, 1.200 mmol) was added and the reaction was heated in a Biotage microwave at high absorption for 3 h at 120° C. It was acidified with 6 N HCl to pH~1. 0.5 mL DMSO was added and concentrated. The crude product was purified by reverse-phase HPLC (with 0.1% TFA condition) to give the title compound (53 mg, 0.100 mmol, 49.9% yield) (69-B1). LC-MS m/z 531.1 (M+H)+, 0.66 min (ret. time)

The compounds in Table 15 were prepared by a method similar to the one described for the preparation of 3-(3-((2-((1,4-oxazepan-4-yl)methyl)-1H-imidazol-1-yl)methyl)-4-methylphenyl)-3-(1,4-dimethyl-1H-benzo[d][1,2,3]triazol-5-yl)-2,2-dimethylpropanoic acid. As is appreciated by those skilled in the art, these analogous examples may involve variations in general reaction conditions.

TABLE 15

| Ex # | Structure | Name | LCMS [M + H]+ | Retention Time (min) |
|---|---|---|---|---|
| Example 139 | 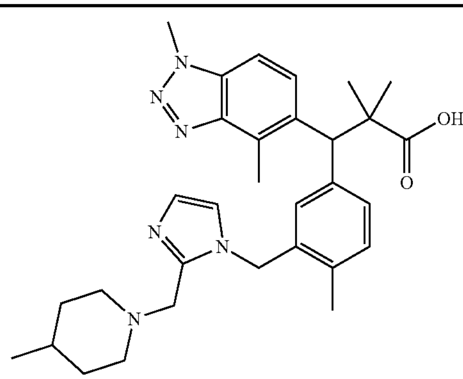 | 3-(1,4-Dimethyl-1H-benzo[d][1,2,3]triazol-5-yl)-2,2-dimethyl-3-(4-methyl-3-((2-((4-methylpiperidin-1-yl)methyl)-1H-imidazol-1-yl)methyl)phenyl)propanoic acid | 529.5 | 0.71 |

TABLE 15-continued

| Ex # | Structure | Name | LCMS [M + H]+ | Retention Time (min) |
|---|---|---|---|---|
| Example 140 | 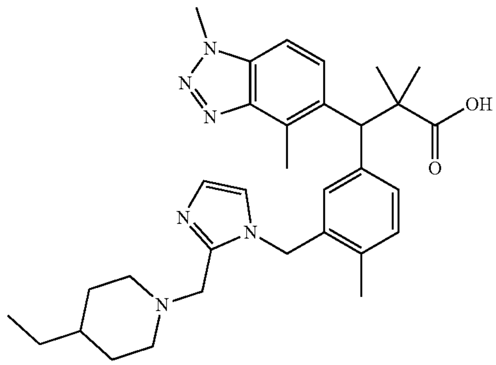 | 3-(1,4-Dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoic acid, formic acid salt | 543.5 | 0.82 |
| Example 141 | 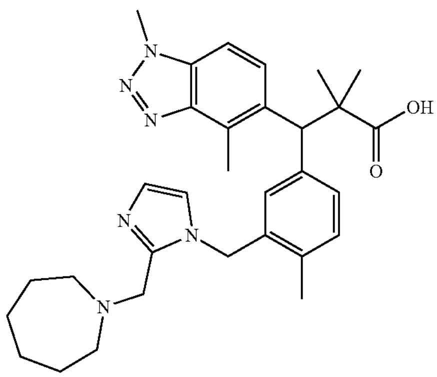 [SMILES: Cc1ccc(C(c2ccc3c(nnn3C)c2C)C(C)(C)C(=O)O)cc1Cn1ccnc1CN1CCCCCC1] | 3-(3-((2-(Azepan-1-ylmethyl)-1H-imidazol-1-yl)methyl)-4-methylphenyl)-3-(1,4-dimethyl-1H-benzo[d][1,2,3]triazol-5-yl)-2,2-dimethylpropanoic acid, trifluoroacetic acid salt | 529.5 | 0.72 |
| Example 142 | 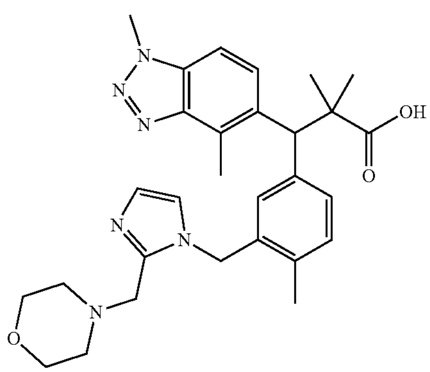 [SMILES: Cc1ccc(C(c2ccc3c(nnn3C)c2C)C(C)(C)C(=O)O)cc1Cn1ccnc1CN1CCOCC1] | 3-(1,4-Dimethyl-1H-benzo[d][1,2,3]triazol-5-yl)-2,2-dimethyl-3-(4-methyl-3-((2-(morpholinomethyl)-1H-imidazol-1-yl)methyl)phenyl)propanoic acid, trifluoroacetic acid salt | 517.4 | 0.75 |
| Example 143 | 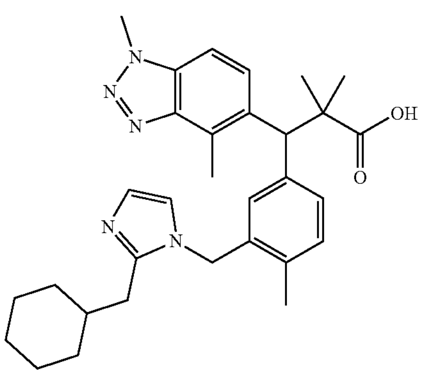 [SMILES: Cc1ccc(C(c2ccc3c(nnn3C)c2C)C(C)(C)C(=O)O)cc1Cn1ccnc1CC1CCCCC1] | 3-(3-((2-(Cyclohexylmethyl)-1H-imidazol-1-yl)methyl)-4-methylphenyl)-3-(1,4-dimethy-1H-benzo[d][1,2,3]triazol-5-yl)-2,2-dimethylpropanoic acid, trifluoroacetic acid salt | 514.4 | 0.90 |

TABLE 15-continued

| Ex # | Structure | Name | LCMS [M + H]+ | Retention Time (min) |
|---|---|---|---|---|
| Example 144 | 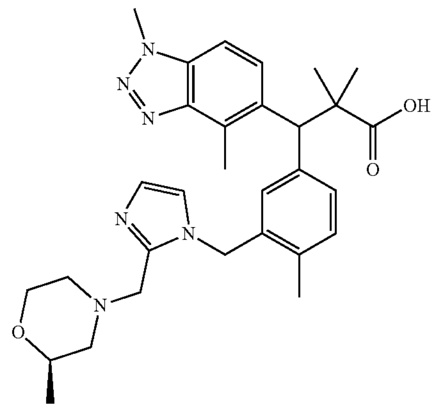 [SMILES: Cc1ccc(C(c2ccc3c(nnn3C)c2C)C(C)(C)C(=O)O)cc1Cn1ccnc1CN1CCO[C@H](C)C1] | 3-(1,4-Dimethyl-1H-benzo[d][1,2,3]triazol-5-yl)-2,2-dimethyl-3-(4-methyl-3-((2-(((R)-2-methylmorpholino)methyl)-1H-imidazol-1-yl)methyl)phenyl)propanoic acid, trifluoroacetic acid salt | 531.4 | 0.70 |
| Example 145 | 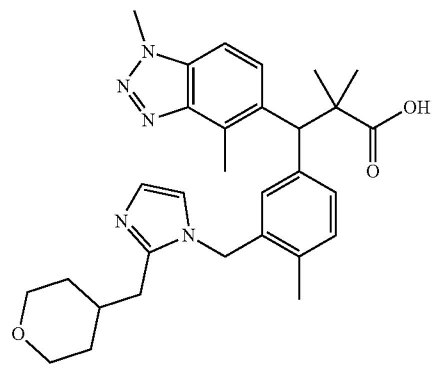 [SMILES: Cc1ccc(C(c2ccc3c(nnn3C)c2C)C(C)(C)C(=O)O)cc1Cn1ccnc1CC1CCOCC1] | 3-(1,4-Dimethyl-1H-benzo[d][1,2,3]triazol-5-yl)-2,2-dimethyl-3-(4-methyl-3-((2-((tetrahydro-2H-pyran-4-yl)methyl)-1H-imidazol-1-yl)methyl)phenyl)propanoic acid, trifluoroacetic acid salt | 516.5 | 0.69 |
| Example 146 | 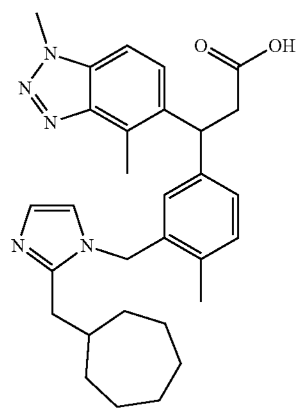 [SMILES: Cc1ccc(C(CC(=O)O)c2ccc3c(nnn3C)c2C)cc1Cn1ccnc1CC1CCCCCC1] | 3-(3-((2-(Cycloheptylmethyl)-1H-imidazol-1-yl)methyl)-4-methylphenyl)-3-(1,4-dimethyl-1H-benzo[d][1,2,3]triazol-5-yl)propanoic acid, formic acid salt | 500.30 | 1.86 |
| Example 147 | 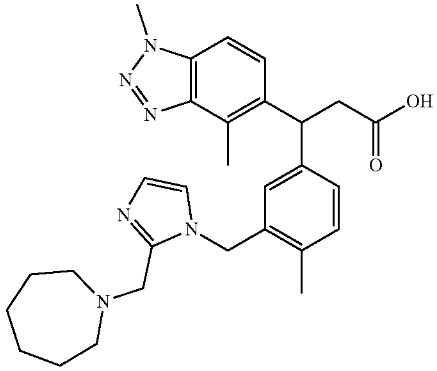 [SMILES: Cc1ccc(C(CC(=O)O)c2ccc3c(nnn3C)c2C)cc1Cn1ccnc1CN1CCCCCC1] | 3-(3-((2-(Azepan-1-ylmethyl)-1H-imidazol-1-yl)methyl)-4-methylphenyl)-3-(1,4-dimethyl-1H-benzo[d][1,2,3]triazol-5-yl)propanoic acid, formic acid salt | 501.4 | 0.66 |

TABLE 15-continued

| Ex # | Structure | Name | LCMS [M + H]+ | Retention Time (min) |
|---|---|---|---|---|
| Example 148 | 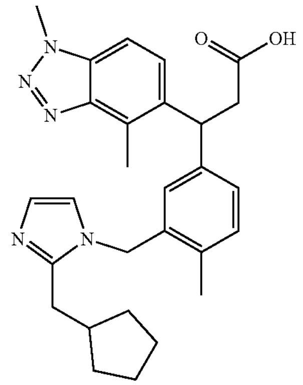 [SMILES: Cc1ccc(C(CC(=O)O)c2ccc3c(nnn3C)c2C)cc1Cn1ccnc1CC1CCCC1] | 3-(3-((2-(Cyclopentylmethyl)-1H-imidazol-1-yl)methyl)-4-methylphenyl)-3-(1,4-dimethyl-1H-benzo[d][1,2,3]triazol-5-yl)propanoic acid | 472.25 | 1.75 |
| Example 149 | 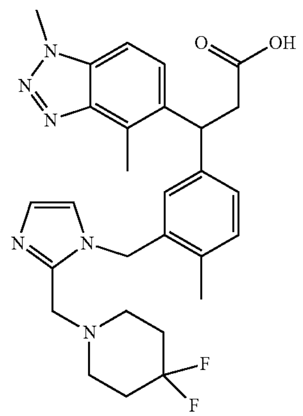 [SMILES: Cc1ccc(C(CC(=O)O)c2ccc3c(nnn3C)c2C)cc1Cn1ccnc1CN1CCC(F)(F)CC1] | 3-(3-((2-((4,4-Difluoropiperidin-1-yl)methyl)-1H-imidazol-1-yl)methyl)-4-methylphenyl)-3-(1,4-dimethyl-1H-benzo[d][1,2,3]triazol-5-yl)propanoic acid | 501.4 | 0.66 |
| Example 150 | 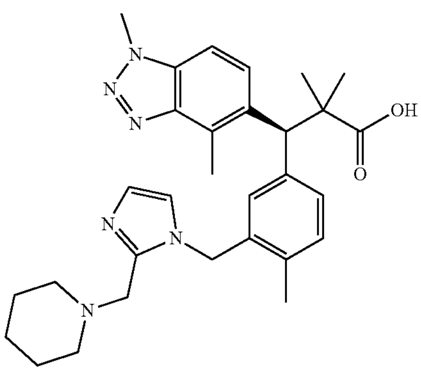 [SMILES: Cc1ccc([C@@H](c2ccc3c(nnn3C)c2C)C(C)(C)C(=O)O)cc1Cn1ccnc1CN1CCCCC1] | (S)-3-(1,4-Dimethyl-1H-benzo[d][1,2,3]triazol-5-yl)-2,2-dimethyl-3-(4-methyl-3-((2-(piperidin-1-ylmethyl)-1H-imidazol-1-yl)methyl)phenyl)propanoic acid | 515.6 | 0.72 |
| Example 151 | 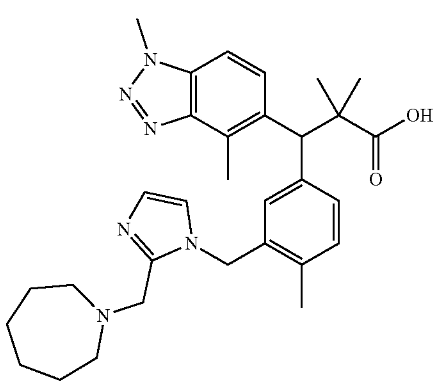 [SMILES: Cc1ccc(C(c2ccc3c(nnn3C)c2C)C(C)(C)C(=O)O)cc1Cn1ccnc1CN1CCCCCC1] | 3-(3-((2-(Azepan-1-ylmethyl)-1H-imidazol-1-yl)methyl)-4-methylphenyl)-3-(1,4-dimethyl-1H-benzo-[d][1,2,3]triazol-5-yl)-2,2-domethylpropanoic acid, 0.3 formic acid salt | 529.3 | 0.87 |

Example 152

(3R)-3-(1,4-Dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2-methylpropanoic Acid, Trifluoroacetic Acid Salt

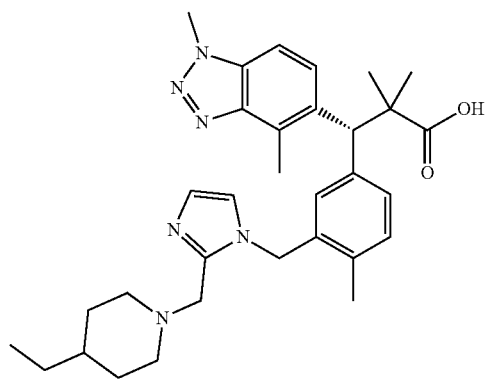 [SMILES: CCC1CCN(Cc2nccn2Cc2cc([C@H](c3ccc4c(nnn4C)c3C)C(C)(C)C(=O)O)ccc2C)CC1]

(3R)-Benzyl 3-(1,4-dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2-methylpropanoate

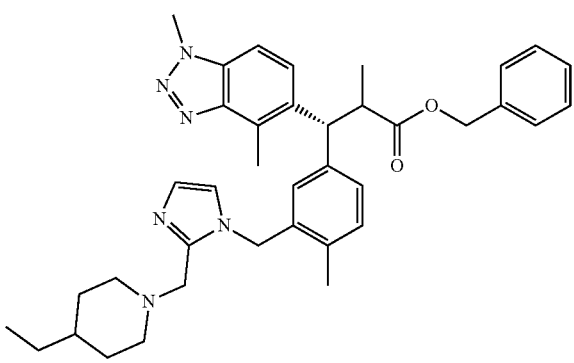 [SMILES: CCC1CCN(Cc2nccn2Cc2cc([C@H](c3ccc4c(nnn4C)c3C)C(C)C(=O)OCc3ccccc3)ccc2C)CC1]

To a solution of 1-((1H-imidazol-2-yl)methyl)-4-ethylpiperidine (36.8 mg, 0.190 mmol) in N,N-dimethylformamide (DMF) (1 mL) at 0° C. was added NaH (8.31 mg, 0.208 mmol). The mixture was stirred at 0° C. for 40 min. (3R)-benzyl 3-(1,4-dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2-methylpropanoate (74 mg, 0.120 mmol, 69.1% yield) in N,N-dimethylformamide (DMF) (1 mL) was added and the mixture was stirred for 21 h. More NaH (8.31 mg, 0.208 mmol) was added and stirred for 5 h. It was quenched with saturated NH$_4$Cl, extracted with ethyl acetate twice. The combined organic layer was concentrated to give the crude product. The crude product was purified by silica gel chromatography. The desired fractions were concentrated to give the title compound (74 mg, 0.120 mmol, 69.1% yield). LC-MS m/z 619.4 (M+H)$^+$, 1.06 min (ret. time)

(3R)-3-(1,4-Dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2-methylpropanoic Acid, Trifluoroacetic Acid Salt

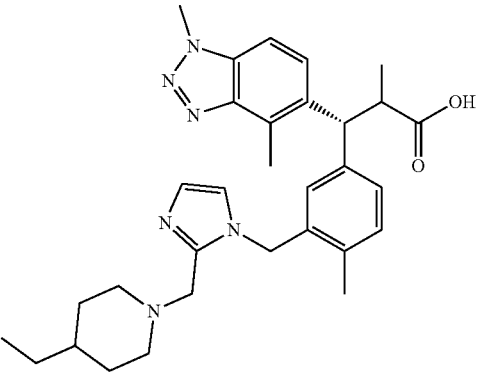 [SMILES: CCC1CCN(Cc2nccn2Cc2cc([C@H](c3ccc4c(nnn4C)c3C)C(C)C(=O)O)ccc2C)CC1]

A solution of (3R)-benzyl 3-(1,4-dimethyl-1H-benzo[d][1,2,3]triazol-5-yl)-3-(3-((2-((4-ethylpiperidin-1-yl)methyl)-1H-imidazol-1-yl)methyl)-4-methylphenyl)-2-methylpropanoate (74 mg, 0.120 mmol) in ethyl acetate (6 mL) was passed through H-Cube (cartridge: Pd/C, 1 mL/min, 25° C.) for 2 h. The solvent was removed under reduced pressure and the sample was purified by reverse-phase HPLC (with 0.1% TFA condition) to give the title compound (26.2 mg, 0.050 mmol, 41.4% yield). LC-MS m/z 529.3 (M+H)$^+$, 0.77 min (ret. time

Example 153

3-(1,4-Dimethyl-1H-benzo[d][1,2,3]triazol-5-yl)-3-(4-methyl-3-((2-(pyrrolidin-1-ylmethyl)-1H-imidazol-1-yl)methyl)phenyl)propanoic Acid, Formic Acid Salt

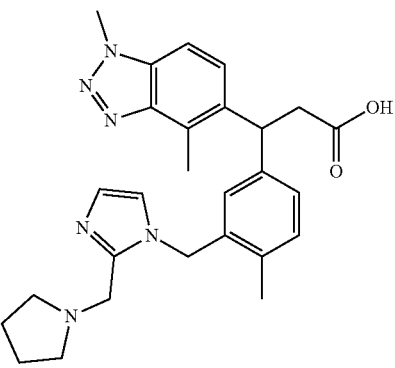 [SMILES: Cc1ccc(C(CC(=O)O)c2ccc3c(nnn3C)c2C)cc1Cn1ccnc1CN1CCCC1]

2-Cyclopentylethanol

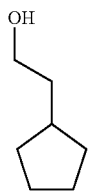

To a solution of 2-cyclopentylacetic acid (5 g, 39.0 mmol) in tetrahydrofuran (THF) (10 mL) at 0° C. was added a solution of BH$_3$.DMS (39.0 mL, 78 mmol) in toluene dropwise. It was stirred at ambient temperature for 16 h. The reaction mixture was cooled to 0° C. and quenched with methanol (10 mL) dropwise. The reaction mixture was stirred at ambient temperature for 3 h and then concentrated. The crude residue was diluted with ethyl acetate (50 mL) and washed with 1N HCl (10 mL), brine solution (10 mL) and dried over anhydrous Na$_2$SO$_4$, filtered and concentrated to give the title compound (4 g, 35.0 mmol, 90% yield). 1H NMR (400 MHz, cdcl3) δ=3.66 (t, J=6.9 Hz, 2H), 1.91-1.72 (m, 3H), 1.64-1.45 (m, 6H), 1.19-1.03 (m, 2H).

2-Cyclopentylacetaldehyde

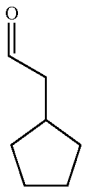

To a solution of 2-cyclopentylethanol (4 g, 35.0 mmol) in dichloromethane (DCM) (50 mL) at 0° C. was added Dess-Martin periodinane (22.29 g, 52.5 mmol). It was stirred at ambient temperature for 4 h. The reaction mixture was filtered through celite. The filtrate was concentrated to give the title compound (2 g, 17.83 mmol, 50.9% yield) as liquid. 1H NMR (400 MHz, CDCl$_3$) δ=9.76 (t, J=2.2 Hz, 1H), 2.44 (dd, J=2.1, 7.1 Hz, 2H), 2.34-2.22 (m, 1H), 1.95-1.80 (m, 2H), 1.71-1.45 (m, 4H), 1.23-1.07 (m, 2H).

2-(Cyclopentylmethyl)-1H-imidazole

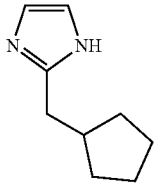 [SMILES: c1c[nH]c(CC2CCCC2)n1]

To a solution of 2-cyclopentylacetaldehyde (2 g, 17.83 mmol) in water (20 mL) at ambient temperature was added glyoxal hydrate (0.749 g, 3.57 mmol) and ammonia (0.386 mL, 17.83 mmol). The reaction was stirred at ambient temperature for 18 h. The reaction mixture was diluted with water and extracted with twice DCM. The organic layer was dried under anhydrous Na$_2$SO$_4$, filtered and concentrated to give the crude compound. It was purified by silica gel chromatography to give the title compound (400 mg, 2.428 mmol, 13.62% yield) as liquid. LC-MS m/z 151.15 (M+H)$^+$, 2.386 min (ret. time)

Ethyl 3-(1,4-dimethyl-1H-benzo[d][1,2,3]triazol-5-yl)-3-(4-methyl-3-((2-(pyrrolidin-1-ylmethyl)-1H-imidazol-1-yl)methyl)phenyl)propanoate

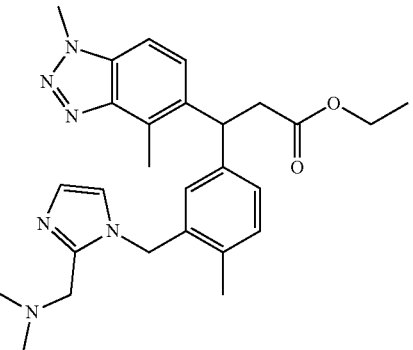

To a solution of 2-(pyrrolidin-1-ylmethyl)-1H-imidazole (37.6 mg, 0.249 mmol) in N,N-dimethylformamide (DMF) (1 mL) at 25° C. was added NaH (10.78 mg, 0.270 mmol). The mixture was stirred at 25° C. for 40 min. Ethyl 3-(3-(chloromethyl)-4-methylphenyl)-3-(1,4-dimethyl-1H-benzo[d][1,2,3]triazol-5-yl)propanoate (80 mg, 0.207 mmol) in N,N-dimethylformamide (DMF) (1 mL) was added and the mixture was stirred for 21 h. It was quenched with saturated NH$_4$Cl and extracted with ethyl acetate twice. The combined organic layer was concentrated and purified by reverse-phase HPLC (with 0.1% TFA condition) to give the title compound (80 mg, 0.160 mmol, 77% yield). LC-MS m/z 501.4 (M+H)$^+$, 0.75 min (ret. time)

3-(1,4-Dimethyl-1H-benzo[d][1,2,3]triazol-5-yl)-3-(4-methyl-3-((2-(pyrrolidin-1-ylmethyl)-1H-imidazol-1-yl)methyl)phenyl)propanoic Acid, Formic Acid Salt

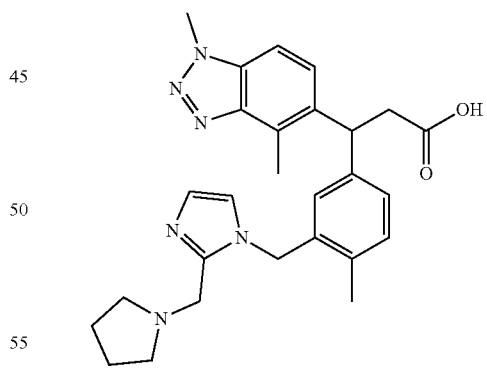

A mixture of ethyl 3-(1,4-dimethyl-1H-benzo[d][1,2,3]triazol-5-yl)-3-(4-methyl-3-((2-(pyrrolidin-1-ylmethyl)-1H-imidazol-1-yl)methyl)phenyl)propanoate (77 mg, 0.154 mmol) and 2M LiOH (0.461 mL, 0.923 mmol) in methanol (2 mL) was heated in a Biotage microwave at high absorption for 30 minutes at 80° C. It was acidified with 6N HCl and 0.5 mL DMSO was added. It was concentrated and purified with preparative HPLC under acidic conditions to give the title compound (29.6 mg, 0.057 mmol, 37.1% yield). LC-MS m/z 473.4 (M+H)$^+$, 0.61 min (ret. time)

Example 154

3-(1,4-dimethyl-1H-benzo[d][1,2,3]triazol-5-yl)-3-(4-methyl-3-((2-(piperidin-1-ylmethyl)-1H-imidazol-1-yl)methyl)phenyl)propanoic Acid, Trifluoroacetic Acid Salt

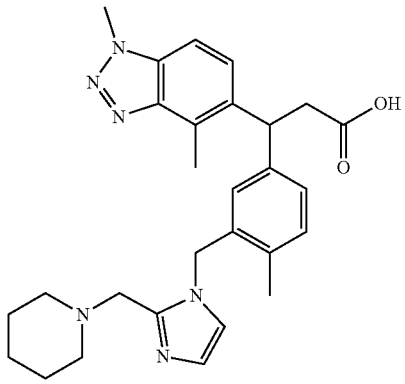 [SMILES: Cc1ccc(C(CC(=O)O)c2ccc3c(nnn3C)c2C)cc1Cn1ccnc1CN1CCCCC1]

Ethyl 3-(3-(chloromethyl)-4-methylphenyl)-3-(1,4-dimethyl-1H-benzo[d][1,2,3]triazol-5-yl)propanoate

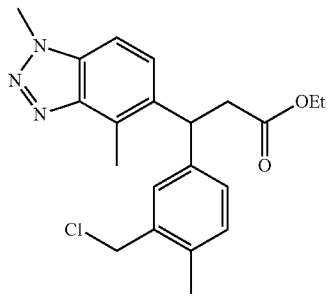 [SMILES: CCOC(=O)CC(c1ccc(C)c(CCl)c1)c1ccc2c(nnn2C)c1C]

Thionyl chloride (0.397 mL, 5.44 mmol) was added to a solution of ethyl 3-(1,4-dimethyl-1H-benzo[d][1,2,3]triazol-5-yl)-3-(3-(hydroxymethyl)-4-methylphenyl)propanoate (1 g, 2.72 mmol) in dichloromethane (DCM) (5.44 mL) at ambient temperature and stirred for 1 hour. The solution was concentrated in vacuo to give the title compound (1.1 g, 2.85 mmol, 105% yield). LC/MS: m/z 386.1 (M+H)$^+$, 1.13 min (ret. time).

3-(1,4-dimethyl-1H-benzo[d][1,2,3]triazol-5-yl)-3-(4-methyl-3-((2-(piperidin-1-ylmethyl)-1H-imidazol-1-yl)methyl)phenyl)propanoic Acid, Trifluoroacetic Acid Salt

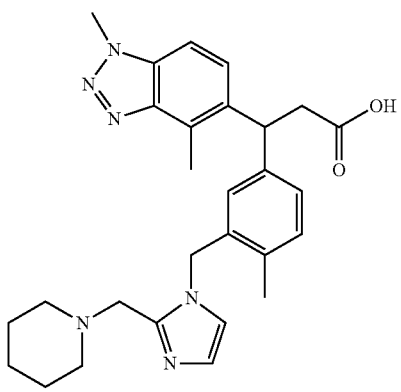 [SMILES: Cc1ccc(C(CC(=O)O)c2ccc3c(nnn3C)c2C)cc1Cn1ccnc1CN1CCCCC1]

Sodium hydride (24.88 mg, 0.622 mmol) was added to a solution of 1-((1H-imidazol-2-yl)methyl)piperidine (34.3 mg, 0.207 mmol) in N,N-dimethylformamide (DMF) (4.146 mL) at 0° C. The solution was allowed to stir for 30 minutes before a solution of ethyl 3-(3-(chloromethyl)-4-methylphenyl)-3-(1,4-dimethyl-1H-benzo[d][1,2,3]triazol-5-yl)propanoate (80 mg, 0.207 mmol) in N,N-dimethylformamide (DMF) (4.146 mL) was added. The reaction was complete after 48 hours. The solution was quenched with saturated ammonium chloride (5 mL) and extracted with ethyl acetate (3×10 mL), washed (brine), and solvent removed in vacuo. The aqueous fraction was concentrated and redissolved in a 4:1 isopropanol/dichloromethane and filtered. The filtrate was concentrated and the crude product was purified by reverse-phase HPLC (with 0.1% TFA) to give the title compound (26.2 mg, 0.044 mmol, 21.04% yield). LC/MS: m/z 487.1 (M+H)$^+$, 0.7 min (ret. time).

Example 155

3-(3-((2-(7-Azabicyclo[2.2.1]heptan-7-ylmethyl)-1H-imidazol-1-yl)methyl)-4-methylphenyl)-3-(1,4-dimethyl-1H-benzo[d][1,2,3]triazol-5-yl)-2,2-dimethylpropanoic Acid, Trifluoroacetic Acid Salt

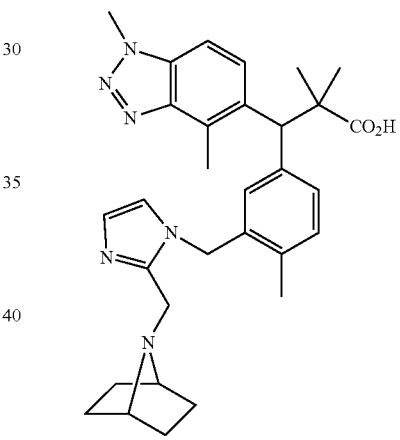

To a solution of methyl 3-(3-(chloromethyl)-4-methylphenyl)-3-(1,4-dimethyl-1H-benzo[d][1,2,3]triazol-5-yl)-2,2-dimethylpropanoate (0.100 g, 0.195 mmol) in acetonitrile (4 mL) was added 7-((1H-imidazol-2-yl)methyl)-7-azabicyclo[2.2.1]heptane (0.035 g, 0.195 mmol) and DIEA (0.136 mL, 0.780 mmol) and stirred at room temperature for 18 h. The reaction was heated to 55° C. for 4 h. The solvent was concentrated and the residue was redissolved in N,N-dimethylformamide (DMF) (4.00 mL). Sodium hydride (0.023 g, 0.585 mmol) was added and stirred at 45° C. for 18 h. The solvent was then concentrated. The residue was redissolved in methanol (1 mL) tetrahydrofuran (THF) (1 mL) and water (1 mL LiOH (0.019 g, 0.780 mmol was added and stirred at room temperature for 22 h. The reaction was heated to 45° C. after which additional LiOH (0.023 g, 0.975 mmol was added and heating was continued for 6 h. The reaction mixture was then transferred to a microwave reaction vial and heated to 150° C. for 1 hour. The solvent was then concentrated, the residue was redissolved in DMSO and acidified with TFA. The residue was purified by reverse phase preparative HPLC under neutral conditions and then acidic conditions to provide the title compound. (0.045 g, 35% yield) LC-MS m/z 526 (M+H)+, 0.68 min (ret. time).

Example 156

3-(3-((2-(8-Azabicyclo[3.2.1]octan-8-ylmethyl)-1H-imidazol-1-yl)methyl)-4-methylphenyl)-3-(1,4-dimethyl-1H-benzo[d][1,2,3]triazol-5-yl)-2,2-dimethylpropanoic Acid, Trifluoroacetic Acid Salt

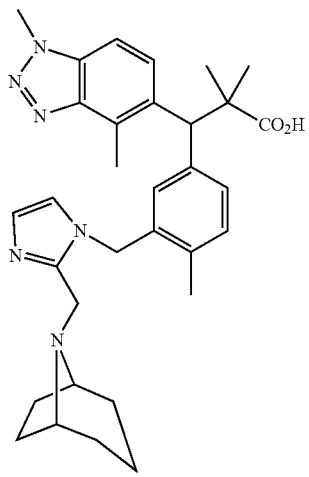 [SMILES: Cc1ccc(C(c2ccc3c(nnn3C)c2C)C(C)(C)C(=O)O)cc1Cn1ccnc1CN1C2CCCC1CC2]

To a solution of methyl 3-(3-(chloromethyl)-4-methylphenyl)-3-(1,4-dimethyl-1H-benzo[d][1,2,3]triazol-5-yl)-2,2-dimethylpropanoate (0.100 g, 0.195 mmol) in acetonitrile (4 mL) was added 8-((1H-imidazol-2-yl)methyl)-8-azabicyclo[3.2.1]octane (0.037 g, 0.195 mmol) and DIEA (0.136 mL, 0.780 mmol) and stirred at room temperature for 18 h. The solvent was concentrated and the residue was redissolved in N,N-dimethylformamide (DMF) (4.00 mL). Sodium hydride (0.023 g, 0.585 mmol) was added and stirred at 45° C. for 18 h. The solvent was then concentrated. The residue was redissolved in methanol (1 mL), tetrahydrofuran (THF) (1 mL), and water (1 mL) and added LiOH (0.019 g, 0.780 mmol) and heated to 45° C. for 25 h. The reaction mixture was then transferred to a microwave reaction vial and heated to 150° C. for 1 hour. The solvent was then concentrated, the residue was redissolved in DMSO and acidified with TFA. The residue was purified by reverse phase preparative HPLC under neutral conditions and then acidic conditions to provide the title compound. (0.065 g, 50 yield %) LC-MS m/z 541 (M+H)+, 0.71 min (ret. time).

Example 157

(3R)-3-(3-((3-(1H-Pyrazol-1-yl)piperidin-1-yl)methyl)-4-methylphenyl)-3-(1,4-dimethyl-1H-benzo[d][1,2,3]triazol-5-yl)propanoic acid (isomer 1)

Isomer 1

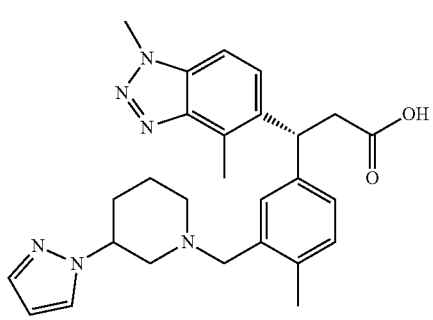

tert-Butyl 3-((methylsulfonyl)oxy)piperidine-1-carboxylate

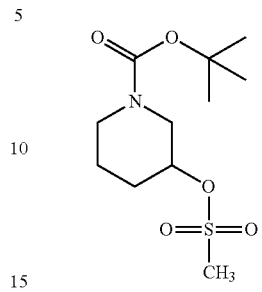

tert-Butyl 3-hydroxypiperidine-1-carboxylate (5 g, 24.84 mmol) was dissolved in dichloromethane (83 mL). Then, triethylamine (5.17 mL, 37.3 mmol) was added and the mixture was cooled to 0° C. (ice/water bath). Following this, methanesulfonyl chloride (2.115 mL, 27.3 mmol) was added and the reaction was allowed to stir for 16 h as the ice bath expired. The organic layer was washed with saturated aqueous NH4Cl solution (2×10 mL), water (10 mL), saturated NaCl solution (2×10 mL), dried (MgSO4), filtered and concentrated to yield the crude title compound as a yellow oil (6.6521 g, 96%) which was used in the next step without further purification. LC-MS m/z 280.1 (M+H)+, 0.80 (ret. time).

tert-Butyl 3-(1H-pyrazol-1-yl)piperidine-1-carboxylate

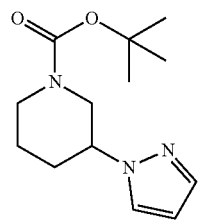 [SMILES: CC(C)(C)OC(=O)N1CCCC(n2cccn2)C1]

1H-Pyrazole (0.975 g, 14.32 mmol) was dissolved in DMF (35.8 mL). The mixture was cooled to 0° C. (ice/water bath). Following this, sodium hydride (60% in mineral oil) (0.573 g, 14.32 mmol) was added. The mixture was stirred at ambient temperature for 15 min after which tert-butyl 3-((methylsulfonyl)oxy)piperidine-1-carboxylate (2 g, 7.16 mmol) in DMF (5 mL) was added. The reaction mixture was allowed to stir at ambient temperature for 72 h. A portion (approximately half) of the reaction mixture was heated in a microwave at 100° C. (high absorption) for 1 h. The two reaction mixtures (ambient temperature conditions and microwave conditions) were combined and quenched by adding saturated aqueous NH4Cl solution (5 mL). The reaction mixture was concentrated. The residue was dissolved in ethylacetate (50 mL) and water (10 mL). The organic layer was washed with water (3×10 mL), saturated NaCl solution (10 mL) and dried (MgSO4) to give the crude material. The crude material was combined with crude material from another batch prepared in a similar manner to that reported here (the other batch was run on a 1 g scale of the mesylate). The combined crude products were purified on a silica cartridge (40 g) with a Combiflash Companion, eluting at 40 mL/min with a gradient running from 100% hexanes to 100% ethyl acetate over 45 min to give the title compound as a colorless oil (0.5808 g, 21.5% overall). LC-MS m/z 252.1 (M+H)+, 0.85 (ret. time).

3-(1H-Pyrazol-1-yl)piperidine, hydrochloride

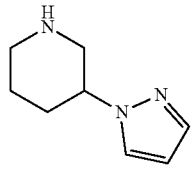 [SMILES: c1cnn(C2CCCNC2)c1]

tert-Butyl 3-(1H-pyrazol-1-yl)piperidine-1-carboxylate (0.5808 g, 2.311 mmol) was dissolved in 1,4-dioxane (5 mL). Following this, 4 M HCl in dioxane (3.47 mL, 13.87 mmol) was added and the reaction mixture was stirred at ambient temperature. After 2 h, additional 4 M HCl in dioxane (3 mL, 12.00 mmol) and 1,4-dioxane (3 mL) were added and the reaction was stirred ambient temperature for an additional 16 h (overall 18 h of stirring). The solvent was removed under reduced pressure to yield crude 3-(1H-pyrazol-1-yl) piperidine, hydrochloride as a white solid (0.3727 g, 86% yield) which was used in the next step without further purification. LC-MS m/z 151.9 (M+H)+, 0.30 (ret. time).

(3R)-Ethyl 3-(3-((3-(1H-pyrazol-1-yl)piperidin-1-yl) methyl)-4-methylphenyl)-3-(1,4-dimethyl-1H-benzo [d][1,2,3]triazol-5-yl)propanoate

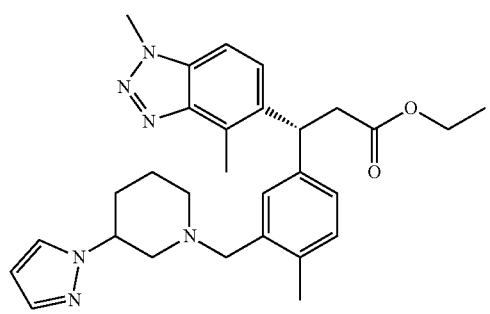 [SMILES: CCOC(=O)C[C@H](c1ccc(C)c(CN2CCCC(n3cccn3)C2)c1)c1ccc2c(nnn2C)c1C]

3-(1H-Pyrazol-1-yl) piperidine, hydrochloride (0.099 g, 0.527 mmol) was added to acetonitrile (2.174 mL). Then, DIEA (0.608 mL, 3.48 mmol) was added. Following this, (R)-ethyl 3-(3-(chloromethyl)-4-methylphenyl)-3-(1,4-dimethyl-1H-benzo[d][1,2,3]triazol-5-yl) propanoate (0.1678 g, 0.435 mmol) was added. The reaction mixture was heated in a microwave at 80° C. (high absorption) for 1 h. The solvent was removed to yield crude (3R)-ethyl 3-(3-((3-(1H-pyrazol-1-yl) piperidin-1-yl)methyl)-4-methylphenyl)-3-(1,4-dimethyl-1H-benzo[d][1,2,3]triazol-5-yl) propanoate (0.4632 g, 213%) which was used in the next step without further purification. LC-MS m/z 501.3 (M+H)+, 0.77 (ret. time).

(3R)-3-(3-((3-(1H-Pyrazol-1-yl)piperidin-1-yl) methyl)-4-methylphenyl)-3-(1,4-dimethyl-1H-benzo [d][1,2,3]triazol-5-yl)propanoic acid (isomer 1)

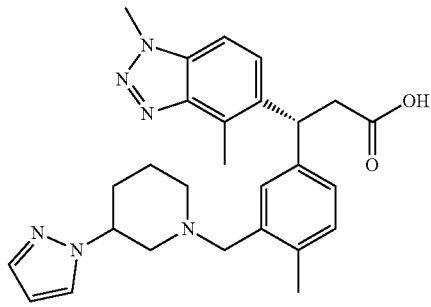

Isomer 1

(3R)-Ethyl 3-(3-((3-(1H-pyrazol-1-yl)piperidin-1-yl) methyl)-4-methylphenyl)-3-(1,4-dimethyl-1H-benzo[d][1, 2,3]triazol-5-yl)propanoate (0.4632 g, 0.925 mmol) was dissolved in methanol (3.08 mL). Then, 1 M NaOH (3.70 mL, 3.70 mmol) was added and the reaction mixture was heated in a microwave at 80° C. (high absorption) for 20 min. The mixture was acidified to pH 4-5 (1 M HCl). The crude mixture of diastereomers was purified by achiral reverse phase preparative HPLC under formic acid conditions (0.1%). Relevant fractions were collected and concentrated. The purified mixture of diastereomers was then separated by chiral SFC (supercritical fluid chromatography). Relevant fractions were concentrated to yield isomer 1 (0.0447 g, 10.22% yield). LC-MS m/z 473.4 (M+H)+, 0.63 (ret. time).

Example 158

(3R)-3-(3-((3-(1H-Pyrazol-1-yl)piperidin-1-yl) methyl)-4-methylphenyl)-3-(1,4-dimethyl-1H-benzo [d][1,2,3]triazol-5-yl)propanoic acid (isomer 2)

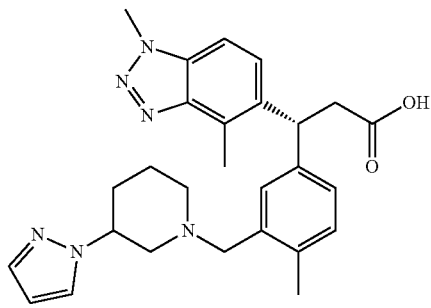

Isomer 2

This is the other isomer (isomer 2) obtained from the diastereomeric separation of (3R)-3-(3-((3-(1H-pyrazol-1-yl)piperidin-1-yl)methyl)-4-methylphenyl)-3-(1,4-dimethyl-1H-benzo[d][1,2,3]triazol-5-yl)propanoic acid. Relevant fractions resulting from the above SFC separation were combined to yield isomer 2 (0.0402 g, 9.19%). LC-MS m/z 473.4 (M+H)+, 0.61 (ret. time).

The compound in Table 16 was prepared by a method similar to the one described for the preparation of (3R)-3-

(3-((3-(1H-pyrazol-1-yl)piperidin-1-yl)methyl)-4-methylphenyl)-3-(1,4-dimethyl-1H-benzo[d][1,2,3]triazol-5-yl)propanoic acid (isomer 1) from (S)-ethyl 3-(1,4-dimethyl-1H-benzo[d][1,2,3]triazol-5-yl)-3-(3-(hydroxymethyl)-4-methylphenyl). As is appreciated by those skilled in the art, this analogous example may involve variations in general reaction conditions.

reaction mixture followed by water (4 mL). The mixture was diluted with water (20 mL) and ethyl acetate (35 mL). More water (10 mL; 30 mL overall) was added. The aqueous layer was extracted with ethyl acetate (2×20 mL). Combined organic extracts were washed with a saturated aqueous solution of NaHCO$_3$ (2×10 mL), saturated aqueous NaCl (10 mL), dried (Na$_2$SO$_4$), filtered, and concentrated under

TABLE 16

| Ex # | Structure | Name | LCMS [M + H]$^+$ | Retention Time (min) |
|---|---|---|---|---|
| Example 159 | 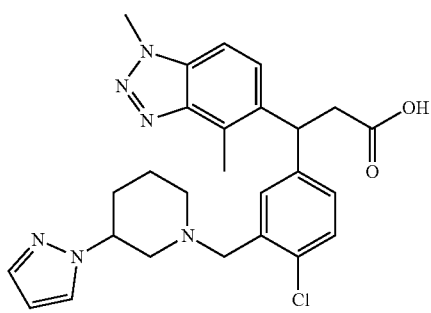 [SMILES: Cc1c(C(CC(=O)O)c2ccc(Cl)c(CN3CCCC(n4cccn4)C3)c2)ccc2c1nnn2C] Isomer 1 | (3S)-3-(3-((3-(1H-Pyrazol-1-yl)piperidin-1-yl)methyl)-4-methylphenyl)-3-(1,4-dimethyl-1H-benzo[d][1,2,3]triazol-5-yl)propanoic acid (isomer 1) | 473.4 | 0.62 |

Example 160

3-(3-((3-(1H-Pyrazol-1-yl)piperidin-1-yl)methyl)-4-chlorophenyl)-3-(1,4-di methyl-1H-benzo[d][1,2,3]triazol-5-yl)propanoic Acid, Formic Acid Salt

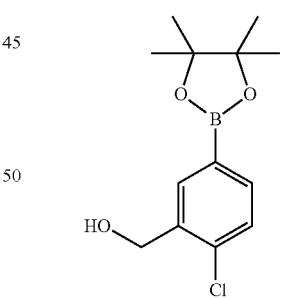

(5-Bromo-2-chlorophenyl)methanol

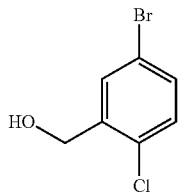

5-bromo-2-chlorobenzoic acid (2.5 g, 10.62 mmol) was dissolved in THF (53.1 mL) and the mixture was stirred at ambient temperature under nitrogen. Then, BH$_3$.THF (1.0 M in THF) (26.5 mL, 26.5 mmol) was added slowly and the light yellow reaction mixture was stirred at ambient temperature for 22 h. Ethanol (2 mL) was added slowly to the reduced pressure to yield the crude product. This crude material was recrystallized from dichloromethane, and the filtrate resulting from the recrystallization was concentrated and purified on a silica cartridge (40 g) with a Combiflash Companion, eluting at 40 mL/min with a gradient running from 100% hexanes to 40% ethyl acetate over 20 min. The pure products resulting from recrystallization and silica gel purification were combined to give the title compound as a white solid (1.6319 g, 69.4%). LC-MS m/z 203.0 (M-OH)$^+$, 0.79 (ret. time).

(2-Chloro-5-(4,4,5,5-tetramethyl-1,3,2-dioxaborolan-2-yl)phenyl)methanol (5-bromo-2-chlorophenyl) methanol (0.5 g, 2.258 mmol) was dissolved in DMF (9 mL). Then, bis(pinacolato)diboron (0.688 g, 2.71 mmol) was added and the mixture was stirred. Potassium acetate (0.665 g, 6.77 mmol) was added quickly followed by PdCl$_2$ (dppf) (0.050 g, 0.068 mmol). The reaction mixture was heated via microwave at 100° C. (high absorption) for 1 h. This procedure was performed two more times to give two additional batches prepared in a similar manner to that reported here. Material from all three batches was combined and the combined reaction mixture was concentrated. The residue was taken up in ethyl acetate (100 mL) and filtered through a short pad of celite (1.5 g). The resulting black solids were discarded. The filtrate was transferred into a separatory funnel and washed with water (4×10 mL gently). The organic layer was then washed with saturated NaCl solution (10 mL), dried (MgSO₄) and filtered. An initial attempt to purify the combined crude material on silica gel with a Combiflash Companion (40 g column, 40 mL/min flow rate, 100% hexanes to 50% ethyl acetate gradient over 23 min) did not produce clean product. Fractions were recombined and the crude material was adsorbed onto isolute and repurified on a silica cartridge (40 g) with a Combiflash Companion, eluting at 40 mL/min with a gradient running from 100% hexanes to 60% acetone over 45 min to yield the title compound as a white solid (0.6382 g, 40.2%). LC-MS m/z 251.0 (M-OH)$^+$, 0.97 (ret. time).

Ethyl 3-(4-chloro-3-(hydroxymethyl)phenyl)-3-(1,4-dimethyl-1H-benzo[d][1,2,3]triazol-5-yl)propanoate

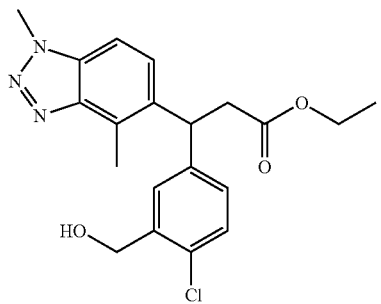 [SMILES: CCOC(=O)CC(c1ccc(Cl)c(CO)c1)c1ccc2c(nnn2C)c1C]

To a suspension of (2-chloro-5-(4,4,5,5-tetramethyl-1,3,2-dioxaborolan-2-yl)phenyl)methanol (1.098 g, 4.09 mmol), (E)-ethyl 3-(1,4-dimethyl-1H-benzo[d][1,2,3]triazol-5-yl)acrylate (3.31 g, 13.49 mmol), and chloro(1,5-cyclooctadiene)rhodium(I)dimer (0.202 g, 0.409 mmol) in water (24 mL) and 1,4-dioxane (9 mL) at ambient temperature was added triethylamine (1.140 mL, 8.18 mmol). The mixture was heated to 75° C. for 2 h then 95° C. for 2.5 h. The reaction mixture was allowed to cool to ambient temperature. The mixture was diluted with ethyl acetate (40 mL) and water (10 mL). The organic layer was washed gently with water (10 mL), saturated NaCl solution (10 mL), dried (MgSO₄), filtered, and concentrated. An initial attempt to purify the crude material on silica gel with a Combiflash Companion (40 g column, 40 mL/min flow rate, 100% hexanes to 100% ethyl acetate gradient over 80 min) did not produce clean product. Fractions were recombined and the crude material was adsorbed onto isolute and repurified on a silica cartridge (24 g) with a Combiflash Companion, eluting at 30 mL/min with a gradient running from 100% hexanes to 50% 3:1 ethyl acetate:ethanol over 65 min to yield the title compound as a light brown solid (0.6382 g, 40.2%). LC-MS m/z 388.2 (M+H)$^+$, 0.87 (ret. time).

Ethyl 3-(4-chloro-3-(chloromethyl)phenyl)-3-(1,4-dimethyl-1H-benzo[d][1,2,3]triazol-5-yl)propanoate

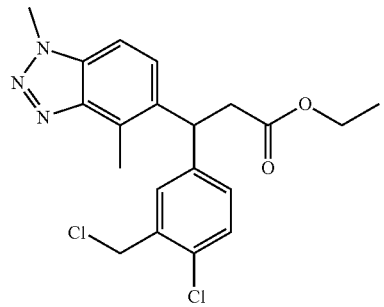 [SMILES: CCOC(=O)CC(c1ccc(Cl)c(CCl)c1)c1ccc2c(nnn2C)c1C]

Ethyl 3-(4-chloro-3-(hydroxymethyl)phenyl)-3-(1,4-dimethyl-1H-benzo[d][1,2,3]triazol-5-yl) propanoate (0.3 g, 0.773 mmol) was dissolved in DCM (2.5 mL). Thionyl chloride (0.113 mL, 1.547 mmol) was dispensed and the reaction mixture was stirred at ambient temperature for 20 minutes. Additional thionyl chloride (0.052 mL, 0.712 mmol) was added to the reaction mixture which was stirred for an additional 20 minutes. The reaction was concentrated to yield crude ethyl 3-(4-chloro-3-(chloromethyl)phenyl)-3-(1,4-dimethyl-1H-benzo[d][1,2,3]triazol-5-yl) propanoate) (0.3545 g, 113% yield) which was used in the next step without further purification. LC-MS m/z 406.2 (M+H)$^+$, 1.12 (ret. time).

Ethyl 3-(3-((3-(1H-pyrazol-1-yl)piperidin-1-yl)methyl)-4-chlorophenyl)-3-(1,4-dimethyl-1H-benzo[d][1,2,3]triazol-5-yl)propanoate

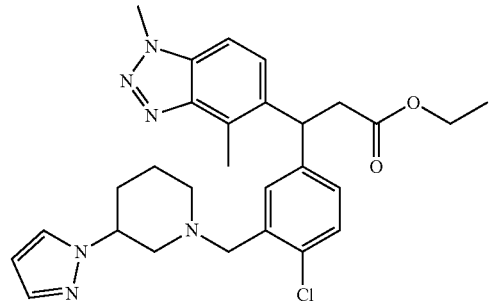 [SMILES: CCOC(=O)CC(c1ccc(Cl)c(CN2CCCC(n3cccn3)C2)c1)c1ccc2c(nnn2C)c1C]

3-(1H-Pyrazol-1-yl) piperidine, hydrochloride (0.02 g, 0.106 mmol) was dissolved in acetonitrile (2 mL). To this mixture was added DIEA (0.060 mL, 0.345 mmol), followed by ethyl 3-(4-chloro-3-(chloromethyl)phenyl)-3-(1,4-dimethyl-1H-benzo[d][1,2,3]triazol-5-yl)propanoate (0.035 g, 0.086 mmol). The resulting reaction mixture was heated on a microwave at 90° C. (high absorption) for 30 min. Additional 3-(1H-pyrazol-1-yl)piperidine, hydrochloride (0.005 g, 0.026 mmol) was added and the reaction was heated in a microwave at 80° C. (high absorption) for 30 min. The reaction mixture was concentrated to yield crude ethyl 3-(3-((3-(1H-pyrazol-1-yl) piperidin-1-yl)methyl)-4-chlorophenyl)-3-(1,4-dimethyl-1H-benzo[d][1,2,3]triazol-5-yl) propanoate (0.0861 g, 192% yield) which was used in the next step without further purification. LC-MS m/z 521.4 (M+H)$^+$, 0.75 (ret. time).

3-(3-((3-(1H-pyrazol-1-yl)piperidin-1-yl)methyl)-4-chlorophenyl)-3-(1,4-dimethyl-1H-benzo[d][1,2,3]triazol-5-yl)propanoic Acid, Formic Acid Salt

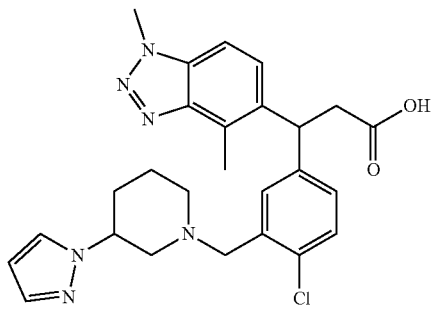 [SMILES: Cc1c(C(CC(=O)O)c2ccc(Cl)c(CN3CCCC(n4cccn4)C3)c2)ccc2c1nnn2C]

Ethyl 3-(3-((3-(1H-pyrazol-1-yl) piperidin-1-yl)methyl)-4-chlorophenyl)-3-(1,4-dimethyl-1H-benzo[d][1,2,3]triazol-5-yl)propanoate (0.0861 g, 0.165 mmol) was dissolved in methanol (2 mL). Then 2.5 M NaOH (0.276 mL, 0.689 mmol) was added and the reaction mixture was heated on microwave at 80° C. (high absorption) for 20 min. The mixture was acidified to pH=3 with 1M HCl, then concentrated. The residue was dissolved in DMSO (1 mL), filtered and purified by reverse phase preparative HPLC under formic acid conditions (0.1%). This yielded the title compound (0.01652 g, 37.5% yield). LC-MS m/z 493.3 (M+H)$^+$, 0.65 (ret. time).

Example 161

3-(4-chloro-3-((3-hydroxypiperidin-1-yl)methyl)phenyl)-3-(1,4-dimethyl-1H-benzo[d][1,2,3]triazol-5-yl)propanoic Acid

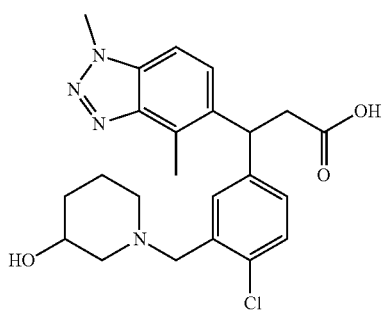

Ethyl 3-(4-chloro-3-((3-hydroxypiperidin-1-yl)methyl)phenyl)-3-(1,4-dimethyl-1H-benzo[d][1,2,3]triazol-5-yl)propanoate

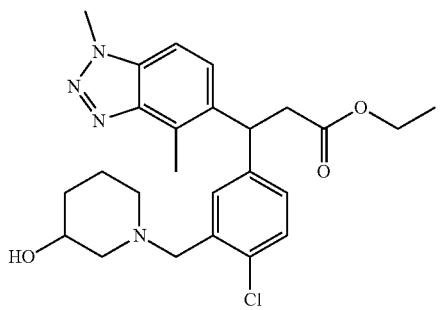 [SMILES: CCOC(=O)CC(c1ccc(Cl)c(CN2CCCC(O)C2)c1)c1ccc2c(nnn2C)c1C]

Piperidin-3-ol (0.025 g, 0.246 mmol) was dissolved in acetonitrile (2 mL). To this mixture was added was added DIEA (0.086 mL, 0.492 mmol). Then, ethyl 3-(4-chloro-3-(chloromethyl)phenyl)-3-(1,4-dimethyl-1H-benzo[d][1,2,3]triazol-5-yl)propanoate (0.05 g, 0.123 mmol) was added. The resulting reaction mixture was heated via microwave at 80° C. (high absorption) for 1 h. The mixture was concentrated to yield crude ethyl 3-(4-chloro-3-((3-hydroxypiperidin-1-yl)methyl)phenyl)-3-(1,4-dimethyl-1H-benzo[d][1,2,3]triazol-5-yl)propanoate (0.0898 g, 155% yield) which was used in the next step without further purification. LC-MS m/z 471.5 (M+H)$^+$, 0.67 (ret. time).

3-(4-chloro-3-((3-hydroxypiperidin-1-yl)methyl)phenyl)-3-(1,4-dimethyl-1H-benzo[d][1,2,3]triazol-5-yl)propanoic Acid

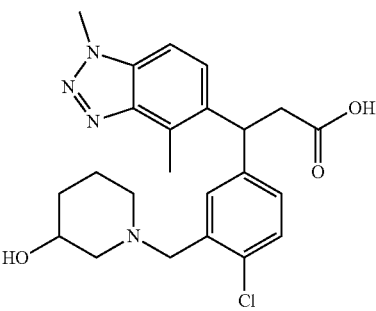 [SMILES: Cc1c(C(CC(=O)O)c2ccc(Cl)c(CN3CCCC(O)C3)c2)ccc2c1nnn2C]

Ethyl 3-(4-chloro-3-((3-hydroxypiperidin-1-yl)methyl)phenyl)-3-(1,4-dimethyl-1H-benzo[d][1,2,3]triazol-5-yl)propanoate (0.0898 g, 0.184 mmol) was dissolved in methanol (2 mL). Then, 2.5 M NaOH (0.394 mL, 0.984 mmol) was added and the reaction mixture was heated via microwave at 80° C. (high absorption) for 20 min. The mixture was acidified to pH=3 with 1 M HCl, then concentrated. The residue was dissolved in 1 mL DMSO, filtered, and purified by reverse phase preparative HPLC under neutral conditions to yield the title compound (0.0181 g, 33.2% yield). LC-MS m/z 443.5 (M+H)$^+$, 0.58 (ret. time).

Example 162

3-(3-((3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic Acid

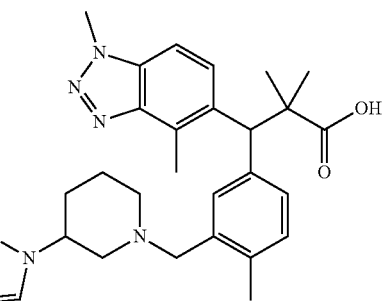

Tert-butyl 3-((methylsulfonyl)oxy)piperidine-1-carboxylate

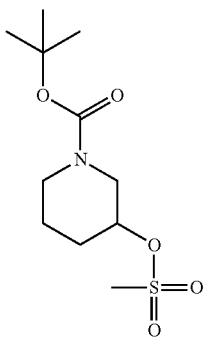

To a solution of tert-butyl 3-hydroxypiperidine-1-carboxylate (1.05 g, 5.22 mmol) and triethylamine (0.792 g, 7.83 mmol) in dichloromethane (DCM) (50 mL), methanesulfonyl chloride (0.657 g, 5.74 mmol) was added. The reaction mixture was stirred at 0° C. to 25° C. for 3 h. Then it was washed with water (3×50 mL) and HCl (1 M), (50 mL), dried over MgSO$_4$, and concentrated to give the title compound tert-butyl 3-((methylsulfonyl)oxy)piperidine-1-carboxylate (1.20 g, 3.87 mmol, 74.1% yield) as a yellow oil. LC-MS m/z 302.1 (M+Na)$^+$, 1.54 min (Ret. time)

Tert-butyl 3-(1H-pyrazol-1-yl)piperidine-1-carboxylate

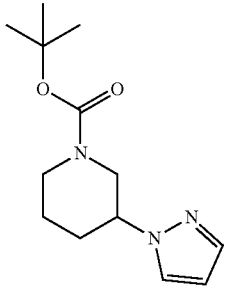 [SMILES: CC(C)(C)OC(=O)N1CCCC(n2cccn2)C1]

To a solution of 1H-pyrazole (0.585 g, 8.59 mmol) in N,N-dimethylformamide (DMF) (10 mL) was added sodium hydride (0.309 g, 12.89 mmol) in small portions at 00° C. After it was warmed to ambient temperature and stirred for 1 h, tert-butyl 3-((methylsulfonyl)oxy)piperidine-1-carboxylate (1.20 g, 4.30 mmol) was added. The reaction mixture was stirred at 100° C. for 18 h. Then it was quenched with saturated NH$_4$Cl, and extracted with EtOAc (3×30 mL). The combined organic layer was washed with water (2×30 mL), brine (2×30 mL), dried over MgSO$_4$ and concentrated. The crude product was purified by silica gel chromatography (EtOAc:petroleum ether=1:5) to give the title compound tert-butyl 3-(1H-pyrazol-1-yl)piperidine-1-carboxylate (222 mg, 0.786 mmol, 18.30% yield) as a yellow oil. LCMS m/z 252.2 (M+H)$^+$, 1.61 min (ret. time)

3-(1H-Pyrazol-1-yl)piperidine hydrochloride

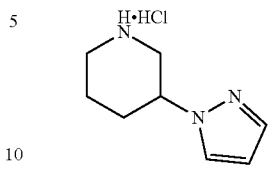

To a solution of tert-butyl 3-(1H-pyrazol-1-yl)piperidine-1-carboxylate (222 mg, 0.883 mmol) in 1,4-dioxane (10 mL) was added hydrogen chloride (292 mg, 8.00 mmol) in 1,4-dioxane (705 mg). The reaction mixture was stirred at 25° C. under the protection of N$_2$ for 2 h. The solid was filtered to give the title compound 3-(1H-pyrazol-1-yl)piperidine hydrochloride (160 mg, 0.836 mmol, 95% yield) as a white solid.

Methyl 3-(3-((3-(1H-pyrazol-1-yl)piperid in-1-yl)methyl)-4-methylphenyl)-3-(1,4-dimethyl-1H-benzo[d][1,2,3]triazol-5-yl)-2,2-dimethylpropanoate

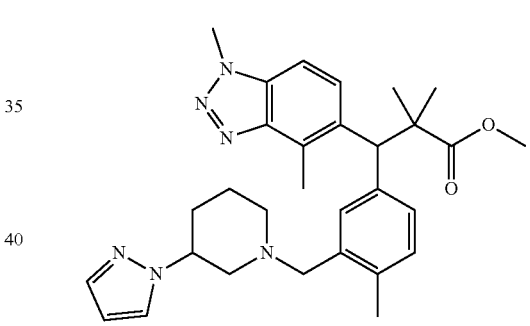

To a solution of 3-(1H-pyrazol-1-yl)piperidine hydrochloride (100 mg, 0.535 mmol) in N,N-dimethylformamide (DMF) (10 mL) was added N-ethyl-N-isopropylpropan-2-amine (323 mg, 2.501 mmol), followed by addition of a solution of methyl 3-(3-(chloromethyl)-4-methylphenyl)-3-(1,4-dimethyl-1H-benzo[d][1,2,3]triazol-5-yl)-2,2-dimethylpropanoate (100 mg, 0.250 mmol) in N,N-dimethylformamide (DMF) (10 mL). The reaction mixture was stirred at 90° C. for 16 h. Then it was poured in saturated NH$_4$Cl solution (10 mL), extracted with EtOAc (3×20 mL), washed with water (2×20 mL), saturated NaCl solution (20 mL), dried over MgSO$_4$, filtered and concentrated to give the title compound methyl 3-(3-((3-(1H-pyrazol-1-yl)piperidin-1-yl)methyl)-4-methylphenyl)-3-(1,4-dimethyl-1H-benzo[d][1,2,3]triazol-5-yl)-2,2-dimethylpropanoate (85 mg, 0.149 mmol, 59.4% yield) as a yellow oil which was carried to the next step without further purification. LCMS m/z 515.2 (M+)$^+$, 1.54 min (ret. time).

371

3-(3-((3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic Acid

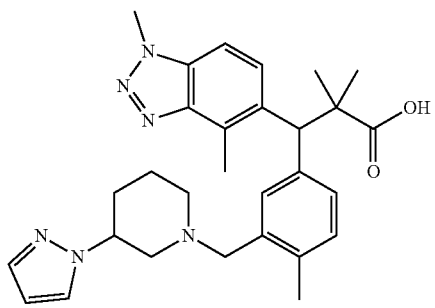 [SMILES: Cc1ccc(C(c2ccc3c(nnn3C)c2C)C(C)(C)C(=O)O)cc1CN1CCCC(n2cccn2)C1]

To a solution of methyl 3-(3-((3-(1H-pyrazol-1-yl)piperidin-1-yl)methyl)-4-methylphenyl)-3-(1,4-dimethyl-1H-benzo[d][1,2,3]triazol-5-yl)-2,2-dimethylpropanoate (85 mg, 0.165 mmol) in tetrahydrofuran (THF) (3 mL) was added lithium hydroxide (39.6 mg, 1.652 mmol) in water (1 mL) and ethylene glycol (3.00 mL). The reaction was heated in a microwave at 125° C. (high absorption) for 4 h. Then the organic solvent was removed. The residue was purified by reverse-phase HPLC (0.05% NH$_4$HCO$_3$/H$_2$O: CH$_3$CN=5-95%) to give the title compound 3-(3-((3-(1H-pyrazol-1-yl)piperidin-1-yl)methyl)-4-methylphenyl)-3-(1,4-dimethyl-1H-benzo[d][1,2,3]triazol-5-yl)-2,2-dimethylpropanoic acid (15 mg, 0.029 mmol, 17.60% yield) as a white solid. LC-MS m/z 501.3 (M+H)$^+$, 1.56 min (ret. time).

Example 163

3-(3-((3-(1H-pyrazol-1-yl)piperidin-1-yl)methyl)-4-methylphenyl)-5-(1-propyl-1H-1,2,3-triazol-4-yl)pentanoic Acid, Formic Acid Salt

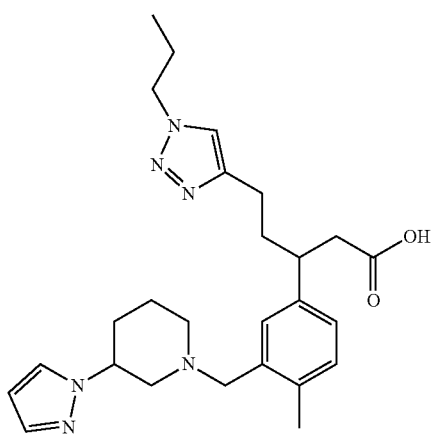 [SMILES: CCCn1cc(CCC(CC(=O)O)c2ccc(C)c(CN3CCCC(n4cccn4)C3)c2)nn1]

372

Ethyl 3-(3-(hydroxymethyl)-4-methylphenyl)-5-(1-propyl-1H-1,2,3-triazol-4-yl)pentanoate

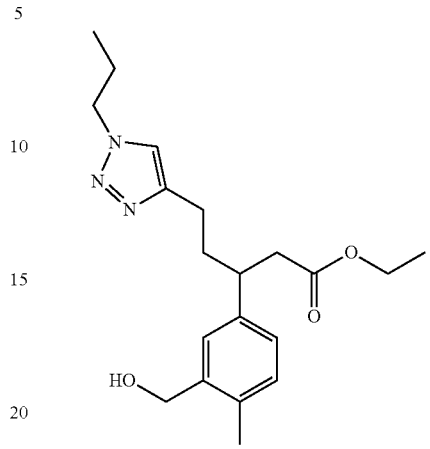

To a solution of (E)-ethyl 5-(1-propyl-1H-1,2,3-triazol-4-yl)pent-2-enoate (300 mg, 1.264 mmol) in 1,4-dioxane (3 mL) and water (2 mL) was added triethylamine (0.264 mL, 1.896 mmol), (2-methyl-5-(4,4,5,5-tetramethyl-1,3,2-dioxaborolan-2-yl)phenyl)methanol (314 mg, 1.264 mmol) and chloro(1,5-cyclooctadiene)rhodium(I) dimer (34.9 mg, 0.071 mmol). The reaction was then heated to 75° C. and stirred for 2 h. The reaction was removed from the heat and filtered through a pad of celite. The filtrate was then concentrated in vacuo and purified by reverse phase preparative HPLC to provide the title compound as a yellow oil. (340 mg, 45.6% yield) LC-MS m/z 360 (M+H)$^+$, 0.90 min (ret. time).

3-(3-((3-(1H-pyrazol-1-yl)piperidin-1-yl)methyl)-4-methylphenyl)-5-(1-propyl-1H-1,2,3-triazol-4-yl)pentanoic Acid, Formic Acid Salt To a solution of ethyl 3-(3-(hydroxymethyl)-4-methylphenyl)-5-(1-propyl-1H-1,2,3-triazol-4-yl)pentanoate (170 mg, 0.288 mmol) in dichloromethane (DCM) (5 mL) was added thionyl chloride (0.042 mL, 0.577 mmol). The resulting mixture was stirred at room temperature for 1 h. The solvent was then removed by evaporation and the residue was redissolved in N,N-dimethylformamide (DMF) (5 mL).

To that solution was added DIEA (0.202 mL, 1.154 mmol) and 3-(1H-pyrazol-1-yl)piperidine (65.4 mg, 0.433 mmol). The reaction mixture was heated to 75° C. and stirred for 18 h. To the reaction mixture was added LiOH (34.5 mg, 1.442 mmol) and water (5.00 mL) and heated to 60° C. for 18 h. The reaction mixture was concentrated and acidified with formic acid. The residue was purified by reverse phase preparative HPLC under acidic conditions to provide the title compound as a light brown oil. (91.7 mg, 66.3% yield) LC-MS m/z 465 (M+H)$^+$, 0.68 min (ret. time).

Example 164

3-(3-((3-(1H-pyrazol-1-yl)piperidin-1-yl)methyl)-4-chlorophenyl)-3-(7-methoxy-1,4-dimethyl-1H-benzo[d][1,2,3]triazol-5-yl)propanoic Acid, Formic Acid Salt

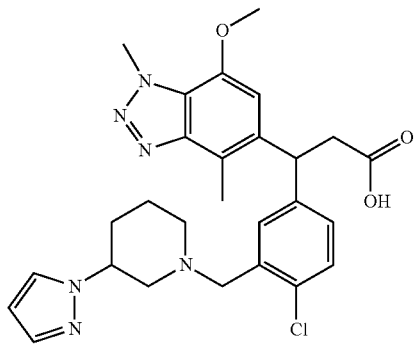 [SMILES: COc1cc(C(CC(=O)O)c2ccc(Cl)c(CN3CCCC(n4cccn4)C3)c2)c(C)c2nnn(C)c12]

5-Bromo-7-iodo-1,4-dimethyl-1H-benzo[d][1,2,3]triazole

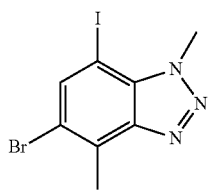

Sodium periodate (0.378 g, 1.769 mmol) was suspended in a stirred mixture of Acetic Acid (2 mL) with Ac$_2$O (2.98 mL, 31.5 mmol) cooled to 5-10° C. Concentrated H$_2$SO$_4$ (1.792 mL, 33.6 mmol) was very slowly added dropwise. Then 5-bromo-1,4-dimethyl-1H-benzo[d][1,2,3]triazole (1 g, 4.42 mmol) was added, and the stirring was continued for 16 h at ambient temperature. The reaction mixture was poured into ice-water containing the previously dissolved Na$_2$SO$_3$. After 15 minutes, the collected precipitate was worked up with EtOAc and Na$_2$SO$_3$ solution. The crude product was then purified on a silica cartridge (40 g) with a Combiflash Companion, eluting at 40 mL/min with a gradient running from 100% hexanes to 80% EtOAc/hexanes over 35 min) to give 286 mg (18.34%) of the title compound. LC-MS m/z 351.9, 353.9 (M+H)$^+$, 1.03 (ret. time).

5-Bromo-7-methoxy-1,4-dimethyl-1H-benzo[d][1,2,3]triazole

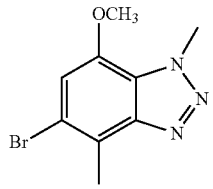

To a solution of 5-bromo-7-iodo-1,4-dimethyl-1H-benzo[d][1,2,3]triazole (286 mg, 0.813 mmol) in methanol (5 mL) at ambient temperature, copper(I) iodide (77 mg, 0.406 mmol) and Cs$_2$CO$_3$ (530 mg, 1.625 mmol) were added. Then the reaction mixture was stirred at 110° C. for 40 minutes. The solvent was evaporated under reduced pressure. The crude product was then purified on a silica cartridge (12 g) with a Combiflash Companion, eluting at 20 mL/min with a gradient running from 100% hexanes to 80% EtOAc/hexanes over 35 min) to give 68 mg (32.7%) of the title compound. LC-MS m/z 256.1, 258.0 (M+H)$^+$, 0.91 (ret. time).

(E)-Ethyl 3-(7-methoxy-1,4-dimethyl-1H-benzo[d][1,2,3]triazol-5-yl)acrylate

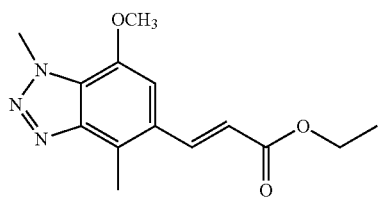 [SMILES: CCOC(=O)/C=C/c1cc(OC)c2c(nnn2C)c1C]

To a solution of 5-bromo-7-methoxy-1,4-dimethyl-1H-benzo[d][1,2,3]triazole (1000 mg, 3.90 mmol) in N,N-dimethylformamide (DMF) (20 mL), ethyl acrylate (2346 mg, 23.43 mmol), tri-o-tolylphosphine (357 mg, 1.171 mmol), N-ethyl-N-isopropylpropan-2-amine (2019 mg, 15.62 mmol) and palladium(II) acetate (131 mg, 0.586 mmol) were added. The reaction mixture was heated in a microwave at 110° C. for 1 h. Water was added to quench the reaction. Ethyl acetate was added, and the layers were separated. The aqueous layer was extracted once with ethyl acetate, and the combined organic layers were washed once with brine. The organic layer was concentrated. The crude product was then purified on a silica cartridge (40 g) with a Combiflash Companion, eluting at 30 mL/min with a gradient running from 100% Hexanes to 80% EtOAc/Hexanes over 35 min) to give 950 mg (88%) of the title compound. LC-MS m/z 276.0 (M+H)$^+$, 0.97 (ret. time).

Methyl 3-(4-chloro-3-(hydroxymethyl)phenyl)-3-(7-methoxy-1,4-dimethyl-1H-benzo[d][1,2,3]triazol-5-yl)propanoate

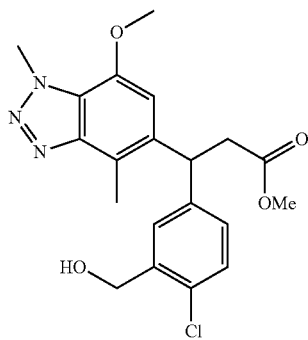 [SMILES: COC(=O)CC(c1ccc(Cl)c(CO)c1)c1cc(OC)c2c(nnn2C)c1C]

To a solution of (E)-methyl 3-(7-methoxy-1,4-dimethyl-1H-benzo[d][1,2,3]triazol-5-yl)acrylate (261 mg, 1 mmol) in 1,4-dioxane (6 mL) and water (2 ml) was added (2-chloro-5-(4,4,5,5-tetramethyl-1,3,2-dioxaborolan-2-yl)phenyl)methanol (403 mg, 1.500 mmol), triethylamine (0.558 mL, 4.00 mmol) and [Rh(cod)Cl]$_2$ (24.65 mg, 0.050 mmol). The resulting reaction mixture was stirred at 90° C. and ambient temperature for 16 h. The solvent was removed under reduced pressure and the crude product purified via flash chromatography to afford product methyl 3-(4-chloro-3-(hydroxymethyl)phenyl)-3-(7-methoxy-1,4-dimethyl-1H-benzo[d][1,2,3]triazol-5-yl)propanoate (119.9 mg, 0.297 mmol, 29.7% yield). LC-MS m/z 404.3 (M+H)$^+$, 0.88 min (ret. time).

3-(3-((3-(1H-pyrazol-1-yl)piperidin-1-yl)methyl)-4-chlorophenyl)-3-(7-methoxy-1,4-dimethyl-1H-benzo[d][1,2,3]triazol-5-yl)propanoic Acid, Formic Acid Salt

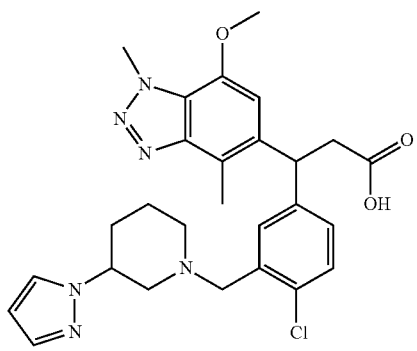 [SMILES: COc1cc(C(CC(=O)O)c2ccc(Cl)c(CN3CCCC(n4cccn4)C3)c2)c(C)c2nnn(C)c12]

To a solution of methyl 3-(4-chloro-3-(hydroxymethyl)phenyl)-3-(7-methoxy-1,4-dimethyl-1H-benzo[d][1,2,3]triazol-5-yl)propanoate (60.6 mg, 0.15 mmol) in dichloromethane (0.50 mL) was added SOCl$_2$ (0.022 mL, 0.300 mmol). The resulting reaction mixture was stirred at ambient temperature for 15 min and the solvent removed under reduced pressure. The residue was dissolved in acetonitrile (1.5 mL) followed by addition of 3-(1H-pyrazol-1-yl)piperidine (34.0 mg, 0.225 mmol), sodium iodide (11.24 mg, 0.075 mmol) and K$_2$CO$_3$ (41.5 mg, 0.300 mmol). The resulting reaction mixture was heated at 40° C. for 21 h and then was filtered. The filter cake was washed with MeCN (2 mL). The combined filtrate was evaporated down under vacuum then was dissolved in methanol (1.5 mL) before adding NaOH (3 N) (0.250 mL, 0.750 mmol). The resulting reaction mixture was heated with microwave at 80° C. for 20 min and then was acidified with HCl (3 N) to pH 4-5, evaporated down under vacuum and purified by reverse phase HPLC to afford product 3-(3-((3-(1H-pyrazol-1-yl)piperidin-1-yl)methyl)-4-chlorophenyl)-3-(7-methoxy-1,4-dimethyl-1H-benzo[d][1,2,3]triazol-5-yl)propanoic acid, formic acid salt (53.1 mg, 0.094 mmol, 62.9% yield). LC-MS m/z 523.3 (M+H)$^+$, 0.76 min (ret. time).

Example 165

(S)-3-(1,4-Dimethyl-1H-benzo[d][1,2,3]triazol-5-yl)-3-(3-((7-methoxy-2,2-dimethyl-2,3-dihydrobenzo[f][1,4]oxazepin-4(5H)-yl)methyl)-4-methylphenyl)propanoic acid, 0.5 Formic Acid Salt

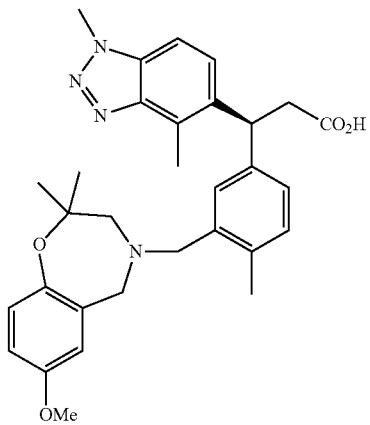 [SMILES: COc1ccc2c(c1)CN(Cc1cc([C@H](CC(=O)O)c3ccc4c(nnn4C)c3C)ccc1C)CC(C)(C)O2]

To the mixture of 7-methoxy-2,2-dimethyl-2,3,4,5-tetrahydrobenzo[f][1,4]oxazepine, hydrochloride (0.133 g, 0.544 mmol) in methanol (4 mL) was added K$_2$CO$_3$ (0.075 g, 0.544 mmol). The resulting reaction mixture was stirred at ambient temperature for 17 h then filtered and concentrated then filtered added acetonitrile (4 mL) and filtered to afford intermediate solution.

To the mixture of (S)-ethyl 3-(1,4-dimethyl-1H-benzo[d][1,2,3]triazol-5-yl)-3-(3-(hydroxymethyl)-4-methylphenyl)propanoate (0.100 g, 0.272 mmol) in dichloromethane (1 mL) was added SOCl$_2$ (0.040 mL, 0.544 mmol). The resulting reaction mixture was stirred at ambient temperature for 20 min and then concentrated then filtered added the above intermediate solution and DIEA (0.190 mL, 1.089 mmol). The resulting reaction mixture was heated via microwave at 100° C. for 1 h. The reaction mixture was concentrated and the residue dissolved in methanol (4 mL). NaOH (3.0 N) (0.726 mL, 2.177 mmol) was added. The resulting reaction mixture was heated via microwave at 80° C. for 20 min and then neutralized with HCl (2 N) to pH~6 then concentrated and purified reverse phase HPLC (formic acid modifier) to afford the title compound (69.5 mg, 0.126 mmol, 46.3% yield). LC/MS: m/z 529.2 (M+H)$^+$, 0.86 min (ret. time).

The compounds in Table 17 were prepared by a method similar to the one described for the preparation of (S)-3-(1,4-Dimethyl-1H-benzo[d][1,2,3]triazol-5-yl)-3-(3-((7-methoxy-2,2-dimethyl-2,3-dihydrobenzo[f][1,4]oxazepin-4(5H)-yl)methyl)-4-methylphenyl)propanoic acid. As is appreciated by those skilled in the art, these analogous examples may involve variations in general reaction conditions.

TABLE 17

| Ex # | Structure | Name | LCMS [M + H]+ | Retention Time (min) |
|---|---|---|---|---|
| 166 | 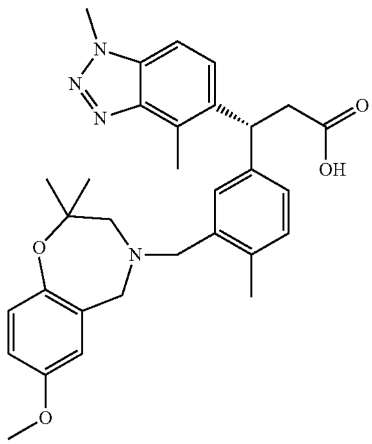 [SMILES: COc1ccc2c(c1)CN(Cc1cc([C@@H](CC(=O)O)c3ccc4c(nnn4C)c3C)ccc1C)CC(C)(C)O2] | (R)-3-(1,4-Dimethyl-1H-benzo[d][1,2,3]triazol-5-yl)-3-(3-((7-methoxy-2,2-dimethyl-2,3-dihydrobenzo[f][1,4]oxazepin-4(5H)-yl)methyl)-4-methylphenyl)propanoic acid | 529.2 | 0.86 |
| 167 | 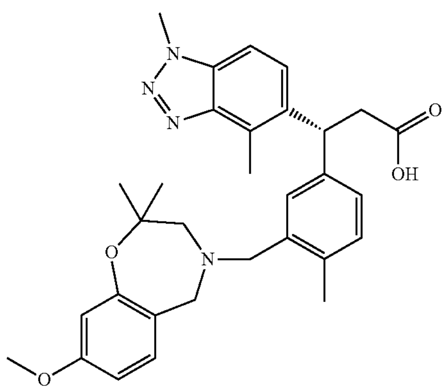 [SMILES: COc1ccc2c(c1)OC(C)(C)CN(Cc1cc([C@@H](CC(=O)O)c3ccc4c(nnn4C)c3C)ccc1C)C2] | (R)-3-(1,4-Dimethyl-1H-benzo[d][1,2,3]triazol-5-yl)-3-(3-((8-methoxy-2,2-dimethyl-2,3-dihydrobenzo[f][1,4]oxazepin-4(5H)-yl)methyl)-4-methylphenyl)propanoic acid | 529.2 | 0.87 |
| 168 | 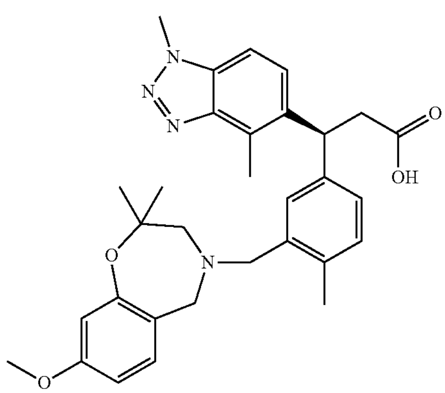 [SMILES: COc1ccc2c(c1)OC(C)(C)CN(Cc1cc([C@H](CC(=O)O)c3ccc4c(nnn4C)c3C)ccc1C)C2] | (S)-3-(1,4-Dimethyl-1H-benzo[d][1,2,3]triazol-5-yl)-3-(3-((8-methoxy-2,2-dimethyl-2,3-dihydrobenzo[f][1,4]oxazepin-4(5H)-yl)methyl)-4-methylphenyl)propanoic acid | 529.3 | 0.87 |

TABLE 17-continued

| Ex # | Structure | Name | LCMS [M + H]+ | Retention Time (min) |
|---|---|---|---|---|
| 169 | 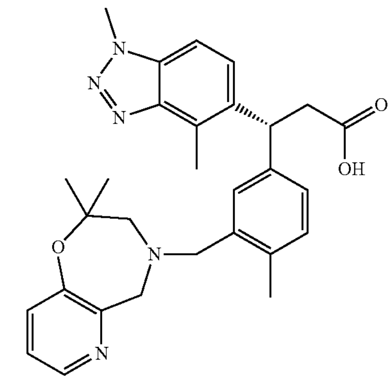 [SMILES: Cc1ccc([C@@H](CC(=O)O)c2ccc3c(nnn3C)c2C)cc1CN1Cc2ncccc2OC(C)(C)C1] | (R)-3-(1,4-Dimethyl-1H-benzo[d][1,2,3]triazol-5-yl)-3-(3-((2,2-dimethyl-2,3-dihydropyrido[2,3-f][1,4]oxazepin-4(5H)-yl)methyl)-4-methylphenyl)propanoic acid, 0.5 Formic acid salt | 500.4 | 0.86 |
| 170 | 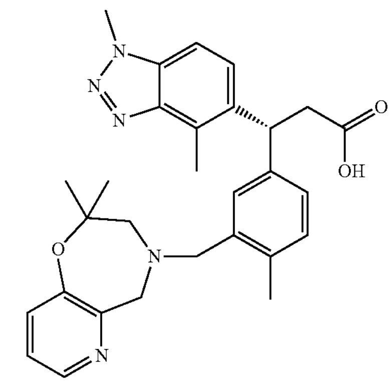 [SMILES: Cc1ccc([C@@H](CC(=O)O)c2ccc3c(nnn3C)c2C)cc1CN1Cc2ncccc2OC(C)(C)C1] | (S)-3-(1,4-Dimethyl-1H-benzo[d][1,2,3]triazol-5-yl)-3-(3-((2,2-dimethyl-2,3-dihydropyrido[2,3-f][1,4]oxazepin-4(5H)-yl)methyl)-4-methylphenyl)propanoic acid, 0.5 Formic acid salt | 500.4 | 0.85 |

Example 171 rel-(R)-3-(3-((7-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic Acid

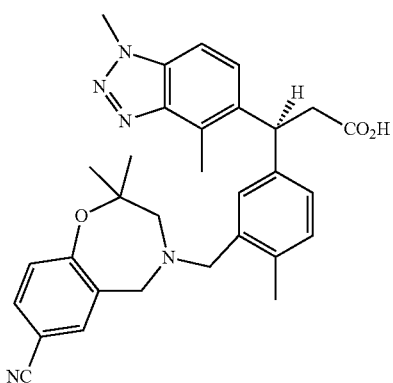 [SMILES: Cc1ccc([C@H](CC(=O)O)c2ccc3c(nnn3C)c2C)cc1CN1Cc2cc(C#N)ccc2OC(C)(C)C1]

To the mixture of 2,2-dimethyl-2,3,4,5-tetrahydrobenzo[f][1,4]oxazepine-7-carbonitrile, hydrochloride (107 mg, 0.450 mmol) in methanol (5 mL) was added K$_2$CO$_3$ (83 mg, 0.600 mmol). The resulting reaction mixture was stirred at ambient temperature for 30 min then concentrated. The resulting residue was taken into acetonitrile (4 mL) and tetrahydrofuran (1 mL) and stirred at ambient temperature for 10 min, and filtered to afford the intermediate solution.

To the mixture of ethyl 3-(1,4-dimethyl-1H-benzo[d][1,2,3]triazol-5-yl)-3-(3-(hydroxymethyl)-4-methylphenyl)propanoate (110 mg, 0.3 mmol) in dichloromethane (1.5 mL) was added SOCl$_2$ (0.044 mL, 0.600 mmol). The resulting reaction mixture was stirred at ambient temperature for 10 min then concentrated and then was added the above intermediate solution and DIEA (0.210 mL, 1.200 mmol). The resulting reaction mixture was heated via microwave at 100° C. for 1 h then added more DIEA (0.105 mL, 0.600 mmol) then heated via microwave at 100° C. for 1 h. The reaction mixture was concentrated then dissolved in methanol (5 mL) then NaOH (3 N) (0.800 mL, 2.400 mmol) was added. The resulting reaction mixture was heated via microwave at 60° C. for 20 min. The reaction mixture was acidified with HCl (3 N) to pH 4~5, concentrated, purified with reverse phase HPLC (formic acid modifier) then with chiral SFC (Column: Chiralpak AD 20×250 mm, 5 u; Co-solvent: 25% EtOH; Flowrate: 50 g/min; Back pressure: 100 Bar) to afford the title compound (31.8 mg, 0.061 mmol, 20.24% yield). LC/MS: m/z 524.5 (M+H)+, 0.90 min (ret. time).

The compounds in Table 18 were prepared by a method similar to the one described for the preparation of rel-(R)-3-(3-((7-cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid. As is appreciated by those skilled in the art, these analogous examples may involve variations in general reaction conditions.

TABLE 18

| Ex # | Structure | Name | LCMS [M + H]+ | Retention Time (min) |
|---|---|---|---|---|
| 172 | 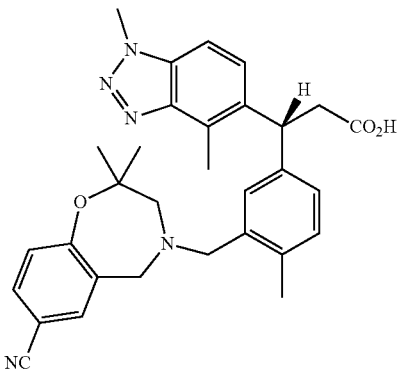 [SMILES: Cc1ccc([C@@H](CC(=O)O)c2ccc3c(nnn3C)c2C)cc1CN1Cc2cc(C#N)ccc2OC(C)(C)C1] | rel-(S)-3-(3-((7-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid | 524.6 | 0.90 |
| 173 | 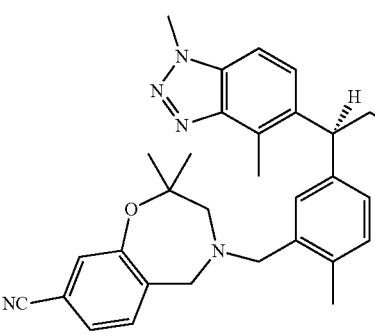 | rel-(R)-3-(3-((8-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid | 524.6 | 0.92 |
| 174 | 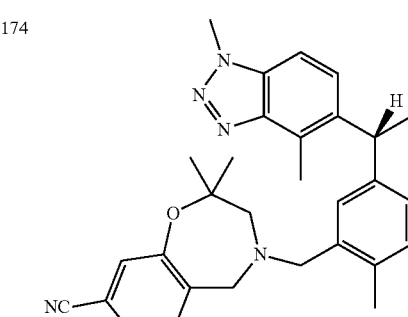 | rel-(S)-3-(3-((8-Cyano-2,2-dimethyl-2,3-dihydrobenzo[f][1,4]oxazepin-4(5H)-yl)methyl)-4-methylphenyl)-3-(1,4-dimethyl-1H-benzo[d][1,2,3]triazol-5-yl)propanoic acid | 524.5 | 0.92 |

Example 175

(R)-3-(1,4-Dimethyl-1H-benzo[d][1,2,3]triazol-5-yl)-3-(4-methyl-3-((2,2,7-trimethyl-2,3-dihydrobenzo[f][1,4]oxazepin-4(5H)-yl)methyl)phenyl)propanoic Acid

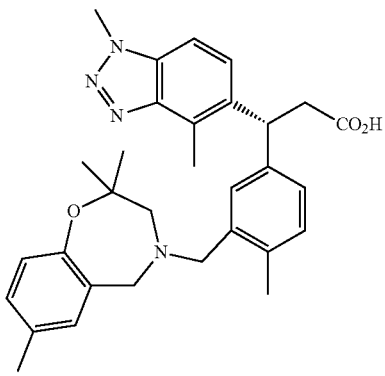 [SMILES: Cc1ccc2c(c1)CN(Cc1cc([C@@H](CC(=O)O)c3ccc4c(nnn4C)c3C)ccc1C)CC(C)(C)O2]

To the mixture of 2,2,7-trimethyl-2,3,4,5-tetrahydrobenzo[f][1,4]oxazepine, hydrochloride (0.044 g, 0.194 mmol) in acetonitrile (2.59 ml) was added DIEA (0.181 ml, 1.037 mmol) and (R)-ethyl 3-(3-(chloromethyl)-4-methylphenyl)-3-(1,4-dimethyl-1H-benzo[d][1,2,3]triazol-5-yl)propanoate (0.05 g, 0.130 mmol). The resulting reaction mixture was stirred at ambient temperature for 12 h then heated via microwave at 80° C. for 60 min. The reaction mixture was concentrated then dissolved in methanol (3 mL) and NaOH (6 M) (0.166 ml, 1.037 mmol) was added. The resulting reaction mixture was heated via microwave at 90° C. for 30 min and acidified to pH 4~5 with HCl (1 N) then concentrated and purified with reverse phase HPLC (neutral) to give the title compound (20.2 mg, 0.039 mmol, 30.4% yield). LC/MS: m/z 513.5 (M+H)$^+$, 0.94 min (ret. time).

The compounds in Table 19 were prepared by a method similar to the one described for the preparation of (R)-3-(1,4-dimethyl-1H-benzo[d][1,2,3]triazol-5-yl)-3-(4-methyl-3-((2,2,7-trimethyl-2,3-dihydrobenzo[f][1,4]oxazepin-4(5H)-yl)methyl)phenyl)propanoic acid. As is appreciated by those skilled in the art, these analogous examples may involve variations in general reaction conditions.

TABLE 19

| Ex # | Structure | Name | LCMS [M + H]$^+$ | Retention Time (min) |
|---|---|---|---|---|
| 176 | 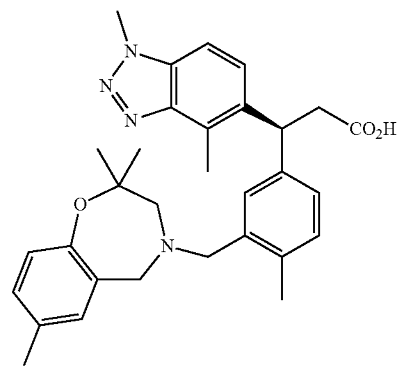 [SMILES: Cc1ccc2c(c1)CN(Cc1cc([C@H](CC(=O)O)c3ccc4c(nnn4C)c3C)ccc1C)CC(C)(C)O2] | (S)-3-(1,4-Dimethyl-1H-benzo[d][1,2,3]triazol-5-yl)-3-(4-methyl-3-((2,2,7-trimethyl-2,3-dihydrobenzo[f][1,4]oxazepin-4(5H)-yl)methyl)phenyl)propanoic acid | 513.5 | 0.95 |
| 177 | 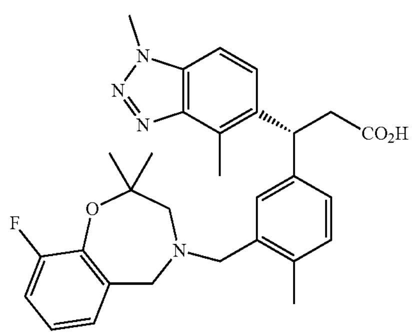 [SMILES: Cc1ccc([C@@H](CC(=O)O)c2ccc3c(nnn3C)c2C)cc1CN1Cc2cccc(F)c2OC(C)(C)C1] | (R)-3-(1,4-Dimethyl-1H-benzo[d][1,2,3]triazol-5-yl)-3-(3-((9-fluoro-2,2-dimethyl-2,3-dihydrobenzo[f][1,4]oxazepin-4(5H)-yl)methyl)-4-methylphenyl)propanoic acid | 517.4 | 0.93 |
| 178 | 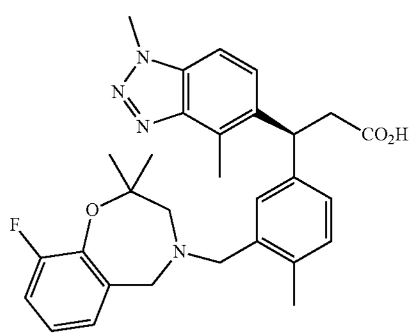 [SMILES: Cc1ccc([C@H](CC(=O)O)c2ccc3c(nnn3C)c2C)cc1CN1Cc2cccc(F)c2OC(C)(C)C1] | (S)-3-(1,4-Dimethyl-1H-benzo[d][1,2,3]triazol-5-yl)-3-(3-((9-fluoro-2,2-dimethyl-2,3-dihydrobenzo[f][1,4]oxazepin-4(5H)-yl)methyl)-4-methylphenyl)propanoic acid | 517.4 | 0.94 |

TABLE 19-continued

| Ex # | Structure | Name | LCMS [M + H]+ | Retention Time (min) |
|---|---|---|---|---|
| 179 | 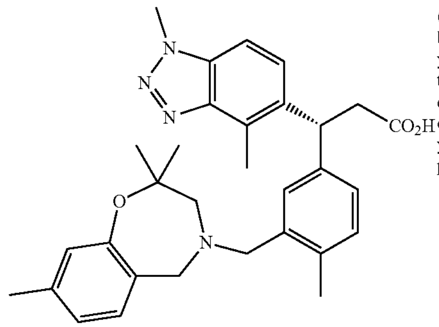 | (R)-3-(1,4-Dimethyl-1H-benzo[d][1,2,3]triazol-5-yl)-3-(4-methyl-3-((2,2,8-trimethyl-2,3-dihydrobenzo[f][1,4]oxazepin-4(5H)-yl)methyl)phenyl)propanoic acid | 513.5 | 0.94 |
| 180 | 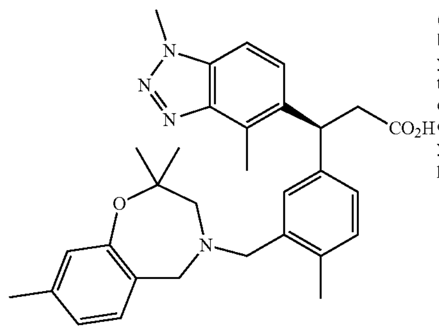 | (S)-3-(1,4-Dimethyl-1H-benzo[d][1,2,3]triazol-5-yl)-3-(4-methyl-3-((2,2,8-trimethyl-2,3-dihydrobenzo[f][1,4]oxazepin-4(5H)-yl)methyl)phenyl)propanoic acid | 513.5 | 0.94 |

Example 181 rel-(R)-3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic Acid

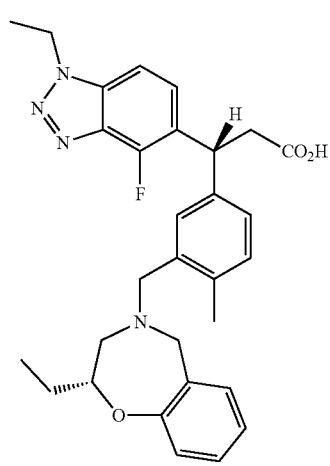 [SMILES: CC[C@@H]1CN(Cc2cc([C@@H](CC(=O)O)c3ccc4c(nnn4CC)c3F)ccc2C)Cc2ccccc2O1]

3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid

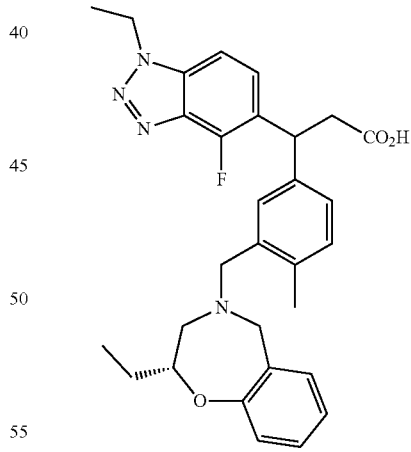

To a suspension of (E)-benzyl 3-(1-ethyl-4-fluoro-1H-benzo[d][1,2,3]triazol-5-yl)acrylate (500 mg, 1.537 mmol), (R)-2-ethyl-4-(2-methyl-5-(4,4,5,5-tetramethyl-1,3,2-dioxaborolan-2-yl)benzyl)-2,3,4,5-tetrahydrobenzo[f][1,4]oxazepine (657 mg, 1.614 mmol), and [RhCl(cod)]₂ (76 mg, 0.154 mmol) in 1,4-dioxane (8 mL) and water (2 mL) at ambient temperature was added triethylamine (0.643 mL, 4.61 mmol). The resulting suspension was heated at 90° C. for 1 h. The reaction mixture was passed through celite and washed with EtOAc. The organic layer was collected and concentrated to give the crude product. It was purified by silica gel chromatography. This intermediate was redissolved in MeOH (8 mL). LiOH (221 mg, 9.22 mmol) was added and heated at 60° C. for 1.5 h. Solvent was removed. 6 N HCl was added until pH~1. 1 mL of DMSO was added. The reaction mixture was concentrated and then purified with preparative HPLC under acidic conditions (using 0.1% TFA as modifier) to give the title compound (400 mg, 0.774 mmol, 50.4% yield). LC/MS: m/z 517.4 (M+H)$^+$, 0.86 min (ret. time).

Methyl rel-(R)-3-(3-(((R)-2-ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoate

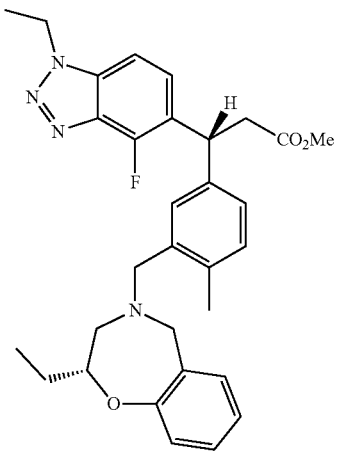 [SMILES: CC[C@@H]1CN(Cc2cc([C@@H](CC(=O)OC)c3ccc4c(nnn4CC)c3F)ccc2C)Cc2ccccc2O1]

To the mixture of 3-(3-(((R)-2-ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid (400 mg, 0.774 mmol) in methanol (8 mL) was added H$_2$SO$_4$ (conc.) (0.413 mL, 7.74 mmol). The resulting reaction mixture was stirred at ambient temperature for 23 h then quenched with Na$_2$CO$_3$ (615 mg, 5.81 mmol), diluted with EtOAc (20 mL), and filtered. The filtrate was dried over Na$_2$SO$_4$, filtered, concentrated then purified with chiral SFC (Column: Chiralpak IA 20×250 mm, 5 u; Co-solvent: 30% MeOH:IPA 1:1; Flowrate: 50 g/min; Back pressure: 100 Bar) to give the title compound (112.4 mg, 0.212 mmol, 27.4% yield). LC/MS: m/z 531.3 (M+H)$^+$, 1.01 min (ret. time).

rel-(R)-3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic Acid

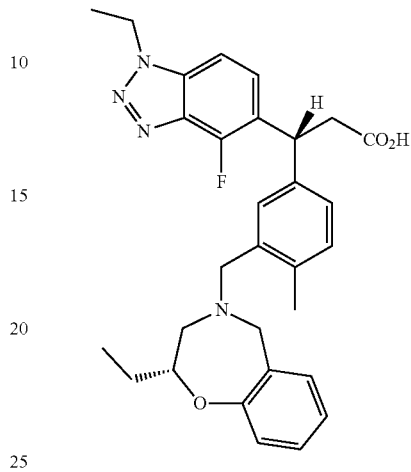

To the solution of methyl rel-(R)-3-(3-(((R)-2-ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoate (110 mg, 0.207 mmol) in methanol (2 mL) was added NaOH (3.0 N) (0.345 mL, 1.036 mmol). The reaction mixture was heated via microwave at 80° C. for 20 min then acidified with HCl (3.0 N) (0.345 mL, 1.036 mmol), concentrated, and extracted with DCM (3×3 mL). The combined organic layer was dried over MgSO$_4$, filtered, and concentrated to give the title compound (106.8 mg, 0.207 mmol, 100% yield). LC/MS: m/z 517.3 (M+H)$^+$, 0.86 min (ret. time).

The compounds in Table 20 were prepared by a method similar to the one described for the preparation of rel-(R)-3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid. As is appreciated by those skilled in the art, these analogous examples may involve variations in general reaction conditions.

TABLE 20

| Ex # | Structure | Name | LCMS [M + H]$^+$ | Retention Time (min) |
|---|---|---|---|---|
| 182 | (structure) | rel-(S)-3-(3-(((R)-2-Ethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid | 517.4 | 0.86 |

Example 183

(S)-3-(3-(((S)-3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic Acid

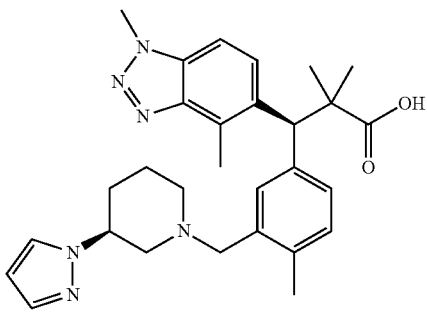 [SMILES: Cc1ccc([C@@H](c2ccc3c(nnn3C)c2C)C(C)(C)C(=O)O)cc1CN1CCC[C@H](n2cccn2)C1]

(S)-Methyl 3-(3-(((S)-3-(1H-pyrazol-1-yl)piperidin-1-yl)methyl)-4-methylphenyl)-3-(1,4-dimethyl-1H-benzo[d][1,2,3]triazol-5-yl)-2,2-dimethylpropanoate

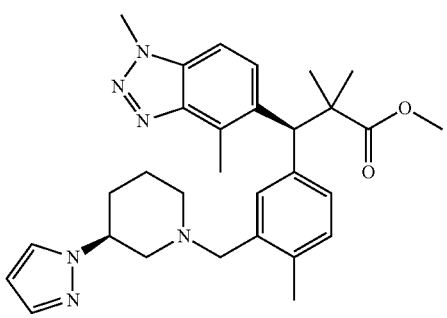 [SMILES: COC(=O)C(C)(C)[C@@H](c1ccc(C)c(CN2CCC[C@H](n3cccn3)C2)c1)c1ccc2c(nnn2C)c1C]

To the mixture of 3-(1H-pyrazol-1-yl)piperidine, hydrochloride (0.2645 g, 1.409 mmol) in acetonitrile (10.38 m) was added DIEA (1.450 m, 8.30 mmol), and (S)-methyl 3-(3-(chloromethyl)-4-methylphenyl)-3-(1,4-dimethyl-1H-benzo[d][1,2,3]triazol-5-yl)-2,2-dimethylpropanoate (0.415 g, 1.038 mmol). The resulting reaction mixture was heated via microwave at 80° C. for 1 h. The reaction mixture was concentrated then purified with reverse phase HPLC (neutral) then further purified with chiral SFC (Column: Chiralpak IA 20×250 mm, 5 u; Co-solvent: 20% IPA; Flowrate: 50 g/min; Back pressure: 100 Bar) to give the title compound (0.124 g, 0.241 mmol, 23.22% yield). LC/MS: m/z 515.4 (M+H)$^+$, 0.89 min (ret. time).

(S)-3-(3-(((S)-3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic Acid

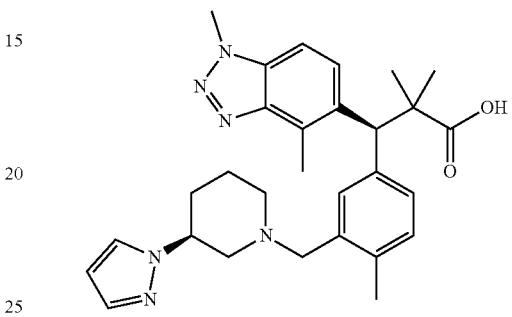

The mixture of (S)-methyl 3-(3-(((S)-3-(1H-pyrazol-1-yl)piperidin-1-yl)methyl)-4-methylphenyl)-3-(1,4-dimethyl-1H-benzo[d][1,2,3]triazol-5-yl)-2,2-dimethylpropanoate (0.124 g, 0.241 mmol) in methanol (4.82 ml) and sodium hydroxide (2 N) (0.602 ml, 1.205 mmol) was heated via microwave at 130° C. for 3 h. To the reaction mixture was added more sodium hydroxide (2 N) (0.361 ml, 0.723 mmol) then heated via microwave at 135° C. for 1 h twice. The reaction mixture was acidified with HCl (1 N) to pH~4-5 then concentrated. The result residue was extracted with ethyl acetate (4×2 mL) and was filtered. The combined organic layer was concentrated to give the title compound (88.3 mg, 0.176 mmol, 73.2% yield). LC/MS: m/z 501.3 (M+H)$^+$, 0.86 min (ret. time).

The compounds in Table 21 were prepared by a method similar to the one described for the preparation of (S)-3-(3-(((S)-3-(1H-pyrazol-1-yl)piperidin-1-yl)methyl)-4-methylphenyl)-3-(1,4-dimethyl-1H-benzo[d][1,2,3]triazol-5-yl)-2,2-dimethylpropanoic acid. As is appreciated by those skilled in the art, these analogous examples may involve variations in general reaction conditions.

TABLE 21

| Ex # | Structure | Name | LCMS [M + H]$^+$ | Retention Time (min) |
|---|---|---|---|---|
| 184 | 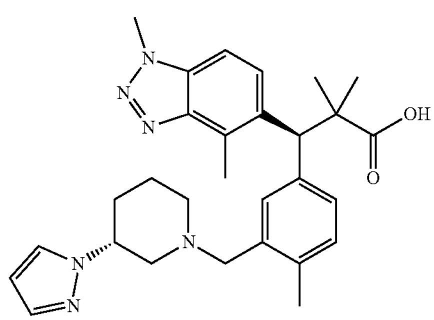 [SMILES: Cc1ccc([C@@H](c2ccc3c(nnn3C)c2C)C(C)(C)C(=O)O)cc1CN1CCC[C@@H](n2cccn2)C1] | (S)-3-(3-(((R)-3-(1H-Pyrazol-1-yl)piperidin-1-yl)methyl)-4-methylphenyl)-3-(1,4-dimethyl-1H-benzo[d][1,2,3]triazol-5-yl)-2,2-dimethylpropanoic acid | 501.3 | 0.84 |

Example 185

3-(1,4-Dimethyl-1H-benzo[d][1,2,3]triazol-5-yl)-3-(4-methyl-3-((3-(phenylsulfonyl)piperidin-1-yl)methyl)phenyl)propanoic Acid

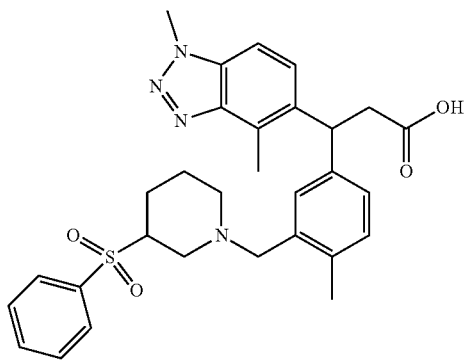 [SMILES: Cc1ccc(C(CC(=O)O)c2ccc3c(nnn3C)c2C)cc1CN1CCCC(S(=O)(=O)c2ccccc2)C1]

tert-Butyl 3-(phenylthio)piperidine-1-carboxylate

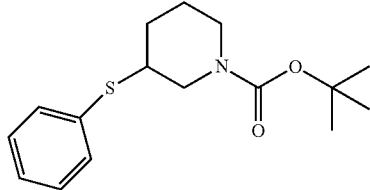 [SMILES: CC(C)(C)OC(=O)N1CCCC(Sc2ccccc2)C1]

To the mixture of NaH (0.042 g, 1.038 mmol) in DMF (2.5 mL) under nitrogen was added benzenethiol (0.085 ml, 0.830 mmol). The mixture was stirred at ambient temperature for 5 min then tert-butyl 3-((methylsulfonyl)oxy)piperidine-1-carboxylate (0.29 g, 1.038 mmol) in DMF (2.5 mL) was added. The resulting reaction mixture was stirred at ambient temperature for 2 h then heated via microwave at 100° C. for 1 h. The reaction mixture was quenched with NH$_4$Cl (2 mL, saturated) then concentrated. The residue was taken up in EtOAc (35 mL) and water (5 mL). After removing the aqueous layer, the organic layer was washed with water (2×10 mL), brine (10 mL) and filtered through an isolute IST (70 mL) phase separator. The filtrate was concentrated and purified by flash chromatography to give the title compound (0.1201 g, 0.409 mmol, 39.4% yield). LC/MS: m/z 294.1 (M+H)$^+$, 1.30 min (ret. time).

3-(Phenylsulfonyl)piperidine, hydrochloride

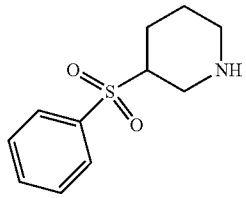 [SMILES: O=S(=O)(c1ccccc1)C1CCCNC1]

To the mixture of tert-butyl 3-(phenylthio)piperidine-1-carboxylate (0.1201 g, 0.409 mmol) in dichloromethane (2.047 ml) was added mCPBA (0.229 g, 1.023 mmol). The resulting reaction mixture was stirred at ambient temperature for 30 min then NaOH (1 N) (3 mL) was added followed by DCM (30 mL) and washed with 1 M NaOH (2×5 mL). The organic layer was filtered through an isolute IST (70 mL) phase separator. The filtrate was concentrated and the residue dissolved in dichloromethane (2.047 ml) then HCl (4 M in dioxane) (1.023 ml, 4.09 mmol) was added. The resulting reaction mixture was stirred at ambient temperature for 1 h then evaporated down under vacuum to give the title compound (0.1116 g, 0.426 mmol, 104% yield). LC/MS: m/z 226.1 (M+H)$^+$, 0.55 min (ret. time).

3-(1,4-Dimethyl-1H-benzo[d][1,2,3]triazol-5-yl)-3-(4-methyl-3-((3-(phenylsulfonyl)piperidin-1-yl)methyl)phenyl)propanoic Acid

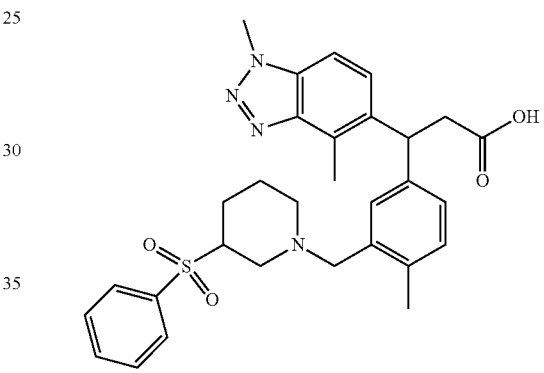

To the mixture of 3-(phenylsulfonyl)piperidine, hydrochloride (0.044 g, 0.168 mmol) in acetonitrile (2.59 ml) was added DIEA (0.181 ml, 1.037 mmol), and ethyl 3-(3-(chloromethyl)-4-methylphenyl)-3-(1,4-dimethyl-1H-benzo[d][1,2,3]triazol-5-yl)propanoate (0.05 g, 0.130 mmol). The resulting reaction mixture was heated via microwave at 80° C. for 1 h then concentrated. The resulting residue was dissolved in methanol (2.5 mL) then NaOH (6 N) (0.124 ml, 0.777 mmol) was added. The resulting reaction mixture was heated via microwave at 90° C. for 30 min then acidified to pH~4 with HCl (1 N), concentrated, and purified via reverse phase HPLC (neutral) to give the title compound (36.9 mg, 0.067 mmol, 52.1% yield). LC/MS: m/z 547.5 (M+H)$^+$, 0.79 min (ret. time).

The compounds in Table 22 were prepared by a method similar to the one described for the preparation of 3-(1,4-Dimethyl-1H-benzo[d][1,2,3]triazol-5-yl)-3-(4-methyl-3-((3-(phenylsulfonyl)piperidin-1-yl)methyl)phenyl)propanoic acid. As is appreciated by those skilled in the art, these analogous examples may involve variations in general reaction conditions.

TABLE 22

| Ex # | Structure | Name | LCMS [M + H]⁺ | Retention Time (min) |
|---|---|---|---|---|
| 186 | 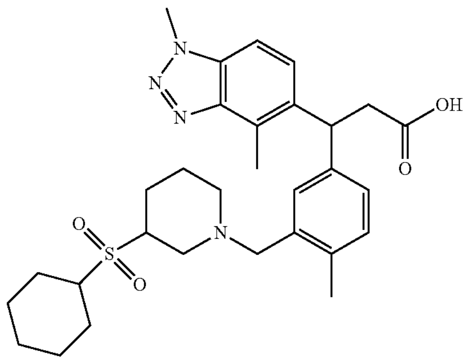 [SMILES: Cc1ccc(C(CC(=O)O)c2ccc3c(nnn3C)c2C)cc1CN1CCCC(S(=O)(=O)C2CCCCC2)C1] | 3-(3-((3-(Cyclohexylsulfonyl)piperidin-1-yl)methyl)-4-methylphenyl)-3-(1,4-dimethyl-1H-benzo[d][1,2,3]triazol-5-yl)propanoic acid | 553.5 | 0.82 |

Example 187

3-(1,4-Dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)-N-(methylsulfonyl)propanamide

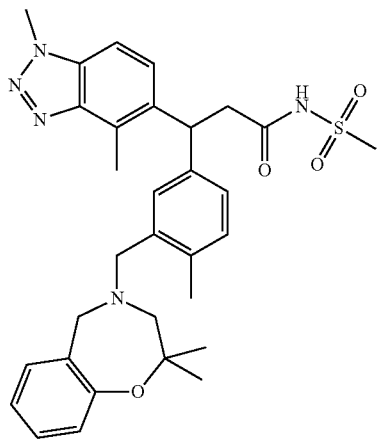 [SMILES: Cc1ccc(C(CC(=O)NS(C)(=O)=O)c2ccc3c(nnn3C)c2C)cc1CN1Cc2ccccc2OC(C)(C)C1]

To the mixture of 2,2-dimethyl-2,3,4,5-tetrahydrobenzo[f][1,4]oxazepine, hydrochloride (0.055 g, 0.259 mmol) in acetonitrile (2 mL) was added DIEA (0.362 ml, 2.073 mmol) then ethyl 3-(3-(chloromethyl)-4-methylphenyl)-3-(1,4-dimethyl-1H-benzo[d][1,2,3]triazol-5-yl)propanoate (0.1 g, 0.259 mmol). The resulting reaction mixture was heated via microwave at 100° C. for 1 h then concentrated and purified by flash chromatography to afford intermediate ethyl 3-(1,4-dimethyl-1H-benzo[d][1,2,3]triazol-5-yl)-3-(3-((2,2-dimethyl-2,3-dihydrobenzo[f][1,4]oxazepin-4(5H)-yl)methyl)-4-methylphenyl)propanoate (0.0833 g, 0.158 mmol, 61.0% yield). This intermediate was dissolved in methanol then NaOH (6 N) (0.332 ml, 2.073 mmol) added. The resulting reaction mixture was heated via microwave at 80° C. for 1 h then acidified with HCl (1 N) to pH 4~5 and then concentrated. The residue was dissolved in EtOAc and DCM (4 mL each) and then filtered. The filtrate was concentrated then dissolved in DCM (3 mL) then EDC (0.04 g, 0.209 mmol), DMAP (0.022 g, 0.180 mmol) and DIEA (0.068 ml, 0.389 mmol) under nitrogen atmosphere were added. This reaction mixture was stirred for 15 minutes then methanesulfonamide (0.0283 g, 0.298 mmol) was added. The resulting reaction mixture was stirred at ambient temperature for 48 h under nitrogen then HCl (1 N) (2 mL) was added. The organic layer was separated and filtered through an isolute IST (70 mL) phase separator. The filtrate was evaporated and purified with reverse phase HPLC (neutral) to give the title compound (16 mg, 0.028 mmol, 10.72% yield). LC/MS: m/z 576.4 (M+H)⁺, 0.84 min (ret. time).

Example 188

(S)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid

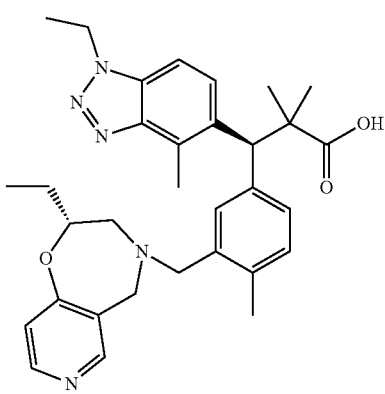 [SMILES: CC[C@@H]1CN(Cc2cc([C@@H](c3ccc4c(nnn4CC)c3C)C(C)(C)C(=O)O)ccc2C)Cc2cnccc2O1]

Example 189

(R)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid

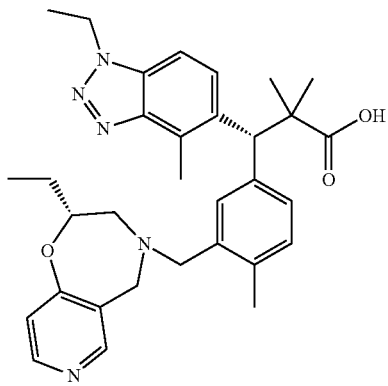 [SMILES: CC[C@@H]1CN(Cc2cc([C@H](c3ccc4c(nnn4CC)c3C)C(C)(C)C(=O)O)ccc2C)Cc2cnccc2O1]

(S)-Methyl 3-(3-(chloromethyl)-4-methylphenyl)-3-(1,4-dimethyl-1H-benzo[d][1,2,3]triazol-5-yl)-2,2-dimethylpropanoate

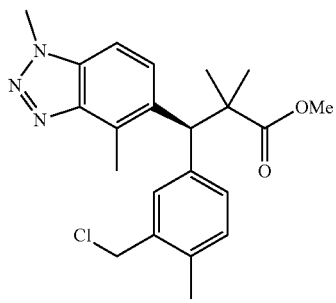 [SMILES: COC(=O)C(C)(C)[C@@H](c1ccc(C)c(CCl)c1)c1ccc2c(nnn2C)c1C]

To a solution of (S)-methyl 3-(1,4-dimethyl-1H-benzo[d][1,2,3]triazol-5-yl)-3-(3-(hydroxymethyl)-4-methylphenyl)-2,2-dimethylpropanoate (710 mg, 1.861 mmol) in dichloromethane (10 mL) at ambient temperature was added thionyl chloride (0.272 mL, 3.72 mmol). The reaction was stirred for 40 min. The resulting mixture was concentrated to give the title compound (750 mg, 1.875 mmol, 101% yield). LC-MS m/z 400.2 (M+H)⁺, 1.21 min (ret. time)

3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid N36149-12

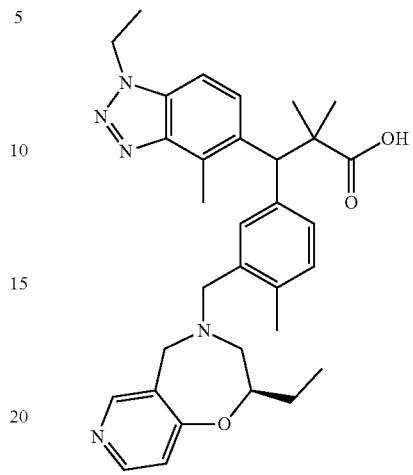

Methyl 3-(3-(chloromethyl)-4-methylphenyl)-3-(1-ethyl-4-methyl-1H-benzo[d][1,2,3]triazol-5-yl)-2,2-dimethylpropanoate (414 mg, 1 mmol), (R)-2-ethyl-2,3,4,5-tetrahydropyrido[3,4-f][1,4]oxazepine hydrochloride (215 mg, 1.000 mmol), and N-ethyl-N-isopropylpropan-2-amine (0.699 ml, 4.00 mmol) in acetonitrile (2 mL) were heated to 120° C. biotage initiator microwave (high power) for 1 h. Solvent was then removed under a stream of nitrogen at 50 C. The crude product was redissolved in methanol (2 mL) and water (1 mL) and lithium hydroxide (479 mg, 20.00 mmol) was added. The solution was heated to 130° C. in a biotage initiator microwave (high power) for 3 hs. DMSO (2 mL) was added to the solution and the methanol and water removed with a V-10 vortex evaporator. The DMSO solution was then acidified with 1 N HCl to a pH of 2. Water was removed with a V-10 vortex evaporator and the DMSO filtered and purified on a Gilson HPLC with formic acid modifier to give the title compound (250 mg, 0.462 mmol, 46.2% yield). LC/MS: m/z 123.4 (M+H)⁺, 0.12 min (ret. time)

(S)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid and (R)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid

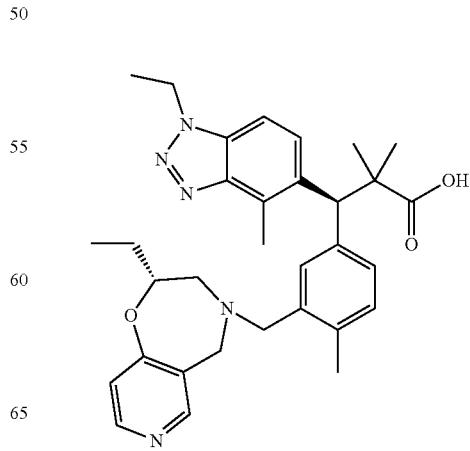

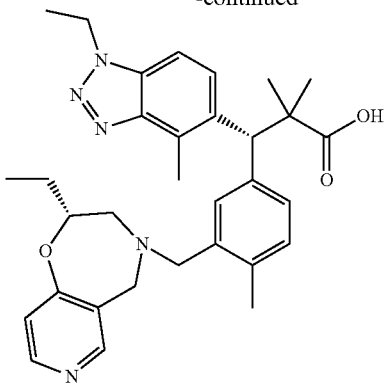

3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid (250 mg, 0.462 mmol) was separated by Chiral SFC (Column: Chiralpak IA 20×250 mm, 5 u; Co-solvent: 20% EtOH; Flowrate: 50 g/min; Back pressure: 100 Bar) to give single enantiomerically pure diastereomer (S)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid (63 mg, 0.116 mmol, 25.2% yield) (chiral SFC ret. time: 4.75 min) and (R)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid (74 mg, 0.137 mmol, 29.6% yield) (chiral SFC ret. time: 6.07 min) LC-MS m/z 542.4 (M+H)$^+$, 0.88 min (ret. time). However, (S)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid was not pure enough. The crude product was purified by reverse phase preparative HPLC using 0.1% formic acid as a solvent modifier to provide the title compound (S)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid, formic acid salt (55 mg, 0.094 mmol, 20.28% yield) as solid. LC-MS m/z 542.6 (M+H)$^+$, 0.93 min (ret. time)

Example 190

(2R,3S)-3-(3-((2,2-Dimethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoic Acid

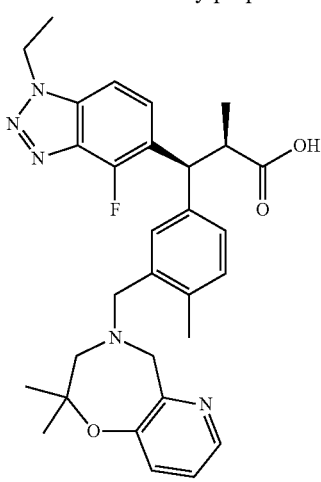

N-Ethyl-3-fluoro-2-nitroaniline

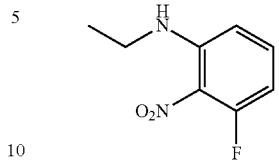

To a solution of 1,3-difluoro-2-nitrobenzene (10 g, 62.9 mmol) in ethanol (300 mL) was added ethanamine (47.2 g, 314 mmol) slowly at 0° C. The reaction mixture was stirred at 0° C. for 0.5 h and then warmed to 25° C. for another 4 h. After removing the solvent, the residue was purified via silica gel chromatography (80 g, PE/EA=5%) to give the title compound (8.0 g, 43.4 mmol, 69.1% yield) as a solid. LC/MS: m/z 185 (M+H)$^+$, 1.70 min (ret. time)

4-Bromo-N-ethyl-3-fluoro-2-nitroaniline

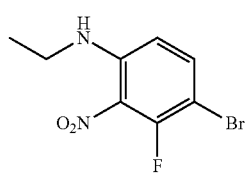

To a solution of N-ethyl-3-fluoro-2-nitroaniline (8.0 g, 43.4 mmol) in DMF (100 mL) at 0° C. was added a solution of N-bromosuccinimide (6.19 g, 34.8 mmol) dropwise. The mixture was stirred at 0° C. for 6 h. The mixture was quenched with water (500 mL) and extracted with ethyl acetate (3×400 mL). The combined organic layer was washed with water (2×100 mL), brine (2×100 mL), dried (Na$_2$SO$_4$) and concentrated. The residue was purified by silica gel chromatography (PE/EA=12%) to give the title compound (8.2 g, 31.2 mmol, 71.8% yield) as yellow oil. LCMS: m/z 263 (M+H)$^+$ 1.80 min (ret. time)

4-Bromo-N1-ethyl-3-fluorobenzene-1,2-diamine

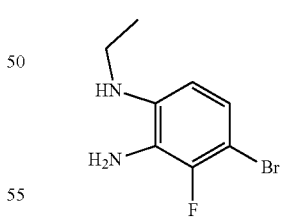

To a solution of 4-bromo-N-ethyl-3-fluoro-2-nitroaniline (8000 mg, 30.4 mmol) in ethanol (100 mL) and 1,2-dichloroethane (DCE) (100 mL) under nitrogen at 0° C. was added Raney nickel (1983 mg, 30.4 mmol, 90% in water) slowly. Hydrazine hydrate (2.237 mL, 45.6 mmol) was added dropwise. The reaction mixture was stirred at 0° C. for 1 h, filtered, and concentrated. The residue was purified by silica gel chromatography (hexane: ethyl acetate=4:1) to give the title compound (6500 mg, 27.9 mmol, 92% yield). LC-MS m/z 233.0 (M+H)$^+$ 1.90 (ret. time)

5-Bromo-1-ethyl-4-fluoro-1H-benzo[d][1,2,3]triazole

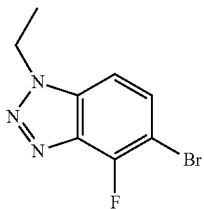

A stirred suspension of 4-bromo-N1-ethyl-3-fluorobenzene-1,2-diamine (6.5 g, 27.9 mmol) and sulfuric acid (5.95 mL, 112 mmol) in water (300 mL) at 0° C. was treated with a solution of sodium nitrite (2.89 g, 41.8 mmol) in water (50 mL). The mixture was stirred at 0° C. for 2 h. The mixture at 0° C. was basified to pH 8 using 2 N NaOH and extracted with DCM (3×200 mL). The combined organics were washed with water (2×80 mL), brine (2×80 mL), dried ($Na_2SO_4$) and concentrated. The residue was purified by silica gel chromatography (120 g, PE/EA=60%) to give the title compound (5.2 g, 21.31 mmol, 76% yield) as a colorless oil. LCMS: m/z 243.9 (M+H)$^+$ 1.63 min (ret. time)

(E)-Benzyl 3-(1-ethyl-4-fluoro-1H-benzo[d][1,2,3]triazol-5-yl)acrylate

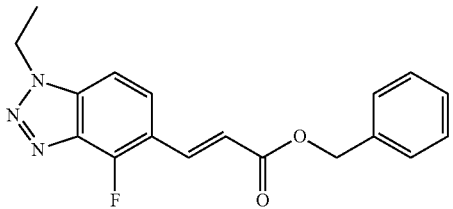 [SMILES: CCn1nnc2c(F)c(/C=C/C(=O)OCc3ccccc3)ccc21]

A mixture of 5-bromo-1-ethyl-4-fluoro-1H-benzo[d][1,2,3]triazole (5.2 g, 21.31 mmol), benzyl acrylate (6.91 g, 42.6 mmol), diacetoxypalladium (0.239 g, 1.065 mmol), tri-otolylphosphine (0.648 g, 2.131 mmol) and triethylamine (14.85 ml, 107 mmol) was heated to 120° C. for 6 h under $N_2$. The reaction mixture was quenched with 200 mL ethyl acetate, and then washed with water (3×100 mL). The organics were dried over $Na_2SO_4$ and the solvent was removed. The residue was purified by silica gel chromatography (120 g, eluted with PE:EA=2:1-1:1) to give the title compound (2.7 g, 8.30 mmol, 39.0% yield) as a solid. LCMS m/z 326.3 (M+H)$^+$, 2.02 min (ret. time)

Benzyl 3-(1-ethyl-4-fluoro-1H-benzo[d][1,2,3]triazol-5-yl)-3-(3-(hydroxymethyl)-4-methyl phenyl)propanoate

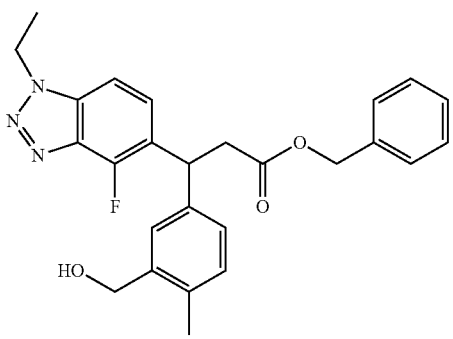 [SMILES: CCn1nnc2c(F)c(C(CC(=O)OCc3ccccc3)c3ccc(C)c(CO)c3)ccc21]

To a solution of (E)-benzyl 3-(1-ethyl-4-fluoro-1H-benzo[d][1,2,3]triazol-5-yl)acrylate (2.7 g, 8.30 mmol) in dioxane (40 mL) and water (20 mL) was added (2-methyl-5-(4,4,5,5-tetramethyl-1,3,2-dioxaborolan-2-yl)phenyl)methanol (6.18 g, 24.90 mmol) and TEA (3.47 mL, 24.90 mmol). The reaction was stirred for 5 min, then chloro(1,5-cyclooctadiene)rhodium(I) dimer (0.205 g, 0.415 mmol) was added under nitrogen. The reaction mixture was stirred at 90° C. for 16 h. The solvent was removed and the residue was purified by silica gel chromatography (PE:EtOAc=6:1) to give title compound (2.0 g, 4.47 mmol, 53.9% yield) as a yellow oil. LC-MS m/z 448.1 (M+18)$^+$, 2.10 (ret. time)

(S)-Benzyl 3-(1-ethyl-4-fluoro-1H-benzo[d][1,2,3]triazol-5-yl)-3-(3-(hydroxymethyl)-4-methylphenyl)propanoate and (R)-benzyl 3-(1-ethyl-4-fluoro-1H-benzo[d][1,2,3]triazol-5-yl)-3-(3-(hydroxymethyl)-4-methylphenyl)propanoate

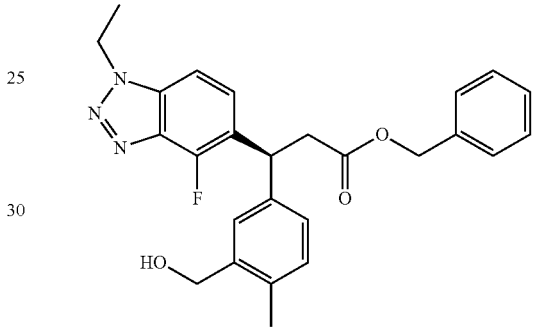

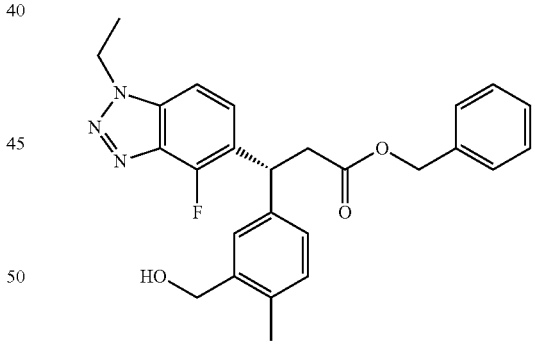

Benzyl 3-(1-ethyl-4-fluoro-1H-benzo[d][1,2,3]triazol-5-yl)-3-(3-(hydroxymethyl)-4-methylphenyl)propanoate (2 g, 4.47 mmol) was separated by Chiral SFC (Column: AS-H 20*250 mm, 5 um; Co-solvent: $CO_2$/MeOH (0.1DEA)=85/15; Flowrate: 80 g/min; Back pressure: 100 Bar) to give single enantiomerically pure (S)-benzyl 3-(1-ethyl-4-fluoro-1H-benzo[d][1,2,3]triazol-5-yl)-3-(3-(hydroxymethyl)-4-methylphenyl)propanoate (0.9 g, 2.011 mmol, 45%) (chiral SFC ret. time: 2.4 min). LCMS m/z 448.1 (M+H)$^+$, 1.69 (ret. time) and (R)-benzyl 3-(1-ethyl-4-fluoro-1H-benzo[d][1,2,3]triazol-5-yl)-3-(3-(hydroxymethyl)-4-methylphenyl)propanoate (0.8 g, 1.788 mmol, 40%) (chiral SFC ret. time: 5.43 min) LCMS m/z 448.1 (M+H)$^+$, 1.69 (ret. time)

401

(S)-benzyl 3-(3-(((tert-butyldimethylsilyl)oxy)methyl)-4-methylphenyl)-3-(1-ethyl-4-fluoro-1H-benzo[d][1,2,3]triazol-5-yl)propanoate

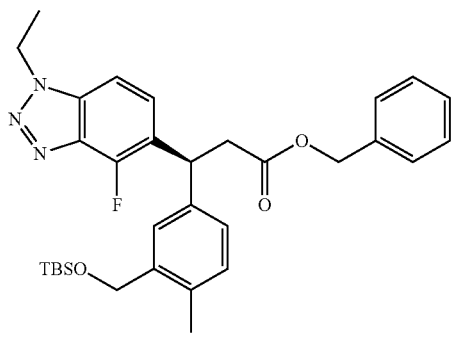 [SMILES: CCn1nnc2c(F)c([C@@H](CC(=O)OCc3ccccc3)c3ccc(C)c(CO[Si](C)(C)C(C)(C)C)c3)ccc21]

To a solution of (S)-benzyl 3-(1-ethyl-4-fluoro-1H-benzo[d][1,2,3]triazol-5-yl)-3-(3-(hydroxymethyl)-4-methylphenyl)propanoate (4000 mg, 8.94 mmol) in dichloromethane (50 mL) at ice bath were added imidazole (669 mg, 9.83 mmol) and tert-butylchlorodimethylsilane (1617 mg, 10.73 mmol). The reaction mixture was stirred at 10° C. for 2 h. The mixture was quenched with water (10 mL) and extracted with DCM (3×20 mL). The combined organic layer was washed with water (2×10 mL) and brine (2×8 mL), dried (Na$_2$SO$_4$), filtered and concentrated. The crude product was purified by silica gel chromatography (80 g, PE:EA=3:1) to give the title compound (4100 mg, 6.93 mmol, 78% yield) as a solid. LCMS m/z 562.1 (M+H)$^+$, 2.12 (ret. time)

(R)-4-benzyl-3-((S)-3-(3-(((tert-butyldimethylsilyl)oxy)methyl)-4-methylphenyl)-3-(1-ethyl-4-fluoro-1H-benzo[d][1,2,3]triazol-5-yl)propanoyl)oxazolidin-2-one

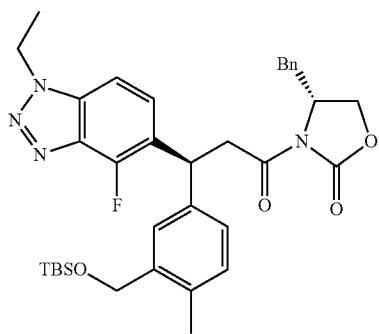 [SMILES: CCn1nnc2c(F)c([C@@H](CC(=O)N3C(=O)OC[C@H]3Cc3ccccc3)c3ccc(C)c(CO[Si](C)(C)C(C)(C)C)c3)ccc21]

(S)-Benzyl 3-(3-(((tert-butyldimethylsilyl)oxy)methyl)-4-methylphenyl)-3-(1-ethyl-4-fluoro-1H-benzo[d][1,2,3]triazol-5-yl)propanoate (640 mg, 1.139 mmol) and Et$_3$N (0.476 mL, 3.42 mmol) in ethyl acetate (20 mL) was passed through a 10% Pd—C cartridge at 1 mL/minute on an H-cube flow hydrogenation instrument set on full H$_2$. After 40 min, the solvent was removed and the residue dissolved in tetrahydrofuran (10.00 mL). Di(1H-imidazol-1-yl)methanone (CDI) (277 mg, 1.709 mmol) was added and the reaction stirred for 16 h. Consumption of the starting material was monitored by TLC. The solution was then diluted with ethyl acetate (10 mL) and washed with brine (2 mL) and dried (sodium sulfate). The solution was concentrated in vacuo and dissolved in acetonitrile (10 mL). 2,3,4,6,7,8,9,10-Octahydropyrimido[1,2-a]azepine (0.034 mL, 0.228 mmol) and (R)-4-benzyloxazolidin-2-one (222 mg, 1.253 mmol) were added and the solution stirred at ambient temperature for 16 h. The reaction was quenched with water, concentrated, then extracted with ethyl acetate (3×). The combined organic fractions were washed (brine) and concentrated. The crude product was purified by silica gel chromatography (Combiflash) (product came out at 30% ethyl acetate in hexane). Desired fractions were concentrated to give the title compound (509 mg, 0.807 mmol, 70.8% yield). LC/MS: m/z 631.5 (M+H)$^+$, 1.64 min (ret. time)

(R)-4-Benzyl-3-((2R,3S)-3-(3-(chloromethyl)-4-methylphenyl)-3-(1-ethyl-4-fluoro-1H-benzo[d][1,2,3]triazol-5-yl)-2-methylpropanoyl)oxazolidin-2-one

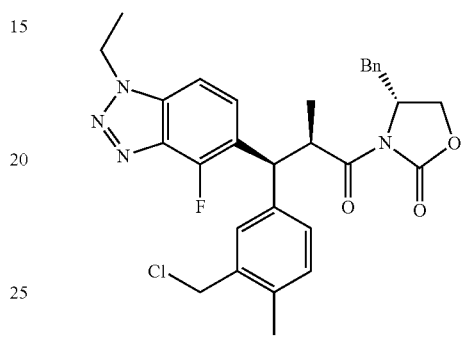

To a mixture of (R)-4-benzyl-3-((2R,3S)-3-(3-(((tert-butyldimethylsilyl)oxy)methyl)-4-methylphenyl)-3-(1-ethyl-4-fluoro-1H-benzo[d][1,2,3]triazol-5-yl)-2-methylpropanoyl)oxazolidin-2-one (400 mg, 0.620 mmol) in dichloromethane (2 mL) was added thionyl chloride (0.091 mL, 1.241 mmol). The reaction was stirred at ambient temperature for 7 h. The resulting mixture was concentrated to give the title compound (393 mg, 0.716 mmol, 115% yield) as a solid. LC/MS: m/z 549.4 (M+H)$^+$, 1.37 min (ret. time)

(R)-4-Benzyl-3-((2R,3S)-3-(3-((2,2-di methyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoyl)oxazolidin-2-one

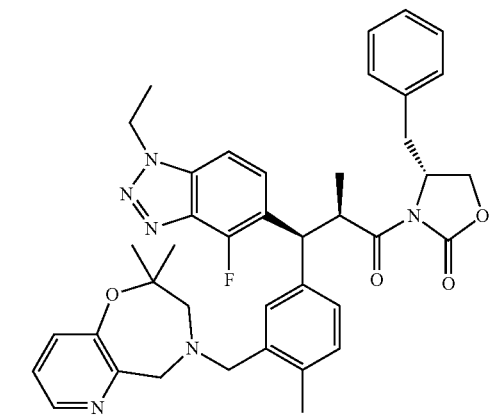 [SMILES: CCn1nnc2c(F)c([C@H](c3ccc(C)c(CN4Cc5ncccc5OC(C)(C)C4)c3)[C@@H](C)C(=O)N3C(=O)OC[C@H]3Cc3ccccc3)ccc21]

To a mixture of (R)-4-benzyl-3-((2R,3S)-3-(3-(chloromethyl)-4-methylphenyl)-3-(1-ethyl-4-fluoro-1H-benzo[d][1,2,3]triazol-5-yl)-2-methylpropanoyl)oxazolidin-2-one (100 mg, 0.182 mmol) in acetonitrile (3 mL) was added 2,2-dimethyl-2,3,4,5-tetrahydrobenzo[f][1,4]oxazepine hydrochloride (78 mg, 0.364 mmol) and N-ethyl-N-isopropylpropan-2-amine (0.095 mL, 0.546 mmol). The reaction was heated via microwave reactor at 120° C. for 1 h. The solvent was removed. The crude product was purified by silica gel chromatography to give the title compound (107 mg, 0.155 mmol, 85% yield). LC/MS: m/z 691.6 (M+H)$^+$, 1.17 min (ret. time)

(2R,3S)-3-(3-((2,2-Dimethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoic Acid

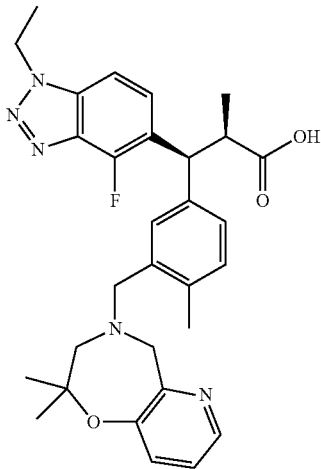 [SMILES: CCn1nnc2c(F)c([C@H](c3ccc(C)c(CN4Cc5ncccc5OC(C)(C)C4)c3)[C@@H](C)C(=O)O)ccc21]

To a mixture of (R)-4-benzyl-3-((2R,3S)-3-(3-((2,2-dimethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoyl)oxazolidin-2-one (107 mg, 0.155 mmol) in tetrahydrofuran (2 mL) and water (0.5 mL) THF/water (4:1) was added hydrogen peroxide (0.127 mL, 1.239 mmol) and 2 M lithium hydroxide (0.232 mL, 0.465 mmol). The reaction was stirred for 2 h. The reaction was quenched with saturated aqueous ammonium chloride (5 mL) and extracted with ethyl acetate twice. The combined organic layer was concentrated then purified with preparative HPLC under acidic conditions (with 0.1% TFA as modifier). Product fractions were combined and concentrated and re-dissolved in ethyl acetate (10 mL), and washed with saturated NaHCO$_3$ twice. The organic layer was dried over sodium sulfate, filtered and concentrated to give the title compound (42 mg, 0.079 mmol, 51.0% yield). LC/MS: m/z 532.4 (M+H)$^+$, 0.90 min (ret. time)

The compounds in Table 23 were prepared by a method similar to the one described for the preparation of (2R,3S)-3-(3-((2,2-dimethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoic acid. As is appreciated by those skilled in the art, these analogous examples may involve variations in general reaction conditions.

TABLE 23

| Ex # | Structure | Name | LCMS [M + H]$^+$ | Retention Time (min) |
|---|---|---|---|---|
| Example 191 | 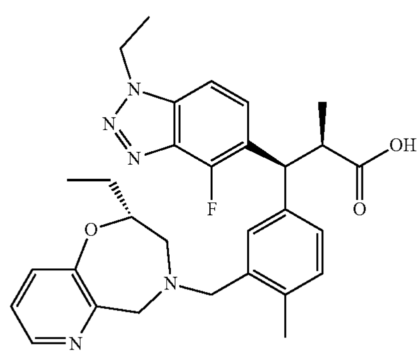 [SMILES: CC[C@@H]1CN(Cc2cc([C@@H](c3ccc4c(nnn4CC)c3F)[C@@H](C)C(=O)O)ccc2C)Cc2ncccc2O1] | (2R,3S)-3-(3-(((R)-2-Ethyl-2,3-dihydropyrido[2,3-f][1,4]oxazepin-4(5H)-yl)methyl)-4-methylphenyl)-3-(1-ethyl-4-fluoro-1H-benzo[d][1,2,3]triazol-5-yl)-2-methylpropanoic acid | 532.4 | 0.87 |

TABLE 23-continued

| Ex # | Structure | Name | LCMS [M + H]+ | Retention Time (min) |
|---|---|---|---|---|
| Example 192 | 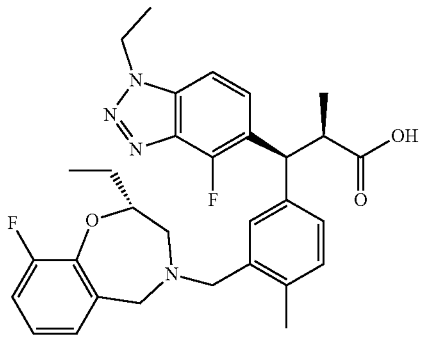 [SMILES: CC[C@@H]1CN(Cc2cc([C@@H](c3ccc4c(nnn4CC)c3F)[C@@H](C)C(=O)O)ccc2C)Cc2cccc(F)c2O1] | (2R,3S)-3-(1-Ethyl-4-fluoro-1H-benzo[d][1,2,3]triazol-5-yl)-3-(3-(((R)-2-ethyl-9-fluoro-2,3-dihydrobenzo[f][1,4]oxazepin-4(5H)-yl)methyl)-4-methylphenyl)-2-methylpropanoic acid | 549.4 | 0.94 |
| Example 193 | 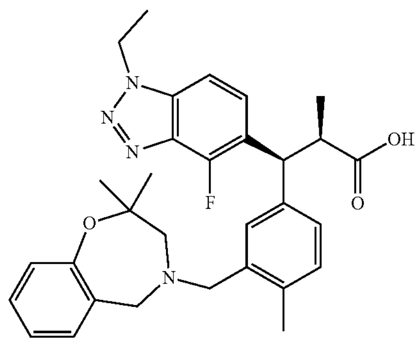 [SMILES: CCn1nnc2c(F)c([C@H](c3ccc(C)c(CN4Cc5ccccc5OC(C)(C)C4)c3)[C@@H](C)C(=O)O)ccc21] | (2R,3S)-3-(3-((2,2-Dimethyl-2,3-dihydro-benzo[f][1,4]oxazepin-4(5H)-yl)methyl)-4-methylphenyl)-3-(1-ethyl-4-fluoro-1H-benzo[d][1,2,3]triazol-5-yl)-2-methylpropanoic acid, Sodium salt | 531.5 | 0.93 |
| Example 194 | 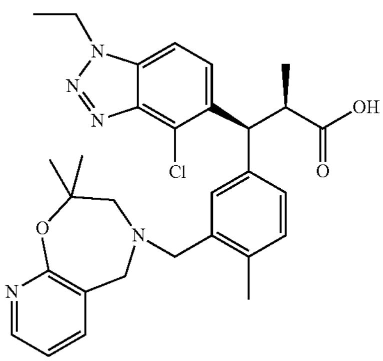 [SMILES: CCn1nnc2c(Cl)c([C@H](c3ccc(C)c(CN4Cc5cccnc5OC(C)(C)C4)c3)[C@@H](C)C(=O)O)ccc21] | (2R,3S)-3-(4-Chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoic acid | 548.3 | 0.86 |
| Example 195 | 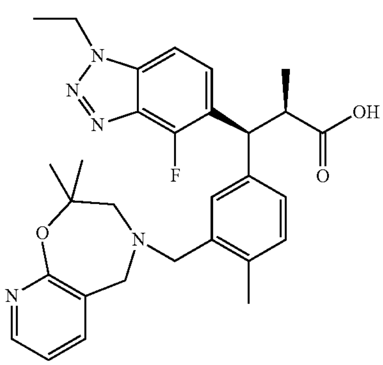 [SMILES: CCn1nnc2c(F)c([C@H](c3ccc(C)c(CN4Cc5cccnc5OC(C)(C)C4)c3)[C@@H](C)C(=O)O)ccc21] | (2R,3S)-3-(3-((2,2-Dimethyl-2,3-dihydropyrldo[3,2-f][1,4]oxazepin-4(5H)-yl)methyl)-4-methylphenyl)-3-(1-ethyl-4-fluoro-1H-benzo[d][1,2,3]triazol-5-yl)-2-methylpropanoic acid | 532.3 | 0.83 |

TABLE 23-continued

| Ex # | Structure | Name | LCMS [M + H]+ | Retention Time (min) |
|---|---|---|---|---|
| Example 196 | 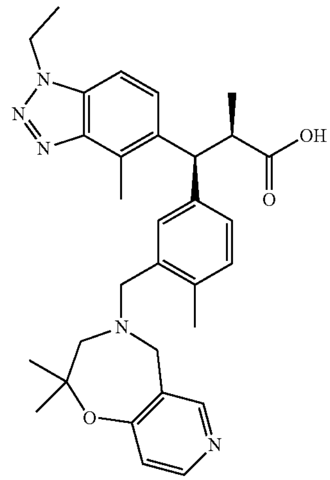 [SMILES: CCn1nnc2c(C)c([C@H](c3ccc(C)c(CN4Cc5cnccc5OC(C)(C)C4)c3)[C@@H](C)C(=O)O)ccc21] | (2R,3S)-3-(3-((2,2-Dimethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoic acid, Trifluoroacetic acid salt | 528.4 | 0.94 |

Example 197

(2S,3R)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoate, Sodium salt

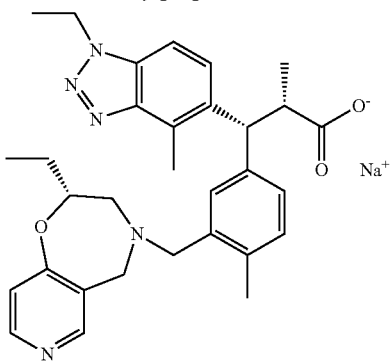

(R)-Ethyl 3-(3-(((tert-butyldimethylsilyl)oxy)methyl)-4-methylphenyl)-3-(1-ethyl-4-methyl-1H-benzo[d][1,2,3]triazol-5-yl)propanoate

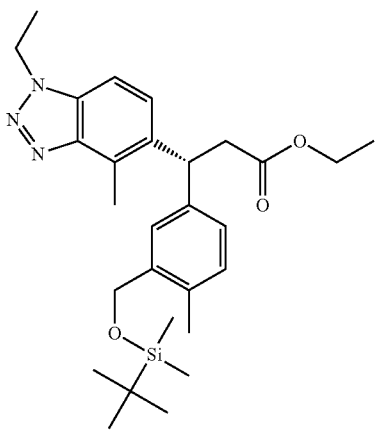 [SMILES: CCOC(=O)C[C@H](c1ccc(C)c(CO[Si](C)(C)C(C)(C)C)c1)c1ccc2c(nnn2CC)c1C]

To a solution of (R)-ethyl 3-(1-ethyl-4-methyl-1H-benzo[d][1,2,3]triazol-5-yl)-3-(3-(hydroxymethyl)-4-methylphe- nyl)propanoate (5 g, 13.11 mmol) in dichloromethane (100 mL) were added imidazole (0.892 g, 13.11 mmol) and tert-butylchlorodimethylsilane (2.173 g, 14.42 mmol). The reaction mixture was stirred at 0° C. to 25° C. for 2 h. The mixture was quenched with water (100 mL) and extracted with DCM (3×150 mL). The combined organic layer was washed with brine (200 mL), dried (Na₂SO₄), filtered and concentrated. The residue was purified with silica gel chromatography (PE:EA=5:1) to give (5.2 g, 9.44 mmol, 72.0% yield) as yellow oil. LC-MS m/z 496.3 (M+H)+, 2.39 (ret. time)

(R)-3-(3-(((tert-Butyldimethylsilyl)oxy)methyl)-4-methylphenyl)-3-(1-ethyl-4-methyl-1H-benzo[d][1,2,3]triazol-5-yl)propanoic acid

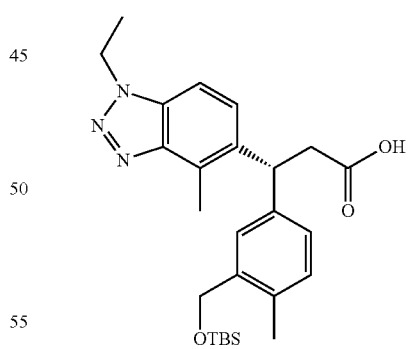

To a solution of (R)-ethyl 3-(3-(((tert-butyldimethylsilyl)oxy)methyl)-4-methylphenyl)-3-(1-ethyl-4-methyl-1H-benzo[d][1,2,3]triazol-5-yl)propanoate (5.2 g, 10.49 mmol) in tetrahydrofuran (10 mL)/methanol (5 mL) was added LiOH (0.462 g, 19.31 mmol) in water (8 mL). The reaction mixture was stirred at 25° C. for 4 h. The organic solvent was removed. The residue was adjusted to pH 5 with HCl (3 M, 5 mL) and extracted with ethyl acetate (2×100 mL). The organic layer was washed with water (50 mL), dried over sodium sulfate, filtered and concentrated to give the title compound (4.8 g, 6.26 mmol, 59.7% yield) as yellow oil. LC-MS m/z 468.3 (M+H)⁺, 1.73 (ret. time)

(R)-Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate

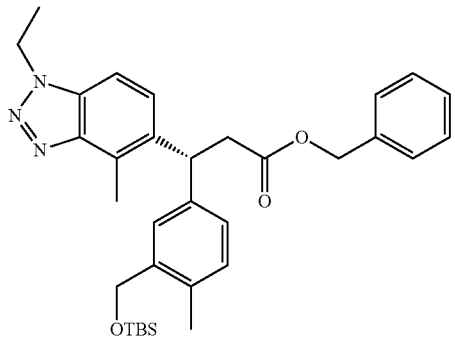 [SMILES: CCn1nnc2c(C)c([C@H](CC(=O)OCc3ccccc3)c3ccc(C)c(CO[Si](C)(C)C(C)(C)C)c3)ccc21]

To a solution of (R)-3-(3-(((tert-butyldimethylsilyl)oxy)methyl)-4-methylenyl)-3-(1-ethyl-4-methyl-1H-benzo[d][1,2,3]triazol-5-yl)propanoic acid (4.8 g, 10.26 mmol) in acetonitrile (30 mL) was added (bromomethyl)benzene (1.931 g, 11.29 mmol) and K₂CO₃ (2.84 g, 20.53 mmol). The solution was stirred at 25° C. for 4 h. The residue was purified by silica gel chromatography (PE:EtOAc=10:1) to give the title compound (4 g, 5.59 mmol, 54.5% yield) as a yellow oil. LC-MS m/z 558.3 (M+H)⁺, 2.54 (ret. time)

(2S,3R)-Benzyl 3-(3-(((tert-butyldimethylsilyl)oxy)methyl)-4-methylphenyl)-3-(1-ethyl-4-methyl-1H-benzo[d][1,2,3]triazol-5-yl)-2-methylpropanoate

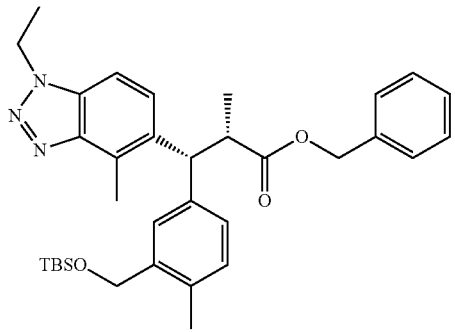 [SMILES: CCn1nnc2c(C)c([C@@H](c3ccc(C)c(CO[Si](C)(C)C(C)(C)C)c3)[C@H](C)C(=O)OCc3ccccc3)ccc21]

Batch 1: To a solution of (R)-benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (500 mg, 0.896 mmol) in tetrahydrofuran (10 mL) was added LDA (1.569 mL, 3.14 mmol) at −78° C. The reaction was stirred for 45 min and MeI (0.112 mL, 1.793 mmol) was added at −78° C. The red wine color turned to light yellow. The reaction was stirred for 45 min. The residue was diluted with EtOAc (75 mL) and water (25 mL). The aqueous layer was extracted again with EtOAc (25 mL) and the combined EtOAc was washed with saturated NaCl (25 mL), dried (Na₂SO₄) and concentrated. Batch 2 to 8 was the same procedure as batch 1. Eight batches were combined. The residue was purified by reverse phase preparative HPLC using 0.05% TFA as a solvent modifier to give the title compound (contained 55% of title compound and 38% (2S,3R)-benzyl 3-(1-ethyl-4-methyl-1H-benzo[d][1,2,3]triazol-5-yl)-3-(3-(hydroxymethyl)-4-methylphenyl)-2-methylpropanoate) as a yellow oil. LC-MS m/z 571.8 (M+H)⁺, 2.32 (ret. time)

(3R)-Benzyl 3-(1-ethyl-4-methyl-1H-benzo[d][1,2,3]triazol-5-yl)-3-(3-(hydroxymethyl)-4-methylphenyl)-2-methylpropanoate

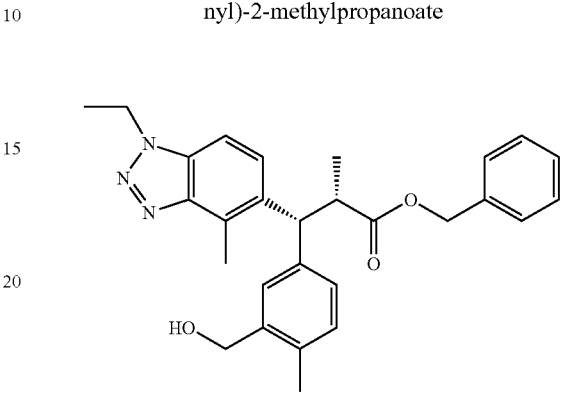

To a solution of (3R)-benzyl 3-(3-(((tert-butyldimethylsilyl)oxy)methyl)-4-methylphenyl)-3-(1-ethyl-4-methyl-1H-benzo[d][1,2,3]triazol-5-yl)-2-methylpropanoate (1.1 g, 1.924 mmol) in tetrahydrofuran (20 mL) at 0° C., TBAF (0.604 g, 2.308 mmol) was added. The reaction mixture was stirred at 0° C. for 1 h. The mixture was quenched with saturated NH₄Cl solution (20 mL) and extracted with ethyl acetate (3×100 mL). The organic layer was washed with brine (100 mL), dried (Na₂SO₄) and concentrated. The residue was purified by silica gel chromatography (PE:EtOAc=1:1) to give the title compound (740 mg, 1.503 mmol, 78% yield) as a colorless oil. LC-MS m/z 457.9 (M+H)⁺, 1.75 (ret. time)

(3R)-Benzyl 3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoate

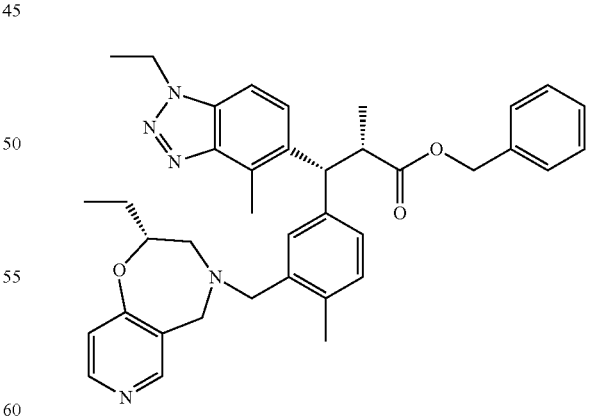

To a solution of (3R)-benzyl 3-(1-ethyl-4-methyl-1H-benzo[d][1,2,3]triazol-5-yl)-3-(3-(hydroxymethyl)-4-methylphenyl)-2-methylpropanoate (200 mg, 0.437 mmol) in dichloromethane (3 mL) was added thionyl chloride (0.064 mL, 0.874 mmol). The mixture was stirred for 40 min. The resulting mixture was concentrated to give (2S,3R)-benzyl 3-(3-(chloromethyl)-4-methylphenyl)-3-(1-ethyl-4-methyl-1H-benzo[d][1,2,3]triazol-5-yl)-2-methylpropanoate. This was re-dissolved in acetonitrile (3 mL). (R)-2-ethyl-2,3,4,5-tetrahydropyrido[3,4-f][1,4]oxazepine hydrochloride (113 mg, 0.525 mmol) was added. The mixture was heated via microwave at 120° C. for 1 h. The resulting mixture was concentrated. The crude product was purified by silica gel chromatography (Combiflash) (product came out at 50% ethyl acetate in hexane). Desired fractions were concentrated to give the title compound (101 mg, 0.163 mmol, 37.4% yield) LC-MS m/z 618.6 (M+H)$^+$, 1.02 min (ret. time)

(2S,3R)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoic Acid

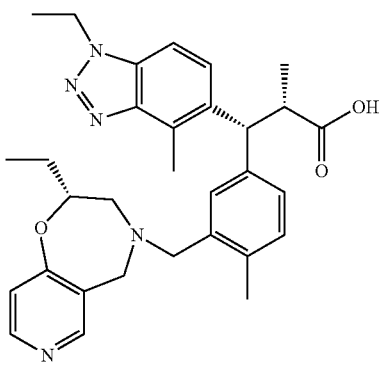 [SMILES: CC[C@@H]1CN(Cc2cc([C@H](c3ccc4c(nnn4CC)c3C)[C@H](C)C(=O)O)ccc2C)Cc2cnccc2O1]

A solution of (3R)-benzyl 3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoate (100 mg, 0.162 mmol) in ethyl acetate (5 mL) was passed through an H-Cube (1 mL/min, 25° C., Pd/C cartridge, 1 bar) for 3 h. The resulting mixture was concentrated and purified by reverse phase preparative HPLC using 0.1% TFA as a solvent modifier to provide the title compound (88 mg, 0.073 mmol, 44.9%). LC-MS m/z 528.3 (M+H)$^+$, 0.80 min (ret. time)

(2S,3R)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoate, Sodium Salt

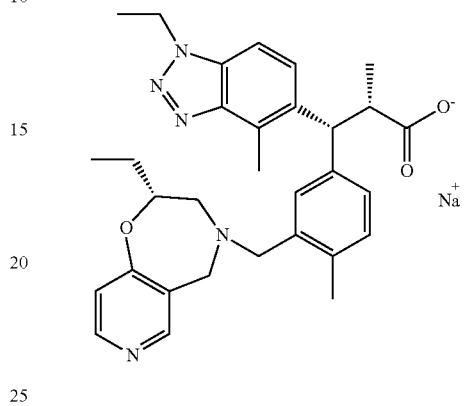

48.5 mg of (2S,3R)-3-(3-(((R)-2-Ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoic acid (6:1 TFA vs. parent) was dissolved in ethyl acetate (8 mL) and washed with saturated NaHCO$_3$. The aqueous layer was washed with ethyl acetate again. The combined organic layer was dried over sodium sulfate, filtered and concentrated to give the title compound (23 mg, 0.042 mmol, 45.5% yield) as solid. LC-MS m/z 528.3 (M+H)$^+$, 0.80 min (ret. time)

The compounds in Table 24 were prepared by a method similar to the one described for the preparation of (2S,3R)-3-(3-(((R)-2-ethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoic acid. As is appreciated by those skilled in the art, these analogous examples may involve variations in general reaction conditions.

TABLE 24

| Ex # | Structure | Name | LCMS [M + H]$^+$ | Retention Time (min) |
|---|---|---|---|---|
| Example 198 | 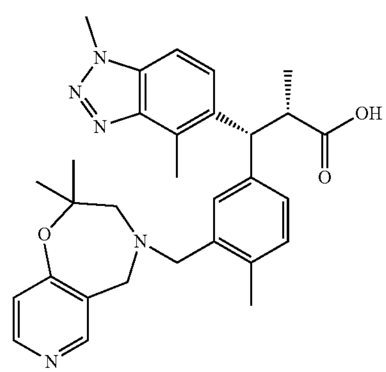 [SMILES: Cc1ccc([C@H](c2ccc3c(nnn3C)c2C)[C@H](C)C(=O)O)cc1CN1Cc2cnccc2OC(C)(C)C1] | (2S,3R)-3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoic acid, 0.1 formic acid salt | 514.5 | 0.93 |

TABLE 24-continued

| Ex # | Structure | Name | LCMS [M + H]+ | Retention Time (min) |
|---|---|---|---|---|
| Example 199 | 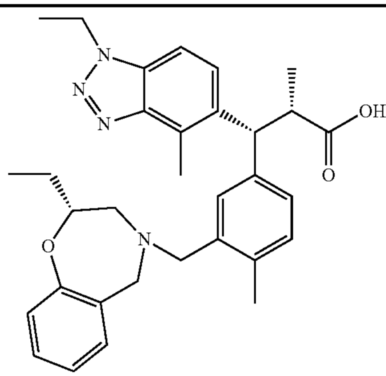 | (2S,3R)-3-(3-(((R)-2-Ethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid | 527.1 | 0.90 |

Example 200

(2S,3R)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic Acid, 2 Trifluoroacetic Acid Salt

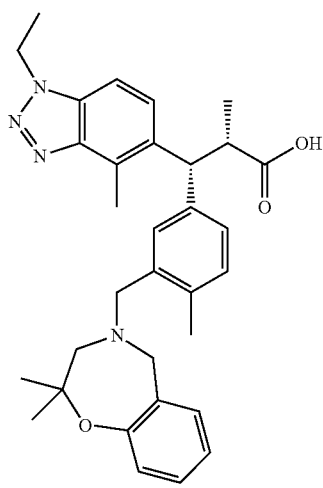 [SMILES: CCn1nnc2c(C)c([C@@H](c3ccc(C)c(CN4Cc5ccccc5OC(C)(C)C4)c3)[C@H](C)C(=O)O)ccc21]

(R)-3-(3-(((tert-Butyldimethylsilyl)oxy)methyl)-4-methylphenyl)-3-(1-ethyl-4-methyl-1H-benzo[d][1,2,3]triazol-5-yl)propanoic Acid

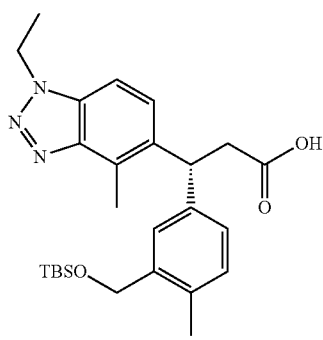 [SMILES: CCn1nnc2c(C)c([C@H](CC(=O)O)c3ccc(C)c(CO[Si](C)(C)C(C)(C)C)c3)ccc21]

(R)-Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (200 mg, 0.359 mmol) in methanol (17.928 mL) was passed through an H-cube flow reactor with a 10% Pd—C cartridge for 1.5 h at 1 mL/min on full H2 mode. The methanol was then removed. The crude material was purified by silica gel chromatography using 0-10% MeOH/DCM to give the title compound (138 mg, 0.295 mmol, 82% yield). LC/MS: m/z 468.2 (M+H)+, 1.41 min (ret. time)

(S)-4-Benzyl-3-((R)-3-(3-(((tert-butyldimethylsilyl)oxy)methyl)-4-methylphenyl)-3-(1-ethyl-4-methyl-1H-benzo[d][1,2,3]triazol-5-yl)propanoyl)oxazolidin-2-one

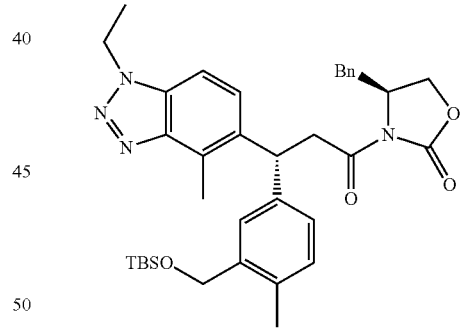

CDI (71.8 mg, 0.443 mmol) was added to a solution of (R)-3-(3-(((tert-butyldimethylsilyl)oxy)methyl)-4-methylphenyl)-3-(1-ethyl-4-methyl-1H-benzo[d][1,2,3]triazol-5-yl)propanoic acid (138 mg, 0.295 mmol) in tetrahydrofuran (2.95 mL) at ambient temperature and the reaction stirred for 16 hs. Consumption of the starting material was monitored by TLC. The solution was then diluted with DCM (10 mL) and washed with water (2 mL) and dried (sodium sulfate). The solution was concentrated and dissolved in acetonitrile (2.95 mL). (S)-4-benzyloxazolidin-2-one (57.5 mg, 0.325 mmol) and DBU (8.90 µL, 0.059 mmol) were added and the solution stirred at ambient temperature for 16 hs. The reaction was quenched with saturated aqueous ammonium chloride and extracted with ethyl acetate (3×). The combined organic fractions were washed (brine), dried (sodium sulfate) and solvent removed in vacuo. The product was purified by silica gel chromatography (EtOAc/hexanes 0-100%) to give the title compound (767 mg, 1.224 mmol, 84% yield). LC/MS: m/z 627.2 (M+H)+, 1.59 min (ret. time)

(S)-4-Benzyl-3-((2S,3R)-3-(3-(((tert-butyldimethylsilyl)oxy)methyl)-4-methylphenyl)-3-(1-ethyl-4-methyl-1H-benzo[d][1,2,3]triazol-5-yl)-2-methylpropanoyl)oxazolidin-2-one

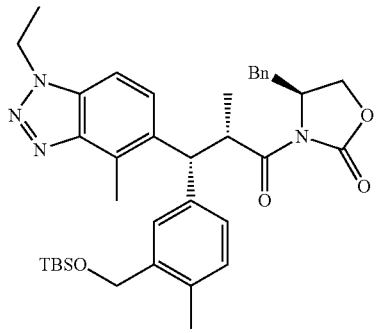 [SMILES: CCn1nnc2c(C)c([C@@H](c3ccc(C)c(CO[Si](C)(C)C(C)(C)C)c3)[C@H](C)C(=O)N3C(=O)OC[C@@H]3Cc3ccccc3)ccc21]

Sodium bis(trimethylsilyl)amide (1.346 mL, 1.346 mmol) was added dropwise to a solution of (S)-4-benzyl-3-((R)-3-(3-(((tert-butyldimethylsilyl)oxy)methyl)-4-methylphenyl)-3-(1-ethyl-4-methyl-1H-benzo[d][1,2,3]triazol-5-yl)propanoyl)oxazolidin-2-one (767 mg, 1.224 mmol) in tetrahydrofuran (12.236 mL) at −78° C. and the reaction stirred for 60 minutes. Methyl iodide (3.06 mL, 6.12 mmol) was then added and the solution stirred for 1 h at −78° C. and then warmed to ambient temperature. The reaction was quenched with saturated aqueous ammonium chloride and extracted with ethyl acetate (3×). The combined organic fractions were washed (brine), dried (sodium sulfate) and solvent removed in vacuo. The product was purified by silica gel chromatography (EtOAc/hexanes 0-100%) to give the title compound (591 mg, 0.922 mmol, 75% yield). LC/MS: m/z 641.2 (M+H)+, 1.68 min (ret. time)

(S)-4-Benzyl-3-((2S,3R)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one

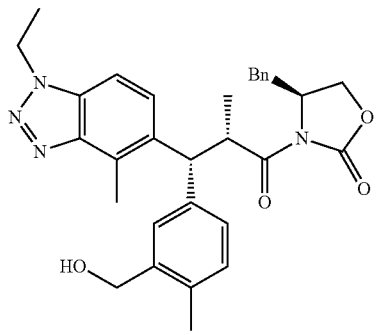 [SMILES: CCn1nnc2c(C)c([C@@H](c3ccc(C)c(CO)c3)[C@H](C)C(=O)N3C(=O)OC[C@@H]3Cc3ccccc3)ccc21]

TBAF (2.029 mL, 2.029 mmol) was added dropwise to a solution of (S)-4-benzyl-3-((2S,3R)-3-(3-(((tert-butyldimethylsilyl)oxy)methyl)-4-methylphenyl)-3-(1-ethyl-4-methyl-1H-benzo[d][1,2,3]triazol-5-yl)-2-methylpropanoyl)oxazolidin-2-one (591 mg, 0.922 mmol) in tetrahydrofuran (18.856 mL) at 0° C. and the reaction stirred for 30 minutes. The desired product was purified by silica gel chromatography to give the title compound (157 mg, 0.298 mmol, 32.3% yield). LC/MS: m/z 527.6 (M+H)+, 1.16 min (ret. time)

(S)-4-Benzyl-3-((2S,3R)-3-(3-(chloromethyl)-4-methylphenyl)-3-(1-ethyl-4-methyl-1H-benzo[d][1,2,3]triazol-5-yl)-2-methylpropanoyl)oxazolidin-2-one

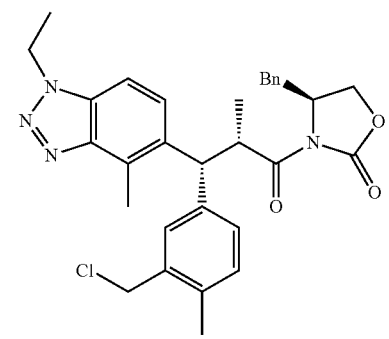 [SMILES: CCn1nnc2c(C)c([C@@H](c3ccc(C)c(CCl)c3)[C@H](C)C(=O)N3C(=O)OC[C@@H]3Cc3ccccc3)ccc21]

Thionyl chloride (0.022 mL, 0.298 mmol) was added to a solution of (S)-4-benzyl-3-((2S,3R)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one (157 mg, 0.298 mmol) in dichloromethane (2.379 mL) at ambient temperature. The solution was stirred for 30 minutes then concentrated. The excess thionyl chloride was removed under reduced pressure utilizing a V-10 vortex evaporator to give the title compound (162 mg, 0.298 mmol, 100% yield). The product was taken to the next step without further purification. LC/MS: m/z 545.3 (M+H)+, 1.39 min (ret. time)

(2S,3R)-3-(3-((2,2-dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid, 2 Trifluoroacetic Acid Salt

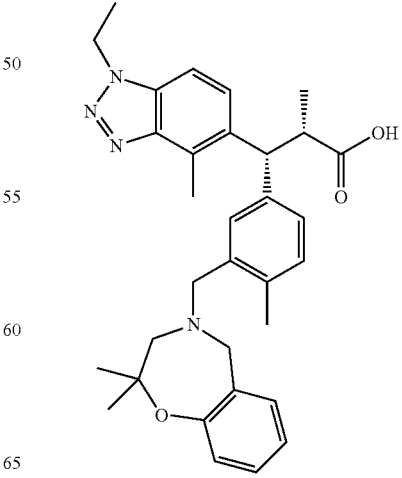

(S)-4-Benzyl-3-((2S,3R)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one (70 mg, 0.133 mmol), 2,2-dimethyl-2,3,4,5-tetrahydrobenzo[f][1,4]oxazepine hydrochloride (56.8 mg, 0.266 mmol), and N-ethyl-N-isopropylpropan-2-amine (69.6 μl, 0.399 mmol) in acetonitrile (1.2 mL) were heated in a biotage microwave reactor (high power) at 120° C. for 2.5 hs. The solvent was removed and the crude product was dissolved in THF/Water (4:1). hydrogen peroxide (0.109 mL, 1.063 mmol) and lithium hydroxide (9.55 mg, 0.399 mmol) were added and the solution stirred for 16 hs. The reaction was quenched with saturated aqueous ammonium chloride (5 mL) and extracted with ethyl acetate (5×20 mL). The combined organic fractions were evaporated and dissolved in DMSO. The residue was purified by reverse phase preparative HPLC using 0.1% TFA as a solvent modifier to provide the title compound (50 mg, 0.066 mmol, 49.8% yield). LC/MS: m/z 527.4 (M+H)+, 0.92 min (ret. time)

Example 201

(2S,3R)-3-(1-Ethyl-4-methyl-1H-benzo[d][1,2,3]triazol-5-yl)-2-methyl-3-(4-methyl-3-((2-(piperidin-1-ylmethyl)-1H-imidazol-1-yl)methyl)phenyl)propanoic Acid

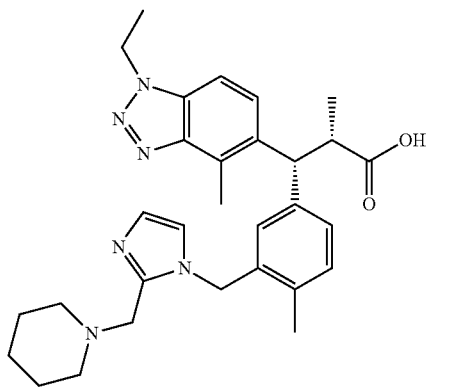 [SMILES: CCn1nnc2c(C)c([C@@H](c3ccc(C)c(Cn4ccnc4CN4CCCCC4)c3)[C@H](C)C(=O)O)ccc21]

Benzyl 3-(1-ethyl-4-methyl-1H-benzo[d][1,2,3]triazol-5-yl)-3-(3-(hydroxymethyl)-4-methylphenyl)-2-methylpropanoate

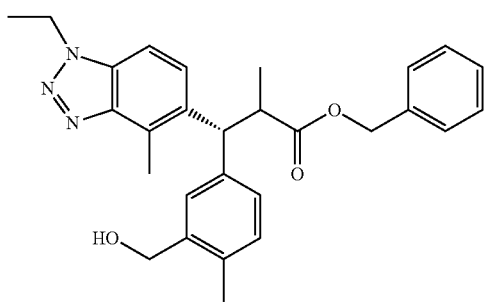

To a solution of (3R)-benzyl 3-(3-(((tert-butyldimethylsilyl)oxy)methyl)-4-methylphenyl)-3-(1-ethyl-4-methyl-1H-benzo[d][1,2,3]triazol-5-yl)-2-methylpropanoate (600 mg, 1.049 mmol) in tetrahydrofuran (10 mL) at 0° C. was added TBAF (329 mg, 1.259 mmol). The reaction mixture was stirred at 0° C. for 1 h. The mixture was quenched with saturated NH₄Cl solution (20 mL) and extracted with ethyl acetate (3×100 mL). The organic layer was washed with brine (100 mL), dried (Na₂SO₄) and concentrated. The residue was purified by reverse phase preparative HPLC using 0.05% TFA as a solvent modifier to provide the title compound (400 mg, 0.857 mmol, 82% yield) as yellow oil. LC-MS m/z 458.0 (M+H)+, 1.77 (ret. time)

(2S,3R)-Benzyl 3-(1-ethyl-4-methyl-1H-benzo[d][1,2,3]triazol-5-yl)-3-(3-(hydroxymethyl)-4-methylphenyl)-2-methylpropanoate and (2R,3R)-benzyl 3-(1-ethyl-4-methyl-1H-benzo[d][1,2,3]triazol-5-yl)-3-(3-(hydroxymethyl)-4-methylphenyl)-2-methylpropanoate

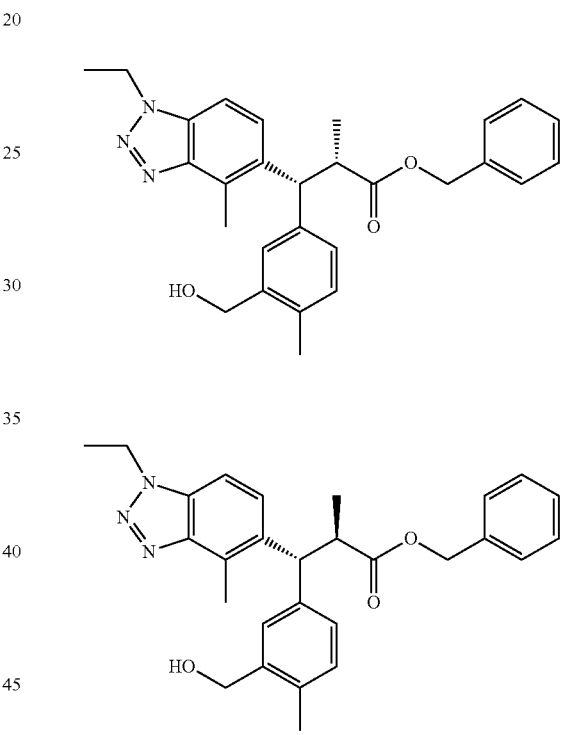

(3R)-Benzyl 3-(1-ethyl-4-methyl-1H-benzo[d][1,2,3]triazol-5-yl)-3-(3-(hydroxymethyl)-4-methylphenyl)-2-methylpropanoate (420 mg, 0.918 mmol) was separated with preparative HPLC under acidic conditions (with 0.1% TFA as modifier). Fractions of each peak were combined and washed with saturated NaHCO₃ and the aqueous layer was extracted with ethyl acetate. The combined organic layer was dried over sodium sulfate, filtered and concentrated to give the title compound (2S,3R)-benzyl 3-(1-ethyl-4-methyl-1H-benzo[d][1,2,3]triazol-5-yl)-3-(3-(hydroxymethyl)-4-methylphenyl)-2-methylpropanoate (185 mg, 0.404 mmol, 44.0% yield) LC-MS m/z 458.4 (M+H)+, 1.06 min (ret. time) and (2R,3R)-benzyl 3-(1-ethyl-4-methyl-1H-benzo[d][1,2,3]triazol-5-yl)-3-(3-(hydroxymethyl)-4-methylphenyl)-2-methylpropanoate (195 mg, 0.426 mmol, 46.4% yield) LC-MS m/z 458.5 (M+H)+, 1.10 min (ret. time)

419

(2S,3R)-Benzyl 3-(3-(chloromethyl)-4-methylphenyl)-3-(1-ethyl-4-methyl-1H-benzo[d][1,2,3]triazol-5-yl)-2-methylpropanoate

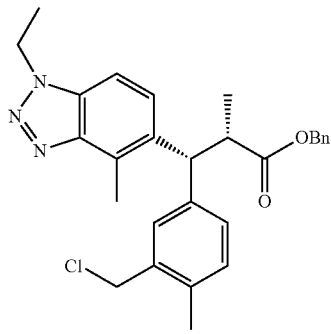 [SMILES: CCn1nnc2c(C)c([C@@H](c3ccc(C)c(CCl)c3)[C@H](C)C(=O)OCc3ccccc3)ccc21]

Thionyl chloride (46.8 mg, 0.393 mmol) was added to a solution of (2S,3R)-benzyl 3-(1-ethyl-4-methyl-1H-benzo[d][1,2,3]triazol-5-yl)-3-(3-(hydroxymethyl)-4-methylphenyl)-2-methylpropanoate (180 mg, 0.393 mmol) in dichloromethane (0.787 mL) at ambient temperature and the reaction stirred for 1 h. Solvent and excess thionyl chloride was removed to give the title compound (184 mg, 0.386 mmol, 98% yield). LC/MS: m/z 476.0 (M+H)$^+$, 1.32 min (ret. time)

(2S,3R)-3-(1-Ethyl-4-methyl-1H-benzo[d][1,2,3]triazol-5-yl)-2-methyl-3-(4-methyl-3-((2-(piperidin-1-ylmethyl)-1H-imidazol-1-yl)methyl)phenyl)propanoic Acid

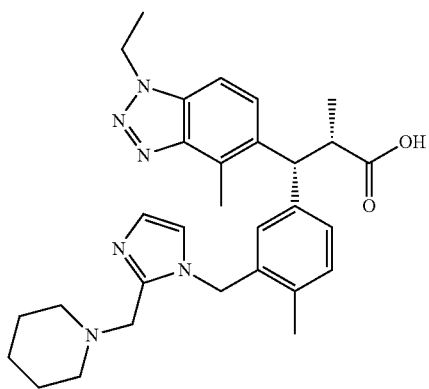 [SMILES: CCn1nnc2c(C)c([C@@H](c3ccc(C)c(Cn4ccnc4CN4CCCCC4)c3)[C@H](C)C(=O)O)ccc21]

[(2S,3R)-Benzyl 3-(3-(chloromethyl)-4-methylphenyl)-3-(1-ethyl-4-methyl-1H-benzo[d][1,2,3]triazol-5-yl)-2-methylpropanoate (150 mg, 0.315 mmol), 1-((1H-imidazol-2-yl)methyl)piperidine (78 mg, 0.473 mmol), and Hunig's base (0.165 mL, 0.945 mmol) in acetronitril (2.86 mL) were heated in a Biotage Initiator microwave reactor at 120° C. for 1 h. The solvent was removed and the crude material re-dissolved in methanol (28.6 mL). The product was passed through an H-cube flow hydrogenation instrument at 1 mL/min through a 10% Pd/C cartridge for 2 hs. The solvent was removed and the product purified by reverse phase preparative HPLC using neutral condition to provide the title compound (30 mg, 0.058 mmol, 18.50% yield). LC/MS: m/z 515.4 (M+H)$^+$, 0.84 min (ret. time)

Example 202

(2R,3S)-3-(4-chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoic Acid

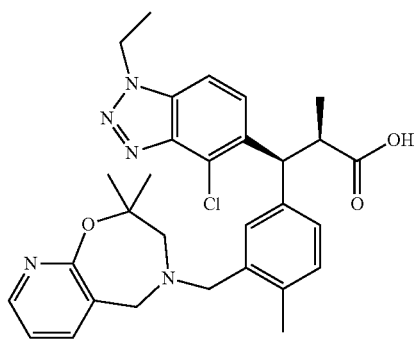 [SMILES: CCn1nnc2c(Cl)c([C@H](c3ccc(C)c(CN4Cc5cccnc5OC(C)(C)C4)c3)[C@@H](C)C(=O)O)ccc21]

(R)-4-Benzyl-3-((S)-3-(3-(((tert-butyldimethylsilyl)oxy)methyl)-4-methylphenyl)-3-(4-chloro-1-ethyl-1H-benzo[d][1,2,3]triazol-5-yl)propanoyl)oxazolidin-2-one

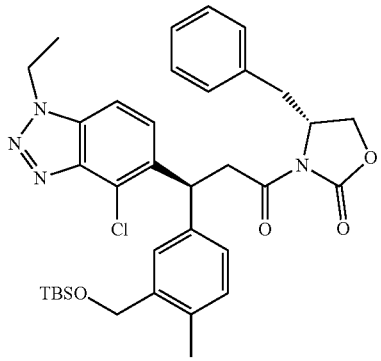 [SMILES: CCn1nnc2c(Cl)c([C@@H](CC(=O)N3C(=O)OC[C@H]3Cc3ccccc3)c3ccc(C)c(CO[Si](C)(C)C(C)(C)C)c3)ccc21]

(S)-Benzyl 3-(3-(((tert-butyldimethylsilyl)oxy)methyl)-4-methylphenyl)-3-(4-chloro-1-ethyl-1H-benzo[d][1,2,3]triazol-5-yl)propanoate (2000 mg, 3.46 mmol) and Et$_3$N (1.446 mL, 10.38 mmol) in ethyl acetate (30 mL) was passed through a 10% Pd—C cartridge at 1 mL/minute on an H-cube flow hydrogenation instrument set on full hydrogen. After 5 h, the resulting mixture was concentrated then re-dissolved in tetrahydrofuran (30.00 mL). Di(1H-Imidazol-1-yl)methanone (CDI) (841 mg, 5.19 mmol) was added and the reaction stirred for 16 h. The solution was then diluted with ethyl acetate (20 mL) and washed with brine (4 mL) and dried (sodium sulfate). The solution was concentrated in vacuo and dissolved in acetonitrile (30.00 mL). 2,3,4,6,7,8,9,10-Octahydropyrimido[1,2-a]azepine (0.103 mL, 0.692 mmol) and (R)-4-benzyloxazolidin-2-one (919 mg, 5.19 mmol) were added and the solution stirred at ambient temperature for 18 h. The reaction was quenched with water and extracted with ethyl acetate (3×20 mL). The combined organic fractions were washed with brine and concentrated. The product was purified by silica gel chromatography to give the title compound (1502 mg, 2.320 mmol, 67.1% yield). LC/MS: m/z 647.6 (M+H)+, 1.61 min (ret. time)

(R)-4-Benzyl-3-((2R,3S)-3-(3-(((tert-butyldimethylsilyl)oxy)methyl)-4-methylphenyl)-3-(4-chloro-1-ethyl-1H-benzo[d][1,2,3]triazol-5-yl)-2-methylpropanoyl)oxazolidin-2-one

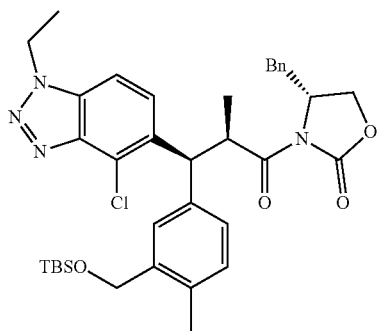 [SMILES: CCn1nnc2c(Cl)c([C@H](c3ccc(C)c(CO[Si](C)(C)C(C)(C)C)c3)[C@@H](C)C(=O)N3C(=O)OC[C@H]3Cc3ccccc3)ccc21]

(R)-4-benzyl-3-((S)-3-(3-(((tert-butyldimethylsilyl)oxy)methyl)-4-methylphenyl)-3-(4-chloro-1-ethyl-1H-benzo[d][1,2,3]triazol-5-yl)propanoyl)oxazolidin-2-one (1500 mg, 2.317 mmol) was dried under vacuum for 19 h then alternately evacuated and filled with nitrogen three times. Tetrahydrofuran (50 mL) was added and evacuated and filled with nitrogen twice. The solution was cooled to −78° C., sodium bis(trimethylsilyl)amide (1M in THF) (2.55 mL, 2.55 mmol) was added and the reaction stirred at −78° C. for 20 minutes. Methyl iodide (1.449 mL, 23.17 mmol) was added and the reaction stirred at −78° C. for 30 min. The reaction was quenched with saturated aqueous ammonium chloride and extracted with ethyl acetate (3×). The combined organic fractions were washed (brine), dried (sodium sulfate) and the solvent was removed. The crude material was purified by silica gel chromatography (Combiflash) (pre-wet column with 0.1% Et₃N in hexane before loading crude material, product came out at 40% ethyl acetate in hexane). The desired fractions were concentrated to give the title compound (1330 mg, 2.011 mmol, 87% yield). LC/MS: m/z 661.6 (M+H)+, 1.70 min (ret. time)

(R)-4-Benzyl-3-((2R,3S)-3-(4-chloro-1-ethyl-1H-benzo[d][1,2,3]triazol-5-yl)-3-(3-(hydroxymethyl)-4-methylphenyl)-2-methylpropanoyl)oxazolidin-2-one

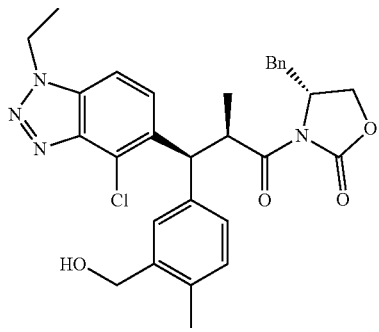

HCl in dioxane (4N) (0.603 mL, 2.413 mmol) was added to a solution of (R)-4-benzyl-3-((2R,3S)-3-(3-(((tert-butyldimethylsilyl)oxy)methy-4-methyl)-4-methylphenyl)-3-(4-chloro-1-ethyl-1H-benzo[d][1,2,3]triazol-5-yl)-2-methylpropanoyl)oxazolidin-2-one (1330 mg, 2.011 mmol) in methanol (20 mL). The reaction was stirred for 20 minutes at which time the reaction was complete. The reaction mixture was concentrated. The crude product was purified by silica gel chromatography (Combiflash) to give the title compound (1.07 g, 1.956 mmol, 97% yield). LC/MS: m/z 547.4 (M+H)+, 1.18 min (ret. time)

(R)-4-Benzyl-3-((2R,3S)-3-(4-chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoyl)oxazolidin-2-one

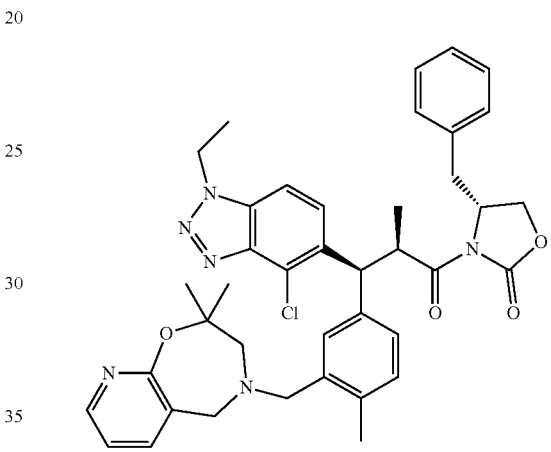

To a mixture of (R)-4-benzyl-3-((2R,3S)-3-(3-(((tert-butyldimethylsilyl)oxy)methyl)-4-methylphenyl)-3-(1-ethyl-4-fluoro-1H-benzo[d][1,2,3]triazol-5-yl)-2-methylpropanoyl)oxazolidin-2-one (120 mg, 0.186 mmol) in dichloromethane (3.00 mL) was added thionyl chloride (0.027 mL, 0.372 mmol). The mixture was stirred at ambient temperature for 1 h. The resulting mixture was concentrated to give (R)-4-benzyl-3-((2R,3S)-3-(4-chloro-1-ethyl-1H-benzo[d][1,2,3]triazol-5-yl)-3-(3-(chloromethyl)-4-methylphenyl)-2-methylpropanoyl)oxazolidin-2-one. This was redissolved in acetonitrile (3 mL), 2,2-dimethyl-2,3,4,5-tetrahydropyrido[3,2-f][1,4]oxazepine (66.3 mg, 0.372 mmol) and N-ethyl-N-isopropylpropan-2-amine (0.098 mL, 0.558 mmol) were added. The reaction was heated via microwave reactor at 120° C. for 1 h. The solvent was removed. The crude product was purified by silica gel chromatography (Combiflash) to give the title compound (81 mg, 0.115 mmol, 78% yield). LC/MS: m/z 707.7 (M)+, 1.15 min (ret. time)

(2R,3S)-3-(4-chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoic Acid

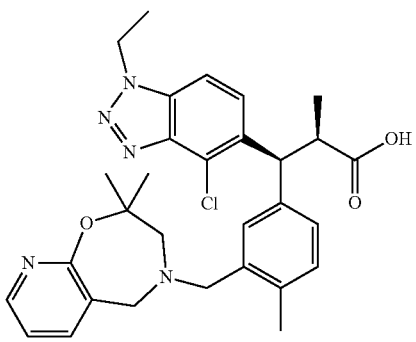 [SMILES: CCn1nnc2c(Cl)c([C@H](c3ccc(C)c(CN4Cc5cccnc5OC(C)(C)C4)c3)[C@@H](C)C(=O)O)ccc21]

To a mixture of (R)-4-benzyl-3-((2R,3S)-3-(4-chloro-1-ethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)-2-methylpropanoyl)oxazolidin-2-one (81 mg, 0.115 mmol) in tetrahydrofuran (2 mL) and water (0.5 mL) THF/Water (4:1) was added hydrogen peroxide (0.094 mL, 0.916 mmol) and 2M lithium hydroxide (0.172 mL, 0.344 mmol). The reaction was stirred for 2 hs. The reaction was quenched with saturated ammonium chloride (5 mL) and extracted with ethyl acetate twice. The combined organic layer was concentrated then purified with preparative HPLC under neutral conditions to give the title compound (11 mg, 0.020 mmol, 17.52% yield) as solid. LC/MS: m/z 548.3 (M+H)$^+$, 0.86 min (ret. time)

Example 203

(2R,3S)-3-(1,4-Dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoic Acid, 0.2 Formic Acid Salt

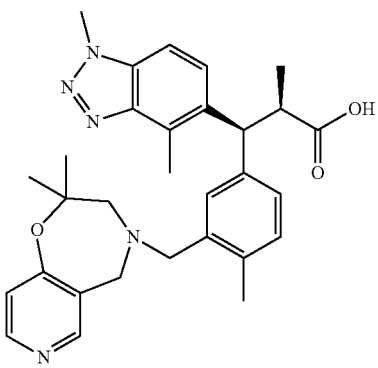 [SMILES: Cc1ccc([C@@H](c2ccc3c(nnn3C)c2C)[C@@H](C)C(=O)O)cc1CN1Cc2cnccc2OC(C)(C)C1]

A mixture of 2,2-dimethyl-2,3,4,5-tetrahydropyrido[3,4-f][1,4]oxazepine (43.4 mg, 0.243 mmol) and DIEA (0.142 mL, 0.812 mmol) in acetonitrile (3 mL) was heated via microwave for 1 h at 120° C. The resulting mixture was concentrated and then purified by silica gel chromatography (product came out at 80% ethyl acetate in hexane). The desired fractions were concentrated under reduced pressure to give (2R,3S)-benzyl 3-(1,4-dimethyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoate. This was dissolved in ethyl acetate (5 mL) and passed through an H-Cube (10% Pd/C cartridge; 1 mL/min flowrate; 25 degree) for 1 h. The resulting mixture was concentrated and purified by reverse phase preparative HPLC using formic acid as a solvent modifier to provide the title compound (13 mg, 0.025 mmol, 12.25% yield). LC/MS: m/z 514.5 (M)$^+$, 0.94 min (ret. time)

Example 204

(R)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic Acid, 0.5 Ethanol

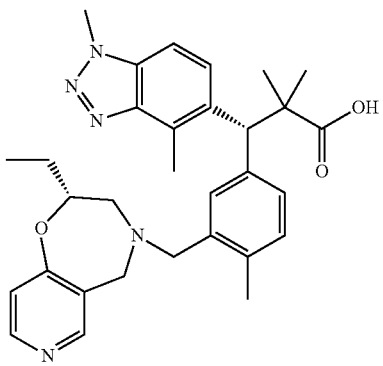 [SMILES: CC[C@@H]1CN(Cc2cc([C@H](c3ccc4c(nnn4C)c3C)C(C)(C)C(=O)O)ccc2C)Cc2cnccc2O1]

To a solution of methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate (2.89 g, 5.34 mmol) in methanol at 25° C. was added 2M LiOH (16.01 ml, 32.0 mmol). The reaction mixture was heated via microwave for 2 h at 120° C. The reaction was acidified with 6 N HCl (pH~1). It was extracted with ethyl acetate twice. The aqueous layer was then basified with saturated NaHCO$_3$ to pH 5. It was extracted with ethyl acetate twice. The organic layer was washed with water twice and then brine. The resulting mixture was concentrated to give the crude product. The water layer was extracted with 4:1 DCM and IPA to obtain another batch. Both batches were purified by reverse phase preparative HPLC using formic acid as a solvent modifier to give the racemic material. The crude product was purified by chiral purification (Column: Chiralpak AD 20×250 mm, 5 u; Co-solvent: 20% EtOH; Flowrate: 50 g/min; Back pressure: 100 Bar) to give (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid, 0.3 Ethanol (783 mg, 1.446 mmol, 27.1% yield) (chiral SFC ret. time: 7.52 min) LC-MS m/z 528.3 (M+H)$^+$, 0.83 min (ret. time) and (R)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (562 mg, 1.065 mmol, 19.96% yield) (chiral SFC ret. time: 10.26 min) LC-MS m/z 528.3 (M+H)$^+$, 0.83 min (ret. time).

Example 205

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(methylsulfonyl)propanamide, Trifluoroacetic Acid Salt

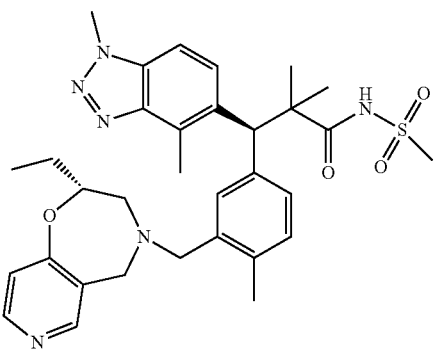 [SMILES: CC[C@@H]1CN(Cc2cc([C@@H](c3ccc4c(nnn4C)c3C)C(C)(C)C(=O)NS(C)(=O)=O)ccc2C)Cc2cnccc2O1]

To a solution of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (60 mg, 0.114 mmol) in dichloromethane (3 mL) at ambient temperature was added EDC (65.4 mg, 0.341 mmol), DMAP (41.7 mg, 0.341 mmol), and DIEA (0.119 mL, 0.682 mmol). The reaction mixture was stirred under nitrogen for 15 minutes after which methanesulfonamide (54.1 mg, 0.569 mmol) in DCM (0.5 mL) was added. The reaction mixture was stirred at ambient temperature for 72 h. More methanesulfonamide (54.1 mg, 0.569 mmol), EDC (65.4 mg, 0.341 mmol), DMAP (41.7 mg, 0.341 mmol), and DIEA (0.119 mL, 0.682 mmol) were added and the reaction stirred at 50° C. for 4 days. The reaction was quenched with saturated NH$_4$Cl and extracted with DCM twice. The combined organic layer was washed with brine and concentrated. The reaction mixture was purified with preparative HPLC under acidic conditions (0.1% TFA as modifier) to give the title compound (15 mg, 0.021 mmol, 18.35% yield) as solid. LC-MS m/z 605.7 (M+H)$^+$, 0.67 min (ret. time)

Example 206 rel-(R)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid [enantiomer A (first to elute from SFC)]

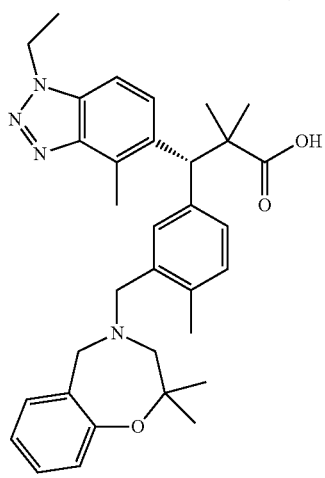

enantiomer A

Example 207 rel-(R)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid [Enantiomer B (Second to Elute from SFC)]

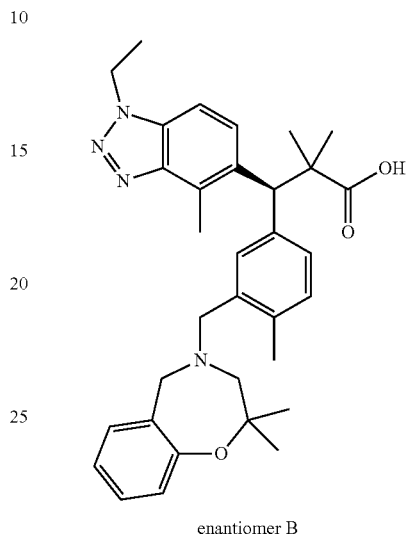

enantiomer B

Methyl 3-(3-(chloromethyl)-4-methylphenyl)-3-(1-ethyl-4-methyl-1H-benzo[d][1,2,3]triazol-5-yl)-2,2-dimethylpropanoate (414 mg, 1 mmol), 2,2-dimethyl-2,3,4,5-tetrahydrobenzo[f][1,4]oxazepine (266 mg, 1.500 mmol), and N-ethyl-N-isopropylpropan-2-amine (0.699 ml, 4.00 mmol) in acetonitrile (2 ml) were heated to 120° C. via microwave for 1 h. The solvent was then removed under a stream of nitrogen at 50° C. The crude product was re-dissolved in water (1 mL) and methanol (2 mL) and lithium hydroxide (479 mg, 20.00 mmol) was added. The solution was heated to 130° C. in a Biotage Initiator microwave for 3 h. DMSO (2 mL) was added to the solution and the methanol and water removed with a V-10 vortex evaporator. The DMSO solution was then acidified with 1 N HCl to pH 2. The water was removed and the DMSO filtered and purified by reverse phase preparative HPLC using 0.1% TFA as a solvent modifier to provide the racemic compound (450 mg). It was then resolved by SFC (Column: Chiralpak IF 20×250 mm, 5 u; Co-solvent: 25% MeOH; Flowrate: 50 g/min; Back pressure: 100 Bar) to give rel-(R)-3-(3-((2,2-dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid (144 mg, 0.266 mmol, 26.6% yield) [enantiomer A (first to elute from SFC)] LC/MS: m/z 541.3 (M+H)$^+$, 0.94 min (ret. time) (chiral SFC ret. time: 6.02 min) and rel-(R)-3-(3-((2,2-dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid (177 mg, 0.327 mmol, 32.7% yield) [enantiomer B (second to elute from SFC)] LC/MS: m/z 541.3 (M+H)$^+$, 0.93 min (ret. time) (chiral SFC ret. time: 7.47 min).

Example 208

(2R,3S)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid, 2 Trifluoroacetic Acid Salt

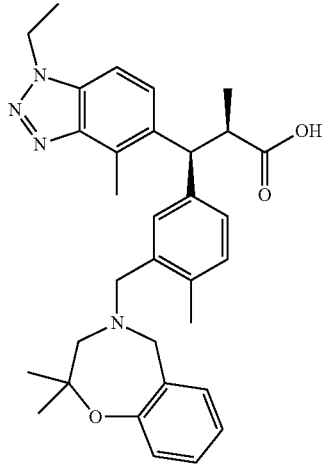 [SMILES: CCn1nnc2c(C)c([C@H](c3ccc(C)c(CN4Cc5ccccc5OC(C)(C)C4)c3)[C@@H](C)C(=O)O)ccc21]

(E)-Ethyl 3-(1-ethyl-4-methyl-1H-benzo[d][1,2,3]triazol-5-yl)acrylate

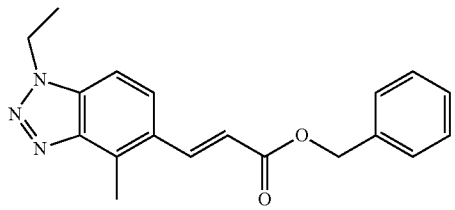 [SMILES: CCn1nnc2c(C)c(/C=C/C(=O)OCc3ccccc3)ccc21]

A mixture of tri-o-tolylphosphine (1.724 g, 5.66 mmol), ethyl acrylate (7.09 g, 70.8 mmol), 5-bromo-1-ethyl-4-methyl-1H-benzo[d][1,2,3]triazole (8.5 g, 35.4 mmol), PdOAc$_2$ (0.636 g, 2.83 mmol), K$_2$CO$_3$ (9.79 g, 70.8 mmol) and N,N-dimethylformamide (200 mL) was stirred at 120° C. for 12 h. The mixture was poured into water and extracted with ethyl acetate (3×30 mL). The organic layer was dried and concentrated. The isolute-adsorbed crude product was purified by silica gel chromatography (hexane:ethyl acetate=4:1). Desired fractions were concentrated to give the title compound (7.24 g, 27.9 mmol, 79% yield) as a solid. LC-MS: 262.0 (M+H)$^+$, 1.71 min (ret. time).

Benzyl 3-(1-ethyl-4-methyl-1H-benzo[d][1,2,3]triazol-5-yl)-3-(3-(hydroxymethyl)-4-methylphenyl)propanoate

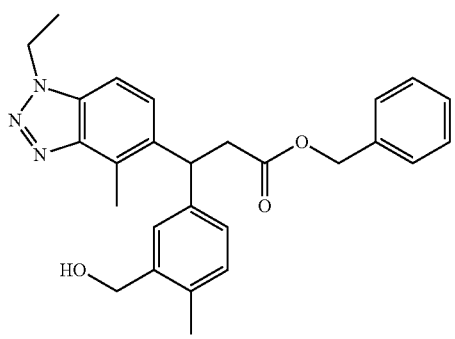 [SMILES: CCn1nnc2c(C)c(C(CC(=O)OCc3ccccc3)c3ccc(C)c(CO)c3)ccc21]

(3-(Hydroxymethyl)-4-methylphenyl)boronic acid (3.49 g, 21.05 mmol) was added to a solution of (E)-benzyl 3-(1-ethyl-4-methyl-1H-benzo[d][1,2,3]triazol-5-yl)acrylate (6.15 g, 19.14 mmol) and triethylamine (8.00 mL, 57.4 mmol) in dioxane (144 mL) and water (47.8 mL). The solution was degassed with Argon for 30 minutes. Chloro (1,5-cyclooctadiene)rhodium(I) dimer (0.472 g, 0.957 mmol) was then added and the solution stirred at 90° C. under nitrogen for 5 hs. The solution was then extracted with ethyl acetate (3×50 mL). The combined organic fraction was washed with brine, dried over sodium sulfate, filtered and concentrated. The crude product was purified by silica gel chromatography to give the title compound (6.15 g, 13.87 mmol, 72.5% yield). LC/MS: m/z 444.0 (M+H)$^+$, 1.12 min (ret. time) 1H NMR (400 MHz, CHLOROFORM-d) d=7.36 (s, 1H), 7.30-7.18 (m, 5H), 7.14-7.03 (m, 4H), 5.01 (s, 3H), 4.68-4.59 (m, 4H), 3.27-3.06 (m, 2H), 2.82 (s, 3H), 2.29 (s, 3H), 1.74 (br. s., 1H), 1.61 (t, J=7.3 Hz, 3H).

Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate

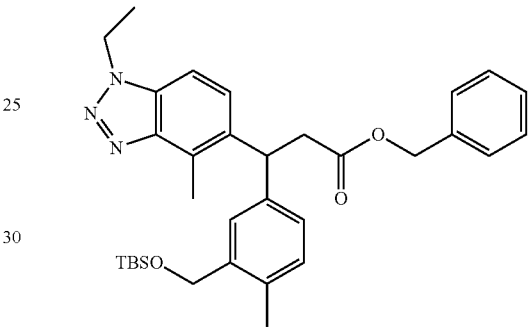

1H-Imidazole (1.477 g, 21.69 mmol) and tert-butylchlorodimethylsilane (3.02 g, 20.02 mmol) were added to a solution of benzyl 3-(1-ethyl-4-methyl-1H-benzo[d][1,2,3]triazol-5-yl)-3-(3-(hydroxymethyl)-4-methylphenyl)propanoate (7.4 g, 16.68 mmol) in dichloromethane (33.4 mL) at ambient temperature. The solution was stirred for 2 hs and then quenched with water, extracted with DCM (3×), washed (brine) and dried (sodium sulfate). The product was purified by silica gel chromatography to give the title compound (8.38 g, 15.02 mmol, 90% yield). LC/MS: m/z 558.2 (M+H)$^+$, 1.71 min (ret. time)

(S)-Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate and (R)-benzyl 3-(3-(((tert-butyldimethylsilyl)oxy)methyl)-4-methylphenyl)-3-(1-ethyl-4-methyl-1H-benzo[d][1,2,3]triazol-5-yl)propanoate

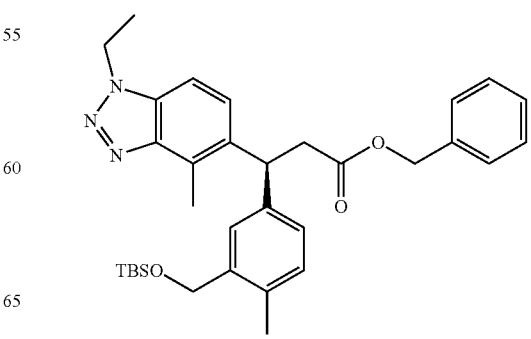

429
-continued

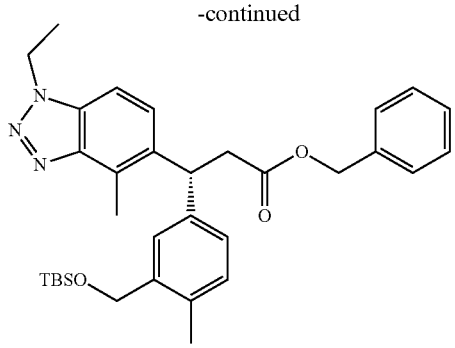

Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (10 g, 17.93 mmol) was separated by Chiral SFC (Column: Chiralpak IA 20×250 mm, 5 u; Co-solvent: 20% EtOH; Flowrate: 50 g/min; Back pressure: 100 Bar) to give a single enantiomerically pure (S)-benzyl 3-(3-(((tert-butyldimethylsilyl)oxy)methyl)-4-methylphenyl)-3-(1-ethyl-4-methyl-1H-benzo[d][1,2,3]triazol-5-yl) propanoate (3.7 g, 6.63 mmol, 46.3%) (chiral SFC ret. time: 3.42 min). LC/MS: m/z 558.3 (M+H)$^+$, 1.70 min (ret. time) and (R)-benzyl 3-(3-(((tert-butyldimethylsilyl)oxy)methyl)-4-methylphenyl)-3-(1-ethyl-4-methyl-1H-benzo[d][1,2,3] triazol-5-yl)propanoate (3.77 g, 6.76 mmol, 47.1%) (chiral SFC ret. time: 6.18 min). LC/MS: m/z 558.4 (M+H)$^+$, 1.71 min (ret. time)

(S)-3-(3-(((tert-Butyldimethylsilyl)oxy)methyl)-4-methylphenyl)-3-(1-ethyl-4-methyl-1H-benzo[d][1,2,3]triazol-5-yl)propanoic Acid

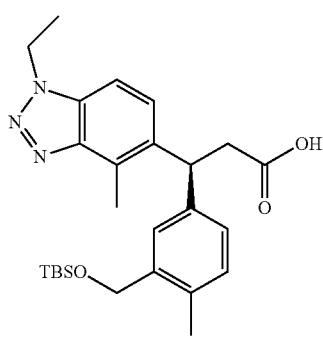 [SMILES: CCn1nnc2c(C)c([C@@H](CC(=O)O)c3ccc(C)c(CO[Si](C)(C)C(C)(C)C)c3)ccc21]

(S)-Benzyl 3-(3-(((tert-butyldimethylsilyl)oxy)methyl)-4-methylphenyl)-3-(1-ethyl-4-methyl-1H-benzo[d][1,2,3] triazol-5-yl)propanoate (3.7 g, 6.63 mmol) in methanol (221 mL) was passed through an H-cube flow reactor with a 10% Pd—C cartridge for 7 h at 1 mL/min on full H$_2$ mode. The methanol was removed in vacuo and the product purified by silica gel chromatography to give the title compound (2.1 g, 4.49 mmol, 67.7% yield). LC/MS: m/z 468.3 (M+H)$^+$, 1.38 min (ret. time)

430

(R)-4-Benzyl-3-((S)-3-(3-(((tert-butyldimethylsilyl)oxy)methyl)-4-methylphenyl)-3-(1-ethyl-4-methyl-1H-benzo[d][1,2,3]triazol-5-yl)propanoyl)oxazolidin-2-one

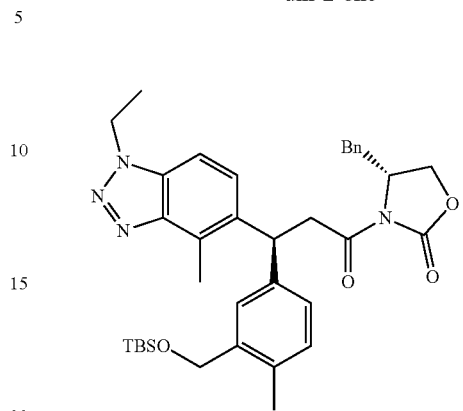

Di(1H-Imidazol-1-yl)methanone (1.092 g, 6.74 mmol) was added to a solution of (S)-3-(3-(((tert-butyldimethylsilyl)oxy)methyl)-4-methylphenyl)-3-(1-ethyl-4-methyl-1H-benzo[d][1,2,3]triazol-5-yl)propanoic acid (2.1 g, 4.49 mmol) in tetrahydrofuran (112 mL) and the reaction stirred at ambient temperature for 16 hs. Water was added and the solution was extracted with ethyl acetate (3×). The combined organic fractions were washed (brine), dried (sodium sulfate), filtered and concentrated. The crude intermediate was re-dissolved in acetonitrile (112 mL), (R)-4-benzyloxazolidin-2-one (0.875 g, 4.94 mmol) and 2,3,4,6,7,8,9,10-octahydropyrimido[1,2-a]azepine (0.135 ml, 0.898 mmol) were added and the solution stirred at ambient temperature for 16 hs. The reaction was quenched with water and extracted with ethyl acetate (3×). The combined organic fractions were washed (brine), dried (sodium sulfate), filtered and concentrated. The product was purified by silica gel chromatography to give the title compound (1.43 g, 2.281 mmol, 50.8% yield). LC/MS: m/z 627.2 (M+H)$^+$, 1.62 min (ret. time)

(R)-4-Benzyl-3-((2R,3S)-3-(3-(((tert-butyldimethylsilyl)oxy)methyl)-4-methylphenyl)-3-(1-ethyl-4-methyl-1H-benzo[d][1,2,3]triazol-5-yl)-2-methylpropanoyl)oxazolidin-2-one

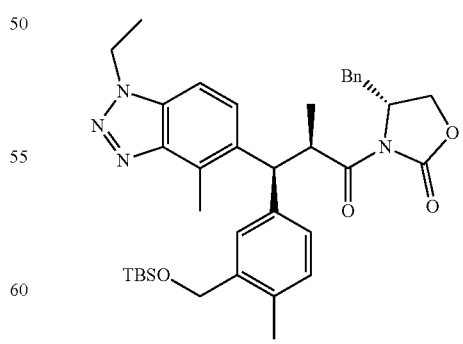

Sodium bis(trimethylsilyl)amide (2.457 ml, 2.457 mmol) was added dropwise to a solution of (R)-4-benzyl-3-((S)-3-(3-(((tert-butyldimethylsilyl)oxy)methyl)-4-methylphenyl)-3-(1-ethyl-4-methyl-1H-benzo[d][1,2,3]triazol-5-yl)propanoyl)oxazolidin-2-one (1.4 g, 2.233 mmol) in tetrahydrofuran (22.33 mL) at −78° C. and the reaction stirred for 30 minutes. Methyl iodide (5.58 mL, 11.17 mmol) was then added and the solution stirred for 3 h at −78° C. and then warmed to ambient temperature. The reaction was quenched with saturated aqueous ammonium chloride and extracted with ethyl acetate (3×). The combined organic fractions were washed (brine), dried (sodium sulfate), filtered and concentrated. The crude product was purified by silica gel chromatography to give the title compound (1.22 g, 1.904 mmol, 85% yield). LC/MS: m/z 641.1 (M+H)+, 1.70 min (ret. time)

(R)-4-Benzyl-3-((2R,3S)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one

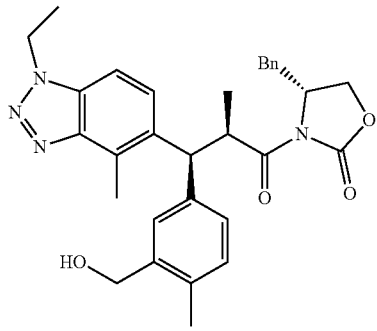 [SMILES: CCn1nnc2c(C)c([C@H](c3ccc(C)c(CO)c3)[C@@H](C)C(=O)N3C(=O)OC[C@H]3Cc3ccccc3)ccc21]

HCl (234 μL, 1.404 mmol) was added to a solution of (R)-4-benzyl-3-((2R,3S)-3-(3-(((tert-butyldimethylsilyl)oxy)methyl)-4-methylphenyl)-3-(1-ethyl-4-methyl-1H-benzo[d][1,2,3]triazol-5-yl)-2-methylpropanoyl)oxazolidin-2-one (300 mg, 0.468 mmol) in methanol (4.68 mL) and the reaction stirred for 5 minutes at which time the reaction was complete. The solution was filtered over sodium sulfate, filtered and concentrated to give the title compound (247 mg, 0.468 mmol, 100% yield). LC/MS: m/z 527.4 (M+H)+, 1.19 min (ret. time)

(R)-4-Benzyl-3-((2R,3S)-3-(3-((2,2-di methyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoyl)oxazolidin-2-one

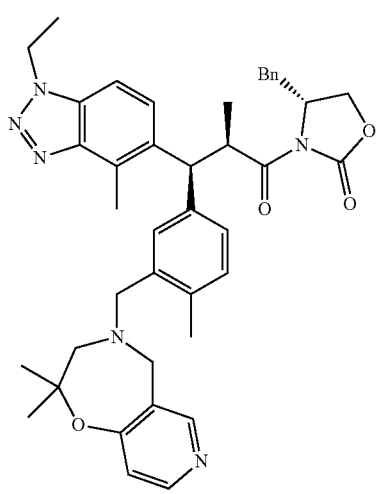 [SMILES: CCn1nnc2c(C)c([C@H](c3ccc(C)c(CN4Cc5cnccc5OC(C)(C)C4)c3)[C@@H](C)C(=O)N3C(=O)OC[C@H]3Cc3ccccc3)ccc21]

Thionyl chloride (41.6 μL, 0.570 mmol) was added to a solution of (R)-4-benzyl-3-((2R,3S)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one (100 mg, 0.190 mmol) in dichloromethane (1.9 mL) and the reaction stirred for 30 minutes. Solvent and excess thionyl chloride was removed. The crude chloride intermediate was then added to a solution of 2,2-dimethyl-2,3,4,5-tetrahydropyrido[3,4-f][1,4]oxazepine hydrochloride (82 mg, 0.380 mmol) and N-ethyl-N-isopropylpropan-2-amine (99 μL, 0.570 mmol) in acetonitrile (1.9 mL) and heated in a Biotage Initiator microwave reactor at 120° C. for 1 h. The solvent was removed and purified by silica gel chromatography to give the title compound (66 mg, 0.096 mmol, 50.6% yield). LC/MS: m/z 687.6 (M+H), 1.19 min (ret. time)

(2R,3S)-3-(3-((2,2-Dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoic acid, 2 Trifluoroacetic Acid Salt

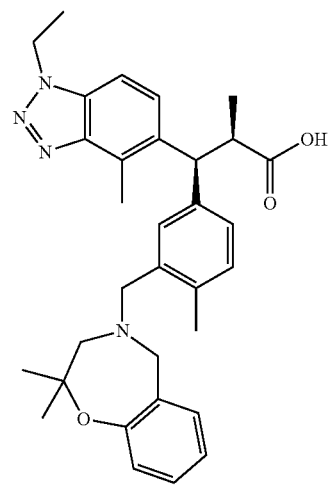 [SMILES: CCn1nnc2c(C)c([C@H](c3ccc(C)c(CN4Cc5ccccc5OC(C)(C)C4)c3)[C@@H](C)C(=O)O)ccc21]

To a solution of (S)-4-benzyl-3-((2R,3R)-3-(3-((2,2-dimethyl-2,3-dihydrobenzo[f][1,4]oxazepin-4(5H)-yl)methyl)-4-methylphenyl)-3-(1-ethyl-4-methyl-1H-benzo[d][1,2,3]triazol-5-yl)-2-methylpropanoyl)oxazolidin-2-one (100 mg, 0.146 mmol) in tetrahydrofuran (1.67 mL) and water (417 μl) at ambient temperature were added hydrogen peroxide (119 μL, 1.166 mmol) followed by lithium hydroxide (0.437 mL, 0.437 mmol). The reaction was stirred for 2 h. The reaction was quenched with saturated aqueous ammonium chloride (2 mL) and extracted with ethyl acetate (3×5 mL). The combined organic layer was dried over sodium sulfate, filtered and concentrated. The crude product was purified by reverse phase preparative HPLC using 0.1% TFA as a solvent modifier to provide the title compound (35 mg, 0.046 mmol, 31.8% yield). LC/MS: m/z 527.4 (M+H)+, 0.89 min (ret. time)

Example 209

(2R,3S)-3-(7-Chloro-1-ethyl-4-methyl-1H-benzo[d][1,2,3]triazol-5-yl)-3-(3-((2,2-dimethyl-2,3-dihydropyrido[3,4-f][1,4]oxazepin-4(5H)-yl)methyl)-4-methylphenyl)-2-methylpropanoic Acid

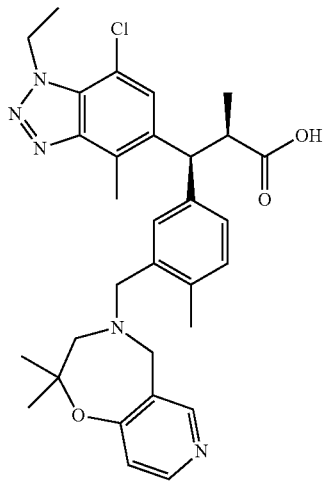 [SMILES: CCn1nnc2c(C)c([C@H](c3ccc(C)c(CN4Cc5cnccc5OC(C)(C)C4)c3)[C@@H](C)C(=O)O)cc(Cl)c21]

To a solution of (S)-4-benzyl-3-((2R,3S)-3-(3-((2,2-dimethyl-2,3-dihydropyrido[3,4-f][1,4]oxazepin-4(5H)-yl)methyl)-4-methylphenyl)-3-(1-ethyl-4-methyl-1H-benzo[d][1,2,3]triazol-5-yl)-2-methylpropanoyl)oxazolidin-2-one (80 mg, 0.116 mmol) in tetrahydrofuran (1.86 mL) and water (466 µL) at ambient temperature were added hydrogen peroxide (47.6 µL, 0.466 mmol) followed by lithium hydroxide (0.175 mL, 0.175 mmol). The reaction was stirred for 2 h. The reaction was quenched with 4 N HCl in diethyl ether. The compound was purified by reverse phase preparative HPLC using 0.1% TFA as a solvent modifier. The title compound (13 mg, 0.023 mmol, 19.86% yield) was obtained. LC/MS: m/z 562.2 (M+H)$^+$, 0.99 min (ret. time)

Example 210

(2R,3S)-3-(1-Ethyl-4-methyl-1H-benzo[d][1,2,3]triazol-5-yl)-2-methyl-3-(4-methyl-3-((2-(piperidin-1-ylmethyl)-1H-imidazol-1-yl)methyl)phenyl)propanoic Acid

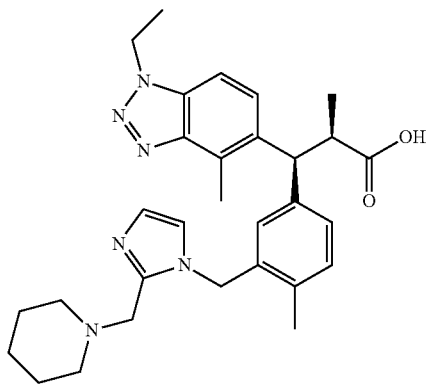 [SMILES: CCn1nnc2c(C)c([C@H](c3ccc(C)c(Cn4ccnc4CN4CCCCC4)c3)[C@@H](C)C(=O)O)ccc21]

[(R)-4-Benzyl-3-((2R,3S)-3-(3-(chloromethyl)-4-methylphenyl)-3-(1-ethyl-4-methyl-1H-benzo[d][1,2,3]triazol-5-yl)-2-methylpropanoyl)oxazolidin-2-one (200 mg, 0.367 mmol), 1-((1H-imidazol-2-yl)methyl)piperidine (91 mg, 0.550 mmol), and Hunig's base (96 µL, 0.550 mmol) in acetonitrile (4 mL) were heated in a Biotage Initiator microwave reactor at 120° C. for 1 h. The solvent was removed and the crude material re-dissolved in tetrahydrofuran (4.1 mL) and water (1 mL). The solution was cooled to 0° C. and hydrogen peroxide (0.150 mL, 1.468 mmol) followed by lithium hydroxide (0.55 mL, 0.550 mmol) were added and the solution stirred at 0° C. for 2 hs. The reaction was quenched with saturated aqueous ammonium chloride (5 mL) and extracted with ethyl acetate (3×15 mL). The combined organic fractions were dried over sodium sulfate, filtered and concentrated. The product was purified by reverse-phase HPLC and silica gel chromatography to give the title compound (7 mg, 0.014 mmol, 3.71% yield). LC/MS: m/z 515.5 (M+H)$^+$, 0.79 min (ret. time)

Example 211

1-((1,4-Dimethyl-1H-benzo[d][1,2,3]triazol-5-yl)(3-((2,2-dimethyl-2,3-dihydropyrido[3,4-f][1,4]oxazepin-4(5H)-yl)methyl)-4-methylphenyl)methyl)cyclopropanecarboxylic acid, Trifluoroacetic Acid Salt

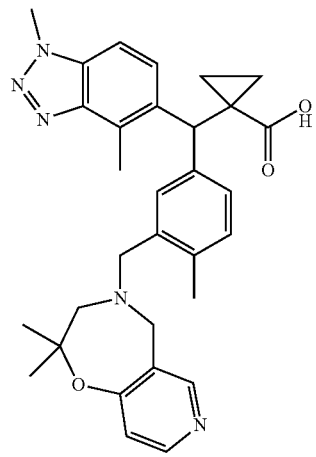 [SMILES: Cc1ccc(C(c2ccc3c(nnn3C)c2C)C2(C(=O)O)CC2)cc1CN1Cc2cnccc2OC(C)(C)C1]

5-(Chloro(3-(((4-methoxybenzyl)oxy)methyl)-4-methylphenyl)methyl)-1,4-dimethyl-1H-benzo[d][1,2,3]triazole

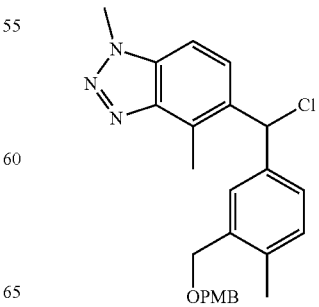

Thionyl chloride (114 µl, 1.557 mmol) was added to a solution of (1,4-dimethyl-1H-benzo[d][1,2,3]triazol-5-yl)(3-(((4-methoxybenzyl)oxy)methyl)-4-methylphenyl)methanol (500 mg, 1.198 mmol) in dichloromethane (12 mL) at ambient temperature and the reaction stirred for 30 minutes. Thionyl chloride was removed under reduced pressure with to give the title compound (522 mg, 1.198 mmol, 100% yield). LC/MS: m/z 418.0 (M+H)⁺, 1.12 min (ret. time)

Methyl 1-((1,4-dimethyl-1H-benzo[d][1,2,3]triazol-5-yl)(3-(((4-methoxybenzyl)oxy)methyl)-4-methylphenyl)methyl)cyclopropanecarboxylate

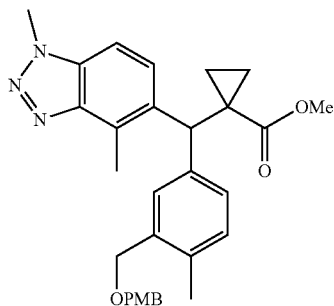

Chlorotrimethylsilane (34.4 µL, 0.034 mmol) was added to a suspension of zinc (67.5 mg, 1.032 mmol) in tetrahydrofuran (1.75 µL) under a nitrogen atmosphere and the reaction stirred for 15 minutes at ambient temperature. Methyl 1-bromocyclopropanecarboxylate (110 µL, 0.860 mmol) was added and the reaction stirred at ambient temperature for 2 hs. This solution was then added by syringe to a solution of 5-(chloro(3-(((4-methoxybenzyl)oxy)methyl)-4-methylphenyl)methyl)-1,4-dimethyl-1H-benzo[d][1,2,3]triazole (150 mg, 0.344 mmol) in tetrahydrofuran (1.75 µL) and the reaction stirred for 45 minutes. The reaction was quenched with saturated aqueous ammonium chloride (2 mL) and the mixture extracted with ethyl acetate (3×5 mL). The combined organic fractions were washed with brine and dried over sodium sulfate, filtered and concentrated. The crude product was purified by silica gel chromatography to give the title compound (100 mg, 0.200 mmol, 58.2% yield). LC/MS: m/z 500.4 (M+H)⁺, 1.31 min (ret. time)

Methyl 1-((3-(chloromethyl)-4-methylphenyl)(1,4-dimethyl-1H-benzo[d][1,2,3]triazol-5-yl)methyl)cyclopropanecarboxylate

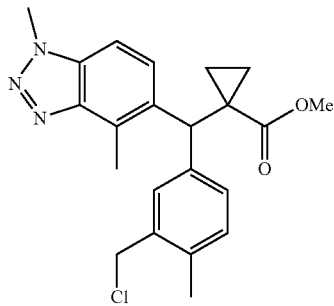 [SMILES: COC(=O)C1(C(c2ccc(C)c(CCl)c2)c2ccc3c(nnn3C)c2C)CC1]

DDQ (91 mg, 0.400 mmol) was added to a solution of methyl 1-((1,4-dimethyl-1H-benzo[d][1,2,3]triazol-5-yl)(3-(((4-methoxybenzyl)oxy)methyl)-4-methylphenyl)methyl)cyclopropanecarboxylate (100 mg, 0.200 mmol) in dichloromethane (2 mL) at 0° C. and the reaction stirred for 2 hs. The reaction was quenched with saturated sodium bicarbonate (5 mL) and extracted with ethyl acetate (4×15 mL). The combined organic fractions were washed (brine), dried (sodium sulfate), filtered and concentrated. The crude product was purified by silica gel chromatography to give the intermediate. This intermediate was dissolved in dichloromethane (2 mL) and thionyl chloride (29.2 µL, 0.400 mmol) was added and the reaction stirred for 30 minutes. Solvent and excess thionyl chloride was removed to give the title compound (35 mg, 0.088 mmol, 43.9% yield).

LC/MS: m/z 398.2 (M+H)⁺, 1.19 min (ret. time)

1-((1,4-Dimethyl-1H-benzo[d][1,2,3]triazol-5-yl)(3-((2,2-dimethyl-2,3-dihydropyrido[3,4-f][1,4]oxazepin-4(5H)-yl)methyl)-4-methylphenyl)methyl)cyclopropanecarboxylic acid, Trifluoroacetic Acid Salt

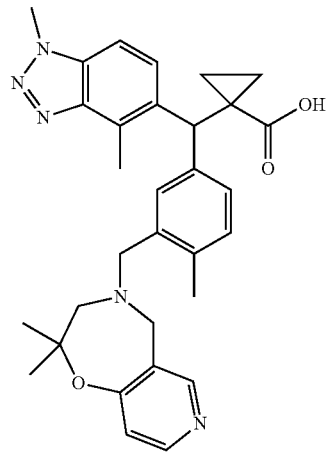 [SMILES: Cc1ccc(C(c2ccc3c(nnn3C)c2C)C2(C(=O)O)CC2)cc1CN1Cc2cnccc2OC(C)(C)C1]

Methyl 1-((3-(chloromethyl)-4-methylphenyl)(1,4-dimethyl-1H-benzo[d][1,2,3]triazol-5-yl)methyl)cyclopropanecarboxylate (35 mg, 0.088 mmol), 2,2-dimethyl-2,3,4,5-tetrahydropyrido[3,4-f][1,4]oxazepine hydrochloride (37.8 mg, 0.176 mmol) and N-ethyl-N-isopropylpropan-2-amine (46.0 µL, 0.264 mmol) in acetonitrile (1.2 mL) were heated in a Biotage Initiator microwave reactor at 120° C. for 1 h. The solvent was evaporated and the crude product was re-dissolved in methanol (1.17 mL) and water (0.6 mL). The solution was heated in a Biotage Initiator microwave reactor at 130° C. for 1.5 hs. The solution was then acidified with 6 N HCl and the solvent was removed. The crude material was dissolved in DMSO and purified by reverse phase preparative HPLC using 0.1% TFA as a solvent modifier to provide the title compound (11.4 mg, 0.018 mmol, 20.26% yield). LC/MS: m/z 526.3 (M+H)⁺, 1.01 min (ret. time)

Example 212

3-(1,4-Dimethyl-1H-benzo[d][1,2,3]triazol-5-yl)-3-(6-(((R)-2-ethyl-2,3-dihydropyrido[3,4-f][1,4]oxazepin-4(5H)-yl)methyl)-5-methylpyridin-2-yl)-2,2-dimethylpropanoic Acid, Formic Acid Salt

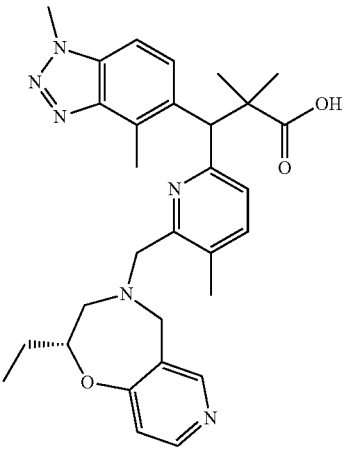 [SMILES: CC[C@@H]1CN(Cc2nc(C(c3ccc4c(nnn4C)c3C)C(C)(C)C(=O)O)ccc2C)Cc2cnccc2O1]

2-(Methoxycarbonyl)-3-methylpyridine 1-oxide

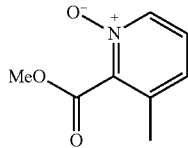

3-Chlorobenzoperoxoic acid (685 mg, 3.97 mmol) was added to a solution of methyl 3-methylpicolinate (500 mg, 3.31 mmol) in dichloromethane (8.269 mL) at 0° C. The solution was allowed to warm to ambient temperature stirring for a total of 12 hs. The product was purified by silica gel chromatography to give the title compound (538 mg, 3.22 mmol, 97% yield). LC/MS: m/z 167.8 (M+H)$^+$, 0.43 min (ret. time). $^1$H NMR (400 MHz, CHLOROFORM-d) δ 8.14-8.10 (m, 1H), 7.26-7.19 (m, 1H), 7.17-7.12 (m, 1H), 4.05 (s, 3H), 2.32 (s, 3H)

Methyl 6-bromo-3-methylpicolinate

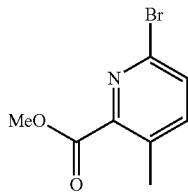

Phosphoryl tribromide (17.15 g, 59.8 mmol) was added to a solution of 2-(methoxycarbonyl)-3-methylpyridine 1-oxide (5 g, 29.9 mmol) in 1,2-dichloroethane (100 mL) and heated to 84° C. for 4 hs. The solution was cooled to 0° C. and quenched slowly with water (50 mL) and extracted with DCM (3×100 mL). The combined organic fractions were washed with water (50 mL), saturated aqueous sodium bicarbonate (50 mL), dried over sodium sulfate, filtered and concentrated. The crude product was purified by silica gel chromatography to give the title compound (600 mg, 2.61 mmol, 8.72% yield). LC/MS: m/z 229.8, 231.8 (M+H)$^+$, 0.82 min (ret. time). $^1$H NMR (400 MHz, CHLOROFORM-d) δ 7.58-7.44 (m, 2H), 3.98 (s, 3H), 2.55 (s, 3H)

6-Bromo-2-(((tert-butyldimethylsilyl)oxy)methyl)-3-methylpyridine

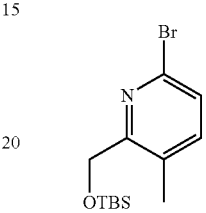

Diisobutylaluminum hydride (6.520 mL, 6.52 mmol) was added dropwise to a solution of methyl 6-bromo-3-methylpicolinate (600 mg, 2.61 mmol) in tetrahydrofuran (13.04 mL) at −45° C. After 1 h, the reaction was quenched with methanol (5 mL) and the solvent removed in vacuo. The crude product was dissolved in dichloromethane (13.04 mL), tert-butyldimethyl chlorosilane (786 mg, 5.22 mmol) and imidazole (391 mg, 5.74 mmol) were added at ambient temperature. The reaction was complete in 1 h and was quenched with water (5 mL) and extracted with DCM (3×10 mL). The combined organic fractions were washed (brine) and dried over sodium sulfate. The crude residue was purified by silica gel chromatography to give the title compound (200 mg, 0.632 mmol, 24.24% yield). $^1$H NMR (400 MHz, CHLOROFORM-d) δ 7.33 (s, 1H), 7.29 (s, 1H), 4.80 (s, 2H), 2.38 (s, 3H), 0.92 (s, 9H), 0.11 (s, 6H)

(6-(((tert-Butyldimethylsilyl)oxy)methyl)-5-methylpyridin-2-yl)(1,4-dimethyl-1H-benzo[d][1,2,3]triazol-5-yl)methanol

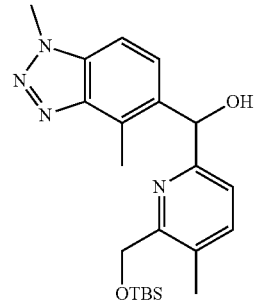 [SMILES: Cc1ccc(C(O)c2ccc3c(nnn3C)c2C)nc1CO[Si](C)(C)C(C)(C)C]

n-Butyllithium (543 μL, 0.869 mmol) was added to a solution of 6-bromo-2-(((tert-butyldimethylsilyl)oxy)methyl)-3-methylpyridine (250 mg, 0.790 mmol) in diethyl ether (7.9 mL) at −78° C. and the reaction stirred for 20 minutes. 1,4-Dimethyl-1H-benzo[d][1,2,3]triazole-5-carbaldehyde (152 mg, 0.869 mmol) in diethyl ether (8 mL) was then added by syringe and the solution stirred at −78° C. for 30 minutes before allowing to warm to ambient temperature. The reaction was quenched with saturated aqueous ammonium chloride and the solution was extracted with dichloromethane (3×25 mL). The combined organic layer was washed with brine (10 mL), dried (sodium sulfate), filtered and concentrated. The crude residue was purified by silica gel chromatography to give the title compound (163 mg, 0.395 mmol, 50% yield). LC/MS: m/z 413.1 (M+H)$^+$, 0.99 min (ret. time)

Methyl 3-(1,4-dimethyl-1H-benzo[d][1,2,3]triazol-5-yl)-3-(6-(hydroxymethyl)-5-methylpyridin-2-yl)-2,2-dimethylpropanoate

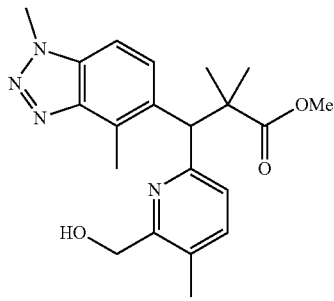 [SMILES: COC(=O)C(C)(C)C(c1ccc(C)c(CO)n1)c1ccc2c(nnn2C)c1C]

2,2,2-Trichloroacetonitrile (77 µL, 0.771 mmol) and 2,3,4,6,7,8,9,10-octahydropyrimido[1,2-a]azepine (2.66 µL, 0.019 mmol) were added sequentially to a solution of (6-(((tert-butyldimethylsilyl)oxy)methyl)-5-methylpyridin-2-yl)(1,4-dimethyl-1H-benzo[d][1,2,3]triazol-5-yl)methanol (159 mg, 0.385 mmol) in acetonitrile (0.3 mL) at ambient temperature and the reaction stirred for 45 minutes. ((1-Methoxy-2-methylprop-1-en-1-yl)oxy)trimethylsilane (0.157 mL, 0.771 mmol) followed by 1,1,1-trifluoro-N-((trifluoromethyl)sulfonyl)methanesulfonamide (10.83 mg, 0.039 mmol) were added and the solution stirred at ambient temperature for 2 h. The reaction was quenched with saturated sodium bicarbonate (10 mL) and extracted with DCM (3×15 mL), dried over sodium sulfate, filtered and concentrated. The residue was re-dissolved in tetrahydrofuran (0.3 mL). The solution was cooled to 0° C. and TBAF (771 µL, 0.771 mmol) was added. The solution was stirred at 0° C. for 1 h at which time LC-MS showed the reaction was complete. The reaction was quenched with saturated sodium bicarbonate (10 mL) and extracted with DCM (3×15 mL) and dried over sodium sulfate. The crude product was purified by silica gel chromatography to give the title compound (103 mg, 0.270 mmol, 70% yield). LC/MS: m/z 383.0 (M+H)$^+$, 0.83 min (ret. time)

3-(1,4-Dimethyl-1H-benzo[d][1,2,3]triazol-5-yl)-3-(6-(((R)-2-ethyl-2,3-dihydropyrido[3,4-f][1,4]oxazepin-4(5H)-yl)methyl)-5-methylpyridin-2-yl)-2,2-dimethylpropanoic Acid, Formic Acid Salt

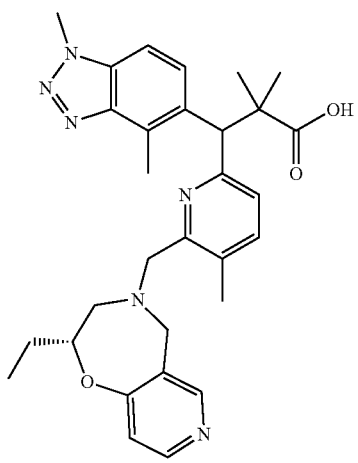 [SMILES: CC[C@@H]1CN(Cc2nc(C(c3ccc4c(nnn4C)c3C)C(C)(C)C(=O)O)ccc2C)Cc2cnccc2O1]

Thionyl chloride (8.02 µL, 0.110 mmol) was added to a solution of methyl 3-(1,4-dimethyl-1H-benzo[d][1,2,3]triazol-5-yl)-3-(6-(hydroxymethyl)-5-methylpyridin-2-yl)-2,2-dimethylpropanoate (21 mg, 0.055 mmol) in dichloromethane (0.39 mL) at ambient temperature and the reaction stirred for 30 minutes. The solvent and excess thionyl chloride was removed to give the benzyl chloride intermediate. This was dissolved in acetonitrile (0.392 mL), (R)-2-ethyl-2,3,4,5-tetrahydropyrido[3,4-f][1,4]oxazepine hydrochloride (17.68 mg, 0.082 mmol) and Hunig's base (29 µL, 0.165 mmol) were added and the mixture heated via microwave reactor at 120° C. for 2 hs. The resulting mixture was concentrated. The crude product was re-dissolved in methanol (0.392 mL) and water (0.196 mL). Lithium hydroxide (26.3 mg, 1.098 mmol) was added and the solution heated via microwave reactor at 130° C. for 1.5 hs. The reaction was acidified with 6N HCl and the solvent removed. The crude product was dissolved in DMSO (1 mL), filtered and purified by reverse phase preparative HPLC using formic acid as a solvent modifier to provide the title compound (16 mg, 0.028 mmol, 50.7% yield). LC/MS: m/z 529.3 (M+H)$^+$, 0.72 min (ret. time)

Example 213

3-(1,4-Dimethyl-1H-benzo[d][1,2,3]triazol-5-yl)-3-(5-(((R)-2-ethyl-2,3-dihydropyrido[3,4-f][1,4]oxazepin-4(5H)-yl)methyl)-6-methylpyridin-3-yl)-2,2-dimethylpropanoic acid, Trifluoroacetic Acid Salt

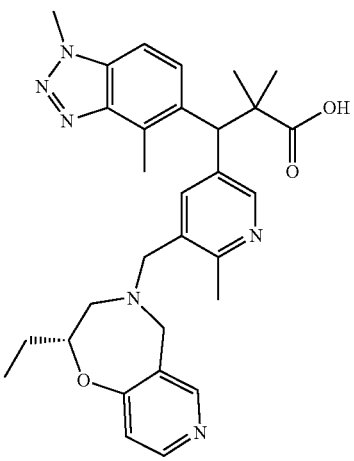 [SMILES: CC[C@@H]1CN(Cc2cc(C(c3ccc4c(nnn4C)c3C)C(C)(C)C(=O)O)cnc2C)Cc2cnccc2O1]

(5-Bromo-2-methylpyridin-3-yl)methanol

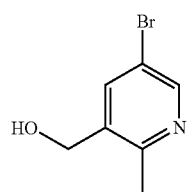

To a solution of ethyl 5-bromo-2-methylnicotinate (5 g, 20.48 mmol) in tetrahydrofuran (50 mL) was added LAH (0.855 g, 22.53 mmol) at 0° C. The mixture was stirred at 0°

5-Bromo-3-(((tert-butyldimethylsilyl)oxy)methyl)-2-methylpyridine

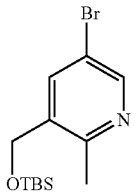

Tert-butyldimethylchlorosilane (746 mg, 4.95 mmol) and imidazole (371 mg, 5.44 mmol) were added to a solution of (5-bromo-2-methylpyridin-3-yl)methanol (500 mg, 2.475 mmol) in dichloromethane (4.949 mL) at ambient temperature and the reaction stirred for 1 h. The reaction was quenched with water (5 mL) and extracted with DCM (3×10 mL). The combined organic fraction was washed (brine), dried (sodium sulfate), filtered and concentrated. The crude residue was purified by silica gel chromatography to give the title compound (758 mg, 2.396 mmol, 97% yield). LC/MS: m/z 315.9, 317.9 (M+H)⁺, 1.39 min (ret. time)

(5-(((tert-Butyldimethylsilyl)oxy)methyl)-6-methylpyridin-3-yl)(1,4-dimethyl-1H-benzo[d][1,2,3]triazol-5-yl) methanol

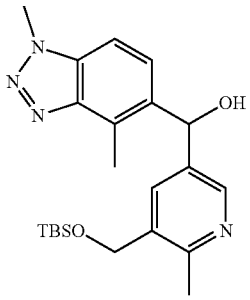 [SMILES: Cc1ncc(C(O)c2ccc3c(nnn3C)c2C)cc1CO[Si](C)(C)C(C)(C)C]

n-Butyllithium (1.498 mL, 2.397 mmol) was added to a solution of 5-bromo-3-(((tert-butyldimethylsilyl)oxy)methyl)-2-methylpyridine (758 mg, 2.397 mmol) in tetrahydrofuran (11.416 mL) at −78° C. and the reaction stirred for 30 minutes. 1,4-Dimethyl-1H-benzo[d][1,2,3]triazole-5-carbaldehyde (280 mg, 1.598 mmol) in tetrahydrofuran (2.0 mL) was added dropwise and the reaction stirred for 30 minutes before allowing to warm to ambient temperature. The reaction was quenched with saturated ammonium chloride (5 mL) and extracted with ethyl acetate (3×10 mL). The combined organic fraction was washed (brine), dried (sodium sulfate), filtered and concentrated. The crude residue was purified by silica gel chromatography to give the title compound (519 mg, 1.258 mmol, 79% yield). LC/MS: m/z 413.1 (M+H)⁺, 0.94 min (ret. time)

Methyl 3-(1,4-dimethyl-1H-benzo[d][1,2,3]triazol-5-yl)-3-(5-(hydroxymethyl)-6-methylpyridin-3-yl)-2,2-dimethylpropanoate

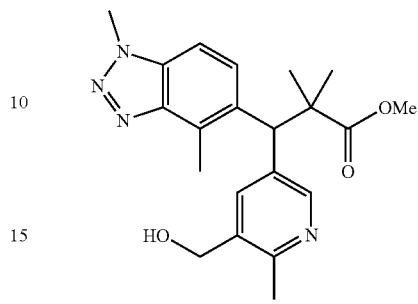

2,2,2-Trichloroacetonitrile (252 µl, 2.52 mmol) and 2,3,4,6,7,8,9,10-octahydropyrimido[1,2-a]azepine (8.70 µL, 0.063 mmol) were added sequentially to a solution of (5-(((tert-butyldimethylsilyl)oxy)methyl)-6-methylpyridin-3-yl)(1,4-dimethyl-1H-benzo[d][1,2,3]triazol-5-yl)methanol (519 mg, 1.258 mmol) in acetonitrile (1.3 mL) at ambient temperature and the reaction stirred for 45 minutes. ((1-Methoxy-2-methylprop-1-en-1-yl)oxy)trimethylsilane (511 µL, 2.52 mmol) followed by 1,1,1-trifluoro-N-((trifluoromethyl)sulfonyl)methanesulfonamide (35.4 mg, 0.126 mmol) were then added and the solution stirred at ambient temperature for 2 hs. LC-MS showed the starting material was consumed with the major product being TBS protected intermediate (LC-MS: m/z 497.2 (M+H)⁺, 1.08 min (ret. time)). The reaction was quenched with saturated sodium bicarbonate (10 mL) and extracted with DCM (3×15 mL), dried over sodium sulfate, filtered and concentrated then re-dissolved in tetrahydrofuran (1.3 mL). The solution was cooled to 0° C. and TBAF (2.5 mL, 2.52 mmol) was added. The solution was stirred at 0° C. for 2 h. The reaction was quenched with saturated sodium bicarbonate (10 mL) and extracted with DCM (3×15 mL), dried over sodium sulfate, filtered and concentrated. The crude product was purified by silica gel chromatography to give the title compound (182 mg, 0.476 mmol, 37.8% yield). LC/MS: m/z 383.1 (M+H)⁺, 0.63 min (ret. time)

Methyl 3-(5-(chloromethyl)-6-methylpyridin-3-yl)-3-(1,4-dimethyl-1H-benzo[d][1,2,3]triazol-5-yl)-2,2-dimethylpropanoate

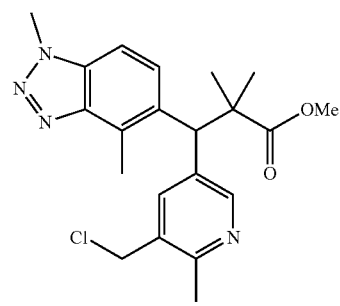 [SMILES: COC(=O)C(C)(C)C(c1cnc(C)c(CCl)c1)c1ccc2c(nnn2C)c1C]

Thionyl chloride (0.069 mL, 0.952 mmol) was added to a solution of methyl 3-(1,4-dimethyl-1H-benzo[d][1,2,3]triazol-5-yl)-3-(5-(hydroxymethyl)-6-methylpyridin-3-yl)-2, 2-dimethylpropanoate (182 mg, 0.476 mmol) in dichloromethane (2.379 mL) at ambient temperature. The solution was stirred for 30 minutes and the DCM was concentrated. The excess thionyl chloride was removed under reduced pressure to give the title compound (191 mg, 0.476 mmol, 100% yield). LC/MS: m/z 401.0 (M+H)$^+$, 0.77 min (ret. time)

3-(1,4-Dimethyl-1H-benzo[d][1,2,3]triazol-5-yl)-3-(5-(((R)-2-ethyl-2,3-dihydropyrido[3,4-f][1,4]oxazepin-4(5H)-yl)methyl)-6-methylpyridin-3-yl)-2,2-dimethylpropanoic Acid, Trifluoroacetic Acid Salt

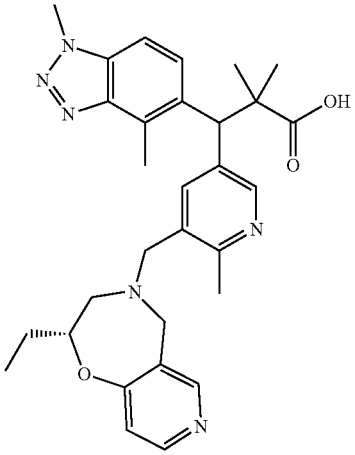 [SMILES: CC[C@@H]1CN(Cc2cc(C(c3ccc4c(nnn4C)c3C)C(C)(C)C(=O)O)cnc2C)Cc2cnccc2O1]

A mixture of methyl 3-(5-(chloromethyl)-6-methylpyridin-3-yl)-3-(1,4-dimethyl-1H-benzo[d][1,2,3]triazol-5-yl)-2,2-dimethylpropanoate (60 mg, 0.150 mmol), (R)-2-ethyl-2,3,4,5-tetrahydropyrido[3,4-f][1,4]oxazepine hydrochloride (48.2 mg, 0.224 mmol), and Hunig's base (105 μl, 0.599 mmol) in acetonitrile (1497 μL) was heated via microwave reactor at 120° C. for 2 hs. The solvent was removed and the residue re-dissolved in methanol (1497 μL) and water (748 μL). Lithium hydroxide (71.7 mg, 2.99 mmol) was added and the reaction heated via microwave reactor at 120° C. for 1 h. The solution was acidified with 6N HCl and the solvent was removed. The crude product was purified by reverse phase preparative HPLC using 0.1% TFA as a solvent modifier to provide the title compound (26 mg, 0.040 mmol, 27.0% yield). LC/MS: m/z 529.2 (M+H)$^+$, 0.60 min (ret. time)

Example 214

3-(5-((2-(Cycloheptylmethyl)-1H-imidazol-1-yl)methyl)-6-methylpyridin-3-yl)-3-(1,4-dimethyl-1H-benzo[d][1,2,3]triazol-5-yl)-2,2-dimethylpropanoic Acid, Trifluoroacetic Acid Salt

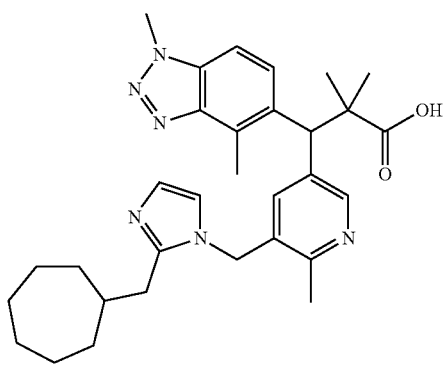 [SMILES: Cc1ncc(C(c2ccc3c(nnn3C)c2C)C(C)(C)C(=O)O)cc1Cn1ccnc1CC1CCCCCC1]

A solution of sodium hydride (14.37 mg, 0.599 mmol), methyl 3-(5-(chloromethyl)-6-methylpyridin-3-yl)-3-(1,4-dimethyl-1H-benzo[d][1,2,3]triazol-5-yl)-2,2-dimethylpropanoate (60 mg, 0.150 mmol), and 2-(cycloheptylmethyl)-1H-imidazole (40.0 mg, 0.224 mmol) in N,N-dimethylformamide (1497 μL) was kept at ambient temperature for 2 hs. The reaction was quenched with methanol and then the solvent was removed. The crude material was re-dissolved in methanol (1497 μL) and water (748 μL). Lithium hydroxide (143 mg, 5.99 mmol) was added and the solution heated via microwave reactor at 120° C. for 1 h. The solution was acidified with 6N HCl and the solvent concentrated. The crude product was purified by reverse phase preparative HPLC using 0.1% TFA as a solvent modifier to provide the title compound (17.5 mg, 0.027 mmol, 18.19% yield). LC/MS: m/z 529.1 (M+H)$^+$, 0.73 min (ret. time).

Example 215

(3S)-3-(3-((3-((1H-Pyrazol-1-yl)methyl)piperidin-1-yl)methyl)-4-methylphenyl)-3-(1,4-dimethyl-1H-benzo[d][1,2,3]triazol-5-yl)propanoic Acid

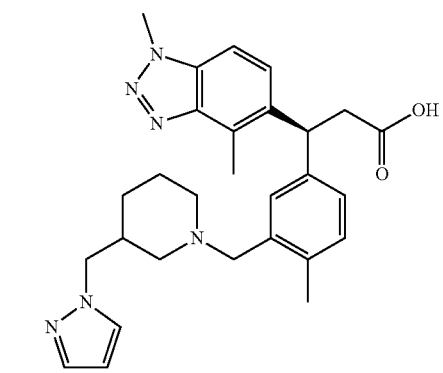 [SMILES: Cc1ccc([C@H](CC(=O)O)c2ccc3c(nnn3C)c2C)cc1CN1CCCC(Cn2cccn2)C1]

tert-Butyl 3-((1H-pyrazol-1-yl)methyl)piperidine-1-carboxylate

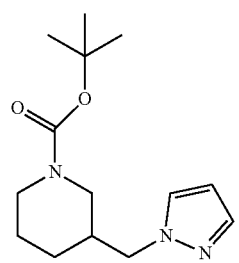 [SMILES: CC(C)(C)OC(=O)N1CCCC(Cn2cccn2)C1]

To a solution of tert-butyl 3-(bromomethyl)piperidine-1-carboxylate (680 mg, 2.444 mmol) and 1H-pyrazole (183 mg, 2.69 mmol) in N,N-dimethylformamide (5 mL) was added NaH (196 mg, 4.89 mmol) portionwise with vigorous stirring. The reaction mixture was heated in a Biotage microwave at high absorption for 5 h at 100° C. The reaction mixture was quenched with water and extracted with EtOAc, washed with brine. The organic layer was dried over MgSO₄ and concentrated to give the title compound (600 mg, 2.261 mmol, 93% yield). LC/MS: m/z 266.1 (M+H)⁺, 0.94 min (ret. time).

3-((1H-Pyrazol-1-yl)methyl)piperidine, 2 Hydrochloride

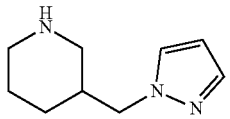 [SMILES: c1cnn(CC2CCCNC2)c1]

Dissolve tert-butyl 3-((1H-pyrazol-1-yl)methyl)piperidine-1-carboxylate (600 mg, 2.261 mmol) in HCl in dioxane (4 M) (5 mL, 165 mmol). The solution was stirred in room temperature for 1 h. The solvent was removed and the residue was washed by EtOAc to give the title compound (539 mg, 2.261 mmol, 100% yield). LC/MS: m/z 166.0 (M+H)⁺, 0.41 min (ret. time).

(3S)-3-(3-(((3-((1H-Pyrazol-1-yl)methyl)piperidin-1-yl)methyl)-4-methylphenyl)-3-(1,4-dimethyl-1H-benzo[d][1,2,3]triazol-5-yl)propanoic Acid

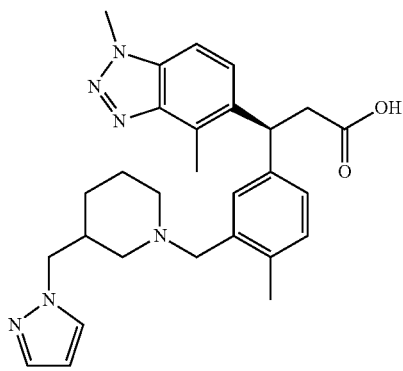 [SMILES: Cc1ccc([C@H](CC(=O)O)c2ccc3c(nnn3C)c2C)cc1CN1CCCC(Cn2cccn2)C1]

To a solution of (S)-ethyl 3-(3-(chloromethyl)-4-methylphenyl)-3-(1,4-dimethyl-1H-benzo[d][1,2,3]triazol-5-yl)propanoate (100 mg, 0.259 mmol) and 3-((1H-pyrazol-1-yl)methyl)piperidine, 2 Hydrochloride (185 mg, 0.777 mmol) in Acetonitrile (3 mL) was added DIEA (0.362 mL, 2.073 mmol). The reaction mixture was heated in a Biotage microwave at high absorption for 1 h at 120° C. The solvent was removed under vacuum and residue was dissolved in ethanol (3.00 mL). NaOH (6M) (0.432 mL, 2.59 mmol) was added. The mixture was heated in a Biotage microwave at high absorption for 20 min at 120° C. The crude product was purified by reverse phase preparative HPLC using 0.1% formic acid as a solvent modifier to provide the title compound (90 mg, 0.176 mmol, 67.8% yield). LC/MS: m/z 487.4 (M+H)⁺, 0.68 min (ret. time).

Example 216

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic Acid

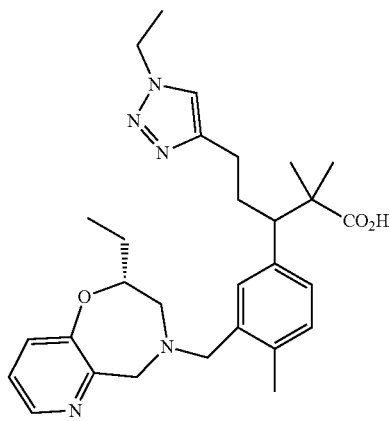 [SMILES: CC[C@@H]1CN(Cc2cc(C(CCc3cn(CC)nn3)C(C)(C)C(=O)O)ccc2C)Cc2ncccc2O1]

Benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate

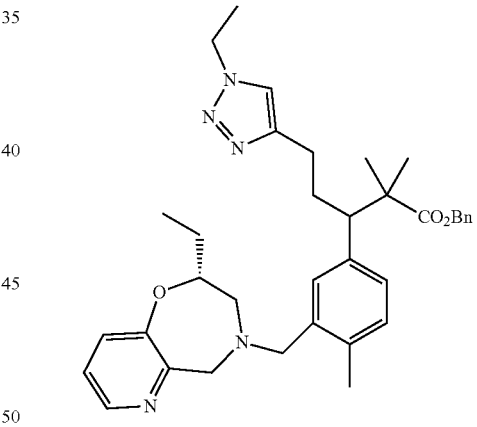

To a solution of benzyl 5-(1-ethyl-1H-1,2,3-triazol-4-yl)-3-(3-(hydroxymethyl)-4-methylphenyl)-2,2-dimethylpentanoate (0.050 g, 0.115 mmol) in dichloromethane (DCM) (2.00 mL) was added thionyl chloride (0.017 mL, 0.230 mmol) and the reaction stirred at ambient temperature for 30 min. The solvent was removed and the residue, in acetonitrile (1.00 mL), was added to a solution of (R)-2-ethyl-2,3,4,5-tetrahydropyrido[2,3-f][1,4]oxazepine (0.023 g, 0.115 mmol) and DIEA (0.080 mL, 0.459 mmol) in acetonitrile (2.00 mL) in a 10 mL microwave reaction vessel. The reaction was heated in a microwave to 120° C. for 1 h after which, additional (R)-2-ethyl-2,3,4,5-tetrahydropyrido[2,3-f][1,4]oxazepine (0.005 g, 0.028 mmol) was added and the solution heated via microwave at 120° C. for 20 min. Isolute was added to the reaction and the solvent was removed. The residue was purified by flash chromatography eluting with 0-40-50% (3:1 EtOAc:EtOH)/hexane to provide the title compound. (0.035 g, 44% yield) LC/MS m/z=596 (M+H)+, 1.07 min (ret. time).

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic Acid

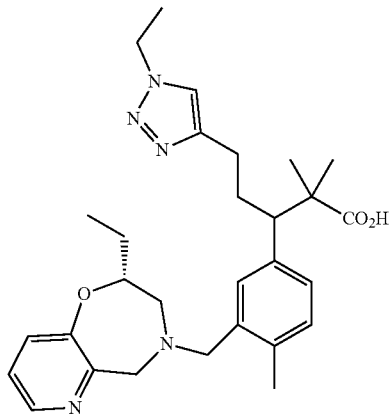 [SMILES: CC[C@@H]1CN(Cc2cc(C(CCc3cn(CC)nn3)C(C)(C)C(=O)O)ccc2C)Cc2ncccc2O1]

A solution of benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (0.035 g, 0.051 mmol) in methanol (10 mL) was hydrogenated on H-Cube using 10% Pd/C cartridge and full H2 pressure for 1 h. The solvent was removed and the residue was purified by reverse phase preparative HPLC under neutral conditions to provide the title compound. (0.009 g, 35% yield) LC/MS m/z=506 (M+H)+, 0.84 min (ret. time).

Example 217

5-(1-Ethyl-1H-1,2,3-triazol-4-yl)-3-(3-(((R)-2-ethyl-2,3-dihydropyrido[3,2-f][1,4]oxazepin-4(5H)-yl)methyl)-4-methylphenyl)-2,2-dimethylpentanoic Acid

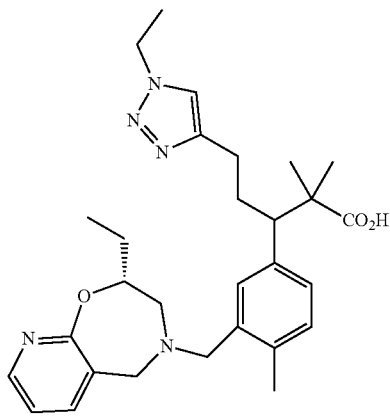 [SMILES: CC[C@@H]1CN(Cc2cc(C(CCc3cn(CC)nn3)C(C)(C)C(=O)O)ccc2C)Cc2cccnc2O1]

(2-Bromopyridin-3-yl)methanamine

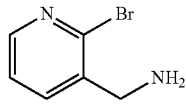

To a solution of 2-bromo-3-(bromomethyl)pyridine, hydrochloride in ethanol (20 mL) heated at 50° C., was added ammonium hydroxide dropwise and stirred at 50° C. for 2 h The solvent was removed and the residue was pumped on high vacuum. The residue was then triturated with dichloromethane and the solid was filtered. The filtered solid was purified by flash chromatography eluting with 0-50% (10% NH4OH-MeOH/DCM)/DCM to provide the title compound. (1.32 g, 59% yield) LC/MS m/z=187 (M+H)+, 0.16 min (ret. time).

(R)-1-(((2-Bromopyridin-3-yl)methyl)amino)butan-2-ol

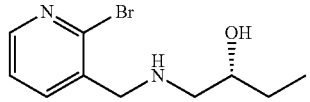

A solution of (2-bromopyridin-3-yl)methanamine (1.27 g, 6.79 mmol) and (R)-2-ethyloxirane (0.490 g, 6.79 mmol) in ethanol (10 mL) in a 20 mL microwave reaction vessel was heated via microwave at 150° C. for 2 hours. The solvent was removed and the residue was purified by flash chromatography eluting with 0-50-90% of (3:1 EtOAc:EtOH)/hexane to provide the title compound. (0.934 g, 53% yield) LC/MS m/z=259 (M+H)+, 0.42 min (ret. time).

(R)-2-Ethyl-2,3,4,5-tetrahydropyrido[3,2-f][1,4]oxazepine

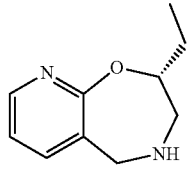

To a solution of (R)-1-(((2-bromopyridin-3-yl)methyl)amino)butan-2-ol (1.365 g, 5.27 mmol) in N,N-dimethylformamide (DMF) (20 mL) was added potassium tert-butoxide (1.773 g, 15.80 mmol) and the reaction heated to 80° C. for 1.5 h. The reaction was cooled, the solids were filtered and washed with DMF and then the solvent was removed. The residue was purified by flash chromatography eluting with 0-5% MeOH/DCM to provide the title compound. (0.89 g, 95% yield) LC/MS m/z=179 (M+H)+, 0.23 min (ret. time).

449

Benzyl 5-(1-ethyl-1H-1,2,3-triazol-4-yl)-3-(3-(((R)-2-ethyl-2,3-dihydropyrido[3,2-f][1,4]oxazepin-4(5H)-yl)methyl)-4-methylphenyl)-2,2-dimethylpentanoate

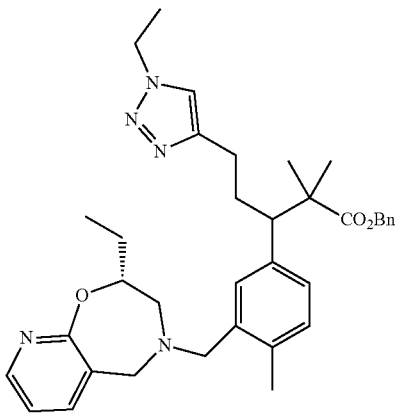 [SMILES: CC[C@@H]1CN(Cc2cc(C(CCc3cn(CC)nn3)C(C)(C)C(=O)OCc3ccccc3)ccc2C)Cc2cccnc2O1]

To a solution of benzyl 5-(1-ethyl-1H-1,2,3-triazol-4-yl)-3-(3-(hydroxymethyl)-4-methylphenyl)-2,2-dimethylpentanoate (0.041 g, 0.094 mmol) in dichloromethane (DCM) (2.00 mL) was added thionyl chloride (0.014 mL, 0.188 mmol) and the reaction stirred at ambient temperature for 30 min. The solvent was removed and the residue, in acetonitrile (1.00 mL), was added to a solution of (R)-2-ethyl-2,3,4,5-tetrahydropyrido[3,2-f][1,4]oxazepine (0.019 g, 0.094 mmol) and DIEA (0.066 mL, 0.377 mmol) in acetonitrile (2.000 mL) in a 10 mL microwave reaction vessel. The reaction was heated in a microwave to 120° C. for 1 h. The solvent was removed and the residue was purified by flash chromatography eluting with 0-40-50% (3:1 EtOAc:EtOH)/hexane to provide the title compound. (0.038 g, 67% yield) LC/MS m/z=596 (M+H)$^+$, 1.03 min (ret. time).

5-(1-Ethyl-1H-1,2,3-triazol-4-yl)-3-(3-(((R)-2-ethyl-2,3-dihydropyrido[3,2-f][1,4]oxazepin-4(5H)-yl)methyl)-4-methylphenyl)-2,2-dimethylpentanoic Acid

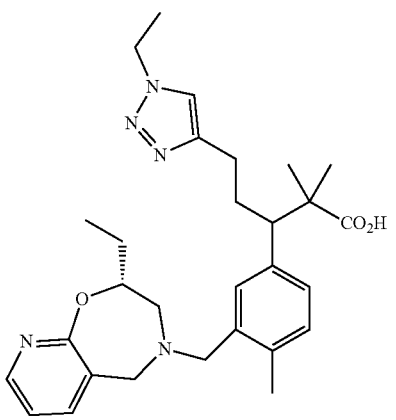 [SMILES: CC[C@@H]1CN(Cc2cc(C(CCc3cn(CC)nn3)C(C)(C)C(=O)O)ccc2C)Cc2cccnc2O1]

A solution of benzyl 5-(1-ethyl-1H-1,2,3-triazol-4-yl)-3-(3-(((R)-2-ethyl-2,3-dihydropyrido[3,2-f][1,4]oxazepin-4(5H)-yl)methyl)-4-methylphenyl)-2,2-dimethylpentanoate

450

(0.038 g, 0.064 mmol) in methanol (10 mL) was hydrogenated on H-Cube using 10% Pd/C cartridge and full H$_2$ pressure, for 1.5 h. The solvent was removed and the residue was purified by reverse phase preparative HPLC under neutral conditions to provide the title compound. (0.008 g, 24% yield) LC/MS m/z=506 (M+H)$^+$, 0.77 min (ret. time).

Example 218

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-2,2-dimethylpropanoic Acid, Trifluoroacetate

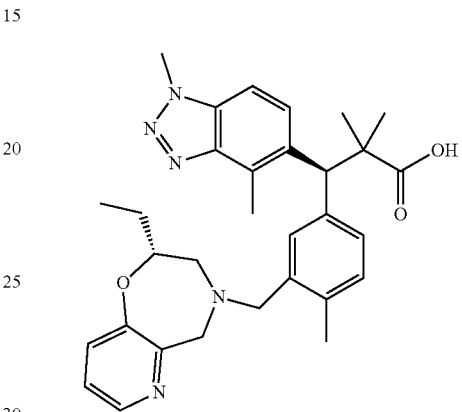

(S)-Methyl 3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-2,2-dimethylpropanoate

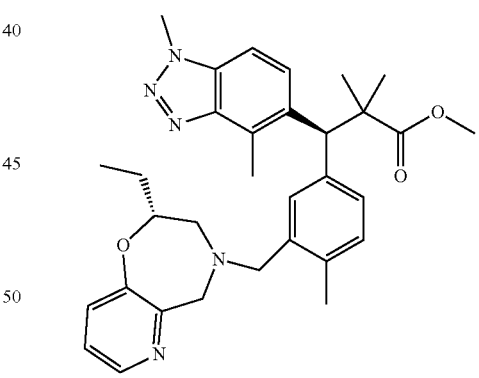

To a solution of (S)-methyl 3-(1,4-dimethyl-1H-benzo[d][1,2,3]triazol-5-yl)-3-(3-(hydroxymethyl)-4-methylphenyl)-2,2-dimethylpropanoate (0.100 g, 0.262 mmol) in dichloromethane (DCM) (3.00 mL) was added thionyl chloride (0.040 mL, 0.546 mmol) and the reaction stirred at ambient temperature for 30 min. The solvent was removed and the residue, in acetonitrile (2.00 mL), was added to a solution of (R)-2-ethyl-2,3,4,5-tetrahydropyrido[2,3-f][1,4]oxazepine (0.054 g, 0.273 mmol) and DIEA (0.183 mL, 1.049 mmol) in acetonitrile (3.00 mL) in a 10 mL microwave reaction vessel. The reaction was heated in microwave to 120° C. for 1 h. Isolute was added to the reaction and the solvent was removed. The residue was purified by flash chromatography eluting with 0-30% (3:1 EtOAc:EtOH)/hexane to provide the title compound. (0.087 g, 61% yield) LC/MS m/z=542 (M+H)⁺, 1.02 min (ret. time).

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-2,2-dimethylpropanoic Acid, Trifluoroacetate

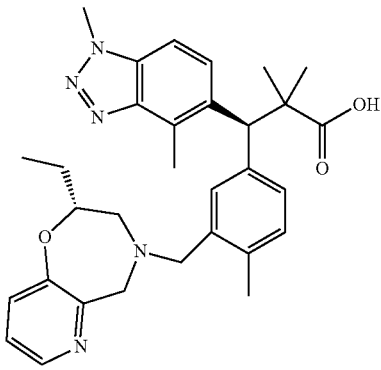 [SMILES: CC[C@@H]1CN(Cc2cc([C@@H](c3ccc4c(nnn4C)c3C)C(C)(C)C(=O)O)ccc2C)Cc2ncccc2O1]

To a solution of (S)-methyl 3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-2,2-dimethylpropanoate (0.087 g, 0.161 mmol) in tetrahydrofuran (THF) (2 mL), methanol (2.000 mL) and water (2.000 mL) in a 10 mL microwave reaction vessel was added lithium hydroxide (0.038 g, 1.606 mmol) and the solution heated via microwave at 150° C. for 1 h. The reaction was acidified with trifluoroacetic acid and, the solvent was removed and the residue was purified by reverse phase preparative HPLC using TFA as a solvent modifier to provide the title compound. (0.097 g, 94% yield) LC/MS m/z=528 (M+H)⁺, 0.88 min (ret. time).

Example 219

(S)-3-(1,4-Dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)-2,2-dimethylpropanoic Acid, Trifluoroacetate

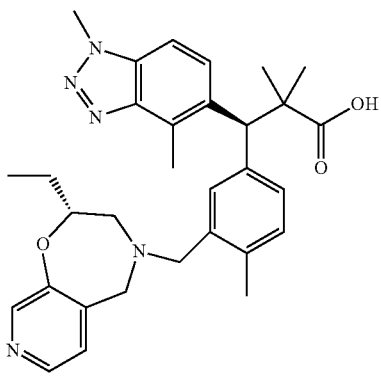 [SMILES: CC[C@@H]1CN(Cc2cc([C@@H](c3ccc4c(nnn4C)c3C)C(C)(C)C(=O)O)ccc2C)Cc2ccncc2O1]

(S)-Methyl 3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)-2,2-dimethylpropanoate

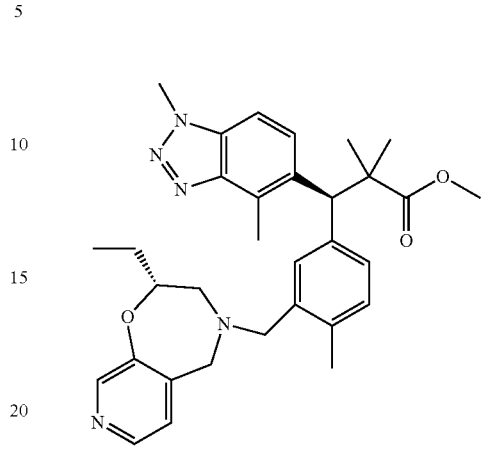

To a solution of (S)-methyl 3-(1,4-dimethyl-1H-benzo[d][1,2,3]triazol-5-yl)-3-(3-(hydroxymethyl)-4-methylphenyl)-2,2-dimethylpropanoate (0.100 g, 0.262 mmol) in dichloromethane (DCM) (3.00 mL) was added thionyl chloride (0.038 mL, 0.524 mmol) and the reaction stirred at ambient temperature for 30 min. The solvent was removed and the residue, in acetonitrile (2.00 mL), was added to a solution of (R)-2-ethyl-2,3,4,5-tetrahydropyrido[4,3-f][1,4]oxazepine (0.052 g, 0.262 mmol) and DIEA (0.183 mL, 1.049 mmol) in acetonitrile (3.00 mL) in a 10 mL microwave reaction vessel. The reaction was heated in a microwave to 120° C. for 1 h. Isolute was added to the reaction and the solvent was removed. The residue was purified by flash chromatography eluting with 0-30% (3:1 EtOAc:EtOH)/hexane to provide the title compound. (0.057 g, 39% yield) LC/MS m/z=542 (M+H)⁺, 0.98 min (ret. time).

(S)-3-(1,4-Dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)-2,2-dimethylpropanoic Acid, Trifluoroacetate

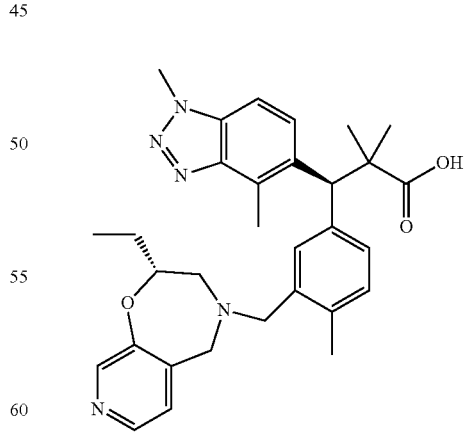

To a solution of (S)-methyl 3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)-2,2-dimethylpropanoate (0.057 g, 0.105 mmol) in tetrahydrofuran (THF) (2 mL), methanol (2.000 mL) and water (2.000 mL) in a 10 mL microwave reaction vessel was added lithium hydroxide (0.025 g, 1.052 mmol) and the solution heated via microwave at 150° C. for 1 h. The reaction was acidified with trifluoroacetic acid and, the solvent was removed and the residue was purified by reverse phase preparative HPLC using TFA as a solvent modifier to provide the title compound. (0.054 g, 80% yield) LC/MS m/z=528 (M+H)$^+$, 0.85 min (ret. time).

Example 220

5-(1-Ethyl-1H-1,2,3-triazol-4-yl)-3-(3-(((R)-2-ethyl-2,3-dihydropyrido[4,3-f][1,4]oxazepin-4(5H)-yl)methyl)-4-methylphenyl)-2,2-dimethylpentanoic Acid, 3.2 Trifluoroacetic Acid Salt

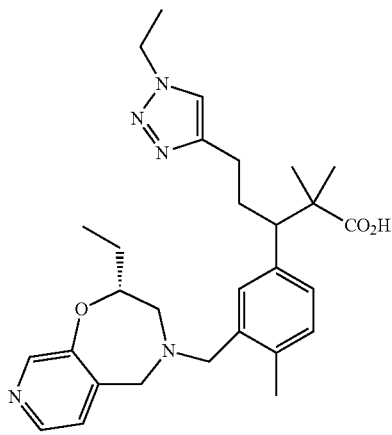 [SMILES: CC[C@@H]1CN(Cc2cc(C(CCc3cn(CC)nn3)C(C)(C)C(=O)O)ccc2C)Cc2ccncc2O1]

Benzyl 5-(1-ethyl-1H-1,2,3-triazol-4-yl)-3-(3-(((R)-2-ethyl-2,3-dihydropyrido[4,3-f][1,4]oxazepin-4(5H)-yl)methyl)-4-methylphenyl)-2,2-dimethylpentanoate

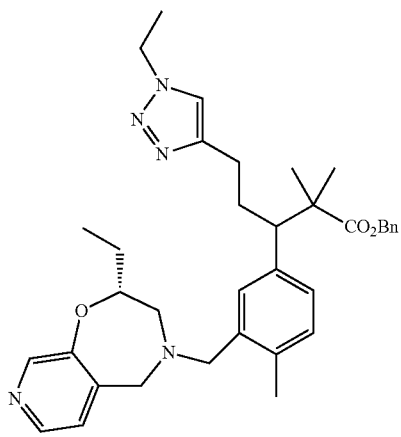 [SMILES: CC[C@@H]1CN(Cc2cc(C(CCc3cn(CC)nn3)C(C)(C)C(=O)OCc3ccccc3)ccc2C)Cc2ccncc2O1]

To a solution of benzyl 5-(1-ethyl-1H-1,2,3-triazol-4-yl)-3-(3-(hydroxymethyl)-4-methylphenyl)-2,2-dimethylpentanoate (0.100 g, 0.230 mmol) in dichloromethane (DCM) (3 mL) was added thionyl chloride (0.034 mL, 0.459 mmol) and the reaction stirred at ambient temperature for 30 min. The solvent was removed and the residue, in acetonitrile (2 mL),was added to a solution of (R)-2-ethyl-2,3,4,5-tetrahydropyrido[4,3-f][1,4]oxazepine (0.045 g, 0.230 mmol) and DIEA (0.160 mL, 0.918 mmol) in acetonitrile (3 mL) in a 10 mL microwave reaction vessel. The reaction was heated in a microwave to 120° C. for 1 h. Isolute was added to the reaction and the solvent was removed. The residue was purified by flash chromatography eluting with 0-40-50% (3:1 EtOAc:EtOH)/hexane to provide the title compound. (0.058 g, 41% yield) LC/MS m/z=596 (M+H)$^+$, 1.07 min (ret. time).

5-(1-Ethyl-1H-1,2,3-triazol-4-yl)-3-(3-(((R)-2-ethyl-2,3-dihydropyrido[4,3-f][1,4]oxazepin-4(5H)-yl)methyl)-4-methylphenyl)-2,2-dimethylpentanoic Acid, 3.2 Trifluoroacetic Acid Salt

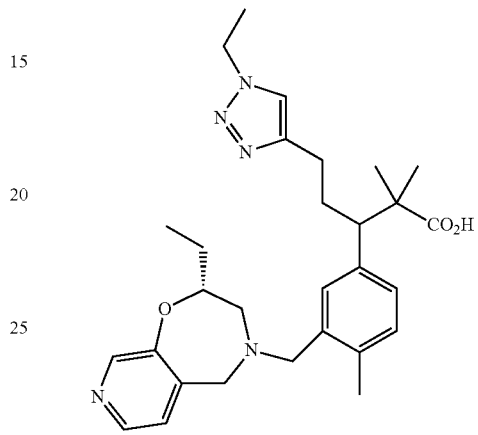

A solution of benzyl 5-(1-ethyl-1H-1,2,3-triazol-4-yl)-3-(3-(((R)-2-ethyl-2,3-dihydropyrido[4,3-f][1,4]oxazepin-4(5H)-yl)methyl)-4-methylphenyl)-2,2-dimethylpentanoate (0.054 g, 0.091 mmol) in methanol (10 mL) was hydrogenated on H-Cube using 10% Pd/C cartridge and 50 bar H$_2$ pressure, for 5.5 h. The solvent was removed and the residue was purified by reverse phase preparative HPLC using TFA as a solvent modifier to provide the title compound. (0.038 g, 48% yield) LC/MS m/z=506 (M+H)$^+$, 0.82 min (ret. time).

Example 221

3-(3-((2,2-Dimethyl-2,3-dihydropyrido[2,3-f][1,4]oxazepin-4(5H)-yl)methyl)-4-methylphenyl)-5-(1-ethyl-1H-1,2,3-triazol-4-yl)-2,2-dimethylpentanoic Acid

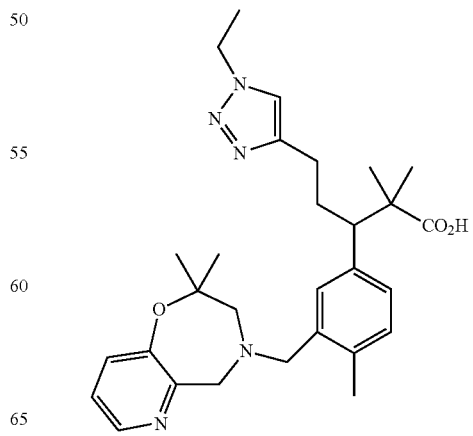

Benzyl 3-(3-((2,2-dimethyl-2,3-dihydropyrido[2,3-f][1,4]oxazepin-4(5H)-yl)methyl)-4-methylphenyl)-5-(1-ethyl-1H-1,2,3-triazol-4-yl)-2,2-dimethylpentanoate

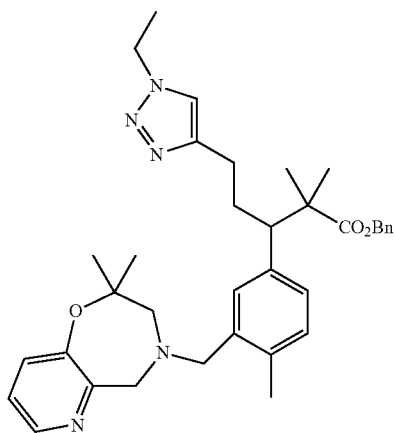 [SMILES: CCn1cc(CCC(c2ccc(C)c(CN3Cc4ncccc4OC(C)(C)C3)c2)C(C)(C)C(=O)OCc2ccccc2)nn1]

To a solution of benzyl 5-(1-ethyl-1H-1,2,3-triazol-4-yl)-3-(3-(hydroxymethyl)-4-methylphenyl)-2,2-dimethylpentanoate (0.050 g, 0.115 mmol) in dichloromethane (DCM) (3 mL) was added thionyl chloride (0.017 mL, 0.230 mmol) and the reaction stirred at ambient temperature for 30 min. The solvent was removed and the residue was dissolved in acetonitrile (5 mL) in a 10 mL microwave reaction vessel. To this solution was added 2,2-dimethyl-2,3,4,5-tetrahydropyrido[2,3-f][1,4]oxazepine, hydrochloride (0.027 g, 0.126 mmol) and DIEA (0.080 mL, 0.459 mmol). The reactions were heated via microwave to 120° C. for 1 h. The solvent was removed and the residue was purified by flash chromatography eluting with 0-40% (3:1 EtOAc:EtOH)/hexane to provide the title compound. (0.051 g, 60% yield) LC/MS m/z=596 (M+H)$^+$, 1.12 min (ret. time).

3-(3-((2,2-Dimethyl-2,3-dihydropyrido[2,3-f][1,4]oxazepin-4(5H)-yl)methyl)-4-methylphenyl)-5-(1-ethyl-1H-1,2,3-triazol-4-yl)-2,2-dimethylpentanoic Acid

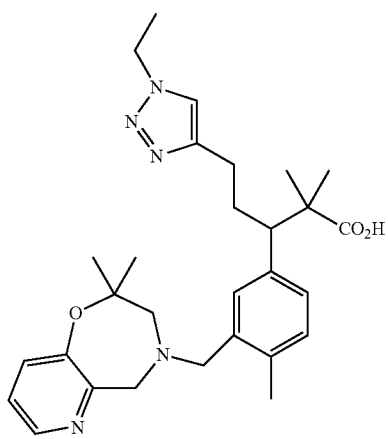 [SMILES: CCn1cc(CCC(c2ccc(C)c(CN3Cc4ncccc4OC(C)(C)C3)c2)C(C)(C)C(=O)O)nn1]

A solution of benzyl 3-(3-((2,2-dimethyl-2,3-dihydropyrido[2,3-f][1,4]oxazepin-4(5H)-yl)methyl)-4-methylphenyl)-5-(1-ethyl-1H-1,2,3-triazol-4-yl)-2,2-dimethylpentanoate (0.051 g, 0.069 mmol) in methanol (10 mL) was hydrogenated on H-Cube using 10% Pd/C cartridge and full H$_2$ pressure, for 30 min. The solvent was removed and the residue was purified by reverse phase preparative HPLC under neutral conditions to provide the title compound. (0.011 g, 31% yield) LC/MS m/z=506 (M+H)$^+$, 0.89 min (ret. time).

Example 222

(S)-3-(1,4-Dimethyl-1H-benzo[d][1,2,3]triazol-5-yl)-3-(3-(((R)-2-ethyl-6-fluoro-2,3-dihydropyrido[3,4-f][1,4]oxazepin-4(5H)-yl)methyl)-4-methylphenyl)-2,2-dimethylpropanoic Acid

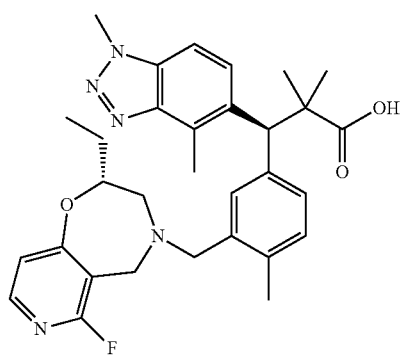 [SMILES: CC[C@@H]1CN(Cc2cc([C@@H](c3ccc4c(nnn4C)c3C)C(C)(C)C(=O)O)ccc2C)Cc2c(ccnc2F)O1]

(S)-Methyl 3-(1,4-dimethyl-1H-benzo[d][1,2,3]triazol-5-yl)-3-(3-(((R)-2-ethyl-6-fluoro-2,3-dihydropyrido[3,4-f][1,4]oxazepin-4(5H)-yl)methyl)-4-methylphenyl)-2,2-dimethylpropanoate

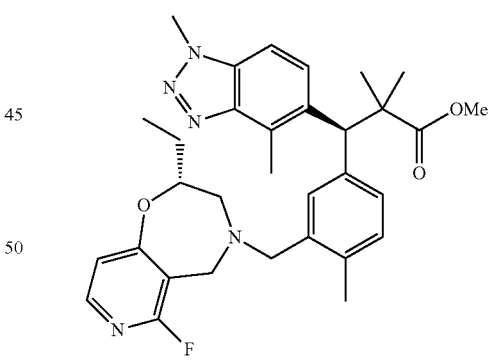

To a solution of (R)-2-ethyl-6-fluoro-2,3,4,5-tetrahydropyrido[3,4-f][1,4]oxazepine (0.030 g, 0.153 mmol) in acetonitrile (10.00 mL) in a 5 mL microwave reaction vessel was added (S)-methyl 3-(3-(chloromethyl)-4-methylphenyl)-3-(1,4-dimethyl-1H-benzo[d][1,2,3]triazol-5-yl)-2,2-dimethylpropanoate (0.061 g, 0.153 mmol) and DIEA (0.080 mL, 0.459 mmol) and heated at 120° C. for 1 h. The solvent was removed and the residue was purified by flash chromatography eluting with 0-25-40% (3:1 EtOAc:EtOH)/hexane to provide the title compound. (0.056 g, 65% yield) LC/MS m/z=560 (M+H)$^+$, 1.01 min (ret. time).

457

(S)-3-(1,4-Dimethyl-1H-benzo[d][1,2,3]triazol-5-yl)-3-(3-(((R)-2-ethyl-6-fluoro-2,3-dihydropyrido[3,4-f][1,4]oxazepin-4(5H)-yl)methyl)-4-methylphenyl)-2,2-dimethylpropanoic Acid

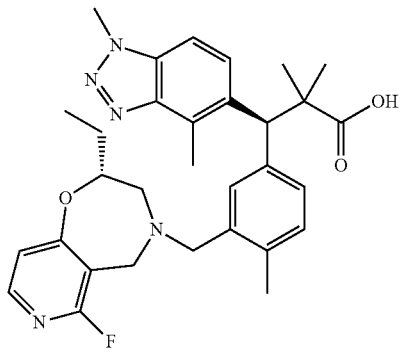 [SMILES: CC[C@@H]1CN(Cc2cc([C@@H](c3ccc4c(nnn4C)c3C)C(C)(C)C(=O)O)ccc2C)Cc2c(ccnc2F)O1]

To a solution of (S)-methyl 3-(1,4-dimethyl-1H-benzo[d][1,2,3]triazol-5-yl)-3-(3-(((R)-2-ethyl-6-fluoro-2,3-dihydropyrido[3,4-f][1,4]oxazepin-4(5H)-yl)methyl)-4-methylphenyl)-2,2-dimethylpropanoate (56 mg, 0.100 mmol) in, methanol (4 mL) and water (2 mL) in a 10 mL microwave reaction vessel, was added LiOH (11.98 mg, 0.500 mmol) and the solution heated via microwave at 120° C. for 7 h. The reaction was acidified with formic acid and the solvent was removed. The residue was purified by reverse phase preparative HPLC using formic acid as a solvent modifier to provide the title compound. (0.004 g, 6.6% yield) LC/MS m/z=546 (M+H)$^+$, 0.92 min (ret. time).

Example 223

3-(3-((2,2-Dimethyl-2,3-dihydropyrido[3,2-f][1,4]oxazepin-4(5H)-yl)methyl)-4-methylphenyl)-5-(1-ethyl-1H-1,2,3-triazol-4-yl)-2,2-dimethylpentanoic Acid

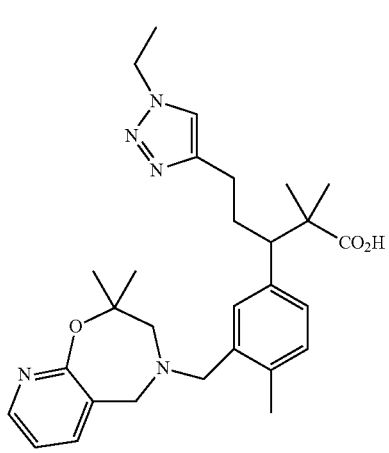 [SMILES: CCn1cc(CCC(c2ccc(C)c(CN3Cc4cccnc4OC(C)(C)C3)c2)C(C)(C)C(=O)O)nn1]

458

Benzyl 3-(3-((2,2-dimethyl-2,3-dihydropyrido[3,2-f][1,4]oxazepin-4(5H)-yl)methyl)-4-methylphenyl)-5-(1-ethyl-1H-1,2,3-triazol-4-yl)-2,2-dimethylpentanoate

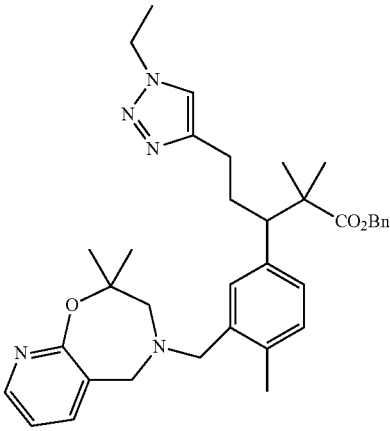 [SMILES: CCn1cc(CCC(c2ccc(C)c(CN3Cc4cccnc4OC(C)(C)C3)c2)C(C)(C)C(=O)OCc2ccccc2)nn1]

To a solution of benzyl 5-(1-ethyl-1H-1,2,3-triazol-4-yl)-3-(3-(hydroxymethyl)-4-methylphenyl)-2,2-dimethylpentanoate (0.050 g, 0.115 mmol) in dichloromethane (DCM) (3 mL) was added thionyl chloride (0.017 mL, 0.230 mmol) and the reaction stirred at ambient temperature for 30 min. The solvent was removed and the residue was dissolved in acetonitrile (5 mL) in a 10 mL microwave reaction vessel. To this solution was added 2,2-dimethyl-2,3,4,5-tetrahydropyrido[3,2-f][1,4]oxazepine (0.045 g, 0.126 mmol) and DIEA (0.080 mL, 0.459 mmol). The reactions were heated via microwave to 120° C. for 1.5 h. The solvent was removed and the residue was purified by flash chromatography eluting with 0-40% (3:1 EtOAc:EtOH)/hexane to provide the title compound. (0.055 g, 80% yield) LC/MS m/z=596 (M+H)$^+$, 1.06 min (ret. time).

3-(3-((2,2-Dimethyl-2,3-dihydropyrido[3,2-f][1,4]oxazepin-4(5H)-yl)methyl)-4-methylphenyl)-5-(1-ethyl-1H-1,2,3-triazol-4-yl)-2,2-dimethylpentanoic Acid

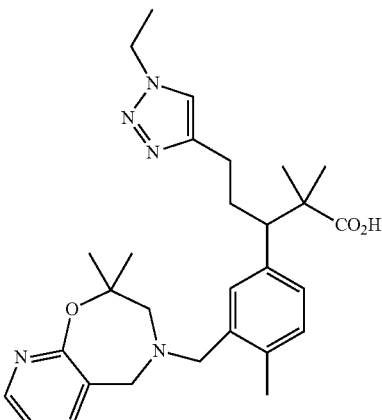

A solution of benzyl 3-(3-((2,2-dimethyl-2,3-dihydropyrido[3,2-f][1,4]oxazepin-4(5H)-yl)methyl)-4-methylphenyl)-5-(1-ethyl-1H-1,2,3-triazol-4-yl)-2,2-dimethylpentanoate (0.047 g, 0.079 mmol) in methanol (10 mL) was hydrogenated on H-Cube using 10% Pd/C cartridge and full $H_2$ pressure, for 20 min. The solvent was removed and the residue was purified by reverse phase preparative HPLC using formic acid as a solvent modifier to provide the title compound. (0.014 g, 35% yield) LC/MS m/z=506 (M+H)$^+$, 0.81 min (ret. time).

Example 224

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2-methylpentanoic Acid, 0.20 Formic Acid Salt

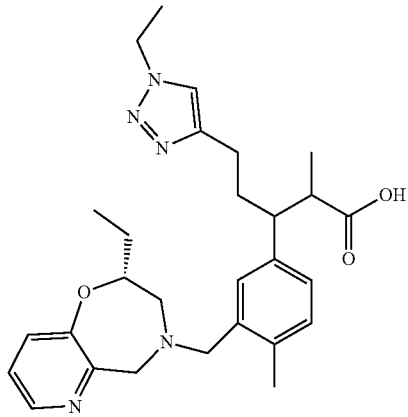 [SMILES: CC[C@@H]1CN(Cc2cc(C(CCc3cn(CC)nn3)C(C)C(=O)O)ccc2C)Cc2ncccc2O1]

tert-Butyl 3-(3-(((4-methoxybenzyl)oxy)methyl)-4-methylphenyl)-2-methyl-7-(trimethylsilyl)hept-6-ynoate

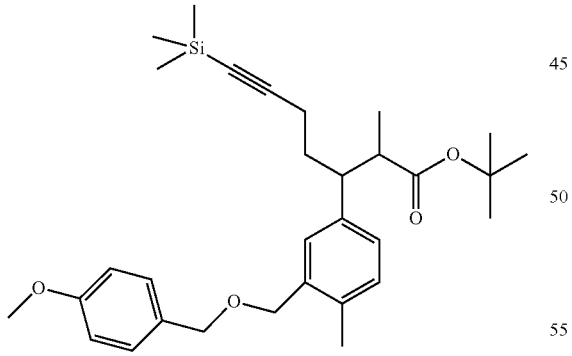

A −70° C. solution of diisopropylamine (0.643 mL, 4.52 mmol) in tetrahydrofuran (THF) (4.5 mL) was treated with 1.6 M n-butyllithium (1.693 mL, 2.71 mmol) and stirred at −70° C. for 1 h. The reaction was warmed to −40° C. (dry-ice acetonitrile) for 10 min, and then recooled to −70° C. Tert-butyl propionate (0.544 mL, 3.61 mmol) in tetrahydrofuran (THF) (4.50 mL) was added to the −70° C. solution dropwise. The reaction was stirred at −70° C. for 45 min, warmed to −50° C. briefly, and then recooled to −70° C. Afterwards, (5-bromo-5-(3-(((4-methoxybenzyl)oxy)methyl)-4-methylphenyl)pent-1-yn-1-yl)trimethylsilane (0.415 g, 0.903 mmol) in tetrahydrofuran (THF) (0.5 mL) was added dropwise to the enolate followed by dry DMPU (2.178 mL, 18.06 mmol) and stirred at −70° C. for 2 h. The reaction was then warmed to −40° C. and stirred for 2 h (dry-ice acetonitrile). The reaction was quenched with 5 mL sat aqueous $NH_4Cl$, diluted with water (20 mL) and EtOAc (75 mL). The phases were separated and the aqueous layer was extracted with EtOAc (50 mL). The combined organic layers were washed with water (3×25 mL), saturated NaCl (25 mL) and then dried with $Na_2SO_4$. The solvent was removed and the residue was purified by flash chromatography eluting with 0-10% EtOAc/hexane to provide the title compound. (0.189 g, 41% yield)
LC/MS m/z=531 (M+Na)$^+$, 1.75 min (ret. time).

tert-Butyl 3-(3-(((4-methoxybenzyl)oxy)methyl)-4-methylphenyl)-2-methylhept-6-ynoate

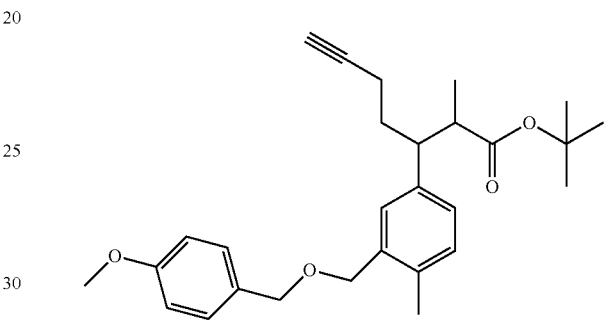

To a solution of tert-butyl 3-(3-(((4-methoxybenzyl)oxy)methyl)-4-methylphenyl)-2-methyl-7-(trimethylsilyl)hept-6-ynoate (0.628 g, 1.234 mmol) in methanol (6.17 mL) was added $K_2CO_3$ (0.853 g, 6.17 mmol) and the reaction stirred at ambient temperature for 2 hours. The reaction was diluted with water and extracted 3× with DCM. Combined organics were washed with water, brine and dried with $MgSO_4$. The residue was purified by flash chromatography eluting with 0-10% EtOAc/hexane to provide the title compound as a mixture of diasteriomers. (0.313 g, 55% yield) LC/MS m/z=459 (M+Na)$^+$, 1.51, 1.54 min (ret. time).

tert-Butyl 5-(1-ethyl-1H-1,2,3-triazol-4-yl)-3-(3-(((4-methoxybenzyl)oxy)methyl)-4-methylphenyl)-2-methylpentanoate

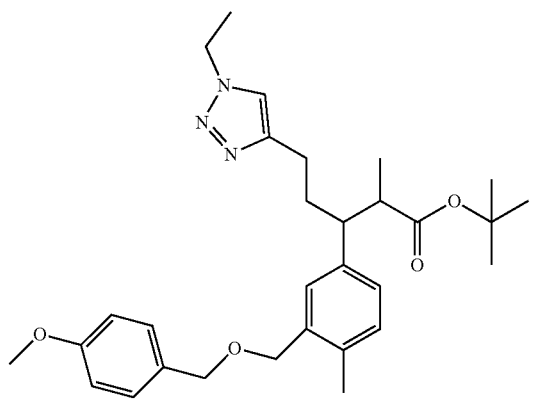 [SMILES: CCn1cc(CCC(c2ccc(C)c(COCc3ccc(OC)cc3)c2)C(C)C(=O)OC(C)(C)C)nn1]

To a solution of tert-butyl 3-(3-(((4-methoxybenzyl)oxy)methyl)-4-methylphenyl)-2-methylhept-6-ynoate (0.331 g, 0.758 mmol) in tert-butanol (2.00 mL) and water (1.50 mL) in a 10 mL microwave reaction vessel was added iodoethane (0.153 mL, 1.895 mmol), copper(I) iodide (0.022 g, 0.114 mmol), sodium azide (0.123 g, 1.895 mmol), and DIEA (0.026 mL, 0.152 mmol). The mixture was heated via microwave at 70° C. for 1 h. The reaction was diluted with water and EtOAc and the layers were separated. The aqueous layer was extracted with 2×EtOAc. The combined organics were washed with water and brine and dried with MgSO$_4$. The residue was purified by flash chromatography eluting with 0-70% EtOAc/hexane to provide the title compound as a mixture of diasteriomers. (0.270 g, 70% yield) LC/MS m/z=508 (M+H)$^+$, 1.34, 1.38 min (ret. time)

tert-Butyl 5-(1-ethyl-1H-1,2,3-triazol-4-yl)-3-(3-(hydroxymethyl)-4-methylphenyl)-2-methylpentanoate

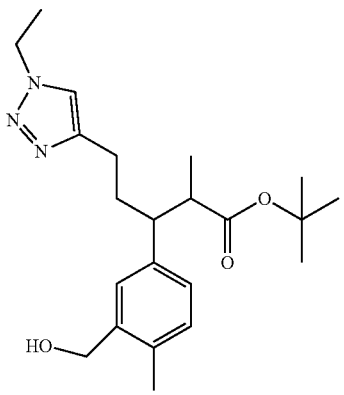 [SMILES: CCn1cc(CCC(c2ccc(C)c(CO)c2)C(C)C(=O)OC(C)(C)C)nn1]

To a solution of tert-butyl 5-(1-ethyl-1H-1,2,3-triazol-4-yl)-3-(3-(((4-methoxybenzyl)oxy)methyl)-4-methylphenyl)-2-methylpentanoate (0.270 g, 0.532 mmol) in dichloromethane (DCM) (10.00 mL) and water (1.00 mL) was added DDQ (0.145 g, 0.638 mmol). The mixture was stirred at ambient temperature for 3 h. The solvent was removed and the residue was purified by flash chromatography eluting with 0-5% MeOH/DCM to provide the title compound as a mixture of stereoisomers. The stereoisomeric mixture was separated by reverse phase preparative HPLC under neutral conditions to provide the title compound as a mixture of enantiomers. (0.124 g, 60% yield) LC/MS m/z=388 (M+H)$^+$, 1.01 min (ret. time)

tert-Butyl 5-(1-ethyl-1H-1,2,3-triazol-4-yl)-3-(3-(((R)-2-ethyl-2,3-dihydropyrido[2,3-f]i[1,4]oxazepin-4(5H)-yl)methyl)-4-methylphenyl)-2-methylpentanoate

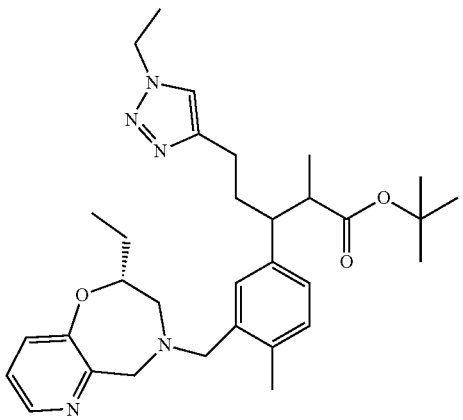 [SMILES: CC[C@@H]1CN(Cc2cc(C(CCc3cn(CC)nn3)C(C)C(=O)OC(C)(C)C)ccc2C)Cc2ncccc2O1]

To a solution of tert-butyl 5-(1-ethyl-1H-1,2,3-triazol-4-yl)-3-(3-(hydroxymethyl)-4-methylphenyl)-2-methylpentanoate (0.062 g, 0.160 mmol) in dichloromethane (DCM) (3 mL) was added thionyl chloride (0.023 mL, 0.320 mmol) and the reaction stirred at ambient temperature for 30 min. The solvent was removed and the residue was dissolved in acetonitrile (4 mL). To this solution was added (R)-2-ethyl-2,3,4,5-tetrahydropyrido[2,3-f][1,4]oxazepine, hydrochloride (0.041 g, 0.192 mmol) and DIEA (0.112 mL, 0.640 mmol) The reaction was heated via microwave to 120° C. for 1 h. The solvent was removed and the residue was purified by flash chromatography eluting with 0-40% (3:1 EtOAc:EtOH)/hexane to provide the title compound. (0.068 g, 78% yield) LC/MS m/z=548 (M+H)$^+$, 1.02 min (ret. time).

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2-methylpentanoic acid, 0.20 Formic Acid Salt

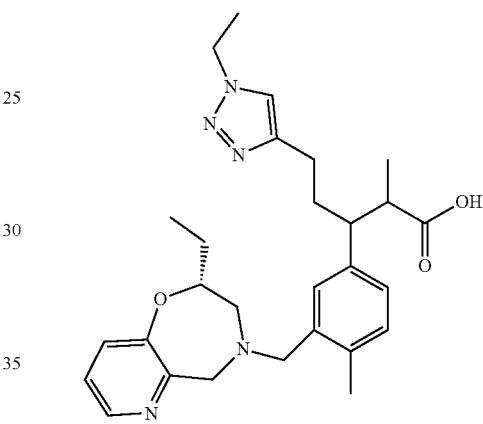

A solution of tert-butyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2-methylpentanoate (0.065 g, 0.114 mmol) in formic acid (1.00 mL, 22.94 mmol) was stirred at ambient temperature for 1 hour and the reaction heated to 50° C. for 8 h. The reaction was then stirred at ambient temperature for 14 h. The reaction was concentrated and the residue was purified by reverse phase preparative HPLC using formic acid as a solvent modifier to provide the title compound. (0.039 g, 69% yield) LC/MS m/z=492 (M+H)$^+$, 0.80 min (ret. time).

Scheme A

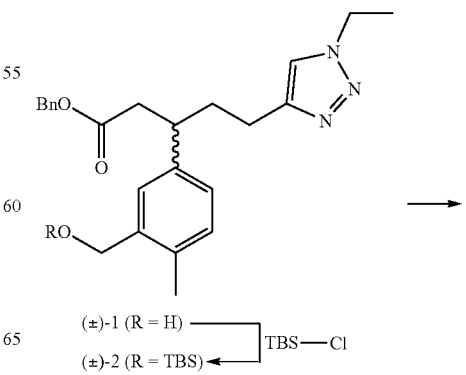

463
-continued
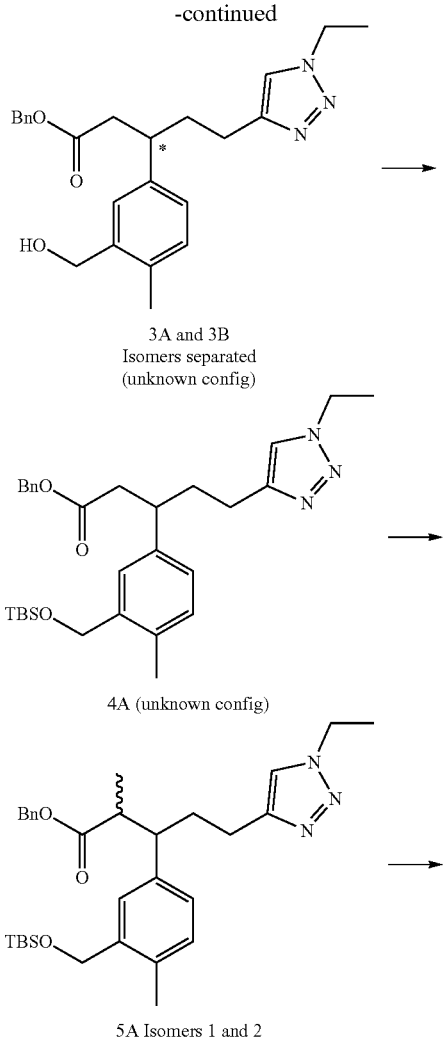
3A and 3B
Isomers separated
(unknown config)
4A (unknown config)
5A Isomers 1 and 2
464
-continued
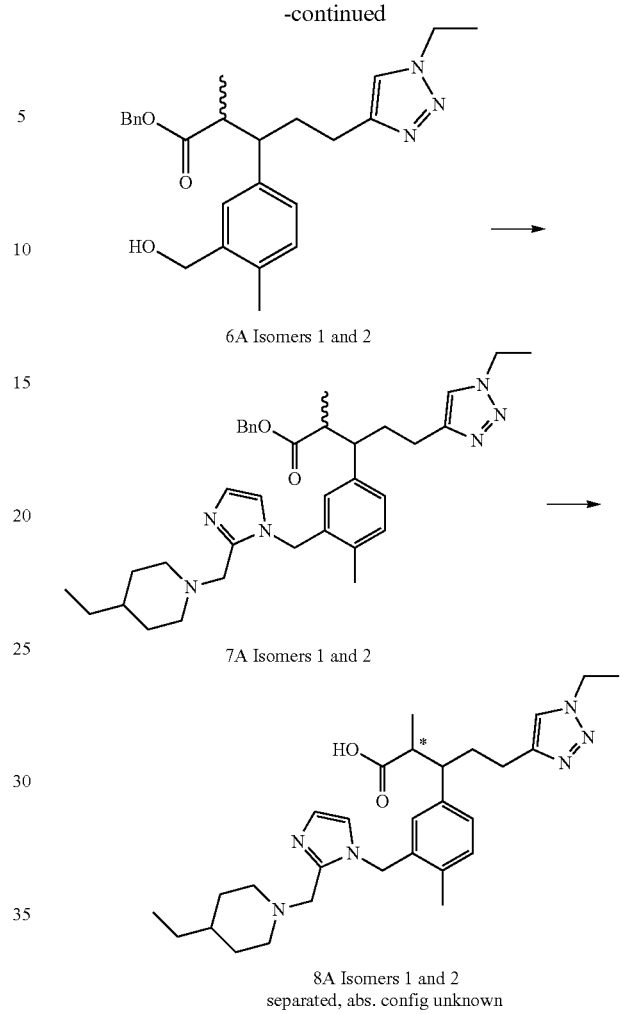
6A Isomers 1 and 2
7A Isomers 1 and 2
8A Isomers 1 and 2
separated, abs. config unknown Scheme B
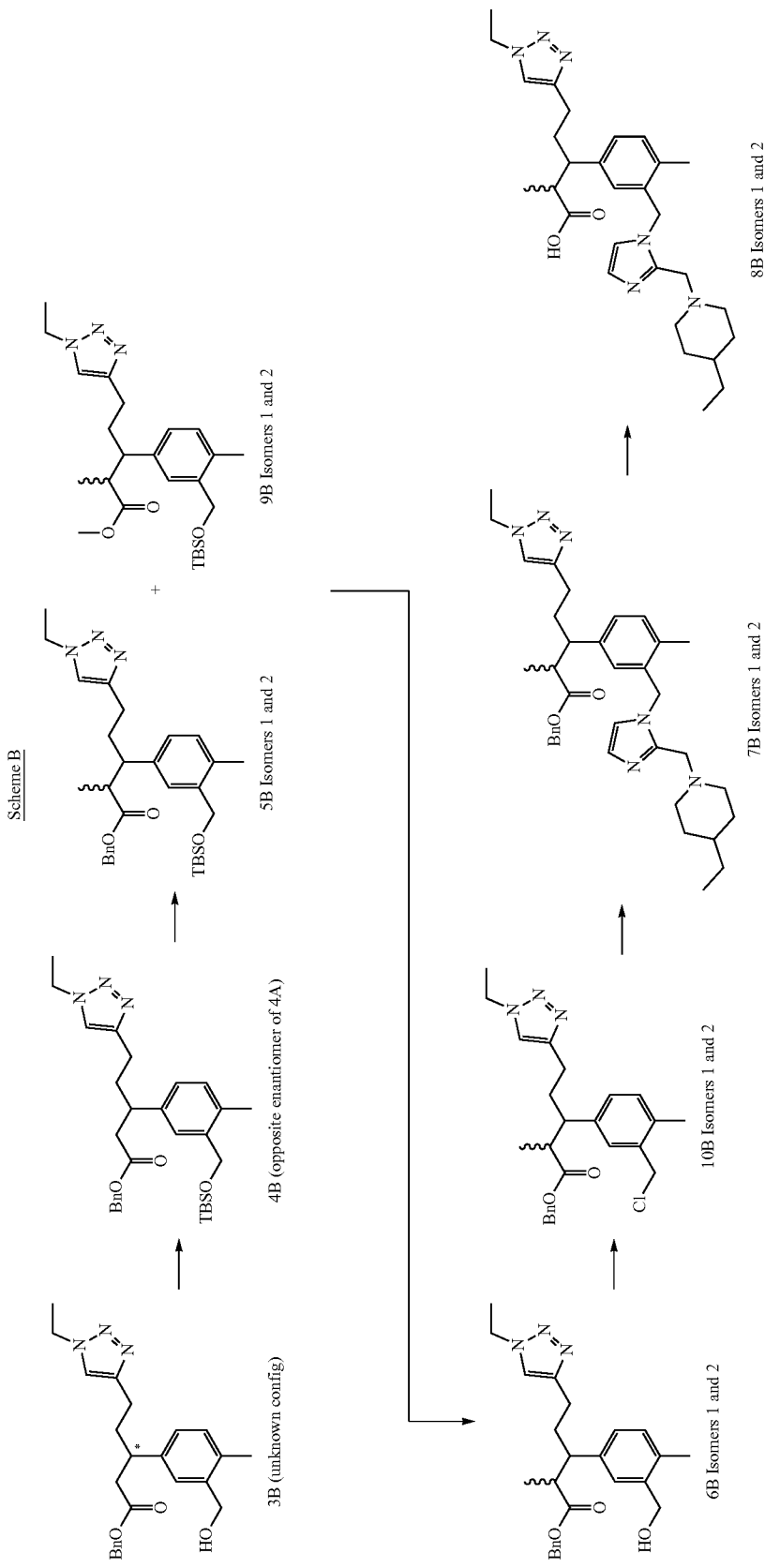

SCHEME C
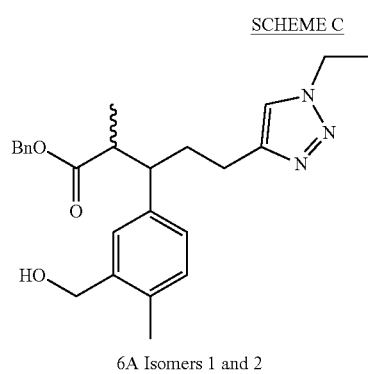
6A Isomers 1 and 2
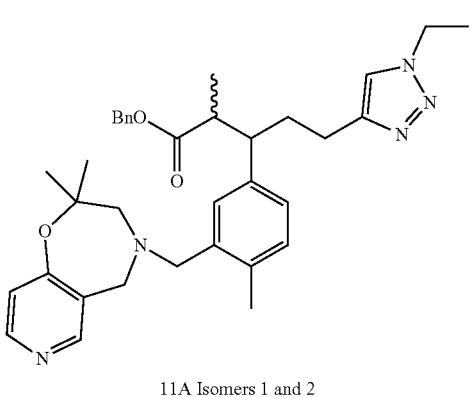
11A Isomers 1 and 2
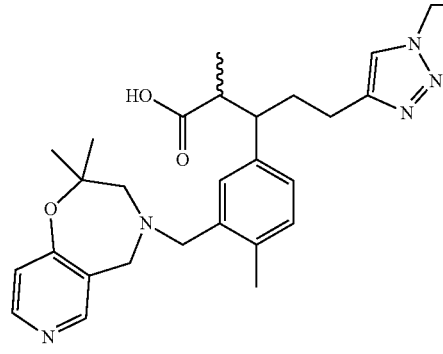
12A Isomers 1 and 2
Scheme D
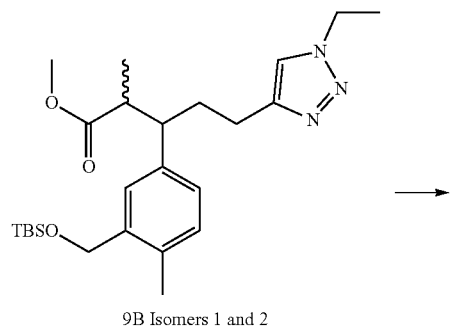
9B Isomers 1 and 2
-continued
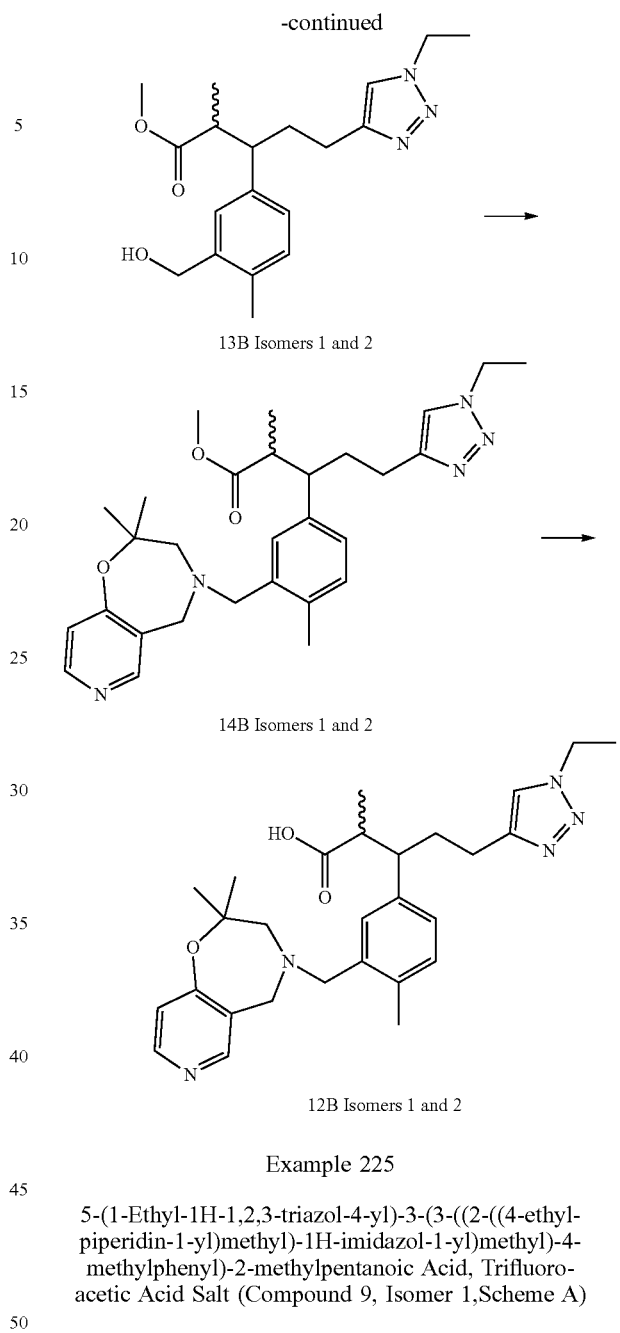
13B Isomers 1 and 2
14B Isomers 1 and 2
12B Isomers 1 and 2
Example 225
5-(1-Ethyl-1H-1,2,3-triazol-4-yl)-3-(3-((2-((4-ethyl-piperidin-1-yl)methyl)-1H-imidazol-1-yl)methyl)-4-methylphenyl)-2-methylpentanoic Acid, Trifluoroacetic Acid Salt (Compound 9, Isomer 1, Scheme A)
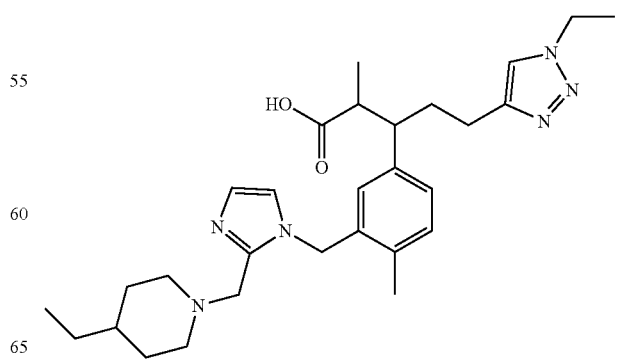

(E)-Benzyl hept-2-en-6-ynoate

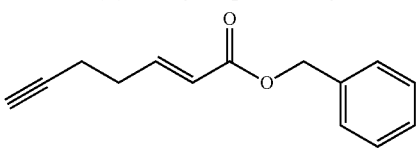 [SMILES: C#CCC/C=C/C(=O)OCc1ccccc1]

To a solution of 3-((2-(dimethoxyphosphoryl)acetoxy)methyl)benzene-1-ylium (51.7 g, 201 mmol) in tetrahydrofuran (THF) (150 mL) was added dium hydride (8.04 g, 201 mmol)) in small portion at 0° C. After it was stirred for 35 min at 00° C., pent-4-ynal (15.0 g, 183 mmol) was added slowly. The reaction mixture was stirred at 0° C. for 50 min. Then 100 mL of saturated NH$_4$Cl was added and the solution was extracted with DCM (2×). The combined organic layer was washed with brine, dried over Na$_2$SO$_4$ and concentrated. The residue was purified by silica gel chromatography (ethyl acetate:petroleum ether=1:50) to give the title compound (E)-benzyl hept-2-en-6-ynoate (12.0 g, 56.0 mmol, 30.7% yield) as an oil.

LC/MS m/z 215.1 (M+H)$^+$, 2.00 min (ret. time)

(E)-Benzyl 5-(1-ethyl-1H-1,2,3-triazol-4-yl)pent-2-enoate

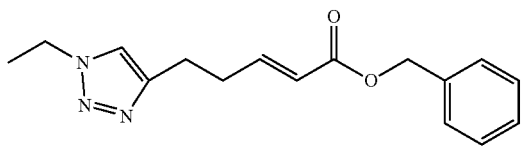 [SMILES: CCn1cc(CC/C=C/C(=O)OCc2ccccc2)nn1]

To a solution of (E)-benzyl hept-2-en-6-ynoate (10.0 g, 46.7 mmol) in tetrahydrofuran (THF) (200.0 mL) and water (200.0 mL) was added sodium azide (9.10 g, 140 mmol), iodoethane (21.84 g, 140 mmol), copper(I) iodide (1.778 g, 9.33 mmol) and NaHCO$_3$ (11.76 g, 140 mmol) slowly under nitrogen. The reaction mixture was stirred at 70° C. for 16 h. The reaction mixture was extracted with ethyl acetate (3×). The organic layer was concentrated and the residue was purified by silica gel chromatography (ethyl acetate: petroleum ether=1:10) to give the title compound (E)-benzyl 5-(1-ethyl-1H-1,2,3-triazol-4-yl)pent-2-enoate (7.5 g, 24.97 mmol, 53.5% yield). LC/MS m/z 286.2 (M+H)$^+$, 1.78 min (ret. time)

Benzyl 5-(1-ethyl-1H-1,2,3-triazol-4-yl)-3-(3-(hydroxymethyl)-4-methylphenyl)pentanoate (Compound (±)-1, Scheme A)

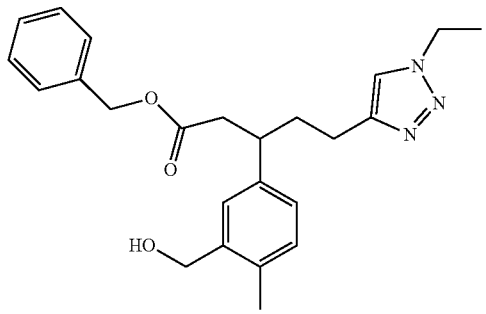 [SMILES: CCn1cc(CCC(CC(=O)OCc2ccccc2)c2ccc(C)c(CO)c2)nn1]

To a solution of (E)-benzyl 5-(1-ethyl-1H-1,2,3-triazol-4-yl)pent-2-enoate (3.0 g, 10.51 mmol) in 1,4-Dioxane (28 mL) and water (11.20 mL) was added (2-methyl-5-(4,4,5,5-tetramethyl-1,3,2-dioxaborolan-2-yl)phenyl)methanol (3.91 g, 15.77 mmol), [Rh(COD)Cl]$_2$ (0.518 g, 1.051 mmol), and triethylamine (4.37 mL, 31.5 mmol). A stream of argon was passed through the mixture for 5 min and then the reaction was heated under Ar at 90° C. for 1.5 h. The reaction mixture was cooled and filtered through a pad of celite, and diluted with EtOAc and water. The layers were separated and the aqueous layer was extracted with 3×EtOAc. The combined organic layers were concentrated and the residue was purified by flash chromatography eluting with 0-40% (3:1 EtOAc:EtOH)/hexane to provide the title compound. (2.66 g, 62% yield) LC/MS m/z=408 (M+H)$^+$, 1.05 min (ret. time).

Benzyl 3-(3-(((tert-butyldimethylsilyl)oxy)methyl)-4-methylphenyl)-5-(1-ethyl-1H-1,2,3-triazol-4-yl)pentanoate (Compound (±)-2, Scheme A)

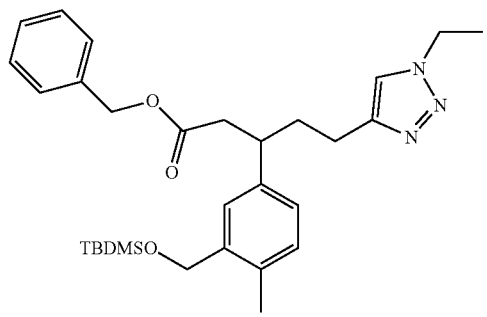 [SMILES: CCn1cc(CCC(CC(=O)OCc2ccccc2)c2ccc(C)c(CO[Si](C)(C)C(C)(C)C)c2)nn1]

To a solution of benzyl 5-(1-ethyl-1H-1,2,3-triazol-4-yl)-3-(3-(hydroxymethyl)-4-methylphenyl)pentanoate (Compound 1, Scheme A) (2.65 g, 6.50 mmol) in N,N-dimethylformamide (DMF) (25 mL) at 0° C. was added imidazole (2.214 g, 32.5 mmol) followed by tert-butyldimethylchlorosilane (2.94 g, 19.51 mmol). The reaction was allowed to stir for 2 h while slowly warming from 0° C. to ambient temperature. The reaction was poured over ice water and extracted with DCM. The combined organic layers were washed with water and concentrated. The residue was purified by flash chromatography eluting with 0-100% EtOAc/hexane to provide the title compound. (3.23 g, 95% yield) LC/MS m/z=522 (M+H)$^+$, 1.54 min (ret. time).

Benzyl 5-(1-ethyl-1H-1,2,3-triazol-4-yl)-3-(3-(hydroxymethyl)-4-methylphenyl)pentanoate (Compound 3A, Scheme A)

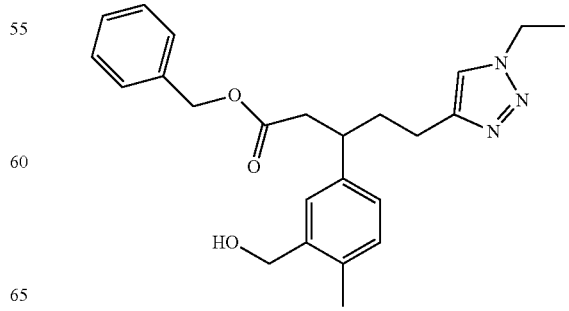

To a solution of benzyl 3-(3-(((tert-butyldimethylsilyl)oxy)methyl)-4-methylphenyl)-5-(1-ethyl-1H-1,2,3-triazol-4-yl)pentanoate (Compound 2, Scheme A) (3.45 g, 6.61 mmol) in tetrahydrofuran (THF) (30 mL) was added TBAF (13.22 mL, 13.22 mmol). The reaction mixture was allowed to stir for 20 h. The reaction was then diluted with EtOAc and washed with 2× water and saturated NaCl. The organic layer was concentrated and the residue was purified by flash chromatography eluting with 0-90% (3:1 EtOAc:EtOH)/hexane to provide 3.23 g of a mixture of stereoisomers of the title compound. This compound was combined with another batch of the same compound prepared by a method similar to the one described here. The combined material was purified by chiral SFC chromatography (Column: Chiralpak AY 20×250 mm; Co-solvent: 25% EtOH; Flowrate: 50 mg/min; Back pressure: 100 Bar) to yield the pure enantiomers of title compounds with unknown absolute configuration. (Compound 3A, Scheme A) (1.48 g) (chiral SFC ret. time: 3.82 min) LC/MS m/z=408 (M+H)+, 1.02 min (ret. time). (Compound 3B, Scheme A) (1.51 g) (chiral SFC ret. time: 5.63 min) LC/MS m/z=408 (M+H)+, 1.01 min (ret. time).

Benzyl 3-(3-(((tert-butyldimethylsilyl)oxy)methyl)-4-methylphenyl)-5-(1-ethyl-1H-1,2,3-triazol-4-yl)pentanoate (Compound 4A, Scheme A)

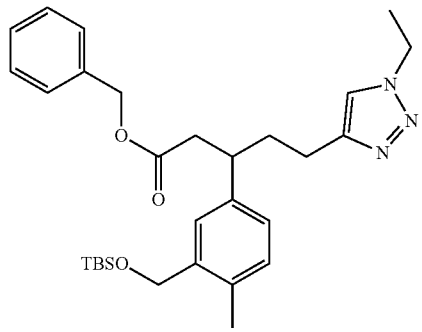 [SMILES: CCn1cc(CCC(CC(=O)OCc2ccccc2)c2ccc(C)c(CO[Si](C)(C)C(C)(C)C)c2)nn1]

To a solution of benzyl 5-(1-ethyl-1H-1,2,3-triazol-4-yl)-3-(3-(hydroxymethyl)-4-methylphenyl)pentanoate (Compound 3A, Scheme A) (1.484 g, 3.64 mmol) in N,N-dimethylformamide (DMF) (20 mL) at 0° C. was added imidazole (1.240 g, 18.21 mmol) followed by tert-butyldimethylchlorosilane (1.647 g, 10.93 mmol). The reaction was allowed to stir for 4 h while warming from 0° C. to ambient temperature slowly. The reaction was poured over ice water and extracted with DCM. The combined organic layers were washed with water and concentrated. The residue was purified by flash chromatography eluting with 0-100% EtOAc/hexane to provide the title compound. (1.55 g, 82% yield) LC/MS m/z=522 (M+H)+, 1.60 min (ret. time).

Benzyl 3-(3-(((tert-butyldimethylsilyl)oxy)methyl)-4-methylphenyl)-5-(1-ethyl-1H-1,2,3-triazol-4-yl)-2-methylpentanoate (Compound 5A, Isomers 1 and 2, Scheme A)

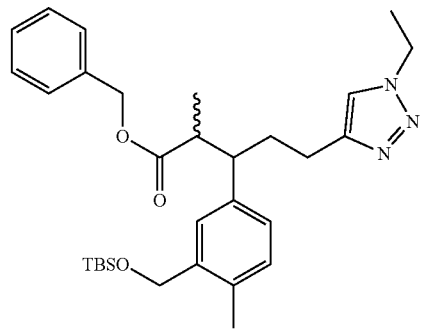 [SMILES: CCn1cc(CCC(c2ccc(C)c(CO[Si](C)(C)C(C)(C)C)c2)C(C)C(=O)OCc2ccccc2)nn1]

To a solution of benzyl 3-(3-(((tert-butyldimethylsilyl)oxy)methyl)-4-methylphenyl)-5-(1-ethyl-1H-1,2,3-triazol-4-yl)pentanoate (Compound 4A, Scheme A) (1.031 g, 1.976 mmol) and 1,3-dimethyl-3,4,5,6-tetrahydro-2(1H)-pyrimidinone (0.238 mL, 1.976 mmol) in tetrahydrofuran (THF) (20 mL) at −78° C. under argon was added 1M LiHMDS (4.94 mL, 4.94 mmol) and the reaction allowed to stir for 50 min. To the reaction mixture was added 2M methyl iodide (6.92 mL, 13.83 mmol) and the reaction mixture was allowed to stir for 25 min at −78° C. before quenching with MeOH and water. The crude product was extracted with DCM and the combined organic layers were concentrated under reduced pressure. The residue was purified by flash chromatography eluting with 0-70% EtOAc/hexane to provide the title compound as a mixture of isomers. (0.810 g, 77% yield) LC/MS m/z=536 (M+H)+, 1.65, 1.69 min (ret. time).

Benzyl 5-(1-ethyl-1H-1,2,3-triazol-4-yl)-3-(3-(hydroxymethyl)-4-methylphenyl)-2-methylpentanoate (Compound 6A, Isomers 1 and 2, Scheme A)

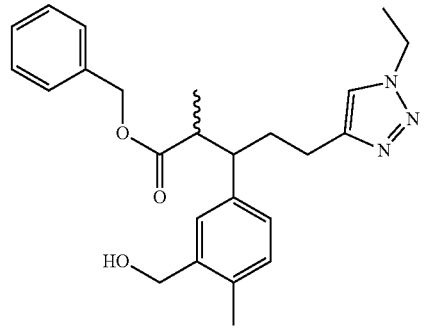

To a solution of benzyl 3-(3-(((tert-butyldimethylsilyl)oxy)methyl)-4-methylphenyl)-5-(1-ethyl-1H-1,2,3-triazol-4-yl)-2-methylpentanoate (Compound 5A, Isomers 1 and 2, Scheme A) (0.810 g, 1.512 mmol) in tetrahydrofuran (THF) (15 mL) was added TBAF (3.02 mL, 3.02 mmol). The reaction mixture was stirred for 21 h. The reaction was then diluted with EtOAc and washed with 2× water and saturated NaCl. Organic layer concentrated and the residue was purified by flash chromatography eluting with 0-90% (3:1

EtOAc:EtOH)/hexane to provide the title compound as a mixture of diasteriomers. (0.490 g, 77% yield) LC/MS m/z=422 (M+H)⁺, 1.06, 1.08 min (ret. time).

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2-methylpentanoate (Compound 7A, Isomers 1 and 2, Scheme A)

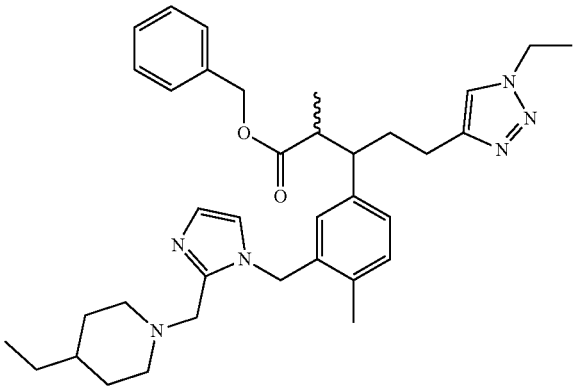 [SMILES: CCC1CCN(Cc2nccn2Cc2cc(C(CCc3cn(CC)nn3)C(C)C(=O)OCc3ccccc3)ccc2C)CC1]

To a solution of benzyl 5-(1-ethyl-1H-1,2,3-triazol-4-yl)-3-(3-(hydroxymethyl)-4-methylphenyl)-2-methylpentanoate (Compound 6A, Isomers 1 and 2, Scheme A) (266 mg, 0.631 mmol) in dichloromethane (DCM) (3 mL), was added DIEA (0.331 mL, 1.893 mmol) followed by the addition of SOCl₂ (0.092 mL, 1.262 mmol) and stirred for 1.5 h at 0° C. The solvent was removed and the residue was redissolved in N,N-dimethylformamide (DMF) (3.00 mL). To the reaction mixture was added 1-((1H-imidazol-2-yl)methyl)-4-ethylpiperidine, trifluoroacetic acid salt (388 mg, 1.262 mmol) and the reaction heated in microwave at 120° C. for 1 h 45 min. The reaction was diluted with water and extracted with DCM. The organic layers were combined and concentrated under reduced pressure. and the residue was purified by flash chromatography eluting with 0-100% (3:1 EtOAc:EtOH)/hexane to provide the title compound as a crude mixture with DMF. LC/MS m/z=597 (M+H)⁺, 1.10 min (ret. time). The compound was carried on to next step without further purification.

5-(1-Ethyl-1H-1,2,3-triazol-4-yl)-3-(3-((2-((4-ethyl-piperidin-1-yl)methyl)-1H-imidazol-1-yl)methyl)-4-methylphenyl)-2-methylpentanoic acid, Trifluoroacetic Acid Salt (Compound 8A, Isomer 1, Scheme A)

The mixture of benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2-methylpentanoate (Compound 7, Isomers 1 and 2, Scheme A) (120 mg, 0.099 mmol), and 5% Pd—C (105 mg, 0.049 mmol) in methanol (30 mL) was hydrogenated at room atmosphere for 5 h. The reaction was filtered and the solvent was removed. The residue was dissolved in methanol and was subjected to H₂ on an H-cube for 2 h at 25° C. using a 10% Pd—C cartridge and a flow rate of 1 mL/min. Afterwards a solution of lithium hydroxide (35.4 mg, 1.478 mmol) in water (5 mL) was added to the solution in methanol (30 mL). This reaction mixture was allowed to stir for 48 h at ambient temperature. The reaction was concentrated and the residue was purified by reverse phase preparative HPLC using TFA as a solvent modifier to provide the two enantiomericly pure title compounds. (Compound 8A, Isomer 1, Scheme A):(0.038 g, 62% yield) LC/MS m/z 507 (M+H)⁺, 0.86 min (ret. time). (Compound 8A, Isomer 2, Scheme A):(0.006 g, 10% yield) LC/MS m/z=507 (M+H)⁺, 0.84 min (ret. time)

Example 226

5-(1-Ethyl-1H-1,2,3-triazol-4-yl)-3-(3-((2-((4-ethyl-piperidin-1-yl)methyl)-1H-imidazol-1-yl)methyl)-4-methylphenyl)-2-methylpentanoic acid, Trifluoroacetic Acid Salt (Compound 8B, Isomers 1 and 2, Scheme B)

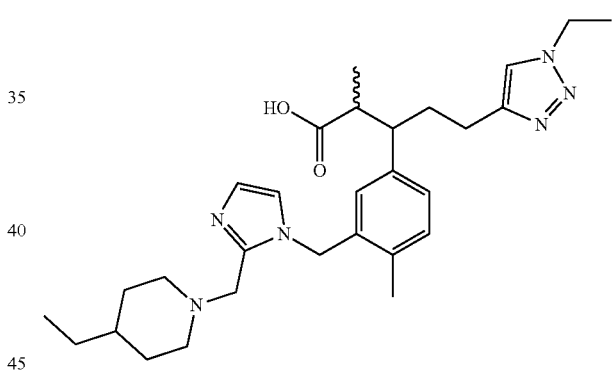

Benzyl 3-(3-((((tert-butyldimethylsilyl)oxy)methyl)-4-methylphenyl)-5-(1-ethyl-1H-1,2,3-triazol-4-yl)pentanoate (Compound 4B, Isomer 2, Scheme A)

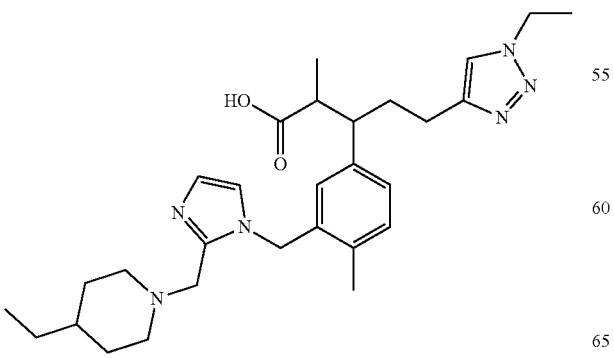

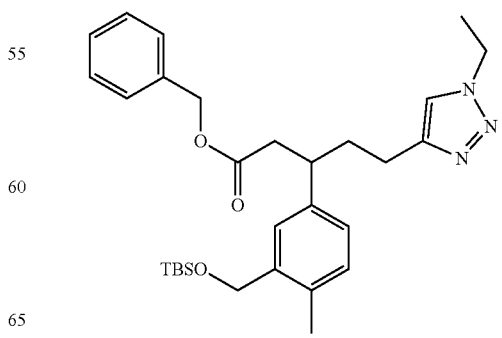

To a solution of benzyl 5-(1-ethyl-1H-1,2,3-triazol-4-yl)-3-(3-(hydroxymethyl)-4-methylphenyl)pentanoate (Compound 3B, Scheme A) (1.511 g, 3.71 mmol) in N,N-dimethylformamide (DMF) (20 mL) at 0° C. was added imidazole (1.262 g, 18.54 mmol) followed by tert-butyldimethylchlorosilane (1.677 g, 11.12 mmol). The reaction was allowed to stir for 4 h while warming from 0° C. to ambient temperature slowly. The reaction was poured over ice water and extracted with DCM. The combined organic layers were washed with water before being concentrated. The residue was purified by flash chromatography eluting with 0-100% EtOAc/hexane to provide the title compound. (1.418 g, 73% yield) LC/MS m/z=522 (M+H)$^+$, 1.63 min (ret. time).

Mixture of benzyl 3-(3-(((tert-butyldimethylsilyl)oxy)methyl)-4-methylphenyl)-5-(1-ethyl-1H-1,2,3-triazol-4-yl)-2-methylpentanoate (Compound 5B, Isomers 1 and 2, Scheme B) and methyl 3-(3-(((tert-butyldimethylsilyl)oxy)methyl)-4-methylphenyl)-5-(1-ethyl-1H-1,2,3-triazol-4-yl)-2-methylpentanoate (Compound 9B, Isomers 1 and 2, Scheme B)

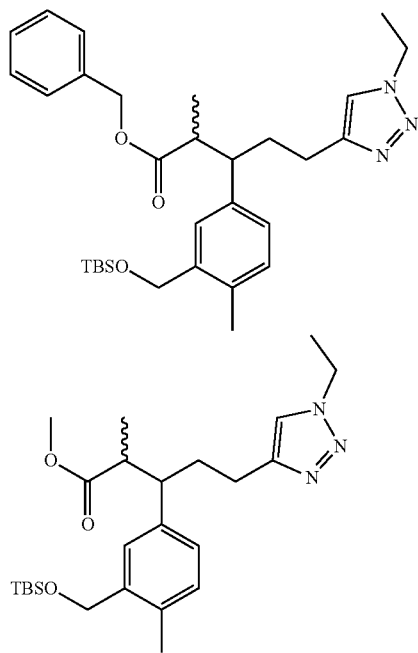

To a solution of benzyl 3-(3-(((tert-butyldimethylsilyl)oxy)methyl)-4-methylphenyl)-5-(1-ethyl-1H-1,2,3-triazol-4-yl)pentanoate (Compound 4B, Scheme B) (1.5 g, 2.87 mmol) and 1,3-dimethyl-3,4,5,6-tetrahydro-2(1H)-pyrimidinone (0.347 mL, 2.87 mmol) in tetrahydrofuran (THF) (20 mL) at −78° C. under argon was added 1M LiHMDS (7.19 mL, 7.19 mmol) and the reaction allowed to stir for 50 min. To the reaction mixture was added 2M methyl iodide (10.06 mL, 20.12 mmol) and the reaction mixture was allowed to stir for 25 min at −78° C. before quenching with MeOH. The reaction was concentrated and the residue was purified by flash chromatography eluting with 0-100% EtOAc/hexane to provide a crude mixture containing the title compounds. This crude material was re-purified by flash chromatography eluting with 0-55% EtOAc/hexane to provide a mixture of the title compounds (0.901 g) This mixture was carried on without further purification. LC/MS [Benzyl ester (Compound 5B, Isomers 1 and 2, Scheme B)] m/z 536.3 [M+H]+, 1.68 min (ret. time). [Methyl ester (Compound 9B, Isomers 1 and 2, Scheme B)] m/z=460.3 (M+H)$^+$, 1.48 min and 1.53 min (ret. time)

Benzyl 5-(1-ethyl-1H-1,2,3-triazol-4-yl)-3-(3-(hydroxymethyl)-4-methylphenyl)-2-methylpentanoate (Compound 6B, Isomers 1 and 2, Scheme B)

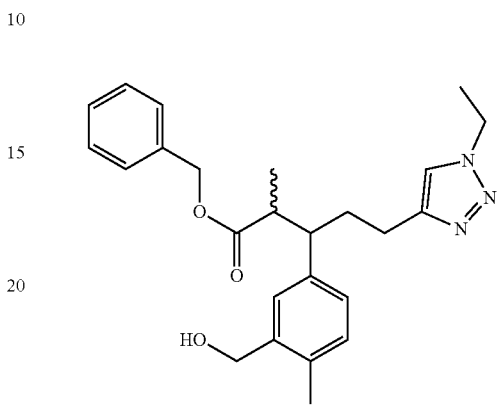

Methyl 5-(1-ethyl-1H-1,2,3-triazol-4-yl)-3-(3-(hydroxymethyl)-4-methylphenyl)-2-methylpentanoate (Compound 13B, Isomers 1 and 2, Scheme D)

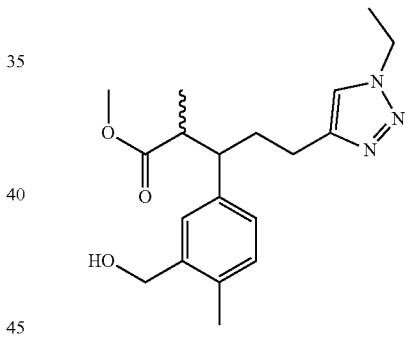

A mixture of benzyl 3-(3-(((tert-butyldimethylsilyl)oxy)methyl)-4-methylphenyl)-5-(1-ethyl-1H-1,2,3-triazol-4-yl)-2-methylpentanoate (Compound 5B, Isomers 1 and 2, Scheme B) and methyl 3-(3-(((tert-butyldimethylsilyl)oxy)methyl)-4-methylphenyl)-5-(1-ethyl-1H-1,2,3-triazol-4-yl)-2-methylpentanoate (Compound 9B, Isomers 1 and 2, Scheme B) (901 mg) were dissolved in tetrahydrofuran (THF) (15 mL) followed by addition of TBAF (1.196 mL, 1.196 mmol). The reaction mixture was allowed to stir for 19 h. The solvent was removed under reduced pressure. The residue was dissolved in EtOAc and washed with 2× water and saturated NaCl. The organic layer was concentrated and the residue was purified by reverse phase preparative HPLC under neutral conditions to provide benzyl 5-(1-ethyl-1H-1,2,3-triazol-4-yl)-3-(3-(hydroxymethyl)-4-methylphenyl)-2-methylpentanoate (Compound 6B, Isomers 1 and 2, Scheme B) (0.091 g) LC/MS m/z 422 (M+H)$^+$, 1.06 min (ret. time), and methyl 5-(1-ethyl-1H-1,2,3-triazol-4-yl)-3-(3-(hydroxymethyl)-4-methylphenyl)-2-methylpentanoate (Compound 13B, Isomers 1 and 2, Scheme D) (0.459 g) LC/MS m/z=346 (M+H)$^+$, 0.78 min and 0.82 min (ret. time)

Benzyl 3-(3-(chloromethyl)-4-methylphenyl)-5-(1-
ethyl-1H-1,2,3-triazol-4-yl)-2-methylpentanoate
(Compound 10B, Isomers 1 and 2, Scheme B)

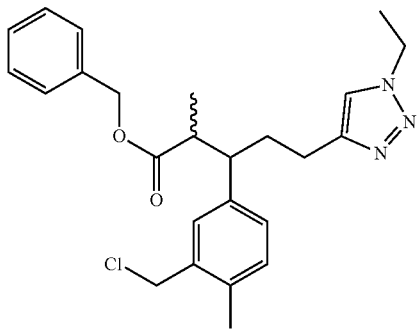 [SMILES: CCn1cc(CCC(c2ccc(C)c(CCl)c2)C(C)C(=O)OCc2ccccc2)nn1]

To a solution of benzyl 5-(1-ethyl-1H-1,2,3-triazol-4-yl)-3-(3-(hydroxymethyl)-4-methylphenyl)-2-methylpentanoate (Compound 6B, Isomers 1 and 2, Scheme B) (95 mg, 0.225 mmol) in dichloromethane (DCM) (3 mL), was added DIEA (0.118 mL, 0.676 mmol) followed by the addition of SOCl$_2$ (0.033 mL, 0.451 mmol) and stirred for 1.5 h in an ice-water bath. The solvent was removed and the residue was purified by flash chromatography eluting with 0-10% MeOH/DCM to provide the title compound as a crude mixture. This mixture was carried on without further purification. (0.079 g) LC/MS m/z=440 (M+H)$^+$, 1.30 min (ret. time).

Benzyl 5-(1-ethyl-1H-1,2,3-triazol-4-yl)-3-(3-((2-
((4-ethylpiperidin-1-yl)methyl)-1H-imidazol-1-yl)
methyl)-4-methylphenyl)-2-methylpentanoate (Compound 7B, Isomers 1 and 2, Scheme B)

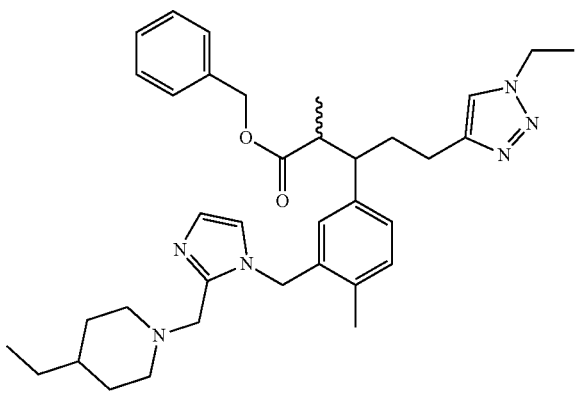 [SMILES: CCC1CCN(Cc2nccn2Cc2cc(C(CCc3cn(CC)nn3)C(C)C(=O)OCc3ccccc3)ccc2C)CC1]

To a solution of 1-((1H-imidazol-2-yl)methyl)-4-ethylpiperidine, trifluoroacetic acid salt (110 mg, 0.359 mmol) in N,N-dimethylformamide (DMF) (3 mL) was added 1M LiHMDS (0.539 mL, 0.539 mmol) and the reaction allowed to stir for 30 min at 0° C. To this reaction mixture was added benzyl 3-(3-(chloromethyl)-4-methylphenyl)-5-(1-ethyl-1H-1,2,3-triazol-4-yl)-2-methylpentanoate (Compound 10B, Isomers 1 and 2, Scheme B) (79 mg, 0.180 mmol). This reaction mixture was allowed to stir for 1 h. To the reaction mixture at 0° C. was added another portion of LiHMDS (0.539 mL, 0.539 mmol). This reaction mixture was allowed to stir for an additional 1 h. To the reaction mixture, at ambient temperature, was added another portion of LiHMDS (0.539 mL, 0.539 mmol). This reaction mixture was allowed to stir for an additional 1 h. The reaction was quenched with saturated aqueous ammonium chloride, diluted with water and extracted with DCM. The organic layers were combined and concentrated under reduced pressure and the residue was purified by flash chromatography eluting with 0-100% (3:1 EtOAc:EtOH)/hexane to provide the title compound. (0.045 g, 42% yield) LC/MS m/z=597 (M+H)$^+$, 1.10 min (ret. time).

(2S,3R)-5-(1-Ethyl-1H-1,2,3-triazol-4-yl)-3-(3-((2-
((4-ethylpiperidin-1-yl)methyl)-1H-imidazol-1-yl)
methyl)-4-methylphenyl)-2-methylpentanoic acid,
Trifluoroacetic acid salt (Compound 8B, Isomers 1
and 2, Scheme B)

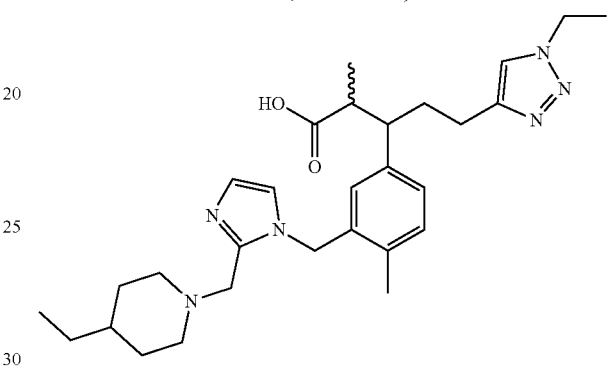

A solution of benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2-methylpentanoate (Compound 16, Isomers 1 and 2, Scheme A) (45 mg, 0.037 mmol), in methanol (10 mL) was hydrogenated in H-cube for 2 h at 40° C. using a 10% Pd—C cartridge and a flow rate of 1 mL/min. The solvent was removed and the residue was purified by reverse phase preparative HPLC using TFA as a solvent modifier to provide the title compound as a mixture of isomers. (0.028 g) LC/MS m/z=507 (M+H)$^+$, 0.76 min (ret. time).

Example 227

3-(3-((2,2-Dimethyl-2,3-dihydropyrido[3,4-f][1,4]
oxazepin-4(5H)-yl)methyl)-4-methylphenyl)-5-(1-
ethyl-1H-1,2,3-triazol-4-yl)-2-methylpentanoic acid,
Trifluoroacetic acid salt (Compound 12B, Isomers 1
and 2, Scheme D)

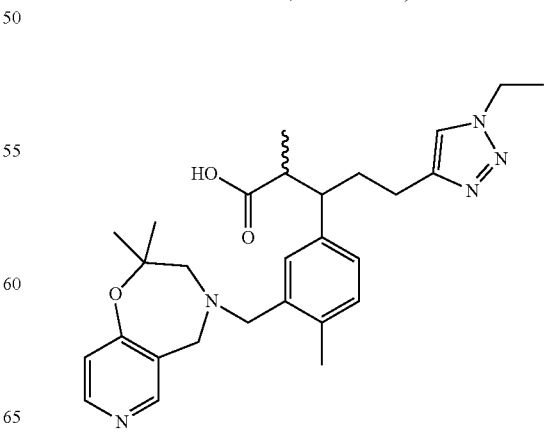

Methyl 3-(3-((2,2-dimethyl-2,3-dihydropyrido[3,4-f]
[1,4]oxazepin-4(5H)-yl)methyl)-4-methylphenyl)-5-
(1-ethyl-1H-1,2,3-triazol-4-yl)-2-methylpentanoate
(Compound 14B, Isomers 1 and 2, Scheme D)

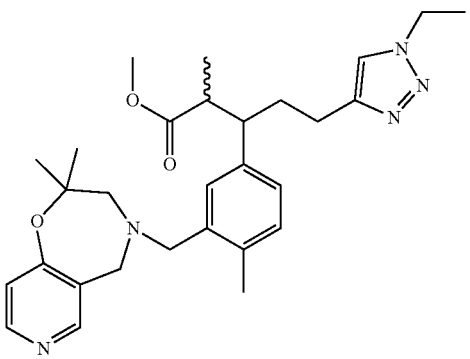 [SMILES: CCn1cc(CCC(c2ccc(C)c(CN3Cc4cnccc4OC(C)(C)C3)c2)C(C)C(=O)OC)nn1]

To a solution of methyl 5-(1-ethyl-1H-1,2,3-triazol-4-yl)-3-(3-(hydroxymethyl)-4-methylphenyl)-2-methylpentanoate (Compound 13B, Isomers 1 and 2, Scheme B) (202 mg, 0.585 mmol) in dichloromethane (DCM) (3 mL), was added DIEA (0.306 mL, 1.754 mmol) followed by the addition of SOCl$_2$ (0.085 mL, 1.170 mmol). This reaction mixture was allowed to stir for 1.5 h in an ice-water bath. The solvent was removed and redissolved in N,N-dimethylformamide (DMF) (3.00 mL). To the reaction mixture was added 2,2-dimethyl-2,3,4,5-tetrahydropyrido[3,4-f][1,4]oxazepine hydrochloride (251 mg, 1.170 mmol) and the reaction heated in microwave at 120° C. for 1 h. The reaction was diluted with water and extracted with DCM. The organic layers were combined and concentrated under reduced pressure. The residue was purified by flash chromatography eluting with 0-80% (3:1 EtOAc:EtOH)/hexane to provide the title compound the title compound as a crude mixture with DMF (0.314 g) LC/MS m/z=506 (M+H)$^+$, 0.91 min and 0.93 min (ret. time). The compound was carried on to next step without further purification.

(2S,3R)-3-(3-((2,2-Dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoic acid, Trifluoroacetic acid salt (Compound 12B, Isomers 1 and 2, Scheme D)

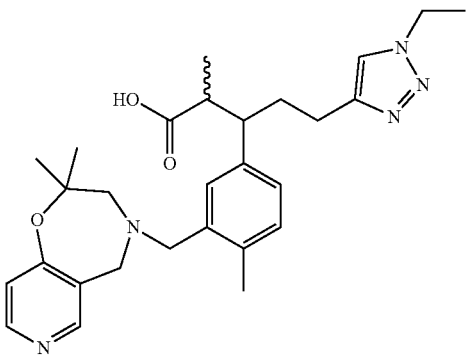 [SMILES: CCn1cc(CCC(c2ccc(C)c(CN3Cc4cnccc4OC(C)(C)C3)c2)C(C)C(=O)O)nn1]

To a solution of methyl 3-(3-((2,2-dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoate (Compound 14B, Isomers 1 and 2, Scheme D) (310 mg, 0.613 mmol) in tetrahydrofuran (THF) (6 mL) was added a solution of LiOH (147 mg, 6.13 mmol) in water (2 mL), followed by the addition of methanol (1 mL). The reaction was allowed to stir at ambient temperature for 19 h. The solvents were evaporated and the aqueous layer was acidified before extracting with DCM. The solvent was removed and the residue was purified by reverse phase preparative HPLC using TFA as a solvent modifier to provide the title compound as a mixture of isomers. (0.094 g, 25% yield) LC/MS m/z=492 (M+H)$^+$, 0.80 min (ret. time).

Example 228

3-(3-((2,2-Dimethyl-2,3-dihydropyrido[3,4-f][1,4]
oxazepin-4(5H)-yl)methyl)-4-methylphenyl)-5-(1-
ethyl-1H-1,2,3-triazol-4-yl)-2-methylpentanoic acid
(Compound 12A, Isomers 1 and 2, Scheme C)

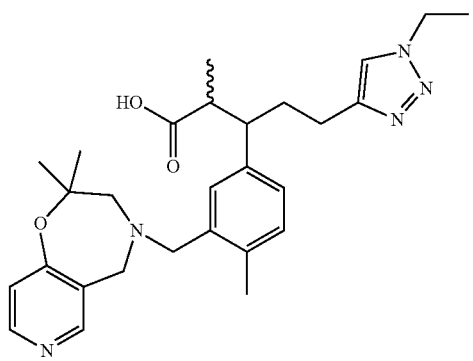 [SMILES: CCn1cc(CCC(c2ccc(C)c(CN3Cc4cnccc4OC(C)(C)C3)c2)C(C)C(=O)O)nn1]

Benzyl 3-(3-((2,2-dimethyl-2,3-dihydropyrido[3,4-f]
[1,4]oxazepin-4(5H)-yl)methyl)-4-methylphenyl)-5-
(1-ethyl-1H-1,2,3-triazol-4-yl)-2-methylpentanoate
(Compound 11, Isomers 1 and 2, Scheme C)

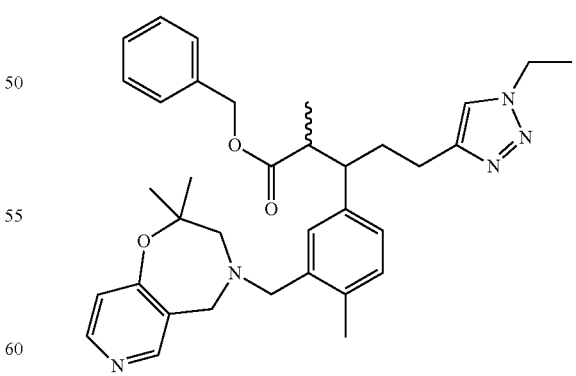

To a solution of benzyl 5-(1-ethyl-1H-1,2,3-triazol-4-yl)-3-(3-(hydroxymethyl)-4-methylphenyl)-2-methylpentanoate (Compound 6A, Isomers 1 and 2, Scheme C) (159 mg, 0.377 mmol) in dichloromethane (DCM) (3 mL), was added DIEA (0.198 mL, 1.132 mmol) followed by the addition of SOCl$_2$ (0.055 mL, 0.754 mmol). This reaction mixture was allowed to stir for 1.5 h in an ice-water bath. The solvent was removed and the residue was redissolved in N,N-dimethylformamide (DMF) (3.00 mL). To the reaction mixture was added 2,2-dimethyl-2,3,4,5-tetrahydropyrido[3,4-f][1,4]oxazepine hydrochloride (162 mg, 0.754 mmol) and the reaction heated in microwave 0 at 120° C. for 1 h. The reaction was diluted with water and extracted with DCM. The organic layers were combined and concentrated under reduced pressure. The residue was purified by flash chromatography eluting with 0-90% (3:1 EtOAc:EtOH)/hexane to provide the title compound the title compound as a crude mixture with DMF (0.245 g) LC/MS m/z=582 (M+H)$^+$, 1.00 min. The compound was carried on to next step without further purification.

3-(3-((2,2-Dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoic acid (Compound 12A, Isomers 1 and 2, Scheme C)

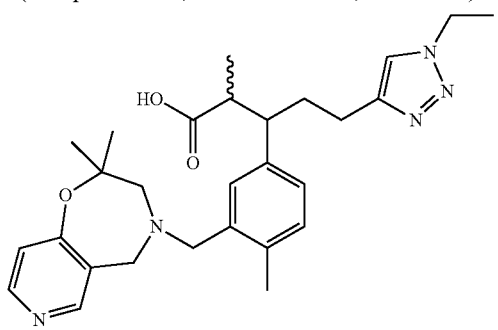

A solution of benzyl 3-(3-((2,2-dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoate (Compound 11A, Isomers 1 and 2, Scheme C) (245 mg, 0.379 mmol) in methanol (15 mL) was hydrogenated in H-cube for 2 h at 30° C. and 20 bar (pressure) using a 10% Pd—C cartridge and a flow rate of 1 mL/min. The solvent was removed and the residue was purified by reverse phase preparative HPLC using TFA as a solvent modifier to provide the title compound. (0.028 g, 15% yield) LC/MS m/z=492 (M+H)$^+$, 0.89 min (ret. time).

Example 229

Benzyl 3-(4-chloro-3-((2-(cycloheptylmethyl)-1H-imidazol-1-yl)methyl)phenyl)-5-(1-ethyl-1H-1,2,3-triazol-4-yl)-2,2-dimethylpentanoate

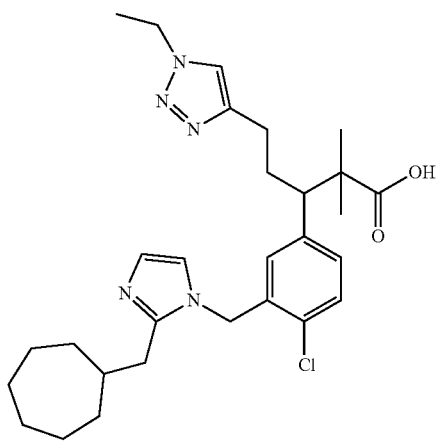 [SMILES: CCn1cc(CCC(c2ccc(Cl)c(Cn3ccnc3CC3CCCCCC3)c2)C(C)(C)C(=O)O)nn1]

(5-Bromo-2-chlorophenyl)methanol

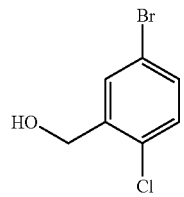

A solution of 5-bromo-2-chlorobenzoic acid (5 g, 21.23 mmol) was dissolved in tetrahydrofuran (THF) (10 mL) at 0° C., then 10M borane-methyl sulfide complex (1.062 mL, 10.62 mmol) was added to the reaction mixture The reaction was warmed to 23° C. and stirred for 14 h. The reaction was cooled on an ice water bath and methanol (2.00 mL) was added slowly. When most of the gas evolution ended the volatile solvents were removed in vacuo. The residue was dissolved in EtOAc (10 mL) and washed with saturated aqueous NaHCO$_3$. The aqueous layer was extracted again with EtOAc (50 mL) and the combined EtOAc was washed with water (5 mL), saturated aqueous NaCl, dried with Na$_2$SO$_4$ and concentrated to provide the title product. (4.624 g, 20.88 mmol, 98% yield) LC/MS m/z=219 (M+H)$^+$, 0.79 min (ret. time).

4-Bromo-1-chloro-2-(((4-methoxybenzyl)oxy)methyl)benzene

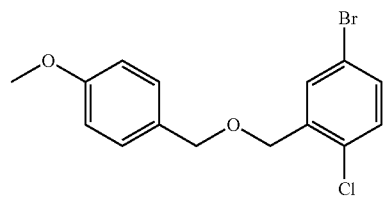 [SMILES: COc1ccc(COCc2cc(Br)ccc2Cl)cc1]

5-bromo-2-chlorophenyl)methanol (5.361 g, 24.21 mmol) was dissolved in N,N-dimethylformamide (DMF) (40 mL) under argon and cooled in an ice-bath at 0° C. 60% sodium hydride (1.936 g, 48.4 mmol) was added carefully in several portions. The reaction was stirred at 23° C. for 1 h then cooled to 10° C., and 1-(chloromethyl)-4-methoxybenzene (4.92 mL, 36.3 mmol) was added. The reaction was stirred at 23° C. for 14 h. The reaction was carefully quenched with water (25 mL) and stirred for 5 min. The reaction was diluted with water (100 mL) and EtOAc (300 mL). The layers were separated and the product was extracted with additional EtOAc (2×200 mL). The combined organics were washed with water (4×100 mL), saturated aqueous NaCl (2×100 mL), and dried with Na$_2$SO$_4$. The solvent was concentrated and the residue was purified by flash chromatography eluting with 0-100% acetone/hexanes to provide the title compound (5.81 g, 15.48 mmol, 63.9% yield) LC/MS m/z=339 (M+H)$^+$, 1.40 min. (ret. time).

5-(Trimethylsilyl)pent-4-ynal

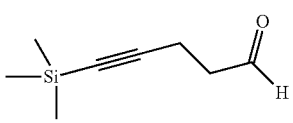

5-(Trimethylsilyl)pent-4-yn-1-ol (6.81 mL, 37.5 mmol) was dissolved in dichloromethane (DCM) (30 mL) and was added portion wise into a solution of Dess-Martin periodinane (19.54 g, 46.1 mmol) in DCM (30 mL) at 0° C. The reaction was diluted with additional dichloromethane (DCM) (10.0 mL) and stirred at ambient temperature for 1 h. The reaction was quenched with sodium thiosulfate (10 g) solution containing NaHCO$_3$. The aqueous layer was washed with DCM (30 mL). The organic layers were combined, dried over Na$_2$SO$_4$, and evaporated. The solvent was concentrated and the residue was purified by flash chromatography eluting with 0-25% acetone/hexanes to provide the title compound (4.78 g, 31.0 mmol, 83% yield). $^1$H NMR (400 MHz, CHLOROFORM-d) δ ppm 0.14 (s, 9H) 2.50-2.57 (m, 2H) 2.63-2.70 (m, 2H) 9.79 (s, 1H)

1-(4-Chloro-3-(((4-methoxybenzyl)oxy)methyl)phenyl)-5-(trimethylsilyl)pent-4-yn-1-ol

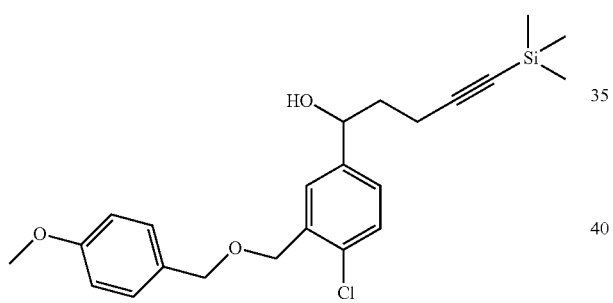

5-(Trimethylsilyl)pent-4-ynal (4.22 g, 27.4 mmol) was dissolved in dry tetrahydrofuran (THF) (81 mL), and stirred with activated molecular sieves for 2 h. In a separate flask, 4-bromo-1-chloro-2-(((4-methoxybenzyl)oxy)methyl)benzene (4.45 g, 13.03 mmol) was dissolved in dry tetrahydrofuran (THF) (81 mL) and stirred with activated molecular sieves for 2 h. This solution was cooled to −78° C. and 1.6M n-butyllithium (9.77 mL, 15.63 mmol) was added to the reaction mixture. Next, 5-(trimethylsilyl)pent-4-ynal (4.22 g, 27.4 mmol) in THF was added slowly and the reaction was stirred in at −78° C. for 2 h. The reaction was diluted with water (25 mL) and EtOAc (75 mL). The aqueous layer was extracted with an additional portion of EtOAc (50 mL) and the combined organics were washed with water (50 mL), saturated aqueous NaCl (50 mL) and dried with Na$_2$SO$_4$. The solvent was concentrated and the residue was purified by reverse phase preparative HPLC under neutral conditions to provide the title compound (1 g, 2.398 mmol, 18.41% yield). $^1$H NMR (400 MHz, CHLOROFORM-d) d ppm 0.11-0.25 (m, 9H) 2.79 (s, 1H) 3.84 (s, 4H) 4.61 (s, 2H) 4.65 (s, 2H) 4.88 (dd, J=7.53, 5.02 Hz, 1H) 6.93 (d, J=8.03 Hz, 3H) 7.24 (d, J=2.01 Hz, 1H) 7.32-7.39 (m, 3H) 7.52 (s, 1H)

(5-Bromo-5-(4-chloro-3-(((4-methoxybenzyl)oxy)methyl)phenyl)pent-1-yn-1-yl)trimethylsilane

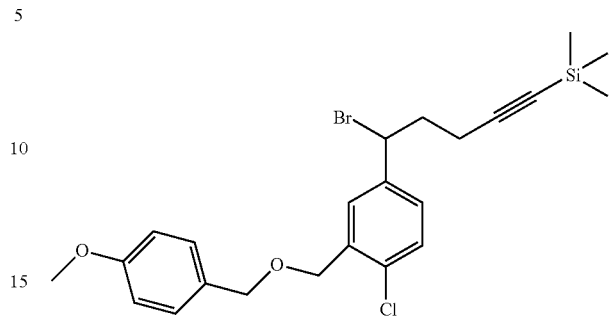

1-(4-Chloro-3-(((4-methoxybenzyl)oxy)methyl)phenyl)-5-(trimethylsilyl)pent-4-yn-1-ol (1 g, 2.398 mmol) was dissolved in dichloromethane (DCM) (48.0 mL). Triphenylphosphine (polymer bound, 2.26 mmol/g) (3.18 g, 7.19 mmol) was added with perbromomethane (0.954 g, 2.88 mmol) and allowed to stir at ambient temperature for 1 h. The solvent was concentrated and the residue was purified by flash chromatography eluting with 0-25% acetone/hexanes to provide the title compound (0.830 g, 1.729 mmol, 72.1% yield). LC/MS m/z=479 (M+H)$^+$, 1.76 min (ret. time).

Benzyl 3-(4-chloro-3-(((4-methoxybenzyl)oxy)methyl)phenyl)-2,2-dimethyl-7-(trimethylsilyl)hept-6-ynoate

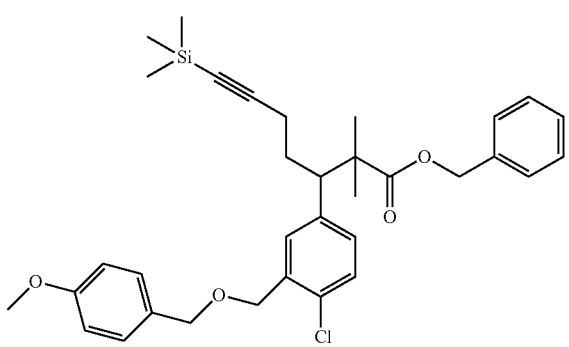 [SMILES: COc1ccc(COCc2cc(C(CCC#C[Si](C)(C)C)C(C)(C)C(=O)OCc3ccccc3)ccc2Cl)cc1]

Diisopropylamine (2.424 mL, 17.29 mmol) was dissolved in tetrahydrofuran (THF) (25.8 mL) and cooled to −70° C. The reaction mixture was treated with 1.6M n-butyllithium (in hexanes) (6.49 mL, 10.38 mmol) and stirred at −70° C. for 15 min, warmed to 0° C. for 15 min, and then re-cooled to −70° C. Benzyl isobutyrate (1.967 mL, 11.07 mmol) in tetrahydrofuran (THF) (25.8 mL) was added to the reaction dropwise and was stirred at −70° C. for 45 min, warmed to −50° C. for 15 min and recooled to −70° C. (5-bromo-5-(4-chloro-3-(((4-methoxybenzyl)oxy)methyl)phenyl)pent-1-yn-1-yl)trimethylsilane (0.830 g, 1.729 mmol), dissolved in tetrahydrofuran (THF) (25.8 mL), was added dropwise to the reaction followed by dry 1,3-dimethyltetrahydropyrimidin-2(1H)-one (4.18 mL, 34.6 mmol). The reaction was stirred for 1 h at −70° C. and then warmed to −45° C. The reaction was diluted with EtOAc (30 mL) and the aqueous phases were extracted with EtOAc (2×). The combined organics were washed with water, saturated aqueous NaCl, and dried with Na$_2$SO$_4$. The solvent was concentrated and the residue was purified by flash chromatography eluting with 0-30% acetone/hexanes to provide the title compound (600 mg, 1.039 mmol, 60.1% yield). LC/MS m/z=578 (M+H)$^+$, 1.83 min (ret. time).

Benzyl 3-(4-chloro-3-(((4-methoxybenzyl)oxy) methyl)phenyl)-2,2-dimethylhept-6-ynoate

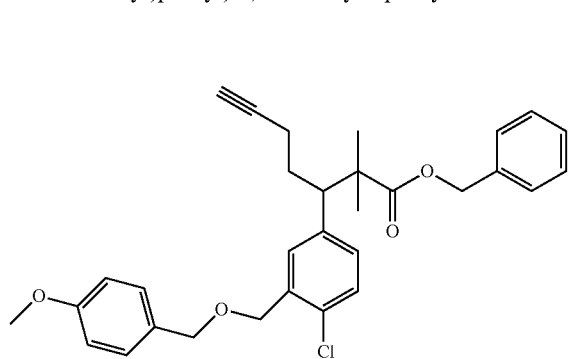

Benzyl 3-(4-chloro-3-(((4-methoxybenzyl)oxy)methyl) phenyl)-2,2-dimethyl-7-(trimethylsilyl)hept-6-ynoate (600 mg, 1.039 mmol) was dissolved in methanol (5.547 mL). Potassium carbonate (718 mg, 5.20 mmol) was added and stirred for 2 h. Afterwards, the solvent was condensed, and the residual oil was diluted with water, and extracted with DCM (3×). The organic layers were dried with MgSO$_4$, and the solvents were removed in vacuo to afford the title compound (400 mg, 0.792 mmol, 76% yield). LC/MS m/z=527 (M+H)$^+$, 1.56 min (ret. time).

Benzyl 3-(4-chloro-3-(((4-methoxybenzyl)oxy) methyl)phenyl)-5-(1-ethyl-1H-1,2,3-triazol-4-yl)-2, 2-dimethylpentanoate

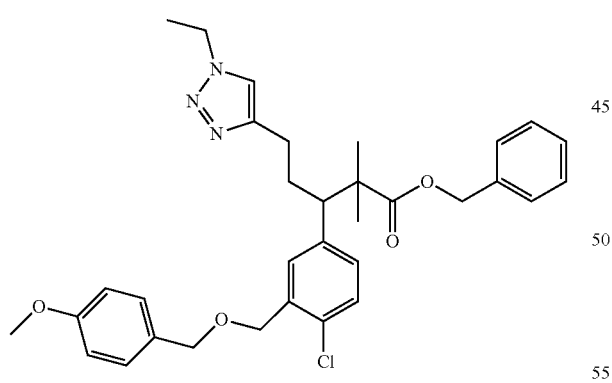

Sodium azide (129 mg, 1.980 mmol), iodoethane (146 μl, 1.822 mmol), copper(I) iodide (22.63 mg, 0.119 mmol), and Hunig's base (27.7 μl, 0.158 mmol) were added to a solution of benzyl 3-(4-chloro-3-(((4-methoxybenzyl)oxy)methyl) phenyl)-2,2-dimethylhept-6-ynoate (400 mg, 0.792 mmol) in tert-butanol (1.9 mL)) and water (1.9 mL) and then heated via microwave at 70° C. for 1 h. The reaction was cooled, diluted with EtOAc (150 mL) and water (50 mL). The aqueous portion was extracted again with EtOAc (75 mL) and the combined organics were washed with water (50 mL), saturated aqueous NaCl (25 mL), and dried with Na$_2$SO$_4$. The solvent was concentrated and the residue was purified by flash chromatography eluting with 0-70% acetone/hexanes to provide the title compound (400 mg, 0.597 mmol, 75% yield). LC/MS m/z=576 (M+H)$^+$, 1.48 min (ret. time).

Benzyl 3-(4-chloro-3-(hydroxymethyl)phenyl)-5-(1-ethyl-1H-1,2,3-triazol-4-yl)-2,2-dimethylpentanoate

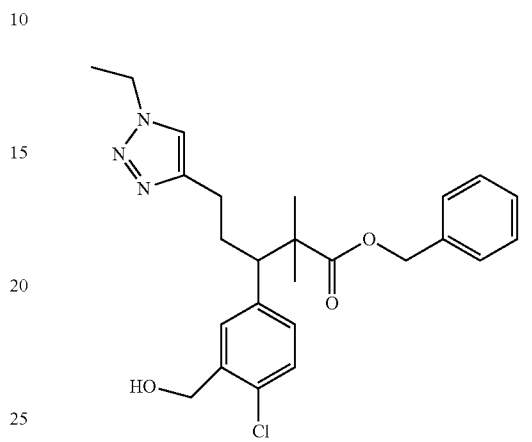

Benzyl 3-(4-chloro-3-(((4-methoxybenzyl)oxy)methyl) phenyl)-5-(1-ethyl-1H-1,2,3-triazol-4-yl)-2,2-dimethylpentanoate (810 mg, 1.406 mmol) was dissolved in acetonitrile (6.5 mL) and was combined with ceric ammonium nitrate (2312 mg, 4.22 mmol) and water (0.725 mL) and stirred 1 h. The reaction was diluted with EtOAc (100 mL) and water (50 mL), and the phases were separated. The aqueous phase was extracted again with EtOAc (50 mL) and the combined organics were washed with water (50 mL), saturated aqueous NaCl and dried with Na$_2$SO$_4$. The solvent was concentrated and the residue was purified by flash chromatography eluting with 0-30% acetone/hexanes to provide the title compound (510 mg, 1.051 mmol, 74.8% yield). LC/MS m/z=456 (M+H)$^+$, 1.11 min (ret. time)

Benzyl 3-(4-chloro-3-((2-(cycloheptylmethyl)-1H-imidazol-1-yl)methyl)phenyl)-5-(1-ethyl-1H-1,2,3-triazol-4-yl)-2,2-dimethylpentanoate

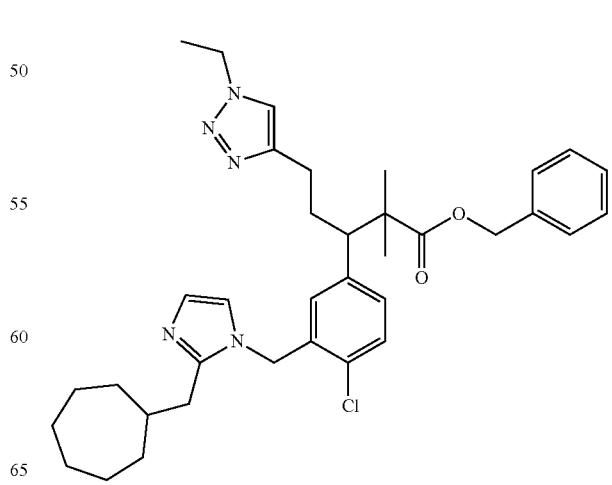

To a solution of benzyl 3-(4-chloro-3-(hydroxymethyl)phenyl)-5-(1-ethyl-1H-1,2,3-triazol-4-yl)-2,2-dimethylpentanoate (40 mg, 0.088 mmol) in dichloromethane (DCM) (6 mL) was added thionyl chloride (0.016 mL, 0.219 mmol) and stirred at ambient temperature for 30 min. The solvent was removed and the residue was dissolved in acetonitrile (6.00 mL). DIEA (0.115 mL, 0.658 mmol) and 2-(cycloheptylmethyl)-1H-imidazole (39 mg, 0.219 mmol) were then added and the reaction was heated via microwave to 120° C. for 2.5 h. The solvent was then concentrated and the residue was purified by reverse phase preparative HPLC under neutral conditions to provide the title compound. (45 mg, 0.073 mmol, 83% yield) LC/MS m/z=616 (M+H)+, 1.2 min (ret. time).

Benzyl 3-(4-chloro-3-((2-(cycloheptylmethyl)-1H-imidazol-1-yl)methyl)phenyl)-5-(1-ethyl-1H-1,2,3-triazol-4-yl)-2,2-dimethylpentanoate

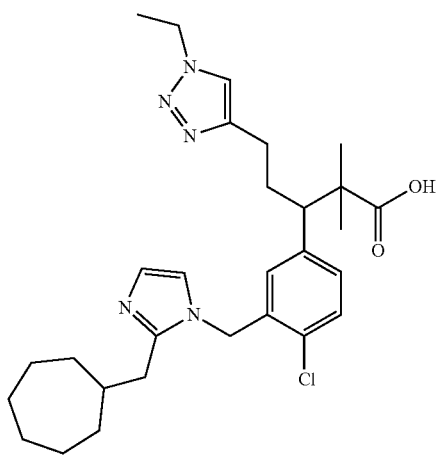 [SMILES: CCn1cc(CCC(c2ccc(Cl)c(Cn3ccnc3CC3CCCCCC3)c2)C(C)(C)C(=O)O)nn1]

Benzyl 3-(4-chloro-3-((2-(cycloheptylmethyl)-1H-imidazol-1-yl)methyl)phenyl)-5-(1-ethyl-1H-1,2,3-triazol-4-yl)-2,2-dimethylpentanoate (40 mg, 0.065 mmol) was dissolved in tetrahydrofuran (THF) (2.000 mL), water (1.000 mL) and methanol (2 mL) in a 2.5 mL Biotage microwave reaction vessel. Lithium hydroxide (7.77 mg, 0.325 mmol) was added and the reaction mixture was heated via microwave at 100° C. for 2 h. The reaction was made acidic using 10% formic acid. The solvent was concentrated and the residue was purified by reverse phase preparative HPLC using formic acid as a solvent modifier to provide the title compound (12 mg, 0.022 mmol, 34.4% yield). LC/MS m/z=575 (M+H)+, 0.93 min (ret. time).

Example 230

3-(4-Chloro-3-((2-((4-ethylpiperidin-1-yl)methyl)-1H-imidazol-1-yl)methyl)phenyl)-5-(1-ethyl-1H-1,2,3-triazol-4-yl)-2,2-dimethylpentanoic Acid

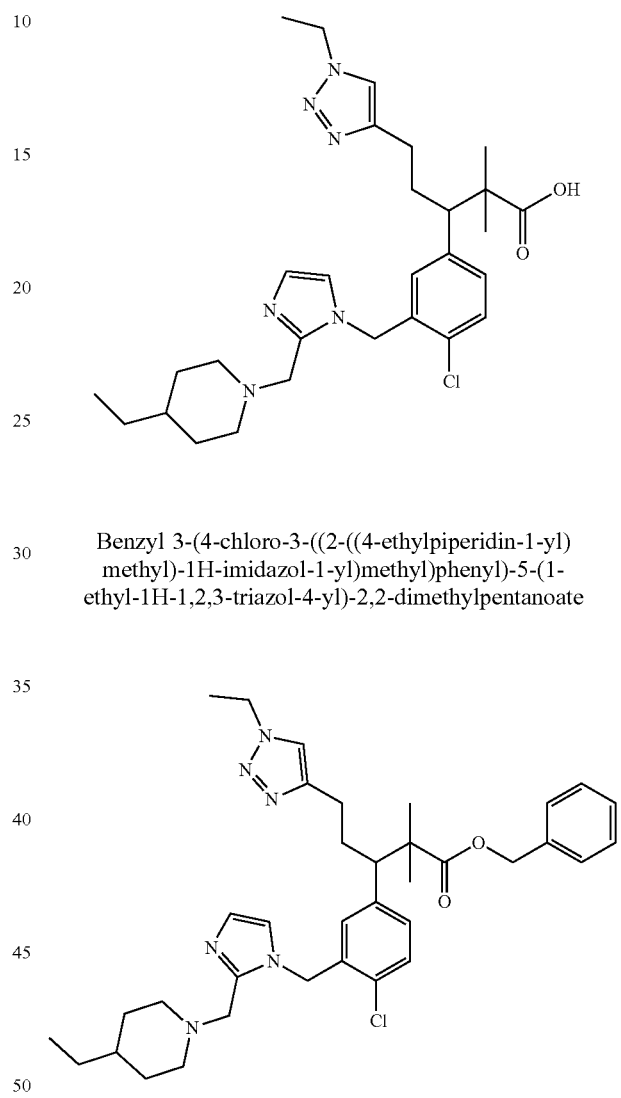

Benzyl 3-(4-chloro-3-((2-((4-ethylpiperidin-1-yl)methyl)-1H-imidazol-1-yl)methyl)phenyl)-5-(1-ethyl-1H-1,2,3-triazol-4-yl)-2,2-dimethylpentanoate To a solution of benzyl 3-(4-chloro-3-(hydroxymethyl)phenyl)-5-(1-ethyl-1H-1,2,3-triazol-4-yl)-2,2-dimethylpentanoate (85 mg, 0.186 mmol) in dichloromethane (DCM) (6 mL) was added thionyl chloride (0.016 mL, 0.219 mmol). The resulting reaction solution was stirred at ambient temperature for 30 min. The solvent was removed and the residue was dissolved in acetonitrile (6.00 mL) and DIEA (0.160 mL, 0.916 mmol) and 1-((1H-imidazol-2-yl)methyl)-4-ethylpiperidine (48.0 mg, 0.248 mmol) was added. The reaction was heated via microwave to 120° C. for 2 h. The solvent was concentrated and the residue was purified by reverse phase preparative HPLC using formic acid as a solvent modifier to provide the title compound (112 mg, 0.177 mmol, 95% yield). LC/MS m/z=631 (M+H)+, 1.09 min (ret. time).

489

3-(4-Chloro-3-((2-((4-ethylpiperidin-1-yl)methyl)-1H-imidazol-1-yl)methyl)phenyl)-5-(1-ethyl-1H-1,2,3-triazol-4-yl)-2,2-dimethylpentanoic acid

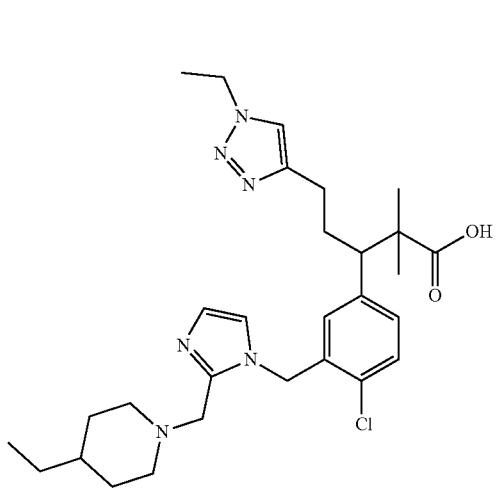 [SMILES: CCC1CCN(Cc2nccn2Cc2cc(C(CCc3cn(CC)nn3)C(C)(C)C(=O)O)ccc2Cl)CC1]

Benzyl 3-(4-chloro-3-((2-((4-ethylpiperidin-1-yl)methyl)-1H-imidazol-1-yl)methyl)phenyl)-5-(1-ethyl-1H-1,2,3-triazol-4-yl)-2,2-dimethylpentanoate (112 mg, 0.177 mmol) was dissolved in tetrahydrofuran (THF) (1.000 mL), water (1.000 mL) and MeOH (2 mL). Lithium hydroxide (21.25 mg, 0.887 mmol) was added to the reaction mixture and the mixture heated via microwave at 100° C. for 1 h. The reaction was quenched using 10% formic acid. The solvent was concentrated and the residue was purified by reverse phase preparative HPLC using formic acid as a solvent modifier to provide the title compound (13 mg, 0.024 mmol, 13.54%). LC/MS m/z=541 (M+H)$^+$, 0.86 min (ret. time).

Example 231

3-(4-Chloro-3-(((R)-2-ethyl-2,3-dihydropyrido[2,3-f][1,4]oxazepin-4(5H)-yl)methyl)phenyl)-5-(1-ethyl-1H-1,2,3-triazol-4-yl)pentanoic Acid

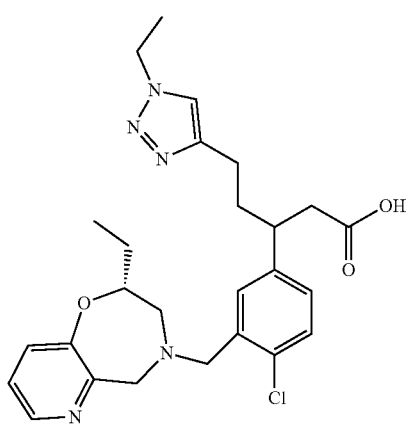 [SMILES: CC[C@@H]1CN(Cc2cc(C(CCc3cn(CC)nn3)CC(=O)O)ccc2Cl)Cc2ncccc2O1]

490

Benzyl 3-(4-chloro-3-(hydroxymethyl)phenyl)-5-(1-ethyl-1H-1,2,3-triazol-4-yl)pentanoate

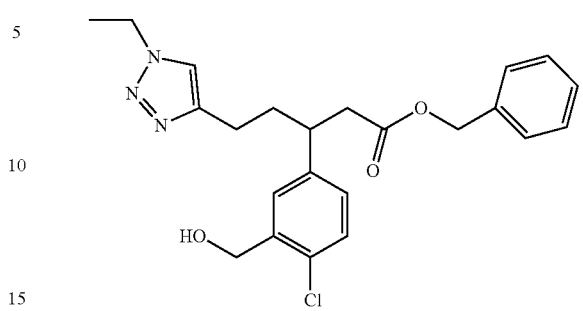

(E)-Benzyl 5-(1-ethyl-1H-1,2,3-triazol-4-yl)pent-2-enoate (0.5 g, 1.752 mmol), (2-chloro-5-(4,4,5,5-tetramethyl-1,3,2-dioxaborolan-2-yl)phenyl)methanol (1.035 g, 3.86 mmol), and chloro(1,5-cyclooctadiene)rhodium(I) dimer (0.086 g, 0.175 mmol) were all dissolved in 1,4-dioxane (10.00 mL) and water (5 mL). The mixture was degassed with argon, after which, triethylamine (1.465 mL, 10.51 mmol) was added. The reaction mixture was heated to 90° C. and stirred overnight. Additional (2-chloro-5-(4,4,5,5-tetramethyl-1,3,2-dioxaborolan-2-yl)phenyl)methanol (1.035 g, 3.86 mmol), chloro(1,5-cyclooctadiene)rhodium(I) dimer (0.086 g, 0.175 mmol) and triethylamine (1.465 mL, 10.51 mmol) were then added and heating was continued at 90° C. for 3 h. The solvent was concentrated and the residue was purified by flash chromatography eluting with 0-90% acetone/hexanes to provide the title compound. (40 mg, 0.080 mol, 4.59% yield) LC/MS m/z=427 (M+H)$^+$, 1.05 min (ret. time).

Benzyl 3-(4-chloro-3-(((R)-2-ethyl-2,3-dihydropyrido[2,3-f][1,4]oxazepin-4(5H)-yl)methyl)phenyl)-5-(1-ethyl-1H-1,2,3-triazol-4-yl)pentanoate

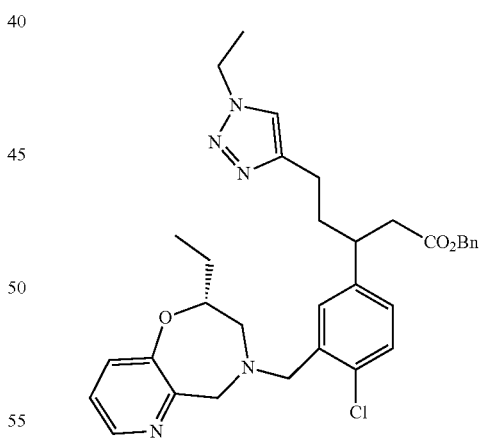

To a solution of benzyl 3-(4-chloro-3-(hydroxymethyl)phenyl)-5-(1-ethyl-1H-1,2,3-triazol-4-yl)pentanoate (0.080 g, 0.187 mmol) in dichloromethane (DCM) (6 mL) was added thionyl chloride (0.027 mL, 0.374 mmol) and stirred at ambient temperature for 30 min. The solvent was removed and the residue was dissolved in acetonitrile (10.00 mL). (R)-2-ethyl-2,3,4,5-tetrahydropyrido[2,3-f][1,4]oxazepine (0.037 g, 0.206 mmol) and DIEA (0.131 mL, 0.748 mmol) were added to the solution and the solution heated via microwave to 120° C. for 1.5 h. The solvent was concentrated and the residue was purified by flash chromatography eluting with 0-40% acetone/hexanes to provide the title compound (0.075 g, 68.2% yield). LC/MS m/z=588 (M+H)+, 1.05 min (ret. time).

3-(4-Chloro-3-(((R)-2-ethyl-2,3-dihydropyrido[2,3-f][1,4]oxazepin-4(5H)-yl)methyl)phenyl)-5-(1-ethyl-1H-1,2,3-triazol-4-yl)pentanoic acid

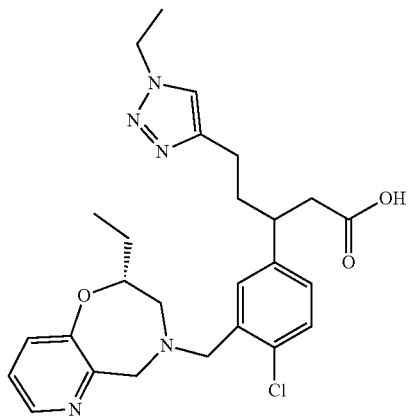 [SMILES: CC[C@@H]1CN(Cc2cc(C(CCc3cn(CC)nn3)CC(=O)O)ccc2Cl)Cc2ncccc2O1]

To a solution of benzyl 3-(4-chloro-3-(((R)-2-ethyl-2,3-dihydropyrido[2,3-f][1,4]oxazepin-4(5H)-yl)methyl)phenyl)-5-(1-ethyl-1H-1,2,3-triazol-4-yl)pentanoate (75 mg, 0.128 mmol) in tetrahydrofuran (THF) (2.0 mL) and water (1 mL) was added lithium hydroxide (15.27 mg, 0.638 mmol). The resulting reaction mixture was stirred at ambient temperature for 1 h. The reaction was acidified with 10% formic acid, the solvent was concentrated and the residue was purified by reverse phase preparative HPLC using formic acid as a solvent modifier to provide the title compound (25 mg, 0.050 mmol, 39.4% yield). LC/MS m/z=498 (M+H)+, 0.84 min (ret. time).

Example 232

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoic Acid

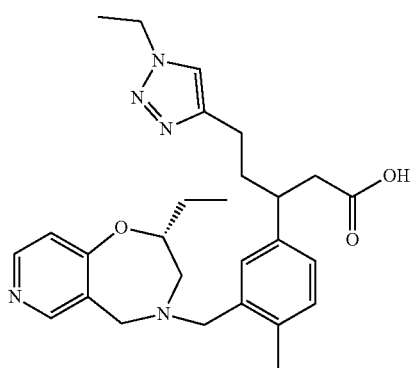 [SMILES: CC[C@@H]1CN(Cc2cc(C(CCc3cn(CC)nn3)CC(=O)O)ccc2C)Cc2cnccc2O1]

Ethyl 5-(1-ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoate

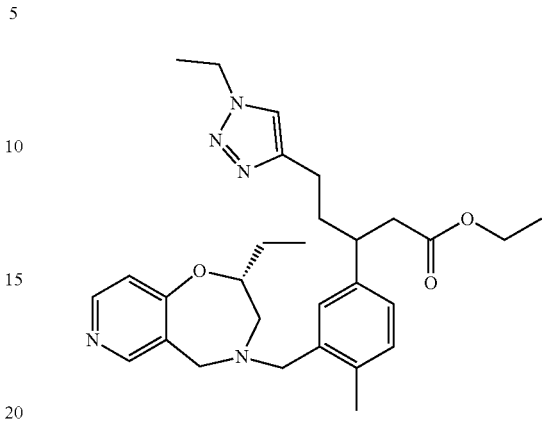

To a solution of ethyl 5-(1-ethyl-1H-1,2,3-triazol-4-yl)-3-(3-(hydroxymethyl)-4-methylphenyl)pentanoate (60 mg, 0.174 mmol) in dichloromethane (DCM) (6 mL) was added thionyl chloride (0.025 mL, 0.347 mmol) and the resulting solution stirred at ambient temperature for 30 min. The solvent was removed and the residue was dissolved in acetonitrile (10.00 mL). To this solution was added (R)-2-ethyl-2,3,4,5-tetrahydropyrido[3,4-f][1,4]oxazepine (49.5 mg, 0.278 mmol) and DIEA (0.182 mL, 1.042 mmol). The reaction was heated via microwave to 120° C. for 2 h. The solvent was concentrated and the residue was purified by flash chromatography eluting with 0-75% acetone/hexanes to provide the title compound (25 mg, 0.046 mmol, 26.5% yield). LC/MS m/z=506 (M+H)+, 0.86 min (ret. time)

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoic Acid

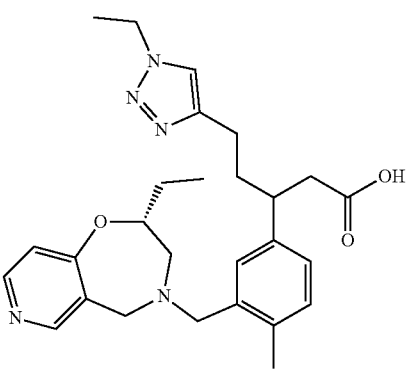 [SMILES: CC[C@@H]1CN(Cc2cc(C(CCc3cn(CC)nn3)CC(=O)O)ccc2C)Cc2cnccc2O1]

To a solution of ethyl 5-(1-ethyl-1H-1,2,3-triazol-4-yl)-3-(3-(((R)-2-ethyl-2,3-dihydropyrido[3,4-f][1,4]oxazepin-4 (5H)-yl)methyl)-4-methylphenyl)pentanoate (20 mg, 0.040 mmol) in tetrahydrofuran (THF) (2.000 mL) and water (1 mL) was added lithium hydroxide (4.74 mg, 0.198 mmol) and the reaction mixture stirred at ambient temperature for 1 h after which time additional lithium hydroxide (0.947 mg, 0.040 mmol) was added to the reaction mixture. The reaction was heated via microwave to 120° C. for 2 h The solvent was concentrated and the residue was purified by reverse phase

Example 233

3-(4-Chloro-3-((2,2-dimethyl-2,3-dihydropyrido[3,2-f][1,4]oxazepin-4(5H)-yl)methyl)phenyl)-5-(1-ethyl-1H-1,2,3-triazol-4-yl)pentanoic Acid

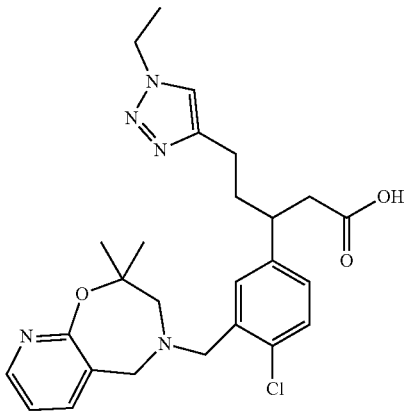 [SMILES: CCn1cc(CCC(CC(=O)O)c2ccc(Cl)c(CN3Cc4cccnc4OC(C)(C)C3)c2)nn1]

Benzyl 3-(4-chloro-3-((2,2-dimethyl-2,3-dihydropyrido[3,2-f][1,4]oxazepin-4(5H)-yl)methyl)phenyl)-5-(1-ethyl-1H-1,2,3-triazol-4-yl)pentanoate

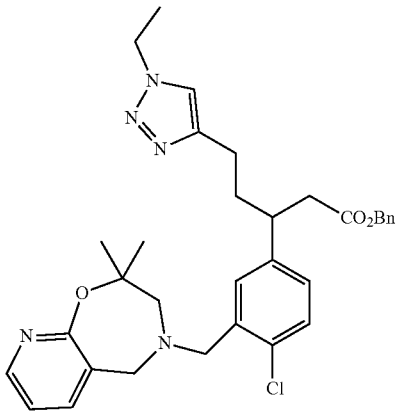 [SMILES: CCn1cc(CCC(CC(=O)OCc2ccccc2)c2ccc(Cl)c(CN3Cc4cccnc4OC(C)(C)C3)c2)nn1]

To a solution of benzyl 3-(4-chloro-3-(hydroxymethyl)phenyl)-5-(1-ethyl-1H-1,2,3-triazol-4-yl)pentanoate (80 mg, 0.187 mmol) in dichloromethane (DCM) (5.00 mL) was added thionyl chloride (0.027 mL, 0.374 mmol) and the solution stirred at ambient temperature for 30 min. The solvent was removed and the residue was dissolved in acetonitrile (10 mL). 2,2-dimethyl-2,3,4,5-tetrahydropyrido[3,2-f][1,4]oxazepine (36.7 mg, 0.206 mmol) and DIEA (0.033 mL, 0.187 mmol) was added to the mixture and the reaction heated via microwave to 120° C. for 1.5 h. The solvent was concentrated and the residue was purified by flash chromatography eluting with 0-40% acetone/hexanes to provide the title compound (0.043 g, 35.6% yield). LC/MS m/z=588 (M+H)⁺, 1.05 min (ret. time).

preparative HPLC using formic acid as a solvent modifier to provide the title compound (1 g, 2.398 mmol, 18.41% yield). LC/MS m/z=478 (M+H)⁺, 0.72 min (ret. time).

3-(4-Chloro-3-((2,2-dimethyl-2,3-dihydropyrido[3,2-f][1,4]oxazepin-4(5H)-yl)methyl)phenyl)-5-(1-ethyl-1H-1,2,3-triazol-4-yl)pentanoic Acid

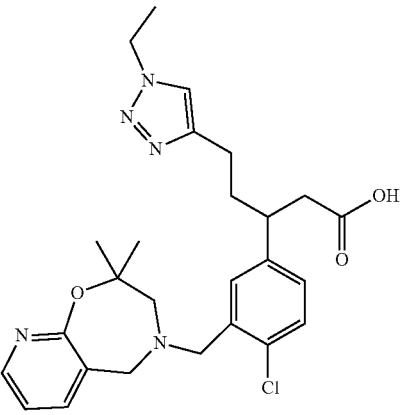 [SMILES: CCn1cc(CCC(CC(=O)O)c2ccc(Cl)c(CN3Cc4cccnc4OC(C)(C)C3)c2)nn1]

To a solution of benzyl 3-(4-chloro-3-((2,2-dimethyl-2,3-dihydropyrido[3,2-f][1,4]oxazepin-4(5H)-yl)methyl)phenyl)-5-(1-ethyl-1H-1,2,3-triazol-4-yl)pentanoate (75 mg, 0.128 mmol) in tetrahydrofuran (THF) (2.0 mL) and water (1 mL) was added lithium hydroxide (15.27 mg, 0.638 mmol) and stirred at ambient temperature for 2 h. The reaction was acidified with 10% formic acid. The solvent was concentrated and the residue was purified by reverse phase preparative HPLC using formic acid as a solvent modifier to provide the title compound (18 mg, 0.036 mmol, 28.3% yield). LC/MS m/z=498 (M+H)⁺, 0.74 min (ret. time).

Example 234

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)-N-(methylsulfonyl)pentanamide

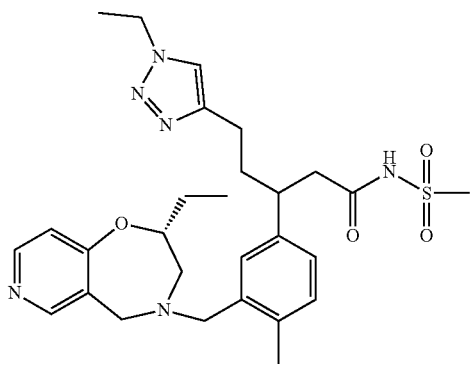 [SMILES: CC[C@@H]1CN(Cc2cc(C(CCc3cn(CC)nn3)CC(=O)NS(C)(=O)=O)ccc2C)Cc2cnccc2O1]

Ethyl 5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoate

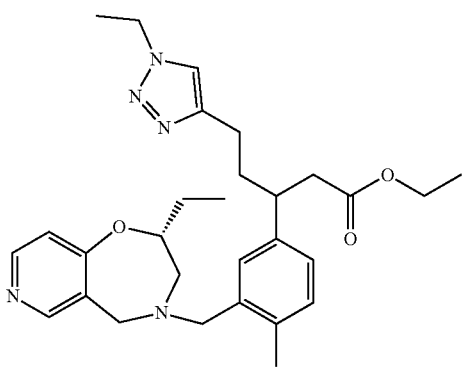 [SMILES: CCOC(=O)CC(CCc1cn(CC)nn1)c1ccc(C)c(CN2Cc3cnccc3O[C@H](CC)C2)c1]

To a solution of ethyl 5-(1-ethyl-1H-1,2,3-triazol-4-yl)-3-(3-(hydroxymethyl)-4-methylphenyl)pentanoate (60 mg, 0.135 mmol) in dichloromethane (DCM) (6 mL) was added thionyl chloride (0.020 mL, 0.271 mmol) and stirred at ambient temperature for 30 min. The solvent was removed and the residue was dissolved in acetonitrile (10.00 mL). (R)-2-ethyl-2,3,4,5-tetrahydropyrido[3,4-f][1,4]oxazepine (38.6 mg, 0.217 mmol) and DIEA (0.142 mL, 0.813 mmol) were added to the reaction mixture which was heated via microwave to 120° C. for 2 h. The solvent was concentrated and the residue was purified by flash chromatography eluting with 0-75% acetone/hexanes to provide the title compound (48 mg, 0.095 mmol, 70.1% yield). LC/MS m/z=506 (M+H)+, 0.88 min (ret. time).

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoic Acid

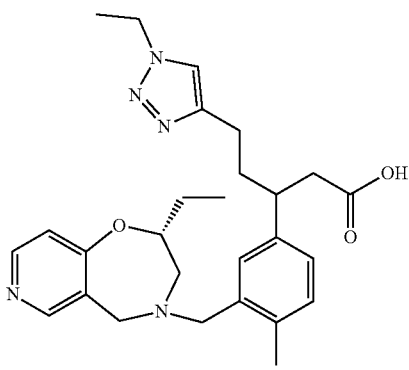 [SMILES: CC[C@@H]1CN(Cc2cc(C(CCc3cn(CC)nn3)CC(=O)O)ccc2C)Cc2cnccc2O1]

To a solution of ethyl 5-(1-ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoate (48 mg, 0.095 mmol) in tetrahydrofuran (THF) (2.000 mL) and water (1 mL), was added lithium hydroxide (11.37 mg, 0.475 mmol) and stirred at ambient temperature after which the reaction mixture was heated via microwave at 70° C. for 1 h. The solvent was concentrated and the residue was purified by reverse phase preparative HPLC using formic acid as a solvent modifier to provide the title compound (20 mg, 0.042 mmol, 44.1% yield). LC/MS m/z=478 (M+H)+, 0.71 min (ret. time).

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)-N-(methylsulfonyl)pentanamide

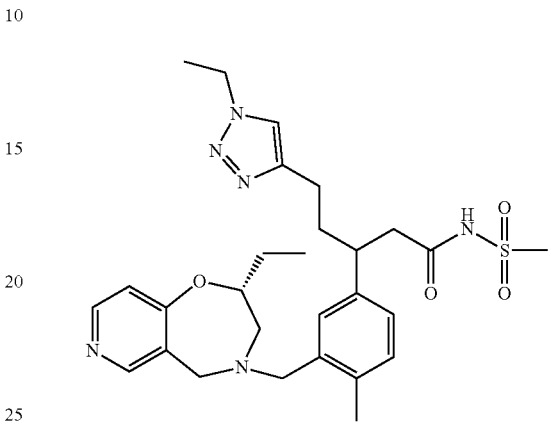

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoic acid (20 mg, 0.042 mmol) was dissolved in dichloromethane (DCM) (2 mL) and added to a solution of EDC (24.08 mg, 0.126 mmol), DMAP (15.35 mg, 0.126 mmol), TEA (0.035 mL, 0.251 mmol) in dichloromethane (DCM) (2 mL). The reaction mixture was allowed to stir for 20 min at ambient temperature. Methanesulfonamide (19.92 mg, 0.209 mmol) was then added and the reaction was allowed to stir for an additional 43 h at ambient temperature. The solvent was concentrated and the residue was purified by reverse phase preparative HPLC using formic acid as a solvent modifier to provide the title compound (10 mg, 0.018 mmol, 43.0% yield). LC/MS m/z=555 (M+H)+, 0.7 min (ret. time).

Example 235

(S)-3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic Acid

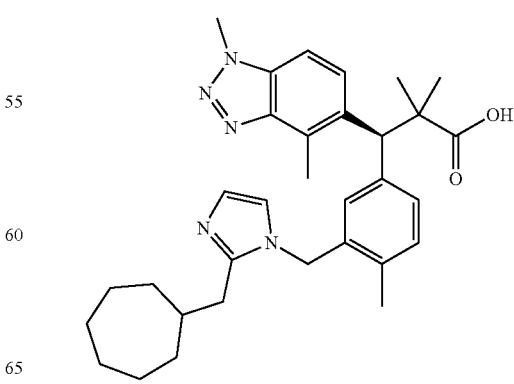

497

Methyl 3-(3-(chloromethyl)-4-methylphenyl)-3-(1,4-dimethyl-1H-benzo[d][1,2,3]triazol-5-yl)-2,2-dimethylpropanoate

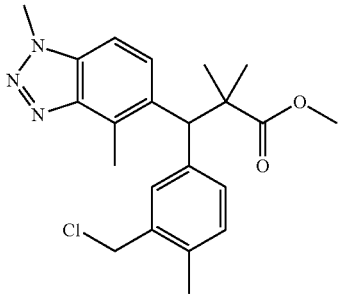 [SMILES: COC(=O)C(C)(C)C(c1ccc(C)c(CCl)c1)c1ccc2c(nnn2C)c1C]

To a solution of methyl 3-(1,4-dimethyl-1H-benzo[d][1,2,3]triazol-5-yl)-3-(3-(hydroxymethyl)-4-methylphenyl)-2,2-dimethylpropanoate (4.0 g, 10.49 mmol) in dichloromethane (DCM) (20 mL) SOCl₂ (1.531 mL, 20.97 mmol) was added slowly. The reaction mixture was stirred at ambient temperature for 1 h and 15 min. The solvent was evaporated to obtain the title compound methyl 3-(3-(chloromethyl)-4-methylphenyl)-3-(1,4-dimethyl-1H-benzo[d][1,2,3]triazol-5-yl)-2,2-dimethypropanoate (4.0 g, 95% yield) which was carried to the next step without further purification. LC/MS m/z 400.0 (M+H)⁺, 1.23 (ret. time).

(S)-Methyl 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate

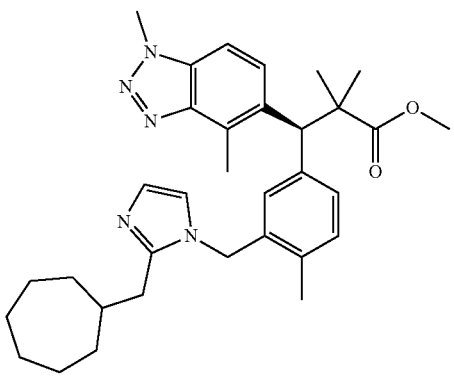 [SMILES: COC(=O)C(C)(C)[C@@H](c1ccc(C)c(Cn2ccnc2CC2CCCCCC2)c1)c1ccc2c(nnn2C)c1C]

To a solution of 2-(cycloheptylmethyl)-1H-imidazole (2.67 g, 15.00 mmol) in N,N-dimethylformamide (DMF) (10 mL), NaH (0.720 g, 30.0 mmol)methyl 3-(3-(chloromethyl)-4-methylphenyl)-3-(1,4-dimethyl-1H-benzo[d][1,2,3]triazol-5-yl)-2,2-dimethylpropanoate (4.0 g, 10.00 mmol) was added slowly at ambient temperature. The reaction mixture was stirred at ambient temperature for 16 h. The reaction mixture was partitioned between ethyl acetate and water. The water layer was extracted with ethyl acetate (2×). The combined organic phase was washed with brine and dried over MgSO₄ and concentrated. The crude product was purified by silica gel chromatography (hexane:ethyl acetate in EtOH=3:1) to obtain methyl 3-(3-((2-(cycloheptylmethyl)-1H-imidazol-1-yl)methyl)-4-methylphenyl)-3-(1,4-

498 dimethyl-1H-benzo[d][1,2,3]triazol-5-yl)-2,2-dimethylpropanoate (5.2 g, 96% yield) which was separated by Chiral SFC (Column: Chiralpak AD 20×150 mm; Co-solvent: 20% MeOH:IPA (1:1); Flowrate: 50 g/min; Back pressure: 100 Bar) to obtain the title compound (S)-Methyl 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate (2.3 g, 42.4% yield) (chiral SFC ret. time: 4.32 min). LC/MS m/z 542.4 (M+H)⁺, 1.03 (ret. time).

(S)-3-(3-((2-(Cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic Acid

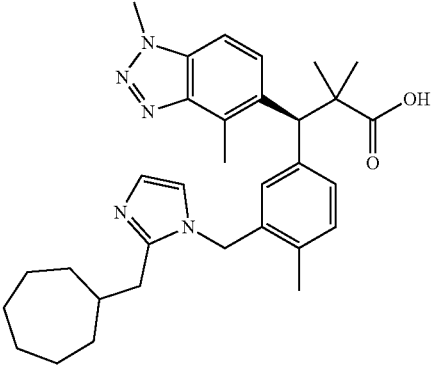 [SMILES: Cc1ccc([C@@H](c2ccc3c(nnn3C)c2C)C(C)(C)C(=O)O)cc1Cn1ccnc1CC1CCCCCC1]

To a solution of (S)-methyl 3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoate (2.3 g, 4.25 mmol) LiOH (2M, 12.74 mL, 25.5 mmol) was added. The reaction mixture was heated via microwave at 120° C. for 2 h 15 min. The solvent was evaporated and the residue was partitioned between 1 N HCl and ethyl acetate. The water layer was extracted with ethyl acetate (2×). The combined organic phase was dried over MgSO₄ and concentrated to get 1.930 g of the crude product which was crystallized from EtOH to obtain the title compound (S)-3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic acid (1.0965 g, 48.1% yield). LC/MS m/z 528.3 (M+H)⁺, 0.91 (ret. time).

Example 236

3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic Acid

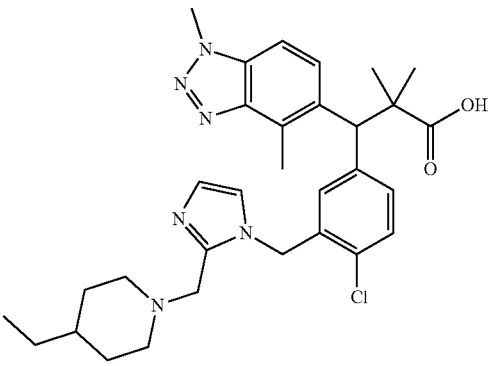 [SMILES: CCC1CCN(Cc2nccn2Cc2cc(C(c3ccc4c(nnn4C)c3C)C(C)(C)C(=O)O)ccc2Cl)CC1]

499

((5-Bromo-2-chlorobenzyl)oxy)(tert-butyl)dimethylsilane

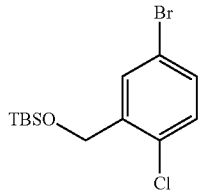 [SMILES: CC(C)(C)[Si](C)(C)OCc1cc(Br)ccc1Cl]

To a solution of (5-bromo-2-chlorophenyl)methanol (12 g, 54.2 mmol) in dichloromethane (DCM) (150 mL), tert-butylchlorodimethylsilane (12.25 g, 81 mmol) and 1H-imidazole (7.38 g, 108 mmol) were added. The reaction mixture was stirred at 0° C. to 25° C. for 2 h. The reaction mixture was quenched with water and extracted with DCM (3×). The combined organic layer was washed with water (2×), brine (2×), dried over Na$_2$SO$_4$ and concentrated. The residue was purified by silica gel chromatography (petroleum ether:ethyl acetate=1:10) to obtain the title compound ((5-bromo-2-chlorobenzyl)oxy)(tert-butyl)dimethylsilane (16 g, 39.1 mmol, 72.1% yield) as a colorless oil. $^1$H NMR (CDCl$_3$, 500 MHz): 7.72-7.71 (m, 1H), 7.35-7.33 (m, 1H), 7.20-7.18 (m, 1H), 4.77 (s, 2H), 1.00 (s, 9H), 0.17 (s, 6H).

3-(((Tert-butyldimethylsilyl)oxy)methyl)-4-chlorobenzaldehyde

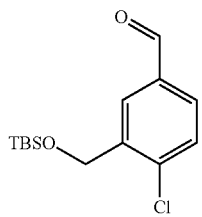 [SMILES: CC(C)(C)[Si](C)(C)OCc1cc(C=O)ccc1Cl]

To a solution of ((5-bromo-2-chlorobenzyl)oxy)(tert-butyl)dimethylsilane (16.0 g, 47.7 mmol) in tetrahydrofuran (THF) (150 mL) was added n-butyllithium (22.87 mL, 57.2 mmol, 2.5 M solution in THF) at −78° C. under nitrogen. After the reaction mixture was stirred at −78° C. for 30 min, DMF (18.45 mL, 238 mmol) was slowly added. The reaction mixture was continuously stirred for 2 h at −78° C. and quenched with saturated NH$_4$CL solution and extracted with ethyl acetate (3×). The combined organic layer was washed with water, brine, dried over anhydrous Na$_2$SO$_4$ and concentrated. The residue was purified by silica gel chromatography (petroleum ether:ethyl acetate=4:1) to obtain the title compound 3-(((tert-butyldimethylsilyl)oxy)methyl)-4-chlorobenzaldehyde (9.0 g, 30.0 mmol, 63.0% yield) as a light yellow oil. $^1$H NMR (CDCl$_3$, 500 MHz): 10.03 (s, 1H), 8.11 (s, 1H), 7.77-7.75 (m, 1H), 7.51-7.49 (m, 1H), 4.85 (s, 2H), 1.01 (s, 9H), 0.19 (s, 6H).

500

(3-(((Tert-butyldimethylsilyl)oxy)methyl)-4-chlorophenyl)(1,4-dimethyl-1H-benzo[d][1,2,3]triazol-5-yl)methanol

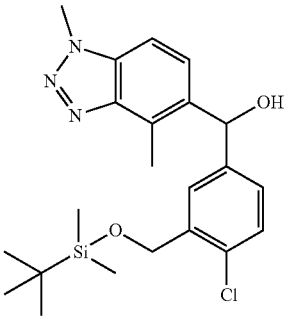 [SMILES: Cc1c(C(O)c2ccc(Cl)c(CO[Si](C)(C)C(C)(C)C)c2)ccc2c1nnn2C]

To a solution of 5-bromo-1,4-dimethyl-1H-benzo[d][1,2,3]triazole (6 g, 26.5 mmol) in tetrahydrofuran (THF) (100 mL) was added tert-butyllithium (20.42 mL, 26.5 mmol, 1.3 M solution in hexane) at −78° C. under nitrogen. After the reaction mixture was stirred at −78° C. for 30 min, 3-(((tert-butyldimethylsilyl)oxy)methyl)-4-chlorobenzaldehyde (7.94 g, 27.9 mmol) in tetrahydrofuran (THF) (100 mL) was added dropwise and continually stirred for 2 h at −78° C. The reaction mixture was slowly warmed to ambient temperature and stirred for an additional 2 h. The reaction mixture was quenched with saturated NH$_4$Cl solution and extracted with ethyl acetate (3×). The combined organic layer was washed with brine and dried over anhydrous Na$_2$SO$_4$ and concentrated. The residue was purified by silica gel chromatography (petroleum ether:ethyl acetate=3:1) to give the title compound (3-(((tert-butyldimethylsilyl)oxy)methyl)-4-chlorophenyl)(1,4-dimethyl-1H-benzo[d][1,2,3]triazol-5-yl)methanol (3.8 g, 6.42 mmol, 24.19% yield) as a light yellow oil. LC/MS m/z 432.1 (M+H)$^+$, 1.97 (ret. time).

Methyl 3-(3-(((tert-butyldimethylsilyl)oxy)methyl)-4-chlorophenyl)-3-(1,4-dimethyl-1H-benzo[d][1,2,3]triazol-5-yl)-2,2-dimethylpropanoate

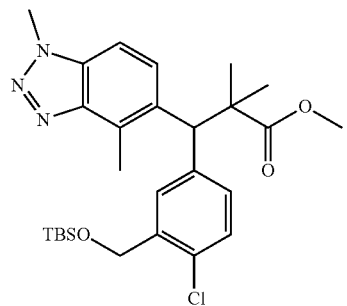 [SMILES: COC(=O)C(C)(C)C(c1ccc(Cl)c(CO[Si](C)(C)C(C)(C)C)c1)c1ccc2c(nnn2C)c1C]

To a solution of (3-(((tert-butyldimethylsilyl)oxy)methyl)-4-chlorophenyl)(1,4-dimethyl-1H-benzo[d][1,2,3]triazol-5-yl)methanol (1.4 g, 3.24 mmol) in dry acetonitrile (30 mL) was slowly added DBU (9.77 μL, 0.065 mmol) and 2,2,2-trichloroacetonitrile (0.561 g, 3.89 mmol) under nitrogen at 25° C. After the reaction mixture was stirred at 25° C. for 30 min, ((1-methoxy-2-methylprop-1-en-1-yl)oxy)trimethylsilane (1.412 g, 8.10 mmol) was added followed by 1,1,1-trifluoro-N-((trifluoromethyl)sulfonyl)methanesulfonamide (0.046 g, 0.162 mmol). The reaction mixture was stirred at ambient temperature for 2 h after which 30 mL of water was added to quench the reaction. The mixture was extracted with ethyl acetate (3×). The combined organic layer was washed with brine and concentrated. The crude product was purified by silica gel chromatography (petroleum ether:ethyl acetate=4:1) to give the title compound methyl 3-(3-(((tert-butyldimethylsilyl)oxy)methyl)-4-chlorophenyl)-3-(1,4-dimethyl-1H-benzo[d][1,2,3]triazol-5-yl)-2,2-dimethylpropanoate (1.2 g, 2.209 mmol, 68.2% yield) as a yellow solid. LC/MS m/z 516.1 (M+H)$^+$, 2.19 (ret. time).

Methyl 3-(4-chloro-3-(hydroxymethyl)phenyl)-3-(1,4-dimethyl-1H-benzo[d][1,2,3]triazol-5-yl)-2,2-dimethylpropanoate

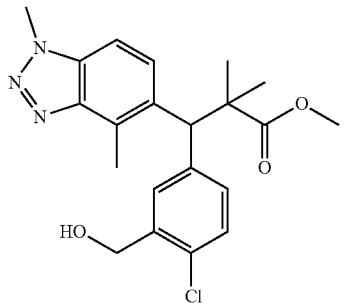 [SMILES: COC(=O)C(C)(C)C(c1ccc(Cl)c(CO)c1)c1ccc2c(nnn2C)c1C]

To a solution of methyl 3-(3-(((tert-butyldimethylsilyl)oxy)methyl)-4-chlorophenyl)-3-(1,4-dimethyl-1H-benzo[d][1,2,3]triazol-5-yl)-2,2-dimethylpropanoate (2.8 g, 4.88 mmol) in tetrahydrofuran (THF) (20 mL) was added TBAF (5.86 mL, 5.86 mmol) slowly under nitrogen at 25° C. The reaction mixture was stirred at 25° C. for 16 h. Water (30 mL) was added and the reaction mixture extracted with ethyl acetate (3×). The combined organic layer was concentrated. The crude product was purified by silica gel chromatography (hexane:ethyl acetate=1:1) to provide the title compound methyl 3-(4-chloro-3-(hydroxymethyl)phenyl)-3-(1,4-dimethyl-1H-benzo[d][1,2,3]triazol-5-yl)-2,2-dimethylpropanoate (1.67 g, 3.95 mmol, 81% yield) as a white solid. LC/MS m/z 402.1 (M+H)$^+$, 1.99 (ret. time).

Methyl 3-(4-chloro-3-(chloromethyl)phenyl)-3-(1,4-dimethyl-1H-benzo[d][1,2,3]triazol-5-yl)-2,2-dimethylpropanoate

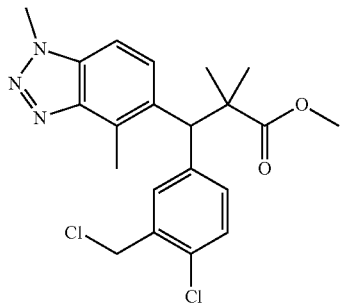 [SMILES: COC(=O)C(C)(C)C(c1ccc(Cl)c(CCl)c1)c1ccc2c(nnn2C)c1C]

To a solution of methyl 3-(4-chloro-3-(hydroxymethyl)phenyl)-3-(1,4-dimethyl-1H-benzo[d][1,2,3]triazol-5-yl)-2,2-dimethylpropanoate (500 mg, 1.244 mmol) in dichloromethane (DCM) (20 mL) thionyl chloride (296 mg, 2.488 mmol) was added slowly. The reaction mixture was stirred at ambient temperature for 1 h. The solvent was evaporated to obtain the title compound methyl 3-(4-chloro-3-(chloromethyl)phenyl)-3-(1,4-dimethyl-1H-benzo[d][1,2,3]triazol-5-yl)-2,2-dimethylpropanoate (500 mg, 96% yield) which was carried to the next step without further purification. LC/MS m/z 420.1 (M+H)$^+$, 1.21 (ret. time).

Methyl 3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate

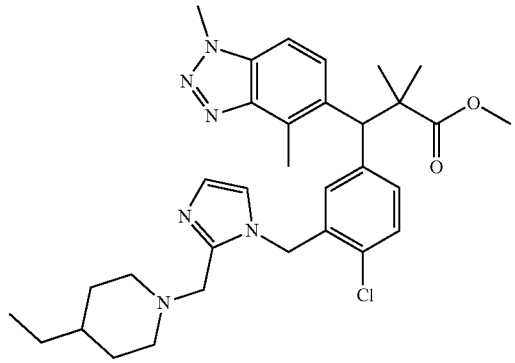 [SMILES: CCC1CCN(Cc2nccn2Cc2cc(C(c3ccc4c(nnn4C)c3C)C(C)(C)C(=O)OC)ccc2Cl)CC1]

To a solution of 1-((1H-imidazol-2-yl)methyl)-4-ethylpiperidine (345 mg, 1.784 mmol) in N,N-dimethylformamide (DMF) (20 mL) sodium hydride (190 mg, 4.76 mmol) was added slowly at ambient temperature under nitrogen. The reaction mixture was stirred for 30 min after which methyl 3-(4-chloro-3-(chloromethyl)phenyl)-3-(1,4-dimethyl-1H-benzo[d][1,2,3]triazol-5-yl)-2,2-dimethylpropanoate (500 mg, 1.190 mmol) was added. The reaction mixture was stirred at ambient temperature for 16 h. The reaction mixture was partitioned between ethyl acetate and water. The water layer was extracted with ethyl acetate (2×). The combined organic phase was washed with brine and dried over MgSO$_4$ and concentrated. The crude product was purified by silica gel chromatography (hexane:ethyl acetate in EtOH=3:1) to obtain the title compound methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate (650 mg, 95% yield). LC/MS m/z 577.5 (M+H)$^+$, 1.05 (ret. time).

3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic Acid

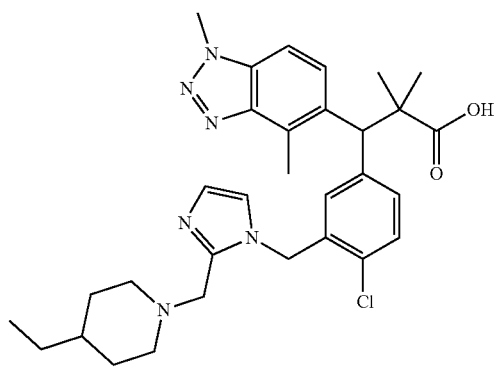 [SMILES: CCC1CCN(Cc2nccn2Cc2cc(C(c3ccc4c(nnn4C)c3C)C(C)(C)C(=O)O)ccc2Cl)CC1]

To a solution of methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate (65 mg, 0.113 mmol) in methanol (5 mL) LiOH (2M, 0.338 mL, 0.676 mmol) was added. The reaction mixture was heated via microwave at 120° C. for 2 h 30 min. The solvent was evaporated and partitioned between ethyl acetate and 1 N HCl after which the water layer was adjusted to pH 5, extracted with ethyl acetate (3×). The combined organic phase was dried over MgSO$_4$ and concentrated to get the title compound (40 mg, 63.1% yield). LC/MS m/z 563.4 (M+H)$^+$, 0.98 (ret. time).

Example 237

(S)-3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic Acid

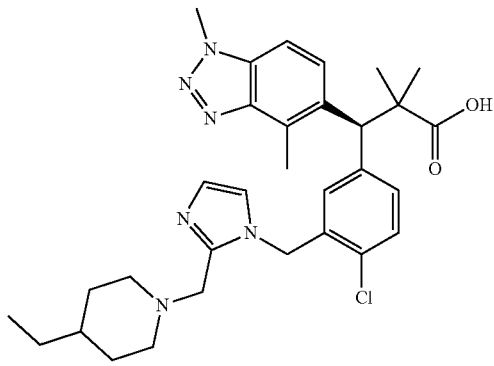 [SMILES: CCC1CCN(Cc2nccn2Cc2cc([C@@H](c3ccc4c(nnn4C)c3C)C(C)(C)C(=O)O)ccc2Cl)CC1]

(S)-Methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate

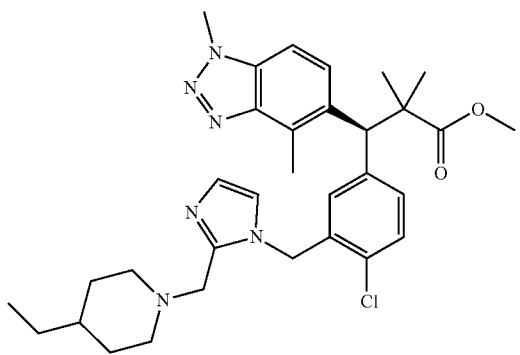 [SMILES: CCC1CCN(Cc2nccn2Cc2cc([C@@H](c3ccc4c(nnn4C)c3C)C(C)(C)C(=O)OC)ccc2Cl)CC1]

Methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate (650 mg) was separated by Chiral SFC (Column: Chiralpak AD 20×150 mm; Co-solvent: 20% MeOH:IPA (1:1); Flow-rate: 50 g/min; Back pressure: 100 Bar) to give single enantiomerically pure (S)-methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate (221 mg, 0.383 mmol, 32.2% yield) (chiral SFC ret. time: 3.62 min) and single enantiomerically pure (R)-methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate (196 mg, 0.340 mmol, 28.5% yield) (chiral SFC ret. time: 5.19 min).

(S)-3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic Acid

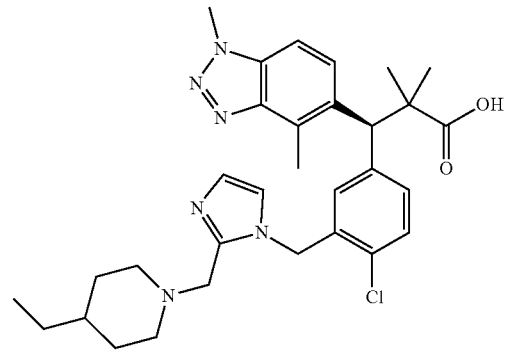 [SMILES: CCC1CCN(Cc2nccn2Cc2cc([C@@H](c3ccc4c(nnn4C)c3C)C(C)(C)C(=O)O)ccc2Cl)CC1]

To a solution of (S)-methyl 3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoate (221 mg, 0.383 mmol) in methanol (6 mL) LiOH (2M, 1.915 mL, 3.83 mmol) was added. The reaction was heated via microwave at 120° C. for 2 h. The solvent was evaporated and partitioned between ethyl acetate and 1N HCl. The water layer was adjusted to pH 5 and extracted with ethyl acetate (3×). The combined organic layer was dried with MgSO$_4$ and concentrated to obtain the title compound (S)-3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic acid (145.1 mg, 67.3% yield). LC/MS m/z 563.4 (M+H)$^+$, 0.86 (ret. time).

Example 238

(R)-3-(4-Chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic Acid

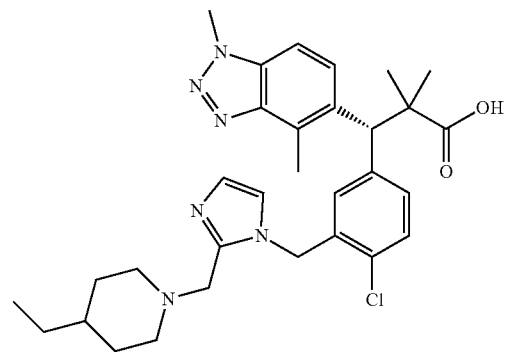 [SMILES: CCC1CCN(Cc2nccn2Cc2cc([C@H](c3ccc4c(nnn4C)c3C)C(C)(C)C(=O)O)ccc2Cl)CC1]

To a solution of (R)-methyl 3-(4-chloro-3-((2-((4-ethyl-piperidin-1-yl)methyl)-1H-imidazol-1-yl)methyl)phenyl)-3-(1,4-dimethyl-1H-benzo[d][1,2,3]triazol-5-yl)-2,2-dimethylpropanoate (196 mg, 0.340 mmol) in methanol (5 mL), LiOH (2M, 1.698 mL, 3.40 mmol) was added. The reaction was heated via microwave at 120° C. for 2 h. The solvent was evaporated and partitioned between ethyl acetate and 1 N HCl. The water layer was adjusted to pH 5 and extracted with ethyl acetate (3×). The combined organic phase was dried over MgSO$_4$ and concentrated to obtain the title compound (R)-3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic acid (163.6 mg, 71.4% yield). LC/MS m/z 563.3 (M+H)$^+$, 0.86 (ret. time).

Example 239

(S)-3-(1-Ethyl-4-methyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoic Acid

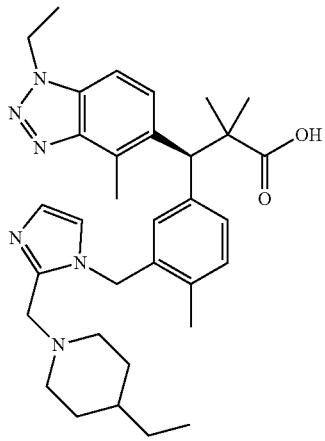 [SMILES: CCC1CCN(Cc2nccn2Cc2cc([C@@H](c3ccc4c(nnn4CC)c3C)C(C)(C)C(=O)O)ccc2C)CC1]

(S)-Methyl 3-(3-(chloromethyl)-4-methylphenyl)-3-(1-ethyl-4-methyl-1H-benzo[d][1,2,3]triazol-5-yl)-2,2-dimethylpropanoate

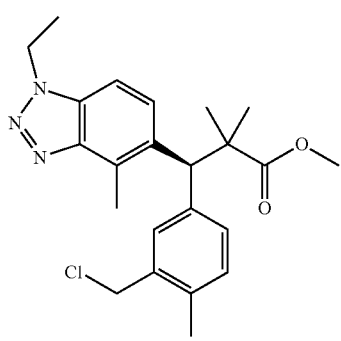 [SMILES: CCn1nnc2c(C)c([C@H](c3ccc(C)c(CCl)c3)C(C)(C)C(=O)OC)ccc21]

To a solution of (S)-methyl 3-(1-ethyl-4-methyl-1H-benzo[d][1,2,3]triazol-5-yl)-3-(3-(hydroxymethyl)-4-methylphenyl)-2,2-dimethylpropanoate (103 mg, 0.260 mmol) in dichloromethane (DCM) (5 mL), thionyl chloride (0.038 mL, 0.521 mmol) was added. The reaction mixture was stirred at ambient temperature for 30 min. The solvent was evaporated to obtain the title compound (S)-methyl 3-(3-(chloromethyl)-4-methylphenyl)-3-(1-ethyl-4-methyl-1H-benzo[d][1,2,3]triazol-5-yl)-2,2-dimethylpropanoate which was carried to the next step without further purification. LC/MS m/z 414.3 (M+H)$^+$, 1.25 (ret. time).

(S)-3-(1-Ethyl-4-methyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoic acid

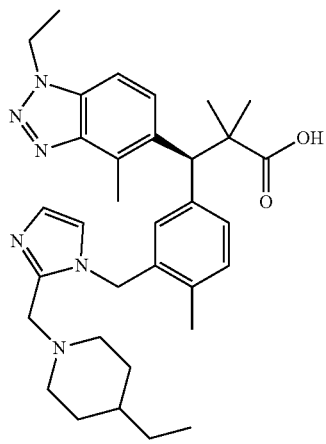 [SMILES: CCC1CCN(Cc2nccn2Cc2cc([C@@H](c3ccc4c(nnn4CC)c3C)C(C)(C)C(=O)O)ccc2C)CC1]

To a solution of 1-((1H-imidazol-2-yl)methyl)-4-ethylpiperidine (117 mg, 0.604 mmol) in N,N-dimethylformamide (DMF) (5 mL) NaH (19.50 mg, 0.488 mmol) was added. After it was stirred for 30 min, (S)-methyl 3-(3-(chloromethyl)-4-methylphenyl)-3-(1-ethyl-4-methyl-1H-benzo[d][1,2,3]triazol-5-yl)-2,2-dimethylpropanoate (100 mg, 0.242 mmol was added. The reaction mixture was stirred at ambient temperature for 2 h. The reaction mixture was partitioned between ethyl acetate and water. The water layer was extracted with ethyl acetate (2×). The combined organic layer was dried over MgSO$_4$ and concentrated to get the crude product which was purified by silica gel chromatography (hexane/ethyl acetate) to obtain (S)-methyl 3-(1-ethyl-4-methyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoate (120 mg, 87% yield).

To (S)-methyl 3-(1-ethyl-4-methyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoate (120 mg, 0.210 mmol) in methanol (5.00 mL) LiOH (1.208 mL, 2.416 mmol) was added. The reaction was heated via microwave at 120° C. for 2 h. The solvent was evaporated and partitioned between ethyl acetate and 1N HCl. The water layer was adjusted to pH 5 and extracted with ethyl acetate (3×). The combined organic phase was dried over MgSO$_4$ and concentrated to obtain the title compound (S)-3-(1-ethyl-4-methyl-1H-benzo[d][1,2,3]triazol-5-yl)-3-(3-((2-((4-ethylpiperidin-1-yl)methyl)-1H-imidazol-1-yl)methyl)-4-methylphenyl)-2,2-dimethylpropanoic acid (96 mg, 71.4% yield). LC/MS m/z 557.7 (M+H)$^+$, 0.88 (ret. time).

Example 240

(3S)-3-(1,4-Dimethyl-1H-benzo[d][1,2,3]triazol-5-yl)-3-(3-((2-ethyl-2-methyl-2,3-dihydrobenzo[f][1,4]oxazepin-4(5H)-yl)methyl)-4-methylphenyl)-2,2-dimethylpropanoic Acid

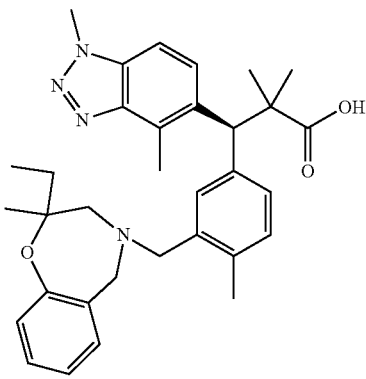 [SMILES: CCC1(C)CN(Cc2cc([C@@H](c3ccc4c(nnn4C)c3C)C(C)(C)C(=O)O)ccc2C)Cc2ccccc2O1]

1-((2-Bromobenzyl)amino)-2-methylbutan-2-ol

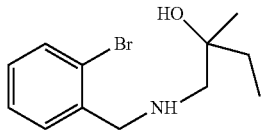

To a solution of 2-bromobenzaldehyde (200 mg, 1.081 mmol) in methanol (5 mL) 1-amino-2-methylbutan-2-ol (134 mg, 1.297 mmol) and sodium hydroxide (4.32 mg, 0.108 mmol) were added. The reaction mixture was stirred for 8 h after which NaBH$_4$ (40.9 mg, 1.081 mmol) was added and the reaction mixture was stirred at ambient temperature for 16 h. After the solvent was evaporated, the residue was partitioned between ethyl acetate and water. The water layer was extracted with ethyl acetate (2×). The combined organic phase was dried over MgSO$_4$ and concentrated to obtain the title compound 1-((2-bromobenzyl)amino)-2-methylbutan-2-ol (275 mg, 93% yield) which was carried to the next step without further purification. LC/MS m/z 274.0 (M+H)$^+$, 0.62 (ret. time).

2-Ethyl-2-methyl-2,3,4,5-tetrahydrobenzo[f][1,4]oxazepine

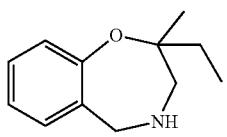

To a solution of 1-((2-bromobenzyl)amino)-2-methylbutan-2-ol (275 mg, 1.010 mmol) in isopropanol (5 mL) cesium carbonate (658 mg, 2.021 mmol) and copper(I) iodide (96 mg, 0.505 mmol) were added. The reaction mixture was stirred while refluxing for 46 h. After it was cooled to ambient temperature, the solid was filtered through celite. The filtrate was evaporated and purified by reverse phase preparative HPLC using TFA as a solvent modifier to provide the title compound 2-Ethyl-2-methyl-2,3,4,5-tetrahydrobenzo[f][1,4]oxazepine (88 mg, 45.5% yield). LC/MS m/z 192.6 (M+H)$^+$, 0.66 (ret. time).

(3S)-3-(1,4-Dimethyl-1H-benzo[d][1,2,3]triazol-5-yl)-3-(3-((2-ethyl-2-methyl-2,3-dihydrobenzo[f][1,4]oxazepin-4(5H)-yl)methyl)-4-methylphenyl)-2,2-dimethylpropanoic Acid

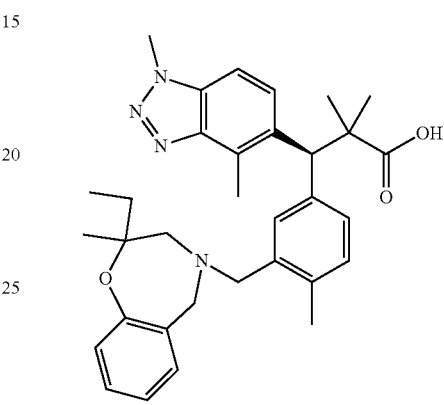

To a solution of 2-ethyl-2-methyl-2,3,4,5-tetrahydrobenzo[f][1,4]oxazepine (78 mg, 0.406 mmol) in N,N-dimethylformamide (DMF) (5 mL) NaH (19.50 mg, 0.488 mmol) was added. After it was stirred for 30 min, (S)-methyl 3-(3-(chloromethyl)-4-methylphenyl)-3-(1,4-dimethyl-1H-benzo[d][1,2,3]triazol-5-yl)-2,2-dimethylpropanoate (65 mg, 0.163 mmol) was added. The reaction mixture was stirred at ambient temperature for 18 h and partitioned between ethyl acetate and water. The water layer was extracted with ethyl acetate (2×). The combined organic layer was dried over MgSO$_4$ and concentrated. The crude product was purified by silica gel chromatography (hexane/ethyl acetate) to obtain (3S)-3-(1,4-dimethyl-1H-benzo[d][1,2,3]triazol-5-yl)-3-(3-((2-ethyl-2-methyl-2,3-dihydrobenzo[f][1,4]oxazepin-4(5H)-yl)methyl)-4-methylphenyl)-2,2-dimethylpropanoate (34 mg, 37.7% yield).

To a solution of (3S)-3-(1,4-dimethyl-1H-benzo[d][1,2,3]triazol-5-yl)-3-(3-((2-ethyl-2-methyl-2,3-dihydrobenzo[f][1,4]oxazepin-4(5H)-yl)methyl)-4-methylphenyl)-2,2-dimethylpropanoate (34 mg, 0.061 mmol) in methanol (5.00 mL)LiOH (0.813 mL, 1.625 mmol) was added. The reaction was heated via microwave at 120° C. for 3 h. The solvent was evaporated. The residue was acidified with 1N HCl, then it was concentrated which was purified by reverse phase preparative HPLC to provide the title compound (3S)-3-(1,4-Dimethyl-1H-benzo[d][1,2,3]triazol-5-yl)-3-(3-((2-ethyl-2-methyl-2,3-dihydrobenzo[f][1,4]oxazepin-4(5H)-yl)methyl)-4-methylphenyl)-2,2-dimethylpropanoic acid (12.2 mg, 12.88% yield). LC/MS m/z 541.4 (M+H)$^+$, 0.95 (ret. time).

Example 241 rel-(S)-3-(3-((1-(Cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic Acid

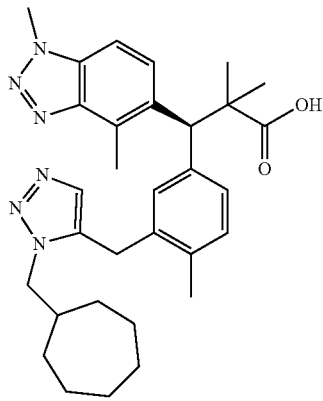 [SMILES: Cc1ccc([C@@H](c2ccc3c(nnn3C)c2C)C(C)(C)C(=O)O)cc1Cc1cnnn1CC1CCCCCC1]

Example 242 rel-(R)-3-(3-((1-(Cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic Acid

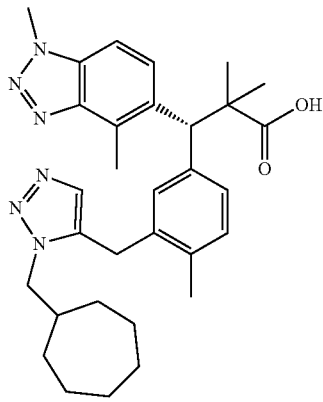 [SMILES: Cc1ccc([C@H](c2ccc3c(nnn3C)c2C)C(C)(C)C(=O)O)cc1Cc1cnnn1CC1CCCCCC1]

Cycloheptylmethyl 4-methylbenzenesulfonate

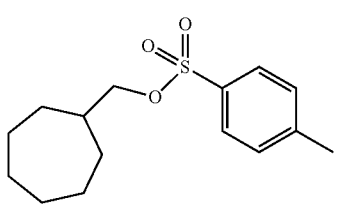 [SMILES: Cc1ccc(S(=O)(=O)OCC2CCCCCC2)cc1]

The mixture of cycloheptylmethanol (3200 mg, 24.96 mmol) and triethylamine (5.22 mL, 37.4 mmol) in DCM (50.0 mL) was stirred at 00° C. under nitrogen, TsCl (4996 mg, 26.2 mmol) was added and stirred at 0° C. for 12 h and filtered and concentrated to give the title compound cycloheptylmethyl 4-methylbenzenesulfonate (3200 mg, 11.33 mmol, 45.4% yield) as an oil.
LC/MS m/z 300.2 (M+H$_2$O)$^+$, 2.20 (ret. time).

1-(Cycloheptylmethyl)-1H-1,2,3-triazole

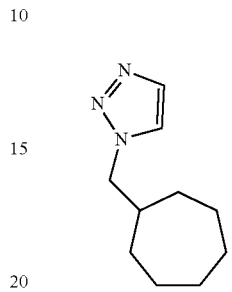

The mixture of cycloheptylmethyl 4-methylbenzenesulfonate (3200 mg, 11.33 mmol), 1H-1,2,3-triazole (783 mg, 11.33 mmol) and Cs$_2$CO$_3$ (3692 mg, 11.33 mmol) in DMF (50.0 mL) was stirred at 00° C. under nitrogen for 2 h and stirred at 100° C. for 8 h. After it was cooled to ambient temperature, the solid was filtered and the filtrate was purified by reverse phase preparative HPLC (50% MeOH/H$_2$O) to provide the title compound 1-(cycloheptylmethyl)-1H-1,2,3-triazole (1500 mg, 8.37 mmol, 73.8% yield) as a solid. LC/MS m/z 180.1 (M+H)$^+$, 1.80 (ret. time).

Methyl 3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoate

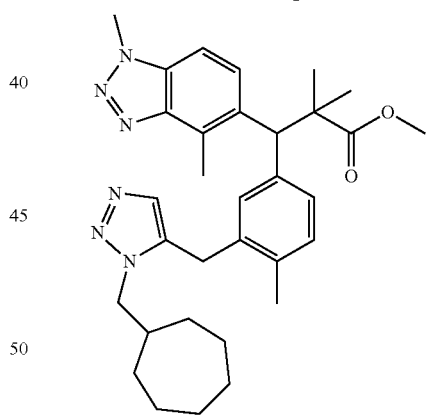

To a solution of 1-(cycloheptylmethyl)-1H-1,2,3-triazole (242 mg, 1.350 mmol) in tetrahydrofuran (THF) (10 mL) was added n-butyllithium (0.540 mL, 1.350 mmol) at −78° C. under nitrogen. The mixture was stirred at −78° C. for 30 min, then methyl 3-(3-(bromomethyl)-4-methylphenyl)-3-(1,4-dimethyl-1H-benzo[d][1,2,3]triazol-5-yl)-2,2-dimethylpropanoate (200 mg, 0.450 mmol) in THF (10 mL) was added dropwise and continually stirred for 2 h at −78° C. The mixture was slowly warmed to ambient temperature and stirred for an additional 2 h. The reaction mixture was quenched with saturated aqueous NH$_4$Cl solution and extracted with ethyl acetate (3×). The combined organic layer was washed with brine and dried over anhydrous Na$_2$SO$_4$ and concentrated. The residue was purified via silica gel chromatography (petroleum ether:ethyl acetate=1:3) to obtain the title compound methyl 3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoate (120 mg, 0.219 mmol, 48.6% yield). LC/MS m/z 543.2 (M+H)⁺, 1.88 (ret. time).

3-(3-((1-(Cycloheptyl methyl)-1H-1,2,3-triazol-5-yl)methyl)-4-methylphenyl)-3-(1,4-dimethyl-1H-benzo[d][1,2,3]triazol-5-yl)-2,2-dimethylpropanoic Acid

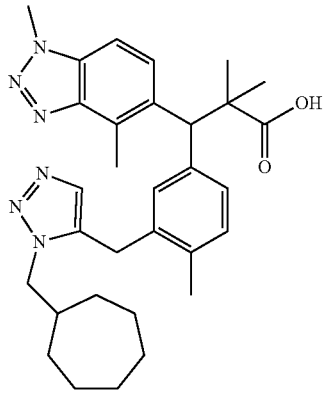 [SMILES: Cc1ccc(C(c2ccc3c(nnn3C)c2C)C(C)(C)C(=O)O)cc1Cc1cnnn1CC1CCCCCC1]

To a solution of methyl 3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoate (200 mg, 0.369 mmol) in ethylene glycol (4 mL) was added lithium hydroxide (17.65 mg, 0.737 mmol) in a mixture of water (1 mL) and tetrahydrofuran (THF) (2 mL). The reaction was heated via microwave at 125° C. for 2 h after which the organic solvent was removed under reduced pressure and the residue was acidified with 1N HCl to pH 5. The white solid was filtered, collected and dried to provide the title compound 3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic acid (180 mg, 0.323 mmol, 88% yield). LC/MS m/z 529.2 (M+H)⁺, 1.76 (ret. time).

rel-(S)-3-(3-((1-(Cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic Acid (Isomer 1)

rel-(R)-3-(3-((1-(Cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic Acid (Isomer 2) N35469-69-A2

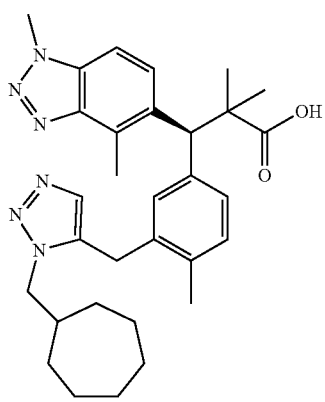

-continued

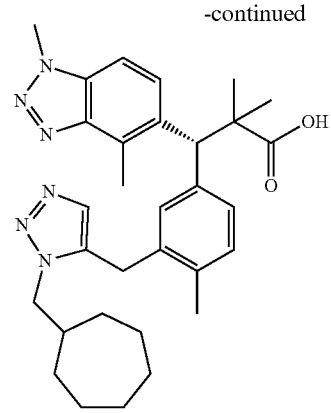

3-(3-((1-(Cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic acid (480 mg, 0.908 mmol) was purified by Chiral SFC (Column: AS-H (4.6*250 mm, 5 um); Co-solvent MeOH (1% Methanol Ammonia); Flowrate: 50 g/min; Back pressure: 100 Bar) to give the title compound (S)-3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic acid (chiral SFC ret. time: 3.45 min) (200 mg, 38.8%) & (R)-3-(3-((1-(cycloheptylmethyl)-1H-1,2,3-triazol-5-yl)methyl)-4-methylphenyl)-3-(1,4-dimethyl-1H-benzo[d][1,2,3]triazol-5-yl)-2,2-dimethylpropanoic acid (chiral SFC ret. time: 4.15 min) (200 mg, 39.6%). LC-MS m/z 529.2 (M+H)⁺, 1.76 min (ret. time)

Example 243

3-(3-((3H-Spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoic Acid

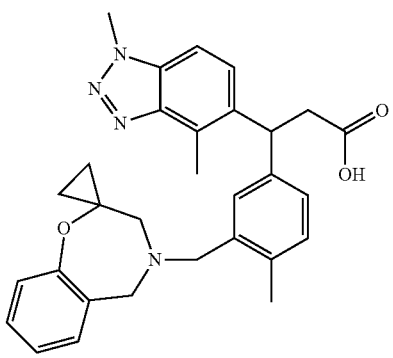 [SMILES: Cc1ccc(C(CC(=O)O)c2ccc3c(nnn3C)c2C)cc1CN1Cc2ccccc2OC2(CC2)C1]

1-Benzoxy-2-((bis-tert-butoxycarbonyl)amino)methyl-benzene

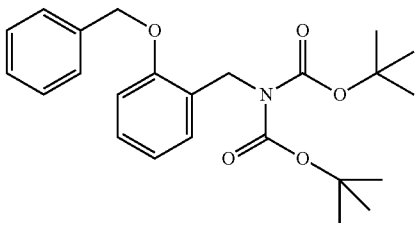 [SMILES: CC(C)(C)OC(=O)N(Cc1ccccc1OCc1ccccc1)C(=O)OC(C)(C)C]

To a solution of (bis-tert-butoxycarbonyl)amine (8 g, 36.8 mmol) in N,N-dimethylformamide (DMF) (200 mL), Cs₂CO₃ (13.27 g, 40.7 mmol) and sodium iodide (0.509 g, 3.39 mmol) were added at ambient temperature. After the reaction mixture was stirred at ambient temperature for 70 min, a solution of 1-(benzyloxy)-2-(chloromethyl)benzene (7.9 g, 33.9 mmol) in DMF (50 mL) was added and the resulting mixture was stirred at ambient temperature for 20 h. The reaction mixture was quenched with water and extracted with ethyl acetate (3×). The combined organic layer was washed with water, brine (2×), dried over Na₂SO₄ and concentrated. The residue was purified by silica gel chromatography (EA:PE=1:2) to obtain the title compound 1-benzoxy-2-((bis-tert-butoxycarbonyl)amino)methyl-benzene (11.6 g, 26.7 mmol, 79% yield) as a white solid.

LC/MS m/z 436.2 (M+Na)*, 2.29 min (ret. time)

1-Hydroxy-2-((bis-tert-butoxycarbonyl)amino) methyl-benzene

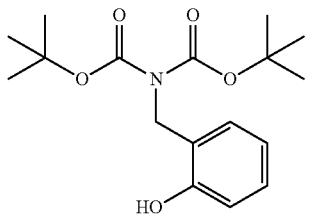 [SMILES: CC(C)(C)OC(=O)N(Cc1ccccc1O)C(=O)OC(C)(C)C]

To a solution of 1-benzoxy-2-((bis-tert-butoxycarbonyl) amino)methyl-benzene (11.6 g, 28.1 mmol) in a mixture of methanol (100 mL) and tetrahydrofuran (THF) (100 mL), palladium/C (10%, 2.99 g, 28.1 mmol) was added. The reaction mixture was stirred at ambient temperature for 6 h under parr shaker at 2 atm. The reaction mixture was filtered through celite. The filtrate was concentrated to obtain the title compound 1-hydroxy-2-((bis-tert-butoxycarbonyl) amino)methyl-benzene (8.9 g, 26.4 mmol, 94% yield) which was carried to the next step without further purification. LC/MS m/z 346.2 (M+Na)⁺, 2.05 min (ret. time)

Methyl 4-bromo-2-(2-(((bis-tert-butoxycarbonyl) amino)methyl)phenoxy)butanoate

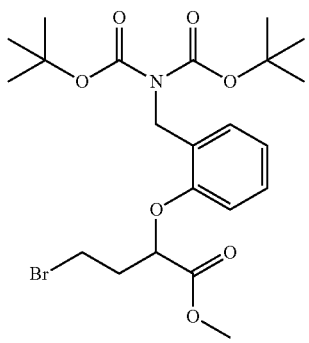 [SMILES: COC(=O)C(CCBr)Oc1ccccc1CN(C(=O)OC(C)(C)C)C(=O)OC(C)(C)C]

To a solution of 1-hydroxy-2-((bis-tert-butoxycarbonyl) amino)methyl-benzene (8.9 g, 27.5 mmol) in acetonitrile (100 mL) was added methyl 2,4-dibromobutanoate (7.87 g, 30.3 mmol) and Cs₂CO₃ (8.97 g, 27.5 mmol). The reaction mixture was stirred at 60° C. for 3 h. The reaction mixture was filtered and concentrated. The crude product was purified by silica gel chromatography (hexane:ethyl acetate=20:1) to obtain the title compound methyl 4-bromo-2-(2-(((bis-tert-butoxycarbonyl)amino)methyl)phenoxy)butanoate (2.6 g, 4.14 mmol, 15.04% yield) as an oil. LC/MS m/z 524.1 (M+Na)⁺, 1.96 min (ret. time)

Methyl 1-(2-(((bis-tert-butoxycarbonyl)amino) methyl)phenoxy)cyclopropanecarboxylate

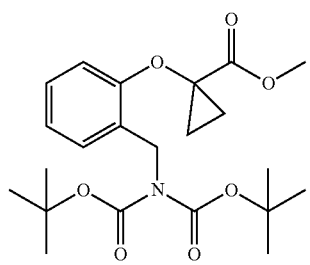 [SMILES: COC(=O)C1(Oc2ccccc2CN(C(=O)OC(C)(C)C)C(=O)OC(C)(C)C)CC1]

To a solution of methyl 4-bromo-2-(2-(((bis-tert-butoxycarbonyl)amino)methyl)phenoxy) butanoate (1.6 g, 3.18 mmol) in tetrahydrofuran (THF) (25 mL), potassium tert-butoxide (4.78 mL, 4.78 mmol) was added slowly under nitrogen at 25° C. The reaction mixture was stirred at 25° C. for 16 h after which 10 mL of aqueous NH₄Cl was added and the mixture extracted with ethyl acetate (3×), dried over Na₂SO₄ and concentrated to obtain the title compound methyl 1-(2-(((bis-tert-butoxycarbonyl)amino)methyl)phenoxy)cyclopropanecarboxylate (800 mg, 0.949 mmol, 29.8% yield) which was carried to next step without further purification. LC/MS m/z 444.0 (M+Na)⁺, 1.60 min (ret. time)

Methyl 1-(2-(aminomethyl)phenoxy)cyclopropanecarboxylate

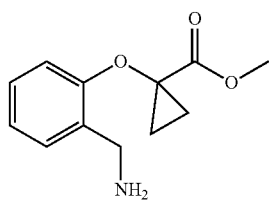 [SMILES: COC(=O)C1(Oc2ccccc2CN)CC1]

A solution of methyl 1-(2-(((bis-tert-butoxycarbonyl) amino)methyl)phenoxy)cyclopropane carboxylate (800 mg, 1.898 mmol) in HCl (10 ml, 20.00 mmol) was stirred at 25° C. for 16 h. The reaction mixture was concentrated and purified by reverse phase preparative HPLC (solvent:H₂O/MeCN) to provide the title compound methyl 1-(2-(aminomethyl)phenoxy)cyclopropanecarboxylate (400 mg, 1.627 mmol, 86% yield) as a white solid. LC/MS m/z 222.2 (M+H)⁺, 1.48 min (ret. time)

4,5-Dihydro-3H-spiro[benzo[f][1,4]oxazepine-2,1'-cyclopropan]-3-one

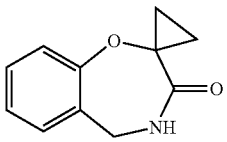 [SMILES: O=C1NCc2ccccc2OC12CC2]

A solution of methyl 1-(2-(aminomethyl)phenoxy)cyclopropanecarboxylate (570 mg, 2.58 mmol) and DIPEA (0.450 mL, 2.58 mmol) in 1,4-dioxane (5 mL) was heated via microwave at 140° C. for 2 h. The reaction mixture was concentrated and purified by reverse phase preparative HPLC (solvent:H$_2$O/MeCN) to provide the title compound 4,5-dihydro-3H-spiro[benzo[f][1,4]oxazepine-2,1'-cyclopropan]-3-one (150 mg, 0.713 mmol, 27.7% yield) as a solid. LC/MS m/z 190.1 (M+H)$^+$, 1.42 min (ret. time)

4,5-Dihydro-3H-spiro[benzo[f][1,4]oxazepine-2,1'-cyclopropane]

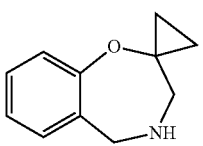

To a solution of 4,5-dihydro-3H-spiro[benzo[f][1,4]oxazepine-2,1'-cyclopropan]-3-one (70 mg, 0.370 mmol) in tetrahydrofuran (THF) (50 mL) was added LiAlH$_4$ (14.04 mg, 0.370 mmol) slowly under nitrogen at 20° C. The reaction mixture was stirred at 20° C. for 4 h after which 10 g of Na$_2$SO$_4$·10H$_2$O was added. The solid was filtered and concentrated to provide the title compound 4,5-dihydro-3H-spiro[benzo[f][1,4]oxazepine-2,1'-cyclopropane] (60 mg, 0.243 mmol, 65.7% yield) which was carried to next step without further purification. LC/MS m/z 176.1 (M+H)$^+$, 1.07 min (ret. time)

Methyl 3-(3-((3H-spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoate

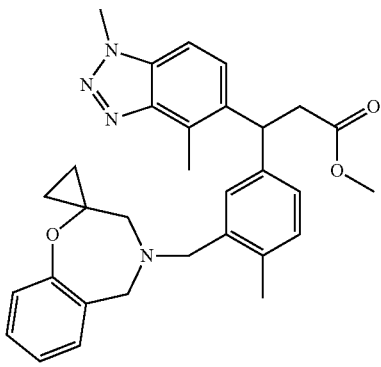 [SMILES: COC(=O)CC(c1ccc(C)c(CN2Cc3ccccc3OC3(CC3)C2)c1)c1ccc2c(nnn2C)c1C]

To a solution of ethyl 3-(3-(chloromethyl)-4-methylphenyl)-3-(1,4-dimethyl-1H-benzo[d][1,2,3]triazol-5-yl)propanoate (100 mg, 0.259 mmol) in acetonitrile (5 mL), 4,5-dihydro-3H-spiro[benzo[f][1,4]oxazepine-2,1'-cyclopropane] (60 mg, 0.342 mmol) and K$_2$CO$_3$ (95 mg, 0.685 mmol) were added slowly under nitrogen at 25° C. The reaction mixture was stirred at 70° C. for 16 h after which 20 mL of water was added and the mixture extracted with ethyl acetate (3×). The combined organic phase was concentrated. The crude product was purified by reverse phase preparative HPLC (solvent:H$_2$O/MeCN) to provide the title compound ethyl 3-(3-((3H-spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoate (45 mg, 0.080 mmol, 23.30% yield). LC/MS m/z 525.3 (M+H)$^+$, 2.19 min (ret. time)

3-(3-((3H-Spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoic Acid

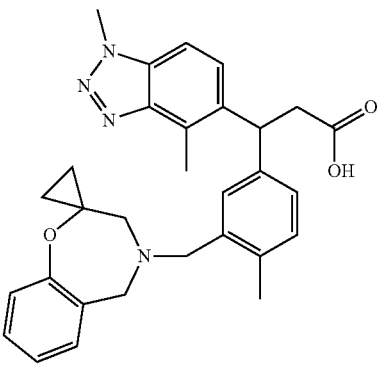 [SMILES: Cc1ccc(C(CC(=O)O)c2ccc3c(nnn3C)c2C)cc1CN1Cc2ccccc2OC2(CC2)C1]

To a solution of ethyl 3-(3-((3H-spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoate (45 mg, 0.086 mmol) in tetrahydrofuran (THF) (2 mL) was added a solution of LiOH (8.22 mg, 0.343 mmol) in water (2.000 mL) slowly under nitrogen at 25° C. The reaction mixture was stirred at 25° C. for 16 h and adjusted to pH 6 with 0.1 N HCl and extracted with ethyl acetate (3×). The combined organic phase was concentrated to provide the title compound 3-(3-((3H-spiro[benzo[f][1,4]oxazepine-2,1'-cyclopropan]-4(5H)-yl)methyl)-4-methylphenyl)-3-(1,4-dimethyl-1H-benzo[d][1,2,3]triazol-5-yl)propanoic acid (30 mg, 0.059 mmol, 69.0% yield). LC/MS m/z 497.2 (M+H)$^+$, 1.33 min (ret. time)

Example 244

3-(3-((3H-Spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoic Acid

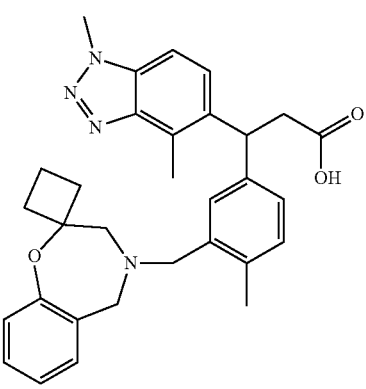 [SMILES: Cc1ccc(C(CC(=O)O)c2ccc3c(nnn3C)c2C)cc1CN1Cc2ccccc2OC2(CCC2)C1]

517

Ethyl 1-(2-formylphenoxy)cyclobutanecarboxylate

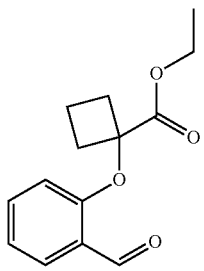 [SMILES: CCOC(=O)C1(Oc2ccccc2C=O)CCC1]

To a solution of 2-hydroxybenzaldehyde (5.3 g, 43.4 mmol) in N,N-Dimethylformamide (DMF) (100 mL) was added NaH (2.60 g, 65.1 mmol) slowly under nitrogen at 25° C. The reaction mixture was stirred at 25° C. for 0.5 h after which ethyl 1-bromocyclobutanecarboxylate (8.99 g, 43.4 mmol) solution in 5 mL of DMF and KI (0.720 g, 4.34 mmol) were added. The reaction mixture was heated at 130° C. for 6 h. After it was cooled to ambient temperature, 100 mL of water was added and the mixture extracted with ethyl acetate (3×). The combined organic layer was concentrated. The crude product was purified by silica gel chromatography (hexane:ethyl acetate=20:1) to provide the title compound ethyl 1-(2-formylphenoxy)cyclobutanecarboxylate (3.4 g, 11.64 mmol, 26.8% yield). $^1$H NMR (400 MHz, DMSO) δ 10.44 (s, 1H), 7.73 (dd, J=7.7, 1.7 Hz, 1H), 7.62-7.51 (m, 1H), 7.09 (t, J=7.5 Hz, 1H), 6.55 (d, J=8.4 Hz, 1H), 4.16 (q, J=7.1 Hz, 3H), 2.78-2.67 (m, 2H), 1.27-1.15 (m, 4H), 1.10 (t, J=7.1 Hz, 3H).

(E)-Ethyl 1-(2-((hydroxyimino)methyl)phenoxy)cyclobutanecarboxylate

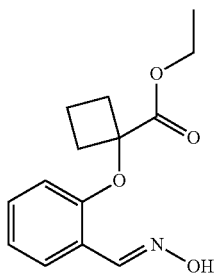 [SMILES: CCOC(=O)C1(Oc2ccccc2/C=N/O)CCC1]

To a solution of ethyl 1-(2-formylphenoxy)cyclobutanecarboxylate (3300 mg, 13.29 mmol) in a mixture of ethanol (15 mL) and water (5 mL) was added hydroxylamine hydrochloride (1847 mg, 26.6 mmol) and ammonium acetate (3074 mg, 39.9 mmol) slowly under nitrogen at 25° C. The reaction mixture was stirred at 25° C. for 12 h after which 30 mL of water was added and the mixture extracted with ethyl acetate (3×). The combined organic phase was concentrated. The crude product was purified by silica gel chromatography (hexane:ethyl acetate=10:1) to obtain the title compound (Z)-ethyl 1-(2-((hydroxyimino)methyl)phenoxy)cyclobutanecarboxylate (1.4 g, 4.79 mmol, 36.0% yield).

LC/MS m/z 264.1 (M+H)$^+$, 1.57 min (ret. time)

518

Ethyl 1-(2-(aminomethyl)phenoxy)cyclobutanecarboxylate

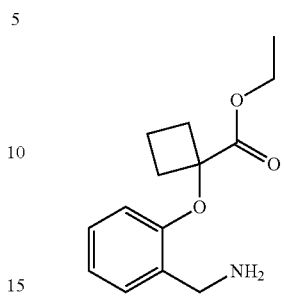

To a solution of (E)-ethyl 1-(2-((hydroxyimino)methyl)phenoxy)cyclobutanecarboxylate (100 mg, 0.380 mmol) in acetic acid (5 mL), platinum(IV) oxide (86 mg, 0.380 mmol) was added slowly at 25° C. The reaction mixture was hydrogenated at 2 atm for 6 h and filtered and concentrated to obtain the title compound ethyl 1-(2-(aminomethyl)phenoxy)cyclobutanecarboxylate (80 mg, 0.263 mmol, 69.3% yield) which was carried to next step without further purification. LC/MS m/z 250.2 (M+H)$^+$, 1.56 min (ret. time)

4,5-Dihydro-3H-spiro[benzo[f][1,4]oxazepine-2,1'-cyclobutan]-3-one

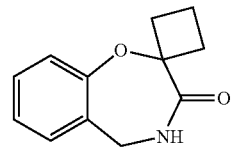 [SMILES: O=C1NCc2ccccc2OC12CCC2]

A solution of ethyl 1-(2-(aminomethyl)phenoxy)cyclobutanecarboxylate (30 mg, 0.120 mmol) and DIPEA (0.021 mL, 0.120 mmol) in 1,4-Dioxane (5 mL) was heated via microwave at 140° C. for 2 h and concentrated and purified by reverse phase preparative HPLC (H$_2$O/MeCN) to provide the title compound 4,5-dihydro-3H-spiro[benzo[f][1,4]oxazepine-2,1'-cyclobutan]-3-one (5 mg, 0.023 mmol, 19.42% yield) as a solid. LC/MS m/z 204.1 (M+H)$^+$, 1.39 min (ret. time)

4,5-Dihydro-3H-spiro[benzo[f][1,4]oxazepine-2,1'-cyclobutane]

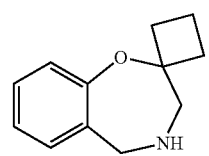 [SMILES: c1ccc2c(c1)CNCC1(CCC1)O2]

To a solution of 4,5-dihydro-3H-spiro[benzo[f][1,4]oxazepine-2,1'-cyclobutan]-3-one (5 mg, 0.025 mmol) in tetrahydrofuran (THF) (5 mL), LiAlH$_4$ (0.934 mg, 0.025 mmol) was added slowly under nitrogen at 20° C. The reaction mixture was stirred at 20° C. for 4 h. 2 g of Na$_2$SO$_4$ 10H$_2$O was added and filtered and concentrated to obtain the title compound 4,5-dihydro-3H-spiro[benzo[f][1,4]ox-azepine-2,1'-cyclobutane] (3 mg, 0.014 mmol, 58.0% yield) which was carried to next step without further purification. LC/MS m/z 190.2 (M+H)+, 1.43 min (ret. time)

Ethyl 3-(3-((3H-spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoate

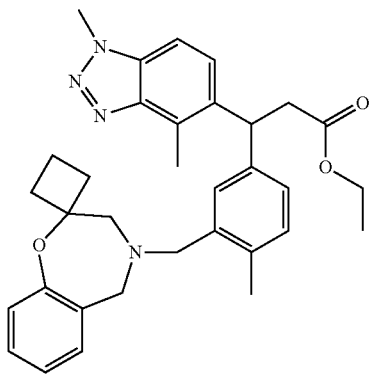 [SMILES: CCOC(=O)CC(c1ccc(C)c(CN2Cc3ccccc3OC3(CCC3)C2)c1)c1ccc2c(nnn2C)c1C]

To a solution of ethyl 3-(3-(chloromethyl)-4-methylphenyl)-3-(1,4-dimethyl-1H-benzo[d][1,2,3]triazol-5-yl)propanoate (100 mg, 0.259 mmol) in acetonitrile (5 mL), 4,5-dihydro-3H-spiro[benzo[f][1,4]oxazepine-2,1'-cyclobutane] (45 mg, 0.238 mmol) and K₂CO₃ (65.7 mg, 0.476 mmol) were added slowly under nitrogen at 25° C. The reaction mixture was stirred at 70° C. for 16 h after which 20 mL of water was added and the mixture extracted with ethyl acetate (3×). The combined organic phase was concentrated and the crude product was purified by reverse phase preparative HPLC (H₂O/MeCN) to provide the title compound ethyl 3-(3-((3H-spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoate (40 mg, 0.070 mmol, 29.4% yield). LC/MS m/z 539.2 (M+H)+, 1.52 min (ret. time)

3-(3-((3H-Spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoic Acid

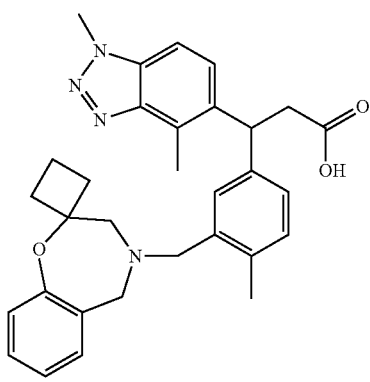 [SMILES: Cc1ccc(C(CC(=O)O)c2ccc3c(nnn3C)c2C)cc1CN1Cc2ccccc2OC2(CCC2)C1]

To a solution of ethyl 3-(3-((3H-spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoate (40 mg, 0.074 mmol) in tetrahydrofuran (THF) (2 mL), a solution of LiOH (7.11 mg, 0.297 mmol) in water (2.0 mL) was added slowly under nitrogen at 25° C. The reaction mixture was stirred at 25° C. for 16 h and adjusted to pH=6 with 0.1 N HCl and extracted with ethyl acetate (3×). The combined organic phase was concentrated to obtain the title compound 3-(3-((3H-spiro[benzo[f][1,4]oxazepine-2,1'-cyclobutan]-4(5H)-yl)methyl)-4-methylphenyl)-3-(1,4-dimethyl-1H-benzo[d][1,2,3]triazol-5-yl)propanoic acid (34 mg, 0.063 mmol, 85% yield) as a solid. LC/MS m/z 511.2 (M+H)+, 1.66 min (ret. time)

Example 245

3-(1,4-Dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoic Acid

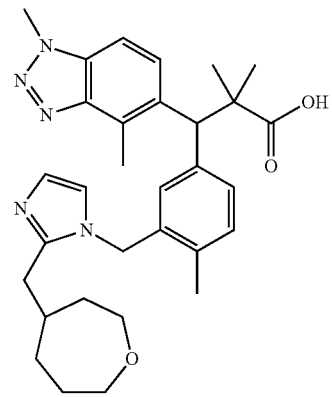 [SMILES: Cc1ccc(C(c2ccc3c(nnn3C)c2C)C(C)(C)C(=O)O)cc1Cn1ccnc1CC1CCCOCC1]

2-(Oxepan-4-yl)acetaldehyde

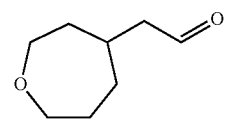

To a solution of 2-(oxepan-4-yl)ethanol (700 mg, 4.85 mmol) in dichloromethane (DCM) (10 mL), PCC (2093 mg, 9.71 mmol) was added. The reaction mixture was stirred at ambient temperature for 12 h. The reaction mixture was filtered. The filtrate was concentrated to obtain the title compound 2-(oxepan-4-yl)acetaldehyde (660 mg, 4.18 mmol, 86% yield) which was carried to next step without further purification. LC/MS m/z 143.1 (M+H)+, 1.36 min (ret. time)

2-(Oxepan-4-ylmethyl)-1H-imidazole

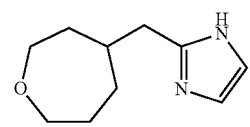 [SMILES: c1c[nH]c(CC2CCCOCC2)n1]

To a solution of 2-(oxepan-4-yl)acetaldehyde (660 mg, 4.64 mmol) in methanol (5 mL) and water (5 mL), oxalaldehyde (1347 mg, 9.28 mmol) and ammonia hydrate (4555 mg, 32.5 mmol) were added. The reaction mixture was stirred at 0° C. for 2 h and at ambient temperature for 18 h. The solvent was removed and the residue was purified by reverse phase preparative HPLC (0.05% NH$_4$HCO$_3$/H$_2$O: CH$_3$CN=5%-95%) to give the title compound 2-(oxepan-4-ylmethyl)-1H-imidazole (500 mg, 2.64 mmol, 56.8% yield) as a brown solid. LC/MS m/z 181.2 (M+H)$^+$, 1.07 min (ret. time)

Methyl 3-(1,4-dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoate

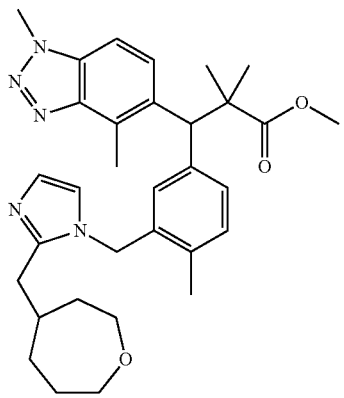 [SMILES: COC(=O)C(C)(C)C(c1ccc(C)c(Cn2ccnc2CC2CCCOCC2)c1)c1ccc2c(nnn2C)c1C]

To a solution of 2-(oxepan-4-ylmethyl)-1H-imidazole (81 mg, 0.450 mmol) in N,N-dimethylformamide (DMF) (5 mL) was added sodium hydride (27.0 mg, 1.125 mmol). After it was stirred at 0° C. for 30 min, methyl 3-(3-(bromomethyl)-4-methylphenyl)-3-(1,4-dimethyl-1H-benzo[d][1,2,3]triazol-5-yl)-2,2-dimethylpropanoate (100 mg, 0.225 mmol) in DMF (2 mL) was added to the mixture slowly and stirred for 1 h at 0° C. Saturated NH$_4$Cl solution was added and the mixture extracted with EtOAc (3×). The combined organic layer was washed with water (2×), brine (2×), dried over Na$_2$SO$_4$ and concentrated to obtain the title compound the methyl 3-(1,4-dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoate (35 mg, 0.061 mmol, 27.2% yield) as a white solid. LC/MS m/z 544.0 (M+H)$^+$, 1.87 min (ret. time)

3-(1,4-Dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoic acid

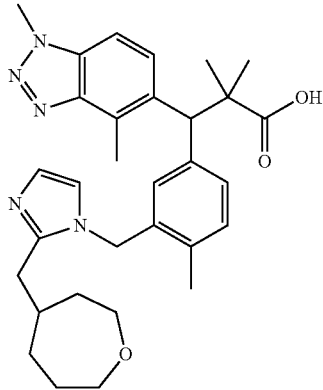 [SMILES: Cc1ccc(C(c2ccc3c(nnn3C)c2C)C(C)(C)C(=O)O)cc1Cn1ccnc1CC1CCCOCC1]

To a solution of methyl 3-(1,4-dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoate (35 mg, 0.064 mmol) in ethylene glycol (2 mL) was added a solution of lithium hydroxide (3.08 mg, 0.129 mmol) in water (0.5 mL) and tetrahydrofuran (THF) (1 mL). The reaction mixture was heated via microwave at 125° C. for 2 h after which the organic solvent was removed. The residue was acidified with 1N HCl to pH 6 and the white precipitate was filtered to give the title compound 3-(1,4-Dimethyl-1H-benzo[d][1,2,3]triazol-5-yl)-2,2-dimethyl-3-(4-methyl-3-((2-(oxepan-4-ylmethyl)-1H-imidazol-1-yl)methyl)phenyl)propanoic acid (25 mg, 0.045 mmol, 69.7% yield). LC/MS m/z 530.3 (M+H)$^+$, 1.58 min (ret. time)

Example 246

3-(3-((7-Cyclopropyl-2-ethyl-1,4-oxazepan-4-yl)methyl)-4-methylphenyl)-3-(1,4-dimethyl-1H-benzo[d][1,2,3]triazol-5-yl)-2,2-dimethylpropanoic Acid

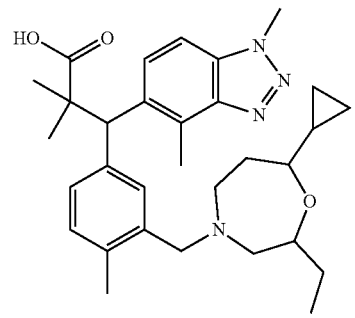 [SMILES: CCC1CN(Cc2cc(C(c3ccc4c(nnn4C)c3C)C(C)(C)C(=O)O)ccc2C)CCC(C2CC2)O1]

3-(4-Methylphenylsulfonamido)propanoic Acid

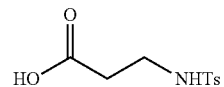

A solution of 3-aminopropanoic acid (9.0 g, 101 mmol) and sodium hydroxide (8.08 g, 202 mmol) in water (40 mL) was heated to 65° C., then 4-methylbenzene-1-sulfonyl chloride (19.26 g, 101 mmol) was added in a portionwise over a period of 0.5 h. Then the reaction mixture was stirred at 65° C. for another 1 h. The reaction mixture was adjusted to PH=1 with HCl (1 N). The solid was filtered to provide the title compound 3-(4-methylphenylsulfonamido)propanoic acid (20 g, 82 mmol, 81% yield) which was carried over to next step without further purification. LC/MS m/z 244.0 (M+H)$^+$, 1.35 min (ret. time)

N-Methoxy-N-methyl-3-(4-methylphenylsulfonamido)propanamide

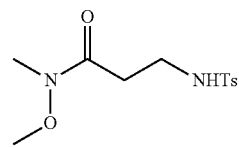

A solution of 3-(4-methylphenylsulfonamido)propanoic acid (5.0 g, 20.55 mmol) and N,O-dimethylhydroxylamine (2.51 g, 41.1 mmol), 1H-benzo[d][1,2,3]triazol-4-ol (2.78 g, 20.55 mmol) and N1-((ethylimino)methylene)-N3,N3-dimethylpropane-1,3-diamine (6.38 g, 41.1 mmol) and N-ethyl-N-isopropylpropan-2-amine (13.28 g, 103 mmol) in dichloromethane (DCM) (100 mL) was stirred at 20° C. for 3 h. The reaction mixture was concentrated. The residue was dissolved in ethyl acetate and washed with 1 N HCl (2×), saturated NaHCO₃ (2×), water, brine (2×), dried over Na₂SO₄ and concentrated to provide the title compound N-methoxy-N-methyl-3-(4-methylphenylsulfonamido)propanamide (5.0 g, 17.46 mmol, 85% yield) as a white solid. LC/MS m/z 287.1 (M+H)⁺, 1.44 min (ret. time)

N-(3-Cyclopropyl-3-oxopropyl)-4-methylbenzenesulfonamide

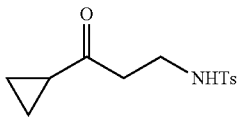

To a solution of N-methoxy-N-methyl-3-(4-methylphenylsulfonamido)propanamide (3.0 g, 10.48 mmol) in tetrahydrofuran (THF) (30 mL), cyclopropylmagnesium bromide (3.04 g, 20.95 mmol) was added at 0° C., and the resulting mixture was stirred at room temperature for 2 h. The mixture was quenched with saturated NH₄Cl solution and extracted with ethyl acetate (3×). The combined organic layer was washed with water, brine (2×), dried over Na₂SO₄ and concentrated. The residue was purified by silica gel chromatography (ethyl acetate:petroleum ether=1:5) to obtain the title compound N-(3-cyclopropyl-3-oxopropyl)-4-methylbenzenesulfonamide (2.15 g, 7.64 mmol, 72.9% yield) as a white solid. LC/MS m/z 268.1 (M+H)⁺, 1.87 min (ret. time)

N-(3-Cyclopropyl-3-hydroxypropyl)-4-methylbenzenesulfonamide

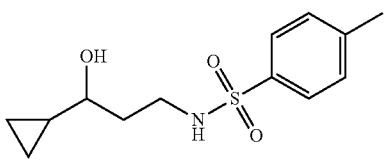 [SMILES: Cc1ccc(S(=O)(=O)NCCC(O)C2CC2)cc1]

To a solution of N-(3-cyclopropyl-3-oxopropyl)-4-methylbenzenesulfonamide (2.0 g, 7.48 mmol) in methanol (20 mL), NaBH₄ (0.425 g, 11.22 mmol) was added in portionwise. The resulting mixture was stirred at room temperature for 2 h. The mixture was poured into ice water and then extracted with ethyl acetate (2×). The combined organic layer was washed with water, brine (2×), dried over Na₂SO₄ and concentrated to provide the title compound N-(3-cyclopropyl-3-hydroxypropyl)-4-methylbenzenesulfonamide (2.0 g, 7.05 mmol, 94% yield) as a white solid. LC/MS m/z 292.2 (M+H)⁺, 1.79 min (ret. time)

N-(3-Cyclopropyl-3-hydroxypropyl)-4-methyl-N-(2-oxobutyl)benzenesulfonamide

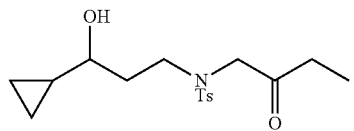 [SMILES: CCC(=O)CN(CCC(O)C1CC1)S(=O)(=O)c1ccc(C)cc1]

To a solution of N-(3-cyclopropyl-3-hydroxypropyl)-4-methylbenzenesulfonamide (2.0 g, 7.43 mmol) in acetone (5 mL), K₂CO₃ (2.052 g, 14.85 mmol) was added, then 1-bromobutan-2-one (1.233 g, 8.17 mmol) was added. The reaction mixture was stirred at room temperature for 16 h. The mixture was filtrated. The filtrate was concentrated. The residue was purified by silica gel chromatography (ethyl acetate:petroleum ether=0 to 30%) to obtain the title compound N-(3-cyclopropyl-3-hydroxypropyl)-4-methyl-N-(2-oxobutyl)benzenesulfonamide (2.5 g, 7.00 mmol, 94% yield) as a white solid. LC/MS m/z 362.1 (M+Na)⁺, 1.78 min (ret. time)

7-Cyclopropyl-2-ethyl-4-tosyl-1,4-oxazepane

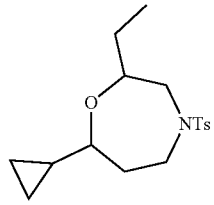 [SMILES: CCC1CN(S(=O)(=O)c2ccc(C)cc2)CCC(C2CC2)O1]

To a solution of N-(3-cyclopropyl-3-hydroxypropyl)-4-methyl-N-(2-oxobutyl)benzenesulfonamide (7.7 g, 22.68 mmol) in dichloromethane (DCM) (100 mL), triethylsilane (2.90 g, 24.95 mmol) and trimethylsilyl trifluoromethanesulfonate (5.55 g, 24.95 mmol) were added at −78° C. The reaction mixture was stirred at −78° C. for 10 min. The mixture was quenched by saturated NaHCO₃, then extracted with CH₂Cl₂ (3×). The combined organic phase was washed with brine, dried over Na₂SO₄ and concentrated. The residue was purified by silica gel chromatography (hexane: ethyl acetate=10:1) to obtain the title compound 7-cyclopropyl-2-ethyl-4-tosyl-1,4-oxazepane (6.1 g, 17.92 mmol, 79% yield) as a white solid. LC/MS m/z 324.3 (M+H)⁺, 2.21 min (ret. time)

7-Cyclopropyl-2-ethyl-1,4-oxazepane

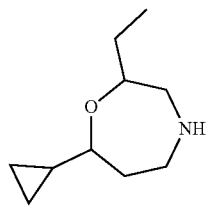

A mixture of sodium (2.452 g, 107 mmol) and naphthalene (16.64 g, 130 mmol) in DME (20 mL) was stirred at room temperature for 2 h. To a solution of 7-cyclopropyl-2-ethyl-4-tosyl-1,4-oxazepane (3.0 g, 9.27 mmol) in DME (20 mL) at −78° C., the sodium naphthalenide solution was added dropwise until a light green colour persisted. Then the mixture was quenched with saturated NaHCO$_3$(20 mL) and DME was removed. The residue was diluted with water and was adjust the PH=1 with HCl (1 N). Then it was extracted with ethyl acetate (3×). The water layer was adjust the PH=8 with saturated NaHCO$_3$ and was extracted with ethyl acetate (3×). The combined organic phase was washed with brine and concentrated to provide the title compound 7-Cyclopropyl-2-ethyl-1,4-oxazepane (1.5 g, 7.98 mmol, 86%) which was carried over to next step without further purification. LC/MS m/z 170.1 (M+H)$^+$, 1.08 min (ret. time)

Tert-Butyl
7-cyclopropyl-2-ethyl-1,4-oxazepane-4-carboxylate

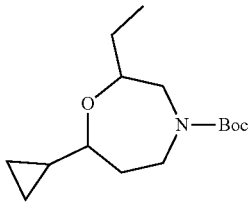

To a solution of 7-cyclopropyl-2-ethyl-1,4-oxazepane (1.5 g, 8.86 mmol) in water (50 mL) was added di-tert-butyl dicarbonate (3.87 g, 17.72 mmol) at ambient temperature. The reaction mixture was stirred for 18 h. The reaction mixture was extracted with ethyl acetate (3×). The combined organic layer was washed with brine and concentrated. The residue was purified by silica gel chromatography (ethyl acetate:petroleum ether=10:1) to obtain the title compound tert-butyl 7-cyclopropyl-2-ethyl-1,4-oxazepane-4-carboxylate (2.17 g, 7.65 mmol, 86% yield) as a light yellow oil. LC/MS m/z 214.2 (M-56+H)$^+$, 1.91 min (ret. time)

7-Cyclopropyl-2-ethyl-1,4-oxazepane

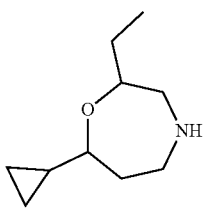

To a solution of tert-butyl 7-cyclopropyl-2-ethyl-1,4-oxazepane-4-carboxylate (2.17 g, 8.06 mmol) in diethyl ether (10 mL) was added hydrogen chloride (0.587 g, 16.11 mmol) at ambient temperature. The reaction mixture was stirred for 18 h. The reaction mixture was concentrated to obtain the title compound 7-cyclopropyl-2-ethyl-1,4-oxazepane, Hydrochloride (1.3 g, 6.00 mmol, 74.5% yield) as a yellow oil. LC/MS m/z 170.3 (M+H)$^+$, 1.22 min (ret. time)

Methyl 3-(3-((7-cyclopropyl-2-ethyl-1,4-oxazepan-4-yl)methyl)-4-methylphenyl)-3-(1,4-dimethyl-1H-benzo[d][1,2,3]triazol-5-yl)-2,2-dimethylpropanoate

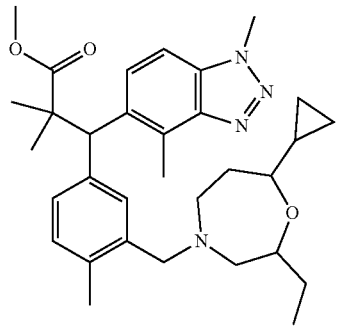 [SMILES: CCC1CN(Cc2cc(C(c3ccc4c(nnn4C)c3C)C(C)(C)C(=O)OC)ccc2C)CCC(C2CC2)O1]

To a solution of methyl 3-(3-(bromomethyl)-4-methylphenyl)-3-(1,4-dimethyl-1H-benzo[d][1,2,3]triazol-5-yl)-2,2-dimethylpropanoate (70 mg, 0.158 mmol) and 7-cyclopropyl-2-ethyl-1,4-oxazepane (32.0 mg, 0.189 mmol) in dichloromethane (DCM) (2 mL) was added N-ethyl-N-isopropylpropan-2-amine (102 mg, 0.788 mmol). The reaction mixture was stirred at ambient temperature for 2 h and concentrated and the residue was purified by silica gel chromatography (ethyl acetate:petroleum ether=3:1) to give the title compound methyl 3-(3-((7-cyclopropyl-2-ethyl-1,4-oxazepan-4-yl)methyl)-4-methylphenyl)-3-(1,4-dimethyl-1H-benzo[d][1,2,3]triazol-5-yl)-2,2-dimethylpropanoate (60 mg, 0.107 mmol, 67.9% yield) as a light yellow solid. LC/MS m/z 533.3 (M+H)$^+$, 1.51 min (ret. time)

3-(3-((7-Cyclopropyl-2-ethyl-1,4-oxazepan-4-yl)methyl)-4-methylphenyl)-3-(1,4-dimethyl-1H-benzo[d][1,2,3]triazol-5-yl)-2,2-dimethylpropanoic Acid

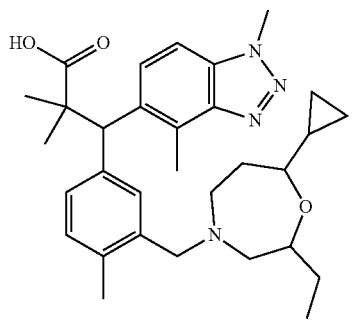 [SMILES: CCC1CN(Cc2cc(C(c3ccc4c(nnn4C)c3C)C(C)(C)C(=O)O)ccc2C)CCC(C2CC2)O1]

To a solution of methyl 3-(3-((7-cyclopropyl-2-ethyl-1,4-oxazepan-4-yl)methyl)-4-methylphenyl)-3-(1,4-dimethyl-1H-benzo[d][1,2,3]triazol-5-yl)-2,2-dimethylpropanoate (60 mg, 0.113 mmol) in ethylene glycol (2 mL) was added a solution of lithium hydroxide (13.49 mg, 0.563 mmol) in water (0.5 mL) and tetrahydrofuran (THF) (1 mL). The reaction was heated via microwave at 125° C. for 10 h after which the organic solvent was removed. The residue was acidified with 1N HCl to pH 6 and the white precipitate was filtered and dried to give the title compound 3-(3-((7-Cyclopropyl-2-ethyl-1,4-oxazepan-4-yl)methyl)-4-methylphenyl)-3-(1,4-dimethyl-1H-benzo[d][1,2,3]triazol-5-yl)-2, 2-dimethylpropanoic acid ((38 mg, 0.07 mmol, 61.8% yield). LC/MS m/z 519.4 (M+H)+, 1.74 min (ret. time)

Example 247

3-(3-((2-((4-Ethylpiperidin-1-yl)methyl)-1H-imidazol-1-yl)methyl)-4-methylphenyl)-2,2-dimethyl-5-(1-propyl-1H-1,2,3-triazol-4-yl)pentanoic Acid

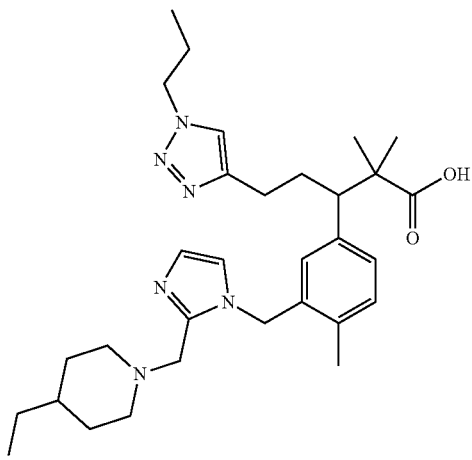 [SMILES: CCCn1cc(CCC(c2ccc(C)c(Cn3ccnc3CN3CCC(CC)CC3)c2)C(C)(C)C(=O)O)nn1]

5-(Trimethylsilyl)pent-4-ynal (Intermediate E)

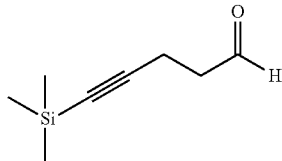

To oxalyl chloride (7.09 ml, 81 mmol) in DCM (100 mL) at −78° C. was added dropwise DMSO (9.58 ml, 135 mmol) in DCM (60 mL) and stirred at −78° C. for 5 min and then 5-(trimethylsilyl)pent-4-yn-1-ol (4.22 g, 27 mmol) in DCM (35 mL) was added dropwise. Stirring continued for 30 min and then another 30 min at −40 C then triethylamine (30.1 ml, 216 mmol) was added rapidly and the stirred solution warmed to 0 C and then poured into satd aq NaHCO₃. Separate phases and wash DCM with water (2×) and again with satd aq NaHCO₃ and dried (Na₂SO₄) and concentrate to an oil. The crude product was purified on a silica cartridge (80 g) with a Combiflash Companion, eluting at 60 mL/min with a gradient running from hexanes to 20% EtOAc/hexanes over 25 min. The desired fractions were pooled based on tlc 95% hexane and EtOAc to afford 5-(trimethylsilyl)pent-4-ynal (3.15 g, 20.42 mmol, 76% yield).

¹H NMR (400 MHz, CHLOROFORM-d) δ 9.82 (s, 1H), 2.64-2.75 (m, 2H), 2.51-2.62 (m, 2H), 0.17 (s, 9H)

1-(3-(((4-Methoxybenzyl)oxy)methyl)-4-methylphenyl)-5-(trimethylsilyl)pent-4-yn-1-ol (Intermediate A)

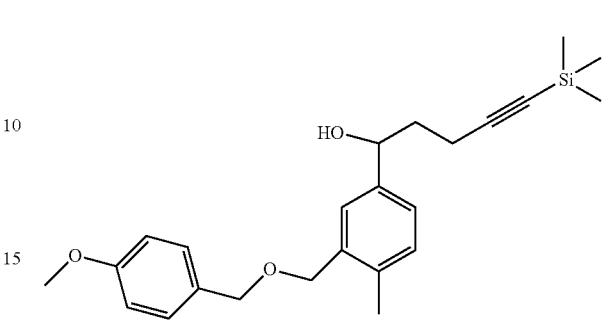

The reaction was under an inert atmosphere (Ar) in Aldrich anhydrous THF (no stabilizer) using glassware dried at 130° C. for >16 h.

4-Bromo-2-(((4-methoxybenzyl)oxy)methyl)-1-methylbenzene (Intermediate 5) (3.28 g, 10.22 mmol) was dissolved in anhydrous tetrahydrofuran (THF) (65 mL) and cooled to −65° C. 2M butyllithium in THF (6.39 mL, 12.78 mmol) was added and the reaction was stirred at −65° C. to −75° C. for 0.5 h. 5-(trimethylsilyl)pent-4-ynal (Intermediate E) (3.15 g, 20.44 mmol) in THF (6 mL) was added dropwise and the reaction was stirred at −65° C. to −75° C. for 2 h. The reaction was diluted with water (25 mL) and EtOAc (75 mL). The aqueous layer was extracted with an additional portion of EtOAc (50 mL) and the combined EtOAc was washed with water (50 mL) and saturated aqueous NaCl (50 mL), dried over Na₂SO₄ and concentrated. The crude product was dissolved in acetonitrile (15 mL) filtered through a 0.45 μm acrodisc, and purified on a Gilson HPLC (Sunfire Prep C18 OBD 5 mm 30×250 mm preparatory column), under neutral conditions to afford 1-(3-(((4-methoxybenzyl)oxy)methyl)-4-methylphenyl)-5-(trimethylsilyl)pent-4-yn-1-ol (3.17 g, 7.99 mmol, 78% yield).

¹H NMR (400 MHz, CHLOROFORM-d) δ 7.26-7.41 (m, 5H), 7.13-7.23 (m, 2H), 6.80-6.97 (m, 2H), 4.76-4.89 (m, 1H), 4.47-4.61 (m, 4H), 3.77-3.93 (m, 3H), 2.25-2.48 (m, 5H), 1.83-2.10 (m, 3H), 0.10-0.25 (m, 9H).

(5-Bromo-5-(3-(((4-methoxybenzyl)oxy)methyl)-4-methylphenyl)pent-1-yn-1-yl)trimethylsilane (intermediate B)

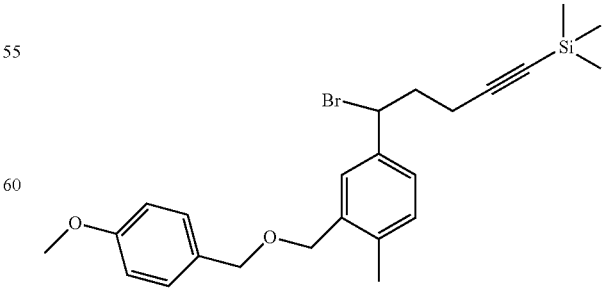

To 1-(3-(((4-methoxybenzyl)oxy)methyl)-4-methylphenyl)-5-(trimethylsilyl)pent-4-yn-1-ol (Intermediate A) (4.3 g, 10.8 mmol) dissolved in dichloromethane (DCM) (300 mL) was added perbromomethane (4.31 g, 13.00 mmol) and then polystyrene-PPh₃ (1.4 mmol/g) (23.21 g, 32.5 mmol) was added. The reaction slowly spontaneously warmed to 30° C. and was stirred with no external cooling or heating for 1.5 h. The reaction was filtered, concentrated and the residue was dissolved in hexane, filtered through an acrodisc filter and injected onto an ISCO 120 g gold column eluting with an Combiflash Rf200 at 85 mL/min with a gradient from 0 to 10% EtOAc in hexane to afford (5-bromo-5-(3-(((4-methoxybenzyl)oxy)methyl)-4-methylphenyl)pent-1-yn-1-yl)trimethylsilane (4.8159 g, 10.48 mmol, 97% yield).

¹H NMR (400 MHz, CHLOROFORM-d) δ7.07-7.52 (m, 6H), 6.80-6.99 (m, 2H), 5.02-5.21 (m, 1H), 4.41-4.69 (m, 4H), 3.65-3.95 (m, 3H), 2.10-2.66 (m, 7H), 0.19 (s, 9H) lcms (1.67 min).

Benzyl 3-(3-(((4-methoxybenzyl)oxy)methyl)-4-methylphenyl)-2,2-dimethyl-7-(trimethylsilyl)hept-6-ynoate (Intermediate C)

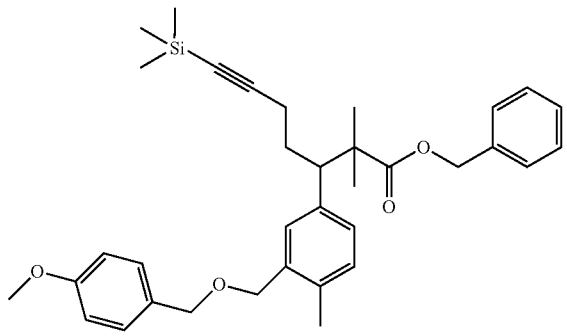 [SMILES: COc1ccc(COCc2cc(C(CCC#C[Si](C)(C)C)C(C)(C)C(=O)OCc3ccccc3)ccc2C)cc1]

The reaction was under an inert atmosphere (Ar) in aldrich anhydrous THF (no stabilizer) using glassware dried at 130° C. for >16 h.

A −70° C. solution of diisopropylamine (12.51 mL, 89 mmol)) in tetrahydrofuran (THF) (38 mL) was treated with 1.6 M n-butyllithium in hexanes (33.5 mL, 53.5 mmol) added at a rate that kept the temperature <−60° C. The resulting solution stirred at −70° C. 15 min, warmed to 0° C. over 15 minutes and cooled to −70° C. after which benzyl isobutyrate (9.45 mL, 53.5 mmol) in tetrahydrofuran (THF) (38.0 mL) was added dropwise while keeping the temperature <−65° C. The reaction was stirred at −70° C. 45 min, warmed to −50° C. for 15 min and then recooled to −70° C. (5-bromo-5-(3-(((4-methoxybenzyl)oxy)methyl)-4-methylphenyl)pent-1-yn-1-yl)trimethylsilane (Intermediate B) (4.1 g, 8.92 mmol) in tetrahydrofuran (THF) (38.0 mL) was added dropwise to the enolate while keeping the temperature <−60° C. This was immediately followed by the addition of 1,3-dimethyltetrahydropyrimidin-2(1H)-one (21.58 mL, 178 mmol) T<−° 60. Stirred 1 h at −70° C. 1 h and then warmed to −45° C. and stirred for 2 h. water (25 mL) was added and the mixture warmed to 23° C. Ethyl acetate (200 mL) was added and additional water (50 mL) and the phases were separated. The aqueous layer was extracted again with EtOAc (75 ml) and the combined extract was washed with water (50 mL) and saturated aqueous NaCl (50 mL) dried (Na₂SO₄), concentrated and the residue was injected as a hexane solution onto an 120 g gold ISCO column eluting with an Combiflash Rf200, at 85 mL/min with a gradient running from hexanes to 10% EtOAc/hexanes over 30 min. The desired fractions were pooled and concentrated to afford benzyl 3-(3-(((4-methoxybenzyl)oxy)methyl)-4-methylphenyl)-2,2-dimethyl-7-(trimethylsilyl)hept-6-ynoate (4.86 g, 8.73 mmol, 98% yield).

¹H NMR (400 MHz, CHLOROFORM-d) 67.23-7.47 (m, 11H), 7.04-7.17 (m, 2H), 6.80-7.02 (m, 3H), 4.91-5.17 (m, 2H), 4.41-4.61 (m, 4H), 3.67-3.94 (m, 3H), 2.95-3.13 (m, 1H), 2.19-2.40 (m, 3H), 1.64-2.16 (m, 4H), 1.03-1.24 (m, 7H), 0.76-0.94 (m, 1H), 0.15 (s, 9H). LC/MS (ES+) [M+Na+]=579.2 (1.74 min)

Benzyl 3-(3-(((4-methoxybenzyl)oxy)methyl)-4-methylphenyl)-2,2-dimethylhept-6-ynoate (Intermediate D)

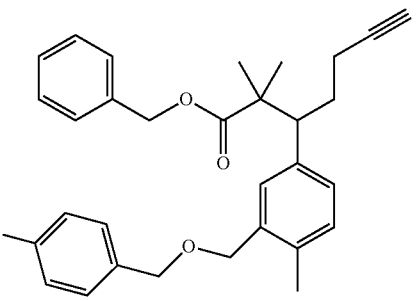

Benzyl 3-(3-(((4-methoxybenzyl)oxy)methyl)-4-methylphenyl)-2,2-dimethyl-7-(trimethylsilyl)hept-6-ynoate (Intermediate C) (2.03 g, 3.65 mmol) dissolved in methanol (18 mL) was combined with potassium carbonate (2.52 g, 18.23 mmol) and stirred for 2 h. The reaction was diluted with water and extracted 3× with DCM. The organic layers were dried with MgSO₄, and volatiles were evaporated in vacuo to afford benzyl 3-(3-(((4-methoxybenzyl)oxy)methyl)-4-methylphenyl)-2,2-dimethylhept-6-ynoate (1.67 g, 3.45 mmol, 95%) LC/MS (ES+) [M+Na]+=507.6 (1.54 min)

Benzyl 3-(3-(((4-methoxybenzyl)oxy)methyl)-4-methylphenyl)-2,2-dimethyl-5-(1-propyl-1H-1,2,3-triazol-4-yl)pentanoate

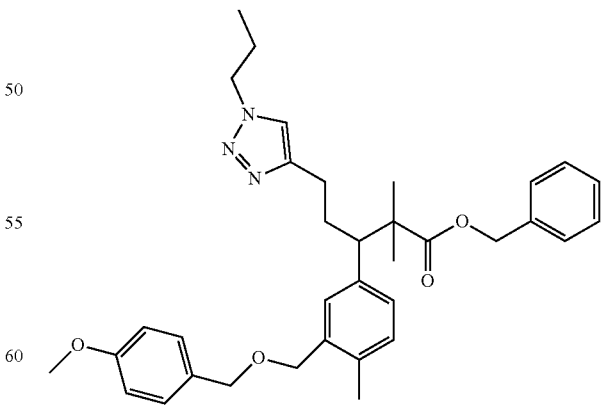

Sodium azide (0.431 g, 6.63 mmol), 1-iodopropane (0.594 mL, 6.10 mmol),copper(I) iodide (0.076 g, 0.398 mmol), and Hunig's base (0.093 mL, 0.530 mmol) were added to a solution of benzyl 3-(3-(((4-methoxybenzyl)oxy)

methyl)-4-methylphenyl)-2,2-dimethylhept-6-ynoate (1.284 g, 2.65 mmol) in tert-butanol (6.50 mL) and water (6.5 mL) and heated via microwave at 70° C. for 1 h. This was repeated for a second equal portion of benzyl 3-(3-(((4-methoxybenzyl)oxy)methyl)-4-methylphenyl)-2,2-dimethylhept-6-ynoate benzyl 3-(3-(((4-methoxybenzyl)oxy)methyl)-4-methylphenyl)-2,2-dimethylhept-6-ynoate for a total of 2.57 g (5.3 mmol) of the starting acetylene. Both reactions were cooled and combined, diluted with EtOAc (150 mL) and water (50 mL). The aqueous layer was extracted again with EtOAc (75 mL) and the combined EtOAc was washed with water (50 mL) and saturated aqueous NaCl (25 mL), dried ($Na_2SO_4$) and concentrated. The crude product was purified on an ISCO 80 g gold column with a Combiflash Rf200 with 0-70% EtOAc in hexane at 60 mL/min to afford benzyl 3-(3-(((4-methoxybenzyl)oxy)methyl)-4-methylphenyl)-2,2-dimethyl-5-(1-propyl-1H-1,2,3-triazol-4-yl)pentanoate (2.21 g, 3.88 mmol, 73% yield). LC/MS (ES+) [M+H]+=570.7 (1.43 min).

Benzyl 3-(3-(hydroxymethyl)-4-methylphenyl)-2,2-dimethyl-5-(1-propyl-1H-1,2,3-triazol-4-yl)pentanoate

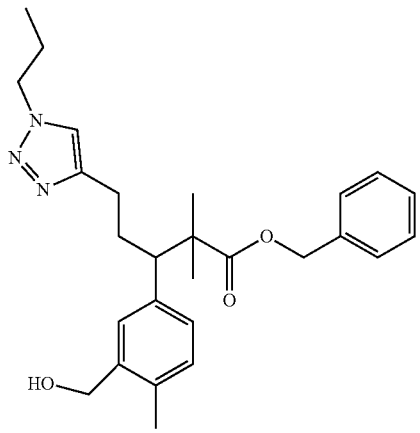 [SMILES: CCCn1cc(CCC(c2ccc(C)c(CO)c2)C(C)(C)C(=O)OCc2ccccc2)nn1]

Benzyl 3-(3-(((4-methoxybenzyl)oxy)methyl)-4-methylphenyl)-2,2-dimethyl-5-(1-propyl-1H-1,2,3-triazol-4-yl)pentanoate (2.28 g, 4.00 mmol) in acetonitrile (18.0 mL) was combined with ceric ammonium nitrate (4.39 g, 8.00 mmol) and water (2 mL) and stirred 90 min. The reaction was diluted with EtOAc (150 mL) and water (50 mL) shaken and the phases were separated. The aqueous layer was extracted again with EtOAc (100 mL) and the combined EtOAc was washed with water (50 mL) and saturated aqueous NaCl (50 mL), dried ($Na_2SO_4$) filtered and the reaction was concentrated and chromatographed on a 40 g gold column with a ISCO Rf200 at 40 ml/min with a gradient from hexane to 100% EtOAc to afford benzyl3-(3-(hydroxymethyl)-4-methylphenyl)-2,2-dimethyl-5-(1-propyl-1H-1,2,3-triazol-4-yl)pentanoate (1.63 g, 3.63 mmol, 91% yield). LC/MS (ES+) [M+H]+=450.6 (1.14 min).

Benzyl 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoate (Propyl Isomer P1)

Benzyl 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoate (Propyl Isomer P2)

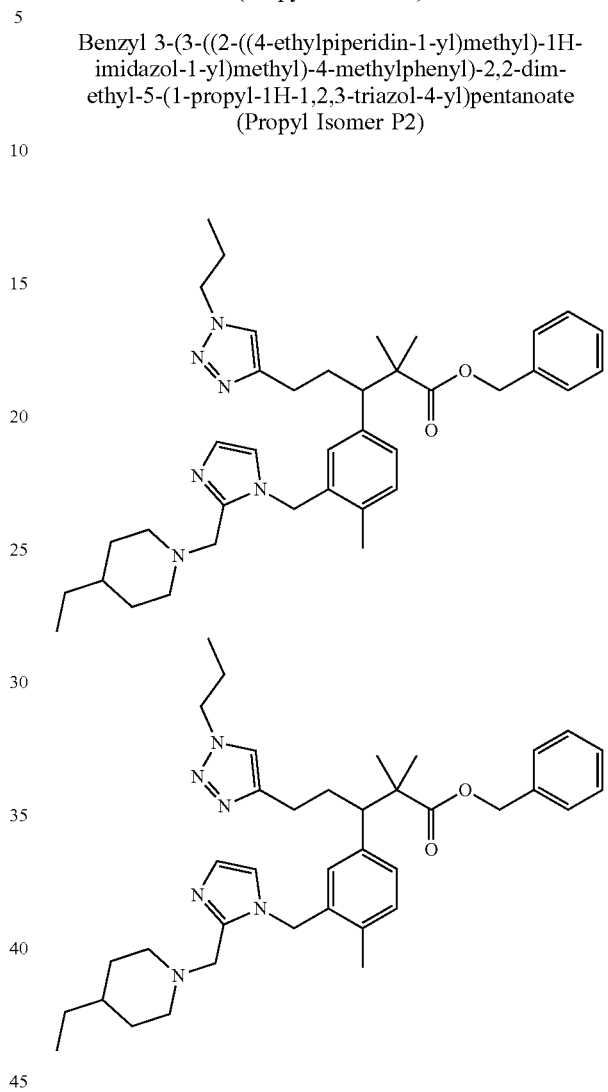

In a 25 mL 2 neck flask under Ar, 1-((1H-imidazol-2-yl)methyl)-4-ethylpiperidine (156 mg, 0.809 mmol) in N,N-Dimethylformamide (DMF) (4.60 mL) was treated with the portionwise addition of 60% sodium hydride in oil (108 mg, 2.70 mmol) and stirred for 30 min to form solution A.

In a separate vial, benzyl 3-(3-(hydroxymethyl)-4-methylphenyl)-2,2-dimethyl-5-(1-propyl-1H-1,2,3-triazol-4-yl)pentanoate (303 mg, 0.674 mmol) in dichloromethane (DCM) (4.6 mL) was treated with thionyl chloride (0.098 mL, 1.348 mmol) and the mixture was stirred at 23° C. for 30 min. The solvent was removed in vacuo and the residue was redissolved in N,N-Dimethylformamide (DMF) (4.60 mL) and the resulting solution was added to solution A described above, and the resulting mixture was stirred for a total of 20 h. The reaction was combined with additional 1-((1H-imidazol-2-yl)methyl)-4-ethylpiperidine (156 mg, 0.809 mmol) and sodium hydride (64.7 mg, 2.70 mmol) and stirred 1 h. The reaction was diluted with EtOAc (100 mL) and water (50 mL). The aqueous layer was extracted with a second portion of EtOAc (100 mL) and the combined EtOAc was washed with water (2×75 mL) and saturated aqueous NaCl, and dried ($Na_2SO_4$) and concentrated to afford a light green oil which was dissolved in DMSO (4 mL) and purified on a Gilson HPLC (Sunfire Prep C$_{18}$ OBD 5 μm 30×250 mm preparatory column), eluting at 30 mL/min with a linear gradient running from 10% CH$_3$CN/ H$_2$O/0.1% TFA to 95% acetonitrile/H$_2$O/0.1% TFA over 15 min to afford purified material as a mixture of isomers (357 mg).

Separation of the enantiomers was effected by chiral SFC, Chiralpak AD 20×250 mm, 5 u, Co-solvent: 20% MeOH, Total flowrate: 50 g/min, Back pressure: 100 Bar to afford benzyl 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoate (propyl isomer P1) (101 mg, 0.162 mmol, 23.98% yield) LC/MS (ES+) [M+H]+=625.7 (1.15 min). sfc Rf=4.44 min and benzyl 3-(3-((2-((4-ethylpiperidin-1-yl)methyl)-1H-imidazol-1-yl) methyl)-4-methylphenyl)-2,2-dimethyl-5-(1-propyl-1H-1,2, 3-triazol-4-yl)pentanoate (propyl isomer P2) (82 mg, 0.131 mmol, 19.47% yield) LC/MS (ES+) [M+H]+=625.7 (1.16 min) sfc Rf=5.43 min.

3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoic Acid (Propyl Isomer 2)

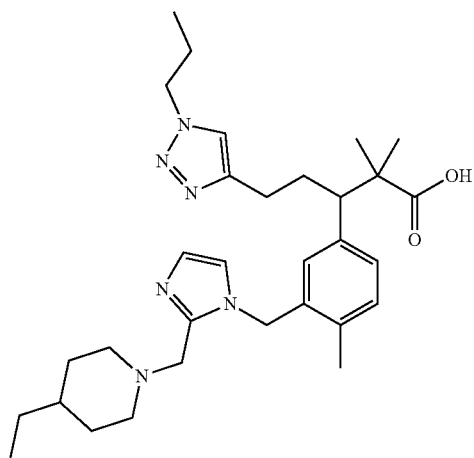 [SMILES: CCCn1cc(CCC(c2ccc(C)c(Cn3ccnc3CN3CCC(CC)CC3)c2)C(C)(C)C(=O)O)nn1]

Benzyl 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoate (propyl isomer P2) (80 mg, 0.128 mmol) was dissolved in methanol (10 mL) and hydrogenated on an H-cube (flow hydrogenator) with the 20% Pd(OH)$_2$ cartridge at 1 atm for 80 min. The solution was concentrated to afford 59.8 mg of a foamy solid. The resulting product was purified by reverse phase preparative HPLC using neutral conditions to afford 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl) pentanoic acid (propyl isomer 2) (32 mg, 0.060 mmol, 47% yield)) as a white solid. LC/MS (ES+) [M+H]+=535.5 (0.90 min).

Example 248

3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoic Acid (Propyl Isomer 1)

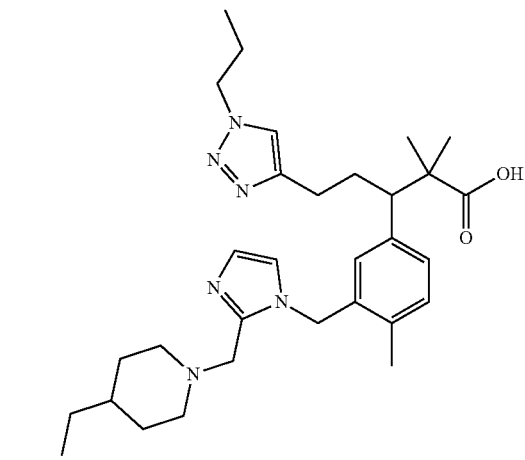 [SMILES: CCCn1cc(CCC(c2ccc(C)c(Cn3ccnc3CN3CCC(CC)CC3)c2)C(C)(C)C(=O)O)nn1]

Benzyl 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoate(propyl isomer P1) (101 mg, 0.162 mmol) was dissolved in methanol (10 mL) and hydrogenated on the H-cube (flow hydrogenator) with the 20% Pd(OH)$_2$ cartridge at 1 atm for 50 min. The solvent was removed in vacuo to afford a clear oil which was purified by reverse phase preparative HPLC using neutral conditions to afford a pure white foamy solid. 3-(3-((2-((4-ethylpiperidin-1-yl)methyl)-1H-imidazol-1-yl)methyl)-4-methylphenyl)-2,2-dimethyl-5-(1-propyl-1H-1,2,3-triazol-4-yl)pentanoic acid (propyl isomer 1) (48 mg, 0.090 mmol, 57%) LC/MS (ES+) [M+H]+=535.5 (0.90 min).

Example 249

5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoic Acid

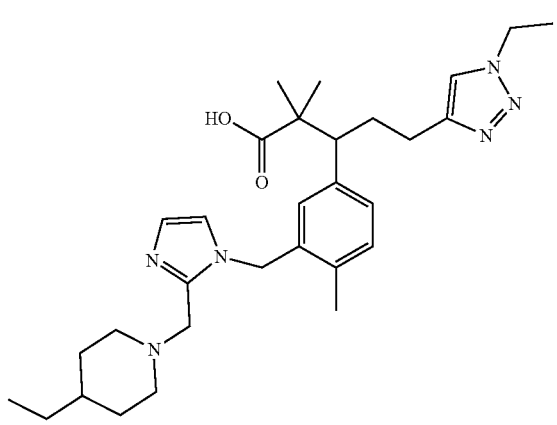 [SMILES: CCC1CCN(Cc2nccn2Cc2cc(C(CCc3cn(CC)nn3)C(C)(C)C(=O)O)ccc2C)CC1]

Benzyl 5-(1-ethyl-1H-1,2,3-triazol-4-yl)-3-(3-(((4-methoxybenzyl)oxy)methyl)-4-methylphenyl)-2,2-dimethylpentanoate

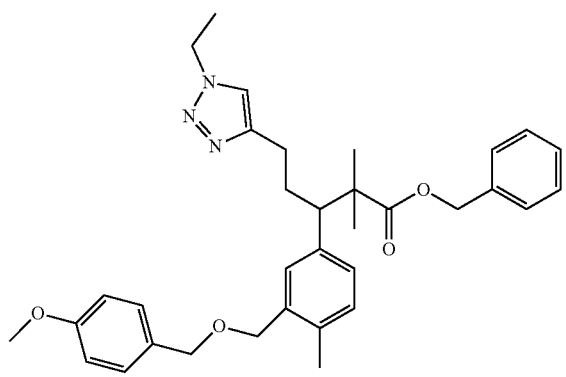 [SMILES: CCn1cc(CCC(c2ccc(C)c(COCc3ccc(OC)cc3)c2)C(C)(C)C(=O)OCc2ccccc2)nn1]

Sodium azide (0.553 g, 8.51 mmol), iodoethane (0.684 ml, 8.51 mmol), copper(I) iodide (0.097 g, 0.511 mmol) and N-ethyl-N-isopropylpropan-2-amine (0.119 ml, 0.681 mmol) were added to a solution of benzyl 3-(3-(((4-methoxybenzyl)oxy)methyl)-4-methylphenyl)-2,2-dimethylhept-6-ynoate (1.65 g, 3.40 mmol) (Intermediate D) in tert-butanol (8.51 ml) and water (8.51 ml). This mixture was heated via microwave to 70° C. for 1 hour. The reaction was diluted with water and EtOAc. The aqueous layer was extracted 3× with EtOAc, and the combined organic layers were dried over MgSO$_4$ concentrated and the crude oil was purified on a silica cartridge (24 g) with a Combiflash Rf200, eluting at 35 mL/min with a gradient running from hexanes to 90% EtOAc/hexanes over 20 min to afford benzyl 5-(1-ethyl-1H-1,2,3-triazol-4-yl)-3-(3-(((4-methoxybenzyl)oxy)methyl)-4-methylphenyl)-2,2-dimethylpentanoate (1.57 g, 2.83 mmol, 83% yield) as a yellow oil. LC/MS (ES+) [M+H]+=535.5 (0.98 min).

Benzyl 5-(1-ethyl-1H-1,2,3-triazol-4-yl)-3-(3-(hydroxymethyl)-4-methylphenyl)-2,2-dimethylpentanoate

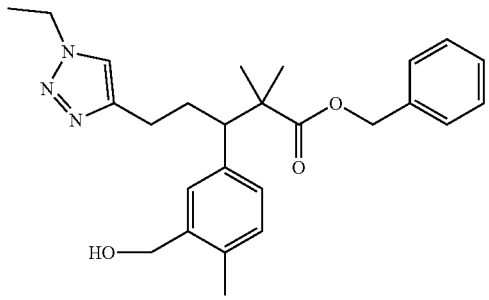 [SMILES: CCn1cc(CCC(c2ccc(C)c(CO)c2)C(C)(C)C(=O)OCc2ccccc2)nn1]

Ceric ammonium nitrate (3.08 g, 5.61 mmol) was added to a solution of benzyl 5-(1-ethyl-1H-1,2,3-triazol-4-yl)-3-(3-(((4-methoxybenzyl)oxy)methyl)-4-methylphenyl)-2,2-dimethylpentanoate (1.56 g, 2.81 mmol) in acetonitrile (12.63 ml) and water (1.404 ml). After 40 min the reaction was diluted with DCM and water. The aqueous layers were extracted 3× with DCM. The combined organic layers were dried with MgSO$_4$ and concentrated. The crude oil was purified on a silica cartridge (12 g) with a Combiflash Rf200, eluting at 30 mL/min with a gradient running from hexanes to EtOAc over 25 min. The desired fractions were isolated to afford benzyl 5-(1-ethyl-1H-1,2,3-triazol-4-yl)-3-(3-(hydroxymethyl)-4-methylphenyl)-2,2-dimethylpentanoate (1.06 g, 2.44 mmol, 87% yield). LC/MS (ES+) [M+H]+=436.5 (1.09 min).

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (Ethyl Isomer P1)

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (Ethyl Isomer P2)

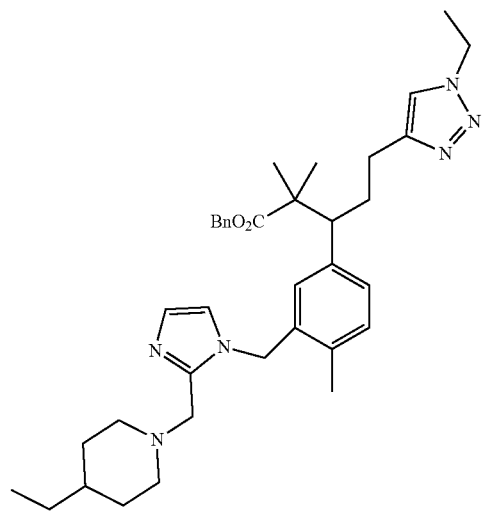

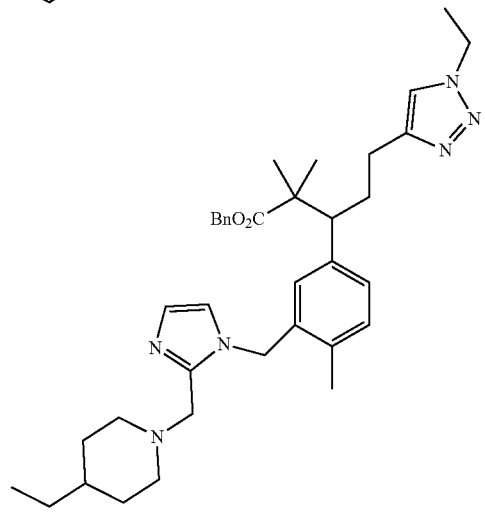

Sodium hydride (55.1 mg, 1.378 mmol) was added to a solution of 1-((1H-imidazol-2-yl)methyl)-4-ethylpiperidine (80 mg, 0.413 mmol) in N,N-Dimethylformamide (DMF) (2.296 mL) at 23° C. to afford solution A.

Thionyl chloride (0.050 mL, 0.689 mmol) was added to a solution of benzyl 5-(1-ethyl-1H-1,2,3-triazol-4-yl)-3-(3-(hydroxymethyl)-4-methylphenyl)-2,2-dimethylpentanoate (150 mg, 0.344 mmol) in dichloromethane (DCM) (2.296 mL) at 23° C. After 30 min, the volatiles were removed in vacuo. The crude chloride was dissolved in DMF and added to the solution of 1-((1H-imidazol-2-yl)methyl)-4-ethylpiperidine (80 mg, 0.413 mmol) and sodium hydride (55.1 mg, 1.378 mmol) in N,N-Dimethylformamide (DMF) (2.296 mL), solution A, described in the paragraph above. The resulting mixture was stirred at 23° C. for 2 hours. The reaction was quenched with NH$_4$C$_1$(aqueous layer), and the aqueous layer was extracted 3× with EtOAc. The organic layers were combined, dried with MgSO$_4$, filtered and concentrated and the residue was dissolved in MeCN, filtered through a 0.45 μm acrodisc, and purified on a Gilson HPLC (YMC C18 5 mm/12 nm 50×20 mm preparatory column), eluting at 20 mL/min with a linear gradient running from 5% CH$_3$CN/H$_2$O to 65% CH$_3$CN/H$_2$O over 10 min. The desired fractions were concentrated under a stream of nitrogen at 50° C., giving the mixture of isomers (110 mg, 0.180 mmol). The sample was combined with a second lot of a mixture of isomers (100 mg) prepared the same way.

This purified material was purified by chiral SFC, Column: Chiralpak AD 20×250 mm, 5 u, Co-solvent: 25% IPA, total flowrate: 50 g/min, Back pressure: 100 Bar to afford Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (ethyl isomer P1) (SFC ret. time 12.19) and Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (ethyl isomer P2) (SFC ret. time 14.12)

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (ethyl isomer P1)

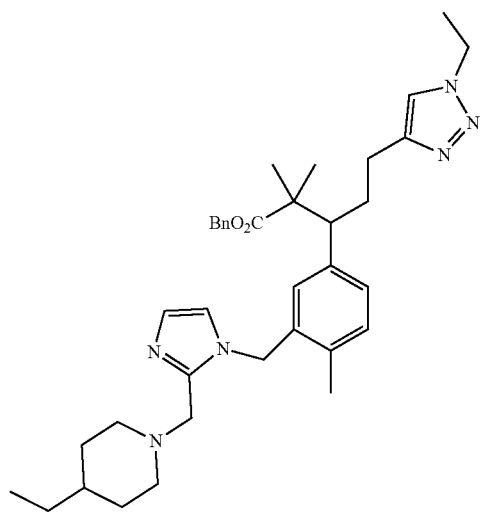

(49 mg, 23%). LC/MS (ES+) [M+H]+=611.4 (1.13 min). Analytical SFC ret. time 12.19.

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (ethyl isomer P2)

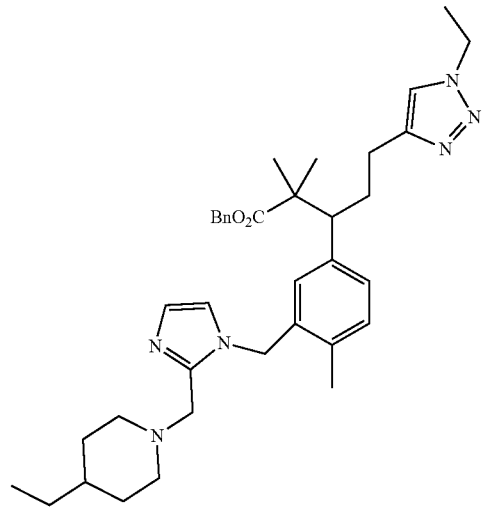

(48 mg, 23%) LC/MS (ES+) [M+H]+=611.4 (1.13 min). Analytical SFC ret. time 14.12

5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoic acid (ethyl isomer 2) G

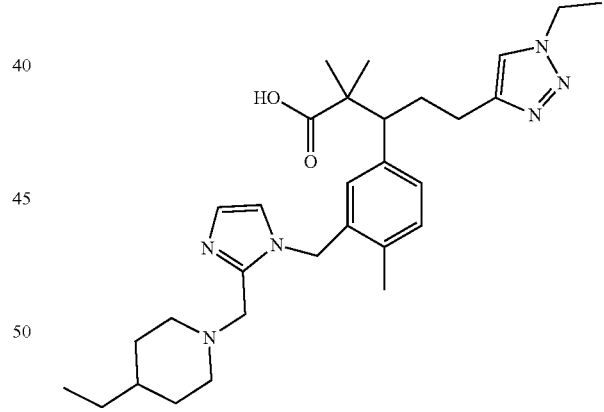

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (ethyl isomer P2) (50 mg, 0.082 mmol) was dissolved in MeOH (10 mL), and passed through an H-cube (flow hydrogenator) at 1 mL/min and 25° C. using a 10% Pd/C cartridge for 1 hour. The methanol was removed in vacuo and the residue was purified by reverse phase preparative HPLC using neutral conditions to afford 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoic acid (ethyl isomer 2) (20 mg, 0.038 mmol, 46.9% yield). LC/MS (ES+) [M+H]+=521.5 (0.89 min).

Example 250

5-(1-ethyl-1H-1,2,3-triazol-4-yl)-3-(3-((2-((4-ethyl-piperidin-1-yl)methyl)-1H-imidazol-1-yl)methyl)-4-methylphenyl)-2,2-dimethylpentanoic acid (ethyl isomer 1)

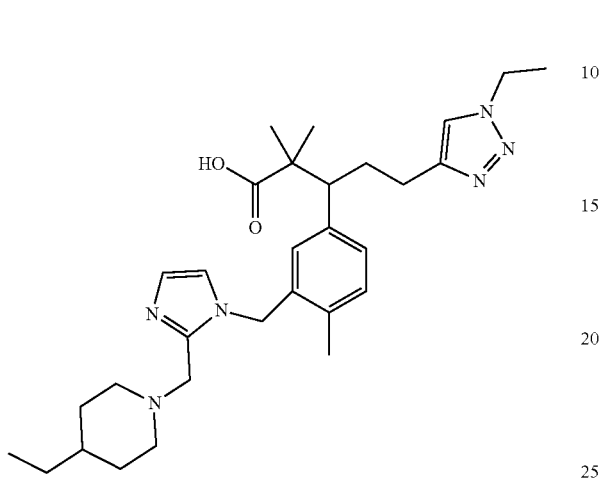

Benzyl 5-(1-ethyl-1H-1,2,3-triazol-4-yl)-3-(3-((2-((4-ethylpiperidin-1-yl)methyl)-1H-imidazol-1-yl)methyl)-4-methylphenyl)-2,2-dimethylpentanoate (ethyl isomer P1) (50 mg, 0.082 mmol) was dissolved in MeOH (10 mL), and passed through an H-cube (flow hydrogenator) at 1 mL/min and 25 C using a 10% Pd/C cartridge for 1 hour. The methanol was removed in vacuo and the residue was purified by reverse phase preparative HPLC using neutral conditions to afford-(1-ethyl-1H-1,2,3-triazol-4-yl)-3-(3-((2-((4-ethyl-piperidin-1-yl)methyl)-1H-imidazol-1-yl)methyl)-4-methylphenyl)-2,2-dimethylpentanoic acid (ethyl isomer 1) (20 mg, 0.038 mmol, 46.9% yield). LC/MS (ES$^+$) [M+H]$^+$ 521.5 (0.90 min).

Example 251

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic Acid

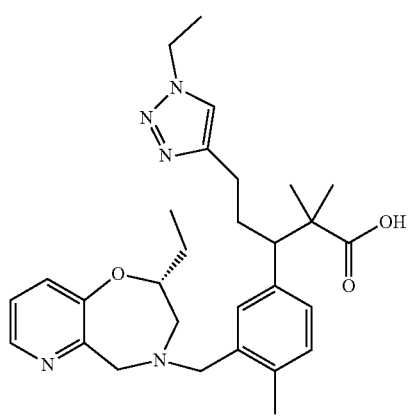 [SMILES: CC[C@@H]1CN(Cc2cc(C(CCc3cn(CC)nn3)C(C)(C)C(=O)O)ccc2C)Cc2ncccc2O1]

5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic Acid

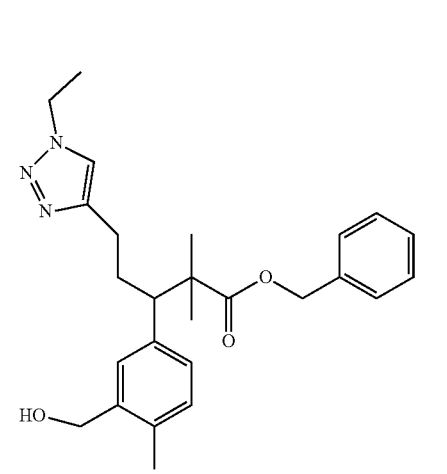

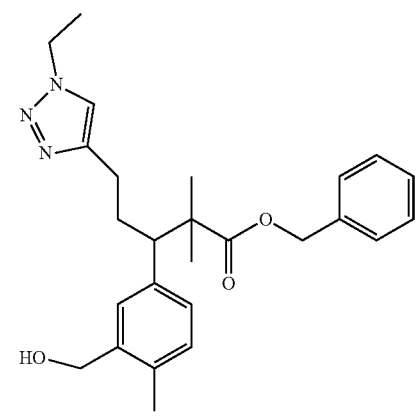

Benzyl 5-(1-ethyl-1H-1,2,3-triazol-4-yl)-3-(3-(hydroxymethyl)-4-methylphenyl)-2,2-dimethylpentanoate (enantiomer A1) and Benzyl 5-(1-ethyl-1H-1,2,3-triazol-4-yl)-3-(3-(hydroxymethyl)-4-methylphenyl)-2,2-dimethylpentanoate (enantiomer A2)

benzyl 5-(1-ethyl-1H-1,2,3-triazol-4-yl)-3-(3-(hydroxymethyl)-4-methylphenyl)-2,2-dimethylpentanoate (998 mg, 2.29 mmol) was submitted to preparative SFC Chiralpak AY 20×250 mm, Co-solvent: 25% EtOH, Total flowrate: 50 g/min, Back pressure: 100 Bar to afford benzyl 5-(1-ethyl-1H-1,2,3-triazol-4-yl)-3-(3-(hydroxymethyl)-4-methylphenyl)-2,2-dimethylpentanoate (enantiomer A1) 301 mg (30%)g. SFC Rf=1.5 min. LC/MS (ES$^+$) [M+H]$^+$ 436.5 (1.09 min) and then eluting benzyl 5-(1-ethyl-1H-1,2,3-triazol-4-yl)-3-(3-(hydroxymethyl)-4-methylphenyl)-2,2-dimethylpentanoate(enantiomer A2) to afford 303 mg, (30%) SFC Rf=2.42 min. LC/MS (ES$^+$) [M+H]$^+$=436.5 (1.08 min).

541

Benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (Isomer 1)

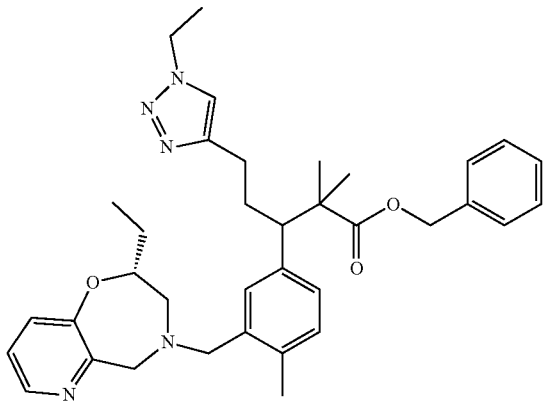 [SMILES: CC[C@@H]1CN(Cc2cc(C(CCc3cn(CC)nn3)C(C)(C)C(=O)OCc3ccccc3)ccc2C)Cc2ncccc2O1]

To a solution of benzyl 5-(1-ethyl-1H-1,2,3-triazol-4-yl)-3-(3-(hydroxymethyl)-4-methylphenyl)-2,2-dimethylpentanoate(enantiomer A1) (273 mg, 0.627 mmol) in dichloromethane (DCM) (10.0 mL) was added thionyl chloride (0.183 mL, 2.507 mmol) and the mixture was stirred at ambient temperature for 30 min to afford the chlorinated product. The solvent was removed and the residue was dissolved in acetonitrile (5.000 mL) and the solution was divided into two equal portions and 1/2 of ((R)-2-ethyl-2,3,4,5-tetrahydropyrido[2,3-f][1,4]oxazepine, hydrochloride (161 mg, 0.752 mmol) (81 mg in each portion) and 1/2 of Hunig's base (0.876 mL, 5.01 mmol) (0.438 mL in each portion) each in acetonitrile (5.000 mL) was added to each of the solutions of the chloride product above. Each of the mixtures were heated in a microwave vial at 120° C. for 1 h. The reaction was concentrated and the residue was shaken with EtOAc (150 mL) and water (50 mL). The aqueous layer was extracted again with EtOAc (50 mL) and the combined EtOAc was washed with water (50 mL) and then saturated aqueous NaCl then dried ($Na_2SO_4$) and concentrated. The crude product was purified on an ISCO gold silica cartridge (12 g) with a Combiflash Rf200, eluting at 30 mL/min with a gradient running from hexanes to 100% EtOAc over 25 min. The desired fractions were pooled and concentrated to afford benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (isomer 1) (283 mg, 0.475 mmol, 76% yield) as a colorless oil. LC/MS (ES$^+$) [M+H]$^+$ 596.8 (1.08 min).

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic Acid (Isomer 1B)

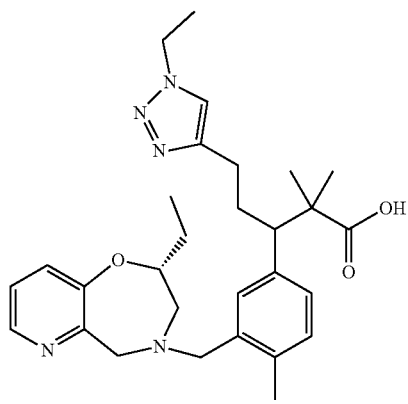 [SMILES: CC[C@@H]1CN(Cc2cc(C(CCc3cn(CC)nn3)C(C)(C)C(=O)O)ccc2C)Cc2ncccc2O1]

542

A solution of benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (isomer 1) (283 mg, 0.475 mmol) in methanol (10 ml) was hydrogenated on the H-cube (flow hydrogenator) using a 10% Pd—C H cube cartridge and full $H_2$ pressure for 45 min. The cartridge was washed with 10 mL methanol and this was combined with the reaction solution and concentrated to afford crude product as a white foam. The sample was purified by neutral Gilson to afford 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid (isomer 1B)(140 mg, 0.277 mmol, 58.3% yield). LC/MS (ES$^+$) [M+H]$^+$=506.3 (0.86 min).

Example 252

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid (isomer 2B)

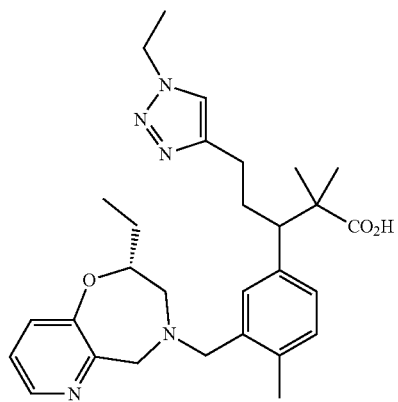 [SMILES: CC[C@@H]1CN(Cc2cc(C(CCc3cn(CC)nn3)C(C)(C)C(=O)O)ccc2C)Cc2ncccc2O1]

Benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (isomer 2)

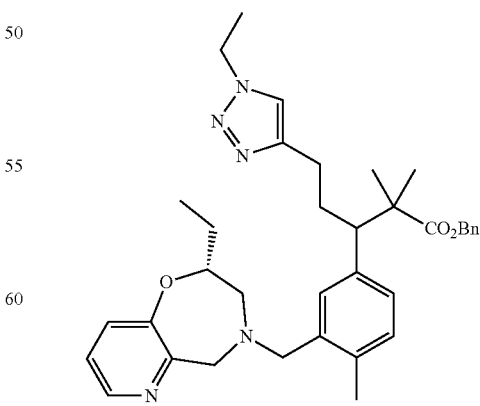

To a solution of benzyl 5-(1-ethyl-1H-1,2,3-triazol-4-yl)-3-(3-(hydroxymethyl)-4-methylphenyl)-2,2-dimethylpentanoate (enantiomer A2) (0.232 g, 0.533 mmol) in dichloromethane (DCM) (10 mL) was added thionyl chloride (0.078 mL, 1.065 mmol) and stirred at ambient temperature for 30 min. The solvent was removed and the residue was dissolved in acetonitrile (5.00 mL). This was divided equally into two 20 mL microwave reaction vessels. To each of these solutions was added one half of a solution of (R)-2-ethyl-2,3,4,5-tetrahydropyrido[2,3-f][1,4]oxazepine, hydrochloride (0.114 g, 0.531 mmol) and DIEA (0.372 mL, 2.131 mmol) in acetonitrile (10.00 mL). The reactions were heated via microwave to 120° C. for 1 h. Additional (R)-2-ethyl-2,3,4,5-tetrahydropyrido[2,3-f][1,4]oxazepine, hydrochloride (0.057 g, 0.266 mmol) and DIEA (0.093 mL, 0.533 mmol) was divided equally between each vessel and heated both on microwave at 120° C. for 20 min. The reactions were combined and the solvent was concentrated. The residue was purified by flash chromatography eluting with 0-40% (3:1 EtOAc:EtOH)/hexane to provide Benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (isomer 2). (0.233 g, 73% yield) LC/MS m/z=596 (M+H)+, 1.11 min (ret. time).

5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid (isomer 2B)

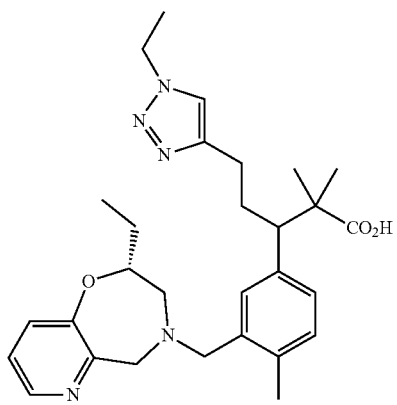 [SMILES: CC[C@@H]1CN(Cc2cc(C(CCc3cn(CC)nn3)C(C)(C)C(=O)O)ccc2C)Cc2ncccc2O1]

A solution of benzyl 5-(1-ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoate (isomer 2) (0.233 g, 0.336 mmol) in methanol (10 mL) was hydrogenated on H-Cube using 10% Pd/C cartridge and full $H_2$ pressure, for 1.5 h. The solvent was concentrated and the residue was purified by reverse phase preparative HPLC under neutral conditions to provide 5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid (isomer 2B). (0.126 g, 74% yield) LC/MS m/z 506 (M+H)+, 0.85 min (ret. time).

Example 253

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

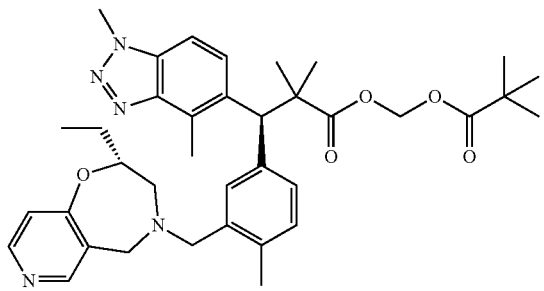 [SMILES: CC[C@@H]1CN(Cc2cc([C@@H](c3ccc4c(nnn4C)c3C)C(C)(C)C(=O)OCOC(=O)C(C)(C)C)ccc2C)Cc2cnccc2O1]

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (100 mg, 0.190 mmol) and cesium carbonate (185 mg, 0.569 mmol) were taken up in DMF (1.7 mL) at 0° C. Iodomethyl pivalate (138 mg, 0.569 mmol) was added. The reaction was stirred at ambient temperature for 18 hrs. The reaction was quenched with brine and extracted three times with EtOAc. The organic layers were dried over magnesium sulfate, filtered, and concentrated in vacuo. The crude residue was purified by flash chromatography (gradient 0-5% MeOH/DCM). (S)-(Pivaloyloxy)methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate (69.8 mg, 0.109 mmol, 57.4% yield) after lyophilization.

$^1$H NMR (400 MHz, CHLOROFORM-d) δ ppm 0.95 (t, J=7.28 Hz, 3H) 1.07 (s, 9H) 1.32 (s, 3H) 1.39 (s, 3H) 1.33-1.44 (m, 1H) 1.59 (d, J=7.28 Hz, 1H) 2.24 (s, 3H) 2.76 (s, 3H) 2.79-2.87 (m, 2H) 3.53 (s, 2H) 3.74 (s, 2H) 3.80-3.94 (m, 1H) 4.25 (s, 3H) 4.85 (s, 1H) 5.49-5.65 (m, 2H) 6.89 (d, J=5.27 Hz, 1H) 7.03 (s, 3H) 7.27 (d, J=8.53 Hz, 2H) 7.60 (d, J=8.53 Hz, 1H) 8.11 (s, 1H) 8.37 (d, J=5.52 Hz, 1H)

LC/MS (ES+): m/z 642.5 (M+H)+

Example 254

(S)-((Diphenoxyphosphoryl)oxy)methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

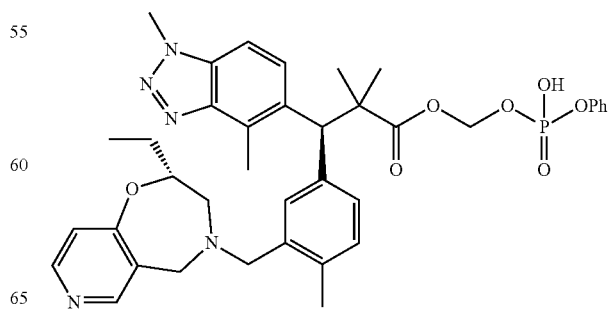

545

Chloromethyl diphenyl phosphate

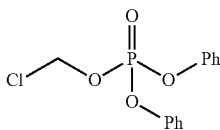 [SMILES: O=P(OCCl)(Oc1ccccc1)Oc1ccccc1]

To a stirring 0° C. solution of diphenyl hydrogen phosphate (10.0 g, 40.0 mmol), tetrabutylammonium hydrogensulfate (13.4 g, 160 mmol) in water (200 mL) was added DCM (100 mL). The resulting mixture was stirred at 0° C. for 10 min and then a solution of chloromethyl sulfochloridate (7.91 g, 48.0 mol) in DCM (100 mL) was added. The resulting solution was stirred for 3 days at ambient temperature. The organic layer was separated and washed with brine, dried over magnesium sulfate, filtered, and concentrated in vacuo. The crude residue was purified by flash chromatography (gradient 0-50% EtOAc/hexanes) to afford chloromethyl diphenyl phosphate (10.37 g, 34.7 mmol, 87% yield) as a colorless oil.

$^1$H NMR (400 MHz, DMSO-$d_6$) δ ppm 6.07 (d, J=16.6 Hz, 2H) 7.21-7.36 (m, 6H) 7.41-7.51 (m, 4H) LC/MS (ES+): m/z 299.0 (M+H)$^+$ (S)-((Diphenoxyphosphoryl)oxy)methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

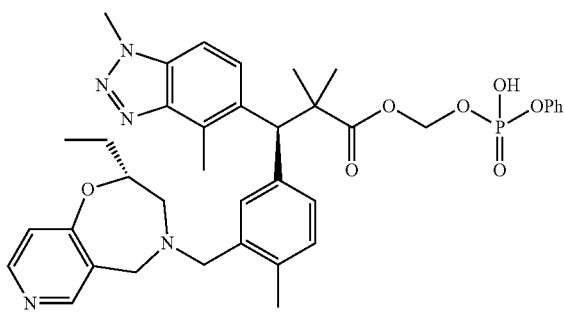 [SMILES: CC[C@@H]1CN(Cc2cc([C@@H](c3ccc4c(nnn4C)c3C)C(C)(C)C(=O)OCOP(C)(=O)Oc3ccccc3)ccc2C)Cc2cnccc2O1]

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (100 mg, 0.190 mmol) and cesium carbonate (185 mg, 0.569 mmol) were taken up in DMF (1.7 mL) at 0° C. Chloromethyl diphenyl phosphate (170 mg, 0.569 mmol) was added. The reaction was stirred at ambient temperature for 18 hrs, at which point the starting material was consumed (>95%). The mono hydrolysis product was the major product. The reaction was quenched with brine and extracted three times with DCM. The organic layers were dried over magnesium sulfate, filtered, and concentrated in vacuo. The crude residue was purified by prep HPLC (20×100 mm Sunfire, 0.1% aq. TFA/CH$_3$CN). Saturated aqueous NaHCO$_3$ was added to the product fractions to free base the product. The product was extracted with DCM (3×) from this aqueous layer. The combined organic layers were dried over magnesium sulfate, filtered, concentrated in vacuo, and lyophilized to provide (S)-((diphenoxyphosphoryl)oxy) methyl 3-(1,4-dimethyl-1H-benzo[d][1,2,3]triazol-5-yl)-3-

546

(3-(((R)-2-ethyl-2,3-dihydropyrido[3,4-f][1,4]oxazepin-4 (5H)-yl)methyl)-4-methylphenyl)-2,2-dimethylpropanoate at 77% purity. Product is a mixture of diastereomers at phosphorus, diastereomeric peaks are denoted in pairs, where applicable, in the NMR characterization.

$^1$H NMR (400 MHz, CHLOROFORM-d) δ ppm 0.94 (t, J=7.53 Hz, 3H) 1.01/1.13 (s, 3H) 1.08/1.18 (s, 3H) 1.27-1.45 (m, 1H) 1.58-1.62 (m, 1H) 1.95 (br.s. 1H) 2.18/2.23 (s, 3H) 2.65/2.73 (s, 3H) 2.79-2.86 (m, 2H) 3.45/3.53 (s, 2H) 3.73/3.86 (s, 2H) 3.80-3.94 (m, 1H) 4.10/4.22 (s, 3H) 4.66/4.76 (s, 1H) 5.17-5.34 (m, 2H) 6.75-7.07 (m, 9H) 7.15/7.24 (d, J=7.78 and 8.78 Hz, respectively, 1H) 7.42/7.57 (d, J=both 8.53 Hz, 1H) 8.04/8.11 (s, 1H) 8.22/8.37 (d, J=3.26 and 5.27 Hz, respectively, 1H) LC/MS (ES+): m/z 714.2 (M+H)$^+$ Example 255

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

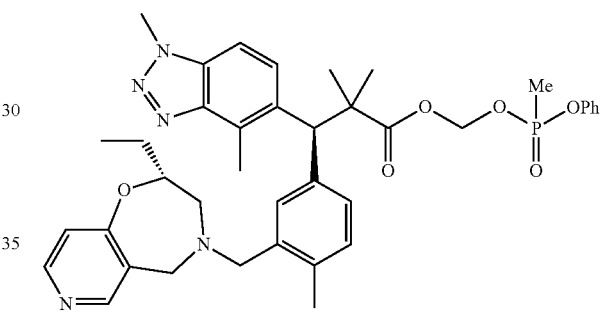

Chloromethyl phenyl methylphosphate

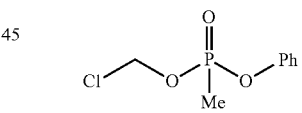

Methylphosphonic dichloride (15.3 g, 115 mmol) was weighed into a dry 500 mL round bottom flask. Phenol (21.7 g, 230 mmol) and DCM (209 mL) were added. The resulting mixture was stirred as it was cooled to 0° C. Triethylamine (64.2 mL, 460 mmol) was added dropwise over 1 hr forming a colorless precipitate. The mixture was allowed to warm to ambient temperature and stirred for an additional 2 hrs. The mixture was carefully poured into ice water (100 mL) The organics were extracted with DCM (2×), dried over magnesium sulfate, filtered, and concentrated in vacuo. The crude product was purified by flash chromatography (gradient 0-50% EtOAc/hexanes) to afford diphenyl methylphosphonate (24.6 g, 99.0 mmol, 86% yield) as a viscous oil. LC/MS (ES+): m/z 249.0 (M+H)$^+$ Diphenyl methylphosphonate (24.6 g, 99.0 mmol) was diluted in water (150 mL). Aqueous sodium hydroxide (2N, 74.4 mL, 149 mmol) was added. The resulting mixture was stirred at reflux for 30 minutes until the organic phase became miscible with the aqueous solvent. The mixture was then cooled to 0° C. and concentrated HCl (16.53 mL, 99.0 mol) was carefully added to neutralize the solution to approximately pH=7. The aqueous phase was washed with DCM to remove the phenol byproduct. The aqueous phase was brought to pH=1 using concentrated HCl. The aqueous phase was extracted with DCM (3×) and the combined organic layers were washed with brine and then dried over magnesium sulfate, filtered, and concentrated to give phenyl hydrogen methylphosphonate (7.17 g, 35.4 mmol, 35.7% yield) as an orange oil, which was carried on to the next step without further purification. LC/MS (ES+): m/z 172.9 (M+H)+

To a stirring 0° C. solution of phenyl hydrogen methylphosphonate (7.17 g, 41.7 mmol), tetrabutylammonium hydrogensulfate (1.41 g, 4.17 mmol) and NaHCO$_3$ (14.0 g, 167 mmol) in water (208 mL) was added DCM (100 mL) The resulting mixture was stirred at 0° C. for 10 min and then a solution of chloromethyl sulfochloridate (8.25 g, 50.0 mmol) in DCM (100 mL) was added and the reaction was stirred for 18 hrs at ambient temperature. The reaction was recharged with chloromethyl sulfochloridate (8.25 g, 50.0 mmol). After 2 hrs, the reaction was at pH=1, so sodium carbonate (8.83 g, 83 mmol) was added. No further progression was observed so chloromethyl sulfochloridate (8.25 g, 50.0 mmol) was added and the mixture was stirred for 18 hr at ambient temperature. A final addition of sodium carbonate (8.83 g, 83 mmol) followed by chloromethyl sulfochloridate (8.25 g, 50.0 mmol) was performed and the mixture was stirred at ambient temperature for 1 hr. The organic layer was separated and concentrated in vacuo. The crude residue was purified by flash chromatography (gradient 0-50% EtOAc/hexanes) to afford chloromethyl phenyl methylphosphonate (3.36 g, 15.23 mmol, 36.6% yield) as a yellow oil. Product is a mixture of diastereomers at phosphorus, diastereomeric peaks are denoted in pairs, where applicable, in the NMR characterization.

$^1$H NMR (400 MHz, DMSO-d$_6$) δ ppm 1.77/1.81 (s, 3H) 5.90/5.94 (m, 2H) 7.17-7.30 (m, 3H) 7.37-7.46 (m, 2H)

LC/MS (ES+): m/z 220.9 (M+H)+

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

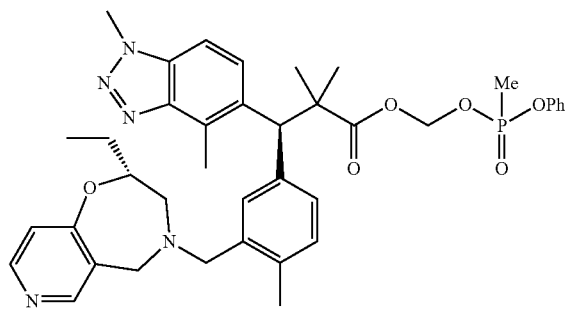 [SMILES: CC[C@@H]1CN(Cc2cc([C@@H](c3ccc4c(nnn4C)c3C)C(C)(C)C(=O)OCOP(C)(=O)Oc3ccccc3)ccc2C)Cc2cnccc2O1]

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4 (5H)-yl)methyl)-4-methylphenyl)-2,2-dimethylpropanoic acid (100 mg, 0.190 mmol) and cesium carbonate (185 mg, 0.569 mmol) were taken up in DMF (1.7 mL) at 0° C. Chloromethyl phenyl methylphosphonate (125 mg, 0.569 mmol) was added. The reaction was stirred at ambient temperature overnight, at which point the starting material was consumed by LC/MS analysis. The reaction was quenched with brine and extracted with DCM (3×). The combined organic layers were dried over magnesium sulfate, filtered, and concentrated in vacuo. The crude residue was purified by reverse phase acidic prep HPLC to separate out the byproduct cleanly (Sunfire, TFA modifier). The purified fractions were washed with saturated NaHCO$_3$ to remove the TFA salt and the product was extracted with DCM. The combined organic layers were dried over magnesium sulfate, filtered, and concentrated to provide (3S)-((methyl(phenoxy)phosphoryl)oxy)methyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate (20.3 mg, 0.029 mmol, 15.05% yield) after lyophilization.

$^1$H NMR (400 MHz, CHLOROFORM-d) δ ppm 0.96/0.97 (t, J=7.30 Hz, 3H) 1.31/1.34 (s, 3H) 1.39/1.40 (s, 3H), 1.36-1.42 (m, 1H), 1.48/1.52 (d, J=6.15 Hz, 3H) 1.56-1.67 (m, 1H) 2.26 (s, 2×3 H, overlapping) 2.77/2.78 (s, 3H) 2.81-2.91 (m, 2H, overlapping) 3.54 (s, 2×2 H, overlapping) 3.75 (s, 2×2 H, overlapping) 3.83-3.96 (m, 1H, overlapping) 4.24/4.25 (s, 3H) 4.84/4.87 (s, 2H) 5.39-5.62 (m, 2H, overlapping) 6.91 (d, J=5.27 Hz, 1H) 6.99-7.10 (m, 3H) 7.11-7.23 (m, 3H) 7.26 (m, 1H) 7.30-7.38 (m, 2H) 7.57/7.63 (d, J=8.78 Hz, 1H) 8.12 (d, J=3.01 Hz, 1H) 8.39 (d, J=5.02 Hz, 1H)

LC/MS (ES+): m/z 712.2 (M+H)+

Example 256

3-((S)-3-(1,4-Dimethyl-1H-benzo[d][1,2,3]triazol-5-yl)-3-(3-(((R)-2-ethyl-2,3-dihydropyrido[3,4-f][1,4] oxazepin-4(5H)-yl)methyl)-4-methylphenyl)-2,2-dimethylpropanoyl)thiazolidin-2-one, Trifluoroacetic Acid Salt

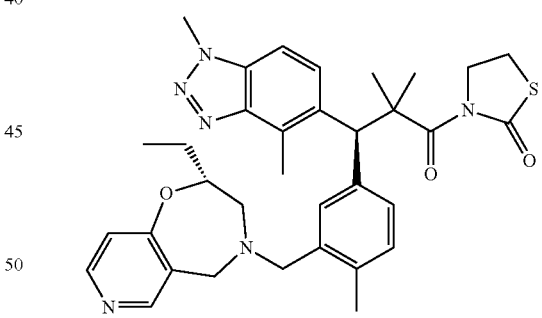

Oxalyl chloride (0.166 mL, 1.895 mmol) was added to a solution of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (100 mg, 0.190 mmol) in DCM (2 mL). Catalytic DMF (2 drops) was added. Additional oxalyl chloride (0.166 mL, 1.895 mmol) was added in order to complete the formation of the intermediate acid chloride, at which point the reaction was concentrated in vacuo to provide the acid chloride hydrochloride salt as a white foam. This crude material was redissolved in DCM (2 mL). DIPEA (0.331 mL, 1.895 mmol) followed by thiazolidin-2-one (98 mg, 0.948 mmol) was added. The reaction was stirred at ambient temperature for 15 minutes, during which time the reaction turned a dark brown color. The reaction was quenched with saturated aqueous NaHCO₃ and extracted with DCM (3×). The organic layers were washed with brine, dried over magnesium sulfate, filtered, and concentrated in vacuo. The crude residue was first purified by flash chromatography (100% DCM) and then further purified by reverse phase acidic prep HPLC (Sunfire, TFA modifier) to provide the trifluoroacetic acid salt of 3-((S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoyl)thiazolidin-2-one (61.6 mg, 0.080 mmol, 42.0% yield) as a white solid after lyophilization.

¹H NMR (400 MHz, CHLOROFORM-d) δ ppm 1.00 (t, J=7.40 Hz, 3H) 1.43 (s, 3H) 1.53 (s, 3H) 1.55-1.67 (m, 1H) 1.67-1.80 (m, 1H) 2.23 (s, 3H) 2.53-2.67 (m, 1H) 2.69-2.78 (m, 1H) 2.80 (s, 3H) 3.00-3.13 (m, 2H) 3.77 (s, 2H) 3.79-3.91 (m, 4H) 4.26 (s, 3H) 4.23 (d, J=15.31 Hz, 2H) 4.44-4.51 (m, 1H) 5.65 (s, 1H) 7.03-7.18 (m, 3H) 7.23 (d, J=6.02 Hz, 1H) 7.32 (d, J=8.78 Hz, 1H) 7.53 (d, J=8.53 Hz, 1H) 8.40 (s, 1H) 8.53 (d, J=6.27 Hz, 1H)

¹⁹F NMR (376 MHz, CHLOROFORM-d) δ ppm −75.72
LC/MS (ES+): m/z 613.4 (M+H)⁺

Example 257

3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate

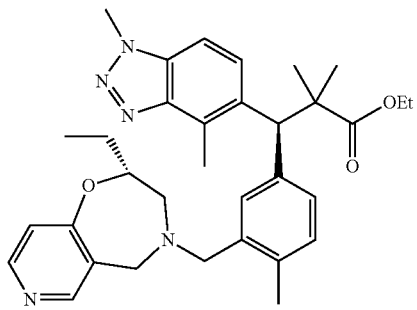 [SMILES: CCOC(=O)C(C)(C)[C@@H](c1ccc(C)c(CN2Cc3cnccc3O[C@H](CC)C2)c1)c1ccc2c(nnn2C)c1C]

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4 (5H)-yl)methyl)-4-methylphenyl)-2,2-dimethylpropanoic acid (86 mg, 0.163 mmol) was taken up in DCM (2 mL). Oxalyl chloride (0.16 mL, 1.828 mmol) followed by catalytic DMF (1 drop) was added and the reaction stirred for 90 minutes. To this reaction mixture was added excess ethanol (2 mL). The reaction was then diluted with saturated aqueous NaHCO₃ and extracted with DCM (3×). The combined organic layers were washed with brine, dried over magnesium sulfate, filtered, and concentrated in vacuo. The crude residue was purified by reverse phase acidic prep HPLC (Sunfire, TFA modifier). The purified product fractions were free based with saturated aqueous NaHCO₃ to remove the TFA salt and the product was extracted from the aqueous layer with DCM. The combined organic layers were dried over magnesium sulfate, filtered, and concentrated in vacuo to provide (S)-ethyl 3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoate (13.4 mg, 0.024 mmol, 14.8% yield) as a white solid after lyophlization.

¹H NMR (400 MHz, CHLOROFORM-d) δ ppm 0.95 (q, J=7.28 Hz, 6H) 1.31 (s, 3H) 1.38 (s, 3H) 1.55-1.65 (m, 1H) 2.25 (s, 3H) 2.78 (s, 3H) 2.79-2.90 (m, 2H) 3.54 (s, 2H) 3.76 (s, 2H) 3.83-4.00 (m, 3H) 4.25 (s, 3H) 4.83 (s, 1H) 6.90 (d, J=5.27 Hz, 1H) 7.00-7.09 (m, 3H) 7.27 (d, J=8.60 Hz, 1H) 7.64 (d, J=8.78 Hz, 1H) 8.16 (s, 1H) 8.39 (d, J=5.02 Hz, 1H)
LC/MS (ES+): m/z 556.2 (M+H)⁺

Example 258

(S)-ethyl 3-(1,4-dimethyl-1H-benzo[d][1,2,3]triazol-5-yl)-3-(3-(((R)-2-ethyl-2.3-dihydropyrido[2,3-f][1,4]oxazepin-4(5H)-yl)methyl)-4-methylphenyl)propionate

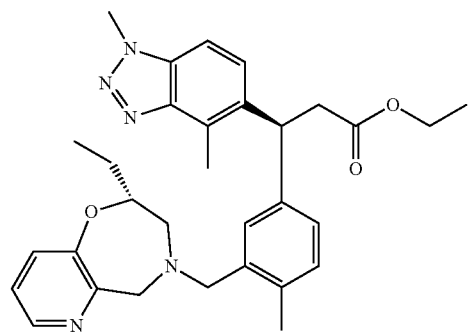 [SMILES: CCOC(=O)C[C@@H](c1ccc(C)c(CN2Cc3ncccc3O[C@H](CC)C2)c1)c1ccc2c(nnn2C)c1C]

To a solution of (S)-ethyl 3-(3-chloromethyl)-4-methylphenyl)-3-(1,4-dimethyl-1H-benzo[d][1,2,3]triazol-5-yl) propanoate (119 mg, 0.308 mmol) and DIEA (0.164 mL, 0.939 mmol) in acetonitrile (2.0 mL) was added (R)-2-ethyl-2,3,4,5-tetrahydropyrido[2,3-t][1,4]oxazepine, hydrochloride (101 mg, 0.469 mmol) and the reaction mixture was stirred at 60° C. for 4 hrs. The reaction mixture was cooled, the solvent evaporated, and the crude residue partitioned between DCM and H₂O, the layers separated and the organic phase dried over Na₂SO₄, filtered and the solvent evaporated under reduced pressure. The crude residue was purified by flash column chromatography (SiO₂; 24 g) eluting with a 100% hexanes to 60% EtOAc-hexanes gradient over 15 min to afford 101.3 mg (61%) of title compound as a white foam.
LC-MS m/z 528.4.

(S)-3-(1,4-dimethyl-1H-benzo[d][1,2,3]triazol-5-yl)-3-(3-(((R)-2-ethyl-2.3-dihydropyrido[2,3-f][1,4]oxazepin-4(5H)-yl)methyl)-4-methylphenyl)propionic Acid

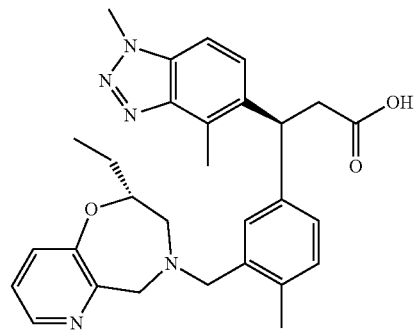 [SMILES: CC[C@@H]1CN(Cc2cc([C@H](CC(=O)O)c3ccc4c(nnn4C)c3C)ccc2C)Cc2ncccc2O1]

To a solution of (S)-ethyl 3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propionate (101 mg, 0.191 mmol) in ethanol (2.0 mL) was added 2N NaOH (0.782 mL, 1.56 mmol) and the reaction mixture was stirred at 60° C. for 18 hrs. The reaction mixture was cooled and the solvent evaporated using a Dry-column nitrogen blowdown unit at 50° C. The crude residue was partitioned between EtOAc and H$_2$O, the pH of the aqueous adjusted to ~pH 6 with 1 N HCl, the layers separated, the aqueous phase extracted with EtOAc (2×), the organics combined, washed with H$_2$O, brine, dried over Na$_2$SO$_4$, filtered and the solvent evaporated under reduced pressure. The crude residue was purified by flash column chromatography (SiO$_2$; 12 g) eluting with a 100% CH$_2$Cl$_2$ to 10% MeOH—CH$_2$Cl$_2$ gradient over 15 min to afford 73.8 mg (77%) of title compound as a white solid. LC-MS m/z 503.2. $^1$H NMR (400 MHz, DMSO-d$_6$) δ: 0.93 (t, J=7.4 Hz, 3H), 1.31 (ddd, J=13.9, 7.3, 4.1 Hz, 1H), 1.42-1.59 (m, 1H), 2.19 (s, 3H), 2.64-2.92 (m, 5H), 3.04 (d, J=7.8 Hz, 2H), 3.51 (s, 2H), 3.73-3.98 (m, 3H), 4.24 (s, 3H), 4.78 (t, J=7.8 Hz, 1H), 7.02-7.07 (m, 1H), 7.08-7.14 (m, 2H), 7.27 (dd, J=8.0, 4.5 Hz, 1H), 7.39 (dd, J=8.0, 1.3 Hz, 1H), 7.45-7.57 (m, 2H), 8.18 (dd, J=4.6, 1.4 Hz, 1H), 12.14 (br. s., 1H).

The compounds in Table 25 were prepared by a method similar to the one described for the preparation of (S)-ethyl 3-(1,4-dimethyl-1H-benzo[d][1,2,3]triazol-5-yl)-3-(3-(((FR)-2-ethyl-2,3-dihydropyrido[2,3-t][1,4]oxazepin-4(5H)-yl)methyl)-4-methylphenyl)propionate. As is appreciated by those skilled in the art, these analogous examples may involve variations in general reaction conditions.

TABLE 25

| Ex # | Structure | Name | LCMS [M + H]$^+$ | Retention Time (min) |
|---|---|---|---|---|
| 259 | 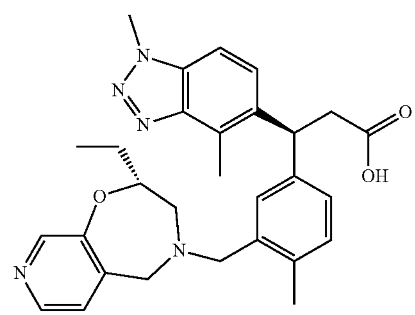 [SMILES: CC[C@@H]1CN(Cc2cc([C@H](CC(=O)O)c3ccc4c(nnn4C)c3C)ccc2C)Cc2ccncc2O1] | (S)-3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-methylphenyl)propanoic acid | 503.2 | 1.32 |
| 260 | 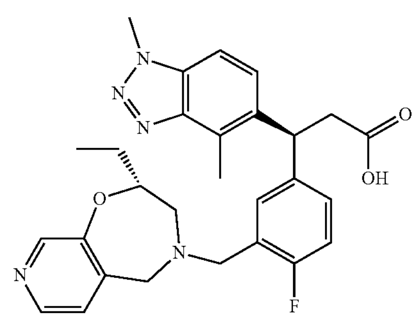 [SMILES: CC[C@@H]1CN(Cc2cc([C@H](CC(=O)O)c3ccc4c(nnn4C)c3C)ccc2F)Cc2ccncc2O1] | (S)-3-(1,4-dimethyl-1H-benzo[d][1,2,3]triazol-5-yl)-3-(3-(((R)-2-ethyl-2,3-dihydropyrido[4,3-f][1,4]oxazepin-4(5H)-yl)methyl)-4-fluorophenyl)propanoic acid | 504.2 | 1.51 |
| 261 | 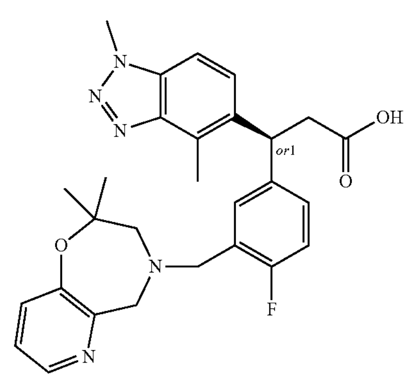 [SMILES: Cc1c([C@@H](CC(=O)O)c2ccc(F)c(CN3Cc4ncccc4OC(C)(C)C3)c2)ccc2c1nnn2C] | rel-(R)-3-(1,4-dimethyl-1H-benzo[d]-[1,2,3]triazol-5-yl)-3-(3-((2,2-dimethyl-2,3-dihydropyrido[2,3-f][1,4]oxazepin-4(5H)-yl)methyl)-4-fluorophenyl)-propanoic acid (isomer 1) | 504.3 | 0.69 |

TABLE 25-continued

| Ex # | Structure | Name | LCMS [M + H]⁺ | Retention Time (min) |
|---|---|---|---|---|
| 262 | 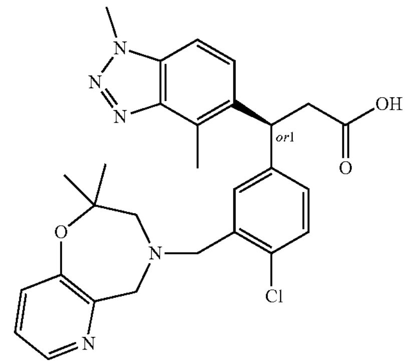 [SMILES: Cc1c([C@@H](CC(=O)O)c2ccc(Cl)c(CN3Cc4ncccc4OC(C)(C)C3)c2)ccc2c1nnn2C] | rel-(R)-3-(4-chloro-3-((2,2-dimethyl-2,3-dihydropyrido[2,3-f][1,4]oxazepin-4(5H)-yl)methyl)phenyl)-3-(1,4-dimethyl-1H-benzo[d][1,2,3]triazol-5-yl)propanoic acid (isomer 1) | 520.3 | 0.8 |
| 263 | 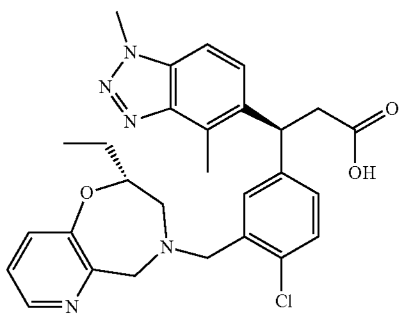 [SMILES: CC[C@@H]1CN(Cc2cc([C@H](CC(=O)O)c3ccc4c(nnn4C)c3C)ccc2Cl)Cc2ncccc2O1] | (S)-3-(4-chloro-3-(((R)-2-ethyl-2,3-dihydropyrido[2,3-f][1,4]oxazepin-4(5H)-yl)methyl)phenyl)-3-(1,4-dimethyl-1H-benzo[d][1,2,3]triazol-5-yl)propanoic acid | 520.2 | 1.62 |
| 264 | 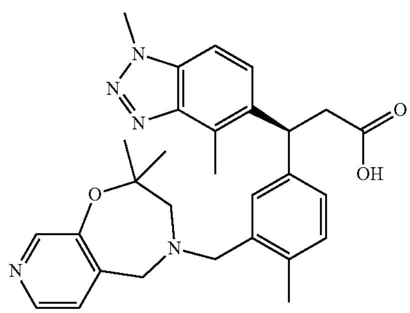 [SMILES: Cc1ccc([C@H](CC(=O)O)c2ccc3c(nnn3C)c2C)cc1CN1Cc2ccncc2OC(C)(C)C1] | (S)-3-(1,4-dimethyl-1H-benzo[d][1,2,3]triazol-5-yl)-3-(3-((2,2-dimethyl-2,3-dihydropyrido[4,3-f][1,4]oxazepin-4(5H)-yl)methyl)-4-methylphenyl)propanoic acid | 500.2 | 1.55 |

What is claimed is:

1. A compound of Formula (I)

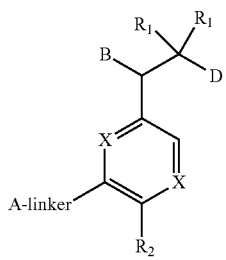

wherein,

B is —(CH₂)₂-triazolyl which is unsubstituted or substituted by 1, 2, or 3 substituents independently selected from —C$_{1-3}$alkyl, —O—C$_{1-3}$alkyl, CN, —(CH₂)₂—O—(CH₂)₂—OR₄ and halo;

D is —C(O)OH, —C(O)NHSO₂CH₃, —SO₂NHC(O)CH₃, 5-(trifluoromethyl)-4H-1,2,4-triazol-2-yl, or tetrazolyl;

R₁ is independently hydrogen, C$_{1-3}$alkyl, F, or the two R₁ groups together with the carbon to which they are attached form a cyclopropyl group;

R₂ is hydrogen, methyl, CF₃, or halo;

R₄ is hydrogen or —C$_{1-3}$alkyl;

Linker is —CH₂—, —CH₂—N(cyclopropyl)—CH₂—, —CH₂—N(CH₃)—CH₂— or —N(CH₃)—CH₂—;

A is tetrahydrobenzoxazepinyl or tetrahydro-pyrido-oxazepinyl, each of which is unsubstituted or substituted by 1, 2, or 3 substituents independently selected from —C$_{1-3}$alkyl, C$_{3-6}$spirocycloalkyl, halo, CN, —O—C$_{1-3}$alkyl, —CH₂—O—CH₃, and OH; and X is CH;

or a pharmaceutically acceptable salt thereof.

2. A pharmaceutical composition comprising a compound of claim 1, or a pharmaceutically acceptable salt thereof, and one or more pharmaceutically acceptable excipients.

3. A method for treating heart failure comprising administering to a human in need thereof, a therapeutically effective amount of the compound, or a pharmaceutically acceptable salt thereof, of claim 1.

4. The method of claim 3 wherein the compound, or a pharmaceutically acceptable salt thereof, is administered orally.

5. The method of claim 3 wherein the compound, or a pharmaceutically acceptable salt thereof, is administered intravenously.

6. A compound which is 5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid:

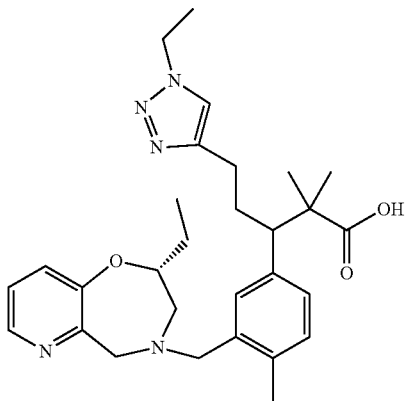 [SMILES: CC[C@@H]1CN(Cc2cc(C(CCc3cn(CC)nn3)C(C)(C)C(=O)O)ccc2C)Cc2ncccc2O1]

or a pharmaceutically acceptable salt thereof.

7. A pharmaceutical composition comprising the compound or a pharmaceutically acceptable salt thereof, of claim 6, and one or more pharmaceutically acceptable excipients.

8. A method for treating heart failure comprising administering to a human in need thereof, a therapeutically effective amount of the compound, or a pharmaceutically acceptable salt thereof, of claim 6.

9. The method of claim 8 wherein the compound, or pharmaceutically acceptable salt thereof, is administered orally.

10. The method of claim 8 wherein the compound, or a pharmaceutically acceptable salt thereof, is administered intravenously.

11. An enantiomer of a compound which is 5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid, or a pharmaceutically acceptable salt thereof.

12. A pharmaceutical composition comprising the compound or pharmaceutically acceptable salt thereof, of claim 11, and one or more pharmaceutically acceptable excipients.

13. A method for treating heart failure comprising administering to a human in need thereof, a therapeutically effective amount of the compound, or a pharmaceutically acceptable salt thereof, of claim 11.

14. The method of claim 13 wherein the compound, or a pharmaceutically acceptable salt thereof, is administered orally.

15. The method of claim 13 wherein the compound, or a pharmaceutically acceptable salt thereof, is administered intravenously.

16. A compound which is 5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid:

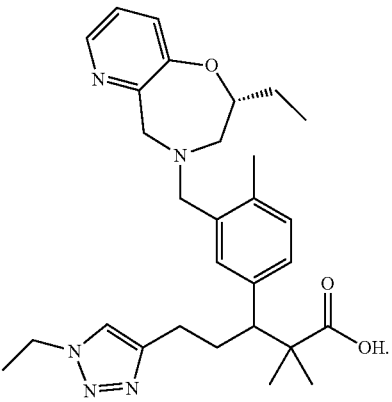 [SMILES: CC[C@@H]1CN(Cc2cc(C(CCc3cn(CC)nn3)C(C)(C)C(=O)O)ccc2C)Cc2ncccc2O1]

17. A pharmaceutical composition comprising the compound of claim 16, and one or more pharmaceutically acceptable excipients.

18. A method for treating heart failure comprising administering to a human in need thereof, a therapeutically effective amount of the compound of claim 17.

19. The method of claim 17 wherein the compound is administered orally.

20. The method of claim 17 wherein the compound is administered intravenously.

21. An enantiomer of a compound which is 5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid.

22. A pharmaceutical composition comprising the compound of claim 21, and one or more pharmaceutically acceptable excipients.

23. A method for treating heart failrue comprising administering to a human in need thereof, a therapeutically effective amount of the compound claim 21.

24. The method of claim 22 wherein the compouind is administered orally.

25. The method of claim 22 wherein the compound is administered intravenously.

26. The compound of claim 1, or a pharmaceutically acceptable salt thereof, which is:
5-(1-Ethyl-1H-1,2,3-triazol-4-yl)-3-(3-((2-ethyl-2,3-dihydrobenzo[f][1,4]oxazepin-4(5H)-yl)methyl)-4-methylphenyl)pentanoic acid;
5-(1-Ethyl-1H-1,2,3-triazol-4-yl)-3-(3-(((R)-2-ethyl-2,3-dihydrobenzo[f][1,4]oxazepin-4(5H)-yl)methyl)-4-methylphenyl)-2-methylpentanoic acid;
5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2,2-dimethylpentanoic acid;
5-(1-Ethyl-1H-1,2,3-triazol-4-yl)-3-(3-(((R)-2-ethyl-2,3-dihydropyrido[3,2-f][1,4]oxazepin- 4(5H)-yl)methyl)-4-methylphenyl)-2,2-dimethylpentanoic acid;
5-(1-Ethyl-1H-1,2,3-triazol-4-yl)-3-(3-(((R)-2-ethyl-2,3-dihydropyrido[4,3-f][1,4]oxazepin- 4(5H)-yl)methyl)-4-methylphenyl)-2,2-dimethylpentanoic acid;
3-(3-((2,2-Dimethyl-2,3-dihydropyrido[2,3-f][1,4]oxazepin-4(5H)-yl)methyl)-4-methylphenyl)- 5-(1-ethyl-1H-1,2,3-triazol-4-yl)-2,2-dimethylpentanoic acid;
3-(3-((2,2-Dimethyl-2,3-dihydropyrido[3,2-f][1,4]oxazepin-4(5H)-yl)methyl)-4-methylphenyl)-5-(1-ethyl-1H-1,2,3-triazol-4-yl)-2,2-dimethylpentanoic acid;
5-(1-Ethyl-1H-1,2,3-triazol-4-yl)-3-(3-(((R)-2-ethyl-2,3-dihydropyrido[2,3-f][1,4]oxazepin-4(5H)-yl)methyl)-4-methylphenyl)-2-methylpentanoic acid;

3-(3-((2,2-Dimethyl-2,3-dihydropyrido[3,4-f][1,4]oxazepin-4(5H)-yl)methyl)-4-methylphenyl)-5-(1-ethyl-1H-1,2,3-triazol-4-yl)-2-methylpentanoic acid;

3-(4-Chloro-3-(((R)-2-ethyl-2,3-dihydropyrido[2,3-f][1,4]oxazepin-4(5H)-yl)methyl)phenyl)-5-(1-ethyl-1H-1,2,3-triazol-4-yl)pentanoic acid;

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)pentanoic acid;

3-(4-Chloro-3-((2,2-dimethyl-2,3-dihydropyrido[3,2-f][1,4]oxazepin-4(5H)-yl)methyl)phenyl)-5-(1-ethyl-1H-1,2,3-triazol-4-yl)pentanoic acid;

5-(1-Ethyl-1H-1,2,3-triazol-4-yl)-3-(3-(((R)-2-ethyl-2,3-dihydropyrido[3,4-f][1,4]oxazepin-4(5H)-yl)methyl)-4-methylphenyl)-N-(methylsulfonyl)pentanamide; and 5-(1-Ethyl-1H-1,2,3-triazol-4-yl)-3-(3-(((R)-2-ethyl-2,3-dihydropyrido[2,3-f][1,4]oxazepin- 4(5H)-yl)methyl)-4-methylphenyl)-2,2-dimethylpentanoic acid.

\* \* \* \* \*